US011060145B2

(12) United States Patent
Jensen et al.

(10) Patent No.: US 11,060,145 B2
(45) Date of Patent: Jul. 13, 2021

(54) METHODS AND COMPOSITIONS FOR IDENTIFYING PRESENCE OR ABSENCE OF HYPERMETHYLATION OR HYPOMETHYLATION LOCUS

(71) Applicant: SEQUENOM, INC., San Diego, CA (US)

(72) Inventors: Taylor Jacob Jensen, San Diego, CA (US); Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 1060 days.

(21) Appl. No.: 14/772,544

(22) PCT Filed: Mar. 13, 2014

(86) PCT No.: PCT/US2014/025132
§ 371 (c)(1),
(2) Date: Sep. 3, 2015

(87) PCT Pub. No.: WO2014/168711
PCT Pub. Date: Oct. 16, 2014

(65) Prior Publication Data

US 2016/0145685 A1    May 26, 2016

Related U.S. Application Data

(60) Provisional application No. 61/780,162, filed on Mar. 13, 2013.

(51) Int. Cl.
*C12Q 1/6883* (2018.01)
*C12Q 1/6811* (2018.01)

(52) U.S. Cl.
CPC .......... *C12Q 1/6883* (2013.01); *C12Q 1/6811* (2013.01); *C12Q 2600/154* (2013.01); *C12Q 2600/16* (2013.01)

(58) Field of Classification Search
CPC ............ C12Q 1/6883; C12Q 1/6811; C12Q 2600/16; C12Q 2600/154
See application file for complete search history.

(56) References Cited

U.S. PATENT DOCUMENTS

| | | | |
|---|---|---|---|
| 4,109,496 A | 8/1978 | Allemann et al. |
| 4,179,337 A | 12/1979 | Davis et al. |
| 4,458,066 A | 7/1984 | Caruthers et al. |
| 4,469,863 A | 9/1984 | Ts'o et al. |
| 4,522,811 A | 6/1985 | Eppstein et al. |
| 4,656,127 A | 4/1987 | Mundy |
| 4,676,980 A | 6/1987 | Segal et al. |
| 4,683,195 A | 7/1987 | Mullis et al. |
| 4,683,202 A | 7/1987 | Mullis |
| 4,851,331 A | 7/1989 | Vary et al. |
| 4,868,103 A | 9/1989 | Stavrianopoulos et al. |
| 4,873,316 A | 10/1989 | Meade et al. |
| 4,965,188 A | 10/1990 | Mullis et al. |
| 5,048,530 A | 9/1991 | Hurwitz |
| 5,075,212 A | 12/1991 | Rotbart |
| 5,118,937 A | 6/1992 | Hillenkamp et al. |
| 5,210,015 A | 5/1993 | Gelfand et al. |
| 5,272,071 A | 12/1993 | Chappel et al. |
| 5,283,317 A | 2/1994 | Saifer et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,536,821 A | 7/1996 | Agrawal et al. |
| 5,541,306 A | 7/1996 | Agrawal et al. |
| 5,547,835 A | 8/1996 | Koster |
| 5,589,330 A | 12/1996 | Shuber |
| 5,605,798 A | 2/1997 | Koster |
| 5,614,622 A | 2/1997 | Iyer et al. |
| 5,631,169 A | 5/1997 | Lakowicz et al. |
| 5,637,683 A | 6/1997 | Usher et al. |
| 5,637,684 A | 6/1997 | Cook |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,700,922 A | 12/1997 | Cook |
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |

(Continued)

FOREIGN PATENT DOCUMENTS

| | | |
|---|---|---|
| EP | 0264166 | 4/1988 |
| EP | 264166 | 4/1988 |

(Continued)

OTHER PUBLICATIONS

Ellinger et al. The Journal of Urology 2009; 182: 324-329 (Year: 2009).*
GenBank Accession No. AC008575.7 for *Homo sapiens* chromosome 5 clone CTC-554D6, complete sequence, Jul. 20, 2001 [online], [retrieved on Jul. 18, 2018], retrieved from the Internet: <URL: www.ncbi.nlm.nih.gov/nuccore/ac008575.7> (Year: 2001).*
GenBank Accession No. NG_028206.2 for *Homo sapiens* prostagladin-endoperoxide synthase 2 (PTGS2), RegfSeqGene on chromosome 1, Sep. 13, 2017 [online], [retrieved on Jul. 18, 2018], Retrieved from the Internet: <www.ncbi.nlm.nih.gov/nuccore/ng_028206.2> (Year: 2017).*

(Continued)

*Primary Examiner* — Angela M. Bertagna
(74) *Attorney, Agent, or Firm* — Kilpatrick Townsend & Stockton LLP

(57) ABSTRACT

Technology provided herein relates in part to methods, processes and apparatuses for non-invasive assessment of genetic variations.

13 Claims, 7 Drawing Sheets
Specification includes a Sequence Listing.

(56) References Cited

U.S. PATENT DOCUMENTS

| | | |
|---|---|---|
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |
| 5,851,770 A | 12/1998 | Babon et al. |
| 5,869,242 A | 2/1999 | Kamb |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,929,226 A | 7/1999 | Padmapriya et al. |
| 5,952,174 A | 9/1999 | Nikiforov et al. |
| 5,955,599 A | 9/1999 | Iyer et al. |
| 5,958,692 A | 9/1999 | Cotton et al. |
| 5,962,674 A | 10/1999 | Iyer et al. |
| 5,976,802 A | 11/1999 | Ansorge et al. |
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,024,925 A | 2/2000 | Little et al. |
| 6,029,041 A | 2/2000 | Takano et al. |
| 6,043,031 A | 3/2000 | Koster et al. |
| 6,045,996 A | 4/2000 | Cronin et al. |
| 6,046,005 A | 4/2000 | Ju et al. |
| 6,057,134 A | 5/2000 | Lader et al. |
| 6,057,143 A | 5/2000 | Lader et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Iyer |
| 6,136,541 A | 10/2000 | Gulati |
| 6,140,053 A | 10/2000 | Koster |
| 6,140,054 A | 10/2000 | Wittwer et al. |
| 6,140,482 A | 10/2000 | Iyer et al. |
| 6,142,681 A | 11/2000 | Gulati |
| 6,143,496 A | 11/2000 | Brown et al. |
| 6,156,501 A | 12/2000 | McGall et al. |
| 6,183,958 B1 | 2/2001 | Stanton, Jr. |
| 6,194,144 B1 | 2/2001 | Koster |
| 6,194,180 B1 | 2/2001 | Joyce |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Koster et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,468,748 B1 | 10/2002 | Monforte et al. |
| 6,610,492 B1 | 8/2003 | Stanton, Jr. et al. |
| 6,664,056 B2 | 12/2003 | Lo et al. |
| 6,723,513 B2 | 4/2004 | Lexow |
| 6,759,217 B2 | 7/2004 | Kopreski |
| 6,794,142 B2 * | 9/2004 | Laird .................. C12Q 1/6848 435/6.1 |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 | 8/2005 | Oefner et al. |
| 7,081,339 B2 | 7/2006 | Slepnev |
| 7,169,314 B2 | 1/2007 | Unger et al. |
| 7,244,567 B2 | 7/2007 | Chen et al. |
| 7,253,259 B2 | 8/2007 | Otagiri et al. |
| 7,285,422 B1 | 10/2007 | Little et al. |
| 7,468,249 B2 | 12/2008 | Xie et al. |
| 7,655,399 B2 | 2/2010 | Cantor et al. |
| 7,709,194 B2 | 5/2010 | Lo et al. |
| 7,709,262 B2 | 5/2010 | Cantor et al. |
| 7,754,428 B2 | 7/2010 | Lo et al. |
| 7,785,798 B2 | 8/2010 | Cantor et al. |
| 7,901,884 B2 | 3/2011 | Lo et al. |
| 8,195,415 B2 | 6/2012 | Fan et al. |
| 8,518,228 B2 | 8/2013 | Marziali et al. |
| 8,706,422 B2 | 4/2014 | Lo et al. |
| 9,074,013 B2 | 7/2015 | Rehli |
| 9,187,780 B2 | 11/2015 | Micallef et al. |
| 9,189,086 B2 | 11/2015 | McGibney et al. |
| 9,222,937 B2 | 12/2015 | Micallef |
| 9,249,464 B2 | 2/2016 | Rehli |
| 9,400,276 B2 | 7/2016 | Micallef |
| 9,709,569 B2 | 7/2017 | Micallef et al. |
| 2001/0008615 A1 | 7/2001 | Little et al. |
| 2001/0051341 A1 | 12/2001 | Lo et al. |
| 2002/0006621 A1 | 1/2002 | Bianchi |
| 2003/0022207 A1 | 1/2003 | Balasubramanian et al. |
| 2003/0082600 A1 | 5/2003 | Olek et al. |
| 2003/0087276 A1 | 5/2003 | Kopreski |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Landes et al. |
| 2004/0014105 A1 | 1/2004 | Schroeder et al. |
| 2004/0081993 A1 | 4/2004 | Cantor et al. |
| 2004/0115684 A1 | 6/2004 | Costa |
| 2004/0137470 A1 | 7/2004 | Dhallan |
| 2004/0203037 A1 | 10/2004 | Lo et al. |
| 2005/0037388 A1 | 2/2005 | Antonarakis et al. |
| 2005/0059003 A1 | 3/2005 | Enoki et al. |
| 2005/0064406 A1 | 3/2005 | Zabarobsky et al. |
| 2005/0064428 A1 | 3/2005 | Berlin |
| 2005/0069879 A1 | 3/2005 | Berlin |
| 2005/0069931 A1 | 3/2005 | Allis et al. |
| 2005/0079521 A1 | 4/2005 | Beaulieu et al. |
| 2005/0112590 A1 | 5/2005 | Van Den Boom et al. |
| 2005/0009059 A1 | 7/2005 | Shapero et al. |
| 2005/0019762 A1 | 7/2005 | Olek |
| 2005/0153316 A1 | 7/2005 | Jeddeloh et al. |
| 2005/0153347 A1 | 7/2005 | Shapero et al. |
| 2005/0164241 A1 | 7/2005 | Hahn et al. |
| 2005/0266473 A1 | 12/2005 | Zhang et al. |
| 2005/0272070 A1 | 12/2005 | Ehrich et al. |
| 2005/0287592 A1 | 12/2005 | Kless |
| 2006/0019278 A1 | 1/2006 | Lo et al. |
| 2006/0094039 A1 | 5/2006 | Rosenfeld et al. |
| 2006/0136142 A1 | 7/2006 | Berlin et al. |
| 2006/0160105 A1 | 7/2006 | Dhallan |
| 2006/0166228 A1 | 7/2006 | Page et al. |
| 2006/0210992 A1 | 9/2006 | van den Boom |
| 2006/0252068 A1 | 11/2006 | Lo et al. |
| 2006/0252071 A1 | 11/2006 | Lo et al. |
| 2007/0048755 A1 | 3/2007 | De Fiore |
| 2007/0059707 A1 | 3/2007 | Cantor et al. |
| 2007/0065823 A1 | 3/2007 | Dressman et al. |
| 2007/0111233 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0275402 A1 | 11/2007 | Lo et al. |
| 2008/0020390 A1 | 1/2008 | Mitchell et al. |
| 2008/0070792 A1 | 3/2008 | Stoughton et al. |
| 2008/0096766 A1 | 4/2008 | Lee |
| 2008/0299562 A1 | 12/2008 | Oeth et al. |
| 2008/0305479 A1 | 12/2008 | Van Den Boom |
| 2009/0026082 A1 | 1/2009 | Rothberg et al. |
| 2009/0029377 A1 | 1/2009 | Lo et al. |
| 2009/0053719 A1 | 2/2009 | Lo et al. |

(56) References Cited

U.S. PATENT DOCUMENTS

| | | |
|---|---|---|
| 2009/0061425 A1 | 3/2009 | Lo et al. |
| 2009/0111712 A1 | 5/2009 | Van Den Boom |
| 2009/0142755 A1 | 6/2009 | Albitar |
| 2009/0202984 A1 | 8/2009 | Cantor |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0184046 A1 | 7/2010 | Klass et al. |
| 2010/0203529 A1 | 8/2010 | Kuslich et al. |
| 2010/0216153 A1 | 8/2010 | Lapidus et al. |
| 2010/0227320 A1 | 9/2010 | Fu |
| 2010/0240054 A1 | 9/2010 | Bischoff |
| 2010/0273165 A1 | 10/2010 | Ehrich et al. |
| 2010/0279295 A1 | 11/2010 | Roy et al. |
| 2011/0033851 A1 | 2/2011 | Rand |
| 2011/0039724 A1 | 2/2011 | Lo et al. |
| 2011/0105353 A1 | 5/2011 | Lo et al. |
| 2011/0151460 A1 | 6/2011 | Klass et al. |
| 2011/0177517 A1 | 7/2011 | Rava et al. |
| 2011/0178719 A1 | 7/2011 | Rabinowirz et al. |
| 2011/0201507 A1 | 8/2011 | Rava et al. |
| 2011/0212846 A1 | 9/2011 | Spier |
| 2011/0224087 A1 | 9/2011 | Quake et al. |
| 2011/0244451 A1 | 10/2011 | Cantor et al. |
| 2011/0266780 A1 | 11/2011 | Komoll et al. |
| 2011/0276277 A1 | 11/2011 | Lo et al. |
| 2011/0288780 A1 | 11/2011 | Rabinowirz et al. |
| 2012/0028613 A1 | 2/2012 | Lewis |
| 2012/0065076 A1 | 3/2012 | Peters et al. |
| 2012/0184449 A1 | 7/2012 | Hixson et al. |
| 2012/0196754 A1 | 8/2012 | Quake et al. |
| 2012/0264618 A1 | 10/2012 | Nygren |
| 2012/0276542 A1 | 11/2012 | Nygren |
| 2012/0277119 A1 | 11/2012 | Ehrich et al. |
| 2012/0282613 A1 | 11/2012 | Patsalis et al. |
| 2013/0012399 A1 | 1/2013 | Myers et al. |
| 2013/0022974 A1* | 1/2013 | Chinnaiyan et al. ............ C12Q 1/6886 435/6.11 |
| 2013/0065254 A1 | 3/2013 | Lunyak |
| 2013/0085681 A1 | 4/2013 | Deciu et al. |
| 2013/0130923 A1 | 5/2013 | Ehrich et al. |
| 2013/0143211 A1 | 6/2013 | Ehrich et al. |
| 2013/0150249 A1 | 6/2013 | Ehrich et al. |
| 2013/0230858 A1 | 9/2013 | Cantor et al. |
| 2013/0237431 A1 | 9/2013 | Lo et al. |
| 2013/0295564 A1 | 11/2013 | Ehrich et al. |
| 2013/0296180 A1 | 11/2013 | Ehrich et al. |
| 2013/0310260 A1 | 11/2013 | Kim et al. |
| 2014/0093873 A1 | 4/2014 | Tynan et al. |
| 2014/0180594 A1 | 6/2014 | Kim et al. |
| 2015/0267263 A1 | 9/2015 | Rehli |
| 2015/0275304 A1 | 10/2015 | Ehrich et al. |
| 2016/0201113 A1 | 7/2016 | Rehli |

FOREIGN PATENT DOCUMENTS

| | | |
|---|---|---|
| EP | 0401384 | 12/1990 |
| EP | 401384 | 12/1990 |
| EP | 1373561 | 2/2009 |
| EP | 1524321 | 4/2009 |
| JP | 2005-514956 | 5/2005 |
| JP | 2007-505641 | 3/2007 |
| JP | 2008-521389 | 6/2008 |
| JP | 2009-529330 | 8/2009 |
| JP | 5727375 | 6/2015 |
| JP | 2015-126748 | 7/2015 |
| JP | 5873434 | 3/2016 |
| JP | 5923571 | 5/2016 |
| WO | WO 91/006667 | 5/1991 |
| WO | WO 94/010300 | 5/1994 |
| WO | WO 97/012058 | 4/1997 |
| WO | WO 97/035589 | 10/1997 |
| WO | WO 97/037041 | 10/1997 |
| WO | WO 98/020020 | 5/1998 |
| WO | WO 98/022489 | 5/1998 |
| WO | 9839474 | 9/1998 |
| WO | WO 98/039352 | 9/1998 |
| WO | WO 98/039474 | 9/1998 |
| WO | WO 98/054364 | 12/1998 |
| WO | WO 99/057318 | 5/1999 |
| WO | 0041147 | 7/2000 |
| WO | WO 00/052625 | 9/2000 |
| WO | WO 00/056746 | 9/2000 |
| WO | WO 00/066771 | 11/2000 |
| WO | WO 00/075372 | 12/2000 |
| WO | WO 01/014398 | 3/2001 |
| WO | WO 01/020039 | 3/2001 |
| WO | WO 01/025485 | 4/2001 |
| WO | WO 01/027326 | 4/2001 |
| WO | WO 01/027327 | 4/2001 |
| WO | WO 01/027329 | 4/2001 |
| WO | WO 01/029259 | 4/2001 |
| WO | WO 02/018616 | 3/2002 |
| WO | WO 02/086163 | 10/2002 |
| WO | WO 03/000919 | 1/2003 |
| WO | WO 2003/020974 | 3/2003 |
| WO | WO 03/057909 | 7/2003 |
| WO | WO 03/062441 | 7/2003 |
| WO | 03070894 | 8/2003 |
| WO | WO 03/080863 | 10/2003 |
| WO | WO 04/013284 | 2/2004 |
| WO | WO 04/076653 | 9/2004 |
| WO | WO 04/079011 | 9/2004 |
| WO | WO 2004/078999 | 9/2004 |
| WO | WO 05/012578 | 2/2005 |
| WO | 2005/023091 | 3/2005 |
| WO | WO 05/021793 | 3/2005 |
| WO | WO 05/023091 | 3/2005 |
| WO | WO 05/035725 | 4/2005 |
| WO | WO 05/040399 | 5/2005 |
| WO | WO 05/098050 | 10/2005 |
| WO | WO 2005/118852 | 12/2005 |
| WO | WO 06/056480 | 6/2006 |
| WO | WO 06/097049 | 9/2006 |
| WO | WO 06/097051 | 9/2006 |
| WO | WO 07/016668 | 2/2007 |
| WO | WO 07/028155 | 3/2007 |
| WO | 2007/092473 | 8/2007 |
| WO | WO 07/092473 | 8/2007 |
| WO | WO 07/100911 | 9/2007 |
| WO | WO 07/121276 | 10/2007 |
| WO | 2007/132167 | 11/2007 |
| WO | WO 07/132166 | 11/2007 |
| WO | WO 07/132167 | 11/2007 |
| WO | WO 07/140417 | 12/2007 |
| WO | WO 07/147063 | 12/2007 |
| WO | WO 08/098142 | 8/2008 |
| WO | WO 08/103761 | 8/2008 |
| WO | WO 08/103763 | 8/2008 |
| WO | WO 08/118988 | 10/2008 |
| WO | WO 08/157264 | 12/2008 |
| WO | WO 09/032779 | 3/2009 |
| WO | WO 09/032781 | 3/2009 |
| WO | WO 09/039507 | 3/2009 |
| WO | WO 2009/030100 | 3/2009 |
| WO | WO 09/046445 | 4/2009 |
| WO | WO 09/091934 | 7/2009 |
| WO | WO 09/114543 | 9/2009 |
| WO | WO 10/004265 | 1/2010 |
| WO | WO 10/033639 | 3/2010 |
| WO | WO 10/065470 | 6/2010 |
| WO | WO 10/115016 | 10/2010 |
| WO | 2010/033639 A9 | 2/2011 |
| WO | WO 2011/018600 | 2/2011 |
| WO | WO 11/034631 | 3/2011 |
| WO | 2011/051283 | 5/2011 |
| WO | WO 11/087760 | 7/2011 |
| WO | WO 11/091063 | 7/2011 |
| WO | WO 11/092592 | 8/2011 |
| WO | WO 11/142836 | 11/2011 |
| WO | WO 11/143659 | 11/2011 |
| WO | 2011/142836 | 1/2012 |

(56) References Cited

FOREIGN PATENT DOCUMENTS

| WO | 2012/071621 | 6/2012 |
|---|---|---|
| WO | WO 12/118745 | 9/2012 |
| WO | WO 12/149339 | 11/2012 |
| WO | WO 13/052913 | 4/2013 |
| WO | WO 13/055817 | 4/2013 |
| WO | 2013/109981 A1 | 7/2013 |
| WO | 2013/131021 | 9/2013 |
| WO | 2013/177086 | 11/2013 |
| WO | WO 14/011928 | 1/2014 |
| WO | WO 14/168711 | 10/2014 |
| WO | 2014/190286 | 11/2014 |
| WO | 2015/040591 | 3/2015 |
| WO | 2015/061359 A1 | 4/2015 |
| WO | WO 15/138774 | 9/2015 |
| WO | 2016/019042 | 2/2016 |
| WO | 2016/067029 | 5/2016 |
| WO | 2017/068371 | 4/2017 |

OTHER PUBLICATIONS

Yamada et al. Genome Research 2004; 14: 247-266 (Year: 2004).*
GenBank Accession No. AL138704.12 for the human DNA sequence from clone RP11-417C20 on Chromosome 13. Dec. 13, 2012 [online], [retrieved on Dec. 8, 2019], retrieved from the Internet: <URL: www.ncbi.nlm.nih.gov/nuccore/AL138704.12> (Year: 2012).*
GenBank Accession No. AP000160.1 for the Homo sapiens genomic DNA, chromosome 21q.22, DSCR region, clone D47-S479, segment 12/16. Jan. 8, 2000 [online], [retrieved on Dec. 8, 2019], retrieved from the Internet: <URL: www.ncbi.nlm.nih.gov/nuccore/AP000160.1>(Year: 2000).*
Office Action dated Mar. 17, 2016 in U.S. Appl. No. 13/940,162, filed Jul. 11, 2013 and published as US 2014-0093873 on Apr. 3, 2014.
Adinolfi et al., "Rapid detection of aneuploidies by microsatellite and the quantitative fluorescent polymerase chain reaction." Prenat Diagn. Dec. 1997;17(13):1299-311.
Agresti, Categorical Data Analysis, 2nd Ed. 2002. Wiley.
Altschul et al., "Basic local alignment search tool." J Mol Biol. Oct. 5, 1990;215(3):403-10.
Altschul et al., "Gapped BLAST and PSI-BLAST: a new generation of protein database search programs." Nucleic Acids Res. Sep. 1, 1997;25(17):3389-402.
Amicucci et al., Clin. Chem. 46:301-302, 2000.
Amir et al., Nature Genet. 23:185-88 (1999).
Anantha et al., "Porphyrin binding to quadrupled T4G4." Biochemistry. Mar. 3, 1998;37(9):2709-14.
Nyren et al. Clin Chem, Oct. 2010, 56(10):1627-1635, Epub Aug. 20, 2010.
Anderson, S., "Shotgun DNA sequencing using cloned Dnase I-generated fragments,"Nucl. Acids Res. 9:3015-3027 (1981).
Antonarakis et al., Am J Hum Genet. Mar. 1992;50(3):544-50.
Antonarakis et al., Nat Genet. Feb. 1993;3(2):146-50.
Aoki E. et al., "Methylation status of the p15INK4B gene in hematopoietic progenitors and peripheral blood cells in myelodysplastic syndromes", Leukemia 14(4):586-593 (2000).
Armour et al., "Measurement of locus copy number By hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Asimakopoulos FA et al., "ABL 1 methylation is a distinct molecular event associated with clonal evolution of chronic myeloid leukemia" Blood 94(7):2452-2460 (1999.
Aston et al. (1999) Methods Enzymol. 303:55-73.
Aston et al. (1999) Trends Biotechnol. 17(7):297-302.
Ausubel et al., Current Protocols in Molecular Biology (Ausubel et al., eds., 1994), (Table of Contents Only).
Banerji et al., "A lymphocyte-specific cellular enhancer is located downstream of the joining region in immunoglobulin heavy chain genes." Cell. Jul. 1983;33(3):729-40.
Bartel et al., Biotechniques 14: 920-924 (1993), (Abstract Only).

Batey et al. (1992) Nucl. Acids Res. 20, 4515-4523.
Batey et al. (1996) Nucl. Acids Res. 24, 4836-4837.
Batzer et al., Nucleic Acid Res. 19:5081 (1991).
Beaucage & Caruthers, Tetrahedron Lett. 22: 1859-1862 (1981).
Beaudet, "Progress toward noninvasive prenatal diagnosis" Clin. Chem. (2011) 57(6):802-804.
Beckman Coulter, Introduction to Capillary Electrophoresis, Beckman Coulter 1991.
Benson G. Tandem repeats finder: a program to analyze DNA sequences. Nucleic Acids Res. Jan. 15, 1999;27(2):573-80.
Bianchi, 'Fetal cells in the mother: from genetic diagnosis to diseases associated with fetal cell microchimerism', In: European Journal of Obstetrics & Gynecology and Reproductive Biology, Sep. 2000, vol. 92(I), pp. 103-108.
Bock et al., "CpG island methylation in human lymphocytes is highly correlated with DNA sequence, repeats, and predicted DNA structure" Plos Genetics (2006) 2(3):e26.
Boguski et al., "Identification of a cytidine-specific ribonuclease from chicken liver." J Biol Chem. Mar. 10, 1980;255(5):2160-3.
Boom et al. (1990), J. Clin. Microbiol. 28: 495-503.
Boom et al. (1991), J. Clin. Microbiol. 29: 1804-1811.
Boyer, L.A. et al. Polycomb complexes repress developmental regulators in murine embryonic stem cells. Nature 441, 349-53 (2006).
Braslaysky et al., "Sequence information can be obtained from single DNA molecules." Proc Natl Acad Sci U S A. Apr. 1, 2003;100(7):3960-4. Epub Mar. 21, 2003.
Brizot et al., "Maternal serum hCG and fetal nuchal translucency thickness for the prediction of fetal trisomies in the first trimester of pregnancy." Br J Obstet Gynaecol. Feb. 1995;102(2):127-32.
Bullinger et al., "Use of gene-expression profiling to identify prognostic subclasses in adult acute myeloid leukemia." N Engl J Med. Apr. 15, 2004;350(16):1605-16.
Burlingame et al. Anal. Chem. 70:647R-716R (1998).
Burnier et al., "Cell-derived microparticles in haemostasis and vascular medicine," Thromb Haemost 2009, 101:439-451.
Byrne et al., "Multiplex gene regulation: a two-tiered approach to transgene regulation in transgenic mice." Proc Natl Acad Sci U S A. Jul. 1989;86(14):5473-7.
Calame et al., "Transcriptional controlling elements in the immunoglobulin and T cell receptor loci." Adv Immunol. 1988;43:235-75.
Caliper LifeSciences, Products and Contract Services, LabChip GX 2010, printed from the internet on Mar. 15, 2011 (http://www.caliperl.com/products/labchip-gx.htm).
Camper et al., "Postnatal repression of the alpha-fetoprotein gene is enhancer independent." Genes Dev. Apr. 1989;3(4):537-46.
Cell Death Detection ELISA Plus Cat. No. 11 774 425 001 "Detection of Post-translational Modifications on Native Intact Nucleosomes by ELISA," Version 11.0, Roche, Content Version: Sep. 2010, pp. 1-19.
Chan et al. (2004) Clin. Chem. 50:88-92.
Chan et al., "Hypermethylated RASSFIA in Maternal Plasma: A Universal Fetal DNA Marker that Improves the Reliability of Noninvasive Prenatal Diagnosis" Clin. Chem. (2006) 52:2211-2218.
Chan et al., Oncogene 22:924-934 (2003.
Chang et al., "LIBSVM: a library for Support Vector Machines," 2001.
Chen et al., "Fluorescence energy transfer detection as a homogeneous DNA diagnostic method." Proc Natl Acad Sci USA. Sep. 30, 1997;94(20):10756-61.
Chen et al., "Template-directed dye-terminator incorporation (TDI) assay: a homogeneous DNA diagnostic method based on fluorescence resonance energy transfer." Nucleic Acids Res. Jan. 15, 1997;25(2):347-53.
Cheson et al, "Report of the National Cancer Institute-sponsored workshop on definitions of diagnosis and response in acute myeloid leukemia" J Clin Oncol 8:813-819, 1990.
Cheung et al. (1994) J. Clin. Microbiol. 32: 2593-2597.
Chirgwin et al. (1979) Biochem. 18: 5294-5299.
Chitty, L. Br Med Bull 54:839-856 (1998).

(56) References Cited

OTHER PUBLICATIONS

Chiu et al., "Effects of blood-processing protocols on fetal and total DNA quantification in maternal plasma." Clin Chem. Sep. 2001;47(9):1607-1613.
Chiu et al., Lancet 360:998-1000, 2002.
Chomczynski and Mackey (1995, Anal. Biochem. 225: 163-164).
Chomczynski and Mackey (1995, Biotechniques 19: 942-945).
Chomczynski and Sacchi (1987, Analytical Biochem. 162: 156-159).
Chomczynski, (1993, Biotech. 15: 532-537).
Chow, K.C., et al., Mass Spectrometric detection of a SNP panel as an internal positive control for fetal DNA analysis in maternal plasma. Clin. Chem. 53, 141-142 (2007).
Chu et al, "A novel approach toward the challenge of accurately quantifying fetal DNA in maternal plasma," Prenatal Diagnosis, 2010; 30:1226-1229.
Colella et al. Biotechniques. Jul. 2003;35(1):1 46-50.
Costa et al., N. Engl. J. Med. 346:1502, 2002.
Costello et al., Restriction Landmark Genomic Scanning (RLGS): Analysis of CpG Islands in genomes by 2D Gel Electrophoresis, Methods in Molecular Biology, DNA Methylation, 2 Methods and Protocols, v.: 507, 2nd eds., pp. 131-148 (2000).
Cross et al., "Purification of CpG islands using a methylated DNA binding column" Nature Genetics (1994) 6(3):236-244.
Cruikshank et al., "A lipidated anti-Tat antibody enters living cells and blocks HIV-1 viral replication." J. Acquired Immune Deficiency Syndromes and Human Retrovirology Mar. 1, 1997;14(3):193-203, (Abstract Only).
Current Protocols in Molecular Biology, John Wiley & Sons, N.Y. , 6.3.1-6.3.6 (1989).
Dai et al., "Detection of Post-translational Modifications on Native Intact Nucleosomes by ELISA," Journal of Visualized Experiments, 2011, pp. 1-4.
D'Alton., "Prenatal diagnostic procedures." Semin Perinatol. Jun. 1994;18(3):140-62, (Abstract).
Das, R. et al. Proc Natl Acad Sci U S A 103, 10713-6 (2006).
Davison., "Sedimentation of deoxyribonucleic acid isolated under low hydrodynamic shear." Nature. Mar. 26, 1960;185:918-20.
Davison., "The Effect of Hydrodynamic Shear on the Deoxyribonucleic Acid From T(2) and T(4) Bacteriophages." Proc Natl Acad Sci U S A. Nov. 1959;45(11):1560-8.
Dayie et al. (1998) J. Mag. Reson. 130, 97-101 (1998).
Dear, "One by one: Single molecule tools for genomics." Brief Funct Genomic Proteomic. Jan. 2003;1(4):397-416.
Deininger, P. L. "Random subcloning of sonicated DNA: application to shotgun DNA sequence analysis," Anal. Biochem. 129(1):216-223 (1983).
Dembo et al., 1994, Ann. Prob. 22: 2022-2039.
Ding C, Cantor CR (2003) A high-throughput gene expression analysis technique using competitive PCR and matrix-assisted laser desorption ionization time-of-flight MS. Proc Natl Acad Sci U S A 100:3059-3064.
Donis-Keller et al., Nucl. Acids Res. 4:2527-2537 (1977).
Donis-Keller., "Phy M: an RNase activity specific for U and A residues useful in RNA sequence analysis." Nucleic Acids Res. Jul. 25, 1980;8(14):3133-42.
Dupont JM, Tost J, Jammes H, and Gut IG. Anal Biochem, Oct. 2004; 333(1): 119-27.
Eads et al., Cancer Res. 59:2302-2306, 1999.
Eckhardt, F. et al. Nat Genet 38, 1378-85 (2006).
Edlund et al., "Cell-specific expression of the rat insulin gene: evidence for role of two distinct 5' flanking elements." Science. Nov. 22, 1985;230(4728):912-6.
Egger et al., "Reverse transcription multiplex PCR for differentiation between polio- and enteroviruses from clinical and environmental samples." J Clin Microbiol. Jun. 1995;33(6):1442-7.
Ehrich et al., "Noninvasive detection of fetal trisomy 21 by sequencing of DNA in maternal blood: a study in a clinical setting," Reports of Major Impact, American Journal of Obstetrics and Gyenocology, Mar. 2011, 205e1-205e11.

Ehrich et al., A new method for accurate assessment of DNA quality after bisulfite treatment, Nucl. Acids Res. (2007) 35(5): e29 1-8.
Ehrich M, et al. (2005) Quantitative high-throughput analysis of DNA methylation patterns by base specific cleavage and mass spectrometry. Proc Natl Acad Sci U S A 102:15785-15790.
Ehrich M, et al. (2008) Cytosine methylation profiling of cancer cell lines. Proc Natl Acad Sci U S A 105:4844-48.
Eiben et al., "First-trimester screening: an overview." J Histochem Cytochem. Mar. 2005;53(3):281-3.
Ernani et al., Agilent's SureSelect Target Enrichment System: Bringing Cost and Process Efficiency to Next-Generation Sequencing Product Note, Agilent Technologies, Mar. 16, 2009.
Eva and Aaronson, Nature, 316:273-275, 1985.
Extended European Search Report dated Apr. 22, 2013 in European Application No. EP10843520 filed: Dec. 20, 2010 based on International Application No. PCT/US2010/061319.
Extended European Search Report dated Jan. 4, 2013 in European Application No. EP10817598.5 filed: Mar. 18, 2010.
Extended European Search Report dated: Apr. 19, 2012 in European Application No. EP 09815148 filed: Sep. 16, 2009.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Fan et al., "Noninvasive diagnosis of fetal aneuploidy by shotgun sequencing DNA from maternal blood." Proc Natl Acad Sci U S A. Oct. 21, 2008;105(42):16266-71. Epub Oct. 6, 2008.
Fan et al., "Working Set Selection Using the Second Order Information for Training SVM" Journal of Machine Learning Research 6 (2005) 1889-1918.
Fan et al., "Analysis of the size distributions of fetal and maternal cell-free DNA by paired-end sequencing" Clinical Chemistry (2010) 56(8):1279-1286.
Fan, Hei-Mun Christina, "Molecular Counting: From Noninvasive Prenatal Diagnostics to Whole-Genome Haplotyping" Dissertation, Stanford University, Nov. 2010.
Feinberg., "Methylation meets genomics." Nat Genet. Jan. 2001;27(1):9-10.
Ferguson-Smith, "Placental mRNA in maternal plasma: Prospects for fetal screening", PNAS vol. 100, No. 8, 4360-4362 Apr. 15, 2003.
Fournie et al. (1986 Anal. Biochem. 158: 250-256).
Frommer et al. Proc. Natl. Acad. Sci. USA 89:1827-1831, (1992).
Futreal, P.A. et al. Nat Rev Cancer 4, 177-83 (2004).
Gardiner-Garden et al., "CpG islands in vertebrate genomes." J Mol Biol. Jul. 20, 1987;196(2):261-82.
Gebhard C, Schwarzfischer L, Pham TH, Andreesen R, Mackensen A, Rehli M (2006) Rapid and sensitive detection of CpG-methylation using methyl-binding (MB)-PCR. Nucleic Acids Res 34:e82.
Gebhard C, Schwarzfischer L, Pham TH, Schilling E, Klug M, Andreesen R, Rehli M (2006) Genomewide profiling of CpG methylation identifies novel targets of aberrant hypermethylation in myeloid leukemia. Cancer Res 66:6118-6128.
Giles et al., "Acute myeloid leukemia." Hematology Am Soc Hematol Educ Program. 2002:73-110.
Go et al. Clin Chem. Dec. 2007;53(12):2223-4.
Go et al., "Non-invasive aneuploidy detection using free fetal DNA and RNA in maternal plasma: recent progress and future possibilities" Human Reproduction Update (2011) 17(3):372-382.
Goeddel, Gene Expression Technology: Methods in Enzymology 185, Academic Press, San Diego, CA (1990).
Gonzalgo & Jones, Nucleic Acids Res. 25:2529-2531, 1997.
Gottesman, S., Gene Expression Technology: Methods in Enzymology, Academic Press, San Diego, California 185: 119-129 (1990).
Grompe et al., Proc. Natl. Acad. Sci. USA 86: 5855-5892 (1989.
Grompe., "The rapid detection of unknown mutations in nucleic acids." Nat Genet. Oct. 1993;5(2):111-7.
Grunau et al., "Bisulfite genomic sequencing: systematic investigation of critical experimental parameters." Nucleic Acids Res. Jul. 1, 2001;29(13):E65-5.
Gupta et al., "Use of specific endonuclease cleavage in RNA sequencing." Nucleic Acids Res. Jun. 1977;4(6):1957-78.

(56) References Cited

OTHER PUBLICATIONS

Haase et al., Methods in Virology, pp. 189-226, 1984.
Haddow, et al.,"Screening of maternal serum for fetal Down's syndrome in the first trimester", In: The New England Journal of Medicine, Apr. 2, 1998, Vol .338(14), pp. 955-961.
Hage & Tweed, J. Chromatogr. B Biomed. Sci. Appl. Oct 10; 699 (1-2): 499-525 (1997).
Hahn et al., (2011) Placenta 32 Suppl: S17-S20.
Hahner et al., "Matrix-assisted laser desorption/ionization mass spectrometry (MALDI) of endonuclease digests of RNA." Nucleic Acids Res. May 15, 1997;25(10):1957-64.
Hames and Higgins eds., Nucleic Acid Hybridization: A Practical Approach, IRL Press, 1985.
Hannish, J. and M. McClelland, "Activity of DNA modification and restriction enzymes in KGB, a potassium glutamate buffer," Gene Anal. Tech 5:105 (1988, (Abstract Only).
Harris et al., "Single-molecule DNA sequencing of a viral genome." Science. Apr. 4, 2008;320(5872):106-9.
Hart et al., J.Biol.Chem., 269:62-65, 1994.
Hasan et al., Nucl. Acids Res. 24:2150-2157 (1996).
Heegaard, J Mol. Recognit. Winter; 11(1-6): 141-8 (1998).
Hennig et al (2007) J. Am. Chem. Soc. 129, 14911-14921, (Abstract Only).
Herman et al. Proc. Nat. Acad. Sci. USA 93:9821-9826, 1996.
Hershey, A. D. and Burgi, E. J. Mol. Biol, 2:143-152 (1960.
Hill, Craig, "Gen-Probe Transcription-Mediated Amplification: System Principles," Jan. 1996 httl://www.gen-probe.com/pdfs/tma_whiteppr.pdf.
HiSeq 2000 Sequencing System Specification Sheet, Illumina Inc. 2010.
Homer, J. et al., Prenat Diagn 23:566-571 (2003).
Hook, E. B. Lancet 2:169-172 (1981).
Hromandnikova, et al., "Quantification of Fetal and Total Circulatory DNA in Maternal Plasma Samples Before and After Size Fractionation by Agarose Gel Electrophoresis,"DNA and Cell Biology, vol. 25, No. 11, 2006, pp. 635-640.
Hu, D. G. et al., "Aneuploidy detection in single cells using DNA array-based comparative genomic hybridization", Mol Hum Reprod 10: 283-289, (2004).
Hua et al., "Quantitative methylation analysis of multiple genes using methylation-sensitive restriction enzyme-based quantitative PCR for the detection of hepatocellular carcinoma" Experimental and Molecular Pathology (2011) 91:455-460.
Huang et al., "Mechanism of ribose 2'-group discrimination by an RNA polymerase." Biochemistry. Jul. 8, 1997;36(27):8231-42, (Abstract Only).
Hulten et al., "Rapid and simple prenatal diagnosis of common chromosome disorders: advantages and disadvantages of the molecular methods FISH and QF-PCR." Reproduction. Sep. 2003;126(3):279-97.
Hunkapiller et al., "A microchemical facility for the analysis and synthesis of genes and proteins." Nature. Jul. 12-18, 1984;310(5973):105-11.
Hyrup et al., "Peptide nucleic acids (PNA): synthesis, properties and potential applications." Bioorg Med Chem. Jan. 1996;4(1):5-23.
Imai et al. , 1992, J. Virol. Methods 36: 181-184).
Imamura et al., "Prenatal diagnosis of adrenoleukodystrophy by means of mutation analysis." Prenat Diagn. Mar. 1996;16(3):259-61.
Innis et al., PCR Protocols: A Guide to Methods and Applications, Innis et al., eds, 1990, Table of Contents Only.
International Preliminary Report on Patentability dated: Dec. 30, 2009 in International Application No. PCT/US2008/066791 filed on Jun. 12, 2008.
International Preliminary Report on Patentability dated: Feb. 18, 2010 in International Application No. PCT/US2008/54470 filed on Feb. 20, 2008.
International Preliminary Report on Patentability dated: Jul. 5, 2012 in International Application No. PCT/US2010/061319 filed on Dec. 20, 2010.
International Preliminary Report on Patentability dated: Mar. 29, 2012 in International Application No. PCT/US2010/027879 filed on Mar. 18, 2010.
International Preliminary Report on Patentability dated: Sep. 3, 2009 in International Application No. PCT/US2008/54468 filed on Feb. 20, 2008.
International Preliminary Report on Patentability dated Mar. 31, 2011 in International Application No. PCT/US2009/057215 filed on Sep. 16, 2009 and published as: WO 10/033639 on Mar. 25, 2010.
International Preliminary Report on Patentability, dated Sep. 23, 2010 in International application No. PCT/US2009/036683 filed on: Mar. 10, 2009 and published as WO 09/114543 on Sep. 17, 2009.
International Search Report and Written Opinion dated Aug. 18, 2008 in International Application No. PCT/US2008/54470 filed on Feb. 20, 2008.
International Search Report and Written Opinion dated Dec. 22, 2008 in International Application No. PCT/US2008/066791 filed on Jun. 12, 2008.
International Search Report and Written Opinion dated Jan. 10, 2012 in International Application No. PCT/US2012/035479 filed on Apr. 27, 2012.
International Search Report and Written Opinion dated Sep. 21, 2011 in International Application No. PCT/US2010/061319 filed on Dec. 20, 2010.
International Search Report and Written Opinion dated Sep. 23, 2008 in International Application No. PCT/US2008/54468 filed on Feb. 20, 2008.
International Search Report and Written Opinion dated Jul. 1, 2013 in International Application No. PCT/US2013/028699, filed on Mar. 1, 2013.
International Search Report and Written Opinion dated Jul. 16, 2013 in International Application No. PCT/US2013/041906, filed on May 20, 2013.
International Search Report and Written Opinion dated Dec. 29, 2010 in International Application No. PCT/US2009/057215 filed on Sep. 16, 2009 and published as: WO 10/033639 on Mar. 25, 2010.
International Search Report and Written Opinion dated Dec. 30, 2010 in International Application No. PCT/US2010/027879 filed on Mar. 18, 2010.
International Search Report and Written Opinion, dated Feb. 24, 2010 in International application No. PCT/US2009/036683 filed on: Mar. 10, 2009 and published as WO 09/114543 on Sep. 17, 2009.
Invitation to Pay Additional Fees and Partial International Search Report dated Dec. 28, 2009 in International application No. PCT/US2009/036683 filed on: Mar. 10, 2009 and published as WO 09/114543 on Sep. 17, 2009.
International Search Report and Written Opinion dated Oct. 23, 2013 in International Application No. PCT/US2013/050145, filed on Jul. 11, 2013.
International Preliminary Report on Patentability dated Nov. 7, 2013 in International Application No. PCT/US2012/035479, filed on Apr. 27, 2012 and published as WO 2012/149339 on Nov. 1, 2012.
International Search Report and Written Opinion dated Jul. 30, 2014 in International Application No. PCT/US2014/025132, filed on Mar. 13, 2014.
International Preliminary Report on Patentability dated Sep. 12, 2014 in International Application No. PCT/US2013/028699, filed on Mar. 1, 2013 and published as WO 2013/131021 on Sep. 6, 2013.
Issa., "CpG island methylator phenotype in cancer." Nat Rev Cancer. Dec. 2004;4(12):988-93.
Iverson et al., 1981, Prenat. Diagn. 9: 31-48.
Iwabuchi et al., Oncogene 8: 1693-1696 (1993.
Jensen et al., "Detection of microdeletion 22q11.2 in a fetus by next-generation sequencing of maternal plasma" Clin Chem (2012) 58:1148-1151.
Jensen et al., "High-throughput massively parallel sequencing for fetal aneuploidy detection from maternal plasma" PLoS One (2013) 8:e57381.
Jing et al. (1998) Proc Natl Acad Sci USA. 95(14):8046-51.
Johansen et al., "An investigation of methods for enriching trophoblast from maternal blood." Prenat Diagn. Oct. 1995;15(10):921-31.

(56) References Cited

OTHER PUBLICATIONS

Jurinke, C., et al., "MALDI-TOF mass spectrometry: a versatile tool for high-performance DNA analysis." Mol. Biotechnol. 26, 147-164 (2004).
Kalinina et al., "Nanoliter scale PCR with TaqMan detection." Nucleic Acids Res. May 15, 1997;25(10):1999-2004.
Kaneko et al., Gut 52:641-646 (2003).
Karlin et al., "Methods for assessing the statistical significance of molecular sequence features by using general scoring schemes." Proc Natl Acad Sci U S A. Mar. 1990;87(6):2264-8.
Kent, "BLAT—the BLAST-like alignment tool." Genome Res. Apr. 2002;12(4):656-64.
Kessel et al., "Murine developmental control genes." Science. Jul. 27, 1990;249(4967):374-9, (Abstract Only).
Kidd JM et al. Mapping and sequencing of structural variation from eight human genomes. Nature. May 1, 2008;453 (7191):56-64).
Kitzman et al., "Noninvasive Whole-Genome Sequencing of a Human Fetus" Science Translation Medicine (2012) 4(137-140):115-122.
Kriegler, Gene Transfer and Expression: A Laboratory Manual (1990), (Table of Contents Only).
Kristensen et al., "PCR-Based Methods for Detecting Single-Locus DNA Methylation Biomarkers in Cancer Diagnostics, Prognostics, and Response to Treatement", Clinical Chemistry, Washington DC, vol. 55, No. 8., Aug. 1, 2009, pp. 1471-1483.
Krueger and Andrews, "Bismark: a flexible aligner and methylation caller for Bisulfite-Seq applications" Bioinformatics (2011) 27:1571-1572.
Kuchino et al., "Enzymatic RNA sequencing." Methods Enzymol. 1989;180:154-63.
Kuhn et al., "DNA Helicases" Cold Spring Harb Symp Quant Biol. 1979;43 Pt 1:63-7, (Abstract).
Kulkarmi et al., "Global DNA methylation patterns in placenta and its association with maternal hypertension in pre-eclampsia," (2011) DNA Cell Biol. 30(2):79-84.
Kumps et al., "RMeseuarlcthi aprtilcelex Amplicon Quantification (MAQ), a fast and efficient method for the simultaneous detection of copy number alterations in neuroblastoma," BMC Genomics 2010, 11:298, pp. 1-10.
Lai et al. (1999) Nat Genet. 23(3):309-13.
Laird, P.W. Nature Reviews Cancer 3, 253-266 (2003).
Langmead et al., "Ultrafast and memory-efficient alignment of short DNA sequences to the human genome" Genome Biol. (2009) 10(3):R25.
Larkin et al., "Clustal W and Clustal X version 2.0." Bioinformatics. Nov. 1, 2007;23(21):2947-8. Epub Sep. 10, 2007.
Lee et al., Fetal Nucleic Acids in Maternal Plasma, In:Fetal and Maternal Medicine Review, 2006, vol. 17,(2), pp. 125-137.
Lee TI, et al. (2006) Control of developmental regulators by Polycomb in human embryonic stem cells. Cell 125:301-313).
Leung et al., "An efficient algorithm for identifying matches with errors in multiple long molecular sequences." J Mol Biol. Oct. 20, 1991;221(4):1367-78.
Li et al. Nucl. Acids Res. 23:4495-4501 (1995).
Li et al., Dynamic Distribution of Linker Histone H1.5 in Cellular Differentiation, PLOS Genetics, vol. 8, Issue 8, e1002879, Aug. 2012, pp. 1-13.
Li et al., "Size separation of circulatory DNA in maternal plasma permits ready detection of fetal DNA polymorphisms." Clin Chem. Jun. 2004;50(6):1002-11. Epub Apr. 8, 2004.
Li et al., "Targeted mutation of the DNA methyltransferase gene results in embryonic lethality." Cell. Jun. 12, 1992;69(6):915-26.
Li, Y., et al., Genotyping fetal paternally inherited SNPs by MALDI-TOF MS using cell-free fetal DNA in maternal plasma: Influence of size fractionation. Electrophoresis 27, 3889-3896 (2006).
Li et al., "Mapping short DNA sequencing reads and calling variants using mapping quality scores" Genome Res. (2008) 18(11):1851-1858.
Lingbeek, M.E., Bruggeman, S.W. & van Lohuizen, M. Cell 118, 409-18 (2004).

Little, et al. Nat Med 3:1413-6 (1997).
Litz C. E. et al., "Methylation status of the major breakpoint cluster region in Philadelphia chromosome negative leukemias" Leukemia 6(1):35-41 (1992).
Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.
Liu et al., "The ribosomal small-subunit protein S28 gene from Helianthus annuus (asteraceae) is down-regulated in response to drought, high salinity, and abscisic acid," American Journal of Botany, vol. 90, No. 4., Apr. 1, 2003, pp. 526-531.
Lo and Chiu, "Prenatal diagnosis: progress through plasma nucleic acids" Nature Reviews Genetics (2007) 8:71-77.
Lo et al. (Nat Med. Feb. 2007;13(2):218-23).
Lo et al., "Maternal Plasma DNA Sequencing Reveals the Genome-Wide Genetic and Mutational Profile of the Fetus," Prenatal Diagnosis, Science Translational Medicine, Dec. 8, 2010, vol. 2, Issue 61, 1-13 Lo et al. (2010).
Lo et al., "Presence of fetal DNA in maternal plasma and serum." Lancet. Aug. 16, 1997;350(9076):485-7.
Lo et al., "Quantitative analysis of fetal DNA in maternal plasma and serum: implications for noninvasive prenatal diagnosis." Am J Hum Genet. Apr. 1998;62(4):768-75.
Lo et al., Clin. Chem. 45:1747-1751, 1999.
Lo et al., Clin. Chem. 45:184-188, 1999.
Lo et al., N. Engl. J. Med. 339:1734-1738 (1998).
Lo, "Recent advances in fetal nucleic acids in maternal plasma." J Histochem Cytochem. Mar. 2005;53(3):293-6.
Lun et al., "Microfluidics digital PCR reveals a higher than expected fraction of fetal DNA in maternal plasma." Clin Chem. Oct. 2008;54(10):1664-72. Epub Aug. 14, 2008.
Lun et al., "Noninvasive prenatal diagnosis of monogenic diseases by digital size selection and relative mutation dosage on DNA in maternal plasma," PNAS, vol. 105, No. 50, Dec. 16, 2008, pp. 19920-19925.
Madura et al., J. Biol. Chem. 268: 12046-12054 (1993).
Majlessi et al., Nucleic Acids Research, 26(9):2224-2229, (1998).
Malik et al., "Polyethylene glycol (PEG)-modified granulocyte-macrophage colony-stimulating factor (GM-CSF) with conserved biological activity." Exp Hematol. Sep. 1992;20(8):1028-35, (Abstract Only).
Mann et al., "Development and implementation of a new rapid aneuploidy diagnostic service within the UK National Health Service and implications for the future of prenatal diagnosis." Lancet. Sep. 29, 2001;358(9287)1 057-61.
Mann, K. Methods Mol Med 92:141-156 (2004).
Mao and Williamson (1999) Nucl. Acids Res. 27, 4059-4070.
Marais et al., EMBO J. 14: 3136-3145 (1995).
Marais et al., J. Biol. Chem. 272: 4378-4383 (1997.
Margulies et al., "Genome sequencing in microfabricated high-density picolitre reactors." Nature. Sep. 15, 2005;437(7057):376-80. Epub Jul. 31, 2005.
Mason et al., EMBO J. 18: 2137-2148 (1999.
McClelland, M. et al., "A single buffer for all restriction endonucleases," Nucl. Acids Res. 16:364 (1988).
McConnell, H. M. et al., Science 257: 1906-1912 (1992)), (Abstract Only).
Meller A. 2007 Clin Chem 53: 1996-2001.
Metzker M., Nature Rev 11:31-46 (2010).
Meyers & Miller, CABIOS 4:11-17 (1989).
Millipore, QIA25 Nucleosome ELISA Kit, Information Brochure, Calbiochem, Feb. 26, 2013.
Mito, Y., Henikoff, J.G. & Henikoff, S. Nat Genet 37, 1090-7 (2005.
Molecular Cloning of PCR Products, Unit 15.4, Current Protocols in Molecular Biology, (2001 John Wiley & Sons, Inc.) 15.4.1-15. 4.11, Supplement 56.
Moudrianakis E. N. and Beer M., Proc Natl Acad Sci USA. Mar. 1965; 53:564-71.
Mouliere et al., "High Fragmentation Characterizes Tumour-Derived Circulating DNA," PLoS ONE, Sep. 2011, vol. 6, Issue 9, e23438, 1-10.
Nakamaye et al., Nucl. Acids Res. 23:9947-9959(1988).

(56) References Cited

OTHER PUBLICATIONS

Nakano et al. "Single-molecule PCR using water-in-oil emulsion;" Journal of Biotechnology 102 (2003) 117-124.
NCBI dbSNP cluster report record for rs16139, accessed Sep. 16, 2013.
Needham-VanDevanter et al., "Characterization of an adduct between CC-1065 and a defined oligodeoxynucleotide duplex." Nucleic Acids Res. Aug. 10, 1984;12(15):6159-68.
Needleman et al., "A general method applicable to the search for similarities in the amino acid sequence of two proteins." J Mol Biol. Mar. 1970;48(3)444-453.
Ng et al. , 2003, Proc. Natl. Acad. Sci. USA 100 : 4748-4753.
Ng et al., 2002, Clin. Chem. 48: 1212-1217.
Nicolaides et al., "One-stop clinic for assessment of risk of chromosomal defects at 12 weeks of gestation." J Matern Fetal Neonatal Med. Jul. 2002;12(1):9-18.
Nicolaides, K. H. et al., Prenat Diagn 22:308-315 (2002)).
Nicolaidis et al., "Origin and mechanisms of non-disjunction in human autosomal trisomies." Hum Reprod. Feb. 1998;13(2):313-9.
Nishizuka et al., "Proteomic profiling of the NCI-60 cancer cell lines using new high-density reverse-phase lysate microarrays." Proc Natl Acad Sci U S A. Nov. 25, 2003;100(24):14229-34. Epub Nov. 17, 2003.
Nolte, "Branched DNA signal amplification for direct quantitation of nucleic acid sequences in clinical specimens." Adv Clin Chem. 1998;33:201-35.
Nosaka, K. et al., "Increasing methylation of the CDKN2A gene is associated with the progression of adult T-cell leukemia", Cancer Res. 60(4):1043-1048 (2000).
Nygren et al., "Quantification of Fetal DNA by Use of Methylation-Based DNA Discrimination," Clinical Chemistry, 56:10, pp. 1627-1635.
Oefner, P. J. et al., "Efficient random subcloning of DNA sheared in a recirculating point-sink flow system," Nucl. Acids Res. 24(20):3879-3886 (1996).
Oeth et al., "Qualitative and quantitative genotyping using single base primer extension coupled with matrix-assisted laser desorption/ionization time-of-flight mass spectrometry (MassARRAY)." Methods Mol Biol. 2009;578:307-43.
Oeth, P. et al., (iPLEX™ Assay: Increased Plexing Efficiency and Flexibility for MassARRAY® System through single base primer extension with mass-modified Terminators. SEQUENOM Application Note (2005).
Ohm, J.E. et al. A stem cell-like chromatin pattern may predispose tumor suppressor genes to DNA hypermethylation and heritable silencing. Nat Genet 39, 237-42 (2007).
Ohtsuka et al., J. Biol. Chem. 260:2605-2608 (1985).
Okano et al., "DNA methyltransferases Dnmt3a and Dnmt3b are essential for de novo methylation and mammalian development." Cell. Oct. 29, 1999;99(3):247-57.
Old RW, "Candidate epigenetic biomarkers for non-invasive prenatal diagnosis of Down syndrom," Reprod Biomed. Online 2007, vol. 15, No. 2, pp. 227-235.
Olek et al., "A modified and improved method for bisulphite based cytosine methylation analysis." Nucleic Acids Res. Dec. 15, 1996;24(24):5064-6.
Oligonucleotides and Analogues, A Practical Approach, F. Eckstein, editor, IRL Press, Oxford, 1991, (pp. 56-57, 137-139, 256-259.
Orita et al., Proc. Natl. Acad. Sci. U.S.A 86: 27776-2770 (1989.
Osborne, et al., Curr. Opin. Chem. Biol.1(1): 5-9 (1997.
Oudejans et al., 2003, Prenatal Diagnosis 23: 111-116.
Padilla et al., "Efficient synthesis of nucleic acids heavily modified with non-canonical ribose 2'-groups using a mutantT7 RNA polymerase (RNAP)." Nucleic Acids Res. Mar. 15, 1999;27(6):1561-3.
Palomaki et al., "Maternal serum screening for Down syndrome in the United States: a 1995 survey." Am J Obstet Gynecol. May 1997;176(5):1046-51.
Palomaki et al., "DNA sequencing of maternal plasma to detect Down syndrome: an international clinical validation study" Genet Med (2011) 13:913-920, and Expanded Methods Appendix A, pp. 1-65.
Pandya et al., "Screening for fetal trisomies by maternal age and fetal nuchal translucency thickness at 10 to 14 weeks of gestation." Br J Obstet Gynaecol. Dec. 1995;102(12):957-62.
Papageorgiou et al., "Sites of differential DNA methylation between placenta and peripheral blood: molecular markers for noninvasive prenatal diagnosis of aneuploidies" The American Journal of Pathology (2009) 174(5):1609-1618.
Papageorgiou et al., "Fetal-specific DNA methylation ratio permits noninvasive prenatal diagnosis of trisomy 21" Nature Medicine (2011) 17:510-513.
Patel, D. J., Curr. Opin. Chem. Biol. Jun;1(1): 32-46 (1997).
Paulin, R. et al. in Nucleic Acids Res. 26:5009-5010, 1998.
Pearson & Reanier, J. Chrom. 255: 137-149 (1983).
Pearson, 1988, Proc. Natl. Acad. Sci. USA 85(5): 2444-2448.
Perry-O'Keefe et al., "Peptide nucleic acid pre-gel hybridization: an alternative to southern hybridization." Proc Natl Acad Sci U S A. Dec. 10, 1996;93(25):14670-5.
Pertl et al., "Rapid molecular method for prenatal detection of Down's syndrome." Lancet. May 14, 1994;343(8907):1197-8.
Peters et al., "Noninvasive Prenatal Diagnosis of a Fetal Microdeletion Syndrome," New England Journal of Medicine, Nov. 10, 2011, pp. 1847-1848.
Petersen and Mikkelsen. Cytogenet Cell Genet. 2000;91(1-4):199-203.
Pinkert et al., Genes Dev. 1: 268-277 (1987).
Poon et al., 2000, Clin. Chem. 46: 1832-1834.
Poon et al., "Differential DNA methylation between fetus and mother as a strategy for detecting fetal DNA in maternal plasma." Clin Chem. Jan. 2002;48(1):35-41.
Porter et al., Biochemistry 34: 11963-11969 (1995).
Qu et al., "Analysis of drug-DNA binding data." Methods Enzymol. 2000;321:353-69.
Queen et al., "Immunoglobulin gene transcription is activated by downstream sequence elements." Cell. Jul. 1983;33(3):741-8.
Radding., "Homologous pairing and strand exchange in genetic recombination." Annu Rev Genet. 1982;16:405-37.
Randen et al., "Prenatal genotyping of RHD and SRY using maternal blood," VOX Sanguinis, vol. 85, No. 4, Nov. 2003, pp. 300-306.
Rashtchian (1994, PCR Methods Applic. 4: S83-S91).
Rivas, G., and Minton, A. P., Trends Biochem Sci Aug;18(8): 284-7 (1993).
Roach et al., "Association between the abnormal expression of matrix-degrading enzymes by human osteoarthritic chondrocytes and demethylation of specific CpG sites in the promoter regions" Arthritis & Rheumatism (2005) 52(10):3110-3124.
Robertson et al., Nature Rev. Genet. 1:11-19 (2000).
Robinson M. D. and T. P. Speed. "A comparison of Affymetrix gene expression arrays." BMC Bioinformatics 8:449 (2007).
Rojo et al., "Cusativin, a new cytidine-specific ribonuclease accumulated in seeds of *Cucumis sativus* L." Planta. 1994;194(3):328-38.
Rollins et al., "Large-scale structure of genomic methylation patterns." Genome Res. Feb. 2006;16(2):157-63. Epub Dec. 19, 2005.
Romero and Rotbard, Diagnostic Molecular Biology: Principles and Applications, pp. 401-406; Pershing et al, eds., Mayo Foundation, Rochester, Minn., 1993.
Roschke et al., "Karyotypic complexity of the NCI-60 drug-screening panel." Cancer Res. Dec. 15, 2003;63(24):8634-47.
Rosenberg, H. S. and Bendich, A. J. Am. Chem. Soc. 82:3198-3201 (1960).
Rossolini et al., Mol. Cell. Probes 8:91-98 (1994).
Sadri & Hornsby Nucl. Acids Res. 24:5058-5059, (1996).
Saito et al., Lancet 356:1170, 2000.
Salgame et al., "An ELISA for detection of apoptosis," Nucleic Acids Research, 1997, vol. 25, No. 3, pp. 680-681.
Sambrook and Russell, Molecular Cloning, A Laboratory Manual (3rd ed. 2001), table of contents.

(56) References Cited

OTHER PUBLICATIONS

Sambrook et al., Molecular Biology: A laboratory Approach, Cold Spring Harbor, N. Y. 1989, chapter 11: pp. 11.2-11.61.
Sanchez et al, "Effects of Sulpiride on Prolactin and mRNA Levels of Steroid 5a-reductase Isozymes in Adult Rat Brain," Neurochem Res (2008) 33:820-825.
Santoro, S. W. and Joyce, G. F. "A general purpose RNA-cleaving DNA enzyme," Proc. Natl. Acad. Sci. USA 94:4262-4266 (1997).
Sargent et al., Meth. Enz. 152:432 (1988).
Sayres et al., "Cell-free fetal nucleic acid testing: A review of the technology and its applications" Obstetrical and Gynecological Survey (2011) 66(7):431-442.
Schlesinger et al., "Polycomb-mediated methylation on Lys27 of histone H3 pre-marks genes for de novo methylation in cancer." Nat Genet. Feb. 2007;39(2):232-6. Epub Dec. 31, 2006.
Schouten et al., "Relative quantification of 40 nucleic acid sequences by multiplex ligation-dependent probe amplification." Nucleic Acids Res. Jun. 15, 2002;30(12):e57.
Schriefer, L. A. et al., "Low pressure DNA shearing: a method for random DNA sequence analysis," Nucl. Acids Res. 18:7455-7456 (1990).
Schroeder et al., "The human placenta methylome" PNAS USA (2013) 110(15):6037-42.
Schuler GD, Sequence mapping by electronic PCR., Genome Res. May 1997;7(5):541-50.
Scott et al. (2004) J. Am. Chem. Soc. 126, 11776-11777.
Sekizawa et al., Clin. Chem. 47:2164-2165, 2001.
Sharma et al., "Mass spectrometric based analysis, characterization and applications of circulating cell free DNA isolated from human body fluids" International Journal of Mass Spectrometry (2011) 304:172-183.
Sheffield et al., "Identification of novel rhodopsin mutations associated with retinitis pigmentosa by GC-clamped denaturing gradient gel electrophoresis." Am J Hum Genet. Oct. 1991;49(4):699-706.
Silverman et al., "Methylation inhibitor therapy in the treatment of myelodysplastic syndrome." Nat Clin Pract Oncol. Dec. 2005;2 Suppl 1:S12-23.
Simoncsits et al., "New rapid gel sequencing method for RNA." Nature. Oct. 27, 1977;269(5631):833-6.
Singer et al., Biotechniques 4:230, 1986.
Sjolander & Urbaniczk, Anal. Chem. 63: 2338-2345 (1991), (abstract only).
Slater et al., "Rapid, high throughput prenatal detection of aneuploidy using a novel quantitative method (MLPA)." J Med Genet. Dec. 2003;40(12):907-12.
Smith et al., "Identification of common molecular subsequences." J Mol Biol. Mar. 25, 1981;147(1):195-7.
Smith et al., "Single-step purification of polypeptides expressed in *Escherichia coli* as fusions with glutathione S-transferase." Gene. Jul. 15, 1988;67(1):31-40.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sousa et al., "A mutant T7 RNA polymerase as a DNA polymerase." EMBO J. Sep. 15, 1995;14(18):4609-21.
Spetzler et al, Enriching for Rare Subpopulations of Circulating Microvesicles by the Depletion of Endothelial-and Leukocyte-Derived Microvesicles, CARIS Life Sciences, Carisome Posters, Papers, Abstracts and Presentations, American Academy of Cancer Research (AACR 2011).

Stanssens et al., "High-throughput MALDI-TOF discovery of genomic sequence polymorphisms." Genome Res. Jan. 2004;14(1):126-33.
Staunton et al., "Chemosensitivity prediction by transcriptional profiling." Proc Natl Acad Sci U S A. Sep. 11, 2001;98(19):10787-92.
Strathdee, et al., Am. J. Pathol. 158:1121-1127 (2001).
Strohmeier, Fred, "A New High-Performance Capillary Electrophoresis Instrument," 10-19, Hewlett-Packard Journal, Jun. 1995.
Supplementary European Search Report dated Jul. 14, 2011 for European Application No. EP 09720284 filed: Mar. 10, 2009 based on internation application No. PCT/US2009/036683.
Szabo et al., Curr. Opin. Struct. Biol. 5: 699-705 (1995).
Tabor et al., "Non-Invasive Fetal Genome Sequencing: Opportunities and Challenges" American Journal of Medical Genetics Part A (2012) 158A(10):2382-2384.
Takai et al., Proc. Natl. Acad. Sci. U.S.A. 99:3740-3745, 2002.
Tang et al. (2002) Analytical Chemistry 74, 226-331.
Terme et al. "Histone H1 Variants Are Differentially Expressed and Incorporated into Chromatin during Differentiation and Reprogramming to Pluripotency," The Journal of Clinical Chemistry, vol. 286, No. 41, Oct. 14, 2011, pp. 35347-35357.
The Cancer Test, Cell Free DNA, 2007, Health Screen Inc. printed from the internet on Mar. 20, 2011 (http://www.thecancertest.com/science-of-cell-free-dna/.
The Human Genome, T. Strachan, BIOS Scientific Publishers, 1992, (table of contents only).
The World Health Organization histological typing of lung tumours, Am J Clin Pathol 1982; 77:123-136, abstract only.
Thorstenson, Y.R. et al., "An Automated Hydrodynamic Process for Controlled, Unbiased DNA Shearing," Genome Research 8:848-855 (1998).
Tolbert and Williamson (1996) J. Am. Chem. Soc. 118, 7929-7940.
Tolbert and Williamson (1997) J. Am. Chem. Soc. 119, 12100-12108.
Tong et al., "Noninvasive Prenatal Detection of Fetal Trisomy 18 by Epigenetic Allelic Ratio Analysis in Maternal Plasma: Theoretical and Empirical Considerations," Clinical Chemistry 52:12, pp. 2149-2202.
Tooke N and Pettersson M. IVDT. Nov. 2004; 41.
Tost et al., Nucl. Acids Res. 37:e50 (2003).
Toyota et al., "Methylation profiling in acute myeloid leukemia." Blood. May 1, 2001;97(9):2823-9.
Toyota et al., Cancer Res. 59:2307-12, 1999.
Tsaliki et al., "MeDIP real-time qPCR of maternal peripheral blood reliably identifies trisomy 21" Prenat. Diagn. (2012) 32:996-1001.
Tsui et al., "Systemic Identification of Placental Epigenetic Signatures for the Noninvasive Prenatal Detection of Edwards Syndrome" PLOS One (2010) 5(11):e15069.
Tungwiwat et al., "Non-invasive fetal sex determination using a conventional nested PCR analysis of fetal DNA in maternal plasma," Clinica Chimica Acta, vol. 334, No. 1-2, Aug. 2003, pp. 173-177.
Tynan et al., "Fractional DNA quantification by massively parallel shotgun sequencing-implications for fetal fraction measurement in maternal plasma," (Sequenom MME) ASHG Poster, 2011.
Uhlmann, K. et al. Electrophoresis 23:4072-4079 (2002).
Valk et al., "Prognostically useful gene-expression profiles in acute myeloid leukemia." N Engl J Med. Apr. 15, 2004;350(16):1617-28.
Valk-Lingbeek et al., "Stem cells and cancer; the polycomb connection." Cell. Aug. 20, 2004;118(4):409-18.
Van der Schoot, C.E., et al., Real-time PCR of bi-allelic insertion/deletion polymorphisms can serve as a reliable positive control for cell-free fetal DNA in non-invasive prenatal genotyping [abstract] Blood 102, 93a (2003).
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Venter et al., "The sequence of the human genome." Science. Feb. 16, 2001;291(5507):1304-51.
Verbeck et al. in the Journal of Biomolecular Techniques (vol. 13, Issue 2, 56-61) (2002).
Verma et al., "Rapid and simple prenatal DNA diagnosis of Down's syndrome." Lancet. Jul. 4, 1998;352(9121):9-12.

(56) References Cited

OTHER PUBLICATIONS

Vincenet et al., "Helicase-Dependent isothermal DNA Amplification," EMBO reports 5(8):795-800 (2004).
Vire et al., "The Polycomb group protein EZH2 directly controls DNA methylation." Nature. Feb. 16, 2006;439(7078):871-4. Epub Dec. 14, 2005.
Vogelstein et al., "Digital PCR." Proc Natl Acad Sci U S A. Aug. 3, 1999;96(16):9236-41.
Volkerding et al., Clin Chem 55:641-658 (2009).
Vu et al. "Symmetric and asymmetric DNA methylation in the human IGF2-H19 imprinted region," Genomics, Mar. 1;64(2):132-143. (2000).
Wada et al., "Codon usage tabulated from the GenBank genetic sequence data." Nucleic Acids Res. May 11, 1992;20 Suppl:21 11-8.
Wald and Hackshaw, Prenat Diagn 17(9):821-829 (1997).
Wang, H. et al. BMC Genomics 7, 166 (2006.
Wapner et al., "First-trimester screening for trisomies 21 and 18." N Engl J Med. Oct. 9, 2003;349(15):1405-13.
Waterman et al., 1980, J. Mol. Biol. 147: 195-197.
Weber et al., Oncogene 19: 169-176 (2000).
Weisenberger, D.J. et al. Nat Genet 38, 787-93 (2006).
Weiss et al., "H1 variant-specific lysine methylation by G9a/KMT1C and Glp1/KMT1D," Epigenetics & Chromatin Mar. 24, 2010, 3:7, pp. 1-13.
White et al., "Detecting single base substitutions as heteroduplex polymorphisms." Genomics. Feb. 1992;12(2):301-6.
Widschwendter, M. et al. Epigenetic stem cell signature in cancer. Nat Genet 39, 157-8 (2007).
Wilkinson, In situ Hybridization, Wilkinson ed., IRL Press, Oxford University Press, Oxford 1998, table of contents.
Winoto et al., "A novel, inducible and T cell-specific enhancer located at the 3' end of the T cell receptor alpha locus." EMBO J. Mar. 1989;8(3):729-33.
Xiong & Laird, Nucleic Acids Res. 25:2532-2534, 1997.
Yamada et al. (Genome Research 14:247-266, 2004).
Yamada et al., "Suppressive effect of epigallocatechin gallate (EGCg) on DNA methylation in mice: Detection by methylation sensitive restriction endonuclease digestion and PCR" Journal of Food, Agriculture & Environment (2005) 3(2):73-76.
Yan et al., "A novel diagnostic strategy for trisomy 21 using short tandem repeats," Electrophoresis 2006, 27,416-422.
Zahra S, et al, Plasma microparticles are not elevated in fresh plasma from patients with gynaecologicalmalignancy—An observational study, Gynecol Onco, Oct. 2011;123(1):152-156.
Zervos et al., Cell 72:223-232 (1993.
Zhang et al., "Histone H1 Depletion Impairs Embryonic Stem Cell Differentiation," PLOS Genetics, vol. 8, Issue 5, e1002691, May 2012, pp. 1-14.
Zhao et al., (2010) Pretat Diag 30(8):778-782.
Zheng et al., "Nonhematopoietically Derived DNA Is Shorter than Hematopoietically Derived DNA in Plasma: A Transplantation Model," Clin Chem 58:2, Nov. 3, 2011.
Zhong et al., Am. J. Obstet. Gynecol. 184:414-419, 2001.
Zhong et al., Prenat. Diagn. 20:795-798, 2000.
Zimmermann Lecturer, et al., 'Serum parameters and nuchal translucency in first trimester screening for fetal chromosomal abnormalities', In: BJOG: An International Journal of Obstetrics & Gynaecology, 1996, vol. 103(1O), pp. 1009-1014.
Zimmermann, B. et al., Clin Chem 48:362-363 (2002).
Zuker "Mfold web server for nucleic acid folding and hybridization prediction," Nucleic Acids Res. 31(13), 3406-3415.
Office Action dated Jan. 28, 2013 in U.S. Appl. No. 13/457,978, filed Apr. 27, 2012 and published as: 2012/0276542 on: Oct. 1, 2012.
Office Action dated Sep. 17, 2012 in U.S. Appl. No. 13/457,978, filed Apr. 27, 2012 and published as: 2012/0276542 on: Oct. 1, 2012.
Office Action dated Feb. 6, 2013 in U.S. Appl. No. 13/458,036, filed Apr. 27, 2012 and published as: 2012/0264618 on: Oct. 18, 2012.
Office Action dated: Sep. 24, 2012 in U.S. Appl. No. 13/458,036, filed Apr. 27, 2012 and published as: 2012/0264618 on: Oct. 18, 2012.
Office Action dated Feb. 5, 2013 in U.S. Appl. No. 13/458,341, filed Apr. 27, 2012.
Office Action dated Sep. 17, 2012 in U.S. Appl. No. 13/458,341, filed Apr. 27, 2012.
Office Action dated Feb. 27, 2013 in U.S. Appl. No. 12/561,241, filed Sep. 16, 2009.
Office Action dated Jun. 15, 2012 in U.S. Appl. No. 12/561,241, filed Sep. 16, 2009.
Office Action dated Apr. 5, 2013 in U.S. Appl. No. 13/495,975, filed Jun. 13, 2012.
Office Action dated Apr. 5, 2013 in U.S. Appl. No. 13/517,532, filed Jun. 13, 2012.
Office Action dated Apr. 12, 2013 in U.S. Appl. No. 12/727,198, filed Mar. 18, 2010.
Office Action dated Mar. 18, 2013 in U.S. Appl. No. 12/401,493, filed Mar. 10, 2009 and published as: 2009/0317817 on: Dec. 24, 2009.
Office Action dated Jul. 19, 2011 in U.S. Appl. No. 12/401,493, filed Mar. 10, 2009 and published as: 2009/0317817 on: Dec. 24, 2009.
Office Action dated Oct. 28, 2010 in U.S. Appl. No. 12/401,493, filed Mar. 10, 2009 and published as: 2009/0317817 on: Dec. 24, 2009.
Office Action dated Aug. 13, 2013 in U.S. Appl. No. 13/517,508, filed Jun. 13, 2012 and published as US 2013-014321 on Jun. 6, 2013.
International Search Report and Written Opinion dated Aug. 14, 2013 in International Application No. PCT/US2013/041354, filed May 16, 2013.
Office Action dated Sep. 20, 2013 in U.S. Appl. No. 13/517,532, filed Jun. 13, 2012 and published as US 2013-0150249 on Jun. 13, 2013.
Office Action dated Sep. 24, 2013 in U.S. Appl. No. 13/495,975, filed Jun. 13, 2012 and published as US 2012-0277119 on Nov. 1, 2012.
Office Action dated Nov. 22, 2013 in U.S. Appl. No. 12/401,493, filed Mar. 10, 2009 and published as US 2009-0317817 on Dec. 24, 2009.
Office Action dated Dec. 31, 2013 in U.S. Appl. No. 12/727,198, filed Mar. 18, 2010 and published as US 2010-0273165 on Oct. 28, 2010.
Office Action dated Jan. 7, 2014 in U.S. Appl. No. 13/517,508, filed Jun. 13, 2012 and published as US 2013-0143211 on Jun. 6, 2013.
Office Action dated Feb. 5, 2014 in U.S. Appl. No. 13/517,508, filed Jun. 13, 2012 and published as US 2013-014321 1 on Jun. 6, 2013.
Office Action dated Mar. 7, 2014 in U.S. Appl. No. 13/801,384, filed Mar. 13, 2013 and published as US 2013-0296180 on Nov. 7, 2013.
Office Action dated Jun. 26, 2014 in U.S. Appl. No. 13/782,857, filed Mar. 1, 2013 and published as US 2013-0310260 on Nov. 21, 2013.
Office Action dated Aug. 8, 2014 in U.S. Appl. No. 13/782,901, filed Mar. 1, 2013 and published as US 2013-0230858 on Sep. 5, 2013.
Office Action dated Sep. 15, 2014 in U.S. Appl. No. 12/727,198, filed Mar. 18, 2010 and published as US 2010-0273165 on Oct. 28, 2010.
Office Action dated Nov. 7, 2014 in U.S. Appl. No. 13/791,466, filed Mar. 8, 2013 and published as US 2013-0295564 on Nov. 7, 2013.
International Preliminary Report on Patentability dated Dec. 4, 2014 in International Application No. PCT/US2013/041906, filed on May 20, 2013 and published as WO 2013/177086 on Nov. 28, 2013.
Office Action dated Dec. 18, 2014 in U.S. Appl. No. 13/517,508, filed Jun. 13, 2012 and published as US 2013-0143211 on Jun. 6, 2013.
Office Action dated Dec. 22, 2014 in U.S. Appl. No. 13/801,384, filed Mar. 13, 2013 and published as US 2013-0296180 on Nov. 7, 2013.
Office Action dated Jan. 30, 2015 in U.S. Appl. No. 13/518,368, filed Feb. 6, 2013 and published as US 2013-0130923 on May 23, 2013.

(56) References Cited

OTHER PUBLICATIONS

International Preliminary Report on Patentability dated Jan. 22, 2015 in International Application No. PCT/US2013/050145, filed on Jul. 11, 2013 and published as WO 2014/011928 on Jan. 16, 2014.
Office Action dated Aug. 3, 2015 in U.S. Appl. No. 13/791,466, filed Mar. 8, 2013 and published as US 2013-0295564 on Nov. 7, 2013.
Office Action dated Aug. 20, 2015 in U.S. Appl. No. 13/940,162, filed Jul. 11, 2013 and published as US 2014-0093873 on Apr. 3, 2014.
International Preliminary Report on Patentability dated Sep. 24, 2015 in International Application No. PCT/US2014/025132, filed on Mar. 13, 2014 and published a WO 2014/168711 on Oct. 16, 2014.
International Preliminary Report on Patentability dated Sep. 22, 2016 in International Application No. PCT/US2015/020250, filed on Mar. 12, 2015 and published as WO 2015/138774 on Sep. 17, 2015.
Extended European Search Report dated Nov. 14, 2016 in European Patent Application No. EP16173137.7, filed on Sep. 16, 2009.
Abyzov, Alexej et al.; "CNVnator: An approach to discover. Genotype, and characterize typical and atypical CNVs from family and population genome sequencing"; Genome Research; vol. 21, No. 6; Feb. 7, 2011; pp. 974-984; 11 pages.
Chen, Shengpei et al.; "A method for noninvasive detection of fetal large deletions/duplications by low coverage massively parallel sequencing"; Prenatal Diagnosis; vol. 33, No. 6; Jun. 17, 2013; pp. 584-590; 7 pages.
Chen, Eric Z. et al.; "Noninvasive Prenatal Diagnosis of Fetal Trisomy 18 and Trisomy 13 by Maternal Plasma DNA Sequencing"; PLoS ONE; vol. 6, Issue 7; Jul. 6, 2011; p. e21791; 7 pages.
Lo, Kitty K. et al.; RAPIDR: an analysis package for non-invasive prenatal testing of aneuploidy; Bioinformatics, vol. 30, No. 20; Jul. 1, 2014, pp. 2965-2967; 3 pages.
Miller, Christopher A. et al.; "ReadDepth: A Parallel R Package for Detecting Copy Number Alterations from Short Sequencing Reads"; PLoS ONE; vol. 6, No. 1; Jan. 31, 2011; p. e16327; 7 pages.
PCT/US2015/054903, "International Search Report and Written Opinion", dated Mar. 30, 2016, 21 pages.
Srinivasan, Anupama et al.; "Noninvasive Detection of Fetal Subchromosome Abnormalities Via Deep Sequencing of Maternal Plasma"; The American Journal of Human Genetics; vol. 92, No. 2; Feb. 7, 2013, pp. 167-176; 10 pages.
Zhao, C et al.; "Detection of Fetal Subchromosomal Abnormalities by Sequencing Circulating Cell-free DNA from Maternal Plasma"; Clinical Chemistry; vol. 61, No. 4; Feb. 20, 2015; pp. 608-616; 9 pages.
Office Action dated Aug. 12, 2016 in U.S. Appl. No. 13/791,466, filed Mar. 8, 2013 and published as US 2013-0295564 on Nov. 7, 2013.
Final Office Action dated Mar. 28, 2019 in U.S. Appl. No. 15/443,051, filed Feb. 27, 2017 and published as US 2017/0321276 on Nov. 9, 2017.
Sancho et al., "Depletion of Human Histone H1 Variants Uncovers Specific Roles in Gene Expression and Cell Growth," PLOS Genetics, 4 (10), e1000227 (2008).
Office Action dated Sep. 26, 2019 in U.S. Appl. No. 15/124,324, filed Sep. 7, 2016 and published as US 2017/0073756 on Mar. 16, 2017.
Extended European Search Report dated Nov. 25, 2019 in European Application No. EP19174694 filed: May 15, 2019 based on International Application No. PCT/US2014/025132.
Final Office Action dated Jan. 21, 2020 in U.S. Appl. No. 15/517,107, filed Apr. 5, 2017 and published as US 2017/0316150 on Nov. 2, 2017.
Flicek et al., "Sense from sequence reads: methods for alignment and assembly," Nature Methods Supplement 6(11s): S6-S12 (2009).
Final Office Action dated Apr. 20, 2020 in U.S. Appl. No. 15/124,324, filed Sep. 7, 2016 and published as US 2017/0073756 on Mar. 16, 2017.

Communication Pursuant to Article 94(3) EPC dated Jul. 5, 2019 in European Application No. EP18174047.3 filed: May 24, 2018 based on International Application No. PCT/US2013/028699.
"H1FOO Antibody (K-14) Date Sheet: SC-9910", Santa Cruz Biotechnology, Available online at: www.scbt.com/datasheet-9918-hfloo-k-14-antibody, html, 2007-2015, 3 pages.
"The Cancer Test, Cell Free DNA", Health Screen Inc., Available Online at: http://www.thecancertest.com/science-of-cell-free-dna/, Accessed from Internet on Mar. 20, 2011, 6 pages.
Assis, P. et al., "Halofuginone Inhibits Phosphorylation of SMAD-2 Reducing Angiogenesis and Leukemia Burden in an Acute Promyelocytic Leukemia Mouse Model", Journal of Experimental and Clinical Cancer Research, 34(65):1-11 (2015).
Aston, C. et al., "Optical Mapping: An Approach for Fine Mapping", Methods Enzymol, 303:55-73 (1999).
Ausubel, F. et al., "Current Protocols in Molecular Biology", John Wiley & Sons, Inc., vol. 1, 18 pages (1994), Table of Contents, Forward, & Preface.
Batey, R. et al., "Improved Large Scale Culture of *Methylophilus methylotrophus* for $^{13}C/^{15}N$ Labeling and Random Fractional Deuteration of Ribonucleotides", Nucleic Acids Research, 24(23):4836-4837 (1996).
Batzer, M. et al., "Enhanced Evolutionary PCR Using Oligonucleotides with Inosine at the 3'-Terminus", Nucleic Acids Res. 19(18):5081 (1991).
Beaucage, S. and Caruthers, M., "Deoxynudeoside Phosphoramidites—A New Class of Key Intermediates for Deoxypolynucleotide Synthesis", Tetrahedron Letters, 22(20):1859-1862 (1981).
Braslavsky, I. et al., "Sequence Information can be Obtained From Single DNA Molecules", Proceedings National Academy of Sciences, 100(7):3960-3964 (2003).
Chiu, R. et al., "Prenatal Exclusion of β Thalassaemia Major by Examination of Maternal Plasma", The Lancet, Research Letters, 360:998-1000 (2002).
Chomczynski, P. and Mackey, K., "Substitution of Chloroform by Bromochloropropane in the Single-Step Method of RNA Isolation", Analytic Biochemistry, 225(1):163-164 (195).
Chow, K. et al., "Mass Spectrometric Detection of an SNP Panel as an Internal Positive Control for Fetal DNA Analysis in Maternal Plasma", Clinical Chemistry, 53(1):141-142 (2007).
Costello, J. et al., "Restriction Landmark Genomic Scanning: Analysis of CpG Islands in Genomes by 2D Gel Electrophoresis", Methods in Molecular Biology, DNA Methylation: Methods and Protocols, 2nd eds, 507:131-148 (2009).
Cruikshank et al., "A Lipidated Anti-Tat Antibody Enters Living Cells and Blocks HIV-1 Viral Replication", J. Acquired Immune Deficiency Syndromes and Human Retrovirology, 14(3)193-203 (1997).
Dai, B., et al., "Detection of Post-translation Modifications on Native Intact Nucleosomes by ELISA", Cell Death Detection ELISA PLUS Cat. No. 11774425 001, Version 11.0, Roche, Sep. 2010, pp. 1-19.
Dayei, K. et al., "3D C(CC)H TOCSY Experiment for Assigning Protons and Carbons in Uniformly $^{13}$C- and Selectively $^{2}$H-Labeled RNA", J. Mag. Reson, 130:97-101 (1998).
Deligezer, U. et al., "Sequence-Specific Histone Methylation is Detectable on Circulating Nucleosomes in Plasma", Clinical Chemistry 54(7):1125-1131 (2008).
Dembo, A. et al., "Limit Distribution of Maximal Non-Aligned Two-Sequence Segmental Score", The Annals of Probability, 22(4):2022-2039 (1994).
Donis-Keller, H. et al., "Mapping Adenines, Guanines, and Pyrimidines in RNA", Nucleic Acids Research, 4(8):2527-2538 (1977).
Donis-Keller, H., "Phy M: An RNase Activity Specific for U and A Residues Useful in RNA Sequence Analysis", Nucleic Acids Research, 8(14):3133-3142 (1980).
Ferguson-Smith, M., "Placental mRNA in Maternal Plasma: Prospects for Fetal Screening", Proceedings National Academy of Sciences, 100(8):4360-4362 (2003).
Finney, M. et al., "Molecular Cloning of PCR Products", Current Protocols in Molecular Biology, Supplement 56, Nov. 2001 pp. 15.4.1-15.4.11.

(56) References Cited

OTHER PUBLICATIONS

Gardiner-Garden, M. and Frommer, M., "CpG Islands in Vertebrate Genomes", Journal of Molecular Biology, 196(2):261-282 (1987).
Giles, F. et al., "Acute Myeloid Leukemia", American Society Hematology Education Program, vol. 2002, No. 1, Jan. 1, 2002, 47 pages.
Goeddel, D., "Systems for Heterologous Gene Expression", Gene Expression Technology: Methods in Enzymology, vol. 185, 1990, pp. 3-7.
Gottesmann, C., "Commentary: GABA Mechanisms and Sleep", Neuroscience, 111(2):231-239 (2002).
Grompe, M., "The Rapid Detection of Unknown Mutations in Nucleic Acids", Nature Genetics, 5(2):111-117 (1993).
Holdenrieder, S. et al., "Circulating Nucleosomes Predict the Response to Chemotherapy in Patients with Advanced Non-Small Cell Lung Cancer", Clinical Cancer Research 10(18):5981-5987 (2004).
Holdenrieder, S., "Circulating Nucleosomes: A New Addition to the Personalized Medicine Toolkit", Personalized Medicine 11(6):565-568 (2014).
Hsu, L. et al., "Denoising Array-Based Comparative Genomic Hybridization Data Using Wavelets", Biostatistics 6(2):211-226 (2005).
Iwabuchi, K. et al., "Use of the Two-Hybrid System to Identify the Domain of p53 Involved in Oligomerization", Oncogene, 8(6):1693-1696 (1993).
Lee, T. et al., "Control of Developmental Regulators by Polycomb in Human Embryonic Stem Cells", Cell, 125(2):301-313 (2006).
Li, H. et al., "Boron-Containing Oligodeoxyribonucleotide 14mer Duplexes: Enzymatic Synthesis and Melting Studies", Nucleic Acids Research, 23(21):4495-4501 (1995).
Li, J-Y et al., "Dynamic Distribution of Linker Histone H1.5 in Cellular Differentiation", PLOS Genetics, 8(8):1-13 (2012).
Mao, H. and Williamson, J., "Assignment of the L30-mRNA Complex Using Selective Isotopic Labeling and RNA Mutants", Nucleic Acids Research, 27(20):4059-4070 (1999).
Marais, R. et al., "Differential Regulation of Raf-1, A-Raf, and B-Raf by Oncogenic Ras and Tyrosine Kinases", Journal of Biological Chemistry, 272(7):4378-4383 (1997).
Mouliere, F. et al., "Multi-Marker Analysis of Circulating Cell-Free DNA Toward Personalized Medicine for Colorectal Cancer", Molecular Oncology 8(5):927-941 (2014).
Ng, E. et al., "mRNA of Placental Origin is Readily Detectable in Maternal Plasma", Proceedings of the National Academy of Sciences, 100(8):4748-4753 (2003).
Nicolaides, K. et al., "Increased Fetal Nuchal Translucency at 11-14 Weeks", Prenatal Diagnosis, 22(4):308-315 (2002).
Nygren, A. et al., "Quantification of Fetal DNA by Use of Methylation-Based DNA Discrimination," Clinical Chemistry, 56(10):1627-1635 (2010).
Oeth, P. et al., "Qualitative and Quantitative Genotyping Using Single Base Primer Extension Coupled With Matrix-Assisted Laser Desorption/Ionization Time-of-Flight Mass Spectrometry (MassARRAY)", Methods in Molecular Biology, 578:307-343 (2009).
Sargent, T., "Isolation of Differentially Expressed Genes", Methods in Enzymology, vol. 152, (1987) 12 pages.
Sayres, L. and Cho, M., "Cell-Free Fetal Nucleic Acid Testing: A Review of the Technology and Its Applications", Obstetrical and Gynecological Survey, 66(7):431-442 (2011).
Strathdee, G. et al., "Primary Ovarian Carcinomas Display Multiple Methylator Phenotypes Involving Known Tumor Suppressor Genes", American Journal of Pathology, 158(3):1121-1127 (2001).
Strauss, W., "Using DNA Fragments as Probes", Wiley & Sons, Current Protocols in Molecular Biology, pp. 6.3.1-6.3.6 (1993).
Takai D. and Jones, P., "Comprehensive Analysis of CpG Islands in Human Chromosomes 21 and 22", Proceedings of the National Academy of Sciences, 99(6):3740-3745 (2002).
Tong, Y. et al., "Noninvasive Prenatal Detection of Fetal Trisomy 18 by Epigenetic Allelic Ratio Analysis in Maternal Plasma: Theoretical and Empirical Considerations", Clinical Chemistry, 52(12):2194-2202 (2006).

Van Der Schoot, C. et al., "Real-Time PCR of Bi-Allelic Insertion/Deletion Polymorphisms Can Serve as a Reliable Positive Control for Cell-Free Fetal DNA in Non-Invasive Prenatal Genotyping", Abstract Blood, 102:93a (2003).
Verbeck, G. et al., "A Fundamental Introduction to Ion Mobility Mass Spectrometry Applied to the Analysis of Biomolecules", The Journal of Biomolecular Techniques, 13(2):56-61 (2002).
Vincent, M. et al., "Hellcase-Dependent Isothermal DNA Amplification", European Molecular Biology Organization Reports 5(8):795-800 (2004).
Wada, K. et al., "Codon Usage Tabulated from the GenBank Genetic Sequence Data", Nucleic Acids Research, 20:2111-2118 (1992).
Wald, N. and Hackshaw, A., "Combining Ultrasound and Biochemistry in First-Trimester Screening for Down's Syndrome", Prenatal Diagnosis 17(9):821-829 (1997).
Widschwendter, M. et al., "Epigenetic Stem Cell Signature in Cancer", Nature Genetics, 39(2):157-158 (2007).
Willenbrock, H. and Fridlyand, J., "A Comparison Study: Applying Segmentation to Array CGH Data for Downstream Analyses", Bioinformatics 21 (22):4084-4091 (2005).
Xiong, Z. and Laird, P., "COBRA: A Sensitive and Quantitative DNA Methylation Assay", Nucleic Acids Research, 25(12):2532-2534 (1997).
Yoon, S. et al., "Sensitive and Accurate Detection of Copy Number Variants Using Read Depth of Coverage", Genome Research 19(9):1586-1592 (2009).
Yu, S. et al., "Size-Based Molecular Diagnostics Using Plasma DNA for Noninvasive Prenatal Testing", Proceedings of the National Academy of Sciences, 111(3):8583-8588 (2014).
U.S. Appl. No. 13/517,508, Non-Final Office Action, dated Aug. 13, 2013, 11 pages.
U.S. Appl. No. 13/782,901, Final Office Action, dated May 28, 2015, 15 pages.
U.S. Appl. No. 13/782,901, Non-Final Office Action, dated Nov. 17, 2015, 8 pages.
U.S. Appl. No. 13/782,901, Non-Final Office Action, dated May 12, 2016, 9 pages.
U.S. Appl. No. 15/124,324, Final Office Action, dated Feb. 13, 2019, 7 pages.
U.S. Appl. No. 15/124,324, Non-Final Office Action, dated Aug. 6, 2018, 8 pages.
U.S. Appl. No. 15/443,051, Non-Final Office Action, dated Aug. 2, 2018, 13 pages.
U.S. Appl. No. 15/517,107, Final Office Action, dated May 26, 2020, 8 pages.
U.S. Appl. No. 15/517,107, Notice of Allowance, dated Sep. 8, 2020, 8 pages.
EP 13709696.2, Office Action, dated Sep. 25, 2015, 3 pages.
EP 13709696.2, Office Action, dated Feb. 16, 2016, 4 pages.
EP 14721601.4, Summons to Attend Oral Proceedings, Sep. 12, 2018, 8 pages.
EP 15753247.4, Notice of Decision to Grant, dated Jul. 2, 2020, 2 pages.
EP 15753247.4, Office Action, dated Aug. 19, 2019, 5 pages.
EP 15753247.4, Office Action, dated Oct. 17, 2018, 6 pages.
EP 15785002.5, Office Action, dated Oct. 10, 2018, 4 pages.
EP 18174047.3, Extended European Search Report, dated Aug. 13, 2018, 8 pages.
EP 19174694.0, Office Action, dated Oct. 12, 2020, 5 pages.
EP 20170556.3, Extended European Search Report, dated Nov. 4, 2020, 9 pages.
EP 20172801.1, Extended European Search Report, dated Sep. 22, 2020, 9 pages.
EP 20187578.8, Extended European Search Report, dated Nov. 11, 2020, 13 pages.
PCT/US2012/035479, International Preliminary Report on Patentability, dated Nov. 7, 2013, 24 pages.
PCT/US2012/035479, International Search Report and Written Opinion, dated Jan. 10, 2013, 20 pages.
PCT/US2013/028699, International Preliminary Report on Patentability, dated Sep. 12, 2014, 8 pages.
PCT/US2013/028699, International Search Report and Written Opinion, dated Jul. 1, 2013, 7 pages.

(56) References Cited

OTHER PUBLICATIONS

PCT/US2013/041354, International Search Report and Written Opinion, dated Aug. 14, 2013, 16 pages.
PCT/US2015/020250, International Search Report and Written Opinion, dated May 28, 2015, 12 pages.
PCT/US2015/054903, International Preliminary Report on Patentability, dated Apr. 20, 2017, 14 pages.

* cited by examiner

METHODS AND COMPOSITIONS FOR IDENTIFYING PRESENCE OR ABSENCE OF HYPERMETHYLATION OR HYPOMETHYLATION LOCUS

RELATED PATENT APPLICATIONS

This patent application is a national stage of international patent application number PCT/US2014/025132, filed Mar. 13, 2014, entitled METHODS AND PROCESSES FOR NON-INVASIVE ASSESSMENT OF GENETIC VARIATIONS, naming Taylor Jensen and Mathias Ehrich as inventors, which claims the benefit of U.S. Provisional Patent Application No. 61/780,162 filed on Mar. 13, 2013, entitled METHODS AND PROCESSES FOR NON-INVASIVE ASSESSMENT OF GENETIC VARIATIONS, naming Taylor Jensen and Mathias Ehrich as inventors. The entire content of the foregoing applications are incorporated herein by reference, including all text, tables and drawings.

REFERENCE TO SUBMISSION OF A SEQUENCE LISTING AS A TEXT FILE

The instant application contains a Sequence Listing which has been submitted electronically in ASCII format and is hereby incorporated by reference in its entirety. Said ASCII copy, created on May 26, 2020, is named SEQ-6063-US_SL.txt and is 157,416 bytes in size.

FIELD

Technology provided herein relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. Identification of one or more genetic variations or variances sometimes involves the analysis of cell-free DNA.

Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma can be a useful mechanism for the monitoring of fetomaternal well-being.

SUMMARY

Provided in some aspects herein are methods for analyzing fetal nucleic acid in a sample, comprising digesting nucleic acid in a nucleic acid sample from a pregnant female, which nucleic acid comprises fetal nucleic acid and maternal nucleic acid, with one or more methylation sensitive cleavage agents that specifically digest the nucleic acid at non-methylated recognition sites, thereby generating digested nucleic acid fragments, and analyzing the digested nucleic acid fragments. In some aspects the analyzing comprises determining the presence or absence of one or more polynucleotides in one or more loci relatively less methylated in fetal nucleic acid than in maternal nucleic acid. In certain aspects the one or more loci are chosen from loci in Table 2AB, Table 2CB, Table 3 and Table 4.

Provided in some aspects herein are methods for analyzing nucleic acid in a sample, comprising: enriching for hypomethylated nucleic acid present in a nucleic acid sample from a pregnant female, which nucleic acid comprises fetal nucleic acid and maternal nucleic acid, thereby generating enriched hypomethylated nucleic acid and analyzing the enriched hypomethylated nucleic acid, which analyzing comprises determining the presence, absence or amount of a polynucleotide in one or more loci chosen from loci of Table 4.

Provided in some aspects herein are methods for enriching for a minority nucleic acid species in a sample, comprising digesting nucleic acid in a nucleic acid sample from a pregnant female, which nucleic acid comprises a minority nucleic acid species and a majority nucleic acid species, with one or more methylation sensitive cleavage agents that specifically digest the nucleic acid at non-methylated recognition sites, thereby generating digested nucleic acid fragments and analyzing the digested nucleic acid fragments.

Provided in some aspects herein are methods for enriching for a minority nucleic acid species in a sample, comprising digesting nucleic acid in a nucleic acid sample from a pregnant female, which nucleic acid comprises a minority nucleic acid species and a majority nucleic acid species, with one or more methylation sensitive cleavage agents that specifically digest the nucleic acid at non-methylated recognition sites, thereby generating digested nucleic acid fragments and enriching the digested nucleic acid fragments relative to non-digested nucleic acid, thereby generating nucleic acid enriched for the minority nucleic acid species.

In some aspects provided herein are methods for analyzing nucleic acid in a sample, comprising enriching for hypomethylated nucleic acid present in a nucleic acid sample from a pregnant female, which nucleic acid comprises a minority nucleic acid species and a majority nucleic acid species, thereby generating enriched hypomethylated nucleic acid and analyzing the enriched hypomethylated nucleic acid, which analyzing comprises determining the presence, absence or amount of a polynucleotide in one or more loci chosen from loci of Table 4.

In some aspects provided herein are methods for preparing a collection of amplification primers, comprising (a) selecting one or more genomic loci, wherein each of the loci comprises three or more or all features selected from: (i) a locus length of about 5000 contiguous base pairs, or less, (ii) a CpG density of 16 CpG methylation sites per 1000 base pairs, or less, (iii) a gene density of 0.1 genes per 1000 base pair, or less, (iv) at least 5 CpG methylation sites, (v) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases, (vi) at least 1 restriction endonuclease recognition site per 1000 base pairs, wherein the at least one restriction endonuclease recognition site can be specifically digested by a methylation sensitive cleavage agent, (vii) a locus comprising a methylation status of 40% or less in fetal nucleic acid, (viii) a locus comprising a methylation status of 60% or more in maternal nucleic acid, and (ix) a locus comprising a difference in methylation status of 5% or more between fetal nucleic acid and maternal nucleic acid, and (b) preparing a plurality of oligonucleotide primer pairs, wherein each primer of each primer pair hybridizes to a portion of a strand of the locus selected in (a) for which the primer pair is specific, whereby a collection of amplification primers is prepared. Any suitable combination of three or more (e.g., 3, 4, 5, 6, 7 or 8) of features (i), (ii), (iii), (iv), (v), (vi), (vii), (viii) and/or (ix) can be utilized in a suitable order for the selection in (a). In some aspects, each of the primers of each of the primer pairs is specific for a target polynucleotide located in one or more of the loci selected in (a). In some embodiments, amplification primer pairs are prepared that amplify a target polynucleotide in one or more loci provided in Table 4.

In certain aspects provided herein is a collection of oligonucleotide primer pairs for identifying the presence or absence of a hypomethylated locus prepared by a process comprising (a) selecting one or more genomic loci wherein each locus comprises three or more or all features selected from (i) 5000 contiguous base pairs, or less, (ii) a CpG density of 16 CpG methylation sites per 1000 base pairs, or less, (iii) a gene density of 0.1 genes per 1000 base pair, or less, (iv) at least 5 CpG methylation sites, (v) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases, (vi) at least 1 restriction endonuclease recognition site per 1000 base pairs, wherein the at least one restriction endonuclease recognition sites can be specifically digested by a methylation sensitive cleavage agent, (vii) a locus comprising a methylation status of 40% or less in fetal nucleic acid, (viii) a locus comprising a methylation status of 60% or more in maternal nucleic acid, and (ix) a locus comprising a difference in methylation status of 5% or more between fetal nucleic acid and maternal nucleic acid and (b) preparing a plurality of oligonucleotide primer pairs, wherein each primer of each primer pair hybridizes to a portion of a strand of the locus selected in (a) for which the primer pair is specific, whereby a collection of amplification primers is prepared. Any suitable combination of three or more (e.g., 3, 4, 5, 6, 7 or 8) of features (i), (ii), (iii), (iv), (v), (vi), (vii), (viii) and/or (ix) can be utilized in a suitable order for the selection in (a). In some aspects of the foregoing, each of the primers of each of the primer pairs is specific for a target polynucleotide located in one or more of the loci selected in (a). In some embodiments, amplification primer pairs are provided that amplify a target polynucleotide in one or more loci provided in Table 4.

In certain aspects presented herein is a collection of amplification primer pairs for identifying the presence or absence of a hypermethylated locus prepared by a process comprising (a) selecting one or more genomic loci wherein each locus comprises three or more or all features selected from: (i) a locus length of about 5000 contiguous base pairs, or less, (ii) at least 5 CpG methylation sites, (iii) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases, (iv) at least 1 restriction endonuclease recognition site per 1000 base pairs, wherein the at least one restriction endonuclease recognition sites can be specifically digested by a methylation sensitive restriction endonuclease, (v) a locus comprising a methylation status of 60% or more in a minority nucleic acid species, (vi) a locus comprising a methylation status of 40% or less in a majority nucleic acid species, and (vii) a locus comprising a difference in methylation status of 5% or more between a minority nucleic acid species and a majority nucleic acid species and (b) preparing a plurality of oligonucleotide primer pairs, wherein each primer of each primer pair hybridizes to a portion of a strand of the locus selected in (a) for which the primer pair is specific, whereby a collection of amplification primers is prepared. Any suitable combination of three or more (e.g., 3, 4, 5 or 6) of features (i), (ii), (iii), (iv), (v), (vi) and/or (vii) can be utilized in a suitable order for the selection in (a). In certain aspects of the foregoing, each of the primers of each of the primer pairs is specific for a target polynucleotide located in one or more of the loci selected in (a). In some embodiments, amplification primer pairs are prepared that amplify a target polynucleotide in one or more loci provided in Table 5.

Also, presented herein, in some aspects, is a method of preparing a collection of amplification primers, comprising (a) selecting one or more genomic loci wherein each locus comprises three or more features selected from (i) a locus length of about 5000 contiguous base pairs, or less, (ii) at least 5 CpG methylation sites, (iii) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases, (iv) at least 1 restriction endonuclease recognition site per 1000 base pairs, wherein the at least one restriction endonuclease recognition site can be specifically digested by a methylation sensitive restriction endonuclease, (v) a locus comprising a methylation status of 60% or more in fetal nucleic acid, (vi) a locus comprising a methylation status of 40% or less in maternal nucleic acid, and (vii) a locus comprising a difference in methylation status of 5% or more between fetal nucleic acid and maternal nucleic acid and (b) preparing a plurality of oligonucleotide primer pairs, wherein each primer of each primer pair hybridizes to a portion of a strand of the locus selected in (a) for which the primer pair is specific, whereby a collection of amplification primers is prepared. Any suitable combination of three or more (e.g., 3, 4, 5 or 6) of features (i), (ii), (iii), (iv), (v), (vi) and/or (vii) can be utilized in a suitable order for the selection in (a). In some embodiments, amplification primer pairs are provided that amplify a target polynucleotide in one or more loci provided in Table 5.

Certain aspects of the technology are described further in the following description, examples, drawings and claims.

BRIEF DESCRIPTION OF THE DRAWINGS

The drawings illustrate aspects of the technology and are not limiting. For clarity and ease of illustration, the drawings are not made to scale and, in some instances, various aspects may be shown exaggerated or enlarged to facilitate an understanding of particular embodiments.

FIG. 7 describes the theoretical enrichment based upon methylation level data described in FIG. 3 derived using HpaII and HinP1I digestion. Fold enrichment as shown on the y-axis was calculated as (Fold enrichment=Fetal fraction after digestion/Fetal fraction before enrichment for each fetal fraction from 0.01-1 at increments of 0.01). The range of enrichment was from about 1 to about 86.3 fold enrichment. Fetal nucleic acid was enriched by digestion of ccf nucleic acid with a methylation sensitive restriction endonuclease followed ligation of linkers and amplification of target polynucleotides.

DETAILED DESCRIPTION

Figure 1:
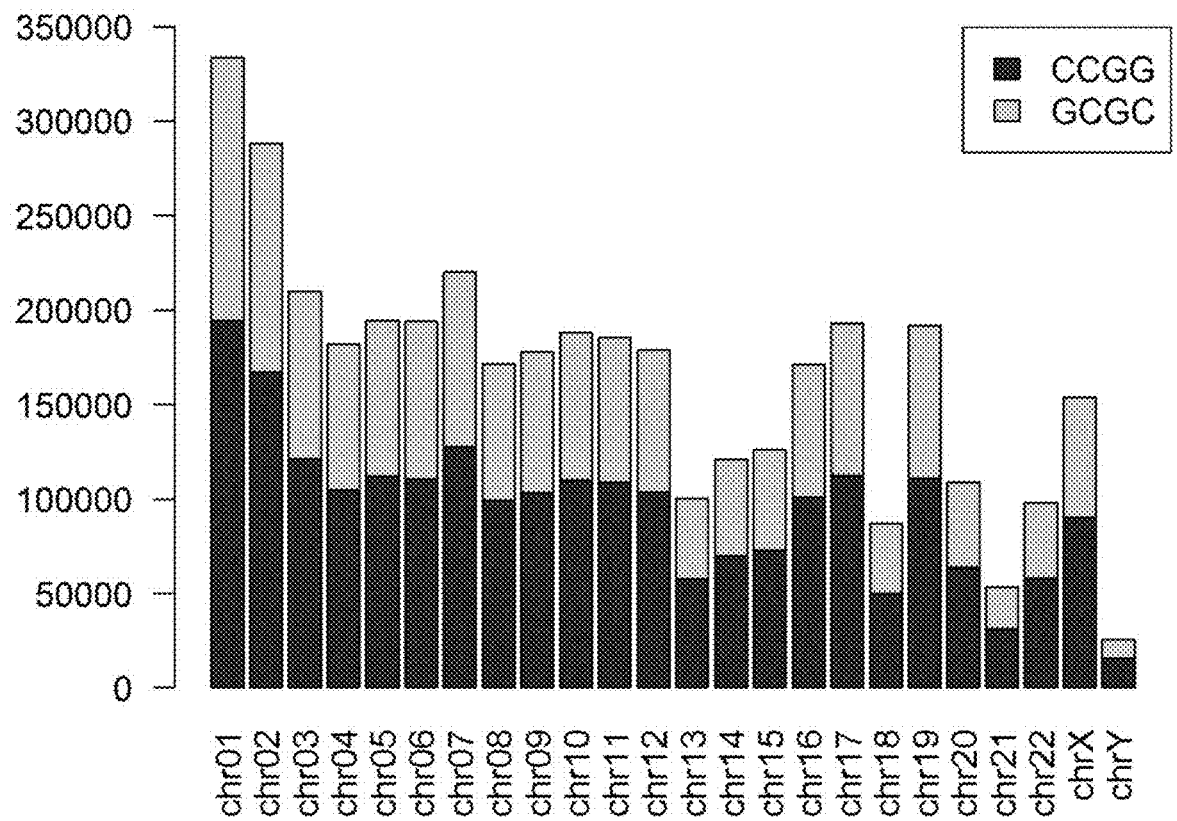
FIG. 1 shows number of restriction sites for HpaII and HinP1I in the human genome for each chromosome.

Provided herein are methods for enriching and/or analyzing a sub-population of cell-free nucleic acid from a larger pool of cell-free nucleic acid in a sample nucleic acid. Cell-free nucleic acid sometimes comprises a mixture of nucleic acids from different sources (e.g., fetal versus maternal tissue, tumor cells versus normal cells). Nucleic acid from different sources sometimes can be differentially methylated. Such differential methylation of certain subpopulations of cell free nucleic acid can be useful for enriching and/or analyzing a particular subpopulation of nucleic acid. Provided herein are methods for enriching and/or analyzing a particular subpopulation of nucleic acid (e.g., fetal nucleic acid) in a sample comprising circulating cell-free (ccf) nucleic acid.

Provided also are methods, processes and apparatuses useful for identifying a genetic variation. Identifying a genetic variation sometimes comprises detecting a copy number variation and/or sometimes comprises adjusting an elevation comprising a copy number variation. In some embodiments, identifying a genetic variation by a method described herein can lead to a diagnosis of, or determining a predisposition to, a particular medical condition. Identifying a genetic variance can result in facilitating a medical decision and/or employing a helpful medical procedure.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject (e.g., a test subject). A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman). In some embodiments a subject is a pregnant human female.

Nucleic acid may be isolated from any type of suitable biological specimen or sample (e.g., a test sample). A sample or test sample can be any specimen that is isolated or obtained from a subject (e.g., a test subject, a human subject, a pregnant female). Non-limiting examples of specimens include fluid or tissue from a subject, including, without limitation, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample is a cervical swab from a subject. In some embodiments, a biological sample may be blood and sometimes plasma or serum. As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain instances, buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be a cellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species are present. The term "minority nucleic acid species" as used herein refers to a nucleic acid species in a sample that is present in an amount that is less than 50%, less than 40%, less than 30%, less than 20% or less than 10% of the total amount of nucleic acid present in the sample. The term "majority nucleic acid species" as used herein refers to a nucleic acid species in a sample that is present in an amount that is greater than greater than 50%, greater than 60%, greater than 70%, or greater than 80% of the total amount of nucleic acid present in the sample. In some embodiments a minority nucleic acid species comprises fetal nucleic acid. In some embodiments a minority nucleic acid species comprises placental nucleic acid. In some embodiments a minority nucleic acid comprises nucleic acid derived from a tumor or malignant cell-type. In some embodiments a minority nucleic acid species comprises hypomethylated nucleic acid, one or more hypomethylated loci or unmethylated nucleic acid. In some embodiments a minority nucleic acid species comprises hypomethylated fetal nucleic acid. In some embodiments a minority nucleic acid species comprises methylated nucleic acid, hypermethylated nucleic acid or one or more hypermethylated loci. In some embodiments a minority nucleic acid species comprises hypermethylated fetal nucleic acid. In some embodiments a majority nucleic acid species comprises maternal nucleic acid. In some embodiments a majority nucleic acid species is derived from normal healthy tissue of a test subject (e.g., non cancerous tissue, non-malignant tissue, non-infected tissue).

For prenatal applications of technology described herein, fluid or tissue sample may be collected from a female (e.g., a pregnant female) at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In some embodiments, a fluid or tissue sample is collected from a pregnant female during or just after (e.g., 0 to 72 hours after) giving birth (e.g., vaginal or non-vaginal birth (e.g., surgical delivery)).

Nucleic Acid Isolation and Processing

Nucleic acid may be derived from one or more sources (e.g., cells, serum, plasma, buffy coat, lymphatic fluid, skin, soil, and the like) by methods known in the art. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid can be a polynucleotide and/or a nucleic acid fragment. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). Nucleic acids sometimes comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of a cellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less). The term "fetal nucleic acid" as referred to herein means any nucleic acid (e.g., polynucleotide) derived from a tissue, cell or fluid originating from a human embryo, fetus, or unborn human child. Non-limiting examples of fetal tissue include umbilical cord, portions of the placenta, fetal organs, fetal skin, fetal hair, fetal blood (e.g., fetal plasma, fetal blood cells), fetal lymphatic fluid, amniotic fluid, the like or combinations thereof).

A nucleic acid sample obtained from blood, serum, plasma or urine often comprises circulating cell free (ccf) DNA (e.g., circulating cell free nucleic acids). Circulating cell free DNA from a pregnant female often comprise fetal nucleic acid and maternal nucleic acid. In some embodiments ccf DNA isolated from a test subject comprises a nucleic acid derived from one or more tumors and nucleic acid derived from normal healthy (e.g., non-cancerous) tissues or cells. Circulating cell free DNA often comprises nucleic acid fragments ranging from about 1000 nucleotides in length or less. In some embodiments the mean, average, median, mode or absolute size of ccf fragments is about 700 nucleotides (nt) or less, 600 nt or less, 500 nt or less, 400 nt or less, 350 nt or less, 300 nt or less, 250 nt or less, 200 nt or less, 190 nt or less, 180 nt or less, 170 nt or less, 160 nt or less, 150 nt or less, 140 nt or less, 130 nt or less, 120 nt or less, 110 nt or less or 100 nt or less. In some embodiments the mean, average, median, mode or absolute size of ccf fragments is associated with a methylation status. For example, in some embodiments ccf fragments of about 250 nt or less, 225 nt or less, 200 nt or less, 190 nt or less, 180 nt or less, 170 nt or less, 160 nt or less, 150 nt or less, 140 nt or less, 130 nt or less, 120 nt or less, 110 nt or less or 100 nt or less in length are derived from a locus that is hypomethylated. In some embodiments ccf fragments of about 150 nt or more, 160 nt or more, 170 nt or more, 180 nt or more, 190 nt or more, 200 nt or more, 250 nt or more, or 300 nt or more are derived from a locus that is hypermethylated.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

The term "amplified" as used herein refers to subjecting a target polynucleotide in a sample to a process that linearly or exponentially generates amplicon nucleic acids having the same or substantially the same nucleotide sequence as the target polynucleotide, or segment thereof. A target polynucleotide is often a portion of a genome or portion of a locus represented in a sample as a polynucleotide fragment. In some embodiments a nucleotide sequence, or portion thereof, of a target polynucleotide is known. The term "amplified" as used herein can refer to subjecting a target polynucleotide (e.g., in a sample comprising other nucleic acids) to a process that selectively and linearly or exponentially generates amplicon nucleic acids having the same or substantially the same nucleotide sequence as the target polynucleotide, or segment thereof. Amplicons that are generated from, and have the same or substantially the same nucleotide sequence as a target polynucleotide, are referred to herein as target specific amplicons. The term "amplified" as used herein can refer to subjecting a population of nucleic acids to a process that non-selectively and linearly or exponentially generates amplicon nucleic acids having the same or substantially the same nucleotide sequence as nucleic acids, or portions thereof, that were present in the sample prior to amplification. In some embodiments, the term "amplified" refers to a method that comprises a polymerase chain reaction (PCR).

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known in the art, which include without limitation, physical, chemical and enzymatic processes. Non-limiting examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Non-limiting examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from portions of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved or non-specifically cleaved by contacting the nucleic acid with one or more enzymatic cleavage agents (e.g., nucleases, restriction enzymes). The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site. Non-specific cleavage agents often cleave nucleic acids at non-specific sites or degrade nucleic acids. Non-specific cleavage agents often degrade nucleic acids by removal of nucleotides from the end (either the 5' end, 3' end or both) of a nucleic acid strand.

Any suitable non-specific or specific enzymatic cleavage agent can be used to cleave or fragment nucleic acids. A suitable restriction enzyme can be used to cleave nucleic acids, in some embodiments. Examples of enzymatic cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid in a sample or mixture can be treated with an agent that modifies a methylated nucleotide to another moiety. In some embodiments nucleic acid in a sample or mixture may be treated with an agent (e.g., a chemical agent), and a modified nucleic acid may be cleaved. Non-limiting examples of nucleic acid modifying agents include (i) alkylating agents such as methylnitrosourea that generate several alkylated bases, including N3-methyladenine and N3-methylguanine, which are recognized and cleaved by alkyl purine DNA-glycosylase; (ii) sodium bisulfite (i.e., bisulfite), which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Nucleic acid may be single or double stranded. Single stranded DNA, for example, can be generated by denaturing double stranded DNA by heating or by treatment with alkali, for example. Nucleic acid sometimes is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

The term "polynucleotide" as used herein refers to all or a portion of a nucleic acid. The term "polynucleotide" as used herein can refer to a portion or all of a genome, chromosome, gene or locus. A polynucleotide is sometimes a nucleic acid fragment (e.g., a fragment of nucleic acid produced from shearing or an enzymatic reaction, a ccf nucleic acid fragment, an amplicon, an extension product, or the like). A polynucleotide can be single or double stranded.

Methylation-Sensitive Cleavage

In some embodiments, a sample nucleic acid (e.g., a sample comprising maternal nucleic acids, fetal nucleic acids or a mixture thereof, (e.g., ccf DNA)) is digested with one or more methylation sensitive cleavage agents. Any suitable sample nucleic acid can be contacted with or digested with a methylation sensitive cleavage agent. Non-limiting examples of sample nucleic acid that can be contacted with or digested with a methylation sensitive cleavage agent include nucleic acid isolated from the blood, serum, plasma or urine of a test subject (e.g., a pregnant female, a cancer patient), nucleic acid enriched for a minority species, nucleic acid enriched for fetal nucleic acid, maternal nucleic acid, or a sample enriched for unmethylated nucleic acid, hypomethylated nucleic acid, methylated nucleic acid or hypermethylated nucleic acid, the like or combinations thereof. In some embodiments sample nucleic acid is contacted with one or more methylation sensitive cleavage agents under suitable conditions (e.g., using a suitable buffer, enzyme concentration, DNA concentration, pH, temperature and/or incubation duration) which often results in digested nucleic acid fragments and/or undigested nucleic acid fragments. Digested nucleic acid fragments can comprise any suitable subset of nucleic acid fragments or target polynucleotides. In some embodiments undigested nucleic acid fragments can comprise any suitable subset of nucleic acid fragments or target polynucleotides. Non-limiting examples of digested or undigested subsets of nucleic acid fragments include fetal nucleic acid, maternal nucleic acid, unmethylated nucleic acid, hypomethylated nucleic acid, methylated nucleic acid, hypermethylated nucleic acid, minority nucleic acid, majority nucleic acid, the like, fragments thereof or combinations thereof. Digested and/or undigested nucleic acid fragments are often enriched, separated and/or analyzed by a method described herein.

In some embodiments, one or more methylation sensitive cleavage agents are methylation sensitive restriction enzymes (e.g., methylation sensitive restriction endonucleases). Methylation sensitive cleavage agents and methylation sensitive restriction enzymes are agents that cleave nucleic acid depending on the methylation state of their recognition site. For example, methylation sensitive DNA restriction endonucleases are generally dependent on the methylation state of their DNA recognition site for activity. In some instances, certain methylation sensitive endonucleases cleave or digest nucleic acid only if it is not methylated at their DNA recognition sequence. Some methylation sensitive endonucleases cleave or digest nucleic acid only if it is methylated at their DNA recognition sequence. Some methylation sensitive endonucleases cleave or digest nucleic acid at their or near their recognition sequence. (i.e. digest at unmethylated or hypomethylated sites). Some methylation sensitive endonucleases cleave or digest nucleic acid 5' and/or 3' of their recognition sequence. Sometimes methylation sensitive endonucleases cleave or digest nucleic acids at random distances (e.g., 5, 10, 20, 50, 100, or 150 base pairs or more) at a site located 5' and/or 3' of their recognition sequences. In some embodiments an unmethylated or hypomethylated DNA fragment can be cut into smaller fragments compared to a methylated or hypermethylated DNA fragment that is not digested. In some embodiments a methylated or hypermethylated DNA fragment can be cut into smaller fragments compared to an unmethylated or hypomethylated DNA fragment that is not digested. For example, the average, mean, median or nominal length of certain digested nucleic acid fragments can be about 20 bases to about 200 bases (e.g., about 30, 40, 50, 60, 70, 80, 90, 100, 150 bases). In certain embodiments nucleic acids in a sample (e.g., genomic DNA or ccf DNA) are digested with an enzyme to produce digested nucleic acid fragments with an average, mean, median or nominal length of about 1000 bases or less, about 500 bases or less, about 250 bases or less, about 200 bases or less, about 150 bases or less or about 100 bases (e.g., 100 base pairs) or less. In some embodiments nucleic acids in a sample are digested to produce nucleic acid fragments with an average, mean, median or nominal length between about 25 bases and about 500 bases, between about 25 bases and about 250 bases, between about 25 bases and about 200 bases, between about 25 bases and about 150 bases, between about 40 bases and about 100 bases, or between about 40 bases and about 80 bases. In some embodiments nucleic acids in a sample are digested to produce nucleic acid fragments with an average, mean, median or nominal length between about 500 bases, about 450 bases, about 400 bases, about 350 bases, about 300 bases, about 250 bases, about 200 bases, about 190 bases, about 180 bases, about 170 bases, about 160 bases, about 150 bases, about 140 bases, about 130 bases, about 120 bases, about 110 bases or about 100 bases.

In some embodiments sample nucleic acids are digested with one or more methylation sensitive cleavage agents resulting in an enrichment of a subset of nucleic acid species (e.g., hypermethylated nucleic acid, hypomethylated nucleic acid, fetal nucleic acid, a minority nucleic acid species, the like or a combination thereof). In some instances, digestion of ccf DNA at certain hypomethylated regions in a genome can provide a mixture enriched for undigested nucleic acid fragments (e.g., enriched for hypermethylated polynucleotides) comprising an average, mean, median or nominal length of 100 bases or more, 120 bases or more, 140 bases or more, 160 bases or more, 180 bases or more, 200 bases or more, 250 bases or more, 300 bases or more, 400 bases or more or 500 bases or more in length. In some instances, digestion of ccf DNA at certain restriction enzyme recognition sequences that are unmethylated can provide a mixture enriched for undigested nucleic acid fragments comprising one or more restriction enzyme recognition sequences that are methylated. In some embodiments, digestion of ccf DNA at certain hypermethylated regions in a genome can provide a mixture enriched for undigested nucleic acid fragments (e.g., enriched for hypomethylated polynucleotides) comprising an average, mean, median or nominal length of 100 bases or more, 120 bases or more, 140 bases or more, 160 bases or more, 180 bases or more, 200 bases or more, 250 bases or more, 300 bases or more, 400 bases or more or 500 bases or more in length. In some embodiments undigested fragments are enriched for fetal nucleic acids. In some instances, digestion of ccf DNA at certain methylated restriction enzyme recognition sequences can provide a mixture enriched for undigested nucleic acid fragments comprising one or more restriction sites that are unmethylated.

The terms "cleave", "cut" and "digest" are used interchangeably herein.

In some embodiments the expected average fragment size of digested fragments for a given restriction enzyme can be estimated based, in part, on the length of the recognition sequence of the restriction enzyme. For example, without being limited to theory, in a genome with 50% GC content and no dinucleotide bias, a four-cutter (e.g., an endonuclease having a 4 base recognition sequence) can be estimated to cut at about every 256 bases, a six-cutter (e.g., an endonuclease having a 6 base recognition sequence) can be expected to cut at about every 4,096 bases, and an eight-cutter (e.g., an endonuclease having a 8 base recognition sequence) should cut at about every 65,536 bases. The expected average fragment size of digested fragments for a given enzyme reaction can be reduced (e.g., frequency of cutting can be increased) by including additional restriction endonucleases in a digestion reaction where each restriction endonuclease has a different recognitions sequence and/or specificity. Sometimes the expected average fragment size of digested fragments for a given restriction enzyme or for a given digestion can be determined empirically for a given sample or sample type (e.g., genomic DNA, ccf DNA). In some embodiments nucleic acid is digested with one or more restriction endonucleases comprising a recognition sequence of 16 bases pairs or less, 12 base pairs or less, 8 base pairs or less, 6 base pairs or less or 4 base pairs or less. In some embodiments nucleic acid is digested with one or more restriction endonucleases comprising a recognition sequence of 4 base pairs or less.

Methylation sensitive restriction enzymes can include any suitable methylation sensitive restriction enzyme described herein or known in the art. For example, a methylation sensitive restriction enzyme can include any suitable Type I, Type II, Type III, Type IV or Type V restriction endonuclease. Type I enzymes are generally complex, multi-subunit, combination restriction-and-modification enzymes that cut DNA at random sites far from their recognition sequences. Type II enzymes generally cut DNA at defined positions close to or within their recognition sequences. Type II enzymes generally recognize DNA sequences that are symmetric, because they often bind to DNA as homodimers, but a some recognize asymmetric DNA sequences, because they bind as heterodimers. Some Type II enzymes recognize continuous sequences in which the two half-sites of the recognition sequence are adjacent, while others recognize discontinuous sequences in which the half-sites are separated. Type II enzymes generally leaves a 3"-hydroxyl on one side of each cut and a 5"-phosphate on the other. Sometimes Type II enzymes (e.g., Type IIS) cleave outside of their recognition sequence to one side. These enzymes generally recognize sequences that are continuous and asymmetric. Some Type II enzymes (e.g., Type IIG) cleave outside of their recognition sequences, recognize continuous sequences and cleave on just one side. Other Type II enzymes cleave outside of their recognition sequences, recognize discontinuous sequences and cleave on both sides releasing a small fragment containing the recognition sequence. Type III enzymes generally cleave outside of their recognition sequences and require two such sequences in opposite orientations within the same DNA molecule to accomplish cleavage. Type IV enzymes generally recognize modified, typically methylated DNA and are generally exemplified by the McrBC and Mrr systems of *E. coli*. Non-limiting examples of restriction enzymes that can be used for a method described herein include AatII, AccII, ACiI, AcII, AfeI, AgeI, AgeI-HF, Aor13HI, Aor51HI, AscI, AseI, BceAI, BmgBI, BsaAI, BsaHI, BsiEI, BspDI, BsrFI, BspT104I, BssHII, BstBI, BstUI, Cfr10I, ClaI, CpoI, EagI, Eco52I, FauI, FseI, FspI, DpnI, DpnII, HaeII, HaeIII, HapII, HfaI, HgaI, HhaI, HinP1I, HPAII, Hpy99I, HpyCH4IV, KasI, MaeII, McrBC, MluI, MspI, NaeI, NgoMIV, NotI, NotI-HF, NruI, NsbI, NtBsmAI, NtCviPII, PaeR7I, PluTI, PmlI, PmaCI, Psp1406I, PvuI, RsrII, SacII, SalI, SalI-HF, ScrFI, SfoI, SfrAI, SmaI, SnaBI, TspMI, ZraI, the like, isoschizomers thereof, or combinations thereof. Non-limiting examples of enzymes that digest nucleic acid according to a non-methylated recognition sequence include HpaII, HinP1I, HhaI, MaeII, BstUI and AciI. In some embodiments, one or more of the restriction enzymes are selected from HHAI, HinP1I and HPAII. In some embodiments, an enzyme that can be used is HpaII that cuts only the unmethylated sequence CCGG. In some embodiments, an enzyme that can be used is HhaI that cuts only the unmethylated sequence GCGC. In some embodiments, an enzyme that can be used is HinP1I that cuts only the unmethylated sequence GCGC. Such enzymes are available from New England BioLabs®, Inc. and from other suitable sources. In some embodiments combinations of two or more methyl-sensitive enzymes can be used. In some embodiments combinations of two or more methyl-sensitive enzymes that digest only unmethylated DNA also can be used. In some embodiments combinations of two or more methyl-sensitive enzymes that digest only methylated DNA also can be used. Suitable enzymes that digest only methylated DNA include, but are not limited to, DpnI, which cuts at a recognition sequence GATC, and McrBC, which belongs to the family of AAA$^+$ proteins and cuts DNA containing modified cytosines and cuts at recognition site 5' . . . Pu$^m$C(N$_{40-3000}$) Pu$^m$C . . . 3' (New England BioLabs®, Inc., Beverly, Mass.).

In some embodiments, one or more restriction enzymes are selected according to the overhangs (i.e., one or more unpaired nucleotides) that result from digestion with a restriction endonuclease. An overhang is generally one or more unpaired nucleotides at the end of a double stranded polynucleotide fragment. In some embodiment, one or more unpaired nucleotides of an overhang extend from the 3' end or 5' end of a polynucleotide strand. Such overhangs sometimes can be referred to as "sticky ends" and can be used, for example, for ligating to an oligonucleotide, adaptor or other molecule as described herein. In some embodiments overhangs are utilizes for hybridization of a primer sequence or part thereof, often for a subsequent amplification process. In some embodiments, one or more restriction enzymes are selected that produce blunt ends (e.g., no overhang). Blunt ends can also be utilized for ligating an adaptor (i.e., adapter). In some embodiment, a restriction enzyme digest produces digested fragments comprising sticky ends, blunt ends and/or a combination thereof. For example, sometimes a digested fragment includes an overhang at both ends, a blunt end at both ends, or an overhang and a blunt end. In some embodiments an overhang can be produced as a result of a polymerase extension (e.g., as a result of a PCR reaction).

Oligonucleotide Ligation

Any suitable overhang or blunt end can be used to ligate an oligonucleotide or adaptor to one end or both ends of a nucleic acid fragment. In some embodiments, digestion of nucleic acid (e.g., methylation sensitive digestion of hypomethylated nucleic acid) generates digested nucleic acid fragments having blunt ends and/or overhangs (i.e., one or more unpaired nucleotides) at the 3' and/or 5' ends of the digested fragments. Such blunt ends and/or overhangs can be ligated to an oligonucleotide, adaptor or other molecule having a complementary overhang sequence (e.g., ligation sequence). For example, a digested fragment having a 5'-CG-3' overhang can be ligated (e.g., using a DNA ligase) to an oligonucleotide having a 3'-GC-S' overhang. Oligonucleotides comprising an overhang used for ligation are often double-stranded. In some embodiments, the oligonucleotide can ligate to substantially all fragments produced by a particular cleavage agent. For example, an oligonucleotide can ligate to at least 90%, 95%, 96%, 97%, 98%, 99%, 99.9% or 100% of the fragments produced by a particular cleavage agent in some embodiments. In some embodiments, different oligonucleotides are used.

In some embodiments ligation is not required for amplification and/or enrichment of nucleic acids digested by a methylation sensitive restriction enzyme. Digested nucleic acid can be amplified by one or more primer sets, often added in excess, comprising a 3' end that is complementary to overhangs produced as a result of a restriction digest or extension. In some embodiments digested nucleic acid can be amplified using target specific primer sets directed to hybridize to nucleic acid sequences (e.g., target polynucleotide sequences) of hypomethylated or hypermethylated loci. In some embodiments, hypomethylated or hypermethylated nucleic acid can be enriched prior to or after restriction digest by a suitable size selection method (e.g., size selection by PEG precipitation, size selection by column chromatograph, size selection by bridge amplification, the like or combinations thereof). In some embodiments, hypomethylated nucleic acid can be enriched prior to, during or after amplification of restriction digested products by a suitable method (e.g., size selection by PEG precipitation, size selection by column chromatograph, size selection by bridge amplification, the like or combinations thereof).

In some embodiment an overhang is not required for enrichment and/or amplification of hypomethylated nucleic acids. For example, hypomethylated nucleic acid can be enriched by precipitation using a methyl-specific binding agent (e.g., an antibody, a methyl binding protein), or by another suitable method followed by digestion of the hypomethylated nucleic acid by a restriction enzyme that produces blunt-ends or overhang ends. In either embodiment, oligonucleotides (e.g., double stranded oligonucleotides) can be ligated to the digested fragments and the ligated sequences can be captured, enriched, amplified, and/or sequenced by using nucleic acid sequences, or a portion thereof, of the newly ligated oligonucleotides.

In some embodiments, an oligonucleotide comprises an element useful for enrichment and/or analysis of the digested nucleic acid fragments. Elements useful for enrichment and/or analysis of the digested nucleic acid fragments may include, for example, binding agents, capture agents (e.g., binding pairs), affinity ligands, antibodies, antigens, primer hybridization sequences (e.g., a sequence configured for a primer to specifically anneal), a suitable predetermined sequence that can be used for enrichment and/or capture (e.g., a sequence that can hybridize to a complementary nucleic acid comprising a binding agent, e.g., biotin), adaptor sequences, identifier sequences, detectable labels and the like, some of which are described in further detail below. For example, an oligonucleotide may be biotinylated such that it can be captured onto a streptavidin-coated bead. In some embodiments, an oligonucleotide comprises an element useful for a targeted enrichment and/or analysis of the digested nucleic acid fragments. For example, certain nucleotide sequences in a sample may be targeted for enrichment and/or analysis (e.g., using oligonucleotides comprising sequence-specific amplification primers). In some embodiments, an oligonucleotide comprises an element useful for global (i.e., non-targeted) enrichment and/or analysis of the digested nucleic acid fragments. For example, certain oligonucleotides may comprise universal amplification hybridization sequences useful for global (e.g., non-target sequence dependent) enrichment and/or analysis of digested nucleotide sequence fragments.

Oligonucleotides can be designed and synthesized using a suitable process, and may be of any length suitable for ligating to certain nucleic acid fragments (e.g., digested nucleic acid fragments) and performing enrichment and/or analysis processes described herein. Oligonucleotides may be designed based upon a nucleotide sequence of interest (e.g., target fragment sequence, target polynucleotides, reference fragment sequence) or may be non-sequence specific (e.g., for a global enrichment process described herein) and/or may be sample-specific (e.g., may comprise a sample-specific identifier as described below). An oligonucleotide, in some embodiments, may be about 10 to about 300 nucleotides, about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. An oligonucleotide may be composed of naturally occurring and/or non-naturally occurring nucleotides (e.g., labeled nucleotides), or a mixture thereof. Oligonucleotides suitable for use with embodiments described herein, may be synthesized and labeled using known techniques. Oligonucleotides may be chemically synthesized according to the solid phase phosphoramidite triester method first described by Beaucage and Caruthers (1981) Tetrahedron Letts. 22:1859-1862, using an automated synthesizer, and/or as described in Needham-VanDevanter et al. (1984) Nucleic Acids Res. 12:6159-6168. Purification of oligonucleotides can be effected by native acrylamide gel electrophoresis or by anion-exchange high-performance liquid chromatography (HPLC), for example, as described in Pearson and Regnier (1983) J. Chrom. 255:137-149.

Primers

A primer is often a strand of nucleic acid (e.g., an oligonucleotide, an oligonucleotide primer) that serves as a starting point for nucleic acid synthesis. The terms "primer" and "oligonucleotide primer" are used interchangeably herein. A primer is often used for nucleic acid sequencing, amplification, fill-in reactions and extension reactions. A portion of a primer is often complementary to, and can hybridize to, a portion of a nucleic acid template (e.g., a target polynucleotide). A portion of a primer that is complementary to a portion of a target sequence which the primer pair is configured to amplify is sometimes referred to herein as a hybridization sequence. In some embodiments, an oligonucleotide primer comprises a hybridization sequence (e.g., a sequence complementary to a portion of a target sequence or template nucleic acid). All or a portion of a primer hybridization sequence can be complementary to a portion of a target polynucleotide or template nucleic acid. In some embodiments a primer, or portion thereof is complementary to an adaptor that was previously ligated to a target polynucleotide or template nucleic acid. In some embodiments a primer, or portion thereof is complementary to an overhang generated by a restriction enzyme cleavage reaction. In some embodiments, a primer is useful for amplification (unidirectional amplification, bi-directional amplification) of certain nucleic acid fragments (e.g., digested nucleic acid fragments). In some embodiments, oligonucleotides comprise hybridization sequences that are specific for certain genomic target sequences (e.g., target polynucleotides). An oligonucleotide primer, primer pair or nucleic acid that is specific for a target polynucleotide often hybridized specifically to the target polynucleotide or a portion thereof under suitable hybridization conditions. In some embodiments, oligonucleotides comprise primer hybridization sequences that are not specific for certain genomic target sequences (e.g., universal primer hybridization sequences configured to anneal to a universal adaptor or linker that is ligated or attached to one or more target polynucleotides). Universal primer hybridization sequences may be useful for global (i.e., non-targeted) amplification of certain nucleic acid fragments (e.g., digested nucleic acid fragments). The term "primer" as used herein refers to a nucleic acid that includes a nucleotide sequence capable of hybridizing or annealing to a target polynucleotide, at or near (e.g., adjacent to) a specific region of interest or universal primer site (e.g., a ligated adaptor, an overhang). Primers can allow for specific determination of a target polynucleotide nucleotide sequence or detection of the target polynucleotide (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide or universal primer for a universal primer hybridization sequence. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer or primer pair can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers can be effected by native acrylamide gel electrophoresis or by anion-exchange high-performance liquid chromatography (HPLC), for example, as described in Pearson and Regnier, J. Chrom., 255:137-149, 1983.

A primer pair refers to a pair of two oligonucleotide primers, oriented in opposite directions and configured for amplifying (e.g., by PCR) a nucleic acid template (e.g., a specific target polynucleotides). A nucleic acid template (e.g., target polynucleotide) can be single and/or double stranded. A primer pair or a collection of primer pairs can be designed by a suitable method that often optimizes or matches various features of each primer of a primer pair. In some embodiments where a collection of primer pairs is used in an amplification reaction, various features of each primer pair in a collection are optimized. Algorithms and methods for designing and optimizing primer pairs, as well as collections of primer pairs for an amplification (e.g., an amplification reaction) are well known. Any suitable method of designing and optimizing primer pairs or collections of primer pairs can be used to design primer pairs or collections of primer pairs for amplification of target polynucleotides. Non-limiting examples of features of oligonucleotide primers that are often used for design and optimization of primer pairs include primer length, GC content and Tm. Primers of a primer pair often comprise a similar Tm. In some embodiments a primer pair is optimized for amplification of a specific target polynucleotide.

All or a portion of a primer nucleic acid sequence (e.g., where a primer comprises naturally occurring, synthetic or modified nucleotides, and/or an identifier) may be substantially complementary to a target polynucleotide, or to an adaptor or linker of a target polynucleotide, in some embodiments. As referred to herein, "substantially complementary" with respect to sequences, refers to nucleotide sequences that will hybridize with each other. The stringency of the hybridization conditions can be altered to tolerate varying amounts of sequence mismatch. Included are target and primer hybridization sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complementary to a target polynucleotide sequence or portion thereof (e.g., linker or adaptor thereof) are also substantially identical to the complement of a target polynucleotide sequence or portion thereof. That is, sometimes primers are substantially identical to the anti-sense strand of a target polynucleotide. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer hybridization sequences and lengths thereof may affect hybridization of a primer to a target polynucleotide sequence, or portion thereof. Depending on the degree of mismatch between the primer and target polynucleotide, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989) or in chapter 11 of Sambrook et al., MOLECULAR CLONING: A LABORATORY MANUAL, second edition, Cold Spring Harbor Laboratory Press, New York (1990), both of which are incorporated by reference herein. Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target polynucleotide sequence that is complementary to the primer.

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primers. A primer, in certain embodiments, may contain a detectable molecule or entity (e.g., a fluorophore, radioisotope, colorimetric agent, particle, enzyme and the like).

A primer also may refer to a polynucleotide sequence that hybridizes to a subsequence of a target polynucleotide or another primer and facilitates the detection of a primer, a target polynucleotide or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

A primer often comprises one or more non-native elements. A non-native element can be any feature of an oligonucleotide primer that is made by the hand of a person. A non-native element associated with an oligonucleotide is often not associated with an oligonucleotide (e.g., DNA or RNA) in nature (e.g., not found in nature). In some embodiments, a non-native element comprises an identifier. Non-limiting examples of an identifier include sequence tags, labels (e.g., a radiolabel (e.g., an isotope), a metallic label, a fluorescent label, a fluorophore, a chemiluminescent label, an electrochemiluminescent label (e.g., Origen™), a phosphorescent label, a light scattering molecule, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody (e.g., a suitable binding agent) or part thereof, a linker, a member of a binding pair), an enzyme substrate (e.g., any moiety capable of participating in an enzyme reaction), a small molecule (e.g., biotin, avidin), a mass tag, quantum dots, nanoparticles, the like or combinations thereof), an amino acid, protein, carbohydrate, fatty acid, lipid, a modified nucleotide (e.g., a non-native nucleotide, e.g., a nucleotide comprising an additional element (e.g., an element of the periodic table of elements), molecule, or a secondary group not found associated with a nucleotide of a DNA or RNA oligonucleotide found in nature), the like, or a combination thereof. For embodiments in which the identifier is a detectable label, the identifier often is a molecule that emits a detectable signal having an intensity different than the intensity of a signal emitted by a naturally occurring nucleotide base under the same conditions (e.g., at the same emission wavelength for a fluorophore). In some embodiments a non-native element comprises or consists of a heterologous nucleotide sequence. A heterologous nucleotide sequence sometimes is synthetic and sometime originates from a type of organism (e.g., a non-human organism or non-mammalian organism) different than the organism from which a sample is derived from. A primer sometimes is a chimeric molecule comprising a hybridization sequence and a heterologous polynucleotide (e.g., heterologous to the hybridization sequence) made by the hand of a person or by a machine and not found in nature. A non-native element can be attached or associated with a primer by any suitable method. In some embodiments a non-native element is attached to a primer by a covalent bond. In some embodiments a non-native element is associated or bound to a primer by a non-covalent bond.

Adaptors

In some embodiments, an oligonucleotide comprises an adaptor sequence and/or complement thereof. Adaptor sequences often are useful for certain sequencing methods such as, for example, a sequencing-by-synthesis process described herein. Adaptors sometimes are referred to as sequencing adaptors or adaptor oligonucleotides. Adaptor sequences typically include one or more sites useful for attachment to a solid support (e.g., flow cell). In some embodiments adaptors comprises one or more binding and/or or capture agents. Adaptors also may include sequencing primer hybridization sites (i.e. sequences complementary to primers used in a sequencing reaction) and identifiers (e.g., indices) as described below. Adaptor sequences can be located at the 5' and/or 3' end of a nucleic acid and sometimes can be located within a larger nucleic acid sequence. Adaptors can be any length and any sequence, and may be selected based on standard methods in the art for adaptor design.

One or more adaptor sequences may be incorporated into a nucleic acid (e.g. oligonucleotide) by any method suitable for incorporating adaptor sequences into a nucleic acid. For example, PCR primers used for generating PCR amplicons (i.e., amplification products) may comprise adaptor sequences or complements thereof. Thus, PCR amplicons that comprise one or more adaptor sequences can be generated during an amplification process. In some instances, one or more adaptor sequences can be ligated to a nucleic acid by any ligation method suitable for attaching adaptor sequences to a nucleic acid. In some embodiments an adaptor, or portion thereof, is ligated to one or both ends of a nucleic acid fragment. Sometimes one or more adaptors are ligated to one or more unpaired nucleotides at the 5' and 3' end of a digested nucleic acid fragment. In some embodiments the sequence of an adaptor ligated to one end of a nucleic acid fragment is different that the sequence of an adaptor ligated at the other end of a nucleic acid fragment. In some embodiments a portion of an adaptor is complementary to a sticky end that remains after digestion of a nucleic acid by a restriction endonuclease. Adaptors used for ligation are often initially double stranded. Sometimes after ligation an unligated strand of an adaptor is removed, discarded or displaced leaving a single strand of the adaptor ligated to its target. Ligation processes may include, for example, blunt-end ligations, ligations that exploit 3' adenine (A) overhangs generated by Taq polymerase during an amplification process and ligate adaptors having 3' thymine (T) overhangs, and other "sticky-end" ligations. Ligation processes can be optimized such that adaptor sequences hybridize to each end of a nucleic acid and not to each other.

The term "modified variant" as used herein refers to a nucleic acid (e.g., a digested nucleic acid fragment) comprising any suitable modification or combination of modifications. Non-limiting examples of suitable modifications of nucleic acids include chemically modified residues, enzymatically modified residues, cleaved fragments of a nucleic acid, a nucleic acid comprising one or more ligated adaptors or linkers, a nucleic acid comprising an identifier, binding agent or capture agent, amplicons or extension products of a nucleic acid or a modified variant thereof, amplicons or extension products comprising a portion of a nucleic acid, amplicons or extension products comprising additional nucleotides and/or modified sequences (e.g., additions, deletions, and/or mutations), the like or combinations thereof.

Identifiers

In some embodiments, a nucleic acid (e.g., an oligonucleotide), protein or binding agent comprises an identifier. An identifier can be any feature that can identify a particular origin or aspect of a nucleic acid fragment (e.g., digested nucleic acid fragment), protein and/or binding agent. An identifier may be referred to herein as a tag, label, index, barcode, identification tag, sequence tag, index primer, and the like. An identifier can be a suitable detectable label or sequence tag incorporated into or attached to a nucleic acid (e.g., a polynucleotide) that allows detection, identification and/or quantitation of nucleic acids and/or nucleic acid targets that comprise the identifier. In some embodiments an identifier allows detection, identification and/or quantitation of nucleic acids and/or nucleic acid targets that are associated with an identifier. For example, in some embodiments a first nucleic acid (e.g., a target) is associated with a second nucleic acid comprising an identifier, the first nucleic acid can hybridized to the second nucleic acid and the first nucleic can be identified, quantified or characterized according to the identifier on the second nucleic acid. An identifier (e.g., a sample identifier) can identify the sample from which a particular fragment originated. For example, an identifier (e.g., a sample aliquot identifier) can identify the sample aliquot from which a particular fragment originated. In another example, an identifier (e.g., chromosome identifier) can identify the chromosome from which a particular fragment originated. A nucleic acid comprising an identifier is sometimes referred to herein as "labeled" (e.g., for a nucleic acid comprising a suitable label) or "tagged" (e.g., for a nucleic acid comprising a sequence tag). In some embodiments an identifier is distinguishable from another identifier. A "distinguishable identifier" as used herein means that a signal from one identifier can be distinguished and/or differentiated from the signal from another identifier. A "signal" as referred to herein can be a suitable detectable read-out and/or change thereof, non-limiting example of which include nucleotide sequence, mass, any detectable electromagnetic radiation (e.g., visible light (e.g., fluorescence, phosphorescence, chemiluminescence), infrared, ultraviolet, radiation (e.g., X-rays, gamma, beta or alpha), anions and ions (e.g., ionization, pH), the like or combinations thereof. In some embodiments a presence, absence or change in a signal can be detected and/or quantified. For example, a change in wavelength or a change in the intensity (e.g., a loss or a gain) of a wavelength of electromagnetic radiation may be a detectable and/or quantifiable read-out. In some embodiments of nucleic acid sequencing, a signal may comprise the detection and/or quantitation of a collection of signals.

Non-limiting examples of detectable labels include a radiolabel (e.g., an isotope), a metallic label, a fluorescent label, a fluorophore, a chemiluminescent label, an electrochemiluminescent label (e.g., Origen™), a phosphorescent label, a light scattering molecule, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody or part thereof, a linker, a member of a binding pair), an enzyme substrate (e.g., any moiety capable of participating in an enzyme reaction), a small molecule (e.g., biotin, avidin), a mass tag, quantum dots, nanoparticles, the like or combinations thereof.

An identifier may be a unique sequence of nucleotides (e.g., sequence-based identifiers) and/or a particular length of polynucleotide (e.g., length-based identifiers; size-based identifiers, a stuffer sequence). Identifiers for a collection of samples or plurality of chromosomes, for example, may each comprise a unique sequence of nucleotides (e.g., a sequence tag). As used herein, the term "sequence tag" or "tag" refers to any suitable sequence of nucleotides in a nucleic acid (e.g., a polynucleotide, a nucleic acid fragment). A sequence tag is sometimes a polynucleotide label. A sequence tag sometimes comprises a heterologous or artificial nucleotide sequence. A sequence tag may comprise a nucleic acid index, barcode and/or one or more nucleotide analogues. A nucleic acid sequence of a sequence tag is often known. In some embodiments a "sequence tag" is a known and/or identifiable sequence of nucleotides and/or nucleotide analogues. In some embodiments a "sequence tag" is a unique sequence. A unique sequence may be a nucleotide sequence (e.g., a "sequence tag"), or reverse complement thereof, that is not present in a sample of nucleic acids where the sequence tag is used. In some embodiments a unique sequence does not hybridize directly, under hybridization conditions, to sample nucleic acids or target polynucleotides.

In some embodiments a sequence tag is configured to hybridize to a target sequence (e.g., a sequence complementary to a sequence tag). In some embodiments a sequence tag is a probe. A probe is often a nucleic acid comprising one or more identifiers that is configured to hybridize to a specific sequence of a target polynucleotide. In some embodiments a sequence tag is a primer or portion thereof. In some embodiments a primer comprises a sequence tag. A primer is often a polynucleotide configured to bind in a sequence-specific manner to a target polynucleotide where the primer is configured for extension by a polymerase while using a portion of the target as a template. In some embodiments a target polynucleotide comprises a sequence tag.

A sequence tag sometimes is incorporated into a target polynucleotide species using a method known in the art. In some embodiments, a sequence tag is incorporated into a target polynucleotide species as part of library preparation. In some embodiments, a sequence tag is native to sample nucleic acid, is predetermined and/or pre-exists within a target polynucleotide. In some embodiments target specific oligonucleotides are designed to hybridize near or adjacent to a predetermined and/or pre-existing sequence tag. For example, a predetermined sequence tag may be a suitable four nucleotide sequence (e.g., ATGC) where the location of the sequence tag within a target polynucleotide (e.g., a chromosome) is known. In certain embodiments one or more target specific oligonucleotides are designed to hybridize to one or more locations on a target polynucleotide (e.g., a chromosome) adjacent to a predetermined and/or pre-existing sequence tag (e.g., ATGC). In such embodiments, the sequence tag (e.g., ATGC) is detected and/or quantified by using the target specific oligonucleotides as a primer and by sequencing the next four nucleotides (e.g., ATGC). In certain embodiments, complementary nucleotides (e.g., or nucleotide analogues, labeled nucleotides) are added by a suitable polymerase. In some embodiments, sequence tags may be detected directly or indirectly by a mass spectrometry method (e.g., using MALDI-TOF). In embodiments where a 3 nucleotide sequence tag is used, 9 potential target polynucleotides may be detected by a suitable DNA sequencing method. Likewise, a 4 nucleotide sequence tag may permit detection of 16 targets, a 5 nucleotide sequence tag may permit detection of 25 targets and so on.

A sequence tag identifier (e.g., sequence-based identifiers, length-based identifiers) may be of any length suitable to distinguish certain nucleic acid fragments from other nucleic acid fragments. In some embodiments, identifiers may be from about one to about 100 nucleotides in length. A sequence tag may comprise 1 or more, 2 or more, 3 or more, 4 or more, 5 or more, 6 or more, 7 or more, 8 or more, 9 or more, 10 or more, 20 or more, 30 or more or 50 or more contiguous nucleotides. In some embodiments a sequence tag comprises about 1 to about 50, about 2 to about 30, about 2 to about 20 or about 2 to about 10 contiguous nucleotides. For example, sequence tag identifiers independently may be about 1, 2, 3, 4, 5, 6, 7, 8, 9, 10, 11, 12, 13, 14, 15, 20, 30, 40, 50, 60, 70, 80, 90 or 100 nucleotides (e.g., contiguous nucleotides) in length. In some embodiments, an identifier contains a sequence of six nucleotides. In some instances, an identifier is part of an adaptor sequence for a sequencing process, such as, for example, a sequencing-by-synthesis process described in further detail herein. In some instances, an identifier may be a repeated sequence of a single nucleotide (e.g., poly-A, poly-T, poly-G, poly-C). Such sequence tag identifiers may be detected and distinguished from each other by any suitable method, for example, by using a suitable sequencing method, mass spectrometry, a nanopore technology, the like or combinations thereof.

An identifier may be directly attached (e.g., by a covalent bond, e.g., by a phosphodiester linkage) or indirectly attached and/or associated with a nucleic acid. Indirect attachment may comprise use of one or more binding pairs (e.g., antibody/antigen, biotin/avidin, the like). Indirect attachment may comprise hybridization (e.g., sequence-specific, non-covalent, base-pairing interactions). An identifier may be covalently bound or non-covalently bound to a nucleic acid. An identifier may be permanently or reversibly attached. In some embodiments an identifier is incorporated into or attached to a nucleic acid during a sequencing method (e.g., by a polymerase). In some embodiments, an identifier is located within or adjacent to an adaptor sequence. In some embodiments, an identifier is located within a portion of one or more primer hybridization sequences. A identifier may permit the detection, identification, quantitation and/or tracing of (i) polynucleotides to which the identifier is attached or incorporated (e.g., a labeled or tagged oligonucleotide, a labeled or tagged primer or extension product thereof), (ii) a polynucleotide to which a labeled or tagged polynucleotide hybridizes, and/or (iii) a polynucleotide to which a labeled or tagged polynucleotide is ligated to.

Any suitable type and/or number of identifiers can be used (e.g., for multiplexing). In some embodiments 1 or more, 2 or more, 3 or more, 4 or more, 5 or more, 6 or more, 7 or more, 8 or more, 9 or more, 10 or more, 20 or more, 30 or more or 50 or more different (e.g., distinguishable) identifiers are utilized in a method described herein (e.g., a nucleic acid detection, quantitation and/or sequencing method). In some embodiments, one, two, three or more identifies are associated with a nucleic acid or a subset of nucleic acids.

In some embodiments identifiers (e.g., sequence tags, labels) are chromosome-specific, locus specific, or gene specific. In some embodiments a locus-specific identifier is used to analyze (e.g., identify, quantify, or the like) a suitable locus (e.g., hypomethylated region, hypomethylated nucleotides, SNPs, the like or a combination thereof) or a collection of loci that are the same or different. For example, a locus-specific sequence tag sometimes is a sequence of nucleic acids that is configured to selectively identify one specific target locus. In some embodiments a locus-specific identifier is configured to selectively identify two or more specific target loci.

In some embodiments, an analysis comprises analyzing (e.g., detecting, counting, sequencing, quantifying, processing counts, the like or combinations thereof) one or more identifiers. In some embodiments, a detection process includes detecting an identifier and sometimes not detecting other features (e.g., sequences) of a nucleic acid. In some embodiments, a counting process includes counting each identifier. In some embodiments, an identifier is the only feature of a nucleic acid that is detected, analyzed and/or counted.

Binding/Capture Agents

In some embodiments a method described herein involves the use of a binding agent and/or a capture agent (e.g., a binding pair). The term "binding agent" as used herein refers to any molecule (e.g., nucleic acid, protein, carbohydrate, lipid, the like or combination thereof) that specifically binds another molecule (e.g., a target molecule (e.g., an antigen), a binding partner). An binding agent "specifically binds" to a corresponding binding partner where the binding agent often has less than about 30%, 20%, 10%, 5% or 1% cross-reactivity with another agent. A binding agent and it's corresponding binding partner are often referred to collectively herein as a binding pair. A binding agent often specifically binds a target molecule or binding partner with a dissociation constant (Kd) on the order of $10^{-6}$, $10^{-7}$, $10^{-8}$, $10^{-9}$, or less. In some embodiments a capture agent comprises a binding agent. In some embodiments a capture agent comprises a binding agent immobilized on a solid support or a binding agent configured to bind a solid support. In some embodiments a capture agent comprises a member of a binding pair immobilized on a solid support or a member of a binding pair configured to bind a solid support. In some embodiments a binding agent binds to a capture agent. In certain embodiments a binding agent is covalently linked to a capture agent or a member of a binding pair. For example, a binding agent may comprise an antibody covalently linked to biotin and a capture agent can comprise avidin immobilized on a solid support where the binding agent is configured to bind to the solid support. Non-limiting examples of binding pairs include, without limitation: avidin/biotin; an antibody/antigen; antibody/epitope; antibody/hapten; operator/repressor; nuclease/nucleotide; lectin/polysaccharide; steroid/steroid-binding protein; ligand/receptor; enzyme/substrate; Ig/protein A; Fc/protein A; Ig/protein G; Fc/protein G; Histidine polymers (e.g., a His tag) and heavy metals; a polynucleotide and its corresponding complement; the like or combinations thereof.

A binding agent and/or corresponding partners can be directly or indirectly coupled to a substrate or solid support. In some embodiments, a substrate or solid support is used to separate certain nucleic acid fragments (e.g., species of nucleic acid fragments, digested nucleic acid fragments) in a sample. Some methods involve binding partners where one partner is associated with an oligonucleotide and the other partner is associated with a solid support. In some instances, a single binding agent can be employed for the enrichment of certain nucleic acid fragments (e.g., digested nucleic acid fragments). In some instances, a combination of different binding agents may be employed for the enrichment of certain nucleic acid fragments (e.g., digested nucleic acid fragments). For example, at least 2, 3, 4, 5, 6, 7, 8, 9, 10, 11, 12, 13, 14, 15, 16, 17, 18, 19, 20, 25, 50, 75 or 100 different binding agents may be used for the enrichment of certain nucleic acid fragments (e.g., digested nucleic acid fragments).

Methods of separation are known in the art. Any suitable method of separation can be used. Non-limiting examples of separation methods include adsorption, centrifugation, chromatography (e.g., affinity chromatography, flow cytometry, various fluid separation methods (e.g., chip based separation), molecular size exclusion, the like or combinations thereof), crystallization, decantation, drying, electrophoresis, flotation, flocculation, filtration, dialysis, magnetic separation, precipitation (e.g., nucleic acid precipitation, immuno-precipitation, solid phase or solid support precipitation, or the like), sedimentation, gravity separation, sieving, the like or combinations thereof. A sample is often subjected to a separation process resulting in one or more separation products. In some embodiments a separation product comprises a minority nucleic acid species. In some embodiments a separation process generates a separation product enriched for minority nucleic acid species (e.g., hypomethylated nucleic acid, fetal nucleic acid, target polynucleotides, tumor nucleic acid). In some embodiments two or more nucleic acid species (e.g., nucleic acid species fragments) are separated by an enrichment process. Non-limiting examples of a separation product comprises an isolated product, a purified or partially purified product, a fractionated product (e.g., an elution fraction, a flow though fraction), an immobilized product, an enriched product, the like or a combination thereof.

In some embodiments, a binding/capture agent is an antibody or a portion thereof, naturally occurring or synthetic (e.g., genetically engineered). Antibodies can be immunoglobulin molecules or immunologically active portions (e.g., binding fragments) of immunoglobulin molecules (e.g., molecules that contain an antigen binding site that specifically binds an antigen). Antibodies, portions thereof (e.g., binding portions), mutants or chimeras thereof can be expressed and/or isolated from any suitable biological organism or source. Non-limiting examples of binding/capture agents include monoclonal antibodies, polyclonal antibodies, Fabs, Fab', single chain antibodies, synthetic antibodies, DNA, RNA, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, peptides, polypeptides, biotin, streptavidin, or combinations thereof. A variety of antibodies and antibody fragments can be generated for use as a specific binding agent. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. In some embodiments a binding/capture agent used herein is an antibody, or fragment thereof that specifically binds 5-methylcytosine. Polyclonal antibodies, monoclonal antibodies, fragments thereof, and variants thereof that bind specific antigens are commercially available, and methods for generating such antibodies are known.

A binding agent also can be a polypeptide or peptide. A polypeptide may include a sequence of amino acids, amino acid analogs, or peptidomimetics, typically linked by peptide bonds. The polypeptides may be naturally occurring, processed forms of naturally occurring polypeptides (such as by enzymatic digestion), chemically synthesized, or recombinant expressed. The polypeptides for use in a method herein may be chemically synthesized using standard techniques. Polypeptides may comprise D-amino acids (which are resistant to L-amino acid-specific proteases), a combination of D- and L-amino acids, beta amino acids, or various other designer or non-naturally occurring amino acids (e.g., beta-methyl amino acids, C alpha-methyl amino acids, N alpha-methyl amino acids, and the like) to convey special properties. Synthetic amino acids may include ornithine for lysine, and norleucine for leucine or isoleucine. In some instances, polypeptides can have peptidomimetic bonds, such as ester bonds, to prepare polypeptides with novel properties. Polypeptides also may include peptoids (N-substituted glycines), in which the side chains are appended to nitrogen atoms along the molecule's backbone, rather than to the alpha-carbons, as in amino acids.

In some embodiments a binding agent is a methyl-specific binding agent. In some embodiments a methyl-specific binding agent selectively and/or specifically (e.g., with high affinity) binds a methylated nucleotide (e.g., 5-methyl cytosine). In some embodiments a methyl-specific binding agent selectively and/or specifically binds a methylation site or locus that is unmethylated (e.g., unmethylated cytosine, unmethylated CpG). In some embodiments a methyl-specific binding agent is an antibody or portion thereof (e.g., a binding fragment thereof). In some embodiments a methyl-specific binding agent comprises a portion of an antibody (e.g., an Fc portion of an immunoglobulin). A methyl-specific binding agent can be an antibody that specifically binds a methylation site or locus that is methylated. A methyl-specific binding agent can be an antibody that specifically binds a hypermethylated locus. Non-limiting examples of antibodies that specifically bind methylated nucleic acid, hypermethylated nucleic acid and/or hypermethylated loci include anti-5-methylcytosine antibody, clone 33D3; anti-5-hydroxymethylcytosine (5hmC) antibody, clone HMC-MA01; anti-5-hydroxymethylcytosine antibody, clone AB3/63.3; anti-5-hydroxymethylcytosine (5hmC) antibody, clone HMC 31, the like or a combination thereof. In certain embodiments, a methyl-specific binding agent can be an antibody that specifically binds a methylation site that is not methylated (e.g., an unmethylated CpG). Often, a methyl-specific binding agent that specifically binds a methylation site that is unmethylated does not substantially bind to a methylation site that is methylated. In some embodiments a methyl-specific binding agent is not an antibody or binding fragment thereof. In some embodiments a methyl-specific binding agent comprises a methyl-specific binding protein (e.g., a methyl-binding domain protein) or a portion thereof. Any suitable methyl-specific binding protein, or portion thereof, can be used for a method described herein. Non-limiting examples of methyl-specific binding proteins include methyl CpG Binding Protein 2 (Rett Syndrome)(MECP2), Methyl-CpG-binding domain protein 1 (MBD1), Methyl-CpG-binding domain protein 2 (MBD2), Methyl-CpG-binding domain protein 4 (MBD4) and Methyl-CpG-binding domain proteins 5-12. Methyl-CpG-binding domain proteins that specifically bind methylated CpG can be isolated, purified or cloned and expressed from a suitable plant, animal, insect, yeast or prokaryote.

In some embodiments a methyl-specific binding agent is an antibody that specifically binds a methylated histone or methylated histone subunit. Antibodies that specifically bind methylated histone proteins, where the histone is associated with a nucleic acid fragment, can be used to enrich for certain nucleic acid species. For example, as shown in Example 2 methylation sites in placenta that are associated with H3K9me3 comprise an intermediate to low amount of methylation (e.g., <75%, <80% methylated) compared to ccf DNA in non-pregnant females. In some embodiments methyl-specific binding agents that specifically bind methylated histones can be used to immunoprecipitate and enrich hypomethylated nucleic acid from a sample (e.g., sample nucleic acid from a pregnant female). For example, methyl-specific binding agents that specifically bind H3K9me3 can be used to immunoprecipitate and enrich hypomethylated nucleic acid from a sample (e.g., sample nucleic acid from a pregnant female). In some embodiments methyl-specific binding agents that specifically bind H3K9me3 can be used to immunoprecipitate and enrich for fetal nucleic acid.

Solid Support

In some embodiments, a binding/capture agent can be linked directly or indirectly to a solid support (e.g., a substrate). In some embodiments, nucleic acid fragments are associated with a solid support, such as the solid supports described below, by one or more binding agents, such as the binding agents described herein. A solid support or substrate can be any physically separable solid to which a nucleic acid, protein, carbohydrate or binding agent can be directly or indirectly attached.

A solid support can be any shape (e.g., flat, concave, convex, a channel, a groove, a cylinder, a tube, a sphere (e.g., a bead)) or size, and can exist as a separate entity or as an integral part of an apparatus or machine (e.g., a collection of beads (e.g., beads in a column), membrane, microwell, matrix, cuvette, plate, vessel, plate, centrifuge tube, slide, chip, wafer, flow cell, the like, or combinations thereof. In some embodiments a solid support comprises a suitable surface, for example as provided by a suitable substrate (e.g., a microarray substrate, a chip). In some embodiments a solid support is a flow cell configured for use in a DNA sequencer. In some embodiments a solid support is configured for a massively parallel sequencing (MPS) method or configured for use in a massively parallel sequencing (MPS) apparatus, machine or device.

A solid support can comprise a suitable material, non-limiting examples of which include glass, borosilicate glass, silica, quartz, fused quartz, mica, silicon (Si), carbon (e.g., diamond) modified silicon, a suitable metal (e.g., gold, titanium, silver, brass, aluminum and the like), steel (e.g., a steel alloy), ceramic, germanium, graphite, plastic, dextran, semiconductor fabrics, high refractive index dielectrics, crystals, a suitable polymer such as (poly)tetrafluoroethylene, (poly)vinylidenedifluoride, polymethacrylate (PMA), polymethyl methacrylate (PMMA), polydimethylsiloxane (PDMS), polystyrene, polycarbonate, polyacrylamide, nylon, latex, cellulose (e.g., activated cellulose), the like or combinations thereof. In some embodiments a solid support comprises particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other suitable chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidene difluoride (PVDF), and the like), polysaccharides, nylon or nitrocellulose, resins, silica or silica-based materials including silicon, silica gel, and modified silicon, Sephadex®, Sepharose®, agarose, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, other fibrous or stranded polymers, the like or combinations thereof. In some embodiments a solid support is a collection of particles. In some instances, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, the solid phase can be a collection of particles. In certain embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$).

In some embodiments a solid support is configured to immobilize a nucleic acid, protein, carbohydrate, a nucleic acid library, a reagent, binding agent, analyte, the like, combination thereof or portion thereof. In some embodiments a solid support comprises a plurality of molecules (e.g., proteins, nucleic acids, functional groups, binding agents, one or members of a binding pair, reactive chemical moieties, the like or combinations thereof). In certain embodiments a solid support comprises a plurality of oligonucleotides (e.g., primers) configured to capture a nucleic acid library or part thereof. In certain embodiments oligonucleotides are attached to a solid support at their 5' ends or at their 3'ends. In some embodiments attachment of an oligonucleotide to a solid support is reversible (e.g., by cleavage with a nuclease or restriction endonuclease). In some embodiments, a plurality of primers are attached or immobilized to a support at their 5' ends. In some embodiments, the 5' end of one or more primers immobilized on a support comprise a single stranded region of about 5 nucleotides to about 30 nucleotides.

In some embodiments a solid support comprises discrete locations (e.g., addresses, mapped locations) where target polynucleotide species are disposed. For example, in some embodiments a solid support may comprises target-specific oligonucleotides immobilized at discrete locations where the target-specific oligonucleotides are configured to capture and/or amplify specific target sequences (e.g., target polynucleotides). In some embodiments target polynucleotides may be amplified at discrete locations on a solid support and the location of the specific amplicons is known (e.g., mapped, e.g., identifiable with a suitable imaging device). In some embodiments amplifying target polynucleotides on a solid support generates cluster of amplified target polynucleotide species at discrete locations on the solid phase.

In some embodiments a nucleic acid library, or portion thereof is immobilized to a suitable solid support. The term "immobilized" as used herein means direct or indirect attachment to a solid support. In some embodiments the term "capture" as used herein refers to immobilization of a nucleic acid, protein, carbohydrate, analyte or reagent. Immobilization can be covalent or non-covalent. Immobilization can be permanent or reversible. In some embodiments immobilization comprises hybridization of complementary nucleic acid sequences. In some embodiments a plurality of oligonucleotides is complementary to one or more universal sequences or sequence tags integrated into a library of nucleic acids. In some embodiments a plurality of nucleic acids comprises specific nucleic acid sequences configured to hybridize, immobilize and/or capture nucleic acids comprising one or more specific loci (e.g., a hyper or hypo methylated locus). In some embodiments nucleic acids are immobilized by use of one or more binding agents (e.g., a binding protein or antibody) that bind specifically to a nucleic acid sequence, protein, carbohydrate, reagent, analyte or portion thereof. For example, a binding agent can specifically bind to and/or immobilize (e.g., capture) polynucleotides comprising specific nucleic acid sequences. In some embodiments a binding agent can specifically bind to and/or immobilize (e.g., capture) polynucleotides comprising specific nucleic acid sequences (e.g., CpG) with a specific methylation status (e.g., a methylated, unmethylated or partially methylated sequence).

Methylated Nucleotides, Sites and Loci

A methylated nucleotide or a methylated nucleotide base refers to the presence of a methyl moiety (e.g., a methyl group) on a nucleotide base, where the methyl moiety is not normally present in the nucleotide base. For example, cytosine can comprise a methyl moiety at position 5 of its pyrimidine ring and can be referred to herein as methylated or as methyl cytosine. Cytosine, in the absence of a 5-methyl group is not a methylated nucleotide and can be referred to herein as unmethylated. In another example, thymine contains a methyl moiety at position 5 of its pyrimidine ring, however, for purposes herein, thymine is not considered a methylated nucleotide. A "methylation site" as used herein refers to a location of a nucleotide (e.g., a cytosine) within a nucleic acid where the nucleotide is methylated or has the possibility of being methylated. For example the nucleic acid sequence CpG is a methylation site where the cytosine may or may not be methylated. Cytosine methylation may also occur at the methylation sites CHG and/or CHH (e.g., where H=A, T or C). Where the particular methylated or unmethylated nucleotide is not specified, "methylation status" (e.g., unmethylated, methylated, hypomethylated, hypermethylated) often refers to cytosine methylation. A CpG island refers to a genomic region that comprises a high frequency of CpG methylation sites that may or may not be methylated.

The term "methylation profile" "methylation state" or "methylation status," are used interchangeably herein and refer to the state of methylation (e.g., methylated, unmethylated, hypermethylated, hypomethylated; percent methylated, or the like) of one or more methylation sites on a polynucleotide (e.g., a nucleic acid, a target polynucleotide), a nucleic acid species or subset, or a genetic locus (e.g., a defined region on a chromosome). A methylation status can refer to a frequency of methylation, relative methylation, differential methylation, absolute methylation, a ratio or percentage of methylation, the like or a combination thereof. A genetic locus comprising one or more methylation sites is sometimes referred to herein as a methylation locus or loci. The term "methylation profile" or "methylation status" refers to the amount or relative amount of methylated or unmethylated methylation sites on a polynucleotide, a nucleic acid species or subset, or locus. A "methylation profile" or "methylation status" sometimes refers to a relative state of methylation for a polynucleotide, a nucleic acid species or subset, or locus between two nucleic acid subsets or samples. For example, a locus can be relatively less methylated in fetal than in maternal nucleic acid. The term "amount" as used herein can refer to a mean, average, median, mode or absolute amount (e.g., quantity, number, count, total, aggregate, sum, quota, group, size, mass, weight, volume, bulk, lot, quantum, moles, concentration, percentage, or the like).

A methylation status of a methylation site can be referred to as unmethylated, methylated, hypomethylated or hypermethylated, for example. Methylation status can be determined by any suitable method. A methylation site comprising a methylated nucleotide is referred to herein as methylated. A methylation site comprising an unmethylated nucleotide is referred to herein as unmethylated. Methylation status of a methylation site is often provided as a percent or ratio. In some embodiments a methylation status of a first methylation site in a sample is a ratio of the quantity of first methylation sites that are methylated to the quantity of first methylation sites that are unmethylated. In some embodiments a methylation status of a first methylation site in a sample is a percentage of the quantity of first methylation sites that are methylated to the quantity of total methylation sites present in a sample or population of nucleic acid. For example, for a given sample, the methylation status for a first methylation site can be 0.3 (e.g., 30%) indicating that 30% of the nucleic acid fragments containing the first methylation site are methylated at the first methylation site, and 70% of the nucleic acids in the sample containing the first site are not methylated at the first methylation site. A hypomethylated site, for example, often refers to a methylation site present on a plurality of nucleic acid fragments in a sample, where the methylation site is methylated on less than 60% (e.g., 0.60), less than 50% (e.g., 0.50), less than 40%, less than 30%, less than 20%, less than 15%, less than 10%, less than 5% or less than 3% of the nucleic acid fragments in the sample that comprise the methylation site. A hypermethylated site, for example, often refers to a methylation site present on a plurality of nucleic acids fragments in a sample, where the methylation site is methylated in greater than 95%, greater than 90%, greater than 85%, greater than 80%, greater than 75%, greater than 70%, greater than 60% or greater than 50% of the nucleic acids fragments in the sample that comprise the methylation site.

In some embodiments the methylation status of a locus is determined. A locus (e.g., a locus targeted for analysis, a methylation locus, a differentially methylated locus) can be any suitable length. A locus often comprises an average, mean, median or absolute length of about 5,000 bp or more, 10,000 bp or more, 15,000 bp or more, 20,000 bp or more, 30,000 bp or more, 40,000 bp or more, 50,000 bp or more, 75,000 bp or more, or 100,000 bp or more. In some embodiments a locus is about 20,000 to about 100,000 bp, or about 20,000 to about 50,000 bp in length. In some embodiments a locus comprises a minimum amount of CpG sites. In some embodiments a locus (e.g., DMR) comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 CpG methylation sites.

The methylation status of a methylation locus (e.g. locus, loci, polynucleotide, region comprising one or more methylation sites) can be referred to as unmethylated, methylated, hypomethylated (e.g., less methylated), hypermethylated (e.g., more methylated), or differentially methylated, for example. A methylation locus comprising one or more methylated nucleotides can be referred to herein as methylated. For example methylated nucleic acids often comprise one or more methylated nucleotides. A methylation locus that does not contain any methylated nucleotides is referred to herein as unmethylated. The methylation status of a locus can be determined by any suitable method. In some embodiments the methylation status of a methylation locus is determined as an average, mean or median of the methylation status of all methylation sites within a locus for a given sample or population of nucleic acid. For example, for a given sample, the methylation status for a first site in a locus can be 0.3 (e.g., 30% of the nucleic acid fragments containing the site are methylated), a second site within the locus can be 0.4 (e.g., 40%), a third site within the locus can be 0.45 (45%) and the mean methylation status of the locus can be calculated as the mean of the methylation status of all sites within the locus (e.g., in the foregoing example, the mean methylation status of the locus is 0.4 or 40%). A hypomethylated nucleic acid or locus often refers to a locus comprising a mean methylation status of less than about 0.75, less than about 0.7, less than about 0.65, less than about 0.6, less than about 0.5, less than about 0.4, less than about 0.3, less than about 0.2, less than about 0.15, less than about 0.10, less than about 0.05 or less than about 0.03 for a given sample. A hypermethylated nucleic acid or locus often refers to a locus comprising a mean methylation status of greater than about 0.95, greater than about 0.90, greater than about 0.85, greater than about 0.80, greater than about 0.75, greater than about 0.70, greater than about 0.65, greater than about 0.60 or greater than about 0.50 for a given sample.

In some embodiments a methylation site, polynucleotide (e.g., target polynucleotide) or locus (e.g., region) is differentially methylated between two or more samples (e.g., sources) or subsets of nucleic acids. A differentially methylated site or locus (e.g., a differentially methylated region (e.g., DMR)), sometimes refers to a difference in the methylation status of a methylation site, region or locus between two or more samples or subsets of nucleic acids (e.g., fetal derived ccf DNA verse maternal derived ccf DNA). In some embodiments a methylation status of a locus is determined as an average, mean or median of the methylation status of a locus obtained from multiple test subjects (e.g., multiple samples) derived from the same source (e.g., enriched fetal nucleic acid). For example a methylation status for a methylation locus can be determined as an average, mean or median of the methylation status of a locus of a first sample, second sample and third sample where all three samples were derived from a different test subject and all three samples were derived from the same source (e.g., enriched fetal nucleic acid). In the foregoing example the presence or absence of a differentially methylated locus can be determined by comparing the methylation status of the first methylation locus derived from multiple samples of a first source (e.g., multiple samples of enriched fetal nucleic acid) to the methylation status of the same methylation locus derived from multiple samples of a second source (e.g., maternal nucleic acid).

In some embodiments a differentially methylated locus comprises a difference in methylation status between two samples or subsets of nucleic acids of about 0.1% or more, about 0.5% or more, 1% or more, about 5% or more, about 7% or more, about 10% or more, about 15% or more, about 20% or more, about 30% or more, about 40% or more, about 50% or more, or about 60% or more. For example a locus in fetal nucleic acid may comprise a methylation status of about 85%, the same locus in maternal nucleic acid may comprise a methylation status of about 90% and the difference in methylation status is about 5%. In some embodiments differentially methylated refers to a statistical difference (e.g., a statistically significant difference) in methylation status of a methylation site or locus between two or more samples or subsets of nucleic acids. In some embodiments methylation sites or loci are determined as differentially methylated or not differentially methylated by a t-test (e.g., a t statistic) or by a suitable statistical method.

In some embodiments analysis (e.g., an analysis of digested nucleic acid fragments, an analysis of enriched fetal nucleic acid) comprises determining the presence, absence or amount of a polynucleotide (e.g., a target polynucleotide) in a locus relatively less methylated in fetal nucleic acid than in maternal nucleic acid. The term "a polynucleotide in a locus" means a polynucleotide comprising a sequence that is present within a particular locus. A locus relatively less methylated in fetal nucleic acid than in maternal nucleic acid can, in some embodiments, refer to a locus that is less methylated in fetal nucleic acid relative to maternal nucleic acid by a difference in methylation status of about 0.1% or more, about 0.5% or more, about 1% or more, about 2% or more, about 3% or more, about 4% or more, about 5% or more, about 6% or more, about 7% or more, about 8% or more, about 9% or more, about 10% or more, about 15% or more, about 20% or more, about 30% or more, about 40% or more, about 50% or more, or about 60% or more. In some embodiments a locus relatively less methylated in fetal nucleic acid than in maternal nucleic acid can refers to a locus that is about 75% or less, about 70% or less, about 65% or less, about 60% or less, about 55% or less, about 50% or less, about 40% or less, about 30% or less, about 20% or less, or about 10% or less methylated in fetal nucleic acid than in maternal nucleic acid. In some embodiments a locus relatively less methylated in fetal nucleic acid than in maternal nucleic acid can refers to a locus that is about 55% or more, about 60% or more, about 65% or more, about 70% or more, about 75% or more, about 80% or more, about 85% or more or about 90% or more methylated in maternal nucleic acid relative to fetal nucleic acid. In some embodiments a locus relatively less methylated in fetal nucleic acid than in maternal nucleic acid is about 60% or more methylated in maternal nucleic acid relative to fetal nucleic acid and about 60% or less methylated in fetal nucleic acid relative to maternal nucleic acid.

In some embodiments the terms "hypomethylated" and "hypermethylated" are relative terms and compare the methylation status of a methylation site, region or locus of different samples, samples obtained at different time points or subsets of nucleic acids derived from different sources (e.g., different cells, different tissues (e.g., fetal vs. maternal, tumor vs. non-tumor, placenta vs. maternal liver)). The term "hypomethylated" is sometimes a relative term and refers to a first subpopulation or subset of nucleic acids that is relatively less methylated when compared to a second subpopulation or subset of nucleic acids. A locus that is hypomethylated in a first subset of nucleic acid relative to a second subset of nucleic acid is, in some embodiments, a locus that is relatively less methylated in the first subset relative to the second subset of nucleic acid. In some embodiments a locus that is hypomethylated in a first subset of nucleic acid relative to a second subset of nucleic acid is relatively less methylated in the first subset compared to the second subset and comprises a difference in methylation status between the first and second subsets of about 0.1% or more, about 0.5% or more, about 1% or more, about 5% or more, about 7% or more, about 10% or more, about 15% or more, about 20% or more, about 30% or more, about 40% or more, about 50% or more, about 60% or more, about 70% or more, about 80% or more, or about 90% or more.

In some embodiments a differentially methylated site or locus of a first sample or subset of nucleic acid is hypermethylated relative to a second sample or subset of nucleic acid. The term "hypermethylated" is sometimes a relative term and refers to a first subpopulation or subset of nucleic acids that is relatively more methylated when compared to a second subpopulation or subset of nucleic acids. A locus that is hypermethylated in a first subset of nucleic acid relative to a second subset of nucleic acid is, in some embodiments, a locus that is relatively more methylated in the first subset relative to the second subset of nucleic acid. In some embodiments a locus that is hypermethylated in a first subset of nucleic acid relative to a second subset of nucleic acid is relatively more methylated in the first subset compared to the second subset and comprises a difference in methylation status between the first and second subsets of about 0.1% or more, about 0.5% or more, about 1% or more, about 5% or more, about 7% or more, about 10% or more, about 15% or more, about 20% or more, about 30% or more, about 40% or more, about 50% or more, about 60% or more, about 70% or more, about 80% or more, or about 90% or more.

Examples of methylation sites and loci that are hypomethylated in placenta relative to nucleic acid of a non-pregnant female (e.g., buffy coats or ccf DNA from a non-pregnant female) are provided in TABLE 2AB, TABLE 2CB, TABLE 3 (e.g., SEQ ID NOs: 1-84) and/or TABLE 4. Methylation sites and loci shown in TABLE 2AB, TABLE 2CB, TABLE 3 (e.g., SEQ ID NOs: 1-84) and/or TABLE 4 are expected to be hypomethylated in fetal nucleic acid (e.g., ccf DNA derived from fetal tissue) relative to maternal nucleic acid (e.g., ccf DNA derived from maternal tissue) in a sample of nucleic acid obtained from a pregnant female subject. Examples of methylation sites and loci that are hypermethylated in placenta relative to nucleic acid of a non-pregnant female (e.g., buffy coats or ccf DNA from a non-pregnant female) are provided in TABLE 2AA, 2B, 2CA and TABLE 5. Information in TABLE 5 is based on the human reference sequence (UCSC Ver. hg19, NCBI Build GRCh37), which was produced by the International Human Genome Sequencing Consortium. Methylation sites and loci shown in TABLE 2AA, 2B, 2CA and TABLE 5 are expected to be hypermethylated in fetal nucleic acid (e.g., ccf DNA derived from fetal tissue) relative to maternal nucleic acid (e.g., ccf DNA derived from maternal tissue) in a sample of nucleic acid obtained from a pregnant female subject.

In some embodiments an analysis comprises determining the presence or absence of a polynucleotide (e.g., a nucleic acid fragment, a target polynucleotide) in one or more loci relatively less methylated in fetal nucleic acid than in maternal nucleic acid. In some embodiments an analysis comprises quantifying (e.g., determining an amount of) a polynucleotide in one or more loci relatively less methylated in fetal nucleic acid than in maternal nucleic acid. In some embodiments an analysis comprises determining the presence or absence of a polynucleotide (e.g., a nucleic acid fragment) in one or more loci relatively less methylated in fetal nucleic acid than in maternal nucleic acid where the loci are chosen from the loci in TABLE 2AB, TABLE 2CB, TABLE 3 (e.g., SEQ ID NOs: 1-84), TABLE 4 or a combination thereof. In some embodiments an analysis comprises determining the presence or absence of a polynucleotide (e.g., a nucleic acid fragment) in one or more loci relatively less methylated in fetal nucleic acid than in maternal nucleic acid where the loci are chosen from a suitable chromosome. For example, the one or more loci relatively less methylated in fetal nucleic acid than in maternal nucleic acid can be chosen from chromosome 13, chromosome 18 and/or chromosome 21. In some embodiments the one or more loci relatively less methylated in fetal nucleic acid than in maternal nucleic acid are chosen from one or more suitable chromosomes in TABLE 4 (e.g., one or more loci in chromosome 13, chromosome 18 and/or chromosome 21). In some embodiments differentially methylated regions or loci are determined according to a suitable statistical test that compares the methylation status of a region or locus between two or more sample or sources. In some embodiments a locus is a differentially methylated region (e.g., DMR) when the methylation status of the locus is statistically different (e.g., a significant statistical difference) between two different samples or sources (e.g., maternal vs fetal). A statistical difference (e.g., a significant difference) can be determined by any suitable statistical method. Non-limiting examples of suitable statistical tests or methods that can compare two or more samples and/or determine a statistical difference include a T-test (e.g., mean, median, or absolute t-statistic), a student's T-test, a Z-test, an F-test, Chi-squared test, Wilcox test, ANOVA, MANOVA, MANCOVA, logistic regression, maximum likelihood, p-values, the like, combinations or variations thereof. In some embodiments one or more loci relatively less methylated in a minority nucleic acid species (e.g., fetal nucleic acid) than in a majority nucleic acid species (e.g., maternal nucleic acid) are chosen according to a suitable statistical test. In some embodiments one or more loci relatively less methylated in a minority nucleic acid species than in a majority nucleic acid species are chosen according to a suitable t-statistic (e.g., a mean, median or average t-statistic).

In certain embodiments a locus in a first sample is differentially methylated compared to the same locus in a second sample when the methylation status of the locus in the first sample is significantly different from the methylation status of the same locus in the second sample. In some embodiments a differentially methylated locus is a DMR (e.g., a locus relatively less methylated in a minority nucleic acid species than in a majority nucleic acid species (e.g., a locus relatively less methylated in fetal nucleic acid than in maternal nucleic acid)). In some embodiments a DMR comprises a t-statistic less than about −1, less than about −2, less than about −3, less than about −4, less than about −5, less than about −6, less than about −7, less than about −8, less than about −9, less than about −10, less than about −11, less than about −12, less than about −13, less than about −14, less than about −14.10, less than about −14.90, less than about −15, or less than about −16. In some embodiments a DMR comprises a t-statistic (e.g., a median t-statistic (e.g., median.tstat)) between about −18 and −2, between about −18 and −3, between about −18 and −4, between about −18 and −5, between about −18 and −6, between about −18 and −7, between about −18 and −8, between about −18 and −9, between about −18 and −10, between about −18 and −11, between about −18 and −12, between about −18 and −13, between about −18 and −14 or between about −17 and about −14. In some embodiments a DMR comprises a t-statistic (e.g., a median t-statistic (e.g., median.tstat)) between about −18.0 and −14.90 or between about −18.0 and −14.10. A locus that is differentially methylated can be determined according to a comparison between two different samples or sources by any suitable method that generates a statistical value that is comparable to, or that can be converted to a t-statistic (e.g., a p-value, Z-score, or the like). A statistical value that can be converted to and/or compared to a certain t-statistic herein, and is determined equal to, or within 5%, 10% or 20% of the value of a certain t-statistic herein, is considered the same as (e.g., equivalent to) the certain t-statistic herein to which it was compared.

In some embodiments a DMR comprises one or more loci relatively less methylated in fetal nucleic acid than in maternal nucleic acid. In some embodiments one or more loci relatively less methylated in fetal nucleic acid than in maternal nucleic acid are chosen from TABLE 4 where the one or more loci comprise a median t-statistic (e.g., median.tstat) less than about −2, less than about −3, less than about −4, less than about −5, less than about −6, less than about −7, less than about −8, less than about −9, less than about −10, less than about −11, less than about −12, less than about −13, less than about −14, less than about −14.10, less than about −14.90, less than about −15, or less than about −16. In some embodiments the one or more loci relatively less methylated in fetal nucleic acid than in maternal nucleic acid are chosen from TABLE 4 where the one or more loci comprise a median t-statistic (e.g., median.tstat) between about −18 and −2, between about −18 and −3, between about −18 and −4, between about −18 and −5, between about −18 and −6, between about −18 and −7, between about −18 and −8, between about −18 and −9, between about −18 and −10, between about −18 and −11, between about −18 and −12, between about −18 and −13, between about −18 and −14 or between about −17 and about −14. In some embodiments the one or more loci relatively less methylated in fetal nucleic acid than in maternal nucleic acid are chosen from TABLE 4 where the one or more loci comprise a median t-statistic (e.g., median.tstat) between about −18.0 and −14.90 or between about −18.0 and −14.10.

In some embodiments a DMR comprises one or more loci relatively more methylated in fetal nucleic acid than in maternal nucleic acid. In some embodiments one or more loci relatively more methylated in fetal nucleic acid than in maternal nucleic acid are chosen from TABLE 5 where the one or more loci comprise a median t-statistic (e.g., median.tstat) less than about −2, less than about −3, less than about −4, less than about −5, less than about −6, less than about −7, less than about −8, less than about −9, less than about −10, less than about −11, less than about −12, less than about −13, less than about −14, less than about −14.10, less than about −14.90, less than about −15, or less than about −16. In some embodiments the one or more loci relatively more methylated in fetal nucleic acid than in maternal nucleic acid are chosen from TABLE 5 where the one or more loci comprise a median t-statistic (e.g., median.tstat) between about −18 and −2, between about −18 and −3, between about −18 and −4, between about −18 and −5, between about −18 and −6, between about −18 and −7, between about −18 and −8, between about −18 and −9, between about −18 and −10, between about −18 and −11, between about −18 and −12, between about −18 and −13, between about −18 and −14 or between about −17 and about −14. In some embodiments the one or more loci relatively more methylated in fetal nucleic acid than in maternal nucleic acid are chosen from TABLE 5 where the one or more loci comprise a median t-statistic (e.g., median.tstat) between about −18.0 and −14.90 or between about −18.0 and −14.10.

Large contiguous genomic regions (e.g., locus) that are differentially methylated (e.g., hypomethylated) in fetal nucleic acid relative to maternal nucleic acid are sometimes associated with gene deserts. In some embodiments a DMR comprises a low gene density. In some embodiments a hypomethylated locus comprises a low gene density. In some embodiments a locus that is hypomethylated in fetal nucleic acid comprises a low gene density. In some embodiments a locus comprising a low gene density comprises a gene density of about 10 genes or less, 9 genes or less, 8 genes or less, 7 genes or less, 6 genes or less, 5 genes or less, 4 genes or less, 3 genes or less, 2 genes or less, 1 genes or less or 0 genes per 50,000 contiguous base pairs. The gene densities provided herein can be scaled according to the size of a particular locus. For example, sometimes a locus comprising a low gene density comprises a gene density of about 0.02 genes/kb or less which is equivalent to about 0.2 genes/10 kb or less or about 2 genes/100 kb or less.

In certain embodiments a DMR or locus (e.g., a differentially methylated locus, a selected locus (e.g., a locus selected for analysis)) is selected and/or analyzed according to a CpG density of the region or locus. In some embodiments a DMR or locus comprises a relatively low CpG density. In some embodiments a hypomethylated locus comprises a relatively low CpG density. In some embodiments a locus that is hypomethylated in fetal nucleic acid comprises a relatively low CpG density. A CpG density can be an absolute, average, mean, median or mode CpG density. In some embodiments a locus comprising a relatively low CpG density comprises a CpG density of about 1000, 950, 900, 850, 800, 750, 700, 650, 600, 550, 500, 450, 400, 350, 300, 250, 200, or 150 CpG methylation sites, or less, per 50,000 base pairs (i.e., which base pairs are contiguous nucleotides in genomic nucleic acid). In some embodiments a locus comprising a relatively low CpG density comprises a CpG density of about 200, 190, 180, 170, 160, 150, 140, 130, 120, 110, 100, 90, 80, 70, 60, 50, 40, or 30 CpG methylation sites or less per 10,000 base pairs (i.e., which base pairs are contiguous nucleotides in genomic nucleic acid). In some embodiments a locus comprising a relatively low CpG density comprises a CpG density of about 20, 19, 18, 17, 16, 15, 14, 13, 12, 11, 10, 9, 8, 7, 6, 5, 4, or 3 CpG methylation sites or less per 1000 base pairs (i.e., which base pairs are contiguous nucleotides in genomic nucleic acid). In some embodiments a locus comprising a relatively low CpG density comprises a CpG density of about 2, 1.9, 1.8, 1.7, 1.6, 1.5, 1.4, 1.3, 1.2, 1.1, 1, 0.9, 0.8, 0.7, 0.6, 0.5, 0.4, or 0.3 CpG methylation sites or less per 100 base pairs (i.e., which base pairs are contiguous nucleotides in genomic nucleic acid). In some embodiments a locus comprising a relatively low CpG density comprises a CpG density of about 0.2, 0.19, 0.18, 0.17, 0.16, 0.15, 0.14, 0.13, 0.12, 0.11, 0.10, 0.09, 0.08, 0.07, 0.06, 0.05, 0.04 or 0.03 CpG methylation sites or less per 10 base pairs (i.e., which base pairs are contiguous nucleotides in genomic nucleic acid). In some embodiments a locus comprising a relatively low CpG density comprises a CpG density of about 0.02, 0.019, 0.018, 0.017, 0.016, 0.015, 0.014, 0.013, 0.012, 0.011, 0.010, 0.009, 0.008, 0.007, 0.006, 0.005, 0.004, or 0.003 CpG methylation sites or less per base pair in a stretch of contiguous nucleotides in genomic nucleic acid (e.g., a stretch of 10 contiguous nucleotides or more, a stretch of 100 contiguous nucleotides or more, a stretch of 10,000 contiguous nucleotides or more, a stretch of about 50,000 contiguous nucleotides or more. For example, one or more loci relatively less methylated in a minority nucleic acid species (e.g., fetal nucleic acid) than in a majority nucleic acid species (e.g., maternal nucleic acid) sometimes comprise a relatively low CpG density.

In certain embodiments a DMR or locus (e.g., a differentially methylated locus, a selected locus (e.g., a locus selected for analysis)) is selected and/or analyzed according to the number and/or spacing (e.g., frequency) of methylation sensitive restrictions sites within a DMR or locus. In certain embodiments a locus (e.g., a locus targeted for analysis, a differentially methylated locus) comprises one or more restriction endonuclease recognition sequence(s) (restriction site(s)) where each restriction site can be cleaved, either in a methylated state or unmethylated state, by a methylation sensitive restriction endonuclease. A restriction endonuclease recognition sequence is often referred to herein as a restriction endonuclease recognition site. A restriction site that can be specifically cleaved, either in a methylated state or unmethylated state, by a methylation sensitive restriction endonuclease is sometimes referred to herein as a "methylation sensitive restriction site". In some embodiments all of the methylation sensitive restriction sites in a locus can be cleaved by the same methylation sensitive restriction endonuclease. In some embodiments a locus comprises methylation sensitive restriction sites that can be cleaved by two or more different methylation sensitive restriction endonuclease. In some embodiments a locus comprises a plurality of methylation sensitive restriction sites. A locus can comprise, on average, one or at least one methylation sensitive restriction site for every 10 bp, every 20 bp, every 30 bp, every 40 bp, every 50 bp, every 60 bp, every 70 bp, every 80 bp, every 90 bp, every 100 bp, every 110 bp, every 120 bp, every 130 bp, every 140 bp, every 150 bp, every 160 bp, every 170 bp, every 180 bp, every 190 or about every 200 bp. In certain embodiments a locus comprises, on average, one or at least one methylation sensitive restriction site for every 30 to about 200 bp, every 40 to about 200 bp, every 50 bp to about 200 bp, every 60 bp to about 200 bp, every 30 to about 150 bp, every 40 to about 150 bp, every 50 bp to about 150 bp, every 60 bp to about 150 bp, every 30 to about 100 bp, every 40 to about 100 bp, every 50 bp to about 100 bp, or every 60 bp to about 100 bp. In some embodiments the average, mean, median or absolute distance between each methylation sensitive restriction site within a locus is about 10 bp, 20 bp, 30 bp, 40 bp, 50 bp, 60 bp, 70 bp, 80 bp, 90 bp, 100 bp, 110 bp, 120 bp, 130 bp, 140 bp, 150 bp, 160 bp, 170 bp, 180 bp, 190 or about 200 bp. In some embodiments the average, mean, median or absolute distance between each methylation sensitive restriction site within a locus is about 30 to about 200 bp, 40 to about 200 bp, 50 bp to about 200 bp, 60 bp to about 200 bp, 30 to about 150 bp, 40 to about 150 bp, 50 bp to about 150 bp, 60 bp to about 150 bp, 30 to about 100 bp, 40 to about 100 bp, 50 bp to about 100 bp, or 60 bp to about 100 bp. Often, for determining the presence or absence of a differentially methylated locus, one or more methylation sensitive restriction endonucleases are selected according to the desired number and/or spacing of corresponding methylation sensitive restrictions sites within a genome or locus. In some embodiments one or more methylation sensitive restriction endonucleases are selected according a the average, mean, median or absolute length of digested fragments that are desired (e.g., digested ccf fragments).

In some embodiments a polynucleotide, comprising one or more methylation sites or methylation loci (e.g., hypermethylated loci), is relatively more methylated in fetal nucleic acid than maternal nucleic. In some embodiments an analysis comprises analyzing enriched methylated nucleic acid and/or enriched hypermethylated nucleic acid. The term "enriched methylated nucleic acid" as used herein refers to one or more polynucleotides in a first sample comprising more methylated nucleotides than polynucleotides of a second sample (e.g., a sample prior to an enrichment process), where the first sample comprises enriched methyl nucleic acid. In some embodiments a first sample comprising enriched methylated nucleic acid comprises 1% or more, 5% or more, 10% or more, 20% or more, 30% or more, 40% or more, 50% or more, 60% or more or 70% or more methylated nucleotides relative to a second sample. In some embodiments enriched methylated nucleic acid is enriched hypermethylated nucleic acid. In some embodiments an analysis comprises determining the presence or absence of a polynucleotide (e.g., a nucleic acid fragment) in one or more loci relatively more methylated in fetal nucleic acid than in maternal nucleic acid. In some embodiments an analysis comprises quantifying a polynucleotide in one or more loci relatively more methylated in fetal nucleic acid than in maternal nucleic acid. In some embodiments an analysis comprises determining the presence or absence of a polynucleotide (e.g., a nucleic acid fragment) in one or more loci relatively more methylated in fetal nucleic acid than in maternal nucleic acid where the loci are chosen from the loci in TABLE 2AA, TABLE 2B, TABLE 2CA, TABLE 5 or a combination thereof. In some embodiments an analysis comprises determining the presence or absence of a polynucleotide (e.g., a nucleic acid fragment) in one or more loci relatively more methylated in fetal nucleic acid than in maternal nucleic acid where the loci are chosen from a suitable chromosome. For example, the one or more loci relatively more methylated in fetal nucleic acid than in maternal nucleic acid can be chosen from chromosome 13, chromosome 18 and/or chromosome 21. In some embodiments the one or more loci relatively more methylated in fetal nucleic acid than in maternal nucleic acid can be chosen from one or more suitable chromosomes in TABLE 5 (e.g., one or more loci in chromosome 13, chromosome 18 and/or chromosome 21).

Identifying a Differentially Methylated Locus

In some embodiments one or more differentially methylated loci are identified by a method described herein. In some embodiments a differentially methylated locus is identified, in part, by digesting a nucleic acid sample with one or more methylation sensitive restriction endonucleases, amplifying the nucleic acid (e.g., specific target polynucleotides within in a locus) after digestion, where amplicons (e.g., target specific amplicons) are generated, and analyzing and/or comparing the amount of amplicons from two or more samples or sources. In certain embodiments sample nucleic are digested by one or more selected methylation sensitive restriction endonucleases at one or more methylation sensitive restriction sites that are unmethylated. In certain embodiment sample nucleic are digested by one or more selected methylation sensitive restriction endonucleases at one or more methylation sensitive restriction sites that are methylated. In some embodiments target polynucleotides in a nucleic acid sample are amplified after a restriction enzyme digestion reaction. Often, target polynucleotides that are left uncut by a methylation sensitive restriction endonuclease are amplified and target polynucleotides that are cleaved a not amplified.

In some embodiments one or more differentially methylated loci (e.g., hypomethylated loci, hypermethylated loci) can be identified, in part, by designing one or more oligonucleotide primer pairs capable of amplifying certain target polynucleotides after a restriction enzyme digestion of sample nucleic acid. A locus often comprises a plurality of target polynucleotides where each target nucleic comprises one or more methylation sensitive restriction sites and where each target polynucleotide can be amplified by a primer pair. In some embodiments a collection of oligonucleotide primer pairs is designed for use in an amplification reaction wherein each primer pair is specific for a target polynucleotide. A primer that is specific for a target polynucleotide can specifically hybridize, under suitable hybridization conditions, to a portion of the target polynucleotide. Each primer of a primer pair that is specific for a target polynucleotide can specifically hybridize, under suitable hybridization conditions, to a portion of a target polynucleotide. Each primer of a pair often hybridizes to opposite strands and at opposite ends of a target polynucleotide. For example, primer pairs are often designed to flank a target polynucleotide of interest. In some embodiments a differentially methylated locus is identified, in part, by designing an oligonucleotide primer pair capable of amplifying a target polynucleotide, where the target polynucleotide comprises at least one restriction endonuclease recognition sequence (e.g., a methylation sensitive restriction site). For example, in some embodiments a collection of oligonucleotide primer pairs is designed for use in an amplification, where (i) each of the primer pairs is specific for a target polynucleotide located within a locus, wherein the locus comprises two or more target polynucleotides, (ii) each of the two or more target polynucleotides comprise at least one restriction endonuclease recognition sequence, and (iii) each of the primer pairs flank the at least one restriction endonuclease recognition sequence. Often a primer pair is designed to flank a methylation sensitive restriction site of a target polynucleotide so that cleavage of the target polynucleotide by a methylation sensitive restriction enzyme inhibits or prevents amplification of the target polynucleotide. For example, in certain embodiments, prior to amplification, nucleic acid of a first sample and a second sample are digested with a methylation sensitive restriction endonuclease that specifically digest the nucleic acid at one or more selected restriction endonuclease recognition sequences. In some embodiments the methylation sensitive restriction endonuclease cleaves only unmethylated recognition sequences. Alternatively, a methylation sensitive restriction endonuclease can be used that only cleaves at methylated recognition sequences. After a restriction digest, samples are often contacted with a collection of oligonucleotide primer pairs designed as described herein, under amplification conditions, thereby providing target specific amplicons. Often amplicons from two samples are analyzed and/or compared and one or more differentially methylated loci can be identified according to the analysis and/or comparison. An analysis sometimes comprises determining an amount of the target specific amplicons from each of two or more samples (e.g., samples comprising nucleic acids derived from different sources). In some embodiments a differentially methylated locus is identified where the amount of target specific amplicons of a locus of a first sample is significantly different from the amount of target specific amplicons of a locus of a second sample. For example, where a methylation sensitive restriction enzyme is used that cuts at unmethylated recognitions sequences, a locus of a first sample that comprises significantly more target specific amplicons than a second sample, is often identified as a hypermethylated locus relative to the same locus in the second sample.

Differentially methylated loci are often identified using sample nucleic acid comprising ccf DNA of an average, mean, median or absolute length 300 bp or less, 250 bp or less or 200 bp or less. In some embodiments the average, mean, median or absolute length of target polynucleotides in a sample nucleic acid is about 40 to 2000, 40 to 1500, 40 to 1000, 40 to 500, or 40 to 250 base pairs.

In certain embodiments a DMR or locus (e.g., a differentially methylated locus, a selected locus (e.g., a locus selected for analysis)) is selected and/or analyzed according to one or more features, non-limiting examples of which include: a size of a locus (e.g., mean, median, average, size range or absolute size); methylation status of a minority species of nucleic acid (e.g., in fetal nucleic acid; e.g., mean, median, average, limit of, span of, range of, or absolute methylation status); a mean, median, average, absolute or relative methylation status of a majority nucleic acid species (e.g., in maternal nucleic acid; e.g., mean, median, average, limit of, span of, range of, or absolute methylation status); a difference in methylation status between a minority nucleic acid species and a majority nucleic acid species; CpG density; number of CpG sites; gene density; number of restriction sites; distance and/or spacing between restriction sites for loci having two or more restriction sites; and amplicon size (e.g., mean, median, average, absolute or range of amplicon size; e.g., amplicon sizes ranging from 40-125 nucleotides in length); the like; or combinations thereof. A differentially methylated locus sometimes is selected and/or analyzed according to 2, 3, 4, 5, 6, 7, 8 or more features described herein.

In certain embodiments a DMR or locus (e.g., a differentially methylated locus, a selected locus (e.g., a locus selected for analysis)) is selected and/or analyzed according to size. For example, a size of a DMR or locus (e.g., mean, median, average, size range or absolute size) can comprise about 50,000, 40,000, 30,000, 20,000, 10,000, 7500, 5000, 2500, 2000, 1750, 1500, 1250, 1000, 750, 500, 250, 200, 150, or 100 contiguous base pairs, or less.

A differentially methylated locus sometimes comprises a CpG density of 0.016, 0.012, 0.008, 0.004, or 0.002 CpG methylation sites per base pair, or less. A CpG density can be provided in any suitable scale and may comprise any suitable units of measure. For example, a differentially methylated locus sometimes comprises a CpG density of 16, 15, 14, 13, 12, 11, 10, 9, 8, 7, 6, 5, 4, 3, 2 or 1, CpG methylation sites per 1000 base pairs, or less. A differentially methylated locus sometimes comprises a CpG density of 160, 150, 140, 130, 120, 110, 100, 90, 80, 70, 60, 50, 40, 30, 20 or 10 CpG methylation sites per 10,000 base pairs, or less. A differentially methylated locus sometimes comprises a CpG density of 800, 750, 700, 650, 600, 550, 500, 450, 400, 350, 300, 250, 200, 150, 100 or 50 CpG methylation sites per 50,000 base pairs, or less.

A differentially methylated locus sometimes comprises a gene density of 0.5, 0.4, 0.3, 0.2, 0.1, 0.08, 0.06, 0.04, 0.02, 0.01 or 0.008 genes per 1000 base pairs, or less. In some embodiments a differentially methylated locus comprises no genes. A gene density can be provided in any suitable scale and may comprise any suitable units of measure. For example, a differentially methylated locus sometimes comprises a gene density of 5, 4, 3, 2, 1, 0.8, 0.6, 0.4, 0.2, 0.1 or 0.08 genes per 10,000 base pairs, or less. A differentially methylated locus sometimes comprises a gene density of 25, 20, 15, 10, 5, 4, 3, 2, 1, 0.5 or 0.4 genes per 50,000 base pairs, or less.

A differentially methylated locus sometimes comprises at least 5, 6, 7, 8, 9, 10, 11, 12, 13, 14, 15, 16, 17, 18, 19 or at least 20 CpG methylation sites. In some embodiments a differentially methylated locus comprises one restriction endonuclease recognition site, or a plurality of restriction endonuclease recognition sites where the average, mean, median or absolute distance between each restriction endonuclease recognition site in the locus is about 20 to about 500, about 20 to about 400, about 20 to about 350, about 20 to about 200, about 20 to about 150, about 30 to about 150, about 40 to about 150, about 20 to about 100 or about 40 to about 100 base pairs. For embodiments in which a locus includes one or more restriction endonuclease recognition sites, each of the one or more restriction endonuclease recognition sites can be recognized and/or digested, depending on the methylation status of the site, by one or more methylation sensitive restriction endonucleases. In some embodiments the average, mean, median or absolute distance between each methylation sensitive restriction endonuclease recognition site on a locus is about 20, 30, 40, 50, 60, 70, 80, 90, 100, 110, 120, 125, 130, 135, 140, 145 or about 150 base pairs. Methylation sensitive restriction endonuclease recognition sites on a locus may be recognized by the same, or two or more different methylation sensitive restriction enzymes. A differentially methylated locus sometimes comprises an average, mean, median or absolute number of at least 0.5, 1, 5, 10, 15, 20, 25, 30, 35, 40, 45, 50, 60, 70, 80, 90 or 100 methylation sensitive restriction endonuclease recognition sites per 1000 base pairs, wherein each of restriction endonuclease recognition sites can be specifically recognized and/or digested by a methylation sensitive cleavage agent.

A differentially methylated locus sometimes comprises a methylation status of about 75% or less, about 70% or less, about 65% or less, about 60% or less, about 55% or less, about 50% or less, about 40% or less, about 35% or less, about 30% or less, about 25% or less, about 20% or less, about 15% or less, or about 10% or less in fetal nucleic acid.

A differentially methylated locus sometimes comprises a methylation status of about 55% or more, about 60% or more, about 65% or more, about 70% or more, about 75% or more, about 80% or more, about 85% or more or about 90% or more in maternal nucleic acid.

A differentially methylated locus sometimes comprises a difference in methylation status between two nucleic acid species or subgroups (e.g., between a minority nucleic acid and a majority nucleic acid, e.g., between fetal nucleic acid and maternal nucleic acid) of about 0.1% or more, about 0.5% or more, about 1% or more, about 2% or more, about 3% or more, about 4% or more, about 5% or more, about 6% or more, about 7% or more, about 8% or more, about 9% or more, about 10% or more, about 15% or more, about 20% or more, about 30% or more, about 40% or more, about 50% or more, or about 60% or more. In some embodiments a difference in methylation status between two nucleic acid species or subgroups can be a statistical difference (e.g., a statistically significant difference) as determined by a suitable statistical test (e.g., a t-test).

Identifying a differentially methylated locus sometimes comprises determining and/or analyzing a methylation status of a locus of a first and a second nucleic acid species or subgroup. In some embodiments, a differentially methylated locus is about 20, 15, 10, or 5% or less methylated in a first nucleic acid species or subgroup (e.g., fetal nucleic acid) and about 50, 60, 65, 70, or 75% or more methylated in a second nucleic acid species or subgroup (e.g., maternal nucleic acid).

Methylation-Sensitive Enrichment, Detection and Quantification

Non-limiting examples of processes for analyzing, detecting and/or quantifying a methylation state of a marker are described in International Application Publication No. WO 2012/149339 published on Nov. 1, 2012 (International Application No. PCT/US2012/035479 filed on Apr. 27, 2012) and in International Application Publication No. WO 2011/034631 published on Mar. 24, 2011 (International Application No. PCT/US2010/027879 filed on Mar. 18, 2010), the entire content of which is incorporated herein by reference, including all text, tables and drawings. In some embodiments, a methylation sensitive procedure is utilized as part of detecting and/or quantifying a marker. Non-limiting examples of methylation sensitive procedures include bisulfite treatment of DNA, bisulfite sequencing, methylation specific PCR (MSP), quantitative methylation specific PCR (QPSP), combined bisulfite restriction analysis (COBRA), methylation-sensitive single nucleotide primer extension (Ms-SNuPE), MethylLight, methylation pyrosequencing, immunoprecipitation with 5-Methyl Cytosine (MeDIP), Methyl CpG Immunoprecipitation (MCIp; e.g., use of an antibody that specifically binds to a methyl-CpG binding domain (MBD) of a MBD2 methyl binding protein (MBD-Fc) for immunoprecipitation of methylated or unmethylated DNA), and methyl-dependent enzyme digestion with McrBC.

Enrichment of a certain nucleic acid subset or species sometimes comprises selectively separating a subset (e.g., subpopulation or species) of nucleic acids from a mixture. In some embodiments a selective separation comprises a method or process that separates, enriches or partially purifies a target subset based on one or more physical characteristics (e.g., methylated or unmethylated nucleotides, a sequence of nucleotides, molecular weight, size, charge, polarity, binding characteristics (e.g., affinity, Kd, on-off rate), an identifier, the like or combinations thereof) unique to, or more predominant in, the target group relative to other components, subsets or species in a mixture. Selectively separating a subset (e.g., subpopulation or species) of nucleic acids from a mixture often results in one or more separation products. A process comprising a selective separation is sometimes not a complete or 100% separation. In some embodiments a selective separation comprises a partial separation where some portion of the target species or components being selectively separated are not separated. In some embodiments the efficiency of a selective separation separates about 60% or more, about 70% or more, about 80% or more, about 85% or more, about 90% or more, about 95% or more, about 97% or more, about 98% or more, about 99% or more or about 100% of the targeted species from a mixture. Methods provided herein can generate separation products that are enriched for a subpopulation of nucleic acid (e.g., enriched for a sub-population of cell-free nucleic acid). In certain embodiments, separation products can be enriched for fetal nucleic acid. In certain embodiments, separation products can be enriched for hypomethylated nucleic acids, hypermethylated nucleic acids, digested nucleic acid fragments, undigested nucleic acid fragments or a minority nucleic acid species. In some embodiments nucleic acid (e.g., a separation product) enriched for hypomethylated loci are often enriched for fetal nucleic acids (e.g., as described herein, e.g., as per Example 2). In some embodiments nucleic acid (e.g., a separation product) enriched for hypomethylated loci are often enriched for a minority nucleic acid species.

In some embodiments enrichment of a certain nucleic acid subset or species comprises exposing nucleic acids (e.g., sample nucleic acid) to conditions that separate certain nucleic acid subsets or species. Enrichment of a certain nucleic acid subset or species sometimes comprises selectively separating digested nucleic acid fragments from non-digested nucleic acid fragments. Digested nucleic acids can be selectively separated from non-digested nucleic acids by any suitable method. Digested nucleic acid fragments are generally shorter polynucleotide fragments of lower molecular weight than undigested nucleic acid in a sample. In some embodiments, undigested nucleic acids can be separated (e.g., selectively separated) from digested nucleic acid fragments by a suitable size or mass-based separation method. Non-limiting examples of size-based and/or mass-based separation methods include size exclusion chromatography, density gradient centrifugation, precipitation, sedimentation, equilibrium sedimentation, polyethylene glycol precipitation, gel filtration, electrophoresis (e.g., gel electrophoresis), the like or a combination thereof. In some embodiments digested nucleic acid are ligated to an adaptor or linker and can be selectively separated from non-digested nucleic acids by certain characteristics of the adaptor or linker. For example, digested fragments comprising a linker or adaptor can be selectively separated according to an identifier (e.g., a fluorescent identifier) or capture agent that is associated with an adaptor or linker. In some embodiments digested fragments comprising a linker or adaptor can be selectively separated according to a nucleic acid sequence of the adaptor or linker, for example by hybridization to a capture agent, where the capture agent is a nucleic acid complementary to a portion of the linker or adaptor.

In some embodiments, selective separation of digested nucleic acids from undigested nucleic acids generates a separation product comprising about 50% or greater digested nucleic acid. For example, a separation product can comprise about 55%, 60%, 65%, 70%, 75%, 80%, 85%, 90%, 95% or 100% digested nucleic acid. In some embodiments, some or substantially all undigested nucleic acid in a sample are separated from digested nucleic acid in the sample, thereby generating a separation product enriched for digested nucleic acid. In certain embodiments, digested nucleic acid fragments are enriched for fragments from fetal origin.

In some embodiments, fetal nucleic acid is enriched without generating of a separation product. In certain embodiments, a separation product can be enriched for fetal nucleic acid by enrichment of digested nucleic acid (e.g., digested hypomethylated nucleic acid, e.g., followed by specific amplification of hypomethylated nucleic acid) and/or by another suitable method. In some embodiments, a separation product comprises about 5%, 10%, 15%, 20% or greater fetal nucleic acid. For example, a separation product can comprise about 25%, 30% 40%, 50%, 60%, 65%, 70%, 75%, 80%, 85%, 90%, 95% or 100% fetal nucleic acid. In some embodiments, some or substantially all undigested nucleic acid is separated from sample nucleic acid, thereby generating a separation product enriched for fetal nucleic acid.

A sample of nucleic acid can be enriched for a nucleic acid species (e.g., a subset or subpopulation of nucleic acids (e.g., a minority nucleic acid species, one or more loci, one or more target polynucleotides, hypomethylated nucleic acid, fetal nucleic acid)) by methods described herein thereby providing or generating nucleic acid enriched for a nucleic acid species. A nucleic acid sample enriched for a nucleic acid species often comprises a greater amount (e.g., concentration, absolute amount, percentage, the like) of the nucleic acid species when compared to the same nucleic acid sample prior to enrichment. In some embodiments the amount of a nucleic acid species in a nucleic acid sample enriched for a nucleic acid species comprises about a 1.5-fold to 1,000-fold increase in the nucleic acid species compared to an amount of the nucleic acid species in a sample prior to an enrichment method. In some embodiments the amount of a nucleic acid species in a nucleic acid sample is increased about 1.5 fold or more, 2 fold or more, 3 fold or more, 4 fold or more, 5 fold or more, 6 fold or more, 7 fold or more, 8 fold or more, 9 fold or more, or about 10 fold or more (e.g., 20, 30, 40, 50, 60, 70, 80, 85, 90, 95, 100, 200, 300, 400, 500, 600, 700, 800 or 900-fold or more). A nucleic acid species in a separation product sometimes is enriched 1.5-fold to 1,000-fold (e.g., 20, 30, 40, 50, 60, 70, 80, 85, 90, 95, 100, 200, 300, 400, 500, 600, 700, 800 or 900-fold enriched) relative to a nucleic acid species in a sample nucleic acid prior to enrichment. In certain embodiments, the relative proportion of (i) fetal nucleic acid to (ii) non-fetal nucleic acid is greater (e.g., enriched) in the separation product than in the sample nucleic acid. For determining such a proportion, non-fetal nucleic acid sometimes is maternal nucleic acid. Fetal nucleic acid sometimes is enriched 1.5-fold to 1,000-fold relative to fetal nucleic acid in sample nucleic acid (e.g., 20, 30, 40, 50, 60, 70, 80, 85, 90, 95, 100, 200, 300, 400, 500, 600, 700, 800 or 900-fold enriched). In some embodiments, fetal nucleic acid can be enriched about 1.5-fold to about 200-fold relative to fetal nucleic acid in sample nucleic acid. For example, fetal nucleic acid can be enriched about 2, 3, 4, 5, 6, 7, 8, 9, 10, 15, 20, 25, 30, 35, 40, 45, 50, 55, 60, 65, 70, 75, 80, 85, 90, 95, 100, 120, 140, 160, 180 or 200-fold (e.g., FIG. 7). Fold enrichment can be calculated by any suitable method. For example, fold enrichment of a minority species (e.g., minority nucleic acid species) can be calculated by dividing the amount of a minority species after enrichment by an amount of the minority species prior to enrichment. n some embodiments, hypomethylated nucleic acid (e.g., in a separation product) is enriched relative to methylated or hypermethylated nucleic acid in sample nucleic acid. In some embodiments, tumor-derived nucleic acid (e.g., in a separation product) is enriched relative to tumor-derived nucleic acid in sample nucleic acid.

A separation and/or enrichment product containing enriched fetal nucleic acid often contains fetal nucleic acid fragments. Fetal nucleic acid fragments in a separation and/or enrichment product often range in size from about 50 base pairs to about 200 base pairs. The entire fetal genome or significant fraction of the fetal genome (e.g., 70% or more of the fetal genome) sometimes is represented in a separation product. Fetal nucleic acid fragments having the same length (e.g., 149 base pair fragment length or 150 base pair fragment length) in a separation product often represent a large number of sequences. There often are many fetal nucleic acid fragments having the same length but different sequences in a separation product. In some embodiments, about 1/15th of the fetal genome is represented by fetal nucleic acid fragments having the same length (e.g., 1/12th to 1/18th (e.g., 1/13th, 1/14th, 1/16th, 1/17th, 1/18th)). Fetal nucleic acid fragments having a particular length in a separation product often are from multiple and distinct regions of the genome. Some or all fetal nucleic acid fragments in a separation product often have sizes separated by one base pair (1-bp), where each fragment is 1-bp larger than the next shorter fragment.

In some embodiments, nucleic acid (e.g., extracellular nucleic acid) is enriched or relatively enriched for a subpopulation or species of nucleic acid using a method described herein and/or one or more additional enrichment methods. Non-limiting examples of nucleic acid species or subpopulations include fetal nucleic acid, maternal nucleic acid, nucleic acid comprising fragments of a particular length or range of lengths, hypermethylated nucleic acid, methylated nucleic acid, hypomethylated nucleic acid, unmethylated nucleic acid, or nucleic acid from a particular genome region (e.g., locus (e.g., hypomethylated locus, hypermethylated locus), a single chromosome, a set of chromosomes, and/or certain chromosome regions). Such enriched samples can be used in conjunction with a method provided herein. Thus, in certain embodiments, methods of the technology comprise a step of enriching and/or analyzing a subpopulation of nucleic acid in a sample, such as, for example, fetal nucleic acid. In some embodiments, certain methods for determining fetal fraction described below also can be used to enrich for fetal nucleic acid. In certain embodiments, maternal nucleic acid is selectively removed (partially, substantially, almost completely or completely) from the sample. In some embodiments, enriching and/or analyzing a particular low copy number species nucleic acid (e.g., a minority species, fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In some embodiments, nucleic acid is enriched for a specific nucleic acid fragment length or range of fragment lengths using one or more length-based separation methods described below. In some embodiments, nucleic acid is enriched for fragments from a select genomic region (e.g., chromosome) using one or more sequence-based separation methods described herein and/or known in the art. Certain methods for enriching and/or analyzing a nucleic acid subpopulation (e.g., fetal nucleic acid) in a sample are described in detail below.

In some embodiments a nucleic acid subpopulation (e.g., fetal nucleic acid, tumor nucleic acid) can be enriched by exploiting epigenetic differences (e.g., methylation differences) between two or more nucleic acid subpopulations (e.g., fetal nucleic acid and maternal nucleic acid). For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Separation and/or enrichment methods sometimes involve contacting a sample nucleic acid with a methyl-specific binding agent (e.g., methyl-CpG binding protein (MBD), methylation specific binding antibodies, the like, portions thereof or combinations thereof). In some embodiments digested nucleic acid fragments or modified variants thereof are selectively separated by a process comprising a methyl-specific binding agent.

In some embodiments a methyl-specific binding agent specifically binds and/or associates with methylated nucleic acid and/or hypermethylated nucleic acid. For example a methyl-specific antibody can specifically bind a methylated portion (e.g., a methylated CpG) of a nucleic acid fragment. In some embodiments a methyl-specific binding agent specifically binds hypermethylated nucleic acid (e.g., hypermethylated locus) comprising one or more methylation sites that are methylated. In certain embodiments a methyl-specific binding agent binds methylated nucleic acid and/or hypermethylated nucleic acid with a higher affinity than it binds unmethylated or hypomethylated nucleic acid.

In some embodiments a methyl-specific binding agent specifically binds and/or associates with unmethylated nucleic acid and/or hypomethylated nucleic acid. For example a methyl-specific antibody can specifically bind an unmethylated portion (e.g., a unmethylated CpG) of a nucleic acid fragment (e.g., a digested nucleic acid fragment). In some embodiments a methyl-specific binding agent specifically binds and/or associates with hypomethylated nucleic acid (e.g., hypomethylated locus) comprising one or more methylation sites on the nucleic acid that are unmethylated. In certain embodiments a methyl-specific binding agent binds unmethylated nucleic acid and/or hypomethylated nucleic acid with a higher affinity than it binds methylated or hypermethylated nucleic acid.

In some embodiments nucleic acid in a sample is contacted with one or more methyl-specific binding agents. In some embodiments enriching for a particular species or subset of nucleic acid comprises contacting nucleic acid in a sample with a methyl-specific binding agent. Specific nucleic acid species, subsets or subpopulations in a sample can be selectively separated by a process comprising contacting the nucleic acid in the sample with one or more methyl-specific binding agents. Non-limiting examples of nucleic acids and/or nucleic acid species that can be selectively separated by a process described herein include fetal nucleic acid, maternal nucleic acid, tumor derived nucleic acid, nucleic acid from healthy tissue, unmethylated nucleic acid, hypomethylated nucleic acid, hypomethylated loci, methylated nucleic acid, hypermethylated nucleic acid, hypermethylated loci, size fractionated nucleic acids (e.g., size fractionated separation products), cleaved nucleic acid (e.g., nucleic acid cleaved by a restriction endonuclease), uncleaved nucleic acid, modified nucleic acid (e.g., chemically treated nucleic acid, sheared nucleic acid, nucleic acid comprising adaptors, linkers, the like, or combinations thereof), amplification or extension products of nucleic acids, the like, combinations thereof or mixtures thereof. Enrichment of a certain nucleic acid subset or species sometimes comprises selectively separating hypomethylated and/or unmethylated nucleic acid from methylated and/or hypermethylated nucleic acid. Enrichment of hypomethylated and/or unmethylated nucleic acid or methylated and/or hypermethylated nucleic acid sometimes comprises exposing nucleic acid in a sample to conditions that separate hypomethylated and/or unmethylated nucleic acid from methylated and/or hypermethylated nucleic acid.

Contacting a mixture of nucleic acid species or a mixture comprising two or more subpopulations with a methyl-specific binding agent often results in bound and unbound nucleic acids. Bound nucleic acids often are non-covalently associated with a binding agent (e.g., a methyl-specific binding agent) with a moderate to high affinity (e.g., $Kd \leq 10^{-6}$ M). Unbound nucleic acids (e.g., free nucleic acids) are often not substantially associated with a methyl-specific binding agent. A sample can be contacted with a binding agent under one or more different conditions (e.g., binding conditions) that determine which subpopulations of nucleic acids in a sample associate or do not associate with a binding agent. In some embodiments a sample of nucleic acid is contacted with a binding agent under conditions where substantially all of the nucleic acids in a sample associate and/or binds to the binding agent. For example, substantially all of the nucleic acids in a sample may comprise at least 90%, 95%, 96%, 97%, 98%, 99%, 99.9% or 100% of the nucleic acids in a sample. In certain embodiments a sample of nucleic acid is contacted with a binding agent under conditions where a portion of the nucleic acids in a sample associate and/or bind to the binding agent. Conditions that determine binding of a particular nucleic acid species to a specific binding agent are often known or can be determined empirically.

In some embodiments a methyl-specific binding agent is soluble in a solution. In some embodiments, a methyl-specific binding agent is immobilized on a solid support or substrate. For example, a methyl-specific binding agent can be immobilized on a bead, chip or flow cells. Sometimes a methyl-specific binding agent is reversibly immobilized on a solid support or substrate. In some embodiments a methyl-specific binding agent is reversibly immobilized on a solid support comprising a capture agent. Sometimes a methyl-specific binding agent comprises a capture agent (e.g., a member of a binding pair, e.g., biotin).

In some embodiments nucleic acid in a sample is contacted with one or more methyl-specific binding agents that specifically bind nucleic acid (e.g., methylated, hypermethylated, unmethylated or hypomethylated nucleic acid), thereby generating bound nucleic acid fragments and unbound nucleic acid fragments. In some embodiments nucleic acids in a sample that are associated with a methyl-specific binding agent (e.g., bound nucleic acids) can be selectively separated from nucleic acids in the sample that are not substantially associated with a methyl-specific binding agent thereby generating one or more separation products. In some embodiments a portion of nucleic acid in a sample that is associated with a binding agent (e.g., a methyl-specific binding agent) can be disassociated and/or selectively eluted from a binding agent using a suitable method, thereby generating one or more separation products. For example, a portion of nucleic acid in a sample that is associated with a binding agent (e.g., bound nucleic acids) can be disassociated or selectively eluted by altering binding and/or elution conditions. Non-limiting examples of elution conditions that can be altered include salt concentration (monovalent or divalent salt concentrations), temperature, pH, volume, flow rate, addition of a competitor that competes for binding to the binding agent, the like or combinations thereof. For example, bound nucleic acids can sometimes be selectively eluted by increasing salt concentration from about 50 mM to about 800 mM. In some embodiments a salt gradient can be used to selectively elute fractions (e.g., separation products) from a binding agent. For example, nucleic acid fragments comprising methylated nucleotides (e.g., methylated nucleic acid, hypermethylated polynucleotides) that are associated with a methyl-specific binding agent (e.g., a methyl-specific binding agent immobilized on a solid support) can be separated (e.g., eluted, step-wise eluted) from a methyl-specific binding agent thereby providing one or more separation products. In the foregoing example, two or more nucleic acids species, where each species comprises different amounts of methylated nucleotides, can be separated and/or fractionated into one or more separation products using a suitable elution process. In some embodiments, generating a separation product does not comprise an elution process. For example, nucleic acids in a sample can be contacted with one or more methyl-specific binding agents thereby generating a separation product comprising unbound nucleic acid fragments. In the foregoing example, the unbound nucleic acids may comprise an enriched minority species of nucleic acid. In some embodiments enrichment comprises contacting a mixture of methylated (e.g., hypermethylated) and hypomethylated nucleic acids with a methyl-specific binding agent that specifically associated with methylated nucleic acid, under conditions that do not permit binding of hypomethylated nucleic acid, and the unbound portion (e.g., unbound nucleic acid) comprises separated and enriched hypomethylated nucleic acid. In the foregoing example the bound fraction of nucleic acid may comprise separated and enriched methylated nucleic acid (e.g., hypermethylated nucleic acid). In some embodiments enrichment comprises contacting a mixture of methylated (e.g., hypermethylated) and hypomethylated nucleic acids with a methyl-specific binding agent that specifically associated with unmethylated nucleotides (e.g., polynucleotides comprising one or more unmethylated nucleotides), under conditions that do not permit binding of methylated nucleic acid (e.g., hypermethylated nucleic acid), and the unbound portion (e.g., unbound nucleic acid) comprises separated and enriched hypermethylated nucleic acid. In the foregoing example the bound fraction of nucleic acid may comprise separated and enriched hypomethylated nucleic acid.

A separation product can be generated before, during or after any step of a method described herein. A separation product can be generated before, during or after a digestion or cleavage reaction. A separation product can be generated before, during or after modification or amplification of nucleic acids in a sample. A separation product can be generated before, during or after an enrichment method. A separation product can be generated before, during or after a process comprising nucleic acid sequencing.

Methods herein also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target polynucleotides (e.g., fetal nucleic acid) relative to non-target polynucleotides (e.g., maternal nucleic acid). In some embodiments, nucleic acid may be selected such that it comprises an allele having a polymorphic site that is susceptible to selective digestion by a cleavage agent, for example. In some embodiments, nucleic acid may be selected such that it comprises an allele having a polymorphic site that is susceptible to selective digestion by a cleavage agent, for example.

In some embodiments digested nucleic acid comprising one or more target loci (e.g., hypomethylated or hypermethylated loci) is selectively enriched and/or amplified. For example, a nucleic acid comprising a target allele (e.g., an unmethylated CpG) is sometimes cleaved with a restriction endonuclease (e.g., a methylation sensitive cleavage agent) that recognizes a nucleic acid comprising a target locus, but generally not a non-target locus; optionally, one or more adaptors is ligated to the cleaved nucleic acid; and cleaved nucleic acid, but not uncleaved nucleic acid, is amplified, where the cleaved, amplified nucleic acid represents enriched target polynucleotides (e.g., fetal nucleic acid) relative to non-target polynucleotides (e.g., maternal nucleic acid). In some embodiments digested nucleic acid fragments comprising linkers or adaptors can be amplified using one or more primers that a complementary to a portion of the ligated linkers or adaptors. Sometimes, for example, where only fragments comprising one or more ligated adaptors are amplified using adaptor specific-primers, the amplification process is referred to as a non-target-based approach. Sometimes amplification comprises a target-based approach, where target specific primers are utilized to selectively amplify specific loci, genes or subsets of nucleic acids (e.g., nucleic acids derived from one or more specific chromosomes). In some embodiments amplification comprises a targeted and non-targeted approached. In some embodiments an analysis of nucleic acids (e.g., an analysis of digested nucleic acid fragments, an analysis of enriched nucleic acid (e.g., enriched fetal nucleic acid, enriched hypomethylated nucleic acid, enriched methylated nucleic acid, enriched hypermethylated nucleic acid)) comprises selective amplification by a targeted and/or a non-targeted approach. For example, digested fragments can be selectively amplified using an adaptor-specific primer and a target specific primer. Some methods for enriching for a nucleic acid subpopulation (e.g., fetal nucleic acid) that can be used with a method described herein include selective enzymatic degradation approaches. Such methods involve protecting target sequences (e.g., target polynucleotides) from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e., non-target) nucleic acid. In some embodiments, the method can be repeated for at least one additional cycle. In some embodiments, the same target-specific primer pair is used to prime each of the first and second cycles of extension, and in some embodiments, different target-specific primer pairs are used for the first and second cycles.

Some methods for enriching and/or analyzing a nucleic acid subpopulation (e.g., fetal nucleic acid) that can be used with a method described herein include massively parallel signature sequencing (MPSS) approaches. MPSS typically is a solid phase method that uses adaptor (i.e., tag) ligation, followed by adaptor decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In some embodiments, certain MPSS-based enrichment methods can include amplification (e.g., PCR)-based approaches. In some embodiments, locus-specific amplification methods can be used (e.g., using locus-specific amplification primers). In some embodiments, a multiplex SNP allele PCR approach can be used. In some embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In some embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain locus-specific forward PCR primers and adaptor sequences incorporated into locus-specific reverse PCR primers, to thereby generate amplicons, followed by a secondary PCR to incorporate reverse capture sequences and molecular index barcodes for sequencing using, for example, the Illumina MPSS system. In some embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both locus-specific forward and locus-specific reverse PCR primers, followed by a secondary PCR to incorporate both forward and reverse capture sequences and molecular index barcodes for sequencing using, for example, the Illumina MPSS system. In some embodiments, a microfluidics approach can be used. In some embodiments, an array-based microfluidics approach can be used. For example, such an approach can involve the use of a microfluidics array (e.g., Fluidigm) for amplification at low plex and incorporation of index and capture probes, followed by sequencing. In some embodiments, an emulsion microfluidics approach can be used, such as, for example, digital droplet PCR.

In some embodiments, universal amplification methods can be used (e.g., using universal or non-locus-specific amplification primers). In some embodiments, universal amplification methods can be used in combination with pull-down approaches. In some embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In some embodiments, pull-down approaches can be used in combination with ligation-based methods. In some embodiments, a method can include biotinylated ultramer pull down with sequence specific adaptor ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In some embodiments, pull-down approaches can be used in combination with extension and ligation-based methods. In some embodiments, a method can include molecular inversion probe (MIP) extension and ligation. For example, such an approach can involve the use of molecular inversion probes in combination with sequence adaptors followed by universal amplification and sequencing. In some embodiments, complementary DNA can be synthesized and sequenced without amplification.

In some embodiments, extension and ligation approaches can be performed without a pull-down component. In some embodiments, a method can include locus-specific forward and reverse primer hybridization, extension and ligation. Such methods can further include universal amplification or complementary DNA synthesis without amplification, followed by sequencing. Such methods can reduce or exclude background sequences during analysis, in some embodiments.

In some embodiments, pull-down approaches can be used with an optional amplification component or with no amplification component. In some embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In some embodiments, a method can include a biotinylated pull-down assay with extension and ligation of adaptor sequence in combination with circular single stranded ligation. For example, such an approach can involve the use of selector probes to capture regions of interest (i.e., target sequences), extension of the probes, adaptor ligation, single stranded circular ligation, optional amplification, and sequencing. In some embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments typically are isolated away from the remaining fragments in the nucleic acid sample. In some embodiments, the separated target fragments and the separated reference fragments also are isolated away from each other (e.g., isolated in separate assay compartments). In some embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome).

In some embodiments, nucleic acid is enriched for a particular nucleic acid fragment length, range of lengths, or lengths under or over a particular threshold or cutoff using one or more length-based separation methods. For example, isolated cell-free nucleic having fragment lengths of about 300 base pairs or less, about 200 base pairs or less, about 150 base pairs or less, about 100 base pairs or less, about 75 base pairs or less or about 50 base pairs or less can be enriched for fetal nucleic acid, in certain instances. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In some embodiments, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. The term "sequence tagging" refers to incorporating a recognizable and distinct sequence into a nucleic acid or population of nucleic acids.

The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In some embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Determining Fetal Nucleic Acid Content

In some embodiments an analysis (e.g., an analysis of nucleic acids) comprises determining an amount of fetal nucleic acid in a nucleic acid sample. An amount of fetal nucleic acid (e.g., concentration, relative amount, ratio, absolute amount, copy number, and the like) in nucleic acid (e.g., a nucleic acid sample or mixture) is determined in some embodiments. In some embodiments, the amount of fetal nucleic acid in a sample is referred to as "fetal fraction". In some embodiments, "fetal fraction" refers to the fraction of fetal nucleic acid in circulating cell-free nucleic acid in a sample (e.g., a blood sample, a serum sample, a plasma sample) obtained from a pregnant female. In some embodiments determining an amount of fetal nucleic acid comprises determining a ratio (e.g., percentage, a percent representation) of fetal nucleic acid to a total amount of nucleic acid in a sample. In some embodiments determining an amount of fetal nucleic acid comprises determining a ratio (e.g., percentage) of the amount of fetal nucleic acid to the amount of maternal nucleic acid in a sample. In some embodiments, a method in which a genetic variation is determined also can comprise determining fetal fraction. Determining fetal fraction can be performed in a suitable manner, non-limiting examples of which include methods described below.

In some embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. The amount of fetal nucleic acid from a maternal sample sometimes can be determined relative to the total amount of nucleic acid present, thereby providing the percentage of fetal nucleic acid in the sample. The copy number of fetal nucleic acid sometimes can be determined in a maternal sample. The amount of fetal nucleic acid sometimes can be determined in a sequence-specific (or locus-specific) manner and sometimes with sufficient sensitivity to allow for accurate chromosomal dosage analysis (for example, to detect the presence or absence of a fetal aneuploidy or other genetic variation).

A fetal quantifier assay (FQA) can be performed in conjunction with any method described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching for fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No.

2007/0065823. In some embodiments, the restriction efficiency can be determined and the efficiency rate is used to further determine the amount of fetal DNA.

A fetal quantifier assay (FQA) sometimes can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. The absolute copy number of fetal nucleic acid in a maternal sample sometimes can be determined, for example, using mass spectrometry and/or a system that uses a competitive PCR approach for absolute copy number measurements. See for example, Ding and Cantor (2003) Proc. Natl. Acad. Sci. USA 100:3059-3064, and U.S. Patent Application Publication No. 2004/0081993, both of which are hereby incorporated by reference.

Fetal fraction sometimes can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. Fetal alleles can be identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target polynucleotide sequence on a reference genome for each of the two alleles of a polymorphic site.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection) methods described herein. For example, to achieve an aneuploidy determination method with a given sensitivity or specificity, a fetal nucleic acid quantification method may be implemented prior to, during or after aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for the presence or absence of aneuploidy or genetic variation, for example. In certain embodiments, determinations of, for example, the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy. In some embodiments, identifying the presence or absence of a chromosome aneuploidy does not require the sequence differentiation of fetal versus maternal DNA. This is because the summed contribution of both maternal and fetal sequences in a particular chromosome, chromosome portion or segment thereof is analyzed, in some embodiments. In some embodiments, identifying the presence or absence of a chromosome aneuploidy does not rely on a priori sequence information that would distinguish fetal DNA from maternal DNA.

Nucleic Acid Amplification and Detection

In some embodiments, nucleic acid fragments (e.g., digested nucleic acid fragments) may be amplified and/or subjected to a analysis and/or detection process (e.g., sequence-based analysis, mass spectrometry). In some embodiments, nucleic acid fragments are (e.g., digested nucleic acid fragments) subjected to a detection process (e.g., sequencing) without amplification. Such methods without amplification typically have less starting material (e.g., less input nucleic acid resulting from an enrichment process herein) for downstream analysis. In some embodiments a nucleic acid or a subset (e.g., subpopulation, species) of nucleic acid is enriched by a process comprising nucleic acid amplification. For example, fetal nucleic acid can be enriched by a process comprising nucleic acid amplification.

Nucleic acid fragments (e.g., digested nucleic acid fragments), or amplified nucleic acid fragment sequences, or detectable products prepared from the foregoing, can be detected by a suitable detection process. Non-limiting examples of methods of detection, quantification, sequencing and the like include mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), direct DNA sequencing, Molecular Inversion Probe (MIP) technology from Affymetrix, restriction fragment length polymorphism (RFLP analysis), allele specific oligonucleotide (ASO) analysis, methyl-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization using at least one probe, hybridization using at least one fluorescently labeled probe, cloning and sequencing, electrophoresis, the use of hybridization probes and quantitative real time polymerase chain reaction (QRT-PCR), digital PCR, nanopore sequencing, chips and combinations thereof. In some embodiments the amount of each nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

Nucleic acid detection and/or quantification also may include, for example, solid support array based detection of fluorescently labeled nucleic acid with fluorescent labels incorporated during or after PCR, single molecule detection of fluorescently labeled molecules in solution or captured on a solid phase, or other sequencing technologies such as, for example, sequencing using ION TORRENT or MISEQ platforms or single molecule sequencing technologies using instrumentation such as, for example, PACBIO sequencers, HELICOS sequencer, or nanopore sequencing technologies.

Nucleic Acid Amplification

In many instances, it is desirable to amplify a nucleic acid sequence or a subset of nucleic acids of the technology herein using any of several nucleic acid amplification procedures which are well known in the art, some of which are listed or described herein. Specifically, nucleic acid amplification is the enzymatic synthesis of nucleic acid amplicons (copies) which contain a sequence that is complementary to a nucleic acid sequence being amplified. In some embodiments amplification comprises ligating one or more adaptors to a nucleic acid target or target subset of nucleic acids (e.g., digested nucleic acid, enriched nucleic acid, separated nucleic acid). Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest. One or more nucleic acids can be amplified in solution or while immobilized on a solid phase. One or more nucleic acids can be amplified prior to and/or after immobilization on a solid support (e.g., a solid support in a flow cell). In some embodiments one or more nucleic acids can be amplified after release from a solid phase.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence (e.g., a target polynucleotide) is typically used in practicing the present technology, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the technology herein, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the technology herein are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

The terms "amplify", "amplification", "selective amplification", "amplification reaction", or "amplifying" refer to any in vitro process for multiplying the copies of a nucleic acid. Amplification sometimes refers to an "exponential" increase in nucleic acid. However, "amplifying" as used herein can also refer to linear increases in the numbers of a select nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, for example, and also may reduce amplification biases due to nucleotide sequence or abundance of the nucleic acid. In some embodiments a one-time primer extension may be performed as a prelude to linear or exponential amplification.

Any suitable amplification technique can be utilized. Amplification of polynucleotides include, but are not limited to, polymerase chain reaction (PCR); ligation amplification (or ligase chain reaction (LCR)); amplification methods based on the use of Q-beta replicase or template-dependent polymerase (see US Patent Publication Number US20050287592); helicase-dependent isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, digital PCR, combinations thereof, and the like. For example, amplification can be accomplished using digital PCR, in certain embodiments (see e.g. Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2; US Patent Publication No. US 20070202525). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation). Reagents and hardware for conducting PCR are commercially available.

A generalized description of a selective amplification process is presented herein. Primers (e.g., a primer pair, a collection of primer pairs) and nucleic acid (e.g., target polynucleotides) are contacted under suitable hybridization conditions, and complementary sequences anneal to one another, for example. Primers can anneal to a nucleic acid, at or near (e.g., adjacent to, abutting, and the like) a sequence of interest. In some embodiments, a primer pair hybridizes within about 10 to 30 nucleotides from a nucleic acid sequence of interest and, under amplification conditions can produce amplified products (e.g., amplicons). In some embodiments, the primers hybridize within a nucleic acid sequence of interest (e.g., a target polynucleotide).

Any suitable amplification conditions can be used to perform an amplification resulting in the production of amplicons. In some embodiments a sample comprising target polynucleotides is contacted with one or more target specific primer pairs (e.g., a collection of primers) under amplification conditions where target specific amplicons are generated. Amplification conditions often comprise a reaction mixture containing a polymerase, at least one primer (e.g., a primer pair), at least one target polynucleotide and additional components (e.g., buffers, salts and nucleotide triphosphates) necessary for polymerase activity. Non-limiting examples of components of an amplification reaction may include, but are not limited to, e.g., primers (e.g., individual primers, primer pairs, a collection of primer pairs and the like) a polynucleotide template, polymerase, nucleotides, dNTPs and the like. In some embodiments, non-naturally occurring nucleotides or nucleotide analogs, such as analogs containing a detectable label (e.g., fluorescent or colorimetric label), may be used for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "genprobe.com/pdfs/tma_whiteppr.pdf"). Other enzyme components can be added, such as reverse transcriptase for transcription mediated amplification (TMA) reactions, for example.

Amplification conditions can be dependent upon primer sequences (e.g., primer hybridization sequences), abundance of nucleic acid, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. Digital PCR is also known in the art; see, e.g., United States Patent Application Publication no. 20070202525, filed Feb. 2, 2007, which is hereby incorporated by reference). Amplification conditions often comprise a plurality of suitable temperature changes (e.g., temperature cycles) and incubation times (e.g., an incubation time for annealing, melting and extension). Amplification is typically carried out as an automated process, often in a thermocycler with a thermostable enzyme. In this process, the temperature of the reaction mixture is cycled multiple times through a denaturing step, a primer-annealing step, and an extension reaction step automatically. Some amplification protocols also include an activation step and a final extension step. Machines specifically adapted for this purpose are commercially available. A non-limiting example of a amplification protocol that may be suitable for embodiments described herein is, treating the sample at 95° C. for 5 minutes; repeating thirty-five cycles of 95° C. for 45 seconds and 68° C. for 30 seconds; and then treating the sample at 72° C. for 3 minutes. A completed amplification reaction can optionally be kept at 4° C. until further action is desired. Multiple cycles frequently are performed using a commercially available thermal cycler. Suitable isothermal amplification processes known and selected by the person of ordinary skill in the art also may be applied, in certain embodiments.

In some embodiments, an amplification product (e.g., an amplicon) may include naturally occurring nucleotides, non-naturally occurring nucleotides, nucleotide analogs and the like and combinations of the foregoing. An amplicon often has a nucleotide sequence that is identical to or substantially identical to a nucleic acid sequence herein, or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification. Nucleic acids in a sample can be enriched by an amplification method described herein. An amplification product (e.g., amplicons) can be generated before, during or after any step of a method described herein. An amplification product can be generated before, during or after a digestion or cleavage reaction. An amplification product can be generated before, during or after a modification of nucleic acids in a sample. An amplification product can be generated before, during or after an enrichment method. An amplification product can be generated before, during or after a separation or purifications step. An amplification product can be generated before, during or after a process comprising nucleic acid sequencing. In some embodiments digested nucleic acids or undigested nucleic acids are enriched by an amplification. In some embodiments enriched and/or separated nucleic acid are further enriched by an amplification. In some embodiments enriched and/or separated methylated, hypermethylated and/or hypomethylated nucleic acid are further enriched by an amplification.

Collection of Primers

In some embodiments a collection of oligonucleotide primers or primer pairs is provided herein for identifying the presence or absence of one or more differentially methylated loci (e.g., hypermethylated loci. hypomethylated loci). In some embodiments a collection of oligonucleotide primers or primer pairs is provided herein for analyzing one or more differentially methylated loci (e.g., hypermethylated loci. hypomethylated loci). In certain embodiments, a collection of primers or primer pairs is provided in a kit. In some embodiments provided herein is a method of preparing a collection of oligonucleotide primers or primer pairs for analyzing or identifying the presence or absence of one or more differentially methylated loci (e.g., hypermethylated loci. hypomethylated loci).

A collection of oligonucleotide primers or primer pairs for analyzing or identifying the presence or absence of a differentially methylated locus (e.g., a hypomethylated locus, a hypermethylated locus) can be prepared by a process comprising selecting one or more genomic loci wherein each locus comprises one or more features, non-limiting examples of which include: a size of a locus (e.g., mean, median, average, size range or absolute size); methylation status of a minority species of nucleic acid (e.g., in fetal nucleic acid; e.g., mean, median, average, limit of, span of, range of, or absolute methylation status); a mean, median, average, absolute or relative methylation status of a majority nucleic acid species (e.g., in maternal nucleic acid; e.g., mean, median, average, limit of, span of, range of, or absolute methylation status); a difference in methylation status between a minority nucleic acid species and a majority nucleic acid species; CpG density; number of CpG sites; gene density; number of restriction sites; distance and/or spacing between restriction sites for loci having two or more restriction sites; and amplicon size (e.g., mean, median, average, absolute or range of amplicon size; e.g., amplicon sizes ranging from 40-125 nucleotides in length); the like; or combinations thereof. A differentially methylated locus sometimes is selected and/or analyzed according to 2, 3, 4, 5, 6, 7, 8 or more features described herein.

For example, in some embodiments a collection of amplification primer pairs for identifying the presence or absence of a hypomethylated locus are prepared by a process comprising selecting one or more genomic loci wherein each locus comprises three or more features selected from: (i) a locus length of about 5000 contiguous base pairs, or less, (ii) a CpG density of 16 CpG methylation sites per 1000 base pairs, or less, (iii) a gene density of 0.1 genes per 1000 base pair, or less, (iv) at least 5 CpG methylation sites, (v) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases, (vi) at least 1 restriction endonuclease recognition site per 1000 base pairs, wherein the at least one restriction endonuclease recognition sites can be specifically digested by a methylation sensitive cleavage agent, (vii) a locus comprising a methylation status of 40% or less in fetal nucleic acid, (viii) a locus comprising a methylation status of 60% or more in maternal nucleic acid, and (ix) a locus comprising a difference in methylation status of 5% or more between fetal nucleic acid and maternal nucleic acid. In some embodiments a collection of amplification primer pairs for identifying the presence or absence of a hypermethylated locus are prepared by a process comprising selecting one or more genomic loci wherein each locus comprises three or more features selected from: (i) a locus length of about 5000 contiguous base pairs, or less, (ii) at least 5 CpG methylation sites, (iii) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases, (iv) at least 1 restriction endonuclease recognition site per 1000 base pairs, wherein the at least one restriction endonuclease recognition sites can be specifically digested by a methylation sensitive restriction endonuclease, (v) a locus comprising a methylation status of 60% or more in a minority nucleic acid species, (vi) a locus comprising a methylation status of 40% or less in a majority nucleic acid species, and (vii) a locus comprising a difference in methylation status of 5% or more between a minority nucleic acid species and a majority nucleic acid species.

Primer pairs are sometimes configured for use in an amplification, where each primer or primer pair is specific for a target polynucleotide located within a loci. Often a locus comprises 1, 2, 3, 4, 5, 6, 7, 8, 9 or 10 or more target polynucleotides. In some embodiments a primer pair is configured to amplify one or more target polynucleotides. In some embodiments a primer comprises a hybridization sequence that is complimentary to a portion of the target sequence which the primer is configured to amplify. In certain embodiments both of the oligonucleotide primers of a primer pair comprises a hybridization sequence that is complimentary to a portion of the target sequence which the primer pair is configured to amplify. In some embodiments a primer comprises a hybridization sequence that is complimentary to a linker (e.g., a universal linker or adapter) or portion thereof that is ligated to a target sequence which the primer is configured to amplify. In some embodiments each of the oligonucleotide primers of a primer pair comprise a different hybridization sequence. In some embodiments each of the oligonucleotide primers of a primer pair comprise the same hybridization sequence, for example, where universal linkers are ligated to a target sequence. Sometimes a target sequence, which a primer pair is configured to amplify, is longer than the combined length of the hybridization sequences of a target specific primer pair.

Target polynucleotides can be single stranded or double stranded. In some embodiments a target polynucleotide comprises a length of about 1000 nucleotides to about 20 nucleotides, about 500 nucleotides to about 30 nucleotides, about 400 nucleotides to about 30 nucleotides, about 400 nucleotides to about 40 nucleotides, about 360 nucleotides to about 40 nucleotides or about 180 nucleotides to about 40 nucleotides. In some embodiments a target polynucleotide is about 1000 base pairs (bp) or less, about 900 base pairs or less, about 800 bp or less, about 700 bp or less, about 600 bp or less, about 500 bp or less, about 400 bp or less, about 300 bp or less, or about 200 bp or less. Target polynucleotides, or portions thereof are sometimes present in circulating cell free DNA. In some embodiments a target polynucleotide is circulating cell free DNA. Circulating cell free DNA sometimes comprises a length of about 1000 nucleotides to about 20 nucleotides, about 500 nucleotides to about 30 nucleotides, about 400 nucleotides to about 30 nucleotides, about 400 nucleotides to about 40 nucleotides, about 360 nucleotides to about 40 nucleotides or about 180 nucleotides to about 40 nucleotides.

In some embodiments each target polynucleotide comprises at least one methylation sensitive restriction site. In some embodiments a collection of oligonucleotide primer pairs is configured for amplification of one or more target polynucleotides where each target polynucleotide comprises at least one methylation sensitive restriction site. In some embodiments each primer pair hybridizes to a portion of a target polynucleotide that flanks at least one methylation sensitive restriction site.

In some embodiments a collection of oligonucleotides primers or primer pairs comprises one or more oligonucleotide primers that comprise a non-native element. A primer of a collection sometimes comprises one or more non-native elements. In some embodiments a non-native element is a heterologous nucleotide sequence. In some embodiments a non-native element is an identifier. In some embodiments a non-native element is or comprises a binding agent (e.g., a member of a binding pair). In certain embodiments a non-native element is a non-native nucleotide or a nucleotide comprising a chemical modification.

In some embodiments a differentially methylated locus is identified by a process comprising (a) digesting one or more target polynucleotides of a first sample and a second sample with one or more methylation sensitive restriction endonucleases that specifically digest a target polynucleotide at restriction endonuclease sites that are unmethylated, where each of the samples comprise one or more selected loci, (b) contacting each sample with a collection of oligonucleotide primers prepared by a method described herein, under amplification conditions, thereby providing target specific amplicons of undigested target polynucleotides and analyzing the target specific amplicons from each sample. In some embodiments a differentially methylated locus is identified according to an analysis comprises comparing and/or determining an amount of target specific amplicons from each sample. The identity (e.g., nucleic acid sequence, detection of an identifier, tag or label) or amount of an amplicon can be by any suitable method (e.g., by nucleic acid sequencing, mass spectrometry, spectrophotometry, the like or combinations thereof). In some embodiments a differentially methylated locus is identified where the amount of target specific amplicons of a first sample are significantly different from an amount of target specific amplicons of a second sample. In certain embodiments nucleic acids of a first sample and a second sample are from different sources (e.g., fetal and maternal sources). Sometimes a first sample and/or a second sample comprise circulating cell free nucleic acid. Sometimes an analysis comprises comparing and/or determining a methylation status of one or more selected loci in a first sample and/or one or more selected loci in a second sample. In some embodiments a first sample comprises a minority nucleic acid species (e.g., fetal nucleic acid). In some embodiments a first sample comprises enriched fetal nucleic acid. In some embodiments a second sample comprises a majority nucleic acid species (e.g., maternal nucleic acid).

In some embodiments a differentially methylated locus (e.g., a locus hypomethylated in a minority species relative to a majority nucleic acid species) is identified where an analysis comprises identifying one or more selected loci 60% or more, 65% or more, 70% or more, 75% or more, 80% or more or 85% or more methylated in a majority nucleic acid species (e.g., maternal nucleic acid) relative to a minority nucleic acid species (e.g., fetal nucleic acid). In some embodiments a differentially methylated locus (e.g., a locus hypomethylated in a minority species relative to a majority nucleic acid species) is identified where an analysis comprises identifying one or more selected loci 45% or less, 40% or less, 35% or less, 30% or less, 25% or less, or 20% or less, 15% or less, 10% or less or 5% or less methylated in a minority nucleic acid species relative to a majority nucleic acid species. In some embodiments a differentially methylated locus (e.g., a locus hypomethylated in a minority species relative to a majority nucleic acid species) is identified where an analysis comprises identifying one or more selected loci, wherein a difference in methylation status between the minority nucleic acid species and the majority nucleic acid species for the one or more selected loci is 5% or more, 10% or more, 15% or more, 20% or more, 25% or more, 30% or more or 40% or more.

In some embodiments a differentially methylated locus (e.g., a locus hypermethylated in a minority species relative to a majority nucleic acid species) is identified where an analysis comprises identifying one or more selected loci 60% or more, 65% or more, 70% or more, 75% or more, 80% or more or 85% or more methylated in a minority nucleic acid species (e.g., fetal nucleic acid) relative to a majority nucleic acid species (e.g., maternal nucleic acid). In some embodiments a differentially methylated locus (e.g., a locus hypermethylated in a minority species relative to a majority nucleic acid species) is identified where an analysis comprises identifying one or more selected loci 45% or less, 40% or less, 35% or less, 30% or less, 25% or less, or 20% or less, 15% or less, 10% or less or 5% or less methylated in a majority nucleic acid species relative to a minority nucleic acid species. In some embodiments a differentially methylated locus (e.g., a locus hypermethylated in a minority species relative to a majority nucleic acid species) is identified where an analysis comprises identifying one or more selected loci, wherein a difference in methylation status between the minority nucleic acid species and the majority nucleic acid species for the one or more selected loci is 5% or more, 10% or more, 15% or more, 20% or more, 25% or more, 30% or more or 40% or more.

Obtaining Sequence Reads

In some embodiments analyzing nucleic acids or nucleic acid fragments comprises sequencing. In some embodiments, nucleic acids (e.g., nucleic acid fragments, digested nucleic acid fragments, sample nucleic acid, cell-free nucleic acid, enriched nucleic acid fragments, fetal nucleic acid fragments, maternal nucleic acid fragments) may be sequenced. In some embodiments, a full or substantially full sequence is obtained and sometimes a partial sequence is obtained. In some embodiments, a nucleic acid is not sequenced, and the sequence of a nucleic acid is not determined by a sequencing method, when performing a method described herein. In some embodiments, nucleic acid fragments (e.g., digested nucleic acid fragments) are sequenced with or without prior amplification as described above. In some embodiments, digested nucleic acid fragments are sequenced via ligated adaptor sequences (e.g., adaptor nucleic acids) as described above. Sequencing, mapping and related analytical methods are known in the art (e.g., United States Patent Application Publication US200910029377, incorporated by reference). Certain aspects of such processes are described hereafter.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

In some embodiments the nominal, average, mean or absolute length of single-end reads sometimes is about 20 contiguous nucleotides to about 50 contiguous nucleotides, sometimes about 30 contiguous nucleotides to about 40 contiguous nucleotides, and sometimes about 35 contiguous nucleotides or about 36 contiguous nucleotides. In some embodiments, the nominal, average, mean or absolute length of single-end reads is about 20 to about 30 bases in length. In some embodiments, the nominal, average, mean or absolute length of single-end reads is about 24 to about 28 bases in length. In some embodiments, the nominal, average, mean or absolute length of single-end reads is about 21, 22, 23, 24, 25, 26, 27, 28 or about 29 bases in length.

In certain embodiments, the nominal, average, mean or absolute length of the paired-end reads sometimes is about 10 contiguous nucleotides to about 50 contiguous nucleotides (e.g., about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), sometimes is about 15 contiguous nucleotides to about 25 contiguous nucleotides, and sometimes is about 17 contiguous nucleotides, about 18 contiguous nucleotides, about 20 contiguous nucleotides, about 25 contiguous nucleotides, about 36 contiguous nucleotides or about 45 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

Sequence reads can be mapped and the number of reads or sequence tags mapping to a specified nucleic acid region (e.g., a chromosome, a bin, a genomic section) are referred to as counts. In some embodiments, counts can be manipulated or transformed (e.g., normalized, combined, added, filtered, selected, averaged, derived as a mean, the like, or a combination thereof). In some embodiments, counts can be transformed to produce normalized counts. Normalized counts for multiple genomic sections can be provided in a profile (e.g., a genomic profile, a chromosome profile, a profile of a segment of a chromosome). One or more different elevations in a profile also can be manipulated or transformed (e.g., counts associated with elevations can be normalized) and elevations can be adjusted.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.01-fold to about 100-fold coverage, about 0.2-fold to 20-fold coverage, or about 0.2-fold to about 1-fold coverage (e.g., about 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In some embodiments an analysis comprises sequencing a portion of nucleic acids in a test sample and sometimes an analysis comprises sequencing substantially all of the nucleic acids in a test sample. In some embodiments a portion of nucleic acids in test sample comprises fetal nucleic acids (e.g., enriched fetal nucleic acids), maternal nucleic acids (e.g., enriched maternal nucleic acids), placental nucleic acids (e.g., enriched placental nucleic acids), tumor nucleic acids (e.g., enriched tumor nucleic acids), hypomethylated nucleic acids (e.g., enriched hypomethylated nucleic acids, hypomethylated loci), hypermethylated nucleic acids (e.g., enriched hypermethylated nucleic acids, hypermethylated loci), minority nucleic acids, majority nucleic acids, the like or a combination thereof. In some embodiments substantially all of an enriched nucleic acid species (e.g., enriched fetal, maternal, placental, hypomethylated, hypermethylated, or tumor nucleic acids) is sequenced. In some embodiments a portion of an enriched nucleic acid species (e.g., enriched fetal, maternal, placental, hypomethylated, hypermethylated, or tumor nucleic acids) is sequenced. In some embodiments an analysis of nucleic acids (e.g., an analysis of digested nucleic acid fragments, an analysis of enriched fetal nucleic acid) comprises targeted sequencing and/or non-targeted sequencing of nucleic acids (e.g., digested and/or enriched nucleic acids). For example, where a targeted sequencing or amplification approach is used, sometimes a portion (e.g., a selected portion) of an enriched nucleic acid species is sequenced. A selected portion can be one or more selected genes, exons, introns, promoters, loci (e.g., hypermethylated loci, hypomethylated loci, polymorphisms, alleles), chromosomes, the like, portions thereof or combinations thereof. In some embodiments modified variants of nucleic acids (e.g., modified variants of digested nucleic acids) are analyzed by targeted sequencing and/or by non-targeted sequencing.

In certain embodiments, a subset of nucleic acid fragments is selected prior to sequencing. In certain embodiments, hybridization-based techniques (e.g., using oligonucleotide arrays) can be used to first select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected set of nucleic acid fragments is sequenced randomly. In some embodiments, the nucleic acid is amplified prior to sequencing. In some embodiments, a portion or subset of the nucleic acid is amplified prior to sequencing.

In some embodiments, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In some embodiments, a ligation-based library preparation method is used (e.g., ILLUMINA TRUSEQ, Illumina, San Diego Calif.). Ligation-based library preparation methods typically use a methylated adaptor design which can incorporate an index sequence at the initial ligation step and often can be used to prepare samples for single-read sequencing, paired-end sequencing and multiplexed sequencing. In some embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template, a single DNA molecule, bin or chromosome. Next generation sequencing techniques capable of sequencing DNA in a massively parallel fashion are collectively referred to herein as "massively parallel sequencing" (MPS). High-throughput sequencing technologies include, for example, sequencing-by-synthesis with reversible dye terminators, sequencing by oligonucleotide probe ligation, pyrosequencing and real time sequencing. Non-limiting examples of MPS include Massively Parallel Signature Sequencing (MPSS), Polony sequencing, Pyrosequencing, Illumina (Solexa) sequencing, SOLiD sequencing, Ion semiconductor sequencing, DNA nanoball sequencing, Helioscope single molecule sequencing, single molecule real time (SMRT) sequencing, nanopore sequencing, ION Torrent and RNA polymerase (RNAP) sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in a method provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes can be fragmented into lengths of several hundred base pairs in preparation for library generation. In some embodiments, library preparation can be performed without further fragmentation or size selection of the template DNA (e.g., ccfDNA). Sample isolation and library generation may be performed using automated methods and apparatus, in certain embodiments. Briefly, template DNA is end repaired by a fill-in reaction, exonuclease reaction or a combination of a fill-in reaction and exonuclease reaction. The resulting blunt-end repaired template DNA is extended by a single nucleotide, which is complementary to a single nucleotide overhang on the 3' end of an adaptor primer, and often increases ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adaptor oligonucleotides are complementary to the flow-cell anchors, and sometimes are utilized to associate the modified template DNA (e.g., end-repaired and single nucleotide extended) with a solid support, such as the inside surface of a flow cell, for example. In some embodiments, the adaptor also includes identifiers (i.e., indexing nucleotides, or "barcode" nucleotides (e.g., a unique sequence of nucleotides usable as an identifier to allow unambiguous identification of a sample and/or chromosome)), one or more sequencing primer hybridization sites (e.g., sequences complementary to universal sequencing primers, single end sequencing primers, paired end sequencing primers, multiplexed sequencing primers, and the like), or combinations thereof (e.g., adaptor/sequencing, adaptor/identifier, adaptor/identifier/sequencing). Identifiers or nucleotides contained in an adaptor often are six or more nucleotides in length, and frequently are positioned in the adaptor such that the identifier nucleotides are the first nucleotides sequenced during the sequencing reaction. In certain embodiments, identifier nucleotides are associated with a sample but are sequenced in a separate sequencing reaction to avoid compromising the quality of sequence reads. Subsequently, the reads from the identifier sequencing and the DNA template sequencing are linked together and the reads de-multiplexed.

After linking and de-multiplexing the sequence reads and/or identifiers can be further adjusted or processed as described herein.

In certain sequencing by synthesis procedures, utilization of identifiers allows multiplexing of sequence reactions in a flow cell lane, thereby allowing analysis of multiple samples per flow cell lane. The number of samples that can be analyzed in a given flow cell lane often is dependent on the number of unique identifiers utilized during library preparation and/or probe design. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). A method described herein can be performed using any number of unique identifiers (e.g., 4, 8, 12, 24, 48, 96, or more). The greater the number of unique identifiers, the greater the number of samples and/or chromosomes, for example, that can be multiplexed in a single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell.

In certain sequencing by synthesis procedures, adaptor-modified, single-stranded template DNA is added to the flow cell and immobilized by hybridization to the anchors under limiting-dilution conditions. In contrast to emulsion PCR, DNA templates can be selectively amplified in a flow cell by "bridge" amplification, which relies on captured DNA strands "arching" over and hybridizing to an adjacent anchor oligonucleotide. In some embodiments digested nucleic acid fragments are amplified by a process comprising bridge amplification. Multiple amplification cycles convert the single-molecule DNA template to a clonally amplified arching "cluster," with each cluster containing approximately 1000 clonal molecules. Approximately $50 \times 10^6$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adaptor sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50 \times 10^6$ clusters per flow cell, the overall sequence output can be greater than 1 billion base pairs (Gb) per analytical run.

Another nucleic acid sequencing technology that may be used with a method described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in a method provided herein is Applied Biosystems' SOLiD™ technology. In SOLiD™ sequencing-by-ligation, a library of nucleic acid fragments is prepared from the sample and is used to prepare clonal bead populations. With this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adaptors are typically universal adaptor sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adaptor sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1. Another nucleic acid sequencing technology that may be used in a method described herein is the Helicos True Single Molecule Sequencing (tSMS). In the tSMS technique, a poly-A sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/ $cm^2$. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in a method provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Additional non-limiting examples of a nucleic acid sequencing technology and/or nucleic acid amplification method that may be used herein include Avalanche™ (Life Technologies) and WildFire (e.g., Life Technologies, US patent publication US20130012399). Avalanche and Wild-Fire are examples of sequencing technologies that utilize solid phase nucleic acid amplification reactions. In some embodiments solid phase nucleic acid amplification methods (e.g., Avalanche™ and Wildfire) produce clusters of like amplicons on a solid phase that are sometimes referred to herein as cluster generation methods.

Another nucleic acid sequencing technology that may be used in a method described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in a method described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Application Publication No. 2009/0026082).

Another nucleic acid sequencing technology that may be used in a method described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M., PNAS USA. 1965 March; 53:564-71). In some embodiments, transmission electron microscopy (TEM) is used (e.g. Halcyon Molecular's TEM method). This method, termed Individual Molecule Placement Rapid Nano Transfer (IM-PRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, International Patent Application No. WO 2009/046445).

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore. A nanopore is a small hole or channel, of the order of 1 nanometer in diameter. Certain transmembrane cellular proteins can act as nanopores (e.g. alpha-hemolysin). Nanopores sometimes can be synthesized (e.g. using a silicon platform). Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or in some instances, methyl-C. The change in the current through the nanopore as the DNA molecule passes through the nanopore represents a direct reading of the DNA sequence. A nanopore sometimes can be used to identify individual DNA bases as they pass through the nanopore in the correct order (see, for example, Soni G V and Meller A. Clin. Chem. 53: 1996-2001 (2007); International Patent Application No. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. The exonuclease enzyme sometimes can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling a target polynucleotide through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median, mode or average length of about 1000 bp or more.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligo to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Mapping Reads

Mapping nucleotide sequence reads (i.e., sequence information from a fragment whose physical genomic position is unknown) can be performed in a number of ways, and often comprises alignment of the obtained sequence reads with a matching sequence in a reference genome (e.g., Li et al., "Mapping short DNA sequencing reads and calling variants using mapping quality score," Genome Res., 2008 Aug. 19.) In such alignments, sequence reads generally are aligned to a reference sequence and those that align are designated as being "mapped" or a "sequence tag." In some embodiments, a mapped sequence read is referred to as a "hit". In some embodiments, mapped sequence reads are grouped together according to various parameters and assigned to particular genome sections, which are discussed in further detail below.

Various computational methods can be used to map each sequence read to a genome section. Non-limiting examples of computer algorithms that can be used to align sequences include BLAST, BLITZ, and FASTA, or variations thereof. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate genome sections (described hereafter), for example.

A "sequence tag" is a nucleic acid (e.g. DNA) sequence (i.e. read) assigned specifically to a particular genome section and/or chromosome (i.e. one of chromosomes 1-22, X or Y for a human subject). A sequence tag may be repetitive or non-repetitive within a single portion of the reference genome (e.g., a chromosome). In some embodiments, repetitive sequence tags are eliminated from further analysis (e.g. quantification). In some embodiments, a read may uniquely or non-uniquely map to portions in the reference genome. A read is considered "uniquely mapped" if it aligns with a single sequence in the reference genome. A read is considered "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, a reference sequence or reference genome often is an assembled or partially assembled genomic sequence from an individual or multiple individuals. In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

Genomic Sections

In some embodiments, mapped sequence reads (i.e. sequence tags) are grouped together according to various parameters and assigned to particular genomic sections. Often, the individual mapped sequence reads can be used to identify an amount of a genomic section present in a sample. In some embodiments, the amount of a genomic section can be indicative of the amount of a larger sequence (e.g. a chromosome) in the sample. The term "genomic section" can also be referred to herein as a "sequence window", "section", "bin", "locus", "region", "partition", "portion" (e.g., portion of a reference genome, portion of a chromosome) or "genomic portion." In some embodiments, a genomic section is an entire chromosome, portion of a chromosome, portion of a reference genome, multiple chromosome portions, multiple chromosomes, portions from multiple chromosomes, and/or combinations thereof. In some embodiments, a genomic section is predefined based on specific parameters. In some embodiments, a genomic section is arbitrarily defined based on partitioning of a genome (e.g., partitioned by size, portions, contiguous regions, contiguous regions of an arbitrarily defined size, and the like).

In some embodiments, a genomic section is delineated based on one or more parameters which include, for example, length or a particular feature or features of the sequence. Genomic sections can be selected, filtered and/or removed from consideration using any suitable criteria know in the art or described herein. In some embodiments, a genomic section is based on a particular length of genomic sequence. In some embodiments, a method can include analysis of multiple mapped sequence reads to a plurality of genomic sections. Genomic sections can be approximately the same length or the genomic sections can be different lengths. In some embodiments, genomic sections are of about equal length. In some embodiments genomic sections of different lengths are adjusted or weighted. In some embodiments, a genomic section is about 10 kilobases (kb) to about 100 kb, about 20 kb to about 80 kb, about 30 kb to about 70 kb, about 40 kb to about 60 kb, and sometimes about 50 kb. In some embodiments, a genomic section is about 10 kb to about 20 kb. A genomic section is not limited to contiguous runs of sequence. Thus, genomic sections can be made up of contiguous and/or non-contiguous sequences. A genomic section is not limited to a single chromosome. In some embodiments, a genomic section includes all or part of one chromosome or all or part of two or more chromosomes. In some embodiments, genomic sections may span one, two, or more entire chromosomes. In addition, the genomic sections may span joint or disjointed portions of multiple chromosomes.

In some embodiments, genomic sections can be particular chromosome portion in a chromosome of interest, such as, for example, chromosomes where a genetic variation is assessed (e.g. an aneuploidy of chromosomes 13, 18 and/or 21 or a sex chromosome). A genomic section can also be a pathogenic genome (e.g. bacterial, fungal or viral) or fragment thereof. Genomic sections can be genes, gene fragments, regulatory sequences, introns, exons, and the like.

In some embodiments, a genome (e.g. human genome) is partitioned into genomic sections based on the information content of the regions. The resulting genomic regions may contain sequences for multiple chromosomes and/or may contain sequences for portions of multiple chromosomes. In some embodiments, the partitioning may eliminate similar locations across the genome and only keep unique regions. The eliminated regions may be within a single chromosome or may span multiple chromosomes. The resulting genome is thus trimmed down and optimized for faster alignment, often allowing for focus on uniquely identifiable sequences.

In some embodiments, the partitioning may down weight similar regions. The process for down weighting a genomic section is discussed in further detail below. In some embodiments, the partitioning of the genome into regions transcending chromosomes may be based on information gain produced in the context of classification. For example, the information content may be quantified using the p-value profile measuring the significance of particular genomic locations for distinguishing between groups of confirmed normal and abnormal subjects (e.g. euploid and trisomy subjects, respectively). In some embodiments, the partitioning of the genome into regions transcending chromosomes may be based on any other criterion, such as, for example, speed/convenience while aligning tags, high or low GC content, uniformity of GC content, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual bins, and/or a targeted search for particular features. A "segment" of a chromosome generally is part of a chromosome, and typically is a different part of a chromosome than a genomic section (e.g., bin). A segment of a chromosome sometimes is in a different region of a chromosome than a genomic section, sometimes does not share a polynucleotide with a genomic section, and sometimes includes a polynucleotide that is in a genomic section. A segment of a chromosome often contains a larger number of nucleotides than a genomic section (e.g., a segment sometimes includes a genomic section), and sometimes a segment of a chromosome contains a smaller number of nucleotides than a genomic section (e.g., a segment sometimes is within a genomic section).

Outcomes and Determination of the Presence or Absence of a Genetic Variation

Some genetic variations are associated with medical conditions. Genetic variations often include a gain, a loss, and/or alteration (e.g., reorganization or substitution) of genetic information (e.g., chromosomes, portions of chromosomes, polymorphic regions, translocated regions, altered nucleotide sequence, the like or combinations of the foregoing) that result in a detectable change in the genome or genetic information of a test subject with respect to a reference subject free of the genetic variation. The presence or absence of a genetic variation can be determined by analyzing and/or manipulating enriched nucleic acids. In some embodiments, the presence or absence of a genetic variation can be determined by analyzing and/or manipulating sequence reads that have been mapped to genomic sections (e.g., genomic bins) as described herein.

An analysis can be a target-based analysis (e.g., targeted analysis) or a non-target-based analysis (e.g., non-targeted). A target-based analysis generally comprises analysis (e.g., sequencing, quantitation) of selected nucleic acids or a selected subset of nucleic acids (e.g., a subpopulation of nucleic acids). In some embodiments a selective nucleic acid subset comprises selected genes, selected loci (e.g., hypomethylated loci, hypermethylated loci), selected alleles (e.g., selected polymorphisms), nucleic acids derived from one or more selected chromosomes, selected fetal nucleic acids, the like or combinations thereof. In some embodiments a target-bases analysis comprises a suitable target specific amplification or sequencing method. A target-based analysis generally comprises use of one or more sequence-specific oligonucleotides (e.g., primers or capture agents) that hybridize to specific selected nucleic acid sequences that are expected and/or known to exist in a test sample (e.g., an unmanipulated sample isolated from a test subject). A non-target-based analysis generally does not comprise a sequence-specific selection process or utilizes oligonucleotides that hybridize to specific selected nucleic acid sequences that are expected and/or known to exist in a test sample. In some embodiments a non-target-based analysis utilizes adaptors and/or adaptor specific primers to amplify and/or sequence nucleic acids or a subset of nucleic acids in a test sample. For example, a non-target-based analysis sometimes comprises ligation of adaptors and/or hybridization of primers to sticky ends that results from restriction enzyme cleavage followed by a suitable capture, primer extension, amplification and/or sequencing method.

Counting

Sequence reads that have been mapped or partitioned based on a selected feature or variable can be quantified to determine the number of reads that were mapped to each genomic section (e.g., bin, partition, genomic segment and the like), in some embodiments. In certain embodiments, the total number of mapped sequence reads is determined by counting all mapped sequence reads, and in some embodiments the total number of mapped sequence reads is determined by summing counts mapped to each bin or partition. In certain embodiments, a subset of mapped sequence reads is determined by counting a predetermined subset of mapped sequence reads, and in some embodiments a predetermined subset of mapped sequence reads is determined by summing counts mapped to each predetermined bin or partition. In some embodiments, predetermined subsets of mapped sequence reads can include from 1 to n−1 sequence reads, where n represents a number equal to the sum of all sequence reads generated from a test subject or reference subject sample. In certain embodiments, predetermined subsets of mapped sequence reads can be selected utilizing any suitable feature or variable.

Quantifying or counting sequence reads can be done in any suitable manner including but not limited to manual counting methods and automated counting methods. In some embodiments, an automated counting method can be embodied in software that determines or counts the number of sequence reads or sequence tags mapping to each chromosome and/or one or more selected genomic sections. As used herein, software refers to computer readable program instructions that, when executed by a computer, perform computer operations.

The number of sequence reads mapped to each bin and the total number of sequence reads for samples derived from test subject and/or reference subjects can be further analyzed and processed to provide an outcome determinative of the presence or absence of a genetic variation. Mapped sequence reads that have been counted sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, genomic section or bin specific], the like and combinations thereof). In certain embodiments, data or data sets can be organized into a matrix having two or more dimensions based on one or more features of variables. Data organized into matrices can be stratified using any suitable features or variables. A non-limiting example of data organized into a matrix includes data that is stratified by maternal age, maternal ploidy, and fetal contribution. In certain embodiments, data sets characterized by one or more features or variables sometimes are processed after counting.

In some embodiments nucleic acids are analyzed. Sometimes enriched nucleic acids, digested nucleic acids, ligated nucleic acids and/or amplified nucleic acids are analyzed. In some embodiments analyzing nucleic acids comprises generating sequencing reads, mapping sequence reads, counting sequencing reads, processing sequencing reads, processing sequencing counts or a combination thereof.

Data Processing

Mapped sequence reads that have been counted are referred to herein as raw data, since the data represent unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative genomic sections or bins (e.g., bins with uninformative data, redundant mapped reads, genomic sections or bins with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments.

The term "noisy data" as used herein refers to (a) data that has a significant variance between data points when analyzed or plotted, (b) data that has a significant standard deviation, (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative bins", and "uninformative genomic sections" as used herein refer to genomic sections, or data derived therefrom, having a numerical value that is significantly different from a predetermined cutoff threshold value or falls outside a predetermined cutoff range of values. A cutoff threshold value or range of values often is calculated by mathematically and/or statistically manipulating sequence read data (e.g., from a reference and/or subject), in some embodiments, and in certain embodiments, sequence read data manipulated to generate a threshold cutoff value or range of values is sequence read data (e.g., from a reference and/or subject). In some embodiments, a threshold cutoff value is obtained by calculating the standard deviation and/or median absolute deviation (e.g., MAD) of a raw or normalized count profile and multiplying the standard deviation for the profile by a constant representing the number of standard deviations chosen as a cutoff threshold (e.g., multiply by 3 for 3 standard deviations), whereby a value for an uncertainty is generated. In certain embodiments, a portion or all of the genomic sections exceeding the calculated uncertainty threshold cutoff value, or outside the range of threshold cutoff values, are removed as part of, prior to, or after the normalization process. In some embodiments, a portion or all of the genomic sections exceeding the calculated uncertainty threshold cutoff value, or outside the range of threshold cutoff values or raw data points, are weighted as part of, or prior to the normalization or classification process. Examples of weighting are described herein. The terms "redundant data", and "redundant mapped reads" as used herein refer to sample derived sequences reads that are identified as having already been assigned to a genomic location (e.g., base position) and/or counted for a genomic section.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set. In some embodiments, one or more processing steps can comprise one or more filtering steps.

The term "filtering" as used herein refers to removing genomic sections or bins from consideration. Bins can be selected for removal based on any suitable criteria, including but not limited to redundant data (e.g., redundant or overlapping mapped reads), non-informative data (e.g., bins with zero median counts), bins with over represented or under represented sequences, noisy data, the like, or combinations of the foregoing. A filtering process often involves removing one or more bins from consideration and subtracting the counts in the one or more bins selected for removal from the counted or summed counts for the bins, chromosome or chromosomes, or genome under consideration. In some embodiments, bins can be removed successively (e.g., one at a time to allow evaluation of the effect of removal of each individual bin), and in certain embodiments all bins marked for removal can be removed at the same time.

In some embodiments, one or more processing steps can comprise one or more normalization steps. The term "normalization" as used herein refers to division of one or more data sets by a predetermined variable. Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference genomic sections to the total number of counts mapped to the chromosome or the entire genome on which the selected genomic section or sections are mapped; normalizing raw count data for one or more selected genomic segments to a median reference count for one or more genomic sections or the chromosome on which a selected genomic segment or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more genomic sections or bins, based on the quality or usefulness of the data in the selected bin or bins). A weighting function can be used to increase the influence of data with a relatively small measurement variance, and/or to decrease the influence of data with a relatively large measurement variance, in some embodiments. For example, bins with under represented or low quality sequence data can be "down weighted" to minimize the influence on a data set, whereas selected bins can be "up weighted" to increase the influence on a data set. A non-limiting example of a weighting function is [1/(standard deviation)$^2$]. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak elevations, determination of peak edge locations, calculation of peak area ratios, analysis of median chromosomal elevation, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median elevations, mean elevations, count distribution within a genomic region, relative representation of nucleic acid species, the like or combinations thereof.

In some embodiments, a processing step can include the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median elevations, mean elevations, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to mathematical and/or statistical manipulation of data that facilitates identification of patterns and/or correlations in large quantities of data. Thus, the term "profile" as used herein often refers to values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a portion or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a genomic section. In certain embodiments, a data point in a profile represents the results of data manipulation for groups of genomic sections. In some embodiments, groups of genomic sections may be adjacent to one another, and in certain embodiments, groups of genomic sections may be from different parts of a chromosome or genome.

Data points in a profile derived from a data set can be representative of any suitable data categorization. Non-limiting examples of categories into which data can be grouped to generate profile data points include: genomic sections based on sized, genomic sections based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile frequently is presented as a plot, and non-limiting examples of profile plots that can be generated include raw count (e.g., raw count profile or raw profile), normalized count (e.g., normalized count profile or normalized profile), bin-weighted, z-score, p-value, area ratio versus fitted ploidy, median elevation versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median elevation versus ratio between fitted and measured fetal fraction, principle components). The terms "raw count profile plot" or "raw profile plot" as used herein refer to a plot of counts in each genomic section in a region normalized to total counts in a region (e.g., genome, chromosome, portion of chromosome).

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected genomic section is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, genomic sections or portions thereof from a set of references known not to carry a genetic variation, (b) removal of uninformative genomic sections from the reference sample raw counts (e.g., filtering); (c) normalizing the reference counts for all remaining bins to the total residual number of counts (e.g., sum of remaining counts after removal of uninformative bins) for the reference sample selected chromosome or selected genomic location, thereby generating a normalized reference subject profile; (d) removing the corresponding genomic sections from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered genomic sections in (b), can be included between (c) and (d).

In some embodiments, the use of one or more reference samples known to be free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected genomic section or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected genomic section or sections is expected to vary significantly from the predetermined value for affected genomic locations.

In some embodiments, analysis and processing of data can include the use of one or more assumptions. Any suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion or genomic deletion; represent the presence or absence of a variation in the physical amount of a sequence associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). Any suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Mass Spectrometry

In some embodiments a mass spectrometer is used to analyze nucleic acids and/or enriched nucleic acids (e.g., enriched fetal or maternal nucleic acids). Analysis of nucleic acids by a mass spectrometer can be a target-based analysis or a non-target based analysis. In some embodiments a mass spectrometer is used quantify nucleic acids and/or specific subsets (e.g., subpopulations) of nucleic acids. In some embodiments a mass spectrometer is used to detect, measure and/or quantify an identifier (e.g., a sequence tag, a label, a mass tag) associated with a selected subset or subpopulation of nucleic acids or associated with a specific target polynucleotide. In some embodiments detection, identification and/or quantitation of a target polynucleotide (e.g., a specific polynucleotide, a target comprising a tag) is determined by mass spectrometry (e.g., by a target-based analysis). In certain embodiments, a sequence of an oligonucleotide or polynucleotide is determined by a mass spectrometer. Mass spectrometry methods typically are used to determine the mass of a molecule, such as a nucleic acid fragment, sequence tag or an identifier. In some embodiments, the length and/or the sequence of a nucleic acid fragment (e.g., a sequence tag) can be extrapolated from the mass of a fragment, tag or a fragment comprising a tag. In some embodiments, the length and/or the sequence of a first nucleic acid fragment and/or a first sequence tag can be extrapolated from the mass of a second nucleic acid fragment that hybridizes to the first fragment or tag. In some embodiments, presence of a target and/or reference nucleic acid of a given length and/or sequence can be verified by comparing the mass of the detected signal with the expected mass of the target and/or a reference fragment. The relative signal strength, e.g., mass peak on a spectra, for a particular nucleic acid fragment and/or fragment length sometimes can indicate the relative population of the fragment species amongst other nucleic acids in a sample (see e.g., Jurinke et al. (2004) Mol. Biotechnol. 26, 147-164).

Mass spectrometry generally works by ionizing chemical compounds to generate charged molecules or molecule fragments and measuring their mass-to-charge ratios. A typical mass spectrometry procedure involves several steps, including (1) loading a sample onto the mass spectrometry instrument followed by vaporization, (2) ionization of the sample components by any one of a variety of methods (e.g., impacting with an electron beam), resulting in charged particles (ions), (3) separation of ions according to their mass-to-charge ratio in an analyzer by electromagnetic fields, (4) detection of ions (e.g., by a quantitative method), and (5) processing of the ion signal into mass spectra.

Mass spectrometry methods are well known in the art (see, e.g., Burlingame et al. Anal. Chem. 70:647R-716R (1998)), and include, for example, quadrupole mass spectrometry, ion trap mass spectrometry, time-of-flight mass spectrometry, gas chromatography mass spectrometry and tandem mass spectrometry can be used with the methods described herein. The basic processes associated with a mass spectrometry method are the generation of gas-phase ions derived from the sample, and the measurement of their mass. The movement of gas-phase ions can be precisely controlled using electromagnetic fields generated in the mass spectrometer. The movement of ions in these electromagnetic fields is proportional to the m/z (mass to charge ratio) of the ion and this forms the basis of measuring the m/z and therefore the mass of a sample. The movement of ions in these electromagnetic fields allows for the containment and focusing of the ions which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as $R=m/delta\ m$, where m is the ion mass and delta m is the difference in mass between two peaks in a mass spectrum. For example, a mass spectrometer with a resolution of 1000 can resolve an ion with a m/z of 100.0 from an ion with a m/z of 100.1. Certain mass spectrometry methods can utilize various combinations of ion sources and mass analyzers which allows for flexibility in designing customized detection protocols. In some embodiments, mass spectrometers can be programmed to transmit all ions from the ion source into the mass spectrometer either sequentially or at the same time. In some embodiments, a mass spectrometer can be programmed to select ions of a particular mass for transmission into the mass spectrometer while blocking other ions.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Mass analyzers include, for example, a quadrupole mass filter, ion trap mass analyzer and time-of-flight mass analyzer.

The ion formation process is a starting point for mass spectrum analysis. Several ionization methods are available and the choice of ionization method depends on the sample used for analysis. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix (e.g., 2,5-dihydroxybenzoic acid, alpha-cyano-4-hydroxycinammic acid, 3-hydroxypicolinic acid (3-HPA), di-ammoniumcitrate (DAC) and combinations thereof). Other ionization procedures known in the art include, for example, plasma and glow discharge, plasma desorption ionization, resonance ionization, and secondary ionization.

A variety of mass analyzers are available that can be paired with different ion sources. Different mass analyzers have different advantages as known in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Ion mobility mass (IM) spectrometry is a gas-phase separation method. IM separates gas-phase ions based on their collision cross-section and can be coupled with time-of-flight (TOF) mass spectrometry. IM-MS is discussed in more detail by Verbeck et al. in the Journal of Biomolecular Techniques (Vol 13, Issue 2, 56-61).

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering.

A quadrupole mass analyzer, as well as the other mass analyzers described herein, can be programmed to analyze a defined m/z or mass range. Since the desired mass range of nucleic acid fragment is known, in some instances, a mass spectrometer can be programmed to transmit ions of the projected correct mass range while excluding ions of a higher or lower mass range. The ability to select a mass range can decrease the background noise in the assay and thus increase the signal-to-noise ratio. Thus, in some instances, a mass spectrometer can accomplish a separation step as well as detection and identification of certain mass-distinguishable nucleic acid fragments.

Ion trap mass spectrometry utilizes an ion trap mass analyzer. Typically, fields are applied such that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector.

Mass analysis can be accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. Control of the number of ions can be accomplished by varying the time over which ions are injected into the trap.

Time-of-flight mass spectrometry utilizes a time-of-flight mass analyzer. Typically, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

Gas chromatography mass spectrometry often can analyze a target in real-time. The gas chromatography (GC) portion of the system separates the chemical mixture into pulses of analyte and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans.

Any suitable mass spectrometer, mass spectrometer format, configuration or technology described herein or known in the art can be used to perform a method described herein, non-limiting examples of which include Matrix-Assisted Laser Desorption/Ionization Time-of-Flight (MALDI-TOF) Mass Spectrometry (MS), Laser Desorption Mass Spectrometry (LDMS), Electrospray (ES) MS, Ion Cyclotron Resonance (ICR) MS, Fourier Transform MS, inductively coupled plasma-mass spectrometry (ICP-MS), accelerator mass spectrometry (AMS), thermal ionization-mass spectrometry (TIMS), spark source mass spectrometry (SSMS) and the like.

For quantification, controls may be used which can provide a signal in relation to the amount of the nucleic acid fragment, for example, that is present or is introduced. A control to allow conversion of relative mass signals into absolute quantities can be accomplished by addition of a known quantity of a mass tag or mass label to each sample before detection of the nucleic acid fragments. See for example, Ding and Cantor (2003) PNAS USA March 18; 100(6):3059-64. Any mass tag that does not interfere with detection of the fragments can be used for normalizing the mass signal. Such standards typically have separation properties that are different from those of any of the molecular tags in the sample, and could have the same or different mass signatures.

A separation step sometimes can be used to remove salts, enzymes, or other buffer components from the nucleic acid sample. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. Salts sometimes can absorb energy from the laser in matrix-assisted laser desorption/ionization and result in lower ionization efficiency. Thus, the efficiency of matrix-assisted laser desorption/ionization and electrospray ionization sometimes can be improved by removing salts from a sample.

Enriched Nucleic Acids

Nucleic acid subsets or subpopulations (e.g., enriched nucleic acid (e.g., an enriched minority nucleic acid species, enriched hypomethylated nucleic acid, enriched fetal nucleic acid, the like or combinations thereof)) that are enriched and/or separated by a method described herein can be analyzed by any suitable analytical method. Non-limiting examples of an analytical methods that can use or analyze enriched nucleic acid include sequencing (e.g., any suitable type of nucleic acid sequencing (e.g., nanopore sequencing), any suitable method of obtaining sequence reads), genetic testing (e.g., gene detection, mutation detection, SNP detection, fetal screening, gender determination and the like), promoter analysis, pathogen analysis (e.g., viral detection and analysis), hybridization studies, cancer analysis (e.g., cancer screening), personalized medicine, cloning, gene therapy, genetic comparison studies (e.g., comparing SNPs between samples), the like or combinations thereof.

Outcome

Enriched nucleic acid (e.g., an enriched minority nucleic acid species, enriched hypomethylated nucleic acid, enriched fetal nucleic acid, the like or combinations thereof) can be used to determine the presence or absence of a genetic variation. A determination of the presence or absence of a genetic variation (e.g., fetal aneuploidy) can be generated for a sample (e.g., for an enriched nucleic acid), thereby providing an outcome (e.g., thereby providing an outcome determinative of the presence or absence of a genetic variation (e.g., fetal aneuploidy)) by a suitable method or by a method described here. Methods of determining the presence or absence of a genetic variation (e.g., a fetal aneuploidy) from sequence reads of ccf DNA obtained from a pregnant female are described, for example, in U.S. Patent Application Publication No. 20130085681 (published on Apr. 4, 2013, entitled "METHODS AND PROCESSES FOR NON-INVASIVE ASSESSMENT OF GENETIC VARIATIONS" naming Cosmin Deciu, Zeljko Dzakula, Mathias Ehrich and Sung Kyun Kim as inventors). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to genomic sections (e.g., genomic bins).

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. Sometimes methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to genomic sections of a reference genome. Counts of sequence reads utilized to determine presence or absence of a genetic variation sometimes are raw counts and/or filtered counts, and often are normalized counts. A suitable normalization process or processes can be used to generate normalized counts, non-limiting examples of which include bin-wise normalization, normalization by GC content, linear and nonlinear least squares regression, LOESS, GC LOESS, LOWESS, PERUN, RM, GCRM and combinations thereof. Normalized counts sometimes are expressed as one or more levels or elevations in a profile for a particular set or sets of genomic sections. Normalized counts sometimes are adjusted or padded prior to determining presence or absence of a genetic variation.

Presence or absence of a genetic variation (e.g., fetal aneuploidy) sometimes is determined without comparing counts for a set of genomic sections to a reference. Counts measured for a test sample and are in a test region (e.g., a set of genomic sections of interest) are referred to as "test counts" herein. Test counts sometimes are processed counts, averaged or summed counts, a representation, normalized counts, or one or more levels or elevations, as described herein. Sometimes test counts are averaged or summed (e.g., an average, mean, median, mode or sum is calculated) for a set of genomic sections, and the averaged or summed counts are compared to a threshold or range. Test counts sometimes are expressed as a representation, which can be expressed as a ratio or percentage of counts for a first set of genomic sections to counts for a second set of genomic sections. Sometimes the first set of genomic sections is for one or more test chromosomes (e.g., chromosome 13, chromosome 18, chromosome 21, or combination thereof) and sometimes the second set of genomic sections is for the genome or a part of the genome (e.g., autosomes or autosomes and sex chromosomes). Sometimes a representation is compared to a threshold or range. Sometimes test counts are expressed as one or more levels or elevations for normalized counts over a set of genomic sections, and the one or more levels or elevations are compared to a threshold or range. Test counts (e.g., averaged or summed counts, representation, normalized counts, one or more levels or elevations) above or below a particular threshold, in a particular range or outside a particular range sometimes are determinative of the presence of a genetic variation or lack of euploidy (e.g., not euploidy). Test counts (e.g., averaged or summed counts, representation, normalized counts, one or more levels or elevations) below or above a particular threshold, in a particular range or outside a particular range sometimes are determinative of the absence of a genetic variation or euploidy.

Presence or absence of a genetic variation (e.g., fetal aneuploidy) sometimes is determined by comparing test counts (e.g., raw counts, filtered counts, averaged or summed counts, representation, normalized counts, one or more levels or elevations, for a set of genomic sections) to a reference. A reference can be a suitable determination of counts. Counts for a reference sometimes are raw counts, filtered counts, averaged or summed counts, representation, normalized counts, one or more levels or elevations, for a set of genomic sections. Reference counts often are counts for a euploid test region.

In certain embodiments, test counts sometimes are for a first set of genomic sections and a reference includes counts for a second set of genomic sections different than the first set of genomic sections. Reference counts sometimes are for a nucleic acid sample from the same pregnant female from which the test sample is obtained. Sometimes reference counts are for a nucleic acid sample from one or more pregnant females different than the female from which the test sample was obtained. In some embodiments, a first set of genomic sections is in chromosome 13, chromosome 18, chromosome 21, segment thereof or combination of the foregoing, and the second set of genomic sections is in another chromosome or chromosomes or segment thereof. In a non-limiting example, where a first set of genomic sections is in chromosome 21 or segment thereof, a second set of genomic sections often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of deviation between the test counts and the reference counts can be generated.

Sometimes a reference comprises counts for the same set of genomic sections as for the test counts, where the counts for the reference are from one or more reference samples (e.g., often multiple reference samples from multiple reference subjects). A reference sample often is from one or more pregnant females different than the female from which a test sample is obtained. A measure of deviation between the test counts and the reference counts can be generated.

A suitable measure of deviation between test counts and reference counts can be selected, non-limiting examples of which include standard deviation, average absolute deviation, median absolute deviation, maximum absolute deviation, standard score (e.g., z-value, z-score, normal score, standardized variable) and the like. In some embodiments, reference samples are euploid for a test region and deviation between the test counts and the reference counts is assessed. A deviation of less than three between test counts and reference counts (e.g., 3-sigma for standard deviation) often is indicative of a euploid test region (e.g., absence of a genetic variation). A deviation of greater than three between test counts and reference counts often is indicative of a non-euploid test region (e.g., presence of a genetic variation). Test counts significantly below reference counts, which reference counts are indicative of euploidy, sometimes are determinative of a monosomy. Test counts significantly above reference counts, which reference counts are indicative of euploidy, sometimes are determinative of a trisomy. A measure of deviation between test counts for a test sample and reference counts for multiple reference subjects can be plotted and visualized (e.g., z-score plot).

Any other suitable reference can be factored with test counts for determining presence or absence of a genetic variation (or determination of euploid or non-euploid) for a test region of a test sample. For example, a fetal fraction determination can be factored with test counts to determine the presence or absence of a genetic variation. A suitable process for quantifying fetal fraction can be utilized, non-limiting examples of which include a mass spectrometric process, sequencing process or combination thereof.

Laboratory personnel (e.g., a laboratory manager) can analyze values (e.g., test counts, reference counts, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Table 1). In some cases a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis).

Analysis and processing of data can provide one or more outcomes. In some embodiments an analysis (e.g., an analysis of nucleic acids) comprises determining an outcome. The term "outcome" as used herein refers to a result of data processing that facilitates determining whether a subject was, or is at risk of having, a genetic variation. An outcome often comprises one or more numerical values generated using a processing method described herein in the context of one or more considerations of probability. A consideration of probability includes but is not limited to: measure of variability, confidence level, sensitivity, specificity, standard deviation, coefficient of variation (CV) and/or confidence level, Z-scores, Chi values, Phi values, ploidy values, fitted fetal fraction, area ratios, median elevation, the like or combinations thereof. A consideration of probability can facilitate determining whether a subject is at risk of having, or has, a genetic variation, and an outcome determinative of a presence or absence of a genetic disorder often includes such a consideration.

An outcome often is a phenotype with an associated level of confidence (e.g., fetus is positive for trisomy 21 with a confidence level of 99%, test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or genomic section from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a profile. In those embodiments in which an outcome comprises a profile, any suitable profile or combination of profiles can be used for an outcome. Non-limiting examples of profiles that can be used for an outcome include z-score profiles, p-value profiles, chi value profiles, phi value profiles, the like, and combinations thereof An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in any suitable form, which form comprises without limitation, a probability (e.g., odds ratio, p-value), likelihood, value in or out of a cluster, value over or under a threshold value, value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. An outcome also can describe any assumptions used in data processing. In certain embodiments, an outcome comprises a value that falls within or outside a predetermined range of values and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative. The term "sensitivity" as used herein refers to the number of true positives divided by the number of true positives plus the number of false negatives, where sensitivity (sens) may be within the range of $0 \leq sens \leq 1$. Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \leq spec \leq 1$. Ideally, the number of false positives equal zero or close to zero, so that no subject is wrongly identified as having at least one genetic variation when they do not have the genetic variation being assessed.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein.

A method that has sensitivity and specificity equaling one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

After one or more outcomes have been generated, an outcome often is used to provide a determination of the presence or absence of a genetic variation and/or associated medical condition. An outcome typically is provided to a health care professional (e.g., laboratory technician or manager; physician or assistant). In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in any suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing.

In some embodiments, presence or absence of a genetic variation (e.g., chromosome aneuploidy) is determined for a fetus. In such embodiments, presence or absence of a fetal genetic variation (e.g., fetal chromosome aneuploidy) is determined. In some embodiments an analysis (e.g., an analysis of nucleic acids) comprises determining the presence or absence of one or more genetic variations (e.g., in a fetus). In some embodiments an analysis comprises determining the presence or absence of one or more chromosome aneuploidies (e.g., a fetal aneuploidy). In some embodiments a fetal aneuploidy is a trisomy. In some embodiments a fetal trisomy is a trisomy of chromosome 13, 18, and/or 21.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by any communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by any other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to any method for obtaining such information, including, without limitation, obtaining the information from a laboratory file. A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

A healthcare professional or qualified individual, can provide any suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Software can be used to perform one or more steps in the process described herein, including but not limited to; counting, data processing, generating an outcome, and/or providing one or more recommendations based on generated outcomes.

Machines, Software and Interfaces

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by any suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, any suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by any suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., data acquisition module, data processing module, data display module). The term "software" refers to computer readable program instructions that, when executed by a computer, perform computer operations. The term "module" refers to a self-contained functional unit that can be used in a larger software system. For example, a software module is a part of a program that performs a particular process or task.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software.

Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium (e.g., a non-transitory storage medium) having a computer readable program code embodied therein, the computer readable program code adapted to be executed to implement a method comprising: (a) obtaining nucleotide sequence reads from a sample comprising circulating, cell-free nucleic acid from a pregnant female, where the sample has been enriched for fetal nucleic acid, (b) mapping the nucleotide sequence reads to reference genome sections, (c) counting the number of nucleotide sequence reads mapped to each reference genome section, (d) comparing the number of counts of the nucleotide sequence reads mapped in (c), or derivative thereof, to a reference, or portion thereof, thereby making a comparison, and (e) determining the presence or absence of a fetal aneuploidy based on the comparison.

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Pen, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for providing an outcome determinative of the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Genetic Variations and Medical Conditions

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms (SNPs)), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In some embodiments, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In some embodiments, a duplication is a mutation (e.g., a genetic aberration) in which a part of a chromosome or a sequence of DNA is copied and inserted back into the genome. In some embodiments, a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In some embodiments, an insertion comprises the addition of a segment of a chromosome into a genome, chromosome, or segment thereof. In some embodiments, an insertion comprises the addition of an allele, a gene, an intron, an exon, any non-coding region, any coding region, segment thereof or combination thereof into a genome or segment thereof. In some embodiments, an insertion comprises the addition (i.e., insertion) of nucleic acid of unknown origin into a genome, chromosome, or segment thereof. In some embodiments, an insertion comprises the addition (i.e. insertion) of a single base.

As used herein a "copy number variation" generally is a class or type of genetic variation or chromosomal aberration. A copy number variation can be a deletion (e.g. microdeletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In some embodiments, a duplication comprises an insertion. In some embodiments, an insertion is a duplication. In some embodiments, an insertion is not a duplication. For example, often a duplication of a sequence in a genomic section increases the counts for a genomic section in which the duplication is found. Often a duplication of a sequence in a genomic section increases the elevation. In some embodiments, a duplication present in genomic sections making up a first elevation increases the elevation relative to a second elevation where a duplication is absent. In some embodiments, an insertion increases the counts of a genomic section and a sequence representing the insertion is present (i.e., duplicated) at another location within the same genomic section. In some embodiments, an insertion does not significantly increase the counts of a genomic section or elevation and the sequence that is inserted is not a duplication of a sequence within the same genomic section. In some embodiments, an insertion is not detected or represented as a duplication and a duplicate sequence representing the insertion is not present in the same genomic section.

In some embodiments a copy number variation is a fetal copy number variation. Often, a fetal copy number variation is a copy number variation in the genome of a fetus. In some embodiments a copy number variation is a maternal copy number variation. In some embodiments, a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" refers to the number of chromosomes present in a fetus or mother. In some embodiments, "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes refers to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of an elevation in a profile (e.g., after normalizing counts of an elevation to an NRV of 1). Thus, an elevation representing an autosomal chromosome pair (e.g., a euploid) is often normalized to an NRV of 1 and is referred to as a ploidy of 1. Similarly, an elevation within a segment of a chromosome representing the absence of a duplication, deletion or insertion is often normalized to an NRV of 1 and is referred to as a microploidy of 1. Ploidy and microploidy are often bin-specific (e.g., genomic section specific) and sample-specific. Ploidy is often defined as integral multiples of ½, with the values of 1, ½, 0, 3/2, and 2 representing euploidy (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploidy (e.g., no copy number variation), a heterozygous deletion, homozygous deletion, heterozygous duplication and homozygous duplication, respectively.

In some embodiments, the microploidy of a fetus matches the microploidy of the mother of the fetus (i.e., the pregnant female subject). In some embodiments, the microploidy of a fetus matches the microploidy of the mother of the fetus and both the mother and fetus carry the same heterozygous copy number variation, homozygous copy number variation or both are euploid. In some embodiments, the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected elevation. For example, sometimes an elevation (e.g., an elevation in a profile, sometimes an elevation that includes substantially no copy number variation) is normalized to an NRV of 1 and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method or apparatus described herein. In some embodiments, a method in which fetal gender is determined can also comprise determining fetal fraction and/or presence or absence of a fetal genetic variation (e.g., fetal chromosome aneuploidy). Determining presence or absence of a fetal genetic variation can be performed in a suitable manner, non-limiting examples of which include karyotype analysis, amniocentesis, circulating cell-free nucleic acid analysis, cell-free fetal DNA analysis, nucleotide sequence analysis, sequence read quantification, targeted approaches, amplification-based approaches, mass spectrometry-based approaches, differential methylation-based approaches, differential digestion-based approaches, polymorphism-based approaches, hybridization-based approaches (e.g., using probes), and the like.

Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In some instances, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In some instances, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenita, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjrg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinits pigmentosa, and azoospermia.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example.

The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "euploid", in some embodiments, refers a normal complement of chromosomes.

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods and apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |

TABLE 1A-continued

| Chromosome | Abnormality | Disease Association |
|---|---|---|
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
| | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |

TABLE 1A-continued

| Chromosome | Abnormality | Disease Association |
|---|---|---|
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |

TABLE 1B-continued

| Syndrome | Chromosome | Start | End | Interval (Mb) | Grade |
|---|---|---|---|---|---|
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, GeneReviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In some instances, preeclampsia also is associated with elevated levels of extracellular nucleic acid and/or alterations in methylation patterns. For example, a positive correlation between extracellular fetal-derived hypermethylated RASSF1A levels and the severity of preeclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff) DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

Placenta hypomethylated domains (PHDs), as described herein, show characteristics consistent with the partially methylated domains and/or global hypomethylation of certain tumors and cancer subtypes. Thus, methods, systems and processes described herein can be directly applied to non-invasive detection and monitoring of various tumors and cancers. The term "tumor nucleic acid" as used herein refers to nucleic acid derived or originating from a tumor or cancerous tissue.

EXAMPLES

The examples set forth below illustrate certain embodiments and do not limit the technology.

Example 1

Enrichment of Fetal DNA Using Methylation-Specific Restriction Digestion

In this example, genome-wide differences in DNA methylation are leveraged to enrich for fetal DNA through methylation-specific restriction digestion. Often, there is a direct relationship between fetal fraction and the ability to detect genetic variations in the fetus (fetal aneuploidies) using cell free DNA analysis. The purpose of this technology is to use the global differences in DNA methylation between maternal and fetal/placental ccf DNA to enrich for fetal DNA.

Figure 2:
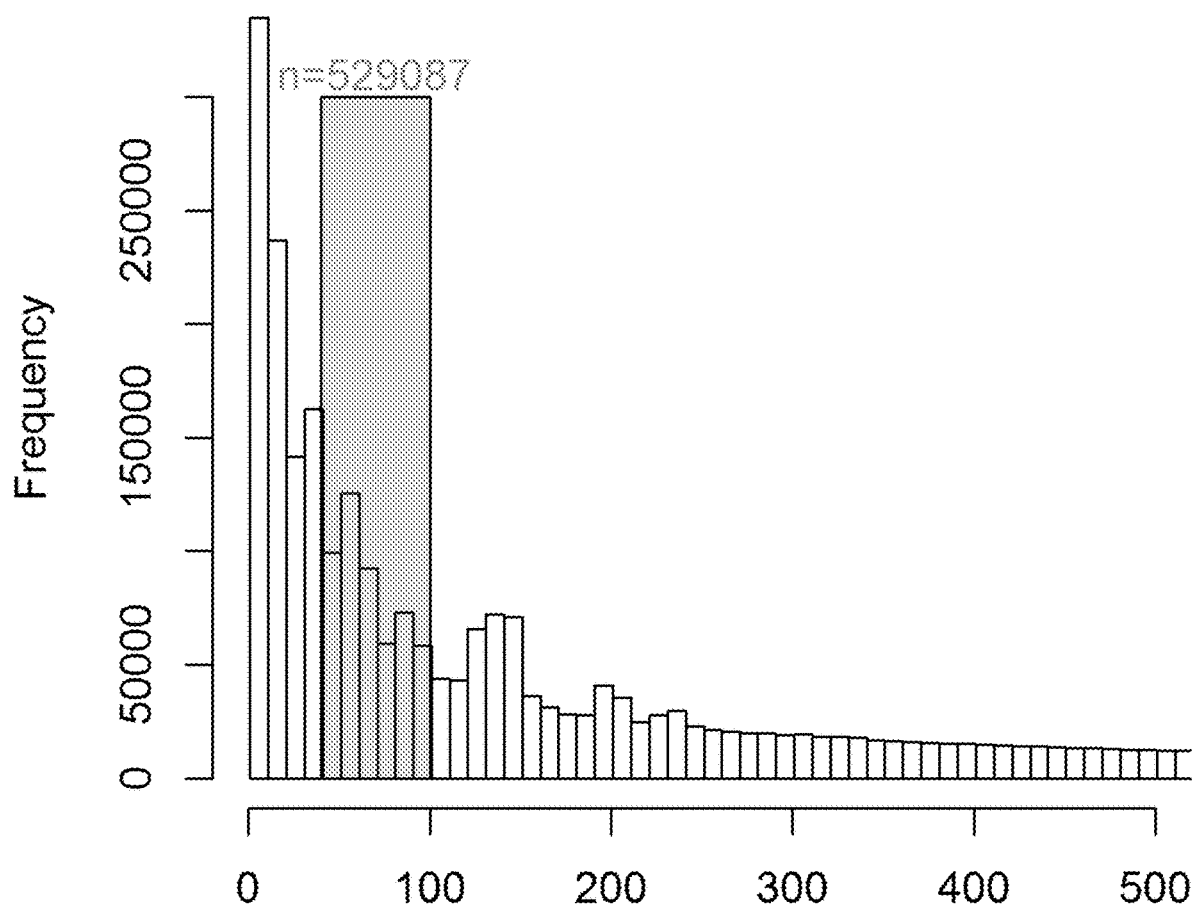
FIG. 2 shows the distance between measured restriction sites when comparing non-pregnant ccf DNA and placenta. Only those points less than 500 bp are shown.

Differences in DNA methylation generally exist between certain contributors to maternal (e.g., buffy coat or PBMC-derived) ccf DNA and fetal (e.g., placenta-derived) ccf DNA. A whole genome bisulfite sequencing experiment was designed to sequence and determine DNA methylation patterns of maternal buffy coat, placenta tissue, non-pregnant female ccf DNA, and pregnant female ccf DNA. The results showed that the placenta was strikingly hypomethylated relative to the buffy coat or maternal plasma (FIGS. 1 and 2). Specifically, almost 95% of the identified differentially methylated regions were more methylated in buffy coat or non-pregnant ccf DNA when compared to placenta tissue (FIGS. 1 and 2).

Figure 3:
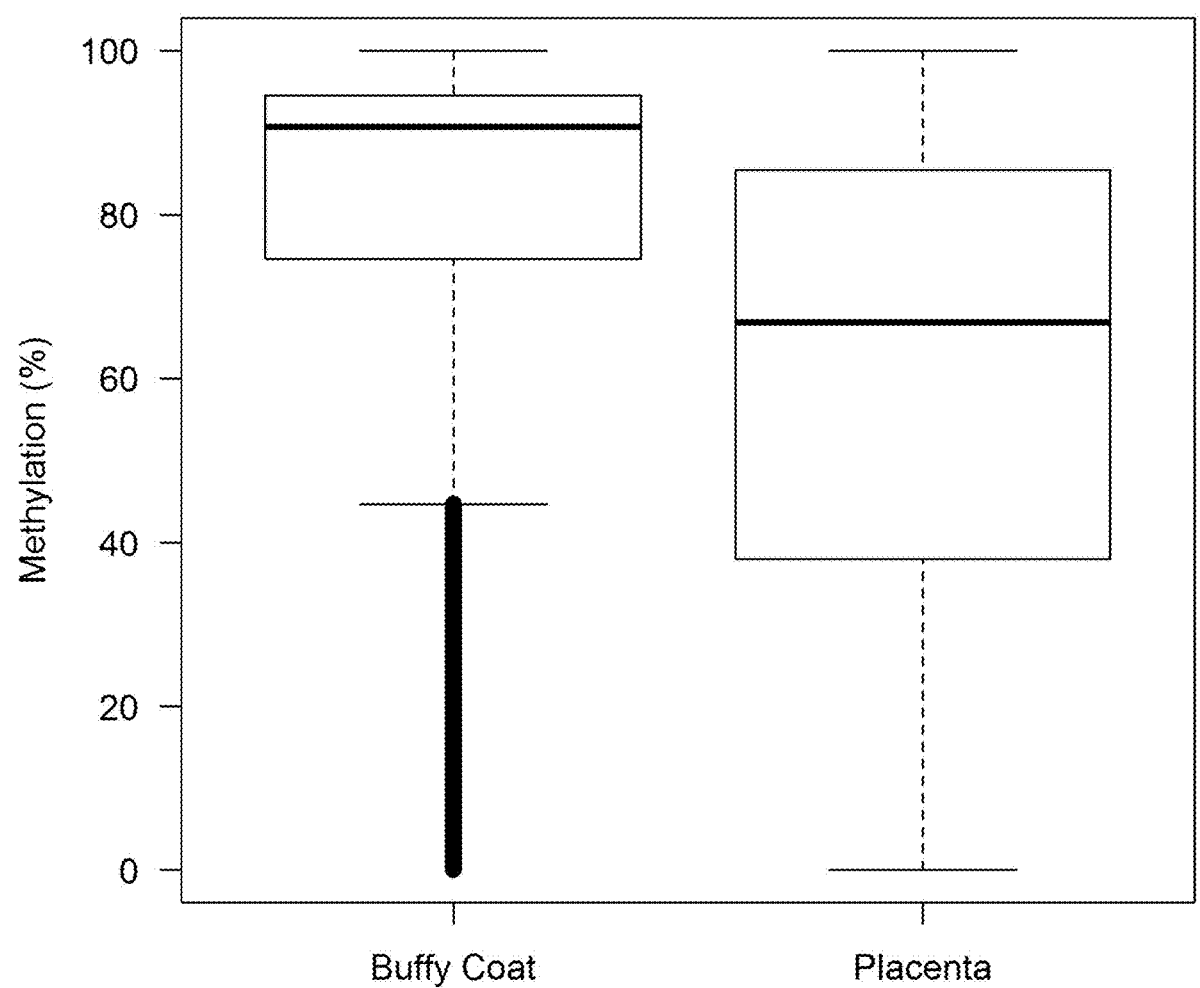
FIG. 3 shows methylation levels of CCGG and GCGC sites in buffy coat and placenta. Only sites where values were obtained from both sample types were used.

Such differential methylation is used to enrich for fetal ccf DNA. To perform such a method, the following steps are performed:

1. Extract ccf DNA from maternal plasma using standard methods.
2. Treat ccf DNA with a combination of methylation sensitive restriction enzymes including, but not limited to, HHAI, HinP1I, and HPAII. In certain instances, HpaII (FIG. 3A) and HinP1I (FIG. 3B) are used because each digestion leaves a 5'-CG-3' overhang that is used for ligating to a directional adaptor sequence.

Because these enzymes generally are inhibited by DNA methylation, methylated DNA fragments (higher proportion of maternal relative to fetal) remain unaffected while unmethylated DNA fragments (higher proportion of fetal relative to maternal) are digested by the restriction endonucleases. Such a method results in a population of DNA fragments enriched for fetal DNA. Such enrichment sometimes leaves fewer input DNA molecules for downstream processing.

3. Ligate a custom oligonucleotide containing a sequence which allows for universal or, in certain instances, targeted PCR, next generation sequencing and/or other detection methodology.
4. Perform a universal or targeted PCR reaction to amplify the digested fragments and select for fragments containing adaptor sequences. PCR is used in certain instances to obtain enough material for downstream processes and to enrich for the properly ligated products.
5. Sequence the resultant library using a suitable sequencing method of nucleic acid sequencing (e.g., high-throughput sequencing, MPS, MPSS, or the like). Upon completion of sequencing, reads are aligned to an entire human genome reference or a reduced portion of the human genome. The number of reads per chromosome is counted and deviations from the expected chromosomal representation is indicative of fetal aneuploidy.

Figure 4:
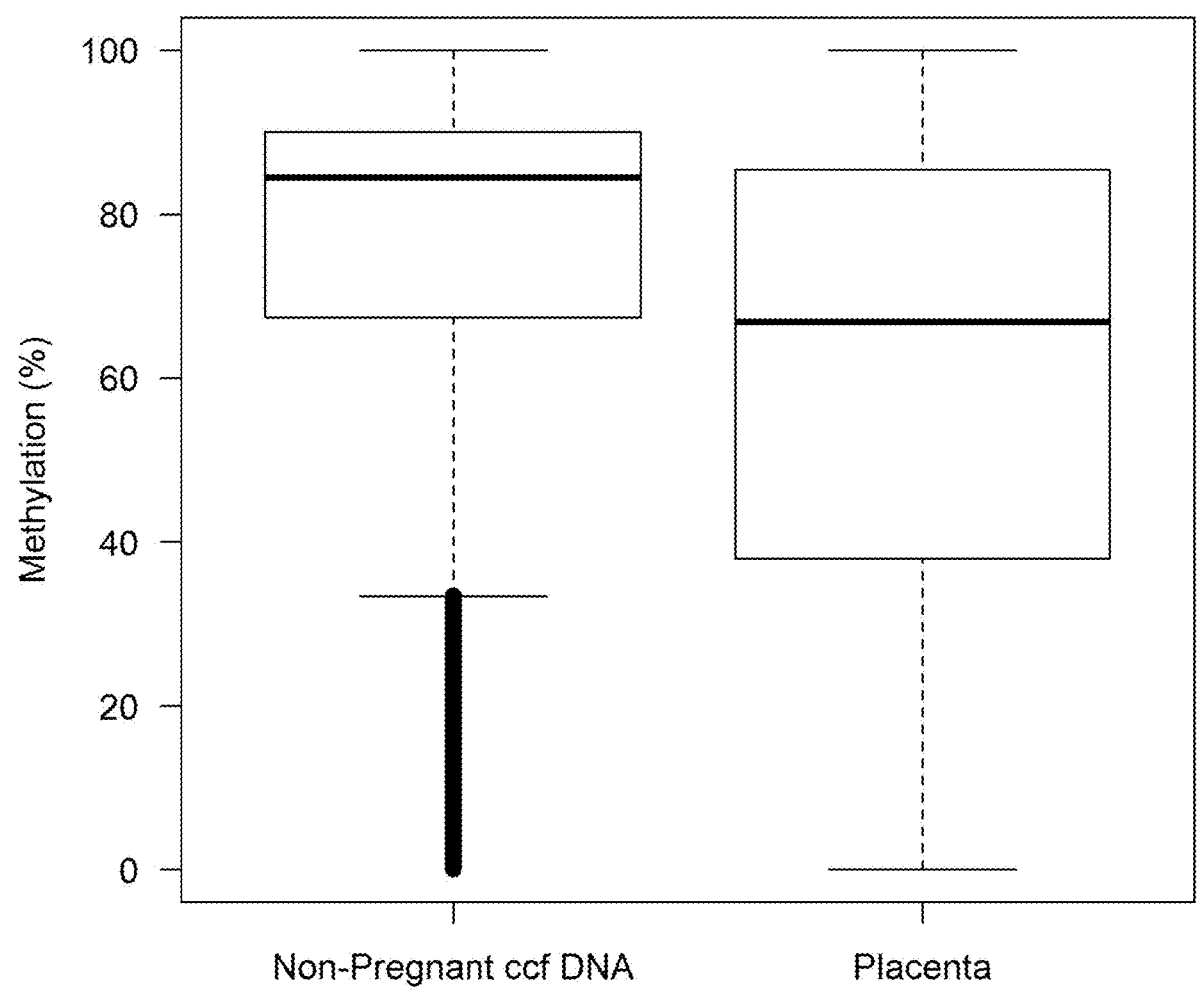
FIG. 4 shows methylation levels of CCGG and GCGC sites in non-pregnant ccf DNA and placenta. Only sites where values were obtained from both sample types were used.

To examine the feasibility of a method described above, the frequency of certain restriction sites was evaluated. Based on the hg19 human genome sequence, a total of 3,953,090 recognition sequences were identified in the human genome for one of the enzymes (FIG. 4).

Figure 5:
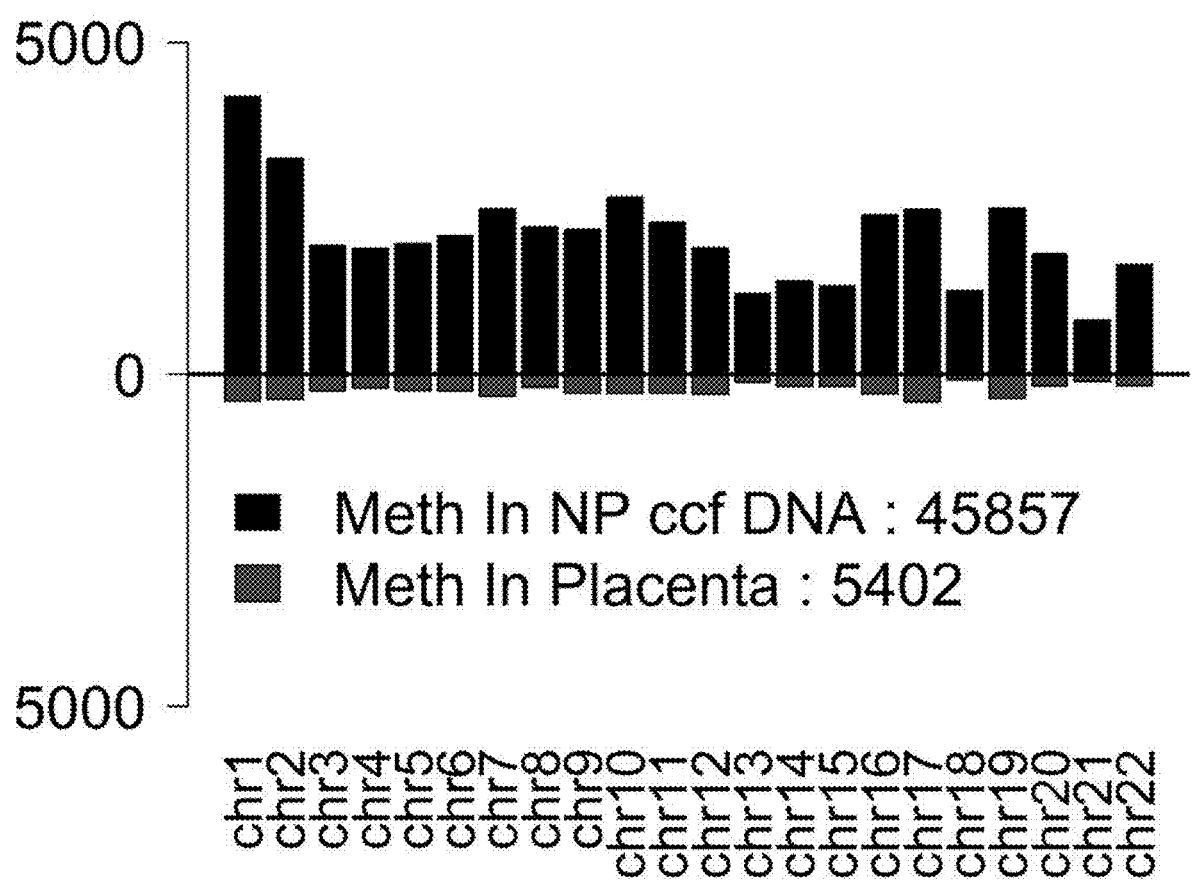
FIG. 5 is directed to methylation patterns in placenta and non-pregnant ccf DNA, and quantifies the number of differentially methylated regions (DMRs) per autosome (Y-axis).

Next, the distance between restriction enzyme recognition sequences was calculated. Since ccf DNA generally is present in maternal plasma within a narrow size window (e.g., typically less than 200 bp in length), the distance between sites is considered when selecting one or more restriction endonucleases. Using the CpG sites for which data was obtained in both non-pregnant ccf DNA and placenta (n=3,562,431), the median distance between adjacent CpG sites was 184 bp. In evaluating the distribution of distances, these analyses show approximately 529,000 fragments generated with a length between 40 bp and 100 bp (FIG. 5).

Figure 6:
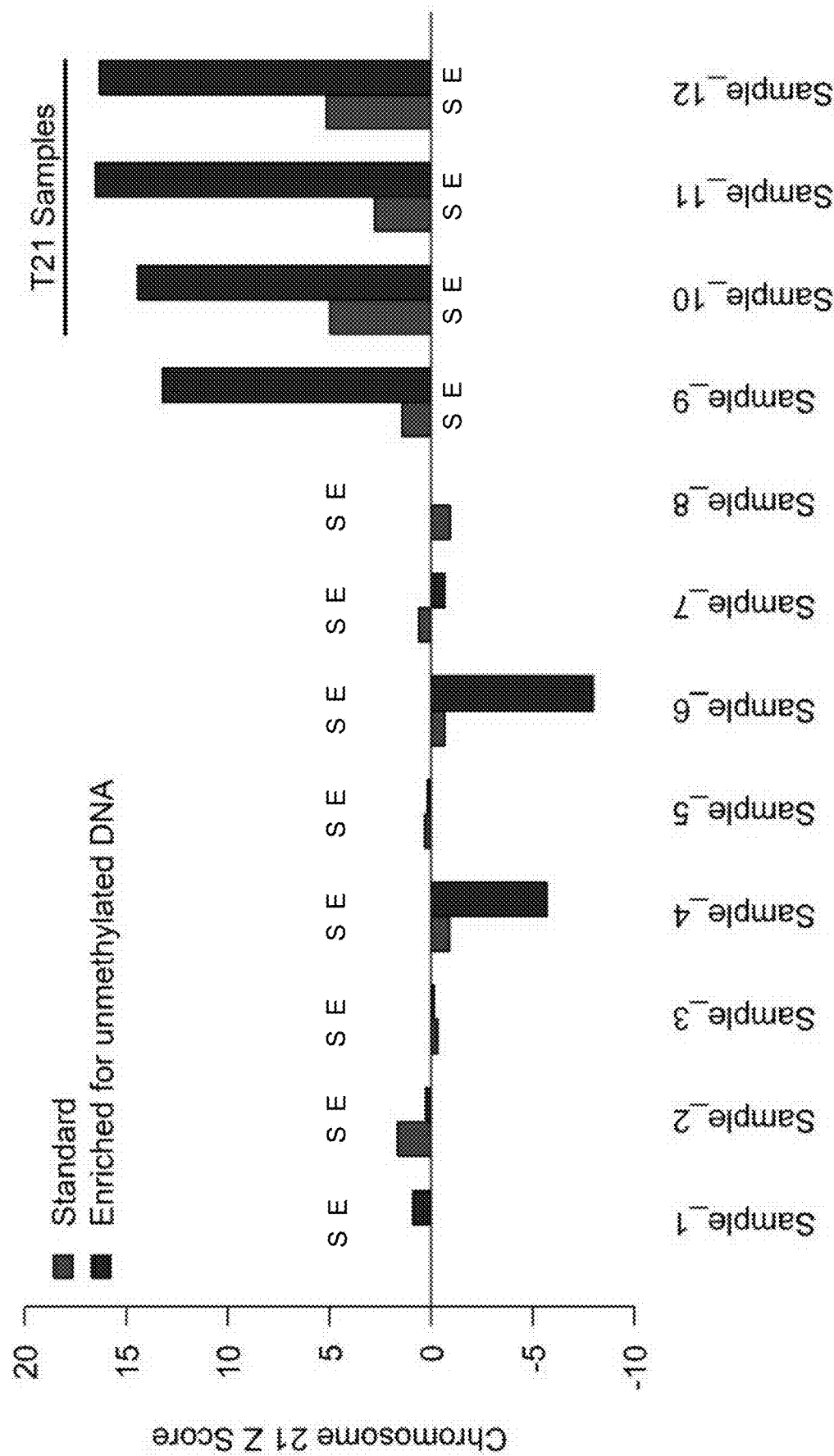
FIG. 6 shows enrichment for hypomethylated DNA enhances aneuploidy detection in twelve trisomy 21 (T21) samples (indicated on x-axis). Barplot shows the chromosome 21 z-score for each of 12 ccf DNA samples obtained from pregnant female donors (9 euploid, 3 T21) and subjected to massively parallel sequencing using either all input ccf DNA (Standard (designated by "S": left histogram of each pair of histogram bars/sample) or only the unmethylated DNA fraction obtained after depletion of the methylated fragments by MCIp (enriched for unmethylated DNA (designated by "E": right histogram of each pair of histogram bars/sample).
Figure 7:
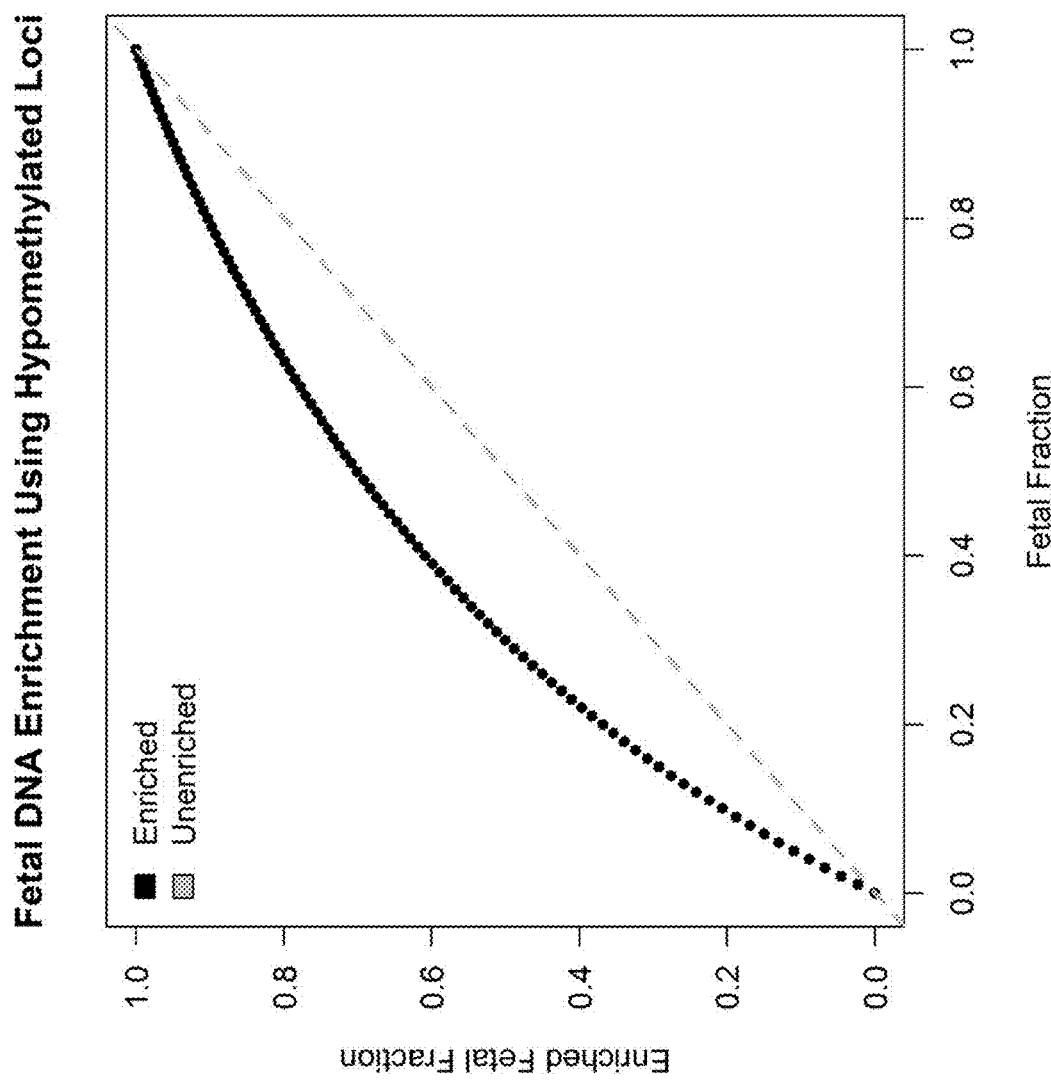
FIG. 7 shows fold enrichment of fetal nucleic acid (y-axis) from samples comprising various amounts of fetal nucleic acid prior to enrichment (x-axis, fraction of fetal nucleic acid to total nucleic acid in a sample).

Next, the mean methylation level of each CpG site within the restriction enzyme recognition sequence was compared between buffy coat and placenta (n=3,566,125). Within these sites, the median methylation level was significantly reduced in placenta relative to buffy coat (FIG. 6). A similar, albeit reduced, pattern is seen when comparing non-pregnant ccf DNA and placenta (FIG. 7).

A more direct comparison of the methylation level at each targeted CpG site revealed that the mean methylation of those sites in buffy coat was greater than the mean methylation in placenta for 80.8% of sites, although there was a large proportion that were unchanged (FIG. 8).

Taken together, these data indicate that selective digestion and ligation of unmethylated fragments globally enriches for placental/fetal DNA in a sample comprising maternal and fetal ccf DNA. Tables 2AA, 2AB, 2B, 2CA and 2CB below present differentially methylated human genomic regions.

TABLE 2AA

| | | | | | Hypermethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA – MATERNAL | RELATIVE METHYL-ATION PLACENTA TO MATERNAL |
| chr13 group00016 | chr13 | 19773745 | 19774050 | chr13: 19773518-19774214 | 0.19 | 0.22 | 0.32 | 0.1 | HYPERMETHYL-ATION |
| CENPJ | chr13 | 24404023 | 24404359 | :- | 0.57 | 0.17 | 0.49 | 0.32 | HYPERMETHYL-ATION |
| ATP8A2 | chr13 | 25484475 | 25484614 | chr13: 25484287-25484761 | 0.81 | 0.16 | 0.43 | 0.27 | HYPERMETHYL-ATION |

TABLE 2AA-continued

| | | | | | Hypermethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA – MATERNAL | RELATIVE METHYL-ATION PLACENTA TO MATERNAL |
| GSH1 | chr13 | 27265542 | 27265834 | chr13: 27264549-27266505 | 0.57 | 0.13 | 0.19 | 0.05 | HYPERMETHYL-ATION |
| PDX1 | chr13 | 27393789 | 27393979 | chr13: 27392001-27394099 | 0.55 | 0.06 | 0.2 | 0.14 | HYPERMETHYL-ATION |
| PDX1 | chr13 | 27400459 | 27401165 | chr13: 27400362-27400744; chr13: 27401057-27401374 | 0.73 | 0.12 | 0.26 | 0.14 | HYPERMETHYL-ATION |
| MAB21L1 | chr13 | 34947737 | 34948062 | chr13: 34947570-34948159 | 0.66 | 0.11 | 0.17 | 0.06 | HYPERMETHYL-ATION |
| RB1 | chr13 | 47790983 | 47791646 | chr13: 47790636-47791858 | 0.18 | 0.45 | 0.48 | 0.03 | HYPERMETHYL-ATION |
| PCDH17 | chr13 | 57104856 | 57106841 | chr13: 57104527-57106931 | 0.46 | 0.15 | 0.21 | 0.06 | HYPERMETHYL-ATION |
| KLHL1 | chr13 | 69579933 | 69580146 | chr13: 69579733-69580220 | 0.79 | 0.09 | 0.28 | 0.2 | HYPERMETHYL-ATION |
| POU4F1 | chr13 | 78079515 | 78081073 | chr13: 78079328-78079615; chr13: 78080860-78081881 | 0.66 | 0.12 | 0.23 | 0.11 | HYPERMETHYL-ATION |
| GPC6 | chr13 | 92677402 | 92678666 | chr13: 92677246-92678878 | 0.66 | 0.06 | 0.19 | 0.13 | HYPERMETHYL-ATION |
| SOX21 | chr13 | 94152286 | 94153047 | chr13: 94152190-94153185 | 0.94 | 0.16 | 0.4 | 0.25 | HYPERMETHYL-ATION |
| ZIC2 | chr13 | 99439660 | 99440858 | chr13: 99439335-99440189; chr13: 99440775-99441095 | 0.89 | 0.13 | 0.35 | 0.22 | HYPERMETHYL-ATION |
| chr13 group00385 | chr13 | 111595578 | 111595955 | chr13: 111595459-111596131 | 0.87 | 0.06 | 0.2 | 0.14 | HYPERMETHYL-ATION |
| chr13 group00390 | chr13 | 111756337 | 111756593 | chr13: 111755805-111756697 | 0.71 | 0.12 | 0.34 | 0.22 | HYPERMETHYL-ATION |
| chr13 group00391 | chr13 | 111759856 | 111760045 | chr13: 111757885-111760666 | 0.86 | 0.11 | 0.36 | 0.25 | HYPERMETHYL-ATION |
| chr13 group00395 | chr13 | 111808255 | 111808962 | chr13: 111806599-111808492; chr13: 111808866-111809114 | 0.96 | 0.13 | 0.35 | 0.22 | HYPERMETHYL-ATION |
| chr13 group00399 | chr13 | 112033503 | 112033685 | chr13: 112032967-112033734 | 0.38 | 0.26 | 0.43 | 0.18 | HYPERMETHYL-ATION |
| PROZ | chr13 | 112855566 | 112855745 | chr13: 112855289-112855866 | 0.29 | 0.15 | 0.3 | 0.16 | HYPERMETHYL-ATION |
| CIDEA | chr18 | 12244327 | 12244696 | chr18: 12244147-12245089 | 0.23 | 0.14 | 0.23 | 0.1 | HYPERMETHYL-ATION |
| chr18 group00091 | chr18 | 12901467 | 12901643 | chr18: 12901024-12902704 | 0.16 | 0.15 | 0.43 | 0.29 | HYPERMETHYL-ATION |
| chr18 group00094 | chr18 | 13126819 | 13126986 | chr18: 13126596-13127564 | 0.41 | 0.07 | 0.34 | 0.27 | HYPERMETHYL-ATION |

TABLE 2AA-continued

| | | | | | Hypermethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA − MATERNAL | RELATIVE METHYL-ATION PLACENTA TO MATERNAL |
| KLHL14 | chr18 | 28603978 | 28605183 | chr18: 28603688-28606300 | 0.83 | 0.07 | 0.19 | 0.12 | HYPERMETHYL-ATION |
| ST8SIA3 | chr18 | 53171265 | 53171309 | chr18: 53170705-53172603 | 1.02 | 0.09 | 0.25 | 0.16 | HYPERMETHYL-ATION |
| ONECUT2 | chr18 | 53254808 | 53259810 | chr18: 53254152-53259851 | 0.74 | 0.09 | 0.23 | 0.14 | HYPERMETHYL-ATION |
| RAX | chr18 | 55086286 | 55086436 | chr18: 55085813-55087807 | 0.88 | 0.11 | 0.26 | 0.16 | HYPERMETHYL-ATION |
| chr18 group00277 | chr18 | 57151972 | 57152311 | chr18: 57151663-57152672 | 0.58 | 0.08 | 0.21 | 0.13 | HYPERMETHYL-ATION |
| NETO1 | chr18 | 68685099 | 68687060 | chr18: 68684945-68687851 | 0.65 | 0.09 | 0.22 | 0.13 | HYPERMETHYL-ATION |
| MBP | chr18 | 72953150 | 72953464 | chr18: 72953137-72953402 | 0.6 | 0.44 | 0.72 | 0.28 | HYPERMETHYL-ATION |
| NFATC1 | chr18 | 75385424 | 75386008 | chr18: 75385279-75386532 | 0.23 | 0.14 | 0.84 | 0.7 | HYPERMETHYL-ATION |
| chr18 group00430 | chr18 | 75653272 | 75653621 | :- | 0.52 | 0.24 | 0.62 | 0.39 | HYPERMETHYL-ATION |
| OLIG2 | chr21 | 33317673 | 33321183 | chr21: 33316998-33322115 | 0.66 | 0.11 | 0.2 | 0.09 | HYPERMETHYL-ATION |
| SIM2 | chr21 | 36994965 | 36995298 | chr21: 36990063-36995761 | 0.83 | 0.08 | 0.26 | 0.18 | HYPERMETHYL-ATION |
| SIM2 | chr21 | 36999025 | 36999410 | chr21: 36998632-36999555 | 0.87 | 0.06 | 0.24 | 0.18 | HYPERMETHYL-ATION |
| DSCR6 | chr21 | 37300407 | 37300512 | chr21: 37299807-37301307 | 0.22 | 0.04 | 0.14 | 0.11 | HYPERMETHYL-ATION |
| DSCAM | chr21 | 41135559 | 41135706 | chr21: 41135380-41135816 | 1.03 | 0.06 | 0.29 | 0.23 | HYPERMETHYL-ATION |
| chr21 group00165 | chr21 | 43643421 | 43643786 | chr21: 43643322-43643874 | 1.14 | 0.16 | 0.81 | 0.65 | HYPERMETHYL-ATION |
| PRMT2 | chr21 | 46911967 | 46912385 | chr21: 46911628-46912534 | 1.08 | 0.04 | 0.25 | 0.21 | HYPERMETHYL-ATION |
| SIX2 | chr2 | 45081223 | 45082129 | chr2: 45081148-45082287 | 1.15 | 0.08 | 0.36 | 0.28 | HYPERMETHYL-ATION |
| SIX2 | chr2 | 45084851 | 45085711 | chr2: 45084715-45084986; chr2: 45085285-45086054 | 1.21 | 0.07 | 0.35 | 0.28 | HYPERMETHYL-ATION |
| SOX14 | chr3 | 138971870 | 138972322 | chr3: 138971738-138972096; chr3: 138972281-138973691 | 1.35 | 0.08 | 0.33 | 0.25 | HYPERMETHYL-ATION |
| TLX3 | chr5 | 170674439 | 170676431 | chr5: 170674208-170675356; chr5: 170675783-170676712 | 0.91 | 0.11 | 0.35 | 0.24 | HYPERMETHYL-ATION |
| FOXP4 | chr6 | 41623666 | 41624114 | chr6: 41621630-41624167 | 1.1 | 0.07 | 0.27 | 0.2 | HYPERMETHYL-ATION |

TABLE 2AA-continued

| | | | | | Hypermethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA – MATERNAL | RELATIVE METHYL-ATION PLACENTA TO MATERNAL |
| FOXP4 | chr6 | 41636384 | 41636779 | chr6: 41636244-41636878 | 1.32 | 0.04 | 0.33 | 0.29 | HYPERMETHYL-ATION |
| chr7 group00267 | chr7 | 12576755 | 12577246 | chr7: 12576690-12577359 | 0.94 | 0.08 | 0.26 | 0.17 | HYPERMETHYL-ATION |
| NPY | chr7 | 24290224 | 24291508 | chr7: 24290083-24291605 | 0.93 | 0.09 | 0.3 | 0.21 | HYPERMETHYL-ATION |
| SHH | chr7 | 155291537 | 155292091 | chr7: 155288453-155292175 | 0.98 | 0.19 | 0.52 | 0.33 | HYPERMETHYL-ATION |
| OSR2 | chr8 | 100029764 | 100030536 | chr8: 100029673-100030614 | 1.21 | 0.08 | 0.43 | 0.35 | HYPERMETHYL-ATION |
| GLIS3 | chr9 | 4288283 | 4289645 | chr9: 4287817-4290182 | 1.24 | 0.06 | 0.24 | 0.18 | HYPERMETHYL-ATION |
| PRMT8 | chr12 | 3472714 | 3473190 | chr12: 3470227-3473269 | 0.86 | 0.07 | 0.23 | 0.16 | HYPERMETHYL-ATION |
| TBX3 | chr12 | 113609153 | 113609453 | chr12: 113609112-113609535 | 1.45 | 0.09 | 0.56 | 0.48 | HYPERMETHYL-ATION |
| chr12 group00801 | chr12 | 118516189 | 118517435 | chr12: 118515877-118517595 | 1.1 | 0.06 | 0.25 | 0.19 | HYPERMETHYL-ATION |
| PAX9 | chr14 | 36201402 | 36202386 | chr14: 36200932-36202536 | 0.89 | 0.11 | 0.32 | 0.21 | HYPERMETHYL-ATION |
| SIX1 | chr14 | 60178801 | 60179346 | chr14: 60178707-60179539 | 0.95 | 0.1 | 0.33 | 0.22 | HYPERMETHYL-ATION |
| ISL2 | chr15 | 74420013 | 74421546 | chr15: 74419317-74422570 | 1.08 | 0.08 | 0.27 | 0.19 | HYPERMETHYL-ATION |
| DLX4 | chr17 | 45397228 | 45397930 | chr17: 45396281-45398063 | 1.25 | 0.1 | 0.32 | 0.22 | HYPERMETHYL-ATION |
| CBX4 | chr17 | 75428613 | 75431793 | chr17: 75427586-75433676 | 1 | 0.07 | 0.27 | 0.21 | HYPERMETHYL-ATION |
| EDG6 | chr19 | 3129836 | 3130874 | chr19: 3129741-3130986 | 1.35 | 0.04 | 0.87 | 0.83 | HYPERMETHYL-ATION |

TABLE 2AB

| | | | | | Hypomethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA – MATERNAL | RELATIVE METHYL-ATION PLACENTA TO MATERNAL |
| chr13 group00005 | chr13 | 19290394 | 19290768 | :- | −0.89 | 0.94 | 0.35 | −0.59 | HYPOMETHYL-ATION |
| CRYL1 | chr13 | 19887090 | 19887336 | chr13: 19887007-19887836 | −0.63 | 0.74 | 0.21 | −0.53 | HYPOMETHYL-ATION |
| IL17D | chr13 | 20193675 | 20193897 | chr13: 20193611-20194438 | −1.01 | 0.53 | 0.13 | −0.39 | HYPOMETHYL-ATION |
| IRS2 | chr13 | 109232856 | 109235065 | chr13: 109232467-109238181 | −0.17 | 0.73 | 0.38 | −0.35 | HYPOMETHYL-ATION |

TABLE 2AB-continued

| | | | | | Hypomethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA – MATERNAL | RELATIVE METHYL-ATION PLACENTA TO MATERNAL |
| chr13 group00350 | chr13 | 109716455 | 109716604 | chr13: 109716325-109716726 | −0.37 | 0.77 | 0.41 | −0.36 | HYPOMETHYL-ATION |
| MCF2L | chr13 | 112724910 | 112725742 | chr13: 112724782-112725121; chr13: 112725628-112725837 | −0.47 | 0.91 | 0.33 | −0.58 | HYPOMETHYL-ATION |
| F7 | chr13 | 112799123 | 112799379 | chr13: 112798487-112799566 | −0.05 | 0.97 | 0.55 | −0.41 | HYPOMETHYL-ATION |
| chr18 group00039 | chr18 | 6919797 | 6919981 | chr18: 6919450-6920088 | −0.38 | 0.88 | 0.39 | −0.49 | HYPOMETHYL-ATION |
| C18orf1 | chr18 | 13377536 | 13377654 | chr18: 13377385-13377686 | −0.12 | 0.95 | 0.69 | −0.26 | HYPOMETHYL-ATION |
| CD33L3 | chr18 | 41671477 | 41673011 | chr18: 41671386-41673101 | −0.34 | 0.49 | 0.44 | −0.05 | HYPOMETHYL-ATION |
| TNFRSF11A | chr18 | 58203013 | 58203282 | chr18: 58202849-58203367 | −0.33 | 0.88 | 0.28 | −0.6 | HYPOMETHYL-ATION |
| chr18 group00304 | chr18 | 70133945 | 70134397 | chr18: 70133732-70134724 | 0.12 | 0.93 | 0.92 | −0.01 | NOT CONFIRMED |
| TSHZ1 | chr18 | 71128742 | 71128974 | chr18: 71128638-71129076 | 0.23 | 0.95 | 0.92 | −0.03 | NOT CONFIRMED |
| ZNF236 | chr18 | 72664454 | 72664736 | chr18: 72662797-72664893 | −0.62 | 0.17 | 0.1 | −0.07 | HYPOMETHYL-ATION |
| chr18 group00342 | chr18 | 74170347 | 74170489 | chr18: 74170210-74170687 | −0.2 | 0.78 | 0.48 | −0.3 | HYPOMETHYL-ATION |
| CTDP1 | chr18 | 75596358 | 75596579 | chr18: 75596009-75596899 | 0.07 | 0.97 | 0.96 | −0.01 | NOT CONFIRMED |
| KCNG2 | chr18 | 75760343 | 75760820 | chr18: 75759900-75760988 | 0.01 | 0.84 | 0.75 | −0.09 | NOT CONFIRMED |
| OLIG2 | chr21 | 33327593 | 33328334 | chr21: 33327447-33328408 | −0.75 | 0.77 | 0.28 | −0.49 | HYPOMETHYL-ATION |
| RUNX1 | chr21 | 35180938 | 35185436 | chr21: 35180822-35181342; chr21: 35182320-35185557 | −0.68 | 0.14 | 0.07 | −0.07 | HYPOMETHYL-ATION |
| AIRE | chr21 | 44529935 | 44530388 | chr21: 44529856-44530472 | −0.55 | 0.62 | 0.27 | −0.35 | HYPOMETHYL-ATION |
| SUMO3 | chr21 | 45061293 | 45061853 | chr21: 45061154-45063386 | −0.41 | 0.55 | 0.46 | −0.09 | HYPOMETHYL-ATION |
| C21orf70 | chr21 | 45202815 | 45202972 | chr21: 45202706-45203073 | −0.46 | 0.96 | 0.51 | −0.46 | HYPOMETHYL-ATION |
| C21orf123 | chr21 | 45671984 | 45672098 | chr21: 45671933-45672201 | −0.63 | 0.92 | 0.43 | −0.49 | HYPOMETHYL-ATION |
| COL18A1 | chr21 | 45754383 | 45754487 | chr21: 45753653-45754639 | −0.18 | 0.97 | 0.72 | −0.25 | HYPOMETHYL-ATION |
| PRRT3 | chr3 | 9963364 | 9964023 | chr3: 9962895-9964619 | −0.85 | 0.9 | 0.09 | −0.81 | HYPOMETHYL-ATION |
| MGC29506 | chr5 | 138757911 | 138758724 | chr5: 138755609-138758810 | −0.63 | 0.93 | 0.17 | −0.76 | HYPOMETHYL-ATION |

TABLE 2AB-continued

| | | | | | Hypomethylation | | | | |
|---|---|---|---|---|---|---|---|---|---|
| GENE NAME | CHROM | START | END | CpG ISLAND | MEAN LOG RATIO MICRO-ARRAY | MEAN MATERNAL METHYL-ATION EPITYPER | MEAN PLACENTA METHYL-ATION EPITYPER | METHYL-ATION DIFFERENCE PLACENTA – MATERNAL | RELATIVE METHYL-ATION PLACENTA TO MATERNAL |
| TEAD3 | chr6 | 35561812 | 35562252 | chr6: 35561754-35562413 | −1.17 | 0.92 | 0.13 | −0.8 | HYPOMETHYL-ATION |
| chr12 group00022 | chr12 | 1642456 | 1642708 | chr12: 1642195-1642774 | −1.33 | 0.66 | 0.09 | −0.57 | HYPOMETHYL-ATION |
| CENTG1 | chr12 | 56406249 | 56407788 | chr12: 56406176-56407818 | −1.07 | 0.95 | 0.19 | −0.77 | HYPOMETHYL-ATION |
| CENTG1 | chr12 | 56416146 | 56418794 | chr12: 56416095-56416628; chr12: 56418745-56419001 | −0.94 | 0.85 | 0.16 | −0.69 | HYPOMETHYL-ATION |

Information in Table 2AA, 2AB, 2B, 2CA, 2CB and Table 3 is based on the March 2006 human reference sequence (UCSC Ver. hg18, NCBI Build 36.1), which was produced by the International Human Genome Sequencing Consortium.

TABLE 2B

Non-Chromosome 21 differentially methylated regions

| Region Name | Gene Region | Chrom | Start | End | Microarray Analysis | EpiTYPER 8 Samples | EpiTYPER 73 Samples | Previously Validated EpiTYPER | Relative Methylation Placenta to Maternal |
|---|---|---|---|---|---|---|---|---|---|
| TFAP2E | Intron | chr1 | 35815000 | 35816200 | YES | YES | NO | NO | Hypermethylation |
| LRRC8D | Intron/Exon | chr1 | 90081350 | 90082250 | YES | YES | NO | NO | Hypermethylation |
| TBX15 | Promoter | chr1 | 119333500 | 119333700 | YES | YES | NO | NO | Hypermethylation |
| C1orf51 | Upstream | chr1 | 148520900 | 148521300 | YES | YES | NO | NO | Hypermethylation |
| chr1: 179553900-179554600 | Intergenic | chr1 | 179553900 | 179554600 | YES | YES | NO | NO | Hypermethylation |
| ZFP36L2 | Exon | chr2 | 43304900 | 43305100 | YES | YES | NO | NO | Hypermethylation |
| SIX2 | Downstream | chr2 | 45081000 | 45086000 | YES | YES | NO | YES | Hypermethylation |
| chr2: 137238500-137240000 | Intergenic | chr2 | 137238500 | 137240000 | YES | YES | NO | NO | Hypermethylation |
| MAP1D | Intron/Exon | chr2 | 172652800 | 172653600 | YES | YES | NO | NO | Hypermethylation |
| WNT6 | Intron | chr2 | 219444250 | 219444290 | YES | YES | NO | NO | Hypermethylation |
| INPP5D | Promoter | chr2 | 233633200 | 233633700 | YES | YES | YES | NO | Hypermethylation |
| chr2: 241211100-241211600 | Intergenic | chr2 | 241211100 | 241211600 | YES | YES | YES | NO | Hypermethylation |
| WNT5A | Intron | chr3 | 55492550 | 55492850 | YES | YES | NO | NO | Hypermethylation |
| chr3: 138971600-138972200 | Intergenic | chr3 | 138971600 | 138972200 | YES | YES | YES | YES | Hypermethylation |
| ZIC4 | Intron | chr3 | 148598200 | 148599000 | YES | YES | NO | NO | Hypermethylation |
| FGF12 | Intron/Exon | chr3 | 193608500 | 193610500 | YES | YES | NO | NO | Hypermethylation |
| GP5 | Exon | chr3 | 195598400 | 195599200 | YES | YES | NO | NO | Hypermethylation |
| MSX1 | Upstream | chr4 | 4910550 | 4911100 | YES | YES | NO | NO | Hypermethylation |
| NKX3-2 | Intron/Exon | chr4 | 13152500 | 13154500 | YES | YES | NO | NO | Hypermethylation |
| chr4: 111752000-111753000 | Intergenic | chr4 | 111752000 | 111753000 | YES | YES | YES | NO | Hypermethylation |
| SFRP2 | Promoter | chr4 | 154928800 | 154930100 | YES | YES | NO | NO | Hypermethylation |
| chr4: 174664300-174664800 | Intergenic | chr4 | 174664300 | 174664800 | YES | YES | NO | NO | Hypermethylation |
| chr4: 174676300-174676800 | Intergenic | chr4 | 174676300 | 174676800 | YES | YES | NO | NO | Hypermethylation |
| SORBS2 | Intron | chr4 | 186796900 | 186797500 | YES | YES | NO | NO | Hypermethylation |
| chr5: 42986900-42988200 | Intergenic | chr5 | 42986900 | 42988200 | YES | YES | NO | NO | Hypermethylation |
| chr5: 72712000-72714100 | Intergenic | chr5 | 72712000 | 72714100 | YES | YES | NO | NO | Hypermethylation |
| chr5: 72767550-72767800 | Intergenic | chr5 | 72767550 | 72767800 | YES | YES | NO | NO | Hypermethylation |
| NR2F1 | Intron/Exon | chr5 | 92955000 | 92955250 | YES | YES | NO | NO | Hypermethylation |

TABLE 2B-continued

Non-Chromosome 21 differentially methylated regions

| Region Name | Gene Region | Chrom | Start | End | Microarray Analysis | EpiTYPER 8 Samples | EpiTYPER 73 Samples | Previously Validated EpiTYPER | Relative Methylation Placenta to Maternal |
|---|---|---|---|---|---|---|---|---|---|
| PCDHGA1 | Intron | chr5 | 140850500 | 140852500 | YES | YES | YES | NO | Hypermethylation |
| chr6: 10489100-10490200 | Intergenic | chr6 | 10489100 | 10490200 | YES | YES | YES | NO | Hypermethylation |
| FOXP4 | Intron | chr6 | 41636200 | 41637000 | YES | YES | NO | YES | Hypermethylation |
| chr7: 19118400-19118700 | Intergenic | chr7 | 19118400 | 19118700 | YES | YES | NO | NO | Hypermethylation |
| chr7: 27258000-27258400 | Intergenic | chr7 | 27258000 | 27258400 | YES | YES | NO | NO | Hypermethylation |
| TBX20 | Upstream | chr7 | 35267500 | 35268300 | YES | YES | NO | NO | Hypermethylation |
| AGBL3 | Promoter | chr7 | 134321300 | 134322300 | YES | YES | NO | NO | Hypermethylation |
| XPO7 | Downstream | chr8 | 21924000 | 21924300 | YES | YES | NO | NO | Hypermethylation |
| chr8: 41543400-41544000 | Intergenic | chr8 | 41543400 | 41544000 | YES | YES | NO | NO | Hypermethylation |
| GDF6 | Exon | chr8 | 97225400 | 97227100 | YES | YES | NO | NO | Hypermethylation |
| OSR2 | Intron/Exon | chr8 | 100029000 | 100031000 | YES | YES | YES | YES | Hypermethylation |
| GLIS3 | Intron/Exon | chr9 | 4288000 | 4290000 | YES | YES | NO | YES | Hypermethylation |
| NOTCH 1 | Intron | chr9 | 138547600 | 138548400 | YES | YES | YES | NO | Hypermethylation |
| EGFL7 | Upstream | chr9 | 138672350 | 138672850 | YES | YES | NO | NO | Hypermethylation |
| CELF2 | Intron/Exon | chr10 | 11246700 | 11247900 | YES | YES | NO | NO | Hypermethylation |
| HHEX | Intron | chr10 | 94441000 | 94441800 | YES | YES | NO | NO | Hypermethylation |
| DOCK1/FAM196A | Intron/Exon | chr10 | 128883000 | 128883500 | YES | YES | NO | NO | Hypermethylation |
| PAX6 | Intron | chr11 | 31782400 | 31783500 | YES | YES | NO | NO | Hypermethylation |
| FERMT3 | Intron/Exon | chr11 | 63731200 | 63731700 | YES | YES | YES | NO | Hypermethylation |
| PKNOX2 | Intron | chr11 | 124541200 | 124541800 | YES | YES | NO | NO | Hypermethylation |
| KIRREL3 | Intron | chr11 | 126375150 | 126375300 | YES | YES | NO | NO | Hypermethylation |
| BCAT1 | Intron | chr12 | 24946700 | 24947600 | YES | YES | NO | NO | Hypermethylation |
| HOXC13 | Intron/Exon | chr12 | 52625000 | 52625600 | YES | YES | NO | NO | Hypermethylation |
| TBX5 | Promoter | chr12 | 113330500 | 113332000 | YES | YES | NO | NO | Hypermethylation |
| TBX3 | Upstream | chr12 | 113609000 | 113609500 | YES | YES | NO | YES | Hypermethylation |
| chr12: 113622100-113623000 | Intergenic | chr12 | 113622100 | 113623000 | YES | YES | YES | NO | Hypermethylation |
| chr12: 113657800-113658300 | Intergenic | chr12 | 113657800 | 113658300 | YES | YES | NO | NO | Hypermethylation |
| THEM233 | Promoter | chr12 | 118515500 | 118517500 | YES | YES | NO | YES | Hypermethylation |
| NCOR2 | Intron/Exon | chr12 | 123516200 | 123516800 | YES | YES | YES | NO | Hypermethylation |
| THEM132C | Intron | chr12 | 127416300 | 127416700 | YES | YES | NO | NO | Hypermethylation |
| PTGDR | Promoter | chr14 | 51804000 | 51805200 | YES | YES | NO | NO | Hypermethylation |
| ISL2 | Intron/Exon | chr15 | 74420000 | 74422000 | YES | YES | NO | YES | Hypermethylation |
| chr15: 87750000-87751000 | Intergenic | chr15 | 87750000 | 87751000 | YES | YES | NO | NO | Hypermethylation |
| chr15: 87753000-87754100 | Intergenic | chr15 | 87753000 | 87754100 | YES | YES | NO | NO | Hypermethylation |
| NR2F2 | Upstream | chr15 | 94666000 | 94667500 | YES | YES | YES | NO | Hypermethylation |
| chr16: 11234300-11234900 | Intergenic | chr16 | 11234300 | 11234900 | YES | YES | NO | NO | Hypermethylation |
| SPN | Exon | chr16 | 29582800 | 29583500 | YES | YES | YES | NO | Hypermethylation |
| chr16: 85469900-85470200 | Intergenic | chr16 | 85469900 | 85470200 | YES | YES | NO | NO | Hypermethylation |
| SLFN11 | Promoter | chr17 | 30725100 | 30725600 | YES | YES | NO | NO | Hypermethylation |
| DLX4 | Upstream | chr17 | 45396800 | 45397800 | YES | YES | NO | YES | Hypermethylation |
| SLC38A10 (MGC15523) | Intron | chr17 | 76873800 | 76874300 | YES | YES | YES | NO | Hypermethylation |
| S1PR4 | Exon | chr19 | 3129900 | 3131100 | YES | YES | YES | YES | Hypermethylation |
| MAP2K2 | Intron | chr19 | 4059700 | 4060300 | YES | YES | YES | NO | Hypermethylation |
| UHRF1 | Intron | chr19 | 4867300 | 4867800 | YES | YES | YES | NO | Hypermethylation |
| DEDD2 | Exon | chr19 | 47395300 | 47395900 | YES | YES | YES | NO | Hypermethylation |
| CDC42EP1 | Exon | chr22 | 36292300 | 36292800 | YES | YES | YES | NO | Hypermethylation |

TABLE 2CA

Chromosome 21 differentially methylated regions-Hypermethylation

| Region Name | Gene Region | Chrom | Start | End | Microarray Analysis | Epi TYPER 8 Samples | Epi TYPER 73 Samples | Previously Validated Epi TYPER | Relative Methylation Placenta to Maternal |
|---|---|---|---|---|---|---|---|---|---|
| chr21: 15649340-15649450 | Intergenic | chr21 | 15649340 | 15649450 | NO | YES | YES | NO | Hypermethylation |
| CHODL | Promoter | chr21 | 18539000 | 18539800 | NO | YES | YES | NO | Hypermethylation |

TABLE 2CA-continued

Chromosome 21 differentially methylated regions-Hypermethylation

| Region Name | Gene Region | Chrom | Start | End | Microarray Analysis | Epi TYPER 8 Samples | Epi TYPER 73 Samples | Previously Validated Epi TYPER | Relative Methylation Placenta to Maternal |
|---|---|---|---|---|---|---|---|---|---|
| NCAM2 | Upstream | chr21 | 21291500 | 21292100 | NO | YES | NO | NO | Hypermethylation |
| MIR155HG | Promoter | chr21 | 25855800 | 25857200 | NO | YES | YES | NO | Hypermethylation |
| chr21: 30741350-30741600 | Intergenic | chr21 | 30741350 | 30741600 | NO | YES | NO | NO | Hypermethylation |
| TIAM1 | Intron | chr21 | 31426800 | 31427300 | NO | YES | YES | NO | Hypermethylation |
| TIAM1 | Intron | chr21 | 31475300 | 31475450 | NO | YES | NO | NO | Hypermethylation |
| TIAM1 | Intron | chr21 | 31621050 | 31621350 | NO | YES | YES | NO | Hypermethylation |
| HUNK | Intron/Exon | chr21 | 32268700 | 32269100 | NO | YES | YES | NO | Hypermethylation |
| OLIG2 | Promoter | chr21 | 33314000 | 33324000 | YES | YES | NO | YES | Hypermethylation |
| RUNX1 | Intron | chr21 | 35320300 | 35320400 | NO | YES | NO | NO | Hypermethylation |
| RUNX1 | Intron | chr21 | 35321200 | 35321600 | NO | YES | NO | NO | Hypermethylation |
| RUNX1 | Intron/Exon | chr21 | 35340000 | 35345000 | NO | YES | YES | NO | Hypermethylation |
| chr21: 35499200-35499700 | Intergenic | chr21 | 35499200 | 35499700 | NO | YES | YES | NO | Hypermethylation |
| chr21: 35822800-35823500 | Intergenic | chr21 | 35822800 | 35823500 | NO | YES | YES | NO | Hypermethylation |
| CBR1 | Promoter | chr21 | 36364000 | 36364500 | NO | YES | NO | NO | Hypermethylation |
| SIM2 | Promoter | chr21 | 36988000 | 37005000 | YES | YES | YES | YES | Hypermethylation |
| HLCS | Intron | chr21 | 37274000 | 37275500 | YES | YES | YES | NO | Hypermethylation |
| DSCR6 | Upstream | chr21 | 37300200 | 37300400 | YES | YES | NO | YES | Hypermethylation |
| DSCR3 | Intron | chr21 | 37551000 | 37553000 | YES | YES | YES | NO | Hypermethylation |
| chr21: 37841100-37841800 | Intergenic | chr21 | 37841100 | 37841800 | NO | YES | YES | NO | Hypermethylation |
| ERG | Intron | chr21 | 38791400 | 38792000 | NO | YES | YES | NO | Hypermethylation |
| chr21: 39278700-39279800 | Intergenic | chr21 | 39278700 | 39279800 | NO | YES | YES | NO | Hypermethylation |
| C21orf129 | Exon | chr21 | 42006000 | 42006250 | NO | YES | YES | NO | Hypermethylation |
| C2CD2 | Intron | chr21 | 42188900 | 42189500 | NO | YES | YES | NO | Hypermethylation |
| UMODL1 | Upstream | chr21 | 42355500 | 42357500 | NO | YES | YES | NO | Hypermethylation |
| PDE9A | Intron | chr21 | 42977400 | 42977600 | NO | YES | NO | NO | Hypermethylation |
| PDE9A | Intron | chr21 | 43039800 | 43040200 | NO | YES | YES | NO | Hypermethylation |
| U2AF1 | Intron | chr21 | 43395500 | 43395800 | NO | YES | NO | NO | Hypermethylation |
| U2AF1 | Intron | chr21 | 43398000 | 43398450 | NO | YES | YES | NO | Hypermethylation |
| chr21: 43643000-43644300 | Intergenic | chr21 | 43643000 | 43644300 | YES | YES | YES | YES | Hypermethylation |
| C21orf125 | Upstream | chr21 | 43689100 | 43689300 | NO | YES | NO | NO | Hypermethylation |
| C21orf125 | Downstream | chr21 | 43700700 | 43701700 | NO | YES | NO | NO | Hypermethylation |
| AGPAT3 | Intron | chr21 | 44161100 | 44161400 | NO | YES | YES | NO | Hypermethylation |
| C21orf29 | Intron | chr21 | 44950000 | 44955000 | NO | YES | YES | NO | Hypermethylation |
| C21orf57 | Intron | chr21 | 46541568 | 46541861 | NO | YES | NO | NO | Hypermethylation |
| C21orf57 | Exon | chr21 | 46541872 | 46542346 | NO | YES | NO | NO | Hypermethylation |
| C21orf57 | Downstream | chr21 | 46542319 | 46542665 | NO | YES | NO | NO | Hypermethylation |
| PRMT2 | Downstream | chr21 | 46911000 | 46913000 | YES | YES | NO | YES | Hypermethylation |
| ITGB2 | Intron | chr21 | 45170700 | 45171100 | NO | YES | YES | NO | Hypermethylation |

TABLE 2CB

Chromosome 21 differentially methylated regions-Hypomethylation

| Region Name | Gene Region | Chrom | Start | End | Microarray Analysis | Epi TYPER 8 Samples | Epi TYPER 73 Samples | Previously Validated Epi TYPER | Relative Methylation Placenta to Maternal |
|---|---|---|---|---|---|---|---|---|---|
| chr21: 9906600-9906800 | Intergenic | chr21 | 9906600 | 9906800 | NO | YES | NO | NO | Hypomethylation |
| chr21: 9907000-9907400 | Intergenic | chr21 | 9907000 | 9907400 | NO | YES | NO | NO | Hypomethylation |
| chr21: 9917800-9918450 | Intergenic | chr21 | 9917800 | 9918450 | NO | YES | NO | NO | Hypomethylation |
| TPTE | Promoter | chr21 | 10010000 | 10015000 | NO | YES | NO | NO | Hypomethylation |
| chr21: 13974500-13976000 | Intergenic | chr21 | 13974500 | 13976000 | NO | YES | NO | NO | Hypomethylation |
| chr21: 13989500-13992000 | Intergenic | chr21 | 13989500 | 13992000 | NO | YES | NO | NO | Hypomethylation |
| chr21: 13998500-14000100 | Intergenic | chr21 | 13998500 | 14000100 | NO | YES | NO | NO | Hypomethylation |
| chr21: 14017000-14018500 | Intergenic | chr21 | 14017000 | 14018500 | NO | YES | NO | NO | Hypomethylation |
| chr21: 14056400-14058100 | Intergenic | chr21 | 14056400 | 14058100 | NO | YES | NO | NO | Hypomethylation |
| chr21: 14070250-14070550 | Intergenic | chr21 | 14070250 | 14070550 | NO | YES | NO | NO | Hypomethylation |
| chr21: 14119800-14120400 | Intergenic | chr21 | 14119800 | 14120400 | NO | YES | NO | NO | Hypomethylation |
| chr21: 14304800-14306100 | Intergenic | chr21 | 14304800 | 14306100 | NO | YES | NO | NO | Hypomethylation |
| C21orf34 | Intron | chr21 | 16881500 | 16883000 | NO | YES | NO | NO | Hypomethylation |
| BTG3 | Intron | chr21 | 17905300 | 17905500 | NO | YES | NO | NO | Hypomethylation |
| chr21: 23574000-23574600 | Intergenic | chr21 | 23574000 | 23574600 | NO | YES | NO | NO | Hypomethylation |
| chr21: 24366920-24367060 | Intergenic | chr21 | 24366920 | 24367060 | NO | YES | NO | NO | Hypomethylation |

TABLE 2CB-continued

Chromosome 21 differentially methylated regions-Hypomethylation

| Region Name | Gene Region | Chrom | Start | End | Micro-array Analysis | Epi TYPER 8 Samples | Epi TYPER 73 Samples | Previously Validated Epi TYPER | Relative Methylation Placenta to Maternal |
| --- | --- | --- | --- | --- | --- | --- | --- | --- | --- |
| chr21: 25656000-25656900 | Intergenic | chr21 | 25656000 | 25656900 | NO | YES | NO | NO | Hypomethylation |
| CYYR1 | Intron | chr21 | 26830750 | 26830950 | NO | YES | NO | NO | Hypomethylation |
| chr21: 26938800-26939200 | Intergenic | chr21 | 26938800 | 26939200 | NO | YES | NO | NO | Hypomethylation |
| GRIK1 | Intron | chr21 | 30176500 | 30176750 | NO | YES | NO | NO | Hypomethylation |
| SOD1 | Intron | chr21 | 31955000 | 31955300 | NO | YES | NO | NO | Hypomethylation |
| chr21: 33272200-33273300 | Intergenic | chr21 | 33272200 | 33273300 | NO | YES | NO | NO | Hypomethylation |
| OLIG2 | Downstream | chr21 | 33328000 | 33328500 | YES | YES | NO | NO | Hypomethylation |
| RUNX1 | Intron | chr21 | 35185000 | 35186000 | NO | YES | NO | NO | Hypomethylation |
| DOPEY2 | Downstream | chr21 | 36589000 | 36590500 | NO | YES | NO | NO | Hypomethylation |
| UMODL1/C21orf128 | Intron | chr21 | 42399200 | 42399900 | NO | YES | NO | NO | Hypomethylation |
| ABCG1 | Intron | chr21 | 42528400 | 42528600 | YES | YES | NO | NO | Hypomethylation |
| chr21: 42598300-42599600 | Intergenic | chr21 | 42598300 | 42599600 | YES | YES | NO | NO | Hypomethylation |
| chr21: 42910000-42911000 | Intergenic | chr21 | 42910000 | 42911000 | NO | YES | NO | NO | Hypomethylation |
| PDE9A | Upstream | chr21 | 42945500 | 42946000 | NO | YES | NO | NO | Hypomethylation |
| PDE9A | Intron | chr21 | 42961400 | 42962700 | NO | YES | NO | NO | Hypomethylation |
| PDE9A | Intron/Exon | chr21 | 42978200 | 42979800 | YES | YES | NO | NO | Hypomethylation |
| chr21: 43130800-43131500 | Intergenic | chr21 | 43130800 | 43131500 | NO | YES | NO | NO | Hypomethylation |
| chr21: 43446600-43447600 | Intergenic | chr21 | 43446600 | 43447600 | NO | YES | NO | NO | Hypomethylation |
| CRYAA | Intron/Exon | chr21 | 43463000 | 43466100 | NO | YES | NO | NO | Hypomethylation |
| chr21: 43545000-43546000 | Intergenic | chr21 | 43545000 | 43546000 | YES | YES | NO | NO | Hypomethylation |
| chr21: 43606000-43606500 | Intergenic | chr21 | 43606000 | 43606500 | NO | YES | NO | NO | Hypomethylation |
| HSF2BP | Intron/Exon | chr21 | 43902500 | 43903800 | YES | YES | NO | NO | Hypomethylation |
| chr21: 44446500-44447500 | Intergenic | chr21 | 44446500 | 44447500 | NO | YES | NO | NO | Hypomethylation |
| TRPM2 | Intron | chr21 | 44614500 | 44615000 | NO | YES | NO | NO | Hypomethylation |
| C21orf29 | Intron | chr21 | 44750400 | 44751000 | NO | YES | NO | NO | Hypomethylation |
| ITGB2 | Intron/Exon | chr21 | 45145500 | 45146100 | NO | YES | NO | NO | Hypomethylation |
| POFUT2 | Downstream | chr21 | 45501000 | 45503000 | NO | YES | NO | NO | Hypomethylation |
| chr21: 45571500-45573700 | Intergenic | chr21 | 45571500 | 45573700 | NO | YES | NO | NO | Hypomethylation |
| chr21: 45609000-45610600 | Intergenic | chr21 | 45609000 | 45610600 | NO | YES | NO | NO | Hypomethylation |
| COL18A1 | Intron | chr21 | 45670000 | 45677000 | YES | YES | NO | YES | Hypomethylation |
| COL18A1 | Intron/Exon | chr21 | 45700500 | 45702000 | NO | YES | NO | NO | Hypomethylation |
| COL18A1 | Intron/Exon | chr21 | 45753000 | 45755000 | YES | YES | NO | YES | Hypomethylation |
| chr21: 45885000-45887000 | Intergenic | chr21 | 45885000 | 45887000 | NO | YES | NO | NO | Hypomethylation |
| PCBP3 | Intron | chr21 | 46111000 | 46114000 | NO | YES | NO | NO | Hypomethylation |
| PCBP3 | Intron/Exon | chr21 | 46142000 | 46144500 | NO | YES | NO | NO | Hypomethylation |
| COL6A1 | Intron/Exon | chr21 | 46227000 | 46233000 | NO | YES | NO | NO | Hypomethylation |
| COL6A1 | Intron/Exon | chr21 | 46245000 | 46252000 | NO | YES | NO | NO | Hypomethylation |
| chr21: 46280500-46283000 | Intergenic | chr21 | 46280500 | 46283000 | NO | YES | NO | NO | Hypomethylation |
| COL6A2 | Intron | chr21 | 46343500 | 46344200 | NO | YES | NO | NO | Hypomethylation |
| COL6A2 | Intron/Exon | chr21 | 46368000 | 46378000 | NO | YES | NO | NO | Hypomethylation |
| C21orf56 | Intron/Exon | chr21 | 46426700 | 46427500 | NO | YES | NO | NO | Hypomethylation |
| C21orf58 | Intron | chr21 | 46546914 | 46547404 | NO | YES | NO | NO | Hypomethylation |

TABLE 3

Hypomethylated locus region sequences

| SEQ ID NO | GENE NAME | SEQUENCE |
|---|---|---|
| 1 | chr13 group-00005 | TAGTAAGGACCACCGAGGGGTGGCTCCTCTCCCTGCGAGCGGCTGTCGCCTTACCATCCTGTAGACCGTGACCTCCTCACACAGCGCCAGGA<br>CGAGGATCGCGGTGAGCCAGCAGGTGACTGCGATCCTGGAGCTGTGCAGCAGCCATCCTGCACGCGGTGAGGCGCCCCCTGCA<br>GGCCCCAGCCGCATCCCCAGCTTCTGGACGCACTGTGAGCGGTTATGCAGCAGCACGCCACTTGGCACGCCACCACCAGGTGCTATGCA<br>GGCCCAGCCGCTCCCACAAAGCCATGGCAGGCGCCGGTGCCGGAGCACGCACTTGGCCCCATGGATCTCTGTGCCCAGGGCTCAGC<br>CAGGCATCTGCCGCTAAAGGTTT |
| 2 | CRYL1 | TCTCATCTGAGCGCTGTGTCTTTCACCAGAGCTCTGTAGGACTGAGGCAGTAGCGCTGAGCGCCCTGCGAGCGCGGTCTGGACGATG<br>CGTCGCGCCCTTCCCATCGCGCGCGTCGGGCGCCCGCCTCGCGGGCCCGCGGGCCGGGTTTCCTCACCCGGGCACCCTCCCCTCGCC<br>CGCACCCGGCCCCAGTCCCTCCCCAGCTTCGCGGGTAGAGCCGTGTCTTTGCCCAGAAGGCCGTCTCCAAGCT |
| 3 | IL17D | CAGTCCCCGAGGCCTCCCCGGGTGACTCTAACCAGGGATTTCAGCGCCGGCCCGGGGGCTTGCCCCCCAGCGCTGACCTGACCTCACCCGTGCT<br>CTCTCCCTGCAGAATCTCCTACGACCCGGCCTGCTCCCAGGTACCTGCCTGAAGCCTACTGCCTGTGCCGGGGCTGCCTGACCGGG<br>CTGTTCGGCGAGGAGACGTGCGCTTCCGCAGCCGCCCCTGTCTACAT |
| 4 | IRS2 | AGAGAGACATTTTCCACGGAGGCCGAGTTGTGGGCGCTTGGGGTTGTGGGCGAAGGACGGGGACACGGGGGTGACCGTTGCTGTGGTGAG<br>GAGAAGGCTCTCGGAACTGTGGCGCGCGAGTGCCTTGGCGCCAGGGACTCTCGCCGGCGATGACTTCGCGCGTGGGGCGTGGGGGCTG<br>GCTGGCCTGCAGGAAGGCCCTCGACTTCCCGACACCTGCTCCTCCCATGAGGCTCAGCCTCTTCACGCCCACGTCGGGCCACGCGGGC<br>AGTTCTCGGCTTCCGGGGGCCCGCGATAGGTTGCGGCCGGACCCCTGGGCGGTGGCCGCCCACACAGCCATCTCGTGTAGTCACCATTGTCCCC<br>GGTGTCCGAGGACAACGATGAGGGCGGCGCCCGGGCCCTGGGCGGTGGCAACGGCCGAGGGCGGGGGCAACGGCGGGGACAGCGGATACGGGAGGAG<br>GCCTCGGGGACCGGCGGGCTGCAAGGAGCGTCCAGGAGCGCCACGGGGACCCACCGGGCTGGCCCTGCGCCGGCCTTAGGAGACTTGGGGAGCTGAAGTC<br>GAGGTTCATGTAGTCGGAGAGCGAGGAGGACGAGCCCCTGCGCCGGCTTCCTCCTGCTCGTTGTGCCCAGCGACCAGGCGGGCTCGCC<br>TGCTGGCGGACAAGAGCGAGGAGCGAGGAGGACGAGCCCGGCGGCCCGAGCCTCTTGGGCTCCAGTGGACGTACTCGTCCATGCTGGGCAGGCTGGGCAGCCCTCC<br>AAAGTTCGATCGTTTGATGTACTCCGCCCGGGCTCTTGGCTCCAGTGGACGTACTCGTCCATGCTGGGCAGGCTGGGCAGCCCCTCC<br>AGGGACAGGCGCGTGGGCCTCCACCGCCGCTGGCCCAAGAAGCCCTCCGGGCGCCTAGGCCGCACGGGCGAAG<br>GCACTACAGGGTGAGGGGTGCCCGGCCGGCCTGCCCGGCCGGCCGGGCCGGAGTCATGAGCACGTACTGGTCGTCCCGCCACAGTGTAGGGGGCCTTGTAG<br>CGTCCTCCTCCAGATGCGCCCACGGGCTGCGTAGCAGCCGGGAACGCCTGGCCAGCAGCCGGGGCTGTGAGCGGCTCCAGGGCTGCAGGGCTGCAGGGTCAGGCTCGGCCAGGAAGTCGG<br>GAGGCGGGCAAGGAGCGTCCCCGTGCGCGGGTGACCGCGTCGCCGGGGAACACGTTGAGGTAGTCCCCGTTGCCATCGCATGCTCCATGGA<br>CAGCTTGGAACCGCACCACATGCCATGTACCCACTCTTCGGCCCCCAGGCCCGGGAGCTCTCGGCGAGCTGGCCTTGTAGCCGCCCCCCCT<br>CGCCGGGAATGTCTGCCCGCCGCAGAGTCTGCTTGGGGCGGACACGCTGGGGCGGACTGGCCTCATGGGGCTCATGTGCGGTCTCCTGCAGCTGCCGCTCCA<br>CTGCCCGGGAGCGGCGCCCTGGCGTGAGCCCGAGCCATGGGCGATGCCCCGCCATGTGCTGCCCCAGGTTCTGTGAGGCCGATC<br>TCGATGTCTCCGTAGTCTCCTGGGTAGGGTGGTTAGCCCCACCTTGGGAGGAGGACGCGGGCTGGGCACCCCGGCTGCCGCGGCTGGCGTGG<br>GCCCGAGAAGGTAGGTCTCTTGCCCGCATCAGGGTGTATTCATCCAGCGAGGCAGAGGGCTCCCCGAGACCCCGGCCGGGCGGGCCCACAGTGGC<br>TCAGGGAGTAGGTCTCGTCATGTACCCGCAGCCTCACCCGCCGCTGGGCTGCCCGCCGTACTCGTCCAGGACATGAAGCCGGGACTCGG<br>GCGTGTTGCTTCGGTGGCTGCAGAAGGGCGCTGCCGCTGAGGGGCCGCTGCAGGTCGCCCGGACCCGTGGGCAGCCGCCGACATGAAGCCGGGACTCGG<br>GGGAGCCCAGAGGCGGAGGCGCTGCCCGAGCCCGAGCCCGGAGCTGGTGCCAGCCCGTGGTGCAGCGGATGCGGCAGAGGCGGGTGCGCTGG<br>CGGGGCGGCGGCGGTAGGAGCCCGAGCCCTGGCCGCTGCTGGACGACAGGGAGC |
| 5 | chr13 group-00350 | TAACCTAAAGAATGAAGTCATGCCCCGGCCTGCACCCGGAAACTGCACACAGCGAAAGATCGCCACTGAGATAAAGAGCTGAAAGCTA<br>TTCCCCAATTCAGCTGTTTCAGCCCTGCCGCTCAACCCTGCCGCTCAACCCGCCGCGTCCCGCTGTCTCACAGACGGCAGCATC |

TABLE 3-continued

Hypomethylated locus region sequences

| SEQ ID NO | GENE NAME | SEQUENCE |
|---|---|---|
| 6 | MCF2L | GTTTCCACAATCCACCTCGTAGCTGGGGCTGCCCGTGCCCCTTGCTCGCTGTCTCCGGCAGAACACTCTTACCTTTAATGGCGACTGAAAAG<br>TTGCCACGAGTTCCTGATCATTGTGTAGGTGCTGCTGAAGCTGAGACCTGCTGAAGCTGCTGAGCCCACATCCCAGGGGCTTTGAGCCCACC<br>GCGGCGGCGCTGAGGGAGGAGGCTTGTCGTATCCACAGGAGGACACAGGCTCGCAGTGTTCACTCACCCAGGGCCTCTTATCATTGGGAT<br>CTGAGGAATTTTCCGAGAGAAGTCGAATTAACAATGAGAAAGGTTTGTGACAGTGAGTGACAGGCACGTTCATTGAGCACTGCATGGG<br>GCAATTATGTGCCACCAGAGACGGGGCAGTCCAAGAGCCTCAAGAGCCTCAGAGAGTTCGGAGGAGTAGAAGTCATCAGAGCACAAT<br>GAAGCCAGACCCTGCAGCCGCTTCCCCTTCGGCTTCAGCCCTTCAAGACTCGGCAGCCAGGATGGGCTCAAGGACATGAGCCCTCAAAGGA<br>GCCGTCACGGTGTGTTGGACGCCCCTGGTCAGGAGAAAAGATATGCTTGTGTGACGTCTGGCCGAAGTGAGAACGCCCACGGAGCCTCGGGGGCCCAGCG<br>GGTTAGGAAGGAGGCAGGGAGGAGAAAAGATATGCTTGTGTGACGTCTGGCCGAAGTGAGAACGCCCACGGAGCCTCGGGGGCCCAGCG<br>ATTGGAGGGTGCGACAAGGACTCGGACGCAAGGGTCCCCCTGTACTGAGGAGAGCGCCACGGAGCCTCGGGGGCCCAGCG<br>TCCCGGGATCACTGATGTGTAAAGCCGCCTGCCTGGCGT |
| 7 | F7 | TCCAGCTGCGCAGCGACGGCGGCCAGCCCCTTCTCCGACCTGCAGGGTAGCGCGGCCTCGGCGCGGCGACCCCGCCGCTGTCTG<br>GGGCTCGGTGCGGTGTGGGGAGGGCGCGGACGCGCCCGACGCCCCCACCCAGGCCACCTCACCGCGCCCACGAGCGCCTGGCCG<br>TGCGGGCTGCAGAGGACCCCCTCCGGGGCAGAGGCAGGTTCACGCAGGGCAGGAAGACCCCGGCTTCCCGGAGACTCCAGAG |
| 8 | chr18group-00039 | ACTTACTGCTTCCAAAAGCTGGGCACAGCCTTATATGACTGACCCCGCCCGAGTCCAGGCCGCTCCAGCGCCCAACCG<br>CCCAACCGCCCACTCCAAAGTCACCAACCACTGCTTCCAGGCCACGGGCTGTCCTCCCCCACGGCTCTAGGGCCCTTCCCCTCCACCGC<br>AGGCTGAC |
| 9 | C18orf1 | TGCCACACACCAGGTACGCCCCCGCGCGAGAGCCCGGACGGCAGGTGGGCCGCGGATGCTCCCAGAGGCCGGCCCAGCAGAGCGATGG<br>ACTTGGACAGGCTAAGATGGAAGTGACCTGAG |
| 10 | CD33L3 | TCGCCAGCGCAGCGCTGGTCCATGCAGTGCCACCCGAGGTGAGCGCGGAGGCAGGCGACGCGGCAGTGCTGCCCTGCACCTTCAC<br>GCACCCGCACCGCCACTACGACGGGCCGCTGACGCCGCTGCTGGGCGCCGGGAGCCCTTCGGGCCGGAGTGTTCCGCTGCG<br>CTGCCCGGCGGGCGGCGGCGAGCTCTCGCGGCAGCCGCCTCCCCTGCCTGACGCGCCGCCTTCCGCGTGCAGGCCAACCCGCCGCAACGAC<br>CTCTGCTGCGCGGTGCAACCGCCACGGCGGCCTCCGCCGCGTCCAGCCCGGCTGCCGCGGCCGCGGCCCTTCCCGACGTCATGACCGC<br>TACGAGAGCCGCCACGGCGCCACCAAGGGCTACGTGGGGTGCCAGGCGTGTCTGAGCCAGGAAGCAGCAAATGCAGAATCCAGGTTCCAGGAAGGGCTGAGGTGGGCCCG<br>GATCCCGCCCCAAGGGCTAGTTTAGGACACACCTGGGAGCTTGACACCAAATGCAGAATCCAGGTTCCAGGAAGGGCTGAGGTGGGCCCG<br>GGAATAGGCACTTGCCGTGACTCTCGTAGAGTGACTGTCCCAGTGGCTCTCAGACGAAGAGCCAGAAAGACAAGTGAATGGCAATCCT<br>AAATATGCCAAGAGTGCAATGTGTGTGCAGACCCGAATATACAAAGATGCTGAACCAGGGTCCCGTCCTAGAGCAGTGGCTCTCACTCTA<br>CCAAGTAGTGCCTAGCACTTTGCCAGACCATTAGCATTTGCTAGGGAGCCCGGAACCTAGTCCAAGCACCACAGAGCCATGAATCTTTCG<br>GCCCCCACCCTGCTCTGCGACAATAATGCCACTTAAGCACTTAGCATTTGCTAGGGAGCCCGGAACCTAGTCCAAGCACCACAGAGCCATGAATCTTTCG<br>CAAATCTTTTCAGCAACCTCTTAAGGCAACTGTATTGGGACGGGGAGGGTGCCCTTTGTGACAGTCACTGCCAAGGGAGCCGGAACTCTCCTTTCTGAGCCGCGCCGATCGTCAACATCTC<br>CCCAAGGCCACATCTGTATTGGGACGGGGAGGGTGCCCTTTGTGACAGTCACTGCCAAGGGAGCCGGAACTCTCCTTTCTGAGCCGCGCCGATCGTCAACATCTC<br>TGGCGTCCAAAGGCTAAGGGAGGGGTGCCCTTTGTGACAGTCACTGCCAAGGGAGCCGGAACTCTCCTTTCTGAGCCGCGCCGATCGTCAACATCTC<br>GGTGCTGCCCAGTCCGGCTCACGCTTCCGCGCGCTTCGCTGCACTGCCAAGGGAGCGGCCCTTCGCCTGGTCCGGCCCGG<br>CCCTGGGCAACAGCTTGCGACGCGTGCGAGGGCCGTGCAAACGCCCTCGGGCCGTCCAGCCGGCAACTGCGTCTACCTGTTCGCTTCCATGGCCACTGACCATG<br>ACGGCCGCTACACGTGTACGCCCGCCAACGCGTAACGCGGCCCTCGGGCCGTCCAGCCGCAACTGCGTCTACCTGTTCGCTTCCATGGCCACTGACCATG<br>CCTCGACGGTTCGCCCTCTCGCTCGCCGCGCTCTCAAGGCGCT |
| 11 | TNFRSF11A | ATGAACTTCAAGACGCACATCATCGTGTCTACTGCAGCCAGACCTCGCAGCGGGCCGGCTGCGAGCCCATGCCGCCGC<br>CCGGTGCAGGAGGAGACCCTTGGCGCCGCAGGACTCCTTCCGGGGAACGCCCGCTTCCGGGGACCCGTGCGGCGGCCCAGGG<br>GCTGCGGGAGCCCGGAGAAGGCCTCGAGGCCGTGCAGGAGCAAGGCGGGGCAAGGCTTGAGCGCCCCCATGCCTGGAGCCCGA<br>AGCTCGGAGC |

TABLE 3-continued

Hypomethylated locus region sequences

| SEQ ID NO | GENE NAME | SEQUENCE |
|---|---|---|
| 12 | ZNF236 | TCAGTGTTATGTGGGAGCGCTAGATCGTGCACACAGTAGGCGTCAGGAAGTGTTTTCCCCAGTAATTTATTCTCCATGTACTTTGCTA<br>AAGTCATGAAATAACTTCAGATTTTGTTTTCAAGGAAGGAGAAAGGCCCAGAATTTAAGAGCAGGCAGCACACAACCGGCACCCCA<br>GACCCTGGCCCTTCCAGCAGTCAGGAATTGACTTGCCTTCCAAAGCCCCGAGCTTGAGGAACGACTTTCCTGCGCAGGGGG<br>ATCGGGGCGCACTCG |
| 13 | chr18 group- 00342 | GTGAAACACAACCTGCCTTCTCCATTGTCTGCGCCTCCAAAACACCCCCCGGCCATCCGTGAGCTGTGTGTTTCTGTTACTACAGG<br>GGCCCGCTGTGGAAATCCCAGACCGCTCCAGACCGCGTGCCGGGCAGGCCAGCC |
| 14 | OLIG2 | TCCACACCTCGGGCAGTCACTAGGAAAAAGGGTCGCCAACTGAAAGGCTGTCAGGAACCAGGATGATACCTGCTCAGTCCCGCGCTG<br>CTGCGAGTGCGCGCTTCTCCTGCGCCCAGCAGCACACGGAGGGCCCTGCCAGACACCCGAGGGCCCTTC<br>AGTTTGCAAACCCTGAAAGCGGGCGGTCTGCAGGACGATCTCGGCAGGGCTGCCAGGCCTCGGGCCTCCTTATTTGGGGTCCT<br>CGGGCAGCCACGTTCTGGGGGAAGACTGCTTAAGGAACTGCCTCTGAACTGCGCGCTGTCCTCTCCGGCCCTCGCTTCC<br>CCGACCCCGCACAGGCTAACGGGAGAGCGCCAGGCCCAGCCCACCGGTTGGAGACCCCGGCCACAATCCGTCACTGGTTGTGGAACGGTT<br>GCAGCTGGGCTTGGACGCGCGCCAGTTTCCTTTGGCGACATTGCAGCGTCGGTGCGGCCACAATCCGTCACTGGTTGTGGAACGGTT<br>GGAGTCCCCAAGAAGAGACACGCAGAGCTTCCCAGAACCGCCTACATGCGCCATGGGCCCAAACAGCCTCCAAGGAGCACCCA<br>GGTCCATGCACCCGAGCCCAAAATCACAGACCCGCTACGGGCTTTTGCACATCAGCTCCAAACACCTGAGTCCACGTGCACAGGCTCTC<br>GCACAGGGACTCACGCACCTGAGTTCGCCTCACAGATC |
| 15 | RUNX1 | CTGCCCTCGCGGATCTCCCCGCCTCGCCGGCTTCCGCCTCTCCGCCTGTCCTCCGGCCAGTACTTGAAAGCGATGGGCA<br>GGGTCTTGTTGCAGCGCCAGTGCGTAGGCAGCACGCAGGAGAAGTTGGGGCTGTCGTGCCCAGCTCGCCCGGGTGGTCGG<br>CCAGCACCTCCACCATGCTGCGGTCGCCGTCCCAGCTTGCCGCTGGAAGCGGCGGCTCGTGCATCTACGGCATACAACAA<br>TCGCTCATCTTGCCTGGGCTCAGCGCGGTGAAGCGCGTGAAGCGGGCGCGGCTCGTGCTGCATCTACGGGACATCGGAGCAGTGCT<br>GCCGATTGAGTTAGGACCCTGCAAACAGCTCCCTACCACGCGCCAAGCAGCTCCCCAAGCAGCTCCCGGAGACCAACA<br>TACACGTTCAGGGGCCTTTATTACTGCGGGGGTGCGGGGGCTGGGGGGGCGGTGGTTAGGGGAGGAGGAGACTAAGTACTACAGTC<br>AGGAGGGGAAAAACGTTCTGGTTCTGCGATCGGCCTCTGACCCAGGATGGGCTTCCTAGCAACCGATTGCTTAGTGCATTAAAAGTGAA<br>GACTATCTTCCACGAATCTTGCTTGCAGAGGTTAAGTTCTGTCTTTGGCTGTTAGAAAAGTTCCTGAAGCAAAATTCTCATCACTTCCTA<br>AAATATTTATGCGAAGAGTAAAACGATCAGCAAACACATTATTTGGAAGTTCCAGTAGTTAATGCCTGTCAGTTTTTTGCAGTGAGTTTG<br>TCTAAAGTCCCAACAGAACACAATATCTCCCGTAACAGAAGGCCGTATCAGGCACTTTTATCATGCAAACTGGCTTCAGTCCCGAAAAGCAAGAGCTGA<br>GACTTCCAAAGGTAGTGCTACTAATGTATGTGCACGTATATATAATATCTACTTCATTAAATGCTTCATTAAAATATTACAATACAATCTGTG<br>GAGAATTTAAACACAAGAAATTCATTAATGTACGTGCAGATTTTTTAAGTAGCCTTGAAAATCAGCTTCAGTAGTTGGAGCAGTGCT<br>GAGCTAGAAGTACTTTGCCTGGGCTTCAGCGGCGGTGAAGCGGTGAAGCGTCGTGCTGGCATCTACGGGACATCGGAGCAGTGCT<br>CTAATCTTAAACACAACAATCATAAGAAGGCCCAGTCGATGACACTCAGGGTTCTACAGCTTCTCCACATCTGTGAACTCGGGTTGGGGA<br>TGTTGGTTAAGTTCTGTGCTGCTCCTGTGTTGTGGAGTTGAGCAGCCCAGAGTCACAGAGTCACACAGTCACACACTCTTCGAAG<br>GCAGCCACTGTCTACATCAGCTGGGTGACTCAGCCCTGACTCGGGCAGCAGCAGAGAGAGAATTCCTCCACCGTGCCCAGCACCCGCC<br>GGTTAGCTGCTCCGAGGCACCGAACACCCCACGGGTCCGGTTACACCCACGCACAGTCGATCAGGGTCTTCTACAGCTTCTCCACATCTGGGTTCAG<br>AGATCAGAACAGACATGCGGCTGCCGGTTACACACGCACAGTCGATGCATGCTGTAAAAGGAAACAATTGGGAGAAAGGGAAAAACAACAAAAAAAGGAAGTCCAACGAGGCCAAGGAGAAG<br>CTCGGACCACAGAAGCAGTTAATTCAAAAGAAGAAAGGGAAAACAATTGGGAGAAAAGACAACAAAAAAAGGAAGTCCAACGAGGCCAAGGAGAAG<br>CAAGAGAAGGTTGACTTCCTTCGGCGTCCCATGCCGCCCCCCCCGGCCCCGCAGGGGCCCGGGCCAGCGGGTGCCCTGG<br>CTGGTCCGGCCCGGGCCCCGCCCCCCGCCCCGCTCTATGAATGAGAGTGCCCTGAAATGAACGTGCTTTTACTGTAA<br>GCCCGCGGGCCCGGAGGAATTCCATTCCCCTCAGCTCGTTTGCATAGGGCGGCCGGCGGCAATACAGGCCTTTCGGCCAGGGC<br>GCGCTCGCCGCCGCCGCCCGGCTCCCCGCCGCGCCCGGCCATCCAAGCCTGCATGCTGGCGACCCCTTTCCGCAGCACA<br>CGCGGAGGCCACCCCGCCCCGCCATCCAAGCCTGCATGCTGGCCACGGGGCTGTGCGACCCCCGGGTGTACGCAGGCCCCGGGCCCCGGGCCACCCCGGGCCACCCCCCGCCAGCAGCAGACCCGGC<br>CGGCCGCCGCCCGCCGAGAGGCCCCACCCCGGGAGCCCCCGAGCCCTGCCAGGCAGGCCGCCGCAGCCAGGCAGGCCCCACGAGTGGCCCACGAGGCTCCCGAACCCGGGCTG |

TABLE 3-continued

Hypomethylated locus region sequences

| SEQ ID NO | GENE NAME | SEQUENCE |
|---|---|---|
| | | CAGCCCGCGACGGCCCCAGATCCTGCGGCCGCCAGGGCCTCCGCTTCCAGGGCTGGGGGTGCGATTTGGCCGCGGGGC |
| | | CCGGGGAGCCACTCCGCCTCCTGCACCGTCCTCCCGCCTCCCGGCTGCCAGCTGCGGCGAAGCGGCGCTGATTCCTTGCATGAGGCCGACGGCG |
| | | TCCGCGGTGCCGTTTGCTTGCTCACTTGCTGCGTCTCCCTTGGGTCGGTTTCTGTAATGGGTGTTTTTACCGCTCGCCCCGGGCCGCGCGGCTCGA |
| | | TCCCTCCGGCGTCTCACTTGCTGCGTCCAGCGCGCAGCGAAGAGTTTCCTAGTGCAGAAGACCCCAAGAACGCGGCTGGAA |
| | | GGAAAGTTGAAAGCAGCCAGCAGCGGCTTGCTCCCAGCCCTTGTAGCGCCGGACCGCCCCAGGTGCGCAGCCGCGGGCCCGC |
| | | GTTCCCCCTCCGGCTTCCGGCTGCCGGAAGCGGCCGCTTCCCCTGCGCCGGTCCGTCCGCGGGCTCGAGCTTTCGCGGACGCTTCGCGGGAGCTGGAGGGCCCCCGC |
| | | GCTTCGCGTGCGGGCGGCCGTGCCAACTCCGACCCCCGTGCCTCCCCAGCCGAGGCTGCTCCCCGTCCACCATGAGTCCCTCCACG |
| | | CCCTCCCTGCCGGGCCCTGCCTCATCGACCTGCGAATCCCGGATCCCAGTCGTGAACCCCGATCCCGCCCGTTCCACC |
| | | GCGGGCTGCTTTGTGTCCCCCAGGGTGCGGAGGCCTTTCCCGCAGGGACTGTGCCGCAGAACGGTCCCTCCACGGGGCCCTGACGC |
| | | CCGTCCTCCCTCCCAGGGTTGACTGGCGTGAGGCCTTTCGGTCCCGGGAAGAACTAGCGTTCGAGGATAAAAGACAGGAAGCCGCCCACTT |
| | | GAGGGGGCCAGGGGCAGCAGCCGCCCCTCCCGAGCGTCCCCGGACGCGCGGGGC |
| | | GCGCAGCCAGCCGAGCCCCCCTTGCAGGAGCTCCGGGGCCCCCGGGCTCCCGGACGGCGGGGGC |
| | | TGTGCGGCCCTCGTGGGCCAAGGCGCGTTTCTCCCGAGGTTCCAATATAGAGTCGCAGCCGGCCAGTGGGGACTCTCGGACTGTGCTTCAGGAGCCC |
| | | TGTGCGGCCCCCGGTCGGGGTCTTCGGTCCGAAGCCCCTCTGTTTCTGGGGCTTGACTCGGGCCTCTTGGCTATCGTCGTTGGCTTCAGGAGCCC |
| | | GGGCTTCCGGGGGCTAAGGCGGGGGCCCTCCAACCCTCCGCCTCTCCGGCCCTCCTGGGACTGCCAAGCAGGGCCAAGTGTCCAGACCCGAGTTCA |
| | | GTTTGTTTTAATGGACTCTCGGGTCTCGGAAAGAAAACTTACTACATTTTCTTTAAATGATTTTTAAGCCTAATTCCAGTTGTAAATC |
| | | CCCCCTCCCCGCCCACTTCTACTTTCTAACTCTGTCCCTGAGAAGAGTGCATGGCCGCCGGAAACCTTTTCGCTCGTCTCCAATGCATTTC |
| | | CCCAGAGATCCCACCCAGGGCTCCTGGGGGCTCCTCGGGATGCATCCCCGGAAATGCCCCGATGTCCGGAGATGCCGGGACACGAGGTGTG |
| | | GCGGCTCAAAAGTAGGCTTTGACTCCAGGGAGAATAGCACAGGGGCTCGGGTGATTGTCGACTCGACCACCGAGTTAGCCGTCAGAGGTCTCGGTCTCCAGGGAGGCTCCTTGG |
| | | GTCTCGGGCCCGCCCTTGCCTAAAACCTAAACCCCAGCCTTGCATGACCCTTGCACCGAGTTGCTGCACCGAGTTAGCCGTCAGAGGCCAGCAGCGTCGTGGGAGCTGCTCAGCTAG |
| | | TTCTTTATCGAGTAAGGAAAGTTGTCCACGAAGTTGTCCGCAGCCTTGCATGCACCCGAGTTTAGCCGTCAGAGGGCCAGCAGCGTCGTGGGAGCTGCTCAGCTAG |
| | | GAGTTTCAACCGATAAA |
| 16 | AIRE | TTCGAAGTGAGAGTTCTCTGAGTCCCGACAGAGCGAGTCTCTGTCCCCAGCCCCAAGGCAGCTGCCTGCCTGTGGGTGAGTCAGGCC |
| | | AGGCCCGGAGACTTCCCGAGAGCGGCCTTTGCTGTCCGGCGATAGGGAGCCCTGCCGGGGGAGGCCCTGCCGTTCTGATT |
| | | GGGGCCGCCCAAGCGGCCGCCCACCGCCGAGGCCCCCAAGGCCCACAGCGCCGCCGTGGCTCGCAGACCGGAGACGG |
| | | GCGGGCCACGCCGGCGCGAGGCCGCCACAGCCCGAGGCCCAAGCAGCCCAGTGTCCCGGGACCCAC |
| | | GCGTCGCGCCCCCAGCCCGGGTCCCCGCGCCCACCCCATGCGCAGACCGGCCTACGCGCCGGCTTCTGAGGCTCCACCCACGGA |
| | | GATCGCGGTGGCCGTGACAG |
| 17 | SUMO3 | ACGCACACTGGGGTGTGATGGAAAGGGGACGCGATGGATAAGGGGACGCCATTAGGAGGGGTGGGCCGCGATGATGGGCGCAC |
| | | ACACTGGGGTGTGATGATGGGAGGAGGGGACGCCAATAGGAGGGGTGGGCCGCACCAAGGGACGCGATGATGGGCGCAC |
| | | ACCAGGTGGCATGATGGGGAGGAGGGGAGTGGGTACACACCATGGGAGGGCCGTGGGGAGGCGTGGGCGTACACCGGGGCGCGATGGG |
| | | GAGGGGTGGGCGCACACCGGGGCGCACACCGGGGACGCGGATGAGGCCAAGGCCAAGCCCAGTGTGGAGGCTAGTGGCACACTGGAGG |
| | | CACGATTGGGGCGCAAGGAGGACAGAGGGTGGGGACCACATGGGCCGGAACGCGATGGCGGAGCACGGATGCGGAGAAGTGGGTGAATA |
| | | CCGGGGTCGCGATGGGGCGCCCCTTGGAGGACGCGTCAGTGCTGCTCACAGGGGGCGCCCCCTTGGGGGTAACCC |
| | | CAGAGCGCTTGTTCTCCCGAGCCGACTCCGTGCACTCGACACAGGATC |
| 18 | C21orf70 | CCACAGGGTGGGGTGCGCCCCACCTGCCCCTGTCCATGTGGCCTTGGGCCTTGCGGGGGAGGGGGAATCAGGACCCCACGAGGCGAGCCC |
| | | CCTCCGTAGCCGCGGCACCGACTGGATCTCAGTGAACACCCGTCAGCCCATCCAGAGGCTAGAAGGGGGA |
| 19 | C21orf123 | TTGAGGTCTCTGCATGCTTGTGCGTACCCGTGATGGCTTTGCCGTGAGGGGTGGCCAGTGCTGTCTGGGTGCCTTTGCCAGACAACTGGTCT |
| | | GCCGGGCCGAGCATTCATGCTGGTC |

TABLE 3-continued

Hypomethylated locus region sequences

| SEQ ID NO | GENE NAME | SEQUENCE |
|---|---|---|
| 20 | COL18A1 | TGACGGCCCCTCTCCCGCAGCTCCACCTGGTTGCGCTCAACAGCCCCCTGTCAGGCCGCATGCGGGGCATCCGCGGGGCCGACTT CCAGTGCTTCCAGCAGG |
| 21 | PRRT3 | AACACACTGTCTCGCACTAGGTGCTCGCGGAAGAGCGCGGCTCGATGCTGGCCTCAGGTTGATGGCGATGGCGGCCGCAGATCC AGTGCTCAGCGATGCGGCCGGTCCACACCGTTGCGGACAGTCCCGGCCACCGCTGGGGCGACCAACGACGCAGCCGA GCCCCAGGGCGCCTGAACTGGGCGTGCGCCAGCTGCCCACTCTCCCGCCGGTTGCGGATGAGGCTCTTGTCGATGTCCAAGCTGCCTGC ACCAACGTTGCTGGGCCCTGCAGCAAGCGTCCTCCGTGGGCGGCCTGGGTCTCCGGCAGCCACCGCCACCGGGCGAGCGCCATGTCAG AGCTTAGCCCAGCAAGCGTCCTCCGTGGGCGGCCTGGGTCTCGGCAGCCACCGCCACCGGGCGAGCGCCATGTCAG CTCCAGGAGGCGCAGCCAGAAGTGGACACCCCAGCAGGAAGCGCTTGGGCCTGGGTACGCCAGAGCG CAGCCGCCAGCTGCAAGCCGCTAGCCAGCAGCCCCAGCGCCAACAGCCGAGGGCTCGCCATCCCAGCC CGTGGGCCGTCCAGCAGGCGGCGACGGCACAGGCGAGCGCACCCAGAGCCAC |
| 22 | MGC29506 | GTCTCGACGAAGCCCGCGGCGGCCTGCAGGGGCGCCAGCACTGTCTCAGGGAACCGGTGCGCAGGAGCAGCCGGGGCGCGGCG CGCCGGCCGCCCTTGGGGACTCGGGCGGGGACTTCCGGGCGCGCGCGCAGCTGTCCGGGCACCAGGGCCTGTCCGGGCCTGCGGC GCCCTCCTCCAGAGCCACCTCCACACACTCGAACTGCGCTGGGGCGCGGCAGGACTTGGCCCACGGGCGCCGCAGCTCTAGGTAGGTGGC CCAGCGGGAGCCACCATCGGGGACACTTGGCACTGAGACGCTGGCCTCCGGGAGAGACTGCTGGGCCAGGGGTCATCAAGGGGCTGATGAAG GCCGGCTCCGTGAACTGTTGTTGCGCCTCGCGATCGTCTGCGCCGGACAGCGCGAACAGGGGTCCGACAGCGGAGATGACTTCCATCT CCCGGCTCCGTGAACTGTTGTTGCGCCTCGCGATCGTCTGCGCCGGACAGCGCGAACAGGGGTCCGACAGCGGAGATGACTTCCATCT CCCGCCACCGGCAGCGTGCGCAGCTGGGGCTGCGGCCGTGGGGCTCGGGCCGTGGGGCTCGCGCCCGCCAGGAGCCCACCCAGGGCCCGTG CCGCTGGCCGTCCGCTATTCTGGGCGTCCGGCCCAACGTCCGGGACCGTCCCGGGAGCTGCGGGGGCTCGGACAGGACCGGGCCAATTCGCTG GCCGCGGGGGCTGACCTGGGCAGTCCGCTCCTCCAGGCAGGGCTCTGCAGCAGGCGAGCTGCGGGGGCGGGGCGGGTCAGCATGGTGGGGCCGGACGC CGTGCACTATCTCCCTCGCATTCGCTCCTCCTGGTGGCGC |
| 23 | TEAD3 | CTGGAGAGAACTATACGGGCTGTGGGAGTCACCGGGCACGCGGACTATACCGGCGACTATCTTGGGCCCACGAGTCACCTCAGAGCCCCCGTT CCGGGCTCCGACCGGGCCAGACTGGGCTGACGACCGGGTGGGCTGACCGGGCTGTCGCCGCCGCCGGGGCTCACCGGGCCGCCAGCAGCGCGGCCACCTCCAGAACCTCCAGGCCGTAGCGCGGAGG AGAGGAGGAGCAGGCGGCGCGGGGGCTCCAAGGTGTGGGCTGGCGCCTGTTAGGGGCGCAGCCCGGCTTGTTATGAGGAGCGCGA GGAGGATCCAGACACACAGGCTTGCGCGCGACTCGCCCCAGCTCGCCCCCGGCACGCACCGTACATCTTGCCCCTGTCGTCTGACAGGATCATC AGGCAGAAGAGAGCAGGGGAGGCAGGGGGCACCACCGTTGGCGCCCCAACTCAGCAGCCAGCAGGAACCTTGGGTGAG AGGCAGAAGAGAGCAGGGGGAGGCAGGGGGCACCACCGTTGGCGCCCCAACTCAGCAGCCAGCAGGAACCTTGGGTGAG TTCCG |
| 24 | chr12 group-00022 | GAGTGCGGAGTGAAGGGGTCACTGGGCACTCAGCGCGGCCCCTTGGGAGGCAGGCCGCGCCCCAGCCTGCCCTCCTCGTCTGGGAAGG CCGTCCAGAAGCAGGAGCCCCGGGAAACAACTGCTGACGCGGGCGGCCTTCAGTGTCTCTCCCAGCCTGAGAGTCGCTTCCCAC CACCTGGCCACGACGAACCTGCTCTGCCATCTCCGGCAAGTTCTCGCCGTCCGGTAAAATGCAGAATCGCTGGCGTCTT |
| 25 | CENTG1 | TCTTCTTTTCCGCCCCTAGGGGGCACAAGCGGCATGTCCAAGCGCCTAGGAGCGCCCCGTACCCGCTGGGACCTCCCCTTCCCGCGAACCCC GAGCGGGTAGAACCCAGAGCAATCCGAGTGTGAAACAATGGAGAGGGGGCTGTGAGCTGGTCTCATGCCTCGTTGGGAGAG GGAGCTGAGTTTGTGTCTTCTTTTGGAAGGCGTCTCGTGCCCTCGTGTGCCGCCCCCGGTGGTGCTCTCCGGTGGCGATCGG AGAGGTGAGTGGTCGCGCTCGTCTGTGCCCAGCGGCGTGCGTCTGCGCCCGCCCGGTGTGCCGCCCGGTGCCCGGGATGGGGGTGTCTCTCCCGCTGG GCAACTATACCAGCGCAACCGGCGCTGCTGGCCCCCTGGCCGCCCCAGGGGTCTGCGCCCGCCCACCCAGCGCCAGCCTGCGCCGTGATGGCGCACAG CTGGCTTCCAGCCTGCGCCGGCCAGCCTGGGGCGTAGAACAGCGCCCACTGCAGCAGCCCCCAGCGCACCCCCAGCCCCACATGCCCAAGCCTATTCGGGTCCCTCT AAACGCGGGCCGCTGGCCGGGCCCCCCAGGCCGTTTCCCGCCGCAGGCGTTCCGAGATGAAGCTCAAAGACCCCTTTTCCTCCCCCAGCTACCCACCCACAGCA GGGAATTGCTGATGACGAGTGGGCGAGCTGGCGCCCAGGGACGAGAGCGCAGCTGTGGGCAGCCCACCCGGGGTCCTTTCCTCAGCCTGTGGGTCTCCTACGCTGTCGTCGAGCG GCAGTTGCTGATGACGAGTGGGCCAAAAGCAGGAGAACAGTAGCTGTCGTACTTGGCCGAATTCACGACTTGCCCTCCTCCGAAGACCAGG TCCTCCGAGTGTCTCAGCCGCCGCCAGCCCAGCCAGCAGGACCCCCCAGCCAGGACCCTCAGGGGACCCTCAGGGGACCCTAGGAGCCGGAAGGCCCACCTCCGAATCCACGAGGTTCCACCACCGGACCGCTCTCAGGTTGCCACACCCTCAGCAACC GATCAACGGAAAAGGCTCTAGGGACCCCGGGAACCCCCCAGCCAGGGACCCCCCAGCCAGGACCCCTCAGGTTGCCACACCCTCAGCAACC |

TABLE 3-continued

Hypomethylated locus region sequences

| SEQ ID NO | GENE NAME | SEQUENCE |
|---|---|---|
| | | CTCCCCCCGCTCTGTTCCCTCACGCTTACCGCGAAGAGTCCGCGAGGGCTTGGCACGGCCTCGCGTGTCGCTTTCCCACACGCGTT |
| | | GGCCGTGTCGTTGCCAATAGCCGTCAGCACCAGGTCAGCTCCGTGGCCAGTCGTCCAAGTCAAGTGAGCGAACGCGGGACAGGTG |
| | | TGTGCCCAGGTTGCGTGGATGCCAGAAACTCGATGCAGATGAGGGCCCAGGTTCAAGCTGGCCCACTGCCCACGTGGGGTCTGCGAAGG |
| | | AGCGTAGAGAGTCGGCTCCCAGCCGGCAGCACAGGCCATTCACTACACTCCCTAGCCCTCCCCGCTGCCTCCTGGCACTCAC |
| | | TGGGGCCCCGCAGTCCACGCAGATTGAATTCCCCTTGGCGTTCCGATCGCCTGGAT |
| 26 | CENTG1 | AGCCAGGTCCAGCCCCCGCCCTGACACCCGGCCGACGTTCCCGGGACGTCGGCGCCAGCTGGCGGGAACTTGGGATCCGGAGCCAT |
| | | CTGCTCCCACCCGCTCCGGAGCCAAACCCCGGGCCTCCGGAGGCCTCCGGGCCGCTCCTCCTCCCGGAGTGTGAGCCGAACCAA |
| | | GAGTCTCCTGCCTATCTCTCCAGTAGGAAAATATAATAATAGAACACCCTGTCCCCCGTAAAAAACACTACCTTCCCCGTACCGCCT |
| | | CCCAAGTCTCCCGGGGTACGGATTGCTTTGCAGCAGTTCCGCCTGACTGCTCACTCCAGGGTCAGCCCTCCAGGTGGGTTTCAATGC |
| | | GGCTCGGGAGGGGGTGGGCAGTGGGCAGTGAGGCTTCCACCGGACACATCACCTGTCTCAGCCCAGGGACGACTAGTCCT |
| | | CCCCGGACTCGGGTACCGCCAATCCGCTTCACCGCACGAGAAAAACATCACTCAGCCTGCTCAGCCCAGGGACGACTAGTCCT |
| | | GGGGAGAAGCTGCCTGCAAGGTGCCTGTCATGCCAAGTGCTCATGGGGAAACTGAGGCTTCCATCCCCTTCACCTTCAA |
| | | CGTCCTCTAAACACGGCAAAGCCCCGTTTCCATGCTCCCAGAGTTCAGCTGAGCTGGAAGTGGGCTCCTCGGGAGCA |
| | | ATTTTCTAGTCACTCTGATCAAGGACGTTACTTTCCAGAAAAGCTCTGAGGCTGAGTCCCTCTGAAATCAAGTCCTTTCTCCTGTCGCACA |
| | | ATGTAGCTACTCGCCCCGTTCAGGACTCCTATTCTTTGCCCAATCTTGACAGAGGGGTGAGCTTGGTTCATCCGCCACCAGAG |
| | | AAAAGCTTCCCTAGTTTCTGACCTCGTCCTCCCCAAGCTGAGCATTCCAAGTACCCTTCTCCCTGTTTCTCAAGCCCTGACTC |
| | | AACTCACTAGGGGAAGCGCGAGCCCTCCTGTCCTCTTGTGAAGATGCCGCTGATAAACTTGCAGATCTTGCCGTCACGAGTGCTCGGCTG |
| | | CCCGGAGCCAAGAGAGCCCCGTTTCAGCCCGAGCTGGAGCTTCAGAGTGATTGGAGGTCAGGCCCCGGGGGGTCGCCGAAGCAGCCGT |
| | | GACAGCAGTGGCTGGACTCGGACTGGCTGTGGAGGGACAACTTCCCTGGGCTCCAGCCCAGCTCCAGCCCCAGCAGAGGTGAAGCTGTAGAG |
| | | CAAGGTCTTATCTCTTTGCCTTTCCGAGGGGACGCCGGTGGCCGGACCGAAGCTCCCAGCCTGCTCTTTGACCCTGGG |
| | | CCCCTCCCCCGGCCGCTTTCGGGCCATGACAGGCGGCTACCCGAGCCTCGGCTGCGAGCAGGGCGCCACTTGGCTCGTGGTCACCGTCTTGCAA |
| | | GGCTTGGGGCCTTCGGGCTTCGGGCTCCCGCCCCGAGAGCCCCACCGGCTCGGCCTGCTCGAGCAGGGGACGCCGGCCGGGGAGA |
| | | GCCGCCCGGCCTTGGGCTTCAGTCCCCCGGAGACGCGGGGGACAGGGCTGGGGGCTTCCCCGGGCTCCGCCGTCGTGCTGATCCAACAG |
| | | CGCATCCTGCCGGTGAAGAGACGTTCGTGCCCGCTTCTTGCCCGGCTGCCAAGGATCCCCAGTCTCGGA |
| | | GCTTCTGGCACCGGCGGCGCGGCCACAGAGAAGAGGCGGCCGGCTACCTCGAGCTTAACCAGGGTCAGC |
| | | GAGATGAGGTAGGTCGTTGTCGGCGACTGCTCAGGGGGCGCCGGACTGCTGAAGCGCGCTGCTGAAGCGCGCTGAGCTCGGGGGAG |
| | | GGGACTCCCCGGACTGCTCCAGGGGCGCCGGCATGGGGCGCCCGCATGGGCGTCCCCAGCCGCGGCCCCGGCGCCCCCTCCCAGCGCCC |
| | | GCCCTGGCCTCCGCTTGTCGCCCCCCACCCTCTTGGACCCCCAGGGAGGACCGTCTCCAGGAGGCGGGGGCGGCCTGGGTGG |
| | | GGGCCCTGAGATGGGTAGGGGGAAACGAACCTGTGCGGGGAGCAGGGGCGGGGATTGGGGCGGGGGGCGCGCGATGCGGTCG |
| | | GAAAGAGGGTCTAGAGGAGGGTGGGAAGCTAGTGG |
| 27 | chr21: 9906600-9906800 | GGGCCGGGCAAAAAGCCGCCCAACAAGCTGCCGCTGACGGGCCGGGCCGGAGCCGGCGCGGCGGAGCCCAAAAAGCCGGGCGGCAA |
| | | AAAGCCACCGTGCGGCCGCGGGAGCCGCCAAAAAGCCGCAAAAATCAGTGGGAGCAGGGCAAAAATCGGGAGCGCAAAAACACAAAA |
| | | AGCCCCGGCCGGCGGCGGGGCAAAAGCCA |
| 28 | chr21: 9907000-9907400 | TGGCTTTGCTTGGAGTGTGATGTGATTAGGAAATGTCAGCCAAAGACAAAAGAAGATGTAAGTAGCTTGACTCATTGCAGTAAGAACCC |
| | | AGATGTTACCTTGAGGGTATTAACTAATAAGCAGTTTAAATCAGAATGGCACATTTCTGATTTGTTTTTGTATGTTCACATTTGGCAGGCAT |
| | | AGATACTGTTTGAAAAGAGAAAAGTCAGTACATAGAGGTTAACAAGCTTAAATATGTGCCAAGTCTAGAAACAAGAGACTAGGGGATAAG |
| | | GACCTTTCGAAATTAAATGCAGATTTGAAAACTTGAAAACTTATTGCTGGGGGATGGAGGCAAAGGCAAGGCTCTTTAAGGTCAATCCCTGTTTTGCTTT |
| | | AAGTTGTTAGCCGGGTGGTTTTATCATATATTGTAGAA |

TABLE 3-continued

Hypomethylated locus region sequences

| SEQ ID NO | GENE NAME | SEQUENCE |
|---|---|---|
| 29 | chr21: 9917800- 9918450 | TTCCTGGGAATGTCAGCTAACCTGAGCCTAGGGGCCTGAGCCCAAGGGCAGACTGAGGCTCCCCAGCACAGGGAGGTGCTGCCTGTG<br>ACAAGGGGTAGTGCTGGCACAGTGCAGGCTACTCCTCAGGCAGATCAGCTTGAATATGCAGGAAGAGCAGGACCCTCGGGCTGAGGCA<br>GAGGTGGAATGGGAAGTGCATGGTGTAATTAGTTCTCCAGAGGCCAGAAGTAGGAGGAGCGGTTGGAATGCTGAGGCCCAAAGGG<br>AAACCCTGGACTACCCTGGCCTCCCCACAGGCTCCATAGTAATTGCGGTCCCTGCAGTGGTGAGGCCAGAAGAGTGTGCCCAATG<br>CTGTCATCATCCAGTCCAGCTCCACCCCACCACTCAACAGATGAGTGATGTCATGAGGTCACCTCATCAGTCATTTGCTCAGTTGTG<br>AAAAGAAATTGTTCAGAGAAGAGCAAAGTGTTTTTCCATGAGCCAAAGGTCAGCCAAGTTATGCTAATGAGGAGGACTGGAGACAGCGT<br>GTCACAGACACCGAGAAGGACACTGGGCAAGGGCACTTCTCCCAGGGCAGAGCCCACAAGAAGCGTCCTGGCACCAGACACTCAGG<br>GAACTGAAGGCTGCAGGGGCCCGCCCAGT |
| 30 | TPTE | TCCCCCAGCTGGTATAAGCAAACTTTCCTGTCTATGGGCCAGAGACCACCATCTAGTTCCCCGCCAAACTTTACATGATTTTAAT<br>TCTGTCTGATGAAGATGAGAGAGATAACAGCCAACAGAGAGGGCAACAGAGGATGGGACTTCCCTTGCTCAGAGACCTCACTTCTAGGTC<br>TTTACCTCCTATTGAGAATAAGTCAGTTCTGTAGTAGAGACTCTGTGCTAAGAACTCCCCAAGAACATCCTAGCGCTCTTGTGATTCTT<br>GTAGAATGGGGAATAGAACGAGCTTGGCCCCAAGACTGCACAGACACTTTTACACTGTTGGGACTGTAAACTAGTTCAACATGGTGAAGTC<br>AAACAACAGTGCTGGAGAGGATGTGGAGAAATAGGAACATTTGACCCCAGCCATTCCCATTACTGGTATATACCCAAAGGACTATAAATCA<br>AGTGTGGCGATTCCTCAGGGATCTAGAAATAGAAATACCATTGACCCAGCCATCCCATTCCTGTTGGTGGACTGTAAACTAGTTCAACATGGTGAAGTC<br>TGCTGCTATACAGACACATGCACACGTATGTTTACTGCACACTATTCACAATAGCAAAGACTTGAACCAACCAAATGTCAACAATGA<br>TAGACTGGATTAAGAGAAATGTGGCACATATACACCATGGAATACTATGCAAGACAAAACTGCATATTCTCACTCATAGGTGGAACTGAACAATG<br>GATGAAATTGGAAATCATTCTCAGTAAAACTATCCAGAGGGAACATCACACTCTGGGGACTCTGTGGTGGGGAGGGGATAGCATTGGGAGATA<br>AGAACACGTGGACCTAGATGAGGAGTTTGTGGGTGCCAGCTGTCCACCAGTTTACATATGTAACCTACCTGCACATGTGCACATGT<br>TACCAAATGCTAGATGAGAGTTTGTGGGTGCCAGCTGTCCACCAGTTTACATATGTAACCTACCTGCACATTGTGCACATGT<br>ACCCTAAAACTTAAAGTATATAAAAACCAGGAACATCACATCTGTTCCCATCAGAGCCAGAGTACTCATTAAAGATGAGGAGGCATGGGGTGGGG<br>GAGAATGTACCCAAAACCCAAAGAACCAGGAGTTTCATCAAGTGTTCAGCTCCTTGTGGGTTACAGAGAATAACCAGAGGGCTCAGTTATGCTCT<br>GATTATTATTTACTCTGATGAAGAAGTTTCATCAAGTGTTCAGCTCCTTGTGGGTTACAGAGAATAACCAGAGGGCTCAGTTATGCTCT<br>CTGAATAACTATGTTTGCTTAGTGTTTCTAAACAATATTAAATTCACATGAAACAAAATAGACAAGGTTGAAGGACTTGGGGCATAACTCATTG<br>ACTCAAGCTATCATTTTATAGGATTGTGAGAAACAAAATAGAATGACATTTAAATACACTCATATTCTGCTAGAAAGAGGATTTTGAAT<br>ATTCTTACATCAAAGACATGGTAAATGTTAAGGCAATGCAATAGTGTTTAAGGCAATGCAATTGTACAATGATTTGAGATATAGAAAAAATAAATTTGACCTGTATAAGAGAATTTGCAACTGCCAAATAGCAAATAAGCAAATGAAAAACTGGTCAT<br>TCACATTGTACCTCATAAATATGTAACAGATACTTGTAACAGATACTTCAATAAGAGAATTTGCAACTGCCAAATAGCAAATAAGCAAATGAAAAACTGGTCAT<br>CCAACTTTTAAAAACGGGCAAAATGCAGATTAAAAACTACAATAAGAAACATGCTGCCCGTCCAGACGCATTGTTTTGACCGTTTCCAACTGT<br>CATCACTATCTATTAGAGAAATGCAGATTAAAAACTACAATAAGAAACAATGCTGCCCGTCCAGACGCATTGTTTTGACCGTTTCCAACTGT<br>CCCAGCCCTTCCCGGGACCATCGCTCGGGACCCTACGCCTGGGACCCTACGCCAAGCCTCCCCCACCGCTCTCCCGACGCGACTGGGCAAATTGGGA<br>GACCGCCCCGCGGGGGCGACCCAACTTTTCGGACAGCACAGCACCCCCAACTTTCGTGCAGCGTGACGGCCGCAGAGCCCCGAGACCCCCCGACCCCCGCTCCCGGCGA<br>GACTCAGGGAACCCCGCACCCCAAGCCCTTCTAAATCGTCAGCGTGACGGCCGCAGAGCCGGATCGCAGCCCGGATCGCCCG<br>CACCTTTCCCGTGGCCGGGGGCCCAAGCACAGCCAGGCTGGGGAGGGCGCTAGAGGAGCGGCTAGAAGCCAGACACGGGAACTCAG<br>GTCATCCTGGGCGGGCGGGGGGGACAAGACAACGAGACCCGGGCGCCCGGACTGAGCCCGGACTGAGC<br>GCTGAGCCACTTCAGGCCGGCGGGCTTCGGCCTTTACCTGCGCGGCTCCTGCGGGCTCATTCTCCACGCGGCCGGCGGCCGGACTGAGC<br>TAACACCACTTCAGGCCGGCGGGCTTCGGCCTTTACCTGCGACACCTCCGGATTCCGCGGCTCCTGCCGGACACCTCCGGATTCCGCGGCCGGCCGG<br>GCGTGCGAGTTTTTCTCGGCATTCGGCAGCGCCCAGCAACTGCCGGATCGCAGCGCCCAGCAACTCCGCGGGCGACGGGAGCCCG<br>CGGGGCGAGGGGTTCAGCCAGTTCAGCGCCTAGTGCTTCACCTCGGGGCGGAGCTAAGTGTAGCAGCTGTTGTGCCCTTGGCCCTCCGTCCCCACC<br>CCTACCCCCGCCGAGTCCCGGCCGTGGGTAACTGTTGGGTAACTGTTGGGTGCCTAGAGCCCGGCCGACC<br>GCGGCAGCGAGTCCCGGCCTGCCTTGGGGTAACTGTTGGGTAACTGTCAGGTAGCAGTGTAGCAGTGTCCCCCTTGCCCTGCGG<br>AGACGCCCCCTGCCTTGAACCGCCCCGCCTCCGCCGAGCGCGCAGCGCCACCAGTCTTGTTCGGCACTCCGCCGTTCGCCCG<br>CGCGCTGCCAGATCCCGCCTCCCGGCCACCCCTCTCCCCGCGAGCGCCTCCGGAGTGTGCCGAGCGTGCAGAAGCGCGCGCGCGACCCGCGCGTACC<br>CGCCGTGGCGGTGCTGGGCGAGGGAGGGGTTGGCCCGCGAACCCCGAACCCCTGGGTCACCCCGAATTACAAACAAAAACTTAAGCCATTGCT<br>CGCGGGTTAGAAGGCAGCTTGCGTGCTCAGGAAAAGAGACCGCCACGCAGGGATACAGTGACGACGAAACA |

TABLE 3-continued

Hypomethylated locus region sequences

| SEQ ID NO | GENE NAME | SEQUENCE |
|---|---|---|
|  |  | CCCAAAATCTCTTTTGAAAGGGAAACCAGGCACAGTGGCTCATGCCTATAATCCCAGCACTTTCGGGGGCCAAGGCGCTCACCTAAACC |
|  |  | CGAGAGTTCAAGACCAGCCTGGGCAATACAGCGAAACCCTGTCTCTACGAAAATATAAAAATTAGCTGGGCATAGGGCTGGGCACGGT |
|  |  | GGCTCACGCCTGTAATCCCAGCATTTTGAGGGCCGAGGCGGGCGGATCACGAGGTCAGGAGTTCGAGACCATCCTGGCTAACACAGTG |
|  |  | AAACCTTCTCTACTAAAAATACAAAAAATTAGCCGGGCGTGGTGGCCAGGTGCCTGTAGTCCCAGCTACTTGGGAGGTTGAGGCAGG |
|  |  | AGAATGGCATGAATCAGGAGGCTGAAGCTGCAGAGTTGCGCCACTGCACTCCAGCCTGGGCGACAGAGTGAGACTCCGTC |
|  |  | TCAAAAAAAAAAAAATAATTAGCTGGGCATGGTGGCATGCCAAGATGGCACTCCAGCTACTCAGGAGGCTGAGGTGGAAGGATCTCTTGAT |
|  |  | CCCGGGAGGTCAAGGCTGCAGTGAGCCAAGATCAATAATACCAACAGCAATTAGTGAGTACTTTTTCCATGGAGTCTGGGAGAGGAATAAATGTTTGT |
|  |  | AGTGGGAAGAAGAAAATGTAATACACAAAATTAATATACCAACAGCAATTAGTGAGTACTTTTTCCATGGAGTCTGGGAGAGGAATAAATGTTTGT |
|  |  | AAAATTAAAATGTTCTACGCTAGAAATCAACTTTCTTCTATGCTTCTTCTTACTTCCACCCCTTATAGCTACTTAGTAAATCTCACAAATCCTA |
|  |  | TCCTTCTGATCTCTCTGAAATGTATGTACCCTTTCTTTCTAGTCCAGAATAACGTTTCACCACCACGTTTCTTTGTTCCTTCTAGCCTCTGTAATAATCTCA |
|  |  | TAATCGCACCTCCTGTACCTGCCTTCTTTCTAGTCCAGAATAACGTTTCACCAATAACCACCACATGGTCCCAGCCAATCTTTCAGCC |
|  |  | TTTCCAAAAAAATTTACTTTCAAATAAGTCAGGCTCCCTCTTTAGGATACAAAACCACCACATGGTCCCAGCCAATCTTTCAGCC |
|  |  | TGATTCACTCAGTATATATATTTATTTCCCAAGAACACAGACATTAAATAAATTAAAATAAATTAAAGAGTGCGCACAAACAAATTGGAT |
|  |  | TCCTCCCCTCATGGAGAATATCATCATGCAGAAAGCATACACAGAATTATCCAAATTTAAATAAAATAGACAACAACTACACATGT |
|  |  | GTATCCTAGAAGAAATATCACTCATGCAGAAAGCATACACAGAATTATCCAAATTTAAATAAAATAGACAACAGGTTGGGCGGTGGCTCACAC |
|  |  | CACCAAAAGAAAATGCCACATAAACTATACAGTTTTAGAATATAGACAACAGGTTGGGCGGTGGCTCACAC |
|  |  | CTGTAATCCCAGCACTTTGGGAAGCCGAGGCGGGTGGATCACAAGGTTCAGGAGTTCAAGACCAGCCTGGCCAACATGGTGAAACCCG |
|  |  | TCTCCTCTAAAAAACAAAAAATCAGCTGGGCACTGGTGGCAGGCGCCTGTAATCCCAGCTACTCAGGAGGACTGAGGCAGGAGAATCGC |
|  |  | TTGAACCCTGGAGGCAGAGGTTGCAGTGAGCCAAGATCGCCACCAGCTCCAGCCTGGGTGACAGAGCAAGACTCCATCTCAG |
| 31 | chr21: 13974500-13976000 | TGTAGGAGTCCTCCGGTCCTGCTCGGAGTCCAGAGCACAGTGAGGCTGAGGCAGGCACGAGCATGGCCAGGGATGCTGCCACAGGAGAC |
|  |  | CTGCCCTGCCATAGTCCGATAGTTCAGTGCTTCAGTGCCTCCGCAGTAAGGCAATGTCTTCCTCCAGATCTGGAGTTCACGGCCTTGTGGGGTGGGTCCT |
|  |  | TTGGTGACTTAGTCCAGGGCCTACCAGGCCGGGGTCCACAGTTGCCACAGTTGCCACAGTTCTGAGGATCTTGAGGAAGGTGGTTCCTGCCTTGCTGT |
|  |  | AGTCCGGGAGGCAGGGGGCCAGGGGTCCTCCTTGTCAGAGTCTTCGTCAGAGCTCCAGGCCGCAGGGCGAGTGGGGGTGGAGGTGGGGGTTTCTATGCGATA |
|  |  | GCCCACGGGTCGGTGAAGCCGGTCCTCCAGTGCCATATCCAGGGCCGAGCGGCGAGCTGGGGACCTGTCTCTGCAGTGGTCAGGCATGTGGGAGT |
|  |  | CGGCAGGACGGGGGTCCTCCAGTGCCATATCCAGGGCCGAGCGGCGAGCTGGGGACCTGTCTCTGCAGTGGTCAGGCATGTGGGAGT |
|  |  | GGTGGTCCTGCTGTGCCTCAGTGGTCTCCAGTGCCTCAGGGCGGTCTGGAATCCAGTGCAGCGCGGGTCAGGGTCTTACCTGCCAAGGTGGTGGCA |
|  |  | CCAGAGAGCCGCCGTGCCATAGTCTAGGGGGCAGGGGCAGGGGTCCCCTCCCCCTGCCATATCCAGGGTCACAGGCAAGGCTGGTGGCA |
|  |  | AGGGTCCTCCCCGTGCCATAGTCTAGGGGCGCACGGGGAGCTCCTGAACCACAGGTCCAGCCTGTGCCAAGGGTGCAGGGAGCCCATGCCAGAGTGTA |
|  |  | TGTGCAGGAGTCCAGGACGTAGCCAGGAGTCTCTGAACGAGCGGTCAGTCCAGGGCTGTCCGGGCGGCGGGAGTCTCAGATGCCAGAGTGTA |
|  |  | GGGCGCCGTTCAGGTGAGGGTCTTGGCGTCGGCGGATCGGAGGGTCCCTGTGCTCTCCCGTGTCTTGTGGGGCAGGGGTAGTCCAGGGGGCGCTCCT |
|  |  | CTGTGCAGAGAGCCCAGTGCCTGCTGGCGGGAGTCAGAGTTCTCCCGTGTCTTGTGGGGCAGGGGTAGTCCAGGGGGCGCTCCT |
|  |  | GTCCAGGGGGGCCGCAGGACAGTCTCGGAACCACAGCCAGGAGTCGAGTGCGCCAGGAGGTAGTCTAGGCAGCGGGCCCAGGTCCT |
|  |  | AGTTGCCGCAGGAGTACTCTGGAACCACAGCCAGGAGGCAGGAGTAGTTCAGGGCGCGGCAGGTCCAGGTCCT |
|  |  | CGGGAGCCAGAGTCCAGGGTGTGGAGGGTGTGGGAGGGTCTCAGGGGCCGGACACACCCGGGGCCGGACAGGGCGGGATC |
|  |  | CTCCCGTGCCTTAGTCCAGGGCTGAGCCGTGGACGCGGAAAGAGGTTCCTTCAGTAGCACACAGTCTAGCCGCACGGGCGTGCAGGTGTCCTCAGTGC |
|  |  | GTCCAGGGGGGCCGCAGGACAGTCTCGGGTCCGGGGATCGGGGAGTCCAGCAGGTCCTGAGGCCAAGTGCTCCTCCTGCCTCCAGTGCTCCTGGTAGCCCA |
|  |  | GTCCAGGGGGGCCGCAGGACAGTCTCGGGTCCGGGGATCGGGGAGTCCAGCAGGTCCTGAGGCCAAGTGCTCCTCCTGCCTCCAGTGCTCCTGGTAGCCCA |
|  |  | CGGGAGCCAGAGTCCAGGGTGTGAGGCTGAGCCGCGGGAGGCTAGCGCCAGTAGTTCAGGGCCGCGGGGATCAGGGCGGGATC |
|  |  | TGGAGGCGGGATCCT |
| 32 | chr21: 13989500-13992000 | GGGTTGGTCCTAGAAAGCTGTGAGGATCGCCGAGTGCACTGCCCTCCCCAGCCTAGGGTCACTCACTCTTCCTTGGCCCCGAGCCCAGAGCTCG |
|  |  | GGGTTTCAGGCGCTGGCTGCCCCTTGCCAGCTGCCCAGAATAGGCTGAGCCAGCTTCCCGCCCTGGCAAGGGATCCAGCAGTGGAATC |
|  |  | CTCACTGCTGTTGGCTGCGCGGGCAGGGCTGTCCATCGCTCCTGCTGGTGCGAGCGGTGCTAGCTGCCAGCTGAGACG |
|  |  | CGTGGCAGAGACTGGCAGGGGCTGGTCTACGAGGGCTAGAGCTCGAGACCCTGAGCCAGCCTCCAGGATGGCGGCATGGCCCTCTCGGGGCATGCCCTCTAGGGTGCTCTTCCTTAG |
|  |  | CCTGCTCCAGGACGCGGTGTACGAGGCCACCGACCGCTGGTCTACAGAGGATCTGGCCCTGGGTACGTCGGCCTGGGCCATGGGGCCTGGGTGCATGGCCTGGGTGCGAGCAGCGGATTCCTGCCTGCTCAGC |
|  |  | TACAGTCTGAATTAGGCGCCACCCGAGTCTCGCCTGCGCCACCCAGTATCTGGCCCTGCTCACGCACAGCAGCGCTCAATCCCCAGCGCTACGAGACATGGACATGGAGATGGGGGCGACCACCTGACTTAG |
|  |  | GCTATGGGCTGAGCAGCCGATTCTCGCCTGCGCCACCCAGTATCTGGCCCTGCTCACGCACAGCAGCGCTCAATCCCCAGCGCTACGAGACATGGACATGGAGATGGGGGCGACCACCTGACTTAG |
|  |  | ATGCCTTGGAGGCATCCGGTTCTCGGGGCTGCTGCTCGTCGGGCAGGGTCTGCGGGCAGGGTATGGACCCAGCGTATGGGACCGACCACTACTGCTGTGCCCATGG |

TABLE 3-continued

Hypomethylated locus region sequences

| SEQ ID NO | GENE NAME | SEQUENCE |
|---|---|---|
| 33 | chr21: 13998500- 14000100 | GCAGGTGCCAGCTGCAGCTGAGTCCGAGGCAGATCTGTCAGGGCTGGTCTGAGGTTGCCTAAGGGTGGCTGAGTGCACCACGCTTCC ACCCCAGGGTCCGTTATTCCTAGGCCAGCTCCCAGATTGCAGGGTTGCCGGCGTTGGACACTGTGCAGCCATGAGGATCTGGTTGGGT GCAGATTCCCGCCCTCCTGCAGCTGAGAAGCCAATCTCATAACAGGCGCTGCAGTGACCTCTGCAGTCTCCGGTCCGGCTGCTGCTGG AGCTGGCAGAGAACAGAGCTGCCACCGCTGCTTCCAGGAGTTGCCAGCTGGCAGCTGCAGGCTGAGCCCTGCCGAGGCTGAAA GGCCTTATTCCAGAAGCCTTGAGGGTCCCGAATGCCAAGGCTCCCACCCTCAGGCTGAAAGTTTCCGCCCTTCCTTGCTCCCAGAGAGTTG GATTCCAGGCGCTGAGCACAGTGCAGTGCTTTGTCATGGGATCCGCACTGCGGTGCTTGCACACGGCTGCCACAGTGCTATAGTT GAGTTATGCCGCCGCGGCTGCACGTGGCAGCCGCCCGAGCCACAGCTGTGCAGGGCTGTCCGCCAGCCGCCTGCAGGCCATTTGCC CGCGCCCAGATCGGCTGGCTGCGTGCGCAGCCTGCCCGGAATCGCTGTCAGGGCACGTTCCCGCTCCTCCTACAGCTGTG GGCCCGACTGCCTGCGATTTGGCCACTAGGTGGAGTCCAGCGAGCTTGAGCCTCTTTCCTTGCGGAGCTTTAGACCAGGACGGCTGCCC ACCCGCTGCCTCCATGAGCAGGTAGCAGCTGCCCCTCTTCCTTCCCTTACCCAGAGCGGGTTGTGGCCCGCTGAGGCTCTGTGCCGGCGC GGAGTGCAGGGTCCTCCCACCCTTCGGGCGGGCGATTGCGTGGACGGCAGGGGTTGCAACTGGCTGAGAGGAGCTGAGGTTCAGTTGCACTCTGACTTAGTCGCCGAACTCTCCCGGGCATCTGGCCTGGGTCACAGCCGCCGCCCGCCATCTGAGAGGACGGTGGGGGATCGACGCCGCCTGCCGTGATCGACGTACGCAGCGGTACGCAGCGGTCGCAGCGCCATCGGCAGCGGCATCGGGCGCAGTCTCGGCCCACCTGCCCCGCCATGCACCTGGCATCCCTGGGTACCGACATGCCACCCTAGGTTACGTCTTTGGCCCGACTGACCACTGGAATTTAGCCTCTACGGCTCGTGGGTTACGGCCTCTGTGCAGCGCGGCCGGGCTGAATTAGCCTCTACGGTCTGTGGGTTACGGCCTCTGTGCAGCGCGGCCGGGCTGAATTAGCCTCTACGGCTCTGTTGAGAGTGCGGCTGGGGATCCGGGGAACACCTGGACCACTGGAATTGCGCCGCGCCATTTGCACCGTCCTGGTAC |
| 34 | chr21: 14017000- 14018500 | TGGGTGGATTGCTTGAGCCCAGGAGTTCGAGACCTTCGACAAATGCAGAAACTCCATGTCTACAAAAAATACAAAAATTAGCCG GGCATGATGGTTCTGCCCTTGAGTCCAGCTACTCCAGGAGCTCAGGAGCGCTTGAGCCCTGAGGCGGAGTTTGCAGTGA GCTGAAGTGCACTGCATTCCAGCCTGGAGACAGGAGCCAGACTCTGTCTACACTATTACTTTGCCACTATTAAACTGGTTTTATCCTGACCAATTGCAGTGAAGATA AAATTGTATTCTGAATACATCTTCTAAAACACTACATTTACTTGCCATTGCGTTTTAGTGGAAGACCCTCCTAAAATTTGAGGACCACCTTTGTCAAATGGTGCCTATTGGTTCTATTTTCTGGTAAGTAGTGAGTGACCATGTCTTCCCCAGGAAGACCCTCCTAAAATTTGAGGACCACCTTTGT |

TABLE 3-continued

Hypomethylated locus region sequences

| SEQ ID NO | GENE NAME | SEQUENCE |
|---|---|---|
| | | TTTCTTCCAGATATTTTTTGTCATCGCTTTCTCGCGCCCAATTCCCATCTGTCTAGCCCTTCTGCCCTCCGCTGGTCTTTTTCGCGAGCC |
| | | TCTCCCCAGCCGCCAGGTATTCGTCTGGGCTGCAGCCCCCTCCATCTCCTGGGGCGTGACCACCTGTCCAGGCCCCCGCCCCGTCGGCGT |
| | | CCGCGGAGACCCGCCCCCTCTGTGTCGCTCGCTGCCGCCTCAGCGCCGAGCGCTGCGAGCGCGTCCCCGCTCGTCGCCCGGCTCGGCGTC |
| | | GGGAGCGCGCTCTGTTGTCGTCTCGCTGCCGCCTCGCCGCAGTGTTGTTGCTGGCTGTGAGAAGGCGGCGGCGGAGCAGCAGGACCAGA |
| | | CTCCCTAGTAGCTCAGGCGCGCTGCTGCCGGCCCGTCGCCAGGAGGCCTGGTGAGATGGTGGAGGAGGAGCTGTCCGTGGCTGG |
| | | CCTTGCTGTGTCCTCGCTGGTTAGAACCCATCCCCGTCTCCCCCGTCCCCATCCTGAGGAGGCAGCGCCCGAAGCTCAGCTGGCAACCTCT |
| | | CCTTGTCCGGCCCGGCCAGGCGGCCAGTGGGAGTGGGAGTGGGAGTGGGAACCTCAGCTGCCAAGCTGCTGCCAAGCTGCTGCCCGGACCTGCCAAGCTGCCAAGGGGGGGGTCCC |
| | | GGGCAGGCGCTGGGAGTGGGAGTGGGACGCCCAGGCGGACCCGGATGGCCCCTGCCAGGTGCCTTCCAGAGCGCCCGGGTTAT |
| | | TCCCACTGACTCCAGGGAGGTGAGTGTGCGCCCCTTCGCTTCGCTGTCTGTGAGGTCATCGTTGCCGAGACTGAGGTCGGG |
| | | GGCCATGGAGCCCCGGGCGAACGGTGGAACGTGGGACATGGGCATTGGAGTGACCGCCTGAGCGTGCAGCAGGACATCTTC |
| | | CTGACCTGGTAATAATTAGGTGAGAAGGATGGTTGGGGGCGGTCGGCGTAACTCAGGGAACACTGGTCAGGCTGCTCCCCAAACGATTA |
| | | CGGT |
| 35 | chr21: 14056400- 14058100 | GTCTCTAGGACACCCTAAGATGCGGCGAGGGAGACGGTGAAGGTTGGCTCCCGCCTGTCCGCCTCTGATCCTCTGTCTCCCCTCC |
| | | CCCTGCGGCCGGCTCATGGCCTGGCGGAGGCCCGGAACCCAAAGACCTTCCGCACCCGCCGTGTACAACGCCGCCCGTGACGGCAAGGGG |
| | | GCAGCTGCTCCAGAAGCTGCTGCTCAGCAGCCGGGAGCTGGACAGCGCGGGCGGAGCCTGGAAGCTGGGACGTAGGTGGCCGGGAGACGCGCGC |
| | | TGCTCATCGCCGCCTGCTACGGCCACCTGAGGTGCGCGCCGCCCTGACGGTGGTGAGTACCTGGGAGTACCTGGGAGTACCTGGGAGCCCGCTCG |
| | | GTGCACTTCGATGGCCGAGACCATGGCCACCGCGAACAACTCCACGCCTCCACCGCCCTGCTTCGAGGGTGTCGGGCCTCCTGGAGGTGGTGCGCTAC |
| | | GGGCCTCGGTGAACTGCACCCAGCCACCGCCAGCAGCCGCCCAACCTGGAGGTGCACGCCACGCGCACACGCGCACACGCGCACAACTGTCCGCCTACCGGAGACCGCCCGTGCTCTAGGCATAACACCGCTCAGGTGCTGCCCCGTTGCTCCCGG |
| | | CTGTCGGCCAGCCACCAGCGCCCAGGTGAGTCGAGGGCGCCCAAGGTGAACTGCGAGCCGCCAAGGGCGGCCAGCGCAGGACGCAACCTGCTAGCCGAGCCTCTGAGC |
| | | GAGATGCCCCGCTACCTGCTGAGAGGCGCCTCCAGCGCCAGGCGCCCAGGAGCCGCCGGTCCTCTGGAGCGGCGCCCCAAGGGCATTCCCAGCGTGATGAGC |
| | | ACCAGCAGCCTGGAGATCCTGGAGATCCTGAGCCGCCTGAGGATCTCATCTGTGAGTGCGTCTGGCAGAGCCCCGAAGGGCAGCCCCCGCCAGCGTAGAGA |
| | | CAGCTGCAGCTGGCGCCGGCCACACACCAACATCGTGGAGTCATCCAGGAGACAGCAGCCCCGCAGCCGCCGCCCGTCGTGCACCCCGTGACGGCCAGCTCATAGGGGTAGAGGCTCAGC |
| | | TTAGGCTGCCCCAAGAAGGTCTCTCCACCAGCCGGGATGGTGACAGCCGGGAAGCTGTGCCAAGCAGAGCGCCACTGCCTAGGTGGCCGCAGCACGCGGCAGCACGCGGCAGCCCCTTGAGGTACT |
| | | GAACGGGAATCTTACCAAGCTGCTGTCCACCAGCCGGAAGCTGTTGATCCGGGAGCCTCCATAAGCAAGCACACAGACAACCTGGAGCCTCTGAGC |
| | | AGAAACGAGATCTGCTTGGGGCCTTAAACGACTATTCCAGGGAGGTCAACAGGGAGCAGGAGGGCCATCGAACACACCCAGCGCCGACGGGCCGACGACGATGAG |
| | | GCCCCACAGCTGGTTCCTGCCTATGACTATTCCAGGGAGCGGACATCCCAGTCCCTGCGACACTTCCTATTGTATCCGTTACAGGGGCGCAGT |
| | | ATGCTATGCAGGCCCCGAGGCCTTTGATCCGGGAGCGATCCAGGAGCGGCGATCCGCAGATCCGCTGTGGACATGCAAGAGAACCTGGAGCCTCTGAGC |
| | | GTACCCGACTCGGGGAATATCGACTGCTACATCCGTCGTGAGTCGATGCCCTGAAGTACGCCCTGGACATCCAACAGAGCCAAACCTGACAAGCAACCTGACATGAGC |
| | | CCCATGAGCGCCAGCAGCTTCTTCCGCCCCATCATCTCCTTCTCCGAACTCTTCTCTCCAACTCTTCCGCCCAGGACCCCGGCTGCTGCCAAAGGCAGCCTGGGCACCC |
| | | AGATCGGCTTTGCAGACCTCATGGGGCTCCTCACCAAGGGGTCCGGAGACTGGAAGTGGAAGTGGAAGTGGAACGCCGCCAGGAGCCTAGAGA |
| | | CTCGGCCCAGTTCAACAAGCCCTGCCCATCATCCTGCCTCAAGGCGCCAGCTGCTCAGCTGCTCCACCCTGCTCCACCCCCAGCCAGGAGCAC |
| | | CTGAAGCACCAGACCATCTATGCGCTCAAGTGCGC |
| 36 | chr21: 14070250- 14070550 | TAAAAATAAATTGTAATAAATATGCCGGCGGATGGTAGAGATGCCGACCTACCGAGGAGGCAGATGGCAGAAACAGAGAGAAACGACGA |
| | | GGAGCAGTTCGAATGCCAGGAACGCTCAAGTGCCAGGTGCAGGTGGGGGCCCCGAGGAGGAGGAGGAGCCCGGGCCTGGTGG |
| | | CCAAGCCGAGCCGTGCAGCCGGTGCGGATGCTCAGGTGCGATTTCCTCCGCCTTCCTCTCTTTGCCGAGCTTCCGCACGGCCGCTCGGAGGA |
| | | CTTCTGCAGGATCCGCAACGAGGCAGAGGCTATTATT |
| 37 | chr21: 14119800- 14120400 | CGGCACCCAGTGCGGGTAGCGCCCATCGCCCCAGCCGTGTCTTCCTTGGTCTCCGTCCGCCGCCGCCCGTGAACTGGACCAC |
| | | AGGGACCATAGTTCTGGAAATTTATCCTTTTCTCCATGAATTCAGCAGCAGTGTCAGCAGCAGTCAATGAATTCATCATTTATGTATA |
| | | TTTTATATAAAGAGCCATATATATTTCTGTGAATTCCCCTTTACTTAAGAATTCATTATCAGCGAATTAGTTTAAGGAGCCTGTTTTGTT |
| | | TAAATATAAAGCCATATATATTTCTGTGAATTCCCCTTTACTTAAGAATTCATTATCAGCGAATTAGTTTAAGGAGCCTGTTTTGTT |
| | | AGAGGCTGTGGTGTTGCATTCAAAAATTGGAATAGGAACAATGACTTGTAAAAATTCAACATTTATTTATTTTGAGATGGAGTCTCGCTCT |
| | | GTCGCCCAGGCTGTAGTGCAGTGGCGCATCTCGGCTCACTGCAACCTCCGCCTCCCGGGTTTAAGGAATTCTCTGCTTCAGCCTCCTG |
| | | AATAGCTGGGATTACAGGCGCATGCCACCACCAAGCCCAGCTAATTTTTTGTATT |

TABLE 3-continued

Hypomethylated locus region sequences

| SEQ ID NO | GENE NAME | SEQUENCE |
|---|---|---|
| 38 | chr21: 14304800- 14306100 | CCCTGAACAGTCAGAGTTTACTGCCCACTTTGCTGGAGGAGAAGCTCCTGAACAACTAGAGAGACTGTGGTTCCCAAAGAGACAGCCTG TAGGCCTGAGGACTGCTTATGACCGGCCTCAGTCCCTGCCTGTCAGTCCCTGCCTCAGTCCTCCCTCCCTCCTTCCCAGGCCTTCTCTG ACTACCAGATCCAGCAGATGACGGCCAACTTTGTGACTCAGTTTGGCTTCAATGATGAGGAGTTTGCAGACCATGACAACAACATCAAGT GAGTCCACTTGGATGCCCCCTGCAGAGGCACGACTCCCCTCCCCTGCCTCGCTGCAAGTCCCATGGGGCAGCTCCCTTAGTCTTGCCG GGAGATAACAGGTGTTTCCAGTTGCATGAGGGGTGCTGAGGGGTGCTGAGGGGAGAACCAGGGGAGGAGCACTGAGGCCTCAGATGAGCACC GGGGAGGAGCCCTGAGGCCCAGATGAGCACCAGGGGAGGAGCACTGAGGCCTGAGGGCTGAGGCTCTGAGGCCCCAGAGCGTTGAAGCC CCAGATGAGCACCAGAGGAGGAGGACCACCGGGGCAGATGAGCACCCGGGGAGGAGCACTGAGCCCCAGAGAGGCGCCCAGAGCGCCCCAGA GAGCGCCCGAGGCCCGAGATGAGCAGCGCCCAGGGGAGCGCCCGAGCCCATCCCCCTTGCTCTTGCAGCGCCCATTTGACAGGATCAACTTCAA TGAGCAGTGGGCGGGGCCAGGGAGCGCCGAGGCCATCCCCCTTGCTCTTGCGGGGTCATGCAGGCACCCGTTCCAGGACACCCTTTCTTGACCCTCCCC CATGCACACTGACAGGACAGTGTGAGCGACGGACAGTGTGCGGGGTCATGCAGGCACCGTGTGAGCTAGGAACAGTCGCTTTTCTTGACCCTCCCC ATGCCTCGGTCTGTGTGGGCTCGTGCGGTGGGGCTGGGAGGAGCCCCTGTGAGCTAGGAACAGTCCCCTGTGGGGAGAGCCTGCTCTCCCCAGAC CCTCTGGAAACTGACCTTGGCGTTTACTCTGCAGCCACCACCCTGCTGTGCTGCCAGTGAGGCCAGAGCCAGGCTGCGGGGCATCCCCTAGAGA ACGAGGACATCTCGAGGACGCAGCAGACACACTTGCTGTGCTGCCAGTGAAGGCCAGAGCCAGTGCGGGGCCATCCCCATCCCCCAAA GCCTCTGCCGAGGAGGTGCAGCCCCCAGAACACCCCGTCAGATGCCCAGATGCCCAGAGGTGTTGTTATGCCGG |
| 39 | C21orf34 | ATTGCCGTACTTTGCTTCCCTTTGTATTCTTGTATGCTGCCGAGTCACTGATGGCTAGCTCTGTCTGGCAAGTAATTCAAAATGCT GTTTATGTAGAAGGAAAGGTAGGGACTTTACCACACTCTGTCATTAAAGGGAGCAATTGAAGAACAAAGGAACTGAGTAAATACCTATAT ATTGCCTTTTGTGTTGCGAAACACTGTAGCACAAACACATTTGTGTTCAGCCACAAATGTTTACTTCCTTTTGTAATAACGATATAGTAGGT TGTCCCACATATGCAAGAGAATCCATATTTATTAAACGTATATAGTCAATTTGTTCATATTTTCATATTTATAGGCTGCAAACATTTCTCAATCTCAAA GACTTTTACATATCCACCTCCACAGCTATTGTTATTATTTAAACATATATGTTAAAATTCATATAAAATATATACTACAATTCCTGTGAAATGA GTTGATTTATTAGCAACTTAAGCAACTTACTTTATTATAAATCATAGGTTTTTTTCATTATCACATAGAAATGATCATTATACAGATT GGTCCACTTCATGTCTTTTGGGTGCTTGGGACTATTAAGAATTGCTAGATAGGCCATTACTTCTCTATCACGTGTGAGCCTGCTGCTCCTGAG ATGAAGGCATAGAATACAATCTAGGGCTATTAAGAATTGCTAGATAGGCCATTACTTCTCTATCACGTGTGAGCCTGCTGCTCCTGAG GTAGGGGATCCAGGATGAGACTGTGCCGAGCTGTTCCCACAACTGCATTTGGAGATCCGTCTTATTGATTGAGTCCGGAAAGGGGTG GGATTCAGGAGTGTGAGGTGCAGGGAGGAGCCAACTGACACTGGCTCAATGAAGCACAAGACATTTCTTCCGGAAAGATGTCAAACAA CTGAGAAACAGCAAGACTGAGGGGAAAGTAGAAAGGTTGAGAAGCACCCTGACAAAGGCTGAAGTGACAGCGTCATGCAAATGCTGAGTCCAGTCCAGCAGG GCTTTTTCTTTCTTTCTTTTTTTGCTTCCATCATCTGACCTGCAAAGGCTAAAAGCCCCCTCCCCCCATTTCCATGAGACAGCCTTGGG TCTGGGAGAGGGTGATGCTAGACTGTGAGTTAATGTTAATGACGACGAGCGCAGTGAAAATACCAGCCGCTGCGCCCGTCGCTCGGGCATCCG GCGTCTGAGTCGACCATCAGATGTTTGCCTGCCTCGTGTGTATCTGCTCTGTGAGGGTAAAAGCCAGTCAGTCAGTGAGAAGGTACGTTGGAGAGC TGTCTAGCCGAGGGAGGGGCTGGCCTGTGAGTGCCGTGAGGGTAAAAGCCAGTCAGTCAGTGAGAAGGTACGTTGGAGAGC AACTAAAATCGACTGATTTCCATCTTTGGAGCATCAGATGTATTCCC |
| 40 | BTG3 | GCAAGCCTCTCCTGAAAAATGTAAGCCATTTCCACTTTGTAAAGCTACGTTTATATTCCACCACGATACGATGAAAAAGAAACCCAAGGC AATTTAATATACGGGTTGGGAAGAAAGTTTTGCTGATGAACTACATTAGCCTCCACTCCAGCAAAGCAAACAAGGAACCACACTAAAGAA ATGTACTGAATCTTTTAA |
| 41 | chr21: 23574000- 23574600 | TCATTATCCGATTGATTTTCCTGGTATCACATCACTTAAGTTTAAGTAGCTCTTTATGTTACTTAGTAATGACTGCAAAACACGAGTTGTGAT GCGGGCAATTTGGATACAAGAAGCCATTAAGTTTGTTCGTTAGTTAACAGTGAAAGCTCAAGTTATTAAGGATAAAAATGCT AGTATATATATATGGTTTGGAACTATACTGCCGATTTTGGATCATAGTCCCATGGAAGCAGGATAATAATCAGGTTGTTTTA AATTCCATGTCTAATGACTTCGTTATCTAGATCACCTGTAGAGCTGTTTTATTGTAGGAGTTTCCTTGGTTTTAATCTTTGATTGTTTT CATGTTAATACTGAAATTTTAAAATTGCATATTGCATATTCCTATATGAAAATTTTACTATGATTATTTATTTTTATTTTCCTTTCCTTTAGG AAGAATTAGTTTGTTCCCTGACAGATTAGAGTAAGGGACAAATTACTTGTCTCTATAAACAACTCAGATGTTTTGAGCCGGTGTTGTAGG GTTATCTTTTTCTGGTTTTGCATTTTATTTATTATAGGACATAGTGCTT |

TABLE 3-continued

Hypomethylated locus region sequences

| SEQ ID NO | GENE NAME | SEQUENCE |
|---|---|---|
| 42 | chr21: 24366920- 24367060 | AGAAAGAAGAAATCCGGTAAAAGATGTGTTATTGAGTTGCAGTTGGTGTTTGATCTTGCACAGATTTCTCAGGGGCCTTAAGACCCG TGCCTTGGAACTGCCATCTGGGCATAGACAGAGAGGGAGCATTTATACGCC |
| 43 | chr21: 25656000- 25656900 | CGAAGATGGCGGAGGTGCAGTCTCCTGGTGCTCGATGGTCGAGGCCATTCCTGGTCCGCCATGTCCTGGGCGCCATCTGCGCTAAACAGGTACT GCTGGGCCGGAAAGTGGTGCTCGTACGCTCGGAAGGCATCAACATTTCTGGCAATTTCTACAGAAACAAGTTGAAGTTACCTGGGTTTCC TCCGCAAGCGGATGAACACCCCACCTTTCCGAGGTCCTTCCTGCAGCCCCCCCAGCCGCATCTTCTGGCCGACCGTGCGAGGTA TGCCCCCCCACAAGACCAAGCGAGGCCAGGCTTCTTCTGGAACCGGCATCCCACGCCCTCGACGACCGCCTACGACAAGAAAAA GCGATGGTGTTCTTCTGCTCCCTCCCAAGGTTGTGCCTCGAAGCCTACAAGAAAGTTGCCTATCTGGGCGCCTGCCTCACGAGGTTGGC TGGAAGTACCAGGCAGTGACAGCCACCCCTGGAGGAGAAGAGGAAAAGAAAGCCAAGATCCACTACTACCGGAAGAAGAAACAGCTCATGA GGCTACGGAAACAGGCCGGAGAAGAACATGGAAGATGCGCTCCTGCCCTTCCTCCGTCGCCTGGAATGTACGGACCCAGGGGCAGCAGTCCA CAATAAAGACTGTTAATTCCTCATGCTGCCTGCCCTTAATCCGTGCCCTAGCGAAGGTCTTAGTCACTGCCTCCCGAAGTTGCTGAAGCACTCGG GGCGCCACAGCAGCCTCGGACACAGGTCTAGCTCAATGCTAGCTACTGAAGGTCTTAGTCACTGCCTCCCGAAGTTGCTGAAGCACTCGG AGAACTGTGCAGGTGTCATTTATCTATGACCAATAGGAAGAGCAACCAGTTACTATTAGTGAAAGGGAGCCAGAGACTGATTGGAGGGC CCTATCTTGTGAGC |
| 44 | CYYR1 | CATAACAAGATCATTCTAATGTGATTATAAAGGACCCGAAGCTTTGCTTTTAAATTCAATACTTAGTAGAAAATGATAAACTTTTC CCTTTGATTTTTATTCACTATTTTATAACACTAGCACCGGATTGGAAATATCATGCCTCTTGATGTTACCTGGGCACCA CTGCATCACAGTCCT |
| 45 | chr21: 26938800- 26939200 | AATAGTAATTGCCAACAGTCAAGATATGTACTACCACCAAATTCCGTGTTATTTGTGATCAAAAGATATACACAGATACTTGAAAACTGATT TCTACGTTGCATATGGGAAAAATAATTTTTCAATCATTTTCAATCAGAGTCCTGCCAAAATGAAAGAATTTGACAGTATGCAGTGATAGTAAGAACAAGCAGATT TGGAACACATCAGCAATATTTGTTCTGCAAAGGGCAGCTGGGTACTGTGTTTTGGTACCTCATTCTTTAAACGTATAATGGAATCTGGTTGGTTCA CGTAGAAACTGTGCTTGCAAAGGGCAGCTGGGTACTGTGTTTTGGTACCTCATTCTTTAAACGTATAATGGAATCTGGTTGGTTCA GGAAAACCCTTGCCTACTTATTATTACTCTGTTTT |
| 46 | GRIK1 | GGCCCATACTTAATGTATTTTAAACGTTTTAAACATTTACTAATTACTAATAGAACCTTCTATTGCCTATTCTTCCTTCTGGTTTATTCCCTTTCCTTCTG TCATTGAAGAAATGTTCTAGTGGTTAGAAATATCCACGATTGAAGAAGAATGTGGAGAAAAGGAGGGCTGGTGGGTAAGAATTGCTCAT GATGTCTCCCTGAATTCTGTGCTCTCACAATGACACTCCAATGTGTGGTTTGACGCCCTGGAAGA |
| 47 | SOD1 | AAGACCTGGAGTTTCCATTCACCCGAATTGGCACTTAATAACTGTTGTCCGAGCATTTCTTAAGCCACATTTCTGTAAAGTGGCTTAAAAT TGCTCTGCCAGTAGGCAGGTTGCTAAGATGGTCAGAGACAAACTTCTGAACGACTCTTGTAAAATATCAGAAATATTTCAGAACTTTTA TCAGTAAAATTACAAAACGTGTTGCAAGGAAGGTGCTTGTGATAACACTGTCCCCAGAACCTTAGTGAAGTTACCAACTGGTGAAAATTT TCTCTTGCACTCGGCTTAAAATCAT |
| 48 | chr21: 33272200- 33273300 | AAGTAACGGGATCAAATTAATTATTATTTTGGTGCCGCTCCTCTTCTCCACCCAAGCCAGGCAAGACTCACCCTGCCCTTGCCCGCC CCAGCATTTCAAATGGAATACCTAGGTGGCCCAGGGGGACCCCAGGCCTCGACCCCTATCCGTTCTTTTCTTGGCTTTTCGCCTTTCCT TGATAAAAGGAGGAGAAGGTGAGAGATAATTAACAAAAAAACATGCCCCCAGGACAATGAAAACAACTGGCCTTGCCGGCCAGAAATGTATCCT GGTTTCTAGGTGAACTTTCCCATCAATCTTTCCTTTAACCCTCTGTTAGTGGAAGCAATAGGAACACCCCGCCCACAATGGGGCCGC ATGCTTTCTTTTTGACTGGAACAAAACAGGGGCTCCGGGCAAGGCTCGAGGTGAAATGGTCTGATGAATGGAACAATCCCCCGATTCAGGCC TGTTCCCCGGCCCCGGGCTTGTGTTTACAACAGGGGGACGAAGAGAAGTGACAAGTAGAGAGTAGAAGCAGCGGGGGGGAATTAAACAAAATGC TACAAACCGATCTTCTGTTCCCACCGAGGGGACAATTCAGAAGCTGCTGCATATTCAGAGCTTATGGAGAAAGGCTTGGAGAGCCTTCAGGAC GCTCGACTAAAAATCTCTGATTTATTGATGAAGCTCAGAAGCTGCTGGAGAAAGGCCTGAGCCTTCTTTTGTCTCCGAATGAAGTACAAT CTTTCTTCTGCCCCTGATTATTGATGAAGCTCAGAAGCTGCTGGAGAAAGGCCTGAGCCTTCTTTTGTCTCCGAATGAAGTACAAT AGGCCACAGCGGGCGGAGATCTCTTGTGATGCTCTGCCTCTCCCTGCCCTCCTGCAAATACCAGCAGCGGTGACAA ACGATTGGTGTGCCTGGGAGGCCGGTGACAAGACTGGGCCACTTGGGCGTATTATGCCCAGGCGACGTTT |

TABLE 3-continued

Hypomethylated locus region sequences

| SEQ ID NO | GENE NAME | SEQUENCE |
|---|---|---|
| | | GTGCTGTGAAGATGCACACTCCATTTGTCAATGGCTCTCATCGGCCCAGATAATGCCCCCTGCCTGCCTGTCAGGGGCGCAGCCGG<br>CCGATTCATGGCGCCCTCGGAGAAAGTA |
| 49 | OLIG2 | CCGGCACGACCCCGACTCCGCCAGGATTGAAGCAGCTGGCTTGGACGCGGCGGCAGTTTTCCTTTGGCGACATTGCAGCGTCGGTGCGGC<br>CACAATCGTCCACTGGTTGTGGGACGGTGGAGTCTCCCCAAGAGGAGACACGCAGAGCTTCCAGAACCGGCTACATGCGCATG<br>GGGCCCAAACAGCCTCCCAAGGAGGAGCACCCAGGTCTCGCACAGGGGACTCACGCACCTGAGTTCGCGCTCACAGATTCCGCACACCGGTTCT<br>CAAACACCTGAGTCCACGTCGCACAGGCTCTCGCACAGGGGACTCACGCACCTGAGTTCGCGCTCACAGATCCACGCACCGGTGCTT<br>GCACACGCAAGGGCCTGAAGCGGCTCTTGACCGCAAGCACGGGCCTTCTGACCATCCTGGTTTACCATCCCTAC<br>TCCTGGAGGCCTGTGACCGGTGTCCTTGACCGCAAGCACGGGCCTTCTGACCATCCTGGTTTACCATCCCTAC |
| 50 | RUNX1 | GGACGGCGGCCCGCTCTAGAGGCAAGTTCTGGGCAAGGAAACCTTTTCCGCCTGGTCTCCAATGCATTTCCCGAGATCCCACCCAGGG<br>CTTGGGCGCCACCCCACGTGACGTCATCCCCCCGAGATGCGGAGGAGAGCGACGAGGGTGTGGCGGCTCCAAAAGTAGGCTT<br>TTGACTCCAGGGGAAATAGCAGGTGATTTGCCCTCGAGGAGGCTCCTGGGCCGCTTGCCTAA<br>AACCCTAAACCCCCGCACCGGGGCTGCGAGTCGGACTCGGCTGCCGTCTCCAGGGGAGTCAAGTTCTTTATCGACTAAGGAAA<br>GTTGGTCCCAGCCTTGCATGCACCCGAGTTTAGCCTGCAGAGGCAGCGTGCTCCTTGACTCGATGGGATCGCGGACATTTGGGTTTCCCCGGAG<br>GAGTTTGAAGCCCGACAAAAAGCTGATAGCAATCACAGCTTTTGCTCTTGACTCGATGGGATCGCGGACATTTGGGTTTCCCCGGAG<br>CGGCCAGCGTGTTAACTCGCGAGCCGGTGCCTCTTGCACACCAGTCGTAACAGAGATCCCACCCTGCCCTTTCCTTACTGAGGATCTAAAAT<br>GAATGAAAGAGGGCAGGGGCTCCGGGAGAAAGGAACCCTCATTTTACGAGGCCCATTTTACGGACTGCACTTTCAAGGACAGCACA<br>GCGTGTACGAAGTGAGGAATTCCTTTCCACCCAGGTGTTTCCCTGGAGTAATGCCAATACAGAATTCCCCTTCCTTTGCCTAAGGAGGAAAGG<br>AAAGGAAACATTACCCAGGTTCATTCCGAGGTTTCCCTGGAGTAATGCCAATACAGAATTCCCCTTCCTTTGCCTAAGGAGGAAAGG<br>TACAACGAAGCGATACGTTGGGCGATCGTTGGGCGATCGTACGTGACAGATTTTCCAAATTTTGTGCGGGGAGAGGGAGGAGAATTGAAAACG<br>GCTCACAACAGGAATGAAATGTA |
| 51 | DOPEY2 | AAACGTTTAAAATATTTCTAAACAGAATGGGCCAATTCAGTCAGTCAGTCACAGTAACTGTTGATCTCCATAGCAGAGCAACCCACAAAGACAGAAC<br>TGATTTTTTCCCATAATCAGGGGTGAAAAATATATCAACTTGTTTCTGAACCAAAACCACAATTTCTGCAGTTTAAAATGTTTCACTGCTAAT<br>ATGGCCCTGTGTAGAAATTATGTAGTTTCTTTTCTTTAAAAAATAAAAAAAATTCCCATCACCTGTCTCAGTAGGGCCTGAGAGTAGTGTGGGG<br>TGTAGATTCTGATCACAAAGCAGCTCAGTTAACCTAAAAAATAAAAAAATTCCCATCACCTGTCTCAGTAGGGCCTGAGAGTAGTGTGGGG<br>AACCCCAGCTTTGTATGGAGAGTCATGCACCCTTGAACCAGATAGAGACCTTGAATAGCCATAGCTGGTGCTTCTCTCAGGATAAACTC<br>TGATGTAGGAAGTATCACCCTCATGAGAGTGGAATTTGGTCATCGCAGGCATATTCCAGTTGACGCAGGCATATTCCATGTCTCTTTCTGAGACACCCAA<br>CCATCCCCACTCACTTCTGCACTCCGTAACAGGCATCCCCAGTTCTCTGCGGTTGATCCTTCTGCAGTCCTGCCAGCTGCCTGATG<br>GAAGAAGTCCATTTCTTCCATAAATAGCATCTCTGAGGGTCCTGAGGGGTCCTGGAGACAGTGCTTGTAGAACAGGGCACCAAGGCCGTACGG<br>CTCTTGAGCTCGATCTCGCGAGATGCGGCTGTACTTGTAGAACAGTGCTTGCGGCTCCTCTGCGCCCACCGCAAGCCGTAGGCCGTACGG<br>CGTAGATGCACCCGTCGCCGTGCCGCCTCCGCCCCCGACCTCTGCCCCCCGACGCTGTCGTTGTTTATTCTAACAGGGTCTCTCTCT<br>GTCGCCCAGGCTGGAGTGCAGTGGCGCGATCTTGGCTCACTGCAACCTCTGCCTCCCGGGTTCAAGCGATTCCTCCTCAGCCTCC<br>CAAGTAGTGGGCATTATAGGTGCCAGCTAACCATGGCCCGGCTAATTTTTTTTTTTTTTGAGACAGAGTCTTGCTCTGTCA<br>CCCAGGCTGGAGTGCAGTGGCGCGATCTCGGCTCACTGCAAGCTCTGCAAAGATAGGGATTTTAACAGCACCATATCTTCATAGTCCATTCATACG<br>TAGCTGGGATTACAGCTATGTACAGCAGTGTCTGCAAAGATAGGGATTTTAACAGCACCATATCTTCATGTTCATAAAAAGTCCTACACG<br>CGTGATGTACGTCTAGATCTTTCCTTTGTCACAGGATATAGCACGGTAGTTACGGATATAGTCTCCGCAGTGCCTGGGTTGACTCAGC<br>TTCCCCACGTACTCCTCGCATATTTTGTCTCCAGTTTGTCTCCATCTTTAAGGTAG |
| 52 | UMODL1/<br>C21orf128 | CACATTTCAGACTCGAGGTGCTGGTGCGGGCAGGTCTCCTGAGCTGTGGGGGTCAGTGGCCAGTGATGGTGACGCCTCAGGCC<br>GTGCATGGCGCGGAGGCGGCCGCCTGCCTGGGAGGCAGCACGAGGCCTGAGCCTGAGCCTGACCGCAGAGTCGGGGAGCAAC<br>CATGGGGGCACCGCCCCCTGCTGGAGGCACGACGCCCAGCTTACGAGGGGACATCCACCCCGCTGAGAGCCCCACC<br>TTCACGGCGAGGATCGTAGAAGAAGACATTTGATTATTACTCGGCAAAAAACAAGAAACAAGAAACAAAAAGAGCTCCTGAAGAA<br>GAAAAGGTATTTGCCTGTGCCCCACCTAGAAATAATGTTGTTGGCACACTAGGACATTCCTCAGTCATTCAGGAGCACTCCCTGCCG<br>TGCGTCCACATGTCCAACCCGATAGATGAGGCGCTGTTCGCCCGTGAGGGGTGTCGACCTTGTGACCTTATCTTTACCCTTAGGCC |

TABLE 3-continued

Hypomethylated locus region sequences

| SEQ ID NO | GENE NAME | SEQUENCE |
|---|---|---|
| | | GTCCATCCCGGGGCCTGGGGTTTCTGCGCAGTCACGGTGGGCGTGTAGGTGGCCATGTGTTCGGTCTTTCCCAGGAGGTACGTA CCATGTGCTGGGAGGCCTGAGGCTGAGCCTGCGCCCCGCGCCCATGAGTTGCACCCTGCACAGCGCGGCCAAACCTCCTGC |
| 53 | ABCG1 | CAGGCTTGAGCGGCGTGACTGGGAGACCCCCGGAATGGAATGGCTCAAATGCTCAAATGTCGTGTGTGGTGTCCGCAGGGAACGCGCCCGCGGGT GTGTGGAGTCTGGCCCTGGGCTTCAGCTGCGTGGGCGACTGCGGGGAATCTTCAGACTCCAGTTTAAATCAGAGAGTGTGTCC ACGAAAAGAGTCAAACTAAAACATT |
| 54 | chr21: 42598300- 42599600 | AACGAGACAGTGCAAAAGCCGCTGCCTGTGACCTGGCATGCAGCTCGGCCTCCACTTGACGGTGATCCACTGAAGACAACAG CTGCCTCTGTACTCACGCTCCCCCCACTCTCCTCTTGCCCCTGGTTTCTCCATCCCTAGATGCCATCCCATGCCCCAAACCATCCG CCAAGCACAATAACCTCGCCCCCACCCCACTCGAGTGTTCACTCCAGTTGACAACCAGATAACAGTTTGTTTTGTTTTGTTTTG TTTGTTGTTTTGAGACGGGGTCTCGCTCTGTCTGCCCAGGCTGGAGTGCAGTGGCAGTGCCACACAGACAGATAATGTTATCTCGGCTCACCACAACCTCCGCCTCCCG GGTTCAAGAGATTCTTCTGCCCTCAGCTGGGATTAGCTGGGATTACAGGCGCGTGCCACCATTCTCAGCTAATTTTGTATTTTAGTA GAGACAGAGTTTCATATATATGCGGGGTTTCACCATGTTAGCCATGCCCAGGCTGGTCTCGAACTCCTCAGCCTCAAGTGCAGGGATTAC AGGCGTGAGCCACCGCACCCATGCCCCAATAGCAATTTGATGACCCATCCCCTCCACTGTGGGAAAAGGCTGGGCACCACTCCATGCA GCTCTCTTTCCCTGGCTCCAGCATCGTGCAGGCGCCACAGACGCGGCCACTGTTCCCACTCTCAGAATCCATGCCTCTGCTTATCGGGCCGCGGCATC CCCTTGTCCGCAGACACTCCATGCAGAATCATGAAGACACGGGCACCGGGCACCCCTTCCGGAGCTTCTCCAGAAAATCCATGAAGTGCCAGCACCCCTTAATC CATCCAGAGCGCTCCATGAAGCACGCGGACCCCTCTGTCCAGATGCTCCAGAAATCCATGAAGTGCCAGCACCCCTTAATC GGAGCGCTCAGAACCGTGCAGCGAGCAGCAGCCCCACAACCCGGAGCGCTCTAGAATCCATGAAGACCAGCAGCACCCCACACCCGGA GTGCTCCAGAATCCACGCAGCAGCGGCATCTTTATCAGAGCGCTCCAGAGTCCATGAGCCAGACAGTCTCCAACGACCCCTGAGATTGTTT CCAGAATCCACGCAGCGTTGGCACATCTTTATCAGAGCGCTCCAGAGTCCATGAGCCAGACAGTCTCCAACGACCCTGAGATTGTTT CTGCAAAAGCCATGCCCTTCATAAATCTGAAAATTTGAAAACATCCTTGAAAATCCTCCTTCGAGTGCTGAGCTGAGCTGAAGCT TTCTGAACCCCAAGCAGAAGAGATATCCAAAATGTAAAAACGTGGGGGCCT |
| 55 | chr21: 42910000- 42911000 | ATAGTGCGACTGTCCGAAGTCTTTATCACAGTTACTGTGGTTGATGCTTTTTTCCAGATGTCTTCGACGTGCACCCATGAGGGCTCCACCT GAGAGTCCCAGGGTCCTGGGATGGGCTTGGTGGTCTTTGAACCCTCACACGGACCGGTGTTTGGCAGGTCCAGTGGCACTCGCCTC GATGGGTCCCAGAGATAGAGGCCAGTGACAGCAGCGCCTTGAACCCTCACACGGACCGGTGTTTGGCAGTCCAGTGGCACTCGCCTC GGTCACACGGAGAATGGGGCTCTGCTGCTGTAAACAGACAAGTGCACAAGACATGCGCCGGCCAGCCGGTCACAGCCGTCTGGGCTGC CCCCACGGCCGGCTCTGCTTGTAAACAGACAAGTGGAGATGCCCAAGGCCCTGCTAAGCTGCAGTGCCGCTGGTGGGGCCGACTGTGGGTGTCTCGGCCTC GGCCCGAAGGTGCCGCCGGGAGCTGTAGCCATCACTCCAGCCCGTGTAGGGCGCCTGCTAAGGGGGCCGACTGTGGTGTGTCTCGGCCTC AGAGCACCCACAGTGAAGCCAGAGACCTTGATGTGAGATCCCAGGCGCCTGCAGTGTTCTCAAAGGGGTCACTCTCGTGGAAGGGAG CACCCCTTCCACAGTCGGTGTGCACATCCCAGTCAGTGACTGACAGTCCCCAGCCAGCAGTCCCCGAGCTGCCATCCCTCACTCCG CCACCCGCCCCGGGGTGATGTCCCGAGCCTGCAGACCACAGAGCCACCGTCCTCTGTCCTGCTCCCCCTTGCCCCCTGCCTCCCC GGGCTTCCTGTGGGCCAGGTGGGGTCTGCAGGGAGCTGCTTG |
| 56 | PDE9A | CACTTGAAAAGCACAACTCATGCGCCTGCCAAAGCTCCACTGGACACGACTCCACTGGAGCCTGTGGGCCAGGGGTGCCAAGGTACCCAGTTCCA AGCCGTTGTATTTGAGAGCGTCCCCCCCATGAGAGACGCCAGGTGGGGAGACATAAAGTGACACAGGATGGACTGGCCAAAGGCTGAG GACGATCACTTACCTGCACAGGATGATGCTCTGTAAAGCCTGCACCGTTCCACCAGGGACGAGCTCTCCACCTTCCCCAGGACGCTGCCACCAGAGC TCCAGATGGCCCTGGGGGTGTCTGTAAAGCCTGGACGTGACCGTCCAGCAGCCCGAGGGAGGAGGAGGGCCCCAGCAGAGCCCGAGGGAGAGTCAGGC ACTGCCCCTGGCACTTAACGATGGAAAGCCGTGCTTGGACCTGCACTTCACTTCCAACGAAACAATAGCAC |
| 57 | PDE9A | AGCACCTCCTACCCCACCTCCCCATTCCTGCCATCCCAGGGTCCCAGGGAGCCCAGATTCCAGGGAAGGGTTGCATTAGCTCCCACTC GGGTGCTGATGCGCAGCAGAGACAGAGACCCCTGGGAGAAGTGAGCATGAATTATTAAGACAAGAACAAGGGTGAGGCCCAGAGAG GGGGTTGGCGAAGGTCATCTTCATGCAGCCGAGACGTTCTTCGAGCTTGAACCGCTATCCAGGCTCAAGCAGATTGCAACTGGCGA GAGGCCTTGAGGCCTTCGTGTGCAGAGTCCTGTCGTGTGCAGAGTCCATCTCAGCACACTTCCTGTTCTTCTGTCGATTTTGCATTT |

TABLE 3-continued

Hypomethylated locus region sequences

| SEQ ID NO | GENE NAME | SEQUENCE |
|---|---|---|
| | | TCAGTCCCTGTGATCCATTATTTATAACAGTGGAGATTGGCCTCAGACACTAGCAGTGAGGAAAACAAAAGCGAAGCTACGCAGAAAAA |
| | | TGACAAGAGTGATGAGCACGCAGTCATGACAACATGAGCCCTGTGCGGAGGCCCGGGATCCGCCAGATGCCGGGCGCGGGGAAATG |
| | | GGGCCCTGAAATCCCACCGTCAGGCCAGGCAGCTCTGAGCGTGACCTGGAGGGCTGTTCAGACGGTCTGGGTAGCCGTGTCTGCGCAT |
| | | GAACATCCTCCGTCGGGAGGAGAATTCCCACGATTATCAGAGCTGCTCCCTCCACCCCCACGTCCACGCGGCCACATCAA |
| | | CTCCCTGCCGAGCCTTGGCCAGCGTCGAGCCCTGCCTCCCCCTTAATGCCTCCTTCACCATCCCTCCCTGAAGTTCCCC |
| | | ATTGCATACACGCGCTGAGGCCTGATCCAAGGACTCCCATTGCTTGCGAAAAAGATTCTCCAGCTCTGAGGATGAGTCCAAAATCTGAA |
| | | CCGCTGTAGCAAATGCCATAAATGCCAGTGTGGGCAGGGCCGCGCTTAAAACAACAGAAACGGATTATCTCCAGACTTAAACCAGGG |
| | | TGCGTGGGCTGAAATCCAGTGTGGACAGGGCCGCGCTCTAAATGCCAGAGCTCCCCTTAGAGGCTCCCCTTCCTTGCCTCTTCCAGCTGCT |
| | | GGTGGCTGCCAGCAGTTTGGGACAATTGCGCCGCATCACACCACCTTTCTTGTTGGACATCCGCCTCCCTGCCGGGGTC |
| | | TTAGATGTCTCTCTTCCTCCACTGAGTTTCACTCACGAATTTGAATTGATTAACTCATGCCATCTTAGGCAACGTGCCCCTCAAATCCTT |
| | | CCACTTAACAGACATTTATTGAAGGTTCCTGTTGCGGGGCCAAGAGAAGGA |
| 58 | PDE9A | CCATCTTCCTAGGCCTGCGTTTCCCCACACCGGGACTTGTGCTGGAAAGAAAAGCTGCGTTGGCAGCCAGGAGCGCGGGAAACTGT |
| | | CCAGGGAGGCATCCTCTGCGATGAAGGCGGGGCCTCGGCGTGGCCCTGCAGCCTGGACCCCGTTCCGCGCTCTGTCCAGCCTGGAGAAGCCCACCCTCAC |
| | | CGAGCTCGAAATACCCCCGGCTGATGACCCGAGACTCATGGCCCGGACCCGCCATCGCAGAGGAAGAGGATGCGGATCCGGCGCTTCCA |
| | | CCACAGCCCCGGCGCACTGGGACGCGAGCGCGAGCCCATCCCGCGGTAGGTGGTGTTTCTGCAGCGCCAGTTTCACCGCGGGC |
| | | GCCCAGGATCCTCAACGGTTCTGTTGATGGATTCCCCTTCGACTTCGTCATTCAGCCTCGTCCCTCAGTCCCCAAATACCGAAA |
| | | GGCAGTCTTTTTTTTTTTTTTGAGACGGAGTTTCACTCTTGTTGCCCAGGCTGGAGTGGCAATGGTGCAATCGGCCACCACGCCCGGTCAACCTC |
| | | CGTCTCCCTGGCTCAAGCGAATTCTCCCCGCTCAGCCTCCAGGAGTGGGATTACAGGCACCTGGAATCCTGATCTCAGGTGATCCTGCCTCCAAA |
| | | TATTTTTAGTAGAGACGGGGTTTCACCATGTTGGCCAGGATGGTCTCGGAACTCCTGACCTCGTGATCCCACCCGCCTCGGCCTCCCAAA |
| | | GTGCTGGGATTACAGGCGTGAGCCACCGCGCCCGGCCTTTTCTTTTCTTTTTGAAGTTAATGAACTTGAATTTATTTATTTATTACAGA |
| | | ATAGCCCCATGAGATACTTGAAGACCCGGTGCAAGGCCTGTGGGCGACAGGCCATGCTGTATTTTCACAACTCTTTCCACTGAACACGACAAT |
| | | GCGCTTCACCCATAACCATGTCACGGCCTATGCATCAACCAAATGAAAAGAGAGCCTGTGCCACATTCCCGTGCCTAGAGTTACAGCTTTTCTTTTCAAAAC |
| | | GAACATTTTCACCCACCCGTATGCATCAACCAAATGAAAAGAGAGCCTGTGCCACATTCCCGTGCCTAGAGTTACAGCTTTTCTTTTCAAAAC |
| | | TTCTGTTTTGCAGGTAATCTTCAGCAAGTTCTCAACTCCAGCGACATCATGGACCTGTTCTCATCGCCACCTGTCTGCCTCCGTGAGT |
| | | GCGCCTGCGGCCTTCGCGCTCTGCCCGTGACGCCCTTTACAAGGGGCTCTTCGAAATCAATCAATGCCGAAATCCGAGGAGCCTC |
| | | GCCCAGGACACCGGCCCTTGTACAAGGGCTGTGTCCACAAGGAGAAACCGTCGGGCTGAATTAAACAGAACCGCCTCCTAAGAGTGTGGTTTTT |
| | | CTGCCGGCCGTGTGTCTCACACCTGTAATCCCAACACTTTGAGAGGCCGAGATCACCTGAGGTCAGGAGTTCGAGACCA |
| | | GC |
| 59 | chr21:<br>43130800-<br>43131500 | TGCTGCACCCCGCTGCCTCCTCCCGTGGCCCGGCAGCACCTTCTCCACCCGGGCCCCCTCTGCTCACAGCGCTCCCCGCCCCCGT |
| | | CTCCCGAGGGCGGGAGCCAGGACATGGCCTGGCCCTGAAAGCTGAAAGCTAGCCTGCCTTGACCTCCACGGCGCCCTCCCCACCCTCCGCC |
| | | CTCTGCCAACCCTGGCGGCCTGGCCGTCCGTGCCGCCTCACGCCTACGGGATGGGCGCAGGTCCTTCTTGGCCTTCTCTTTACCCACTCTCAGTCACCTG |
| | | GGGGGTCCTGGCGTCTTCCCTGCGGCCACCCCAGTTTCTGTGCAGCCAGGCTCCTGCGGGGCCGGTGATCCAAGACCCGGGT |
| | | AGGGGGCCCGTCGGATCTCTCCCCGCCCAGTTTCCGCCCCAAATGCACCGGCCTCGCGCGCCCCTTAGGAGGAGCTCCCATGGCCGCCC |
| | | CCAGGAGGCCGCCGATCTCCGCCTCGGACTACAGCCCGCCCCGCCGGCCCGCTTGCTCGCGCCCTGTTGCTCATCACCACCAGCAGCCCTGG |
| | | CAGGGGCCGTCTGGCCGTCCTCTTCCACAGCCCGCTGCGCCCACCCTTCCCCCGAGGTGCTGTCATTGTTTAGCTGGGCCCCCTCAGCCTCCG |
| 60 | chr21:<br>43446600-<br>43447600 | CAGGTGCCGGCCACCACCCGGCTAATTTTGTGTTTTTAGTGAGACAGGGTTTCGCCATGTTGGCCGGGCTGGTCTCAAACTCCTG |
| | | ACCTCAGTGATCCACCCGCCTCGGCCTCCCAAAGTGCTGGGATTACAAGTGTGGATTACAAGTGTAAGCCACTGCGCCCGGCCAAGAGTGAAGTTCTGATA |
| | | GCTGGGTAAGAAAGGCCGTGGGAACAGGCCGGTTTCAGACACGCTGGGTTCAAGACACCTCGGCATCCAATGG |
| | | TAGGACGAAGTAGAGGATGGAAGCCAAGCACCGGAGCCAGCGCACAGGAAATAGGAACGTGATGAGCTCAACCGGCTGGTCAAGTG |
| | | CCGCGCATCCTGGAGCCAGTGGAGCCAGTGCCCGTGCCCGCCGCTGACAGCCGCCCGTGCCCCAGGAGGGCCGGGAGGCC |

TABLE 3-continued

Hypomethylated locus region sequences

| SEQ ID NO | GENE NAME | SEQUENCE |
|---|---|---|
| 61 | CRYAA | TGGAGCCGAGGGCCCCGCGTGGCAATGTGGAGAGACATTTGGTGGAGTCATGGGGCCACAGCCTGATTGTGAGAACAGGAAGGGA<br>AATTGCAGATGGGCCTGGGCCTGGCCTCCCGCATACTCCAGGACCTGGGCCTGAGTCATCGTTCACCGTGTGACCAGGGCCCCGT<br>GTGGCCGGCTGTCACTCGGTATCCAGTTACCCTGGGCAGACCACTGGCCGCACCCCAGCCAGAGGCCCAGAGACCAACACACGCCT<br>GCAGGCGACCAGGCCGGACTGCATGCCCCGTGGGGAACTGAGGGCGTTTCAGTAACAGAGTGTTAGGGACACGGGTTGGGTGGCT<br>TGGAAAGGGCCTAAGGTGGGTTGTTTTAGATTGGGGTGGTGAGGGCCGAGGCCTAGGATTCTTCAACAGGGCAGCAGCCAC<br>TCATTTAGCAACAGGAGGAGGCGCTCCAGCGTTTCGTGGCT<br>ACCCAACCACAGGCCTCCTTCTCGACGGGTCGAGCCGGTGAGCCGGTGAGCCGGTTCTGCTGTTTCTGAGGGCCTGAGTCCACCCAGCACCTCAT<br>AAACAGGGTCCTCCCCAGGCTGCTGCAGCGGCATCAACGACCCAGGCCTCAAAATGCCTCAGAGGCCCAAGGCTGAGCCAGGGAGT<br>GAGAAGGAGCATGTGGAAGTGCGTTTTGGAGAGGCAGCTCCAGCCAGGCTCCGGCCGCTTCTATAGACACGATGACACC<br>AAGGGCAGTGACCTCATTCCACAGGCTGAGTCCAGCCAGCCAGCCAAGCATCACCAGCCAGACGATTGACCCTAACGACCAACCAAC<br>CCGTAACGACCCCCTCCTACCATAACCAGTAGCCAGCCAGCCCATAACCAGCCAACTTATCTATAACCAGCCACCTGACCATAGCCAAACA<br>ACCAGGCGACCAGTAGCATTCACCCCAGCTCAGCTGCCCTGAGCCTGAGGTGGAGACAGGTGGAGACATCTGTGTCTGTCCAGGAG<br>ACAGTCACAGGCCCCCAGAAAGCTCTGCCCCACTTGTGTGTGGGAGAAGAGGCCGGTCAGGTGACCGAAGCATCTCTGTTCTGATAACC<br>GGGACCCGCCCTGTCTCTGCCAACCCAGCAGGACGGACACTTCTCCCGGAGGACAGTCCTCACCGTGAAGGTGCAGGACACTTTGTGGAAGATCCG<br>CACGGAAAGCACAACGAGCGCCAGTAGCGCCAGGCACTTCGAGAGGTGGGAAGAGGTGGGAAGACAGGGGTCA<br>CGGCGGGCACGACCGGGCCTGCACACCTGCACATGCCTTCAACCTGGGAGAGAGGACGCTCTCCAGGGAATCAGGCTG<br>GCTTTTCCCAAGGAGGGGCCGTGCCCACCTGAGCCAGCCCCCGTGGACAGGTCACCATTCCGAGCTAATGTGGCT<br>CAGGGATCCAGGTTAGGGTCCCTTCCCCGGTGGCCCTCCAGTGTACATCTTCACATGAACCTACCTGAGAAGCCAGTCC<br>AAGAACCCCAGGAAGTGGGAGTGGCCCGGGTGCCCGTGAGCTTTACAGGCATGACATCTTCGCTCACAGCAGCACTTTTGAACAGTGTCTCATTAT<br>CCGACGGCATAGCTGCATCCCTCGTTGAATGTCTTACAGGCATTGACAATGTCCCGGTGCTCCAGCCTGCTGGGTCCAGCCAGTAGTACCGGGACCGGGAGCTTCTCCCCA<br>CAGTCACCCTTGGGGACAAGGGGGTCCTCAGCCTGCTGGGAGCCTCGGATCTCCGGTGTTGAGGGAGCCGGGACACTGGAGCCTGGTGA<br>CCTGCATCTCCTGCGAGCCCGGAGTCATGGAAGTCATGAGAGTCAAGATGCAAGTCAGGTGAGAAGGTGGTGTCGGGGGGTGAACG<br>GAAGGTGGAACTCTTAGCCAAAGTTCTGGTTTTCTTTGCCAGGATCCCGTAAAGCCCCAGTAGCCCAGCCTGGAACATGCTTCCTGAGC<br>CTGACCTCTCATGTGCTGCCCTCCCGCTGGGGCTGGAGGAGGCTCAGCCCAGGGAGCTGAGTCTGCGGTTAGGCGTCCAGGGACGTGGAA<br>TCCCAGCTCTTGGTCTTTGGCCACCCAATTAGGTAGGGCTGCGATTTTGCAGATTTGAGCGAGGACAGACATGATGGGGACACTGGCT<br>GCATGTGGCTCGTCTGACTGCTGGCCATTGGCGATTTGACGACGAGACAAAATGCATCATAAATCCAGGGGCTGGAAGGGACTGGAA<br>GAGGTGCGGCCTGCTCTGAATGATCCTGAGTGCCAGGTCCAGAGAAGCAGGGCATGAATCCATAAATCATAGCTGGCC<br>CGGCAAGTGCCACCAGGCCAGGCTGAGTCCCCGCAGGCTGCGCCCCTTCTGGGATCTCGGGGCCAGCTTCTCTGGCCATGGATGC<br>TGGCTGCACCCGGCCCCTGTGAGAGCCCCGACTGGCCCCCTCGACTGTGCGCCCTCTTGCGCCATGGGCATGCGGAGACAATTCCGCTCATTTTCCCGTGAGTTCCACC<br>GCCGCTACCGGGCCAACGTGAACCACCACGCCGAGCGAGCCATCCCGTGTCGCGGAGGAGAGCCACCTCCAGCTCCCCATGCATGGGCGCGCCTCCGGCCCTCCAACTCTGC<br>GATCCAGATGGCCTCGGATGCCACACCGCCGAGCGAGCCATCCCGTGTCGCGGAGGAGAGCCACCTCCAGCTCCCCATGCATGGGCGCGCCTCCGGCCCTCCAACTCTGC<br>AGCAGGCATTGCCTCGGCTTCCACCTTCTCCACATGGAATGAGGGTTTGAGGAGCAGCCAGCCTGAGAGCCTTAGGGTCTCAGGGTGTCCCAGACCCC<br>TCCCTTTTTCCTTTCCAGTGCTGCAGGCCGGCAGGCCGGCGGGGGTTCCCGGCCAGGTCCCTGGGGCTTCTGTGCACCTGCACACACCTCCAGCCTCGCGGCCTCCTCTTCTCAGCCGTCTTCCTCCAAACCC<br>TCCTGGGCGCGTGAGGCCGTCTTGGGACCCCGTGGGGAGCCCTCTTTGGGAGGACCTCGTCGGGGCCTGAGGGCTTCGTGCACCCATGAGGGGCCAGCCGGGGCGGCAATCAATAAACAGCAGGTGATACAAGCAACC<br>CGCCCTTGCTCTGCTGTGTCTCATCAGGGCGGCCAGGGCGTGACCTTCAGGCGGGTGACCTTCCTGAGGGCAAACAGGGAGG<br>GTTGGACCCGGTGGCCTCGAACGATGG |
| 62 | chr21: 43545000-43546000 | TTTTTGTGTTTTAGTAGAGATGGGATTTCACCATGTTGGCCAGGCTGGTCTCAAACTCCTGGCCTCATGCAATCCTCCGCCTCAGTAGT<br>AGTAGTTGGGATTACAAGGTTGAGCTGCCATGCCCAGCCAGCTGCAGGCGGTCAGGTGCGGAAGCTGGGGCTCCAGGCTGCCGGT<br>GAGGAGCGGGCATGGCCGGGAGAGCTCGGGAGAGCTTGACTTCGGCAGCGACTTCGAGCGGAGGGAGCTGAGGTGCTGGAGCGTGACCCTTCCTGAGGGCAAACAGGGAGG |

TABLE 3-continued

Hypomethylated locus region sequences

| SEQ ID NO | GENE NAME | SEQUENCE |
|---|---|---|
| | | GCCTTGGAGCCCGGCGCTCAGGACAGGCCCCTGCTGGCCCGGCAGCCTGAGCTTCCACACTTTTCCAGGGCGTCTCGAGTTCGCCCAC |
| | | AGAGCTGTTTGTTCAGGAGATAAAAAATGCCCTTGTATTCCACGTTCCAGTTCAGAGGCCCGTTCGTTCCCAAGAGCGGAGGCGTCAGCCG |
| | | CATGAGTCCCACCCGGAAGCCGGGTTGCCGGGTCCCCGTCCCCTGCCTGCCTGCCACGCATTCCGGAGCCCCTCGAGTTGCACACGCCTGCCTG |
| | | GCTCTCCCAGGCCTGCCTGCCTTCCGACGAGGGCTTCCGAGGCATGCTCATCCTACGTGACTGGCCCGAGTTGTGCACACGCCTGGCCGTG |
| | | TGTGGGCGTGCCTGGGGCCCGACTCAGGGACAGAACCAAGCCTGCGTGACCAAGCCAGTAGCAGCTTGTCGAAACAAGCTGCGTCAATG |
| | | CAGGCAAGCTGAACAGCACAGGGCTGCTTTTTCAGCCTGACAACCCTGGAACCTTGGAACCTTGGAACTCGGAGGGCTGGGAGGAGCAAGGGGCCGTTCCCT |
| | | GCCCACACAGCACAGCACACGACACCCCTCAGCCACCAGATTCGGGGCTGCTGGACTTGTTCTCAAACCTGCACAGTGAGTGACGTGCTGAGA |
| | | CGGAGGTCTCAGGACGTCAGGTGAATCAGCAT |
| 63 | chr21: 43606000- 43606500 | TCCTTATTTTTAGTTCTCAAGCCCTGTAGGGTGTTTTCGGTCGCAGTTGTTTGGGCTGCAGTTCTGCAGTTGTTTGGCAGTTCTGACCCTCCTGAGTTCCAGTGGCTCT |
| | | GTTCAGGAGAGCTGCCTGGGGCCTGCGGACTTTCTGAAACACACTGAGCCACACTGTACATATAAAATAACTTGTAGCCGAGAACAGGATGGGGCGGG |
| | | TTGTGTCGATGTCAGATAGGGCCGTTGCACGTTCAGATGACCTCAGTGACACTTGTACATATAAAATAACTTGTAGCCGAGAACAGGATGGGGCGGG |
| | | GAGGAGGGGAGGCAGAACTACCACAGCAGACAGAAGTCACTGTGATGCGTTCAGCTTTCATCACTGGAGGGTTTTTAAACCTAGCCCTG |
| | | CCGAGCAGCCCTCTCCTGGTCCGGAGAACGATGGGAGAGAGCTGGCGTTCAGCTTTCATCACTGGAGGCCGTTCTCTTCTTCCGGCCG |
| | | CCCGAGGGGCCTGTCCATGATCCATCACTTGTCTTGTTTCCGGGGTGGCCTCGTGAC |
| 64 | HSF28P | GGAACGGAGAGCCGCCAGGCCCAAACCTCCCAGAATTGCGCAGTATTCTCGGCTAGAGAGCGAGGAGTGGCCTTGGCAGGTCCCT |
| | | CTTTGGCTCTTCTGGCTTAGCCGGGGTTTTAAACTTGTTATCTGCAAAGCAGAAGGAAAAGTCAGCCCCTGATGTAAGTGTCAAGTAAAATA |
| | | AATCGGATGGGTCCTTTCCTGTTTGGCGAGGAAATGCGCGTTCAAATGGGACTGCGTTCAAATGGGCAGTCTTTGCTGGAAACCTCGCCT |
| | | CCGCCGCCCTTCCCTCCGATTCAGGCGCTTTCAGGCGTTTAAGGGTTGAGTGACCTAGTCATTAACTTGCCCACAGGCACCTCGGGAGGTCGCCTAGAC |
| | | AACTGAGCGGAGCAACTGAGATAACCCCCCCTACTGTGAGTGACCTAGTCATTAACTTGCCCAGCACGCCCCTGAGTCCCAACTCCC |
| | | ATATAGGATGCGCGTGCTCGGGTTTAGATGAACCCAAAGCTAAGATTCTTTCCCTCTGGAATTAGCAAGCAGGCTCCGGGTAGGGCGCACC |
| | | CTGAAGCGCCGTGCTCCGCCAAGCCTGCGCCAGGCCTCGGAGCCCTCCCAGGGCTCCAACAGGCCCAGGGTCCGGCCTTTCCTTCCAGTCTC |
| | | GATCTGCCCAAGCCTCTGCAGGCCCGGGGCCTGCCACAGTTAAAAACTCCACCCACCGAGATCGCAGGTAAGCTGCTGGCTCAACGAGGGTGCT |
| | | AAATGGGATTAAAGATCTGACCCTGGCCAGCTTGGGCGTCGAGACTGGGAGAATCCACATAGCGAGGAGATCGATCGAGTCTGGAGGTCGAGCCAGGATCA |
| | | TGCTTGAGCCCAGGAGTTTCAGCTACTTGGGCCGTCAAGTCCTAAGTCCTAACCCTGGCTCAAGATCCAGTCAGCACCCTGAATTTGCAACCGAAAGCAGCGCCG |
| | | CGCCAAGATGCGCACTGCATTCCAGCCTGGGCACATGGGAGCAGGAGACCCTGTCTCAAAAACAACCTGAATTTTGCAACCGAAAGCAGCGCCG |
| | | ACAGCCTTCCGCTCTCTCTGGTCAAGTCCGCCGCTCAAGCCTGCCAGGGCCACTGCCGCGCTCACT |
| | | GCGCCACGTGCACACGGGCTGGGCCTGCCAGGGCCACTGCCGCGCTCACT |
| 65 | chr21: 44446500- 44447500 | CACAGCCCAGCTTCAAGCCTGGCCGCCACCAGTCTGGCATGAAGACCCCCGGCAGGGCTGGCGTGTCTGGAATCCACCCGAAGT |
| | | TTCCTGCCCCTTGGGCTGCCCACCAGTTCCCTTTCTGCTCTGATCAAGCTGGACAAAACGTCGTGGGGCCACACCAGGGGCCAA |
| | | CGCAAGCTGGGATGCTAGACGTTAGGAAATCCAAGGAAGAAGGGACACATTCGGAGACGTCGGACACGTCGAAGCA |
| | | GCGGACAGGCACCCTCTGTGGACAAGGCACTGGCGCGGCAGATTCCGAGATTCCTTCTCCACAGACCTCCACGTGTGG |
| | | CTGCCAGTCCAGTCCGGGTCCCCCTACCCTGTCTGCCTTGCTGCGGGTCCCTTCACGGCGTGACCAGAGGCGTTCGGAGGGTTGGGTG |
| | | GCCAAGGGTCGAGCTGACCACCACGCGCCAAGACGCCCTCTCCCAGCCCAGCCCCAGGAAGGCGTGAAACAACCTCTGTTCTCTCCGTTG |
| | | ACTCTCACGACTGACTCCAGGAGATGATGCAACACACATCCTGTTGGAGCCCAGAAGTGCGGATGCAGCCGCGGATGCAGACATACAGTAGAAGC |
| | | AAATCCGTTCTCCAGGAGATGATGCAACCTAAGGACAGACTTTGTTCTTGCCCTGTGCCCTGTGGGCCCTGTGGACCATACAGTAGGTG |
| | | CTCAGTAAATGCTTGCAGGCCGATCGCCAGACCTTAGCCCTCATCATGTGAGCTCGGCAGCGTCGGCAGACATACAGTAGGTG |
| | | AGGTTGCGTGGGGGCGTGCTGCTTGGTCTGTTCGTGGCGGACACCGGAAGCGCCCATCAGTGCGTCAGAGTGCA |
| | | AACTCGGAGCGTCCTTCTCTGGAAAACGAAT |

TABLE 3-continued

Hypomethylated locus region sequences

| SEQ ID NO | GENE NAME | SEQUENCE |
|---|---|---|
| 66 | TRPM2 | GGGAGGGGGCGTGGCCAGCAGGCAGCTGGTGGGCTGAGCCAGGGCGATCCGACCCCGAACCCGAGCTTTGAGTCCC<br>TGTACTCAGAGGTCTCCTGCAGCCGGAGTCCCACTGTCGTGTCCCTGGCAGCCAGCACCCCAGCTTCTCCGTCAAGGTT<br>GAGGACGGAGCACTCCTGCCTCTGATTAACTGCAGGAGAAGCAGTTGCTTTAATCCGAGCCTTGAGTTGGACAGATAATGAGT<br>CATTCAACCAGATTTTCCAAGGACACCACTAACTTTGGTATGATGCGTGTGCCCTGAATCCACGTGGTCAGGAAAGCCAGGAACAC<br>TGGCCTGTGACTCACTGAGCAGGTTCCCTTGTTACCCCGAGGGTGATTTACTCCTCTGACAGTGACACGACACTGTGCGTCATTCC<br>CCGGGCGGCAGGACACTCCCAGATGCCCACAGAGGGGCCCAGCAAGCACTGGCCA |
| 67 | C21orf29 | CTGCAGGACCTGCTCGTTCACAGATGTTCTCTAGAAGCAGAAGCTGTTTCTTGTGCAAACAAATTGCTGTGTCCTGTCTTAGGAGTCT<br>CACCTGAATTTACCAAGGATGCATCTGTGCTTGGGGATGCCTCGGTTTGAGGGCTCTGAGGAGGCCGCTCCCTCTGATCCTTTCCTCCCC<br>AGGAGCCCACCTGCCAGTGTCAGCGTGCAGCCCCACATCTCAAGATGGAGAATGGAGTGAAGCCATGCAAGCCACGCAGGCGTCCTG<br>CTGACATGCAGGCCAGGCCGGCGGTGCCTCTGTATTCAGCAGCCTCAGGCTGTGGCCAGTTCAGGCAGCAGAGGGCCTCATCCCGGTG<br>CTTCCCTGCAGCAGTTGTGGCGCAGGGCCATGGGCCTTGGGAGGCAGGGGATCACAGAGGGTGTCCAGTG<br>ACAGGCAGGGCGGCAGAGCCCATGGGCCTTGGGCTCCGTGCCAGCCCGTCGCTGCCAGCTCAGGGTGACATCTGAGACGCCACCTCCATTAATG<br>GTGGGTTATGATTTGGTTCCATGCAGCCCGTCCAGCTGCTGGGAGGAGGACGAGGACGCCTGTGATC |
| 68 | ITGB2 | CAGGAACCACGGAGCCTGCTGCTAGCGGCCCTGTTCCACCCTTGGCCTGCGGCCCTGCCAAAATGTTTAGGCTTCATAAGGTTTGCCCAGGGTC<br>ACAAATTTAACTCACAGCAAACAATGAAATCAGCCATGATTTTCGAGCCCTGTGGTCTACCCTCCCTTCTCCTCTGCATGG<br>GCAGCAGCAGGGTGAGGAGCTGCTCTCCCACACTGGGAACCTGGGAACTCTGCGGCAGGCCCTCAGACGACCTGCCGGCCAGGGTACCCCCTGCCCCA<br>CACAGCGCTGACACAGAGCCCCCCACACTGGGAACGCTGGGGACACCCAAGCAGGGGCACCCCAAGCAGGGCAGCGCCTCACCGGGCACGGCGACCTGC<br>ATCATGGGCTTCAGCCACCCCAGCCTTCCGGGTGCATCCAGGTTTCCGGAAATCAGCTGCTTTCCGGAACTCGGTCTGAAACTGGTTGGAGTTGTT<br>GGTCAGCTTCACGAACGGTCTTGTCCACGAGCAAACGGGGCTGCCAGAGGACCCGAAGGACCTGCACTGTTTCGCAGCTTATCAGGGTGC<br>GTGTTCACGAACGGCAGCACGGTCTTGTCCACGAGGACCCGAAGCCCTGCAGGGCACATGGAGGGCTGG |
| 69 | POFUT2 | GCTGGGGAACTGAAGGAAGGGCTGTGGAGCCTGGAGCTCTGGGCCTGAAGCCTGGGACCTGGGCCAACCTGGGAGCCCTCATCCGGCAACCTGGGATCCTGCCGTGTCTCAT<br>CTCCACCTCCTGGACCCCCAGCTCATCCGGCAACCTCGGGAGCCCGGACAGTTGAGGAGCCCTCCTGCCGTGTCTCAT<br>GGGGCCCCCTCCAGGTCCTTGTGCCTCTCCACCGTCCCAGGTCGGACAGTGCCTGTGAGATCTGACCTCCCCGCCCACCCAAGTAGGAGAAA<br>CCCGGAGCATGAGCCCTCGTCTTCACCGTCCCGGGACAGGAGGCAGGGGGACAGCGCTGCGGGCTGACAGGCCAACGTGGCAGAA<br>GCTCCAGCTTCACAGGAAGCCAGTGACCATGACGATCGAGAGTCTGTAGCTGTAACGAAGCCACAGAGCTGTGCTTTCTTTCCCCTTCAGCTCTA<br>GGAAAGGTTATCTGCCGCACAGATCTCCGGAGGCCTGCCTGCTGCGCAGGCATCAGAGACGACATCAGACTGATTATCGTAAGAAAAATAATCTCTGC<br>AGACACATTCCTTGCTAGAGACAGGGGACAAAGCCCAGCTTCAAAGACAATTCCACACAGACACAATTCCACACACAGGAGCCTCA<br>GGGTGGAGCAGAGCCCCTTGCAGCCGCGGCTCAGCCGGGCTGAAGGACACAGCTGCCCCCCATTCCCGGGCCTCATCTCCACAGTGAGACGTGGAC<br>AAGGCACACCAACCCACCGTCTCTTTAGAACCTCCCCTCATCCGGCAGCAGTTCGGGCAGCCCAGGGCAGCCAGGGGAAACCCTGCCGAGT<br>GCCTCTGGGCCGCCACAGACCGCAGAGCCCTGGCCCTGACCCAGCCACCATCTGGGACCCAGGTTGCACGTCACGCCTGCAAAGCTCCTGCCCCACCCC<br>CCTGGGACAGGGGAGCCGGGGGTCGGTTGTAGACACCTTTGCAGGTCCTGGACCCAGCAGTCGCTCAGCCAGCAGGCCAGGTTATAGACCAGGT<br>CATGTGCCGGCCGCCGCCCCAGAACCCAGGAGCAGAGCCAAGGCTCGCCATGAGATCCTCCATGCTGGCGCGGCCGCAGGAGCCATCCTCGG<br>CCTCTGCAGGTCCTGCAGGTCCTCTGTGGGAAACCCGGGGGACACGTGGGGCCACTGTCCCGCGGGATCAGAGACGCTTCCACGGCTGTTGTCTCAGGCAGCGATGCC<br>CCACCTGGAACAGCCGAGGGCCGAGCCTTCCCACGGCTTCCACGCTGTTGTCTCAGGCAGCAGATGCC<br>TTCTTCGTTTCAATAGCTGTGGAAGAACCCTGGTCCTGAAAGAACCCAGATGCAGCAATGACAAGGCCTTCTGAGACTCTA<br>GAACCTTGCTGCCATCTCAGACAGGAAGGCCCGTGAGGACGGTTTCAGTCAAAGGACGGGCAGGTGGGCAGCTGC<br>ACACCCAGGGCCTCCACCGGCCCTCTTCCCGGTCTTCCCGGAGGCTGGCGCTCTGGTCATCACCCTGTCTGCCTCTCACTCTGTCCCACGCG<br>GCCAGGTCCCACCGGCCCTGAGCTCAACAGACCAAAAGCTGCCCCGACCCCCGACCCCTGGATAGACAAACTAAGGTCAAAAGCACCTTCTGCACACAGTGCACACACTG<br>CAGAAAAGTAAAAGATCATTTATTCATTCTGTTTCTAGATAGCAAAACACGTTCCCAAGGTTGAGCTGGTTCCGGAGCATGAGGAGCCGCTGAGGGCCCTGAGC<br>GCCAGGGTCCTGTTCCCCAAGGTTGAGCTGGTTGTTCCCGGACATGAGTCCCGGGTGATGAGGAGCCGCTGAGGGCCCTGAGC<br>TGCACGTGCTAATGATTAACGCCCCGTCTGCCCGTTTCTCAAATGCCTCTGACGATTGCGC |

TABLE 3-continued

Hypomethylated locus region sequences

| SEQ ID NO | GENE NAME | SEQUENCE |
|---|---|---|
| 70 | chr21: 45571500- 45573700 | GGCCTGAGGAGTCAAACGGTGCAAACCCTGCCCCACTCTGTTTGGGAAGCACCTGTCTGTGTGGCAGGACCTGCCTGTTGCTGGGGA<br>TAGACCATGGGAAGAAGACACAGAAGAAACCTGCCCTGCTCTCAAGGAACCAGGCCCTGGGGCGGCCAGGGCAGAGAGTCAGTCCAAGGCAGA<br>CACCCACACAGTGGCGTAATGACAGTGCTTATGCGGAGACTTGCCTGCACAGCAGGTCAGCAGCAGGTGTTCAGGTGACACTGGGG<br>GCACCGAGAGACCCCAGGGAGAGTGGATTGACAGGAGGACCTGGGCAATGTCCCGAGGCCTGAGGTGAGTTGCGGAGGAGGAG<br>GCTGCCGGGCAGAGGCGCAGAGAGCTTTGCAGTGTTGGCAGAGAGTTGGCAGATCTGAGAGCTGTGAGAGTCCAGGCTCCTCAGCTGGGA<br>GGGCCATAGAAGGATCTGGGCTGGCCAGGTCGGACATGCTGGTGCAGACTGGAGGCTGGTCAGGTCCACAGGCCTGGACCACC<br>CAGGGGAGTGGCCCAGGTGGGCTTGTGTTGCTCCTGTGGGCAGTGTGGCACAGTGCGGCAGCAGTGGCGGAATGAAGTGGGCGGGTT<br>GGTGTGAGGAGGTGTCTTCCCTTTGTTGGAACCGTGTGGTGCAAGCTGCCATTTGAGTTTGAGTTGCTCTGAGGGTCTGGCAGGGACA<br>CTGGGATGGGTTGGAGACCTTCCACCCAGGATGGAGTGAGTTTCCCAGGGACCCAGGTGGCTTGGCCTGAGAACAGCTCCACTCCCAGATGTGTGGGAA<br>CACAGGAATCACACAGGATGGAGTGAGTTTCCCAGGGACCCAGGTGGCTTGGCCTGAGAACAGCTCCACTCCCAGATGTGTGGGAA<br>GCCCTCGGCACCAAGCCTCAGCCTCTGCCATCTGTGAAATGGAGACAACGTCACTGGACTTGCAGCTGTCCATGAGGGTGATGCGATCA<br>GAAAGGGTGGAGTTCCTGAACGCCCCGGGGTTCCGAACCTGTCTAAACTGACACTGGCCCATGGGCGTGCCTCATGGAAGCTACCTG<br>TCCGAGCGCCCAGTCCTGCCACCTGTCTGCCACTGTCTGCAAGTCTGCACTGTGCCCAGAGGCCCTCAAGGCCCTCAAGCAGACAGCCCACACTCTCGGA<br>CGCCGCCCCAGCACGGTCCTTGTGTGAGGTGGACACTCCTTCTAGGGAAGGAGTAGTAACTCTTGGGTGGTCGGGTAGTTGCCAT<br>TGGACGCCGCCCAGTACGGTCCTTGTGTGAGGTGGACACTCCTTCTAGGGAAGGAGTAGTAACTCTTGGGTGGTCGGGTAGTTGCCAT<br>GGAAAGGGCAGTAATGCCCAGGTATTGCCGTGGCAACCTGAACTGACATGGCCACTGGAGGGCGTGCCTCATGAGAAAGCTACCTG<br>TGCCCCTGCCCCTGTGTTAGCTAGGCCTCAATGTGGTTCAGTATCTGAGACATGGCCTCAGAGATGTTCCCTCTGTCACCCCATTA<br>CCAGGGCGGCACTTCGGGTTCCTTTCGGGATAAACCAGGCACGTGGCCGCGCCACCATTTCCACCGCCCAGCGGTGGAGAGTTGCCAGCCT<br>ACCCAGGTCCTCACCTCTCGGGTTCCTTTCGGGATAAACCAGGCACGTGGCCGCGCCACCATTTCCACCGCCCAGCGGTGGAGAGTTGCCAGCCT<br>TGCAGGAAAACAGCTCTCATGCCAGCAGGACATCCTATTCAAGTTTTCAGGGCTGCCAGCACAAATGCTCATGCCGGGCGCT<br>TCCTCAGCAGACCGTTGTTTCTCTGCGTCTCCCTGGGTCTCCGCAGGGCTGACGTGCCAGTCCCGTGTGCAGCCCGTTCCTCCCGAGCCTC<br>CTTGGCTTGTGGGCGGCGTTCTCCTTCCTCTGCCCTAAGGACTGAATTTTACCTTAACCTCTTAAAAGCTGTCTCCAAATACAGTCACCTTCTGGGG<br>GGCAGACTGGATCAGGGCCTGCCTGAACAGGGGTGCCTGAATTTTGGGCGACTGGATTTGGGCAGAGTCGCAGCCCCATCCTCCAGCCTGCCTTGCCTTTACCATGGGG<br>TCCTGGCTGTTAGGGCTTTGATGCATGGATTTGGGCGACTGGATTTGGGCAGAGTCGTCGTGGCCAGGCGACCCCTCAGCCTGCTCCAGCCGACCTGCTT<br>CTGACCCAGCCCTGCAGGAGTCCCCTGGTTTGATGTCTGCTGTGCCACGGCGACCCTCAGCCTGCTCCAGCCGACCACTGTGCTT |
| 71 | chr21: 46090000- 46106600 | GGGGAGTCTCCAGGGGCTGGGGCTGGAGCCGCATCAGAGAGGAGAAAGGGGTGTTTGAAAAGGGCAGGGCCTGGGACCCAGGAAACT<br>GTTCTTCCAGAGACACCCCGTGAAGCTGAAGCTGAGCTTTGCCTTCAGGGAAGCTGAGGCTGACCCCACGGGTGCTGCCCAGAGATGGGCCAGGT<br>GGAGCCAAGATGGACTGGAATTCCCGACGGGACAGGGCCTTGGGAGGGGACAAGAGGCAAGGCGTGGGCCTCAGCCCTGCACTCCCAGGAGAA<br>TTTCTCCTGAAAAACAGAGGCAGTGATCCCGGCCAGTCAATTCCAGCAGACTCTCAGCAGACTGCCTTGCCCTCGTCTGATGAATGGTCAGGTTTGCTT<br>AAGAGCAGATGGGACTCGCCAGCATCCTCACGGACAGGGCCCGGTCATTGCCCCTGCCCCTCGAGTTGGGACCGGATGTGAGAATGAGGCTGTGGGCGGG<br>CAGATACGCAATGCTGCCATGCCGATTTCTGCGCCCCGATTTCGCGCCCCCGATTTCTGGGCCAGGTGGCCAGGTTGGGCCAGGTCGGGCCATAGGGG<br>GCTCCTTCAAGCCCGTCCCTCCCTGTCAAACCCGAGGAGCTCAAACCCAGGAGCTCACCGGGCCATAGTGAGCGGCCATAGTGCCGGCCA<br>AGCCAGCGTCACCGGGCCATAGTGAGCGGCCAAGTGCGGCCATAGTGAGCGGCCAAGCCGCCAAGCCAGCGCCAGCCAGCTGAGCCAGCCATCAGCCCATAGT<br>GAGCCGCCAAGCCAGTGTCACCGGGCCATAGTGAGCGGCCAAGTTGGCAGCCCTTGGGAGGGGAGAAGAGGCAAGGCGTGGGCCACCAGAAGGATTTCTGGGTC<br>CCCAGTTCCTGGAGGAGCACACAGTTTACACCAGGCCTTGGGAGGGGAGAAGAGGCAAGGCGTGGGCCAGCCCGCACTCCCCAGGAGAA<br>ACCCTGTTTTGACGGAGAATGGACTGGAATTCCCAGGGCGGCGGGATCCTGGAGAGAGAAAACCGGAATTCATCCACGAGAGGC<br>GTTCACCCAGAGGAGAGACCCCGAGCTTCTCCAGGAGGCTGGATTGCTCCAACAGGGCCCTGAGGAGCTGATGGCAAGAGCGGAAG<br>GCAGCTCTGACTCGTGCCTCTGACTCCAGGAGTGCCACCGTTGGGCGTACAGTGGACCAGCCCTGCTGTTGTCACTGAACCCACAAAGCCT<br>GCAGCTCGGGACGGCGGCGGCTTTTCAGTTCCTTTTATCTTGAATAGCCCTTTGGGGAGATTTTGGGGGAGCCAGAACATCTGAGTTCAAAGCCCAGGAGAG<br>TGTGGGAACCTGACATTTTATCCCTCACCTCACGTCAGAAATCAGGGTTCCAGGCCCTTGGTTTTTCTTGGCCCAGCGCGTTGGCCATGAGCCCGGCGCTGGCACCCATGACCCTGTGTCTTCTATG<br>ACATCAGGAGTTTTATCCCTCACCTCACGTCAGAAATCAGGGTTCCAGGCCCTGTAATCCCAGCACTTTGGAAGGCCAAGGCGGGTGATCACGAGGTCAGGAGTTCGA<br>GACCAGCGCAACATGGCAA |

TABLE 3-continued

Hypomethylated locus region sequences

| SEQ ID NO | GENE NAME | SEQUENCE |
|---|---|---|
| 72 | COL18A1 | GCTCCTCAGGGGAGTTCGGGGCCTTTGTCTCTGGACTTGGGCAGCAGAAAGGAAACATCCCTGGGGGCCTGTGGTGACCCCATC
CTCCCAGGGTGGTCTGGCAGGGACACTGTTTTCAAAGCAAAGCCAGAGGCTCTCGGATTCACGAGATCCACATTTAT
CCAAGTTAGAACAGCACATTCGTGCTGCAAACTTCATTCTGACTTCGGCCGCTGTCCTTCTTGCCCAAAGCACCGTGAGGCCTCATC
CCTGCATCCCTGTTGCTTCTTTCATGTGGATGAGAACCCAGGAAGGGCTGAGTGTGACTCCTCTGGTTTTAGAGAGCACTGCCCCC
GCCCGCTCCCCTCTGCTTCCCCACCTTTCACAGTTGCGTGTGGGGCTGAAGTAAGTGAATTGACAGCATTAGTTGAGTGACTTTGAG
TTACTTTTTTTCTTTTTTGAGACAGAGTCTCGCTCTGTCGCCCAGGCTGGAGTCGCAGTGGTGTAATCTTGGCTCACTGCAACCTCTACCT
CCCGGGTTCAAGCGATTCTCACATCTCAGCCTCTCCGAGTAGCTGGAATTACAGGCGCCCACCACACCGGCCTGGCTAATTTTGTGTTTTT
AGTAGAGATGGGGTTTCAGCCATGTTGGCCAGGCTGGTCTCGAACTCCTGACCTCAGGTGATCCGCCTGCCTTGGCCTCCAAAGTGCTG
GGATTACAGGTGTGAGCCACCAGGCCTGGCCTGGAGTTATTTGGAGAGGCAGTTCAGCGTGGCGAGGCTGCGCTGCT
CTCCGGGCGGGCGTCCACACCTCCTCGCCGAGATGGAGAAGCCAAAACCCTGCAGCCTCCCCCATCACGTCGGCCCTGGAAG
CCCCGCGGAAACCTGCCACGCCCTGAGTGGGACAGCGCAGGTCCCTTCGGCCCTGAAGCCCCCAGAAACCCTGGGTGCAGGC
CTGCTCCGGACAGGTTGGGAGCTTGGCTGCATCCTCCGACACCGGACTCAGCCTTCCGCCACGTGCTCCGATTGCCA
CTTCGTCGAGGTTGGGGCAGCTTGGCTGCATCCTCCGACACCGGCGTGTAGGGCCTGTGACTCACTGAGTATATCTGACTGTTAATGGC
AGCCACGCTGGGGGCTGGGCCAGTTTCTGTCCTCCAGTGCCATATCCAGCCCTTTCTCCTCGGGGAATCTTAAGGCTG
AATCACAGTGCACCTCCCCCTGCTCTCCAGTGAGCCCCTAGTAACTACAGCAGTCCCTGAGGCTTCTGCTCCCCACCAGCCTCCAT
GCATTGAATCAGGAGGCCAGATGTGGCCCACAGCAGTGTCTGCCAGCAGTCCTGATGACTGCCTCCCATGGCCTGGTCCTGTTCTGT
GTTGCCTCCAGACTTCCCTTGACCCACCGGAGCCTTGCGGCACTGATCAAGACGCACCAGCTGTGCGCCCGCCATGCCTCCGCCAGGCAG
GCCCCCTCTTGCTCCCGCGGCCACCTGCTCTTGACTCTGCGGGTTGCCGGGTCTGTTGAGTCGCATGCTTGTCATGCTCGTGAGGG
GCGAATTCCAGGCTCTTGGCGCCTTTGCACAGACAACTGGTCTGCCGGCCAGAGCACCTGGTGCCATCAGCTGGTCCCATGCTGC
TGGCCAGTGCTCTGGGTGCCTTTGGGTCGACAGGCCAAGGGCGGACAAGGCAGGCGCAACGCGGGGCTCTGTGGCCCATCAGACTGGGCCATGAGC
CCTGGCCCTGGGTTGGGGTCAGGAGGTGCCCCAGCCCCCGGAGCTTCCTGACTGCCCCATCCTCTGTGGGGCCTGGCAGCTGAGTGTGCATC
TCAGGCTGCTAATGACAAGGACCAGCAGCGGAGACGAGGCTCTGCAGGCAGGCGGTCTGGGCCGCGTCTGAGAGTTTGAGGAGCGTGTGG
GGGAGATGTTGTCCCTGGCCGTCGGCCACCACCTCCTCATGAAGCCTTCCTGACTGCCCCATCCTCTGTGGGCCAGCTGAGTGTGCATC
CGCCGCGCCAAGGCCCGTCGGCCACACTCCTGCGCCTCCTGCAGGAACCCCGGGGCGTCTGGCCGCGTGGCCGCGTTCCTCCTATTCCCCTGCT
TTGAGTGCTGTGCCAGTTGGGGTCTGCAGGACGCAGCACCGGAACGCAGGCCCGCCTGTCAGGGACTCTCAGAGTTTGAGAGCGTGTGG
TGAGGGTGGCCTCGGGCCTCAAAGACGCAGCGTGTGACCAGCAGCGTGCCCAGGCGTGACCAGGGATGGGGTTCTGGGATCAGAGACTTCAGTAGCAGC
CACCCTCAGCTGACCCGCCGTCAGGGGTGACCAGCTGCATTTTCCATCTTTTGAAGACTGGAAACGATTGGATTCTTAACTTTTAAGTTGAGGT
CAGGACCGAGGCCACCCAGTTCCACCCTGGCCATTTTCCATCTTTTGAAGACTGGAAACGATTGGATTCTTAACTTTTAAGTTGAGGT
GAAATTCACAACCGCATAAATTAACCATCTTAAGCGAACAATTCGGTGACATTTAGTACAGCCAGAAGGCTGTGCAGCCATCACCACTG
CCCAACTCTAGAACCTTCACACGCCGAGAGAGGAGCCCTGACCCATCACGCCGGCCTCCAGACCTGAAGAACCTGCGAGTTCA
CTTTCCACCTCTGGATCGGCGGTTCATGCAGGTTCATGCAGCCCACAATTCATCCCTTTCATGGTGTGTAATAGTCCACCATAGATTCTCTACGTT
TCACGTTTCAGGTACGTGCTGGTGTTGTCAGAACGTCTCTGCACTCGAGATATACCCTGCTCTACTATAACCTGCCTCCAGTTCAACTGATTCTTTTGCCTC
GTTCTGTCTGTTTTCAGGCTGGAGTGCAGTGGTGACTGGACTCAGTAGGCGCGAATCCCGGCCTCGGCCTCCCAAATTGTTTTAGTAGAGATGGGTTCATCATGTTGG
AGCCTCCCGAGTAGCTGGGACTATAGGCGCCCACCCACCGCGCCCGGCCTAATTTTTGTATTTTTAGTAGAGATGGGTTCATCATGTTGG
CCAGGATGGTCTCGATCTTCCGACCTTGTGATCTGCCCGAGTCTCTCCCTGTCTCCTTTCCAAATTGTTCCCTGTCTCTTTTCCTTTGGAAAACATTTCAGCCAGG
GCTCCCCAAGTGAGAAAGCCCAGAGCTCCACGAGGTGCAGGATCGAGTCTGCCGTGCACAGCTGCAGAAGATGGCCTGGTATGGTGCTGTC
AGCGATGGCTGTGCAGGTCCCTGTGAGGAGGGGCAGTCCACAGCAGGCTCGGCTGCCAAGCAGAGAGGAGGAGTCAGCGACGTTGATTGGCAGTGCC
GCCATTCCATCATTCAGTCACCCAGTCTGCACCCAGCACCGGAGGCATCTTCTAGTTTTGAGTTCGAACATGGCCCAGGAAGCTCCACTTCCTGTC
TCCTCTTCTCCCCCTCCAGTTCATGATGGGGCTGGAGCTGGACTGCGGAGCTGGTGACTAATGAACATGCTCAGCATCCTCATGAGCAGGCG
GCAGGATCCCAGGACGGTGGAGCTGGAGCTGGACCCCCGTGACTGCCGGCCTGGCACCGTCAGCATCCTCTTCCAGGGCA
TGTGAAAGCCAGTGTGTCCTCAGCTGCCCAGTGCCAGTCAGTCCCCCATGCTCCACCCTCTGTACGGGACCTCGGGGCTCCCCAACCAA |

TABLE 3-continued

Hypomethylated locus region sequences

| SEQ ID NO | GENE NAME | SEQUENCE |
|---|---|---|
| | | GCCTGCCCGCCCTTGGTTCAGCAGAACGGCTTCCTGTCTCTACAGCGGTGCCAGGCCAGGAGTGCTGTGTCTGTGAAGCGGGGTCATGGT<br>TTTGGGGGCCCTCATCTCCCTGCGCCCCTCTCATTGGGGACCCCCTAGCCCTCTCCAGCGTTCTCTCGCCCTTCCACATGTGCTGTGTCT<br>GTGAAGCGGGGTCATGGTTTGGGGCCCCATCTCCCTAGCGCCCTTCTCGTTGGGGACCCCCGTTCTCTCGCCCTCTCCCTAGCGCCCTTCTCCTGTTTGGGGACCCCCATCTCCCTAGCGCCCTTCTCCATGAA<br>GTGGGGTCATGTTTGGGGCCCCTCTCGCCCTTCTCTGAGCGTGAGACACAGCCTTTTCATAGGCTCACCCCTCTGTATGTGAAGTGGGGTCATGGTTTGGGGCCGCC<br>ATCTTTCTAGCGCCCTCACCCTGAATGCTCTGGGAGGACACAGCCTTTTCATAGGCTCACCCCTCTGTATGTGAAGTGGGGTCATGGTTTGGGGCCGCC<br>CGGTGCCCTCTGCTGCCTGCCTGCTTGGGCTGCTTGGGCTGCTAAGTCTCTGGAAGCCTGCTTCTGCTCACCCG<br>GAGGAGGACCGGGTGGCATCCACTCTGGCCAGGTTGACAGCGGTCACAAGGCTGATGAGC<br>GCGTGGGTGGCGCTAAGTCTCTGGAAGATGGAGATGTGGAGATGGGGCGTCAGTGCCCGGATGCAGGGCTCTCCGGCTGGTCTGGAGAA<br>CACCAAAGCAAGCTCCTTTGTAGGCAGGAGGCTGACTGCAAGGAGGCGTCAGTGCCCGGATGCAGGGCTCTCCGGCTGGTCTGGAGAA<br>AGCTCGGAGGCAAGGCGGATCAGAGACACTGTAGACAGGAACACCTGCAGCTCTGCGGCCCCCCATGCAGGGTCACCCCATGAGGCAGGGTC<br>GTAGAAAGACCTAGAAATAAGTCCCGGGGTGCCCTTTGCCTGTTGACGGGGGCCCGAGCAGGACTGTTCAGGCAGGCACTGGTCTC<br>TTGGCTTCCAGGTGTGTTGTTGCTGGTTTGAGCGTGGGGTCTGCTCTTGCCACAGCCATTCATTCATTAGCGGCTTAT<br>GGGCCAAGGACAGAGGGTCAGTGTTTGCAGAGACCTGGGTGAGGGCCCAGTGACCTCACCGAGACCTGCTGTCTGCAGGGCCAGTG<br>CTGGCTGCAGAGACCCGGCCAGGGGCGTGTGTGACGGCCCGGCGGCCCAGGGAGGGGCAGGACCGCGGCCGCCAGGGGAGGGGG<br>GCAGGCAGGAGCCCGGCCAGGCAGGAGCGCCCAGGGAGGTGGCGGCCCAGGGAGGACTCGGCGGCCAGGGTGGACTCATTCCTGAAGCC<br>ACCAGGCCGGCCCCTGGGGGTTCAGGGTGAGGGTCAGGGGGCTAGACCGGGCACCCCAAGGCCTAGACGACACCCCAAGACAATCCCAGCTGGCTCTCGCGCTCTCGGTGTCT<br>GCCATTTGAGACAATTGGGACACAGGCGGGGGTTACCAGCGGGGGGCTGCTCTCATTGCTCCATTCCCAGATGGTGGAGGCAGCCTGTTGG<br>CTCTCAGCTCCCGGTACCAGCGGGGGTTACCAGCGGGGGCTGCTCTCATTGCTCCATGTAAAGGGTGTCATAAGCTACTTTCCGGCCCATCCTA<br>TTTGCACTTGCTGCGCTGCGCCCCTCCACAGTGAGACCCTCCACAGTGTTCCAGTCTGCCGGTGCAGGGCCTGTAAAGGGTGTCATAAGCTACTTTCCGGCCCACTGCCTCTT<br>CCAGCACTTTAGAGCAGAGACCCGCCCTTGGGATGGGGACCTCTCAGGGATAAGGGGTGCAGGTCTGAAGGTCAGAGCTTGCAGATGCCGTTGCAGAGGCCTGG<br>GCCTTGGGCGGAGGCCACATTCCAGGGTCTCAGGTTCCTCAGGTTTAAATCAGGTGATATTTACCTACAGGCCTATGCAGGCCCTATGCAGGGCCATTTCATG<br>TGTGGGTGATGTGTCCATTGATTGCCTCGAGGGCCCACATTCCAGGTTGACACCAGGCTGACCACAGGCCTATGCAGGCCCTGTGCCACAGGGCCTGG<br>AGTGGGATGGACTGGGGGTCAGCTGGAGAACCCCCTGCAGGTTCCTAAATCAGGAATTAACTTAGCCCGCAGCAGCCTATGCCAGGCCTGG<br>TTTCATCACCCACTTTTTGGGTGAGAACCCCCTGCAGTCCTAAACATCTGCCGCATCTCAGAGCCTGTGCCTCAGTCAGACATCTGAAC<br>CATACTGCTGGGGTCAGAGCGCGGCAGGACAATGGC |
| 73 | COL18A1 | TGCCACCACCATCTTCAGGTAGAGCTTCTCTCCTTGCTGGGCGGGGCCCCTCTGGGGAAGCCTGCAGGACCCAGACAGCCA<br>AGGACTCTGCCCGCGCAGCCGCTCCCAGCCAGCAGCTCCAGCAGCCTTCAACGCCTGAGCTCGCCCACCGCCACTTCTGCACCCCTGGT<br>GATGGGCTCCCAAGCACGCGGGCTCCCAAGCTTGGGCTCCTCCTGCGCGCACCGCGCCAGGTCCAGTCACCACTTTA<br>ACCAGGACGGTGCTTCTGGGCCCCGTGGGTGCTAACTCTGTGGCCTCTAATAACTCTGCCTGTCGGGGCTGACC<br>CCGAGGCCCCCGCCCGGTCGTCGCCGGCGCCGGCGGTCCTGCAGTCCGCCACCGGCATCTCACGCTTCTGCCTGCCA<br>ACCACCTCCACCACGAGAGCCGGCGAGCAGTGCGCCCCATGCGGGCACGCAGCGTCTGCAGACCGCACTGCCACCCCTTC<br>CCCTGCCAGGATGCGTCTGCAGTGGCAGCCCGCCGTGCCGTGCCCCTGGCCCTGTGCCCTGCCCGACCCAGAGGATGGGTACT<br>GTGTGCTCATTGGGCCGGCTGTACAGGTTCCCCCACATCTACGTTCAGGAAGGCCGCGATCTCCCCGATCTCCCACGTTCAGGGGCCCGTGCCCTGCAGGAGGTGGAGAGCTGGGAG<br>GCTGACGTGAGCCTGGTGTCAGGTAACTGCCCCCACATCTACGTTCAGGAGCCGGTCACCTGGAGGCCCCGCGATCTCCCCGATCTCCCTGGGCCTGGGCCTGG<br>GAGGCGTCTCCATTTAGCCATTTTAGCCATTAGCCGGACCACCCCCAGGCACACCCCCAGGGAGCCGGAGGTCCTGACAGGAAGCCGGATACCCTGCATGCCCCGAGTCACAGAGGGAAACT<br>GAGGCGTGGGGCAGTGGGGCACTACCCCCAGGGAGCCGAGATTCCCGCTCAGGTGTGGGCTGCATCGACCTTGCTCCGGTCACTAAG |

TABLE 3-continued

Hypomethylated locus region sequences

| SEQ ID NO | GENE NAME | SEQUENCE |
|---|---|---|
| 74 | COL18A1 | CTGCACGGTTCGATCGCTTCTCTGGGAGCCCCAGCTGCTCGGGCCAAGGGTGCTGCCGCGTGGGCAGTCAGAGACCCTACCAGCG<br>TGGGACCAGGGAGGTCTGCAGGGCCCGTCCTGAGAGGGAGCCTTTCATGTCCCCCATCCTGAAGCACACAGCCTCCCTGCCA<br>CAGTGGGGCCGCTTCTGGGCCCAGGGGACGTTGCCCCATCACCGTGCCTGCCCTGCCCTTGTTGCTGGCTGGACAGTTGGGGGCAGGA<br>AGAGGAGGGAAAGGGGGACTCTTTAACCTCCTGGGGGCAGGGCAGCCCAGAAAGGACCCCAGCAGATCCCTCCTCTGTGTCCGGGA<br>GTAGACGGGGCCCC<br>GGGCTCCACAGCGGCCTGTCTCCTCACAGGGTTCAGCCCCAGTCTGTCTCTCACTCATTTGCTGATTCATTCTTCATTCAGCCAGTCAATA<br>GTCATGGCCCCCTCGTGTGCCGGGTGGCCATGGATATTGCCTGGGTAACACACAGCCTGGCCCTGTGGAGCAGACAGTGGGACAG<br>CCATTGGCACAGGGTGCAGGTGACAGTGACAGCTGGGTCCAGAGAGGGCCGTGGGCAAAGGTGCAGAATCAATAGGG<br>GCATCCGACTGGGGTGCAGGCCCTGGCTGGGATTTCTAGGGTGGAGGTCACCTCTGAGGGAGACAGAGCAAGGCCCTGGGAGAT<br>TAGAAGGTCGAAGGTCGCCGTGTTGAGGTCAGGGGCTCGTGGGGCCTGAAATTGGAGCCGCGGACAGAGAGGCAGGTCAGGGCACGTGGTAG<br>TGATTGCTGCGGCTTCTGACACGGCCTTGCCTACCCCAGGGACCCAGAGTGGGCCTGAGCAGAGGTGACCCTGCCTGCCAGTCAGAGCCCAGCCTCTC<br>CCACCCTTGCTGCTCCTACCCCCAGGGCAGCCCAGATGGGGAGGGGCACCCGGAGGGGTCCCCCGCACAGGCTCTCCACCTGCAGGAC<br>ACCCAGCCCAGAGGAGGACACAGATGGAGAGAGGGGACCCCCGTGTGAGCTGCAGCCCCCTGCCCCTGCCACGACAGCAGAACCCTACCCGGCGGAGCACCCCCACCACCGCG<br>CGGCCCTGGCGGGGCAGATGACATCTGGCCAGCCCCCTGCCTGGCCAGCAACCCTACCCGGCGGAGCACCCGGAGCCCCACCACAGCTCC<br>TACGTGCACCTGCGCCGGCCGACCCACAGCCTGGGTCCAGATGGCCTGCAAGTTCCAGCCGGTGAGTGCCCCCAAAG<br>TGGGCTTGGCTCCATCTAGCCCTCTCGGCAGCAGAAGAGGGCCCAGCCCTGCAGAGCTTGCCTCTGTGGGCCAAGCAGTGGTCAT<br>CATGGTGGGGGTCTGGCGGCTCAGGGCCACTCAGGAACCGGCTACCTCCGGTCTGGGCCAGCTGGGCCACCTGGGGGCTG<br>GAAAGTCCAGCCGCTGTCACATCCTTGAGGAACCCAGGCTGCTCCCCCTCAGTGTCACTTGCGCGCCCTGGCCCTCGGCCCTGC<br>CTCTGACCTGCCAGCGTATGGGGCTGCTGCCCCGGCCGGGGATGCCCGGGCCGGGGTGGTTGCGCCCCGGGCCAGCGTGGGCAGCGTGGGACACAGCCCGTGACGGCCCCC<br>TCTCCCCGACCCAGCTCCACCTGTTGCCCTCAACAGCCCCTTCCGGCACCTTCAAGGTGGGTCAGTTCCAGTCCAGTTGTCCAGTTCCAGTGCTTCCA<br>GCAGGCGCGGGCCGTGGGCTGGCCGGACCATGCTCAACCTCAAGGTGGGTCACCTTCAGTCCAGTCAGTTGCGCCCCCACTTGACCTCT<br>CGAGCCGCGCCATCGTCAACCCCAGCCCCCCCCTGACCCCCGGTGCCCCATCGCGGGGAGCTCCGCCTGTCAACTTGCCGCCATCCAT<br>GGGGTGAACTCCCAGCGGGGAGCTCCTCAACCTCCAGGCCTCAGGCCAGCCTCCAGCCCCCCAGTGCCCCTCAGGCCAGTGCCCATGCCCATGCTCAACACAG<br>GGGCAGGGCTCCGGGTGGGTCACACCCCCTGACCCCCGTGCCCCCGTGCCCCCATCGTCACACCCCTGACCCCCGTAGTGCCATGCGGGCTGGTGCCCCTGCCA<br>GTGATAGGGCTCACATACAAGCCTGAATCAGGAACCGTCCTTTTGGGCTCTAGTGCCATGCGGGCTGGTGCCCCTGCCA |
| 75 | chr21: 45885000-45887000 | GCCTGGAGTGTAGTCTCGCTGAAGGCCAGAGACCACACACTCCACCCAGACTCCCGATCTCCCTCCCCAGCAGGGGATGGAGGCCCT<br>GCCCCTGGAGTGCTGGTGTTATGTGGAAGGGCTGGGCTTCTCCAGGGCTCCTCAGGGCCTAAACATCTTGCAAGGTTTGACGTTAA<br>TTACTATTAGATTGCTTTCTGTGTTACTGTTTTCCCCACACTTAGCCACACTTGGAGCCTAATGTGAGCTACAGAAGGCCCTCGCCCCCTACCCCT<br>CCAGATGTCCAGCCCATGACAGCAAGGACAGGGAGACTTCCTGGGCTGGATCTGAACCTGAACATCATTCCAAGCAGATGATA<br>ACCTGCCTTCCAGATTTCCAAACCCACAGCAAGACACCCTGGAGTTATTATAAATGCGAGCCCCCTGGGTGCACTTCTGACGGACCAG<br>CACCCTGACGGCCATGAGAGGGTGAGACAGCCGCACCCCAGCCCGAGCTCAGGGAGGCAGGAAACTCTGACCTGAGGCGGCACCATGA<br>GGGACACGTCCAGGGCCAGCTGCAGGGATGAGATGTGCCCCGCCTGGAGCCCTGCCCGCAGGCAAACCCAGAAACCAGGCCGGATCAGC<br>GTGTGTCAAGAGCGTCAGGGCTGCTGCTCTTTTTCCACAGAGGTTGGCAGGAACTGCAAATAATAGAAAGTCTTTAGGGT<br>CTAACACGCTCAGAAAACATATCATTACTTTCTAATGACTAACTGTCTTTCAGCGTGCTTTCAGCTGACAGTGCTCTGCCAGAGGCCAGGCAGCCCCAGAGCCCAGCCCCAGCT<br>CTCCCGACAGCGGGGAGGCTGGCAGCCTGGCAGCCTGTAATCTGGGGGCGCTGACAGTGCTGCTGCCAGACCCTCGCGCAGCCTTCCCTCTCTCCT<br>TTTCTAAAAACAGAGTCTCACGAATGTTCCACGGGTCTCCATGCGGGTCCAAGCGATCCTTCTGCCTCCATGGCTCCTCCCAAAGCGTT<br>GGGATTAAGGGCGCAGCCACCGCGCCCGGCCTCCCCTTCCTCATTCTCATTCTCCCCGAAACCGCCAAGCGCTCCAAAGCACGGGTTCGCCAA<br>TCCACCAGGCTGCAGGCCTTGCCTCCCACTCCACATTCCTTTCCCGCCGACTCAGCCTCAGCCTCGCGACGGCCCCTCGCCAGCCAGG<br>CTTTTTTTTTTTTCCTCATTTTAAGGTTTGCTTTAAGGTGTTCTTTAAGGACACAAGCGACACATTTGAGACAAAAGGACACATCCTTCCTGACCCAC<br>CTCCAACCCCCAGCTGACGGCCGCCCAGCCCGAGCCTGCCTAGACGCTGGGCTGGACGTTCCCTCCCATCCCGAACCCCTGT |

TABLE 3-continued

Hypomethylated locus region sequences

| SEQ ID NO | GENE NAME | SEQUENCE |
|---|---|---|
| | | CCCCGCCGCTCCGGGGGTGCTCGGGGGCCGGTGGGGTCTGTGACTGCCTCGAGGCTGCATCCGGTGACCCGGCAGCCC |
| | | CTGGCCTCCGCGGAGGCGGGCGGGCCGGACCCCAGGCTTTCCGGCTCAGCCCTGCAGCTGCTGCCGCCCAGCTCCCA |
| | | TGTCTGAGGTCTCGGCGGCGGGCGAGGACGTTTCTCCGGCTCAGCCCCTCCTGCCTCTGCCGCCCCACCCAGCTCCCA |
| | | CGGACGCCAAGAGGCCTTCCCACCCGGCGAGGACTCCCCGGGCCCAGGCGGGGCCAGCCTGCCGCTCAGCTGCGGAGGACGCGCCTCG |
| | | GCCCAGCCGCCTGTCTCGGGGCGCCTCGCTGCCCCAGCCGCGGGGCGCCTGCAGCGCCGCAGAGAAAACGCCCGG |
| | | GCGGGGACGCACAGCGAGGCGGGCTTCCGCGGGAAGTACCCGGGAAAACGCGCGAGCGGAACAG |
| 76 | PCBP3 | TGGAGCAATCCCAGAGAGGTGTTCAGGCTGGGTGGCCCCAGATGCACACGAGAGCTGTTCAGAAGCCAGTCCTCACACC |
| | | CTCTCCCTGCCAGAGGCTCCAGCACCTGTCTGGCCCTCCCTCCCTCCCCTGTGGTCTCTGTCCCTCACCCCACCCCGTCTGC |
| | | ATGTGCACCCGTCACCGGAGATGCGTCTACTAGGGCCGGAGTCGGGGACAGTGCTCAGAAGGACACAGGAAAGAGGAATCC |
| | | CATAACAGAACATTATCCGGCAGGAGTAATTAACAGGAGGACTGGAGGCTTTGTTTTTGTTTTTGCTTAAAAACAGTGGTATTTAAATT |
| | | AATGGCATGGAAGACTATTCAGTGAAGACATCGGTCATTGAGGTATCTATTCAAAACACCGTTAGTACTCTGCCACACCGAAC |
| | | GCAACGCCACAGCAGCCATAGAAGCGGTTGTTTAACGTGGTCTTTTTGGGAGGCATCCTAGGCAGGCAGGCGTGAAGG |
| | | GAAGGCGCGGACGAACAAAACGCGGGCACACGGGCCAACGGCTGCTGCCGGATCTGAGGCCAGCCTGTGGGAGCAGCAACAT |
| | | CGCTCGAGGACAGCGATGAGCCCCCACGATGTAGTCACCAGCATACAGGACCTGACACGGGGCTGCGGGCAGGGTGTGCCGGTACGGGT |
| | | ACGGATGACCCGAAAGACTTCCCAGTGACGGAGTGCGGCCGTCACCCACCGGAGGGTGCGGCCGTGAAGGTTATACATGCAAATATCTTCCA |
| | | CCAGCCAGTTCTCTTCCAGGAAGTGCTCTTCCTTGTGTTGTGCACAGACATGGTCCAGTGTTTGCGACGTGATTGTTATCAG |
| | | AGAGAGAAGGACAGCAGTCTCCAGGCTCGTAGCTGCAGAAGACTCGCCCTCCGAGGCTGCGCCCATCGTGGAGACGATAGTGTCTCTCAT |
| | | GGCACAGGACAGCAAGTCCCAGCCAGAGAGGGCCAGCCGGACCAGGCTCCACCGGGAATTCTGCTCTGTGTGTAAGAGGAAGAGCGATAG |
| | | CTTCAGCCTGGGCGGCCATTTCTGCGGGCATTTCTGCAGCCTGTCCTGGCCAGCACCTTCCAGACATTGTCCACAT |
| | | CCCCGTTGCACGTCCCCCCTCACCGGAAACTGCAGCCCACCCTCGGGAAGAACACTGGGAAGAAGCCAGGCGTTAGGACGGGTGGCCG |
| | | AGACAGGGAAGGAGCCATGGCGGACGTCTCGGTGACACTTCTTTCAGATCCTCCGCCACAGCAAAGCTTCACTTCTTCCAGGACCGTG |
| | | GGGTTTGGCTTTGGGACGGCTTTTGGGACGTCGGGCCGCCACCCTCTCCCTCCCCCGGTGTACTGACAGGAGCCCCGCAGGACGTG |
| | | CTAAGAACAAATTCAACAATTCAGACGCCCCTGGCCTGAGCTTTATTTATGGGTTCGTGAAGTTTATTCTGCGGTATTTAGGTGTGTTATGAATAA |
| | | AGGTGTGCGTTCTGCCAAGTAGAAATACAGAGCTTGTCTTTCAGCCAGGCTGATGGAGGTTGTGGAGATTAACAGGCCGTCAGCGGATTGAAGCTGCG |
| | | AACAAACCAAACCATTAAACATGAATTAGATGAGGCAGGGTCAGGCTGTAATCCGGGAGCATCTGGCTGGGACAGTGGGACAGCGTCTGGCTG |
| | | CACATCGCTGGGATGCTGCTGCGGAGGATTCGGTCTACTTCTTCCGCCTGGGCCATCTGAGCCCCTGTCTGACCCACCCTGGGG |
| | | CTTGAAGGTATGAAGGTTGTGGCCTTTGCTTCCCCCATCAGTCTCTTGGGGTGACCGCGTCTCGTCCTGTCTCTCGCCTGCAGGTGG |
| | | TCATCTTCAGCTCCCTGGGACTGCAGTCGACAGTAGCTGCAGGGTGCAGCTCCGCCCGCTCTCACGTGACCGAGTCAGCAGACCCTGGCAGGTGG |
| | | CTGCTCCCTGGACTGCAACATGGCATGTGGGCTGCAGCCCTGCAGGACGCGTCAGTGCAGCTGTCAGTGCAGCTCCGTCCGTCCCCACCCCTCCA |
| | | TCATGCTGTCAACATGCATGTGGGCTGCAGCCCTGCAGGACGCGTCAGTGCAGCTCCGTCCGTCCCCACCCCTCCAGTGCCAGG |
| 77 | PCBP3 | ATCTTGTCTTCCTTGTCCCAGTCCTGGAACCAGCCACTGCCCCAGCAGCTCCTGTGTGTGGCATGTTCTGAAGCCAGGATGCATG |
| | | GTGCTCCTGGGCTGCTGTGGGCTTGGGCTGTGGGCTTCCGGAGCTGCTGTGGGTCCCCAGTGCTCAGCCCCTGCAGATCTCCTTC |
| | | CATGTTCAGCTCCTCTATATGGAACCCCAGTTCAGCCCCAGCAGGACACAGGGTCCCCAGGTGTCACCCAGGTGTGCACCACGAGGA |
| | | ATCCAACTGCCAGTATCTGTCGTGCCTCCCGCCGGTGGCCTCCCCCCATCAGGCTCAGCCTCAGCTGCCACAGCACTGGCACACATCC |
| | | TAGATTTCCGGAAGACACGGCCTCCTCCCCCGAAGGTGGTGGTGGTGCCCACACCAGGCATTCATTCCTGCAGTGGAGAGACAGAGG |

TABLE 3-continued

Hypomethylated locus region sequences

| SEQ ID NO | GENE NAME | SEQUENCE |
|---|---|---|
| | | GACCTGCCTCTCCAACTGTGGGTGTCAGGAGCCAAGGCGCATGGTAAATGGGCTCTCTGTGAGGCCAGTGCAGGCCCCATCTCCA |
| | | GCAGCAGGCGGCCATGCCACCCAGCTGCACTCTGTGTGGGAGGTGCCATGATTGACGGGGCCCCTCCCTGTCCAGTGTCCTCCTCC |
| | | CCTCTGCACACCGGCCCCTGCACACCGTCCTCCTCACAGTCCTCTGCACCGTCCTCACAGCCTCCCTCTGCACACCATCTCATGGTCTC |
| | | CATCCTCATGTCTCCCTCTCCTCCTCCACAGACCCTCTGTCTGCACCATCCTCAGCCTCCCTCGTCTGACAGGGCCCTCCCTTCTCCTCCTCCTCCACCGTCCTCCTCCACACCGCCTCTCCACCGTCCTCACACACTG |
| | | TCCTCCAGCCTCCCTGCCCCCTCTGACACACCGTCCTCCTCCACGCCATCCTCACAGCCTCCCTCTGCACCGCCGTCTCACGGCCTCCCTCTG |
| | | CCTCCACGGGCCCCTCCCTCTGCACACCGCCGTCCTCACGGCCTCCCTCTGCACCGGCCATGCCGTCCATGCCTCCACGGCCTCCCTCTC |
| | | TCTCCACGGGCCCCTCCTCTGCACGGCCCCTCCTGCACGGCCCCTCCTCACGGCCCTCCTCACGGCCTCCCTCTTT |
| | | TTCCACAGACCCCTCTGCACGCCGTCCTGCCGTCCTCCTCCACGGGCCGTCCTCCTCACAGCCGTCCTCACAGCCTCACCGAGCT |
| | | CACCATTGCTGGCCCCCGCTTCAGGTGACAGGCCACAGTAGCACCTGGCACAGAACCTGGGCAGCATCTTCCAGCGTTCCTTTTAACAGGCT |
| | | CAGCCCAGCGGGGAACGTGTCCCGAATTGCACGAGCAATTGCAGTGCTAAGTTTCTTAAGTCACACAATTGAAGGAGGCTTTATTTTCACACATTTCTT |
| | | GCCGTTGGAATAGGAGTCACCAGCAATTGCAGTGCTAAGTTTCTTAAGTCACACAATTGAAGGAGGCTTTATTTTCACACATTTCTT |
| | | CCAGAGTTTCTGTGGTAGCCTGAGTCATGGTGATGCCCCCCCAGGTGTATTTATCAGGGCAGCCAGCTGCCTCCCCCGGGGCACTTAC |
| | | AGTCAGCCCATCTGTCTCTGGTCAGGTGGGCGCCAAGGAAGACCCGGCTCGGAAGGTTCCCTTCTGCACTCATACCGGGAGGTAGGCAGGTTT |
| | | CCCTCCCACCAGCAGATTCTGAATTCTCCCTTTCATGCACACCGGGAAGGTTCCCTTCTGCACTCATACCGGGAGGTAGGCAGGTTT |
| | | CGGTAGTGCCCTCCCAGTGTTTTTCCTCCTCTATGACATCATCTTTCTGTGATTTTTTCTTGCAGGAAGTTGAAGCATCA |
| | | TCGGGAAGGTAATTATTGATTGAATCTCCTCTCTGGGTCTGTGTTCCATGAAGACAGGACCCCAGAGTGTCGCCCCTCGCTTATGCTGTATG |
| | | GGCACCCAGTAGGTGCGCCTTTCCCAGTTGCGTGCGTGCTGAGGGAAGGGTTCACTCAGCTGCCTGGTTCATCAGCCTGTGTAGTCTGGTGTCTC |
| | | ACATTGAAGCTGGTCCTCCTGCCTCTGCGTGCCGTCTGAGGGGAAGGGTTCACTCAGCTGCCTGGTTCATCAGCCTGTGTAGTCTGGTGTCTC |
| | | GGTGCCAGTCCTTCTTCCCGTTGAAGACCCCAGAGAATGATTTCTTCAAATCCTTCCACGGGTCGCCGGCTGTGTAGTCTGGTGTCTC |
| | | CAGGAGTGCCAGTGGAGGGCAGCAGCCCCAGACAATTCCTTCTGTCTTCATCACATTTTCACCGCTTCGGGGAAGTAAGGCCCAGTTGGAAGCC |
| | | TGCTGCCCCGGAGGCCGAGCAGTGAGGGCCACCTGGGGGCCACCTGGGGGAAGGCCACCTGGGTGAAGCCCCGGGGGCCACCTGGGGCTAGGAAGCC |
| | | CCATGGGGCGCC |
| 78 | COL6A1 | GCTGACACCTCTGAGAGCTGGCCCTGAGGCTGAAGCCTGAAGCCCTGAGGGCCCCTGTGGACAAAGTCAAGTCTTCACCAAGGCTTCATC |
| | | GACAACCTGAGGGACCAGGTAGGAGGGACCGCCTCCTGCTTCCTCTGTGCTTCTTGGAGGGAGGGTGGGGCCCAGG |
| | | GGAACAGGGGTGCGACGGCCTCAACCTCCTCCAAGGTTGGGCGAGCGTTGCCCCTGACCGGCGTTCCTGAGCGTTCCTCCAGCCGCTTCCAGAGTCAGG |
| | | CCGGGGCCCTTTCCGGCGCCCTCCAGAGTGAGCTGGTCGTGAGGCCTGAGGATGAGGCCCCGCTGGGCGCAGCGCCCTTCCCAGAGTCCTCG |
| | | CGGGGCTGCCACCTGTTCAGAGGGCCGAGGTGACAGTGGACAGTAGGAGAGAAGAGGCTCCGAGGCGTCCGAGGCTCCGAGAGGG |
| | | CTCAGCGCACTGGCCTACCTGGGCTCCTGCCTCCTGCCTCGAGGGCCCCTCACTAACCACCTGACCTGAGCCGTCGCTCGAGGACCCAGG |
| | | TGAGAGCCTCTACTTGGGTCCTGATCCCACGTTCGAAGGTCCCGAGGTCAGGGAGGCAGGAGGGGGTCGCCTCGACCCGCCGAGAACCGGGGTGCAGGGGTCTCAGCCCCCAGGG |
| | | CCCCCAGGCTTGGTTCTGGTGGTGACACGGGCACCGGGCATGTAGAACGGGGCTCCCACTGAGACGGGTCTGGCA |
| | | AGAGGGGAGTGCAGTCAGCTTAGCCGGCGTAGGAACAGCCAGGGCATGTAGAACGGGGCTCCCACTGAGACGGGTCTGGCA |
| | | GTGGGGACACAGTCAGCTTAGCCGGCGTAGGAACAGCCAGGGTCGACCTTCCAGCCACCACGTGCCCAGCAGGGCCCATTGTACCAGGAACC |
| | | AGGGGGCACAGTCAGGCTCGACGGCCTCAACCTCCTAAAGTTGGGCGAGCGTTCCTGACCGCCGTTCCTGAGCGTTCCTCCAGGTGAGG |
| | | CGGGCCCTTAGGGACATGGCCAGGCCCGTGCCGGAGCCCTCTGGTTTGGGGGGCAGATGCAGCGGGGCTGCTCCGGGCCCGCG |
| | | TGGCCCAGGCCCCGGAGGCCCCCTTTGTTGCCCTTTGTGCCCTTTACTCAGTCTCCCCATGACTCAGTTCCACCCTGTGAAATGGGCGGAGTCATC |
| | | CCCATGTCGCTGGATTCCTGCAGGCCGAGACCCTCAGGCTCACTCTGGGTCACTCTCAGTTGGATGGAGGGGCAGGTCAGAGGTGGGCCAC |
| | | CCAGGCTGGGGCAGAGCAGACTGTCATGCTGGCTGCCCACTGCAGGCCCCCCAGCAGGCCAGCCCAGGCAGCGAGGGGGCTGCTCAGATCCCGGGGTG |
| | | GCCTGAGGATCGGGCCGCAGGCTGCCTGGCCACACCAGCCTGTCATCCAGGCAGACCACCTGGTGACGTGCGCCCCGGGCCGCCAGGCA |
| | | AGTCAGCTGTGTCAGCCACGGCTGGGGCCAGGTGGGGCAGGCAGCCTGTTCCTGGCAGGTATACCCGTGACCGGCCGCACACAAACCGTCTGGGTAGCGGGTAGCGGATGGCGCCCC |
| | | AGGGCGCCCCGCCTCACCGGCTGGGGCCAGGTGCCTGTTCCTGGCAGGTATACCCGTGACCGGCCGCACACAAAGCAGCGTGGCCCCAGCCTC |
| | | GCAGTACAGTGAGGTGGAGATCATCAAGGCCTACAATGCCCTATCACCGACTGCGCATGCCTTCACGCACGCCGCCGCCACTCAAAGCAGCGTGGCCCCAGCCTC |
| | | CAAGTACTTTGGGAAGGACATCGACGAGATCAAGAGGCAGCTGGACGCTCCTCGTGGGTGAGTGGCGCGCGCGCAGCGCT |
| | | CTGCCCACGCCAGTTCTCACGCGGTGTACCCAGCCTGGGCTGGCCTGGGCTTGGCCTGGGGCTGGGTTGGCCTGCGTGCGCGGCTCCAGCGCCTC |

TABLE 3-continued

Hypomethylated locus region sequences

| SEQ ID NO | GENE NAME | SEQUENCE |
|---|---|---|
| | | TCTCTTGGAGGCTGCACGGCCTCCCTGACCCACTTTGTGGGCAGGAAAGACAGAGACAGACAGAGAGACAGAGAAACAGG
GAGAAACAGACACAGAGAGACAGAGAGAGACAGAGAGTAGAGACAGAGACAGAGACAGAGACAGAAAGAGTGACAGAGGACCAA
GACAGGCAGAGCAGACAGAGACAAACAGAGAGACAGAGACCACAGAGAGACAGAGAGACCAGAGACAGAGACAGGCAGAC
AGAGACAGAGAGAGAGACAAACAGAGAGAGAGACAGAGAGACAGAGAGACAGAGAGAGACAAGAGACAGAGACAGACA
AACAGAGAGCAGAGACAGAAACAGAGGACAGAGAGAGACAGAGACAGAGAAAAGACACAGAGAGAGACAGAGATAGAAAA
GACAGAGGGCAGAGACAGACAGGCAGACAGAGAGAAGACAGAGACAGCAGAAACAGAGACAGAACATACAGAGACAGAGACAGA
GACAGAGGGACGAGACAGACAGGAGAGACAGAGATAGAGACAGAGAGAGACAGAGAAGAGACAAGACAGAGGCAGAGAGACAG
AGAAGCAGAGACAGACAGAGACAGAGAAGCCAGAGACAGACAGAGACAGCAGAAATAGACAGAGATAGAGACAGA
GGGCAGAGACAGATAGACAGAGAGAGACAGAGAGATAGAGACAGAGACAGAGAGATAAGACAGAGAGGCAGAGAGACAG
AGAGAGAAGCACAGACAGAGACAGGGACAGAGAGAGAGACACCCGAAACAGAGGCAGAGAGACTGAGAGAC
TGAGAGAGACGGGGTGGTTTTCCCACAGCATCAACACAAGCAGGGCTAGGATCACTGAGAATCAGACTTCATCAGACCCGAAGCATGCG
CTTTCTCGGGGTTTTCTGAGCTGGCCTCCACACCACGTGGCCTCCCGACTGTCCAGGATCCCCAGTGTGGGGACGGCAAGCCCGCAAGCCCGGAGTGTC
CAGAGGGAACGTGGCCTTCAGCGTCCCCGACTGCCCGGATCCCAGTGGGGTACCGAGGGTGCCTGTCCAGCCA
GGCGGTGCCGGGGGTTTGGGAGAGCCTCTCCCCCAGAGTCGGTCTTCAGAGGGGCTCTCAGAGGGGCATTCCTTTCC
AATGTTGTGCCCACTTCCCTCCAGAGTTGGTGGCCAAGCTGGGACCTGGGGACTTGGAGTCTCAGGAGTCGTCCGCTGTCTGCAGG
GGGTCATGGGGGATGTGGCCACACGTCAGATGCGCCCCTGTAGGGACCAGACAGACGACTCCCCTAAATGAGCTCGC
CCTTCTGCCAGATGCTCAGCGTCCCAGCCTGTGCCCGACTGCCCCGACTGGTCCCCTTCTGCTCCCCACTTTCCCTTT
CGGGAAGTGCTGGGATTGGGGCATCAGGGATGCCCTGTTGTTTGCTCATCACACCCATTTCCTGCCAAGCCACGGTGACCAGCAGC
CTGAGTTGAGGCAGCTTGTGGGTAGACGCGGCCCCCAGGGAACCCAGAGCCTCCTTTGGGGTCCTCCTCGGAGGGTCATGGGTGCCTCCAGCCTCAGTGATTTTCCAAAGCA
GTTTAGAGAAATGAGACCCACCACCCAGGCGTTATTTCCCATGGTGAGGTTCTTTTCAGTAAACCCGTAACCCTATAGCCAGGATCAGCAAAGAGAG
GCGCGTCTCGCAGAGCTGAGACAGGGACCAGCCTTCCCACTGGAGGAGAATAAGTACCTGATTGTGTGACCGAACACCTCCTGCAAAGTTCTTCGGTGGCCATCACACCCGACCA
CCTGGTAGCACCGGCTCTGAAGGATGTGAACGAGGCCAAGCACAGGGAGTGCCCCACCTGGGCGTCAAGGCCCGTGGCCAGCTGGGACCGTCTTT
GGTCCTCGGGAGGGTGTGGTTCTCAGCGCGTCCTGTGGAAGCGGCCGCCCAGCCACACCCCTGCCCCGACGGCCAGCCCTCCAGCCACCCTGAACACTGCCCCCA
GCCCAGCCGCGGTCGAGCATCATCGCCACGGACCACGATCACGAGGCCCACATTGATCGTGAGGCCCTTGCCCAGGAGACGCAATCTCACGGCCTGACTGGGCCAGACGCGACGGCGAGAGC
AGGTGAAAGTAATTCTGCCTTCCCCAGCATCTTCCCACCACCGTCCCATTCTCTTTCCAGAAAAAAAATAACGTGGAGCAAGTTGGTAAGAGCCCTCCCCACCCCCAGCCGT
GAGTCGCACACGTCTGCCCGTGCGGCCCCGGATGTGTGTCCCCCGATGTGTCCACCTGTGCTGGCCATGCTGGACGATGTCATATCCCGGGACACATGTC
CCCTGCGTGTTCTGCCCGTGCCCGGATGTGTCCCGATGGTCCCCCGATGTGTGTCCGATGTGTGCTCCATCACTGCCCATGTTCCCGAGCCATGTTCCTGCTGCCCATGTCCCGCC
CTGTGCGTCCATCCGTGTCTTCCCCCCACAGTGCTCGTCTGCCCATGTGCTGCCCATGCCAGGTGAGTGTCACCCGCATGTCACCCTGAACCCGCCCTGCACC
ACTCGTCTCCATGCTTTCCCCCCAGTGTCTGCCTCTGCTGAATGCCAGGGAGTGTGTCCCCTTGCCCTTGCAGCCCTTGCCCTGTGTTGACCCGTATGTCCGGGGCGACCTCCCCACTG
CTGGGAACCTGAGTCTGGGGGTTCCCTCCTGCTGAATGCCAGGGAGTGGGCTCGGAGTGGGGTGGGCAGGACGGCAGAAGGCTCTGGGCGACCCCG
GCTTTGAGGTGAGTGGTGATCAGAGGATCCAGAGGGGACGCGGGGGTCCAGATGAGGGGACGGCGGGGTCCAGATGGAGGGGACGTTCGGGGATGGA
AAGTCCACCATGAGGGATGCCAGAGGGGACGCGGGGGTCCAGATGGAGGGCACGGCGGGGTCCAGATGAGGGGACGGCCGGGGATGG
CAGATGAGGGGATGGCCAGATGGAGGGGACGGCGGGGTCCAGATGGAGGGGACGCGGGGGTCCAGATGAGGGGACGTCCAGAT
CGGGGGTCCAGATGGGGGGACGGCGGGGTCCAGATGAGGGGACGTCGGGGGTCCAGATGAGGGGACGTCGGGGTCCAGAT
GGGGACGCGGGGGTCCAGATGGAGGGGACGTCCGGGGCTCCAGATGGAGGGGACGGCGCGGGGTCCAGATGGAGGGGACGCGGGG
GGCAGGGTCCAGATGGAGGGGACTTCGGGGCTCCAGATGGAGGGGCTCCAGATGGAGGGACGCGGGGGTCCAGATGAGGAGGGAC
GGAGGGGACGGCGGGGTCCAGATGGAGGGGTCCAGATGGAGGGGACGGCGGGGTCCAGATGGAGGGGACGCGGGGTCCAGAT
GTCCAGATGAGGGGACGGCGGGAGTCCAGATGAGGATGGGGGTCCAGATGAGGAGGGATGTCGGGGTCCAGATGAGGGGTCCAGATGGAGGGG
ACGTCGGGGCTCCAGATGGAGGGGCTCCGGGCGACTGTCCAGATGGAGGGGCTTCGTGCTCCCGCCTGCCCTCAGCCA
GGCAGGCTCCCGGGATGGAGGGAGGTGCGACTTCCCCGGGGCGCCTGGGGCGCTTCAGGGTGTCTGTCCGCCCTGACCTCAGCCG
CACTCTGTTCAGAAGGACCTTTCTGAGGTAGGAGGGTGAGAATGGGTCCCCTGCTTCTGTGGCTCAC |

TABLE 3-continued

Hypomethylated locus region sequences

| SEQ ID NO | GENE NAME | SEQUENCE |
|---|---|---|
| 79 | COL6A1 | GGCCGGGGAGGCGGGAGGCTGCCCCAAGAGTAAAAGCTTTCTGACGTGCGCAGGACGCGGCCCTGACTGGTCTAACTGACTCTTTC<br>TCTTCTCCTCAGCTTGCTGTGGTGAGACCCAGGCTCTAGCTCTTCAGCTCCTGAGAGAATGGATCCCGGGGGGTCGGGGAGCGAGGCCTGGGGTCCA<br>CACATGTCACAGGACAGCACATGGCACTTGGCTCCCTGCCCCCTCTTTCACCCATAACTGAAATAACCAGGAGCAGGTTGGGGGCCTCCTGTCTCC<br>GCAGGGTTCCCGGGTGTTGGGCTGGCCCCCGCCCCCTCTTTCACCCATAACTGAAATAACCAGGAGGAGGTTGGGGGCCTCCTGTCTCC<br>ATCATTCTGGCCCACAGGCCCCACCCTAGCCTGACCTGAGCAACGCCAGCCCTGACCAGCGCCGACAGAGAGCAGCCTTTACGGGCCA<br>TGGAGGGGGTGGGCTTTTCGGGCTGACTGGAGGGGGACATTGGGAGGGGCCTGCTCTGCTCAGCACCGCCGTCAGAATGCAAGTGCGGCCCA<br>GGTGAGGGAGGAGGGGCACTGGAGGGGCACATTGGGGGCGCTGCACCGCCGTCAGAATGCAAGTGCGGCCCA<br>TCGACCTCCTCTTGTCGTTCGCTCAGAGACATTGCCGTGGACTTCAGAGACTTCGTCGTCAAGGATTGCTCAAGGTCATCGAC<br>CGGCTGAGCCGGGACGAGCTGGTCAAGGTGAGGCCCTGGCCTTTCTCAAGCCTCAGCTGCACCCCGACCCTGCCGGCGC<br>CCCTGCCCGGCCCAGAACTTCCAGCCTTCCAGGCCACGGCTGGCCATCCCTGTGACTTCCTGACTTCCCTACTCATGACAAGGATGCAGGCACGGCC<br>AGCCCGTCCAGGCCCTTCCAGGCTGGCCGAGGCTGGCCATCCCTGTGACTTCCCTGTGACAGAACCAGAGGGCTTCATCACCAAGGAAGAT<br>AAGGAGGGTAGTCTGGGGTCCTGAGTGCTGTCCACCCCTCCCTGTGTCCCTGTTGCAGCACCCTGAGACCTGAGCCCAATGCAGTCTCTGCGAGCCAATCGCAGGGTACCCACCCTGGGCACCCGCAGC<br>TGCTTTGCAGGGTACCCAGGTCCGTGCACCCAGAGCCAATGCAGGGTCCTGAGGTCCTGAGGTGCCATGCCACCCTGGGCACCCGCAGC<br>TGCCACCCTCTGTGCACCCAGAGCCAATGCAGGGTCCTGAGGTCCTGAGGTGCCATGCCACCCTGGGCACCCGCAGC<br>CAATAGAGTCACCCTTGGGAAGTCGACACTCGGGTCCTGACCCTCGCAGCACTCGGGTCCGTTCCACAGTTCGAGCCAGGG<br>CAGTCGTACGCGGGTGTGGTGCAGTACAGCCAGGTCAGATGCGAGAGCACGTGACTCTGTCGCAGCCCATCCGAACGTGCAG<br>GAGCTCAAGGAGTGAGTGCCACCGCAGGACCCTCCACCCTTCGCTGCCCTTCTGCCCTTTGCTACAGAGCCCATCAAGAGACCTGCC<br>CTGATCCCAGGTGGGCTCGGCCTCACGTGGCGGCAGTACACGCGGGAGGCCCTGCAGTACAGCTGCTGCCGCCAGCCGAACAACCGCATC<br>AGTGATGGCGGGCGGCACCTTCACGGGGAGGCCCTCAGCACTGCTCAGCCAGGGGCATCCGAGTCCTGCAGCCCGCCATCCAGGTGGGGT<br>GCCCTGGTCATCACTGACAGCGGCTGCTCAGACATGTACAGGGACGCCACACCCCCGCCAGCCAGTGCCAGATCTGCTAGGTGCCGCGG<br>GGCCACCCCCAGCCTGCACCTCTAGGGCGCCCCCGCCAGGACGCCGCCGGGCCCAGGCAGTCCCAGATCTCGTAGGTGCACGCGGGCG<br>CCCAGGGCCGCACCCGTGAGGTCGCACGGGCCCCGAGAGCATCCTCCTCCCGGCTCCGCTCGTCGTGACTCGCGGGGC<br>GCACGGCCACCCCTGTGCTCGGCCGGAGGTCCTGTCACATTCCTTGCGGGGTTATAGGTGGAGCAGTGGGCTCACACTGCACGGCTTT<br>TCTCTTTACAGACAAGAAGTGTCAGATTACACCTGCCCAGTGAGTTACCTCGGCGGGACACGTGGGAGGCACCCGTGG<br>TTGGGGCGAGGGCTCTGAGGACCTGGCGGCTCTGAGGAGGGGCCTGGCGCGTCAGATGACGCCCATGTCATGCTCACTCCGTGGCTG<br>AGCACCACCTGCCGTGCCCCTGTGGGAGGCTTAGACGCCTCTGGCGCTGCATCACCAGGCCTGCATCACCAGGGCCTCATCATGCTAACG<br>GCTGCCCCACCCCGCCACGCTTCGCCAAGCGCTTGCCAAGCGCCACGCCGCTTCTCCCCGGCTGACATCACCATCTGCTGACGGCTCCGCAGCTGGGCAGCCACAA<br>CTTTGACACAAGCGCTTCGCCAAGCGCTTGCAAGCGCCAGCGCAGGACGCACCCCGCCCACGACGTGCGGGT<br>GGCCGGTGGTGCAGTACAGCCGCACCGGCCGCAGCGCCAGAGCGCCCAGCGCCACGCCCAGTTCCTGCAGAACTACACGGCCCCTGGCCA<br>GTGCCGTCGATGCCATGACTTATCAACGACGCACGGCACCAGACGTCAAGATGCCTGGCTATGTGACCCGCTTCTACCGCAGGCCTC<br>GTCCGGCGCTGCCAAGAAGAGGCTCTGCTCTTCGTGGTGTCGTGGTCGCAGCACAATCGCCAGGGCCCACATCCGCGTCCTGTCACCGG<br>GGAAGCCCGCAGGCAGCAGAATCTTCGTGAGTCAGCGCTCAGCCTGCCCCCCACACATCGCCAGCCCTGGCTCAGGCTCCAGGCTCAGCTGGC<br>CAAGACGCCGAGTACGACGTGGCCTGGCCACCTGGCGAGAGCCACCGTGTCCGTCCAGGTTGCCACCGGCGCCCACCCTGTCTCCGGTGTCTTCCAC<br>CAGACAGTCTCCAGAAGGTGGCGCTGGCCAGCCACCGCTGTCCACCCTGCGCCAGCCAGACGTCCCCCACTCATCAC<br>TAAACAGAGTAAAATGTGATGGAATTTTCCGACCAAACCTGATTGGCTAGATTTTTTAAGGAAAAGCTTGGAAAAGCAGGACACAACG<br>CTGCGCTGCCTTTGTGCAGGGCTCGCAGGCGTACCATCACCGAGTTTGCCTCACTGCAGGCGTCAGCCCTGAGCT<br>AGTGTCACCTGCACAGGCCCCTTCTGAGGCTCAGCCCTGCCCCTGAGCTGGTCACTGCTCAGCCGCCCTCCTGCCCAGCTCCTGCCCAGCTTCTCCTGCAGCTCCGG<br>CTCACCTGGGTTCCCACCCCGGCTCTCCTGAGGCTACGGCCTGCGAGACGCCACCTGTTCCGTGCACCAGCTCCGCCAGCCGCCCCGCGAGCCACCTGT<br>TGTCCTGCATCCACCAGCCTCAGCCTGAGCAAGCACTTGCGCCTAGCCACCGCTGTGCCGACCTAGCCTCTTCCTCCGCACTAGCCTGTCCCCATAGCTGGTTT<br>TTCCACCAATCCTCACCTAACAGTTACTTTACAATTAAACTCAAAGCAAGCTTCTTCCTCAGCTTGGCAGCCATTGGCCTCTGTCTC<br>GTTTTGGGAAACCAAGGTCAGGAGGCCCCGTTGCAGACATAAATCTCGGACCTCCGCCCCCGTCCTGAGGGTCCTGCTGTGACCGGC |

TABLE 3-continued

Hypomethylated locus region sequences

| SEQ ID NO | GENE NAME | SEQUENCE |
|---|---|---|
| | | CTGGACCTTGCCTCTACAGCCCTGGAGGCGCTGCTGACCAGCACTGACCCGACTCAGAGAGTACTCCAGGGCGCTGGCTGCA |
| | | CTCAAGACCCTGGAGATTAACGGTCTAACCCCGTCTGCTCCTCCCCGAGAGACTGGGGCCTGGACTGGACATGAGAGCCCTT |
| | | GGTGCCACAGAGGGCTGTGTCTTACTAGAACACACCAAACCTCTCCTTCCTCAGAATAGTGATGTGTTGACGTTTATCAAGGCCCC |
| | | CTTTCTATGTTCATGTTAGTTTTGCTCCTTCTGTGTTTTTTTCTGAACCATATCCATGTTGCTGACTTTTCCAAATAAAGGTTTTCACTCCTCT |
| | | CCCTGTGGTTATCTTCCCCACAAGTAAAATCTCCCAGGCTGACCTGTGCCCAAAGGAAGTTCCACAGAGGAGTTGGGGCGTGTCGTGCGTG |
| | | CTCACTCCCAACCCCATCACCACCAGTCCCAGGCCAGAACCAGGGCTGCCTTGGCTACAGCTGTCTCATCCATGCCCCTTATCTGCGT |
| | | CTGCCTCGGTGACATGGAGACATGCTGGGCTGGGGCCCACCATCCACCGAGTCAACCACGAGAGGCCGGCCACACAGGTTCTAGGCTTGGTACTGAAATAC |
| | | ATCAGGCCTCAGTGGGCTGGGGCTGGGAGTTAGATATCTGGACAGAGAAGAAGTCTTGGGGACTGCAGAGGAAGAA |
| | | CCCTGGGAGCTCGGAAGGGGAGTTAGATATCTGGACAGAGAAGAAGTCTTGGGGACTGCAGAGGAAGAA |
| | | GTCTTTGGGAGGCTCCACCTTTGGGCAGATCCGGGGTGCACGGCTGTTCTGGGGGTCACAGGGATCGGCCGAGGGGTGGGCTGGA |
| | | GGAGGGCAGCAGGAGGATGGGCCGGCTGAGGGTGAGGGTGGGGCTTCCTGAAGGCTTCACCTGCCGGGACCCGCCCAGT |
| | | GCCCAGGCAGGGACGACCTCGCTCAGCAGCACCACCATGTGCCACCAGAGCTGCGGGAAATGCTGGGGACCCTGCATTTCCGT |
| | | TTCAGTGGCCAGCAAGCGCCCCCTCACAGAACTGCAGGTAGAGACGCGGGCCCGGGCAGGAGGCCGTGAGGGTGGGCTGGAC |
| | | GGCAGATGCAGTGAGGGCCCGGGCAGAGCCCGGGGCAGAGGCCAGACCGAGTGGGGCGCGGGGGCCCGGGCAGACGCAG |
| | | TGGGGGGCCCGGGGCAGAGGCAGCGGCCCCGGGGCCAGACGGCAGACGCAGTGAGGCGCCCGGGCAGTGGGGGCGCGGGGTAG |
| | | TGCGCAGTAGGTGGTGGGCCCGGGGCCCCAGGCAGTGAGGTGGTGGGGCAGCATGTGGGCCCGGGGCAGGCGGCGTGGGAG |
| | | GACGGTCCCTCACGCGCTGAGGCGCAGTCTCCCCGTGCCCAGTCCTTCCGCTACCCTGCTTTGCGCTACCGCCAGTGCTGAGGGCTCC |
| | | TCCAGCCCCAGCCGCCCCGGCCCGCCCCGGCTTCCTCCCGGCTTCCTCCCGTAAGCTGGGTGAAGGACTCCATGCAACCACCTGAGAGGGTTGGCGAGG |
| | | GCCGGCCCTGAGCCCTCGTGCCCACGACCCCCAGGACCCTGTCCAGGACCCCTGGGCATGGCCGCCCATGGTGGGCCCCTTCCTGCCCCTTCCCCCCCAAGTCCGGCAAGTGCGCCTGCTCACCG |
| | | GTCCTGAGGAGGCCCAGGACCCTGTCGTGACACACTGGGGTTCAGGGTGCACACTGGGTCGCAGGATTCCAGGCAGGAAGCTCCGGCGGTGGGG |
| | | GTTACCAAGGCCCGGGTTGCCATGCAGAGAACAGGAGACTGGAGCCAGAGCCCCCACAGGGCCCAGGAAGCTCGGAGAAGGGGCCGGTGGGG |
| | | ACTTCACACTTCCTGTGGGGCAGATCTCCAAGGTTCCGGCCCTCATCTTGTAGAAACTGAGGCACCAGGAGGGACACACACTCCCACG |
| | | GCCGGTCACCCGTGCCCCCCAGCCCCACTGACTCCCCACTTCCCAGCCGGGACACCTGCAGGCTCAGGCTGCACAGCCTCAGCCTGCGGC |
| | | CCCTGCTCCGTGGCCCCAGCCCAGCTCCATGCAGGAGGCGGAACCTGCTGCCCAGCCTGGAGGCCCGCCGCCAACCCCCCTACAACCTATCAGCCCCTTTGCCTC |
| | | TCAACAGCAAACTACTTTTTCAGGCTGCAGCTGGCAACCCTTGGTCATCCCAAGCACACCCTGTGTGTTGGGATGCGATGCTGCTGAGCCCC |
| | | CCAGGACGGAGACCCCACCATCAGGTCCGCAGGTTCATCCCAAGCACACCCTGTGTGTTGGGATGCGATGCTGCTGAGCCCCC |
| | | TGCATCC |
| 80 | chr21:<br>46280500-<br>46283000 | AGGGCGTTTGGGAACACCCTCCCCGAGGGGGTGAGGCGGCCGCCTCCCGAGGAGCACAGGTTTCTGCTGCGAACCTGCA |
| | | GACATGGCCATAACAGCCACAGCTGCTCCGGCCCCACACCTGACCCACCATGGCCCTGTCTCACCTCCTCAGGGCAGGCTTCAGG |
| | | GCCTCGACCCTAGAGGCTTGCCGCCCTCTGCCCCTCCTCCAGCATTCCAGACCACACAAACCACTCTGGGCTAAAACGAGGCATGCCAGAGACATCCACTTCC |
| | | GATGAACCCCCGCCTCTGCGCCTCTGCCCCTCCTCCAGCATTCCAGACCACACAAACCACTCTGGGCTAAAACGAGGCATGCCAGAGACATCCACTTCC |
| | | TCGGAAAGCTGACGGCGTCGGGGACCAGGCGTGTAGGGCACCGTGGGGCTCTTTGAGATACTGAGGGGCACAGA |
| | | CATGGAGTGACAGAGCGTCGGGGACCAGGCGTGTAGGGCACCGTTGAGTGTGCTGGGAGAGACAGTGGGGGCCTCAGCTG |
| | | GGTGAGCAGCTGGAGCTGAGCCAGGAGTCAGGAGCGCAGGGGCTGTGATGGTGCTGCCAACCTAGAGGTGCCGGCCCACCCAGATAACCCCAAAGAACT |
| | | GCCCCCCCAGGGCCCTGAGGCGGCAGATGCCAGAGGTGCAGGGCAGAGGAGCAGCGTCCTGCTCGTCAGCAGAACCCATGAT |
| | | GGGCTGGCCCAAGGCTCTGAAGGTGAAGGCTCACACATTCTGCCCGCTGACCGCTTCTTGGGCGTCGGGGTGTGTA |

TABLE 3-continued

Hypomethylated locus region sequences

| SEQ ID NO | GENE NAME | SEQUENCE |
|---|---|---|
| | | ACAAACGCCAAGACGCCATTGTAAAGAAGGAAGCCTGCGTTTCCATCACCGGCTTAATATCAAACAAAAGTGCAATTTGAAAAATGTAGTCC |
| | | AAGGTTTCTGTGGTGCCGAAAATGGCCAGGCCAGGCACCCTCCCGTGGGTGGTTCCTTCCTGTCCACGTCAGCCGCCTACATCCACACTGTGG |
| | | GCACCATGACCTCACATGCGGAGCGGAGCGGAGCCGGCCGCCGGAGAGCCAGGCTGGTCACGAACGAGGCCTAGAGGGCTCAGGC |
| | | CCCAAAGCACTCACAGGCTTCTCCTCCTGTCCTCGGGGCCTTCAGACACTGCCATGCCGATTCAGCCACCCGCGCGCCGATTCCC |
| | | CTGGCCATGGGGTTTCCAAAGTGTGCTCAGAGACAGTTCCTCCAGATGACCTTCTGTCCTCAGTGCCTTGCTGAGGCACAGCGTGCG |
| | | TGCTGGGTCCCGGTCTGAATGCTTCCAACGATTTACCCAGTTCCTTTTCTCCACTCAGGAGGCGTTTGCTGAGAGGCACAGGCTGAGC |
| | | CCCCTGCTGATGCCACGACCGAGGGAACGGGTCTCCCTGTCCGGCGTGAACTGACCCGGCTTCGGCAGAACACGAGGCGCCCTCCACACGCG |
| | | TCCCGGGCACGTGGGCCTGTCATGAAAAAGCTGGATGTGCAGCTTCACCACAGAATCCGTTTGAAGGACGCCGTGAGACATG |
| | | ATCCACCCTAAGTTGTGATCCTGGGTGAGCCGCCGCCGGCCGACACCCCCTGGCTTGCACCTCTGAGGGTCCCTTCACCCACTTTATTCTCCAGAAACCCTGCC |
| | | CATCAGGGCTGAGTCCCACGCCTATCTGGAGGAAGTGGGAGGCGAGTCTGGGGCTCTGCCCTGAGGATGACCACAGGGGACCCACAGCGTCACAGTCCACAC |
| | | AGGCAGAGGCCCTACGGCTTCATGGAGGAAGCGGAGCCCGCTCAGGCAGCCTTCCGGCCAAGACCCGGCCCAGGCCCTCACCGTGGG |
| | | AGAGACACACGGGTGCCTTCCCAGAAGGGCTGAGCCTGGAGTGCCTTTCCCGGGACTGGATGGAGGCAGAGTGAGAGAGCCTGG |
| | | CAGCAGGGCTTCAGGGCTTCCCAAGGTGTGTGGGGGACGGGGCAGCACTGCATCCTCCAGAAGCTGCATCGTCAATTCTGTCTCCAAATCTCTTCTTGTATTTCATGTATTCACAGAGTGACG |
| | | TAAGTTAAGACATTAACTCCCATTGTCAAGGTGCCATCGTCAAGAGCCAAGAGCCCGGCCAGGCCCACGCGCTGCACCCAGG |
| | | CTCCGTGTTTCGTTCAGCCTGCAGGCCTGCAGGCCAATGGGGATGGGCCAAGAGCCCGGCCAGGCCCACGCGCTGCACCCAGG |
| | | ACGGGATTCATGCCCCATGCCTGGCTTCTCAGCATCGGGCAGCGAGTGCCTTTCCCGGGACTGGATGAGGGCAGAGTGAGAGAGCCTGG |
| | | AGCAAGTGTTTGGACCACAGTGATCAAACACGGAGCCCCGTGGG |
| 81 | COL6A2 | AAGAAAGGCCAGACCGGGCACGGTGGCTCACGCCTCGTAATCCCAACACTTGGGAGGCCGAGGCGGGCAGATCACTCGAGGTCAGGA |
| | | GTTCGAGACCAGCTGGCCAACAGGGTGAAACCCCGTCTCTACTAAAAATACAAAAAAAATTAGCCGGGCGTGGTGGCAGGCACCTGT |
| | | AATCCCAGCTAATCGGGAGGCTGAGCAGGAGAATCACTTGAACCTGGAGGCGGAGGTTGCAGTGAGCCGAGATCGCGCCACTGC |
| | | ACTCCAGCCTGGGTGAGGAGCGAGACTGTCTCAAAAGGAAAGAAAAGCCCCGTGAGATGCTTTCTC |
| | | TTAAACACCGGCCCTGCACGTTGAGTTGCTGCCTCCTCATGGAAGGCGCCCAGCCCGGCGATTTATGCAAAGTCGGCGCCCTGATGCGGGGCTCACCCG |
| | | CCAAGCAGGGTCTCGTTCTGCTCATGGAGGAGGCCCTTCTGGCCTGCCAGTGGAGGCGTGTAATGGCAGGGTGTGCAGGGGTGTAGGGAATCCAG |
| | | CCCAGATCCAAAACACCTGCCCTGCTCTTAGAAGGGCCGACATCTGGGTCCAGAGGTCAGAAACGTCAGATGCCCATCCCAGAAGTGCGGGGA |
| | | CTCACAGGGCGCCTGCTCTTAGAAGGGCCGACATCTGGGTCCAGAGGTCAGAAACGTCAGATGCCCATCCCAGAAGTGCGGGGA |
| 82 | COL6A2 | GGGTCGAATGAGTAGATGTAGAGATGTGAGTAGGTGGGTCAGTAGGTGGGTAGGTGTAGTGGATGGGTGATGATGGTGTGTGGTTAGATGATGATG |
| | | GCTGAATGGATGAGTGGGGATGATGGGTGAGTGGGTGTATGTATGGATGGGTTAGTGGGTGTAATGGATGATGGGTGCATA |
| | | AAGGATGGATGGATCGAATGAGTTAGTGGGTTGGCAGATGATGAGTCAGTGGATGGTCAGTGGATGTCAGTGGATGGATAGAGGA |
| | | TGGATGGTTGGGTAGGTGATGGGTGATAGAGTGGTATGTGAGTAGGTATGGGTGATGGGGGATGGTAGGTGGTGATGGATGGTT |
| | | AGTGGAATGAGTGGATGGACAGAGCAGATGGGTGGTTGGGTGGCATGGATCGACGATGAACGATGATGGATGGATGGTG |
| | | GATGAAATGGATGAGGTGATTGGGTGGTCGTGGGAATGGGCGAATGGGTGATTGGGTGCTGCTATTTCTGGGGACACCCAGTTCTGGATGGATGGATGCTG |
| | | GGTGATAATGGATGGATGAGATGGAATTGGAATGAGCTGTTTGGCTGCATTGGCTCGAGTGGGATGATGGGTGACCACCCAGGGGGATTCAAGCGTGAGGAGTTGGGCGCAGGCT |
| | | CTGACGGTCACTCATGCCTTTCTAGCTCTGACATATGGAAGGAGGAGGACACGGCACCCTGTCTTGTATCTCCTTGCCACCTGTTA |
| | | GCCCCCCCCCACCTGTTCTGTTCCTTCTCAGCGGGATCCTGCTCCCCCACCCTGGAGCCAGGGCAACACACAACCTCCGGGGCCCTGTGTTCCCCAGGGACTGCCAGGGGCCACTG |
| | | AAGCCCACCTGTTCTGTTCCTTCTCAGCGGGATCCTGCTCCCCCACCCTGGAGCCAGGGCAACACACAACCTCCGGGGCCCTGTGTTCCCCAGGGACTGCCAGGGGCCACTG |
| | | CCCACGTATCCGTGGCCAGTGCCCTCGGAGGTAGGTGGTCAGTCAGCCAGCCTCCAGCCTGCCCCAGCCTTGCCCCCAGCCAGGG |
| | | TGAGCCCGGCCCCCGGCCCCCTGGAGACCCCCGGTCTCACGTAGGTGTCACATGGGCAGAATCAGTCGTCCCCAAAACTAGACACC |
| | | AAGAGCAGCAGCGGGGTGGGGAGGCAGTCAGCTGCACGTCGACATCTGGCAGCCAAGAGAGAGCAAGGGGCAAGGTCAGAGAGACAA |
| | | GCTTGGTTGGGAGGTCACAGGGGCACGGTTGGGGGGAGGAGGTGCAGCCAGGGTTGGTTAGGGACGAGGTTCGTGTGGGAAACTCTTCGTGGGCCCCCGG |
| | | CCGGATGCGCCTGCCTGCCGTGCATTGCAGAGTTGACGTCATGACCGTCATGACGTCAGGACCTCGGGGACCCTCGCGCGTGCGTGAGGCACT |
| | | GGGACTACCCCTGCTGCCCTGCCGTGCATTGCAGAGTTGACGTCATGACCGTCATGACGTCAGGACCTCGGGGACCCTCGCGCGTGCGTGAGGCACT |

TABLE 3-continued

Hypomethylated locus region sequences

| SEQ ID NO | GENE NAME | SEQUENCE |
|---|---|---|
| | | GCCCACGGCAGGGTCGGGGCCCATCACCCGGTGAGGGTGGAGCAGGGCTGGTCATGCTCCTGCATGTGCACG
TGACCCTAGGGTCTGAGGTCTGAGCAGCTGCCCCCGATGACCCTGCCAGACTGTGAGAAGCGTGGCCCTGACGT
GGTCTTCGTCATCGACAGCTCCGAGAGCATTGGGTACACCAGGAGAACTTCGTCATCAACGTGGTCAACAGGCTGG
GTGCCATCGCTAAGGACCCCAAGTCCAGACAGTTCGAGACGCGGCGTTGCAGCATTGCGCGGGGCGGGGCGTGG
GAGGGCGATGAGAGATGGGAGGAGAAGCGTCCAGACGCGTCCCTCCAACGAGGGGCGTCCATGGCTGGGAGTAGCCCCAAGGCCTTG
GCAACGACCTTCACGCGTGCCGGCTTCCAGGGACGCGTGTGGGCGTGGTGCAGTACGACCACGAGGGCCATCCAGCTG
CCCTCAAGTTTGCCTCTACGACCCTCATCAAGGAGGAGCCCGGACGCCAGAAGACACACGTGTTTGCGGTGTCATCACGGACGGGCCA
CGACCCTCGGGACGACGATGACCTCAACTTGCCGCCGTGTGCACCGCAGCCATTCGGCGCCATCGGCCACATGTTTCCA
CGAGAAGCACGAGAGTGAAAACCTCACTCCATCCCTGCGACAAGCCCACAGCAGGTGCCCAACATGACCCGTGTTCTCCGACCTGTC
GCTGAGAAGTTCATCGATGACATGAGGAGACGTCTCTGCCCAGGACACCCCTCACCTGAGCCTGAGGGATGAATGTGCAGCCCAGGATCTTGGGCGTGTGGGTGGGAAAG
GGGTCGCCCCTCTCGCAGACGCTGTCCAGAGCCCTGAGTGAAGGCCTGTCTAGGCAGATCAGTGAACGCGCTGAGGGTTC
GCTAGGGACTGACCCTGGCCTGGCCCCGACCACCACCCCAGATAGCAAAGCAGCCTGTCCTCTTCCTCTCCTGCCAAACAGGTA
ATGCAGGGCACCCCGGGGGCGCCGGCGAGCCACTGCGGAGCCTGCTCTCTTAGGGAGATGGCCAGCAGGGGAGGG
GCTTGGGGAAGCAGGCTCCCAGGAACGCAGGACCATGAGGCCATGAGGTGGGTGCTGCTAGCCTGCGTGTCTCGGCA
TGTGCCACTGGTCTTGAAGGCCTGAGTTCAGTGAGTGGAAACCATCCCGGGTGAAGCACTGACACCCCCAGCTCCCCATGGGGCCGTGTGCCCAAC
ACTCGGAGAAGCCCTGAGCTGCCTCTGCGGCTCTCACATCTCCGGGTGGAGTGGGGAGCCCATGCTGCCTGATGTGGCCACGTGGGTGTG
CCTGCCTGCCTCCAGGAGCTCGGGAGCCTGAGTCCCAGGCTCTCCAGGCTGTCCGTCCAGGCTGGTGCCATACGTCGCTGCTGCACCGAGCGTGGCCCACAGG
AAGCTGGAGCTGGGGTGCCGTCCAGGGCGTTAGGAGCTGAGTCCCCATACCTGGGCCCTGCGGCTCCCCAGGGTCTGCTGCCCTTCAGCAG
AGTGCCCGGGGGCTTGAGACCTGAGACCACCAGGCAGGAGAACCAGACTTGGCTTCTCTCTGCGTCCCCCAGGGCGCACCCCCGTGTTCCTGACCCCATCAGCAGGG
TGGGAGGGTCCGACCTGGAGGAGAACCAGGAGAAACCTCAGGCTCTGCGGTTCCATGGAGGCTCCCGGTTGGGTAGCCCTGCACACCACTCGAGGCCTGCCACTGCGGGGA
TGTGCCGTTCGGCCGTTCCATGGAGGCTCAGAGCCGAGGTTCCCATACGTGGTCACCAGGCTCACAGAGCTTCGACCAACCTCCCTTCAGCAG
GAGGCCGTGAGCTGGGGTCCGCCTCGGCCTCCTGCTGCAGAGAACCTAGGGCTTGCAGCCTGTCTCGCCGTCCTCCCCAGGGTCCCACATCAGCAGAG
GCGGGCAGCCTGGGCACCCCAACAGTGGGGCTGCGTGTCTTCTCCCCCAAGTGACGGCGTCTCCTTCGTCTCCTGATGGGCAGGGAAGTCTCGGACC
CCATGATGGGCGACATGGCGATGGTCACTGCCCTCCACAGTTCTATCTGTGGATAGAGGTAGGTGCCTCCTGCCCCAGTGTGAGTG
GCCCTATGGCTTTCCCCCCACCCAAGTTCTATCTGTGAGTGAGTGGCCGTCGCCGATGATCGTCAGTGTTGAGGCACTGAGCTGCGCGGGATAAACCCACCT
TATCATTGTAGTTGGGAGTTAGTTAGCCCGTTGAGCCTCATTGAATTTCGCTGATTCGCTGAGGGTTGCCGGGATAAACCCACCT
GGCCCTGGTCGTGTGGCCCTGTTTATGCACCTGGGCCCTGATGCCTGCAGGGTGACGTGGCCTCGTAGGGTCCGTGGGCAGCATCAGCCT
GCACTTTTCTTTCTCGTGATCTCTCCTGGTTCTGCCTCTGGAGTGGGTCACTCAGGCACCAGGGAAAGCAGCCAGGAGGACACGG
GACATGGAGTGAGCCCCATTCTCCCCTTCCTCGGAGTGGGTCACTCAGGCACCAGGGAAAGCAGCCAGGAGGACACGG
AGGGCCTTGAGCTCTGCTCCTCTTCTGAGGACTGTCCAGGACCTGGAAGCCTTGGCAGAGCCCCCTTCCCCCTCTCTCG
GCCGCCCTGACACCTCATCCCGACACTCAGAGCTCATCTCCCAGCTGTTTCAATTTCAAAGTGAACTGACCTTGTGCCTCCA
GGAGATGCAGCAGGGACAGTGTTAAATCGGCTTCTCCAGACAGCCCGTCCACCCAGCCATCCCTCCTGGGCACTGGGGTGGAC
ACCACTGTGTGGCCCTGGCCCTGCCCTGTTCCACCCAAGCCACCCTGGGCCTGCAGGAGGCCTGTG
GAGTTCTCAGTTGCGTGCGCTGCTGTGAGAAACAACCAGCGCAGTCAGGGCAGGGCCAATCAGCGA
TAAGAGCTGCATAGGGGCGTAACCTGAGCTCCAGTCGGTGGAAAAGAAAAGGCAGAGACTTGGCCAAGCTTTCTCAGGCGGGCTCTTG
GGGAAGACAGTTCTGGGTGTAGAGGACTCACATCCCAGAGAGGCCACTGAAGCCTACTGAGTTTGGCCTTCTCGGCACAGGTTTGACG
AGGGTGGCTTGAGGGCTTTCTTCGGAGGTCTTCGAAAGGTTTTCGAGGCTGCCTGGTGTCCCCAAAGGTCGCTCCGGTCCCTGAGCTTC
CTGTCCCTGTGCTCACTGCCCCAGCCCTCCGTGCCAAGCGCGAGCCAGGCCACACACCCCCGTCACCTCGATTCCTCTACCTGACTCGCAGCC
CAAATGCCGCTCTTCACTCTGGCCTCCGCTGGAGCGGCTCGGGCCGCTGGGGCCAGCCCCCGGTCACCTTCCTCCGACGGAAGGGGCCGGACGCACCT
CTGGACGCGTCCCCTTGCAGATGCACCCTCCAGTGCACCAGTGCTAAACCCCCGGGCAAGTAACCTTCAACAACCTTTGCAAGTTCCTGTCTCTTCT
TCCCAGGACCATTCCCCTGATCCAACACAGTTCGCCCCGAGCGGGCCAAGTTCGCCACCGGGGCCTACGCAGCTGGTGCCCGT
GCTGGTCTACACGCCGAGCGGGCCAAGTTCGCCACCGGGGCTACAAGCGGATGGAGCTGTTCATTGACACCTTTAAGCTG |

TABLE 3-continued

Hypomethylated locus region sequences

| SEQ ID NO | GENE NAME | SEQUENCE |
|---|---|---|
| | | GTGCCACAGGGACATCGTGGGGACACCCGAGACCGGCTGCCCTGCTAAAGCCCGGCACCCCAGCCGGGCTGGGCCTCC
CTGCCACACTAGCTTCCCAGGGCTGCCCCCGACAGGCTGGCTTCCATGCTGGTCCTCCAGTGGAGGCCAGAGATCTGGAATCGGGGCTGCAGCGGGCTACA
GTCCTTCCAGGGGCTCTGGGCAGCTCTGGCCCGCTCTCTTTATAAGAACCTGGTCAGCTCCTTCCCATGCTGGTGCCACCCCAAGTGCCACCTGTCCCATCTTCCAGTCTCT
CCTCCGTCTTCCTGGGCCCGCTCTCTTTATAAGAACCTGGTCAGCTCATTGAATTTAAGGCCACAGGCTCCAGATGACCTCGCAAGACCC
TTAACTCACTCCCGTCTGCAGAGTCCTTCTTTGCTGCATCAGGTCACGTCTCCCAGGCTTGGGTGTGAAGTCTTTGAGGC
CCTTACTTAGCGGCCCAGCTGGGCTTGCCGTGCGTCTGGGATGAGGGCTGAGGGAGGGTGCTGCCAGGTGTGGAGGATGTTCCAGCA
CCAGTTCAGCGGAGCCTCGGAGAACAGGCCCAGTGGCAGTGAAGGCTTCCGGTTGGGCAGCAGATAGTCCTGGGGAAGCTGGAGTCCTGGCACCA
TGGGGCTCACGGCCCACCTGGTGCTGCAGTGAAGATGGCTCCAGCGCGAATGCCTGCCAGCACCTGGGGGTGTCTGCACCCTT
TGACGTATCTGGCTGTGTCATGCACAGTAGGGCGAATGGCTCACAGTCGGGGAGCATCCACCAGGCACAACCTCTGCGCTCCTCAGAGACTGAGCAGAGA
CCAGCCCAAACCTCTGGGTCTTCCAAAAGCACAGTCGGGGAGCATCCACCAAAGGGAGCGGCCCCCACGCGAGCTGACCCGACGTTCTGAC
ATCCCAGGGTCCACAATGTTGGGAGGCGGCAGGATCACCATCCAAAGGGAGCGGCCCCCACGCGAGCTGACCCGACGTTCTGAC
TGCAGGAGCCCTATCCAGCCTGGGCTTCCAGCCTGTGACCATTTCTCAGGGCCCAGGTTCTCTGTCCCCACACCACTGCA
CAGGGCAGCCAGGCTGGTCTTCCCACCTGTGACCATTTCTCAGGGACCCAGCGTTCCCATGCTGCAGAACCCCAACAGAGAGTCCACAGACATCCAACAG
CCTCAGCCTCCCTGTGCTTGCCCTGGCCGCCCACAGCTTCCCTCCAGCCCCTCAGCCTCCTGACACTGTTATTAGTTTGAGGGGTTTGGGAAGCCCAGC
AAACCAGCTGCCCCTTGCATGTCTGTCTCCATATGTTGGTGACAGCAGTGAAAATGTTATTAGTTTGAGGGGTTTGGGAAGCCCAGC
GGTACCTGAGGAGTTTCTGACATTTAAGCCGGTTCCTAGGTGTGGCCTTTAACAGGGAGCTGCCCTTCCTTTCACTGAATGAGCTGCG
TCACATCATAAGCTCACTGAGGGAACCCCATCTGCCAGCTCTGGTCGTCTCAGACGCGTCCATGTCTCAAGCGTTCTGTGAAGGCTGCG
GTGCAGCGTGAGGTCACCCTGCTGTGTTCAGAGCTTTGCTCACTGCCCTGTGACCGTTGCACGTCCAGGGGTTGGGCTGAGAAGCAGAC
GAGTTTCGGGTCAGGGTCTCTGTGCATTCGGGGGGCCTGTCAGTCGGGCTGGAGGGTCTGGTGCTTCAAGCGCCAGGGGTCAGGGGCCAGGGCCAGGGTGAGAGGAGGAGATGCCGCAGGAGGCTTGGGGGTTCTGGATGGCCAGG
ACCCTTGGGGAAATGGCTCTGCTGTCTCCTCCCATCCCAGGGCTCGGGGGTTCTTGGTTGAGGCCCAGGGGCCAGGGCCAGGTCCACGCAAGG
ACTGTCCGTCTCCTCCGTCTCTGCGCTCCGAGCGGCCCATTCTGCGCCCCACCACGTGTGGCTGTATTGTAACAGAGTCATAGGGCAGAAC
GGCCCCCAAAGCTGTCCCCAGGGCTGGCCCCCCTGCTCCCCACCATCCCCAGGGCTGTCGCCCCAATGCAGGCCAGGAGATTGGGACCAGGATGCTTTG
CCACCTGGGCTGCCACCAGGAGACGGCCCAGAGCCCCAGCAGCCCCCTTAAGTACCCCACACTACCAGATCAGAGAGTCAGGCTGGGGGCGTCAG
TTCCGGAGGGACCTGGGCTTCCTCCGCCAGGCAGCAGCCCCCAGCTGTCAGCAGCAGCCCCTTTTGGGCAGCAAATTCTTGAGCCATGAAGGATGCTTTG
AGCAGCCCTGCTTCCCCCAGCGACCTGGGCCAGGCAGGCCTGTGGAGGTTGCAGGCAGGTTGGAGGCAGTCTCAGCAGGTAGGCAGGGCCCTGTGTCAGGGTCTGCAGC
CTGGAGGAGCACCCAGCAGGAGGAGATGGCGCCAGTGGTTCTGCAGGCCCAGGTGTGAGGTTGCAGGCAGGTGCGAATGGAAGGGCACAGGTGCCGGGGCCTGGCACCTG
GCAGAAACGCCCCCGAGAGCCCCCTCCCCCAGCCCAGCTGTCTGTGAGGTTGCAGGCAGGTGCGAATGGAAGGGCACAGGTGGGGGGGCTGGCACCTG
CCCGTTCCTGCCCACTTCCCCAGCCCAGCTGCTCCCCCAGCTGTCCGTTGCAGCGGCTGTCGCAGCTGCACGCAGCGGCCCGT
GGACATCGTCTTCTGCTGACGGCTCCGAGCGGCTGTGAGACGCAGAACTTCCACAAGGCCACGTCGTGGAGCAGTGGCGCG
GCGGCTGACCGCTGGCCCGGACGAGGACGACACCCTCTCAACGACACCCTCTGCGCAGTTTGTGGCCCCGGAGCAGCAGG
TGGCCTTCCCGCTGAGCCACAACTCACGGCCATCCACCAGGGCGCTGGAGACACCACAATAACTGAACTCCTTCTCGCACGTGGGCGC
AGGGCTGGGTGCACGCCATCAATGCCATCGTGCCGACCCGAGGGCACGCAGAGCTGTCCTTCGTGTTCCTCAC
GACGGCGTCACGACAACTCGACAGTCTCGCGACCCTCGCCACCAGCTCATGCGCCAAGCACAGCTGTACCCACCGTCGCCAGTGTGCTTGGG
CAGCGACGTGGACATGGACATTCTTCGACCGCTTCATCGGTCCAGATCGTCGTGGATCTGCTGACCGCGCCAGGTGAGGAAGACTATGACAGCCTGG
GCAACCCGGCTTCTTCGACCGGTCTAAGCGCGGGCCCGAGGTCCAGCACGCTGCACTGCTGCAGAGCGCTTCACCTGGGCCTGCGACTCCTCCAGCTC
CTCCCAGGTGTCCCCGTAAGCGGGGCCCCGACCCCCCAGCCCCGAGGTCTCCCGCAGGTCCTCACTCCGCAGGCCTCCGCCCTCCCCCTG
CAGCCATCCCAAGGCTCTGTGCCAGGAGACTCGACCTCTGAACGTCTTGTGCCAGGAGGGAAAACTGCAGCTGTCGCTGCCACCAGGGTC
CTTGCGAGTTCTGTGCCAGGAGACTCGACCTCTGAACGTCTTGTGCCAGGAGGGAAAACTGCAGCCCGCTGTGCTGCGGACGCATG
AATGCTCCCCGGGCCCAGCTCGACCCTCTAGGACATCAACTGCCTAGAGTCTCTAAGAAGTGTCACCATGCTGCGGACGCATG
TCAGCAAACTCCTCCAGCCCAGCCCCAGCCCAAAGTGCTGTAGCGTGTGAGCCTGGTGAGCTCTAAGAAGTCTTCAGTGAGATCTCAGTGAGTTTTGCTCAGACCCCAGGG
ATTAACACTAGACGGGAGAGACAGGCCCCAACAGCAGGTGCTGAACAACTAGCAGTATTGGGCACAGGCTGAGGCATCAGCCGGGCATGCTTCCTCTGGAGGGC
TCCTTCAGGCTCAGCTCAGGGTTGAACAACTAGCAGTATTGGGCACAGGCTGAGGCATCAGCCGGGCATGCTTCCTCTGGAGGGC
ACAGGGACCACCACAGACACAGCTTGAACAACTAGCAGTATTGGGCACAGGCTGAGGCATCAGCCGGGCATGCTTCCTCTGGAGGGC
TAGAGGACTAGAGAAGGCCTCAGCCTGCCCCTCTCCCCAGCATCCCAGCCCCCAGGGTTCCTGATCCTCCTGATTAAGGATACAAGTCACCACA
CTGGACTGGGCTCAGCTCTCTCTAGAATACCTCACCTAAGTCACGTGACCATCCCAAGTGACCAGGCTCAGCCTGCTCTTAAGGTGAGCTCTAAGGTGAGCTACCCAGAC |

TABLE 3-continued

Hypomethylated locus region sequences

| SEQ ID NO | GENE NAME | SEQUENCE |
|---|---|---|
| | | ACTGGACCAGAGATCAGCCTATCCTGGGATAAGCTCACCCGAGTCACACTGGACCAGGGCTCAGCCTATTCCGGGATGAGCTCACCCG AGTC |
| 83 | C21orf56 | GACACTTCCATGACTGCAGCTGACCAGTCCACCTGCCAGCGGTTGACCACTCCCACTTCGCCAGCGACCGAAGGGAGGGAGGGGC CTCACCTGAGGGCAACAGCAGACAGAACCACCACCACCTGTCTTGCTTTACTCAGACCTGAGGGTGTGAAAGGTGCCCGTGACCTCCCGCATCA GGGAGCTGGCCGCCACCCTCGACTTCCCGGGAGCAGGCGTCTCCCGCGACCCCCTCATCTACCAGGCCATCTGAGCTGGGCGGCCCTC ACCTCCGCTCCCGGGGAGCCGCCTCAGGTAGGCATGCGCCTGGGTGGGAGCAGGTCGTGGCCGCCGCCCTCCTGGCAGCTCT GGCTGAGCAGCCGCCGCAGCCATCTGATTCTCCTTCAGGAGGGCGACCTGCTTCTTCAGGTCCGCGTTCTCGCTCAGGAGCCGGCTCAT CAGCTCGCCGCCTTCAGCCATGGCGGGTGCGTCCCCTTGTCCCTCACGGCTCTGCAGCCCCATGGAGGTGGGAGCCCAGAGCCC GCAGGCACCACAGAAACAGCCCAGGCACGGAGTTCCGTAGCCACCCGAGCCCTTCCACGCCTTGTGATGTCACTGCCCTAGTGATGAGG TGCCCAGCACCCTGCCCCCTGCCCCCGCGATGCTCATGGCCCCGTTGAGGCAGTGAAGCTGGAGGCCGTGGCGTGCACAGGCAGCCAC TCCCACATTATGACCAGGGCCCGAGAATGCCAAGGACATTAGGCAGCTACGGATGTAGCGACTGTACTCCAAGAGGGCGTCCAAGC CACTCCCCATTGA |
| 84 | C21orf58 | ATGTCTGCAGGGAAGAAGCAGGGGGACCCTGAATAAAGTTTCCGTTTTTCCTATTTGTTAAAGTGATAGAGCATTATAGGACCAGAGAAC AGGTGTGTCTGTACACTGTGCAGGTCCCCCGGAGTCCAGGCTCTGCAGTCCGTCTGCACACGGTGCGGGTCCCCGGGTGCCCTGAGCC CGTCTGCACACGGTGCGGGTCCCCGGGCGCCCTGAGCCCGTCTGCACACGGTGCGGGTCCCCGGGCGCCCTGAGCCCGTC TGCACACGGTGCGGGTCCCCGGGCGCCCTGAGCCCGTCTGCACACGGTGCGGGTCCCCGGGGCGCGCCCTGAGCCCCTCTGCA CACGGTGCGGGTCCCCGGGCGCCCGCGCCCTGAGCCCGTCTGTACACGGTGCGGGTCCCCGGGGCGCGCCCTGAGTCTCTACTAAAATA CAAAAATTAGCCAGGCGTGGTGGTTCAAGCCTGTAATCCCAGCTCCTTGGGAGG |

Additional hypomethylated loci are presented in TABLE 4, which includes genomic regions in chromosomes 13, 18 and 21 that are significantly hypomethylated in the placenta when compared to non-pregnant circulating cell free DNA. Additional hypermethylated loci are presented in TABLE 5, which includes genomic regions in chromosomes 13, 18 and 21 that are significantly hypermethylated in the placenta when compared to non-pregnant circulating cell free DNA. Chromosome numbers in TABLE 4 and TABLE 5 are indicated in the column labeled "chr". In TABLE 4 and TABLE 5 chromosome-specific start ("start.pos" in TABLE 4 or "DMR Start" in TABLE 5) and end positions ("end.pos" in TABLE 4 or "DMR End" in TABLE 5)) reference nucleotide base positions from the hg19/GRCh37 build of the human reference genome. Each start and end position marks a specific chromosome region or locus. The data for these regions were obtained by performing whole genome bisulfite sequencing on 5 placenta and 9 non-pregnant ccf DNA samples. The regions are ranked according to the median t-statistic (median.tstat) or mean t-statistic (mean.t-stat) of the region when comparing the methylation status of placenta nucleic acid to non-pregnant ccf DNA. In TABLE 4, a negative median t-statistic value indicates a locus that is less methylated in placenta relative to non-pregnant ccf DNA. In TABLE 5, a negative mean t-statistic value indicates a locus that is more methylated in placenta relative to non-pregnant ccf DNA. In TABLE 4 and TABLE 5 a large negative value (e.g., −17) indicates a greater significant difference in methylation status than a smaller negative value (e.g., −5) for mean or median t-statistic. In TABLE 5, each value in the "mean.diff" column is the difference between a first value and a second value: (i) the first value is the mean of mean methylation levels for CpG sites in the specified region for placenta, and (ii) the second value is the mean of mean methylation levels for CpG sites in the specified region for non-pregnant female plasma samples. The number of CpG sites in each locus is indicated by the column labeled "num.cg" in TABLE 4. The length of each locus is indicated in the column labeled "dmr.size" (TABLE 4) or "size" (TABLE 5). The first column on the left of the table is an internal identifier of each locus.

Example 2

Identification of DMRs

Whole genome bisulfite sequencing (WGBS) was performed, in part to characterize the methylome of ccf DNA from eight non-pregnant and seven pregnant female donors. In addition, seven genomic DNA samples isolated from buffy coat and five placenta samples were sequenced at single base resolution. This produced single-base resolution DNA methylome maps of ccf DNA for each sample type. This analysis demonstrated a link between local DNA methylation levels and ccf DNA fragment size and showed large, continuous regions of hypomethylation in the placenta (Placenta Hypomethylated Domains or PHDs), an epigenetic phenomenon, until recently, only described in tumor samples. Hypomethylated DMRs identified are provided in Table 4 and hypermethylated DMRs identified are provided in Table 5.

Whole genome bisulfite sequencing was performed on a set of unmatched samples including ccf DNA from 8 non-pregnant ((NP; n=8) and 7 pregnant (n=7) female donors and genomic DNA from 7 buffy coat (n=7) and 5 placenta (n=5) samples. CpG cytosines within longer fragments were determined more likely to be methylated, linking DNA methylation and fragment size in ccf DNA. Comparison of the methylomes of placenta and NP ccf DNA revealed many of the 51,259 identified differentially methylated regions (DMRs) were located in domains exhibiting consistent placenta hypomethylation across millions of consecutive bases. These regions were termed placenta hypomethylated domains. DMRs identified when comparing placenta to NP ccf DNA were recapitulated in pregnant ccf DNA, which confirmed the ability to detect differential methylation in ccf DNA mixtures.

Results

Single base resolution methylome maps of ccf DNA isolated from the plasma of 8 non-pregnant female donors were produced using WGBS. About 269-551 million paired monoclonal reads per sample were generated, enabling >10× coverage of 74-92% of the ~28 million genomic CpG sites. Cytosine methylation was evaluated in each of the previously identified genomic contexts (CpG, CHG, and CHH). Almost all cytosine methylation occurred in the CpG context with 74.5-75.3% of all CpG cytosines being methylated; methylation in each of the other contexts was minimal (<0.25%). This data generated eight comprehensive genome-wide CpG cytosine methylation maps of ccf DNA which served as a foundation for subsequent comparisons within this study.

WGBS was performed on DNA obtained from buffy coat cells obtained from 7 distinct female donors. Methylation levels at 37775 CpG sites were confirmed by MassARRAY in an independent cohort of 8 buffy coat samples (Pearson correlation=0.953). Nearly all CpG sites in buffy coat showed either low (9.7%) or high (79.8%) levels of methylation, similar to the distribution in non-pregnant ccf DNA.

Next, the link between histone tail modifications and DNA methylation was examined. Using publically available PBMC ChIP-Seq data from the ENCODE project, CpG methylation in non-pregnant ccf DNA was examined within regions enriched for four distinct histone H3 modifications. In regions enriched for H3K4me3, 89.9% of cytosines showed less than 20% methylation while only 5.2% of unenriched sites were similarly unmethylated. Conversely, 84.9% of CpG sites were methylated (>75%) in H3K9me3 enriched regions as compared to 76.3% in unenriched regions. Distinct differences were also observed when comparing H3K4me1 and H3K27me3 enriched regions to corresponding unenriched CpG sites. Taken together, these data suggested a link between particular histone marks and CpG methylation in buffy coat. Comparison of the methylomes of buffy coat and non-pregnant ccf DNA indicated high similarity (Pearson correlation=0.954)); however, 152 differentially methylated regions (DMRs) (139 more methylated in buffy coat) were detected, suggesting there are additional sources of cell free DNA distinct from buffy coat present in circulation. This data linked histone modifications to CpG methylation in buffy coat and suggested that the majority of ccf DNA is derived from the hematopoetic compartment with minimal contributions from alternative tissues.

Since the fetal portion of ccf DNA in pregnant plasma is derived from the placenta, WGBS of 5 placenta samples was performed to identify placenta specific DMRs. Methylation levels of 37775 CpG sites were also measured using MassARRAY in a separate sample cohort and showed high concordance (Pearson correlation=0.897). Comparison of the distribution of methylation in placenta to the distribution in non-pregnant ccf DNA or buffy coat revealed a significant difference (p<2.2e-16; Kolmogorov-Smirnov Test). While only 15.5% and 10.5% of CpG sites exhibited intermediate methylation (20%-75%) in non-pregnant ccf DNA and buffy coat, respectively, 46.6% of CpG sites showed intermediate methylation in placenta tissue. Comparison of CpG sites between placenta and buffy coat revealed that the majority of the intermediate methylated regions in placenta were highly methylated in both non-pregnant ccf DNA and buffy coat. CpG methylation was compared to gene expression determined by microarray analysis on an independent cohort of 8 placenta samples. Transcription start sites (TSS) were generally unmethylated independent of gene expression level, while promoter and intragenic regions were linked to gene expression.

Differential methylation between placenta and each of the aforementioned sample types was then analyzed. The analysis identified 51,259 DMRs between placenta and non-pregnant ccf DNA, of which 89.5% were more methylated in ccf DNA, consistent with the observed distribution differences (FIG. 5). Using MassARRAY, 243 of the putative DMRs were assayed and 98.8% (240/243) were confirmed ($p<0.05$; Wilcox Rank Sum). Interestingly, these DMRs overlapped with CpG islands in only 7.9% of cases and frequently occurred within intragenic and intergenic regions. In addition, 105,874 DMRs were identified between placenta and buffy coat with a similar overrepresentation (94.7%) of buffy coat specific methylated regions. The majority (93.6%) of DMRs identified between ccf DNA and placenta were also identified as DMRs between placenta and buffy coat. Comparison of methylation between buffy coat and placenta in the context of ENCODE defined histone modifications revealed an interesting pattern. Little difference in methylation was observed within H3K4me3 regions while a dramatic difference occurred in H3K9me3 and H3K27me3 enriched regions. These differences possibly indicated differential histone modification profiles within the placenta relative to buffy coat or differences in the correlation between these marks in the placenta. This data provided a genome-wide map of placenta specific DMRs when compared to either non-pregnant ccf DNA or buffy coat.

Examination of the genomic distribution of differential methylation uncovered large contiguous genomic regions with significant placenta hypomethylation relative to non-pregnant ccf DNA, termed placenta hypomethylated domains (PHDs). PHDs were typically located in gene deserts and were characterized by high, largely invariant levels of DNA methylation in non-pregnant ccf DNA and placenta hypomethylation, often approaching 50%. Using a window size of 50 kbp, PHDs were detected on each autosome that covered as many as ~10 million bases. A number of these regions were located on chromosome 16 with particular focus upon a 10 Mbp PHD located on chromosome 16q. Since the presence of a PHD was consistently observed in regions of relatively low CpG density, the link between CpG density and methylation levels was further examined. Indeed, the magnitude of placenta hypomethylation in relatively low CpG density regions far surpasses that observed in more dense regions. A similar pattern was observed when comparing CpG methylation to gene density. Moreover, the magnitude of differential methylation was linked to the local CpG Density. This data identified large genomic regions which were consistently hypomethylated in the placenta and linked these regions to low CpG and gene density, perhaps underscoring a lack of heterochromatin formation during early placenta development or allele specific methylation of regions with relatively low CpG density in the placenta.

The methylome of ccf DNA derived from the plasma of seven pregnant female donors was measured to determine if the DMRs identified between placenta and non-pregnant ccf DNA could be detected. Overall methylation levels in pregnant and non-pregnant ccf DNA were similar for non-CpG cytosines (<0.25%); however, overall methylation within a CpG context was significantly reduced from 74.5-75.3% to 71.0-74.0% ($p=3e-04$, Wilcoxon rank-sum). Since pregnant ccf DNA comprises maternal and fetal ccf DNA, different methylation patterns were expected between non-pregnant ccf DNA and placenta tissue. To address this, the mean methylation level of each CpG site within DMRs identified between non-pregnant ccf DNA and placenta was evaluated. CpG sites within identified DMRs exhibited significantly ($p<2e-16$; Wilcoxon rank-sum) different methylation levels in pregnant ccf DNA relative to non-pregnant ccf DNA. Hierarchical clustering confirmed these results by clustering pregnant and non-pregnant ccf DNA samples as single branches on a dendrogram. Overall, these data confirmed the differential methylation identified when comparing non-pregnant ccf DNA and placenta tissue.

Previous reports have indicated that fetal ccf DNA is shorter than its maternal counterpart. Since hypomethylation is linked to an open chromatin structure and thus increased accessibility to native endonucleases during apoptosis, the relationship between CpG methylation and ccf DNA length in non-pregnant plasma was assessed to determine if this contributed to the observed size difference. In each of the samples analyzed, the most prominent length was about 168 bp. After accounting for the differences in the number of analyzed bases for each size fraction, CpG cytosines within longer fragments (>200 bp) were found, on average, 12.3-fold more likely to be methylated. Interestingly, a similar pattern was also found for cytosines in the CHG (31.5-fold) and CHH (95.5-fold) contexts, although their overall occurrence was much lower than methylated CpG cytosines. Methyl-CpG immunoprecipitation (MCIp)-Seq was performed on an independent set of two non-pregnant ccf DNA samples to confirm the observed size differences for CpG cytosines. MCIp enabled the separation and collection of both the unmethylated and methylated fractions of a sample. Sequencing both fractions from each sample revealed a distinct size difference with the most striking difference between fractions occurring at ~320 bp, roughly the size of two nucleosomes.

Non-invasive prenatal aneuploidy detection is sometimes linked to the fraction of fetal (placental) DNA in a sample. It was hypothesized that the global hypomethylation of the placenta may allow enrichment of fetal DNA. ccf DNA was isolated from the plasma of 12 pregnant donors, three of which were confirmed to be carrying a fetus affected with trisomy 21, and measured each sample with and without enriching for unmethylated DNA. Data from a subset of placenta hypomethylated regions showed that enriching for unmethylated DNA resulted in a 3.99-fold (range: 2.9-5.9 fold) increase in chromosome 21 z-scores in trisomy 21 samples relative to the same samples without enrichment; one sample from a euploid pregnancy showed a similar level of enrichment (FIG. 6). Overall, while the sample size was small, this data suggested that placenta hypomethylation may be leveraged to increase the effective fetal fraction in pregnant ccf DNA samples.

Discussion

Whole genome methylome maps were created for a total of 27 samples from 4 distinct sample types, enabling a comprehensive characterization of the methylome of ccf DNA from pregnant plasma and each of its primary cellular and non-cellular contributors. A total of 152 DMRs were identified when comparing non-pregnant ccf DNA to DNA isolated from buffy coat, thought to be the primary cellular contributor to this nucleic acid pool. While the DNA methylation patterns were similar (Pearson correlation=0.954), the differences identified were consistent with additional minority contributors to non-pregnant ccf DNA. Sources of additional contributors may include organ systems with extensive bloodstream contact including the kidneys, liver, or endothelium. By comparing placenta to non-pregnant ccf DNA, 51,259 DMRs were identified. While placenta hypermethylated regions were identified across the entire genome, this study also suggested that leveraging the global hypomethylation of the placenta has utility.

While evaluating the genomic distribution of DMRs, large regions of placenta hypomethylation were unexpectedly observed. Further characterization of hypomethylated regions indicated that they were present in regions with low CpG and gene density. Regions with these characteristics were often located within heterochromatin domains, pointing to a reduction in the formation or re-distribution of heterochromatin in the developing placenta. This was supported by the observed decrease in CpG methylation in the placenta within regions containing the H3K9me3 mark in PBMC. The identified PHDs showed characteristics consistent with the partially methylated domains and/or global hypomethylation previously described in cancer subtypes. Commonalities between the placenta and tumors were previously described and included an increased proliferation rate, the ability to migrate, and invasive potential. These data indicated that the parallels between cancer and the placenta extend to their epigenomes and may provide an experimental opportunity for elucidating the molecular source of these similarities. In addition, the similarities suggested that lessons learned from this study may be directly applicable to non-invasive tumor detection and monitoring.

Methods

Blood Processing and DNA Extraction.

Plasma samples were collected under two separate Investigational Review Board (IRB) approved clinical protocols (BioMed IRB 301-01 and Western IRB 20090444). Buffy coat and placenta tissue was collected from consented subjects under a Western IRB approved protocol (20111833, study #1128724) and in accordance with the FDA Guidance on Informed Consent for in vitro Diagnostic Device Studies Using Leftover Human Specimens that are Not Individually Identifiable (Apr. 25, 2006). All subjects provided written informed consent prior to undergoing any study related procedures. All information was anonymized prior to processing. Blood was processed and DNA extracted as previously described (Ehrich M, et al., *Am J Obstet Gynecol* (2011) 204:205 e201-211; Palomaki G E, et al., *Genet Med* (2011) 13:913-920; Jensen T J, et al., *Clin Chem* (2012) 58:1148-1151).

Library Preparation of Ccf DNA

For libraries created from ccf DNA, DNA was subjected to end repair, mono-adenylation, and ligation as previously described (Jensen T J, et al., PLoS One (2013) 8:e57381, Jensen T J, et al., *Clin Chem* (2012) 58:1148-1151). Since ccf DNA exists as small fragments, no size selection was required prior to sequencing and the length of each library insert represents a native DNA fragment length. Ligated products were treated with sodium bisulfite (EpiTect; Qiagen) using a cycling incubation of 95° C. for 5 minutes, 60° C. for 25 minutes, 95° C. for 5 minutes, 60° C. for 85 minutes, 95° C. for 5 minutes, and 60° C. for 175 minutes followed by 3 cycles of 95° C. for 5 minutes, 60° C. for 180 minutes. Each reaction was purified according to the manufacturer's instructions (Qiagen). Converted product was amplified using Pfu Turbo Cx Hotstart DNA polymerase (Agilent) and the TruSeq primer cocktail (Illumina) using the following cycling parameters: 95° C. for 5 minutes; 98° C. for 30 seconds; 14 cycles of 98° C. for 10 seconds, 65° C. for 30 seconds, 72° C. for 30 seconds; and 95° C. for 5 minutes.

Library Preparation of Genomic DNA

For libraries created from buffy coat or placenta tissue, genomic DNA (10 μg) was fragmented by sonication and column purified (Qiagen). Three ligated products were prepared from each sample (2.5 μg each) by performing end repair, mono-adenylation, and adaptor ligation according to the manufacturer's protocol (TruSeq; Illumina). Bead-based purification (AMPure XP; Beckman Coulter) was performed after the end repair and ligation processes. Ligated products were pooled and 2 distinct bisulfite conversion reactions were performed as described above. Eluted products from each sample were pooled and concentrated using a column-based method (Qiagen). Finally, 40% of each converted sample was amplified as described above. PCR products were purified using magnetic beads (AMPure XP; Beckman Coulter).

Methyl-CpG Immunoprecipitation (MCIp) Library Preparation

Ccf DNA was isolated from the plasma of either two non-pregnant female donors or twelve pregnant female donors and subjected to methyl-CpG immunoprecipitation according to the manufacturer's instructions (EpiMark; New England Biolabs). Briefly, DNA was incubated with the MBD-Fc protein in the presence of 150 mM NaCl. DNA which did not bind to the protein was collected and characterized as the unmethylated fraction. The protein-DNA complex was washed three times with 150 mM NaCl and DNA was eluted by heating to 65° C. for 15 minutes. Resultant unmethylated and methylated fractions from each donor sample were subjected to library preparation using a modified version of the manufacturer's protocol. Due to low input amounts, adaptor ligation was performed using a diluted adaptor oligonucleotide (1:10 for unmethylated; 1:100 for methylated). Resultant ligated ccf DNA was amplified using TruSeq PCR Master Mix and TruSeq primer cocktail (Illumina) using the following cycling parameters: 98° C. for 30 seconds; 10 cycles of 98° C. for 10 seconds, 65° C. for 30 seconds, 72° C. for 30 seconds; and 72° C. for 5 minutes.

Massively Parallel Sequencing

Library quantification and flow cell clustering were performed as previously described (Ehrich M, et al., *Am J Obstet Gynecol* (2011) 204:205 e201-211; Palomaki G E, et al., *Genet Med* (2011) 13:913-920; Jensen T J, et al., *Clin Chem* (2012) 58:1148-1151). Paired end sequencing was performed for 100 cycles for all whole genome bisulfite samples and 36 cycles for all MCIp-seq samples.

Whole Genome Bisulfite Sequencing Analysis

Libraries prepared from Phi-X were sequenced upon each flow cell to ensure accurate base calling. All methylation analysis was performed using v0.9.0 of the Illumina bisulfite sequencing analysis program. Bismark v.06.3 (Krueger F, Andrews S R, *Bioinformatics* (2011), 27:1571-1572) was utilized to align each sequenced read to a bisulfite converted human genome (hg19) using Bowtie v.0.12.7 (Langmead B, et al., *Genome Biol.* (2009), 10:R25) and simultaneously perform cytosine methylation calls. Prior to alignment, each read was trimmed to remove contaminating adaptor sequences. Each trimmed sequence read was then aligned to each of four bisulfite converted genomes, each derived from the conversion of each strand and the corresponding complement. Alignment was determined by the single best alignment score to one genome. Methylation was subsequently called for each covered cytosine and summary statistics calculated using the Bismark methylation_extractor script.

MCIp Sequencing Analysis

Data were aligned to a February, 2009 build of the human genome (hg19) allowing for only perfect matches within the seed sequence using Bowtie. All paired reads with an insert size greater than 500 bp or with discordant chromosome mapping results were discarded prior to analysis. Size was calculated as the distance between the start site of each of the two paired end reads.

Post Analysis Processing

Post analysis processing was performed using custom scripts in an R or Perl programming environment. Under the assumption that strand specific methylation is uncommon in ccf DNA, methylation calls mapped to the reverse strand were converted to their corresponding forward strand positions and methylation levels recalculated prior to all analyses. The location of each genomic region was obtained from the hg19 build of the UCSC genome browser. Length of each read was calculated by subtracting the distance of the start position of each paired read. The ENCODE data for the four histone tail modifications in PBMC samples was downloaded as narrowPeak files from the UCSC genome ENCODE site.

DMR Identification

The mean and standard deviation were calculated for each covered CpG site for each sample type. A t-statistic was then calculated for each CpG site for all comparisons. All sites with a t-statistic with an absolute value less than 5 were removed. CpG sites were grouped if there was less than 300 bp between them after t-statistic filtering. A region was then considered a DMR if there were 9 or more CpG sites present.

EpiTYPER (MassARRAY) Analysis

EpiTYPER analysis was performed as previously described (Novak P, et al., PLoS One (2012) 7:e52299). Primers were designed to regions of interest using EpiDesigner software (epidesigner.com). Briefly, genomic DNA sequences were obtained from the UCSC genome browser and loaded in to EpiDesigner. Primer sequences were exported from EpiDesigner and primers were ordered from Integrated DNA Technologies (Coralville, Iowa) and were received after standard desalting at a concentration of 100 µM. Genomic DNA was subjected to sodium bisulfite conversion using the Zymo EZ DNA Methylation Kit (Zymo, Orange, Calif.). EpiTYPER biochemistry was then performed as previously described [29]. Methylation values were exported from EpiTYPER and analysis performed in an R programming environment. Poor quality data were removed prior to further analysis.

Gene Expression Analysis

RNA was extracted from placenta villi according to manufacturer's protocol (Qiagen) and hybridized to Affymetrix Human Exon 1.0 ST microarrays. All raw data files (.CEL) were subjected to rma-sketch normalization using Affymetrix Power Tools scripts. Specifically, expression level was calculated at the whole gene level using the "apt-probeset-summarize" command. Subsequent to normalization, results were merged with the annotation information resulting in a total of 22011 gene expression values. Results were subsequently filtered to remove all transcripts which were not included as part of the main array design (4219) and transcripts without a defined gene (329), leaving a final set of 17,463 genes. Gene positions were downloaded from the UCSC genome browser for both refseq and Ensembl genes and transcription start sites from these tables were used to reflect the TSS of the expressed gene. All genes without a defined TSS as part of the refseq or Ensembl gene lists or those not located on autosomes were discarded, leaving a final set of 16,231 genes. These genes were subsequently tiered into the high (5,410), low (5,411), and intermediate (5,410) expressing genes.

MCIp Trisomy Evaluation

Ccf DNA was extracted from two aliquots of plasma (4 mL each) collected from 12 pregnant female donors, three of which were carrying a fetus affected with trisomy 21. The ccf DNA from each sample was then pooled to minimize any collection bias and subsequently separated into two aliquots. Aliquots were then either left untreated or subjected to MCIp to enrich for unmethylated DNA. Sequencing libraries were prepared and sequenced as described above. All data which aligned within a subset of the identified placenta hypomethylated regions were used for downstream analysis. The median and median absolute deviation (MAD) were calculated using data from known euploid samples only for both unenriched and enriched samples independently. Depending on the group (unenriched vs. enriched), chromosome 21 z-scores were calculated using a robust method as follows: Z=(Chr 21 Fractionsample-Chr 21 FractionMedian)/Chr 21 FractionMAD.

Example 3

Enrichment and Detection of Hypomethylated Nucleic Acid

Nucleic acids containing unmethylated and methylated cytosine residues can be distinguished in a number of ways including, but not limited to, methylation sensitive or methylation specific restriction enzyme treatment, sodium bisulfite conversion, and incubation with a protein, substrate, or other moiety capable of binding methylated or unmethylated DNA with differing affinity, for example an antibody to methylated cytosine or a protein containing a methyl binding domain (MBD).

As described herein, placenta nucleic acid (e.g., fetal nucleic acid derived from placenta) generally is hypomethylated relative to most tissues in the body. This feature of fetal nucleic acid is exploited to enrich a sample of nucleic acid obtained from maternal blood for fetal nucleic acid. A protein capable of distinguishing between methylated and unmethylated DNA can be used to differentially bind to methylated nucleic acid or hypomethylated nucleic acid. A non-limiting example of such a protein is MBD-Fc, which comprises the methyl binding domain of MBD2 fused to the Fc domain of human IgG1 (Gebhard C, et al., (2006) Cancer Res 66:6118-6128).

In a particular enrichment method, circulating cell-free (ccf) DNA is isolated from the plasma of non-pregnant female donors or pregnant female donors and subjected to methyl-CpG immunoprecipitation (e.g., EpiMark; New England Biolabs). Briefly, DNA is incubated with MBD-Fc protein in the presence of 150 mM NaCl. DNA that does not bind to the protein is collected and characterized as the unmethylated fraction. The protein-DNA complex can be washed three times with 150 mM NaCl and DNA can be eluted by heating to 65° C. for 15 minutes, yielding methylated nucleic acid.

Since it has been shown that fetal fraction enhances the ability to discriminate euploid from aneuploid samples in ccf DNA, it stands to reason that such a method would act to increase the discriminatory power of various non-invasive prenatal testing assays, thereby increasing test accuracy. Resultant unmethylated and methylated fractions from each donor sample may be subjected to further biochemical modifications (e.g., library preparation for massively parallel sequencing). Enriched and separated subsets of nucleic acids (e.g., generated as described above), can be analyzed using a number of methods including, but not limited to, massively parallel sequencing, digital PCR, or mass spectrometry.

Example 4

Examples of Embodiments

Listed hereafter are non-limiting examples of certain embodiments of the technology.

A1. A method for analyzing fetal nucleic acid in a sample, comprising:
(a) digesting nucleic acid in a nucleic acid sample from a pregnant female, which nucleic acid comprises fetal nucleic acid and maternal nucleic acid, with one or more methylation sensitive cleavage agents that specifically digest the nucleic acid at non-methylated recognition sites, thereby generating digested nucleic acid fragments; and
(b) analyzing the digested nucleic acid fragments.

A2. The method of embodiment A1, which comprises prior to (b) enriching the digested nucleic acid fragments relative to non-digested nucleic acid, thereby generating nucleic acid enriched for the fetal nucleic acid.

A3. A method for enriching for fetal nucleic acid in a sample, comprising:
(a) digesting nucleic acid in a nucleic acid sample from a pregnant female, which nucleic acid comprises fetal nucleic acid and maternal nucleic acid, with one or more methylation sensitive cleavage agents that specifically digest the nucleic acid at non-methylated recognition sites, thereby generating digested nucleic acid fragments; and
(b) enriching the digested nucleic acid fragments relative to non-digested nucleic acid, thereby generating nucleic acid enriched for the fetal nucleic acid.

A4. The method of embodiment A3, comprising (c) analyzing the enriched fetal nucleic acid.

A4.1. The method of embodiment A1, A2 or A4, wherein the analyzing comprises a target-based analysis.

A4.2. The method of embodiment A1, A2 or A4, wherein the analyzing comprises a non-target-based analysis.

A4.3. The method of any one of embodiments A1, A2 and A4 to A4.2, wherein the analysis comprises sequencing.

A4.4. The method of embodiment A4.3, wherein the sequencing comprises sequencing a portion of the enriched fetal nucleic acid.

A4.5. The method of embodiment A4.4, comprising sequencing a portion of the enriched fetal nucleic acid that is hypomethylated.

A4.6. The method of embodiment A4.4, comprising sequencing a portion of the enriched fetal nucleic acid that is hypermethylated.

A4.7. The method of embodiment A4.3, comprising sequencing substantially all of the enriched fetal nucleic acid.

A4.8. The method of embodiment A4.3, wherein the sequencing method comprises sequencing by synthesis.

A4.9. The method of any one of embodiments A1, A2 and A4 to A4.2, wherein the analyzing comprises mass spectrometry.

A4.10. The method of embodiment A4.9, wherein the mass spectrometry analysis comprises a targeted-mass spectrometry.

A5. The method of any one of embodiments A1, A2 and A4 to A4.10, wherein the analyzing comprises determining the presence or absence of one or more polynucleotides in one or more loci relatively less methylated in fetal nucleic acid than in maternal nucleic acid.

A5.1. The method of any one of embodiments A1, A2 and A4 to A5, wherein the analyzing comprises determining the amount of one or more polynucleotides in one or more loci relatively less methylated in fetal nucleic acid than in maternal nucleic acid.

A5.2. The method of any one of embodiments A1, A2 and A4 to A5, wherein a difference in methylation status between fetal nucleic acid and maternal nucleic acid for the one or more loci relatively less methylated in fetal nucleic acid than in maternal nucleic acid is 5% or more.

A5.2.1. The method of embodiment A5.2, wherein the difference in methylation status between fetal nucleic acid and maternal nucleic acid is determined by a statistical method chosen from a t-test, Z-test, Chi-square, Wilcox, ANOVA, MANOVA, MANCOVA and logistic regression.

A5.2.2. The method of embodiment A5.2.1, wherein the difference in methylation status between fetal nucleic acid and maternal nucleic acid is determined by a t-test.

A5.2.3. The method of embodiment A5.2.2, wherein the difference in methylation status between fetal nucleic acid and maternal nucleic acid for the one or more loci relatively less methylated in fetal nucleic acid than in maternal nucleic acid comprise a median t-statistic between −18.0 and −7.0 or comprise a statistical difference comparable to a t-statistic between −18.0 and −7.0.

A5.3. The method of any one of embodiments A2 to A5.2.3, wherein the nucleic acid enriched for fetal nucleic acid comprise one or more polynucleotides in one or more loci that are 60% or less methylated in fetal nucleic acid and 61% or greater methylated in maternal nucleic acid.

A6. The method of any one of embodiments A5 to A5.3, wherein the one or more loci are chosen from loci in Table 2AB, Table 2CB, Table 3 and Table 4.

A6.1. The method of embodiment A6, wherein the one or more loci are chosen from loci having genomic coordinates from human reference genome hg18, NCBI Build 36.1 of: chr13: 19290394-19290768, chr13: 19887090-19887336; chr13: 20193675-20193897; chr13: 109232856-109235065; chr13: 109716455-109716604; chr13: 112724910-112725742; chr13: 112799123-112799379; chr18: 6919797-6919981; chr18: 13377536-13377654; chr18: 41671477-41673011; chr18: 58203013-58203282; chr18: 70133945-70134397; chr18: 71128742-71128974; chr18: 72664454-72664736; chr18: 74170347-74170489; chr18: 75596358-75596579; chr18: 75760343-75760820; chr21: 33327593-33328334; chr21: 35180938-35185436; chr21: 44529935-44530388; chr21: 45061293-45061853; chr21: 45202815-45202972; chr21: 45671984-45672098; chr21: 45754383-45754487; chr3: 9963364-9964023; chr5: 138757911-138758724; chr6: 35561812-35562252; chr12: 1642456-1642708; chr12: 56406249-56407788; and chr12: 56416146-56418794.

A6.2. The method of embodiment A6, wherein the one or more loci are chosen from loci having genomic coordinates from human reference genome hg18, NCBI Build 36.1 of: chr21: 9906600-9906800; chr21: 9907000-9907400; chr21: 9917800-9918450; chr21: 10010000-10015000; chr21: 13974500-13976000; chr21: 13989500-13992000; chr21: 13998500-14000100; chr21: 14017000-14018500; chr21: 14056400-14058100; chr21: 14070250-14070550; chr21: 14119800-14120400; chr21: 14304800-14306100; chr21: 16881500-16883000; chr21: 17905300-17905500; chr21:

23574000-23574600; chr21: 24366920-24367060; chr21: 25656000-25656900; chr21: 26830750-26830950; chr21: 26938800-26939200; chr21: 30176500-30176750; chr21: 31955000-31955300; chr21: 33272200-33273300; chr21: 33328000-33328500; chr21: 35185000-35186000; chr21: 36589000-36590500; chr21: 42399200-42399900; chr21: 42528400-42528600; chr21: 42598300-42599600; chr21: 42910000-42911000; chr21: 42945500-42946000; chr21: 42961400-42962700; chr21: 42978200-42979800; chr21: 43130800-43131500; chr21: 43446600-43447600; chr21: 43463000-43466100; chr21: 43545000-43546000; chr21: 43606000-43606500; chr21: 43902500-43903800; chr21: 44446500-44447500; chr21: 44614500-44615000; chr21: 44750400-44751000; chr21: 45145500-45146100; chr21: 45501000-45503000; chr21: 45571500-45573700; chr21: 45609000-45610600; chr21: 45670000-45677000; chr21: 45700500-45702000; chr21: 45753000-45755000; chr21: 45885000-45887000; chr21: 46111000-46114000; chr21: 46142000-46144500; chr21: 46227000-46233000; chr21: 46245000-46252000; chr21: 46280500-46283000; chr21: 46343500-46344200; chr21: 46368000-46378000; chr21: 46426700-46427500; and chr21: 46546914-46547404.

A6.3. The method of embodiment A6, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; chr1: 209819233-209819714; chr15: 99270658-99271954; chr9: 110581951-110582676; chr11: 76039765-76040736; chr21: 37607430-37607980; chr2: 100226464-100227140; chr21: 40278885-40279778; chr20: 40125800-40126325; chr14: 96964341-96965236; chr1: 94566367-94567508; chr6: 32120324-32121235; chr6: 2158961-2159107; chr2: 85833089-85833413; chr4: 147936346-147936831; chr2: 33107594-33108530; chr22: 43407118-43407581; chr21: 39492468-39494149; chr9: 124359818-124360534; chr6: 164167085-164167560; chr4: 4674762-4675733; chr1: 23890894-23891476; chr15: 57844015-57844457; chr16: 68766035-68766853; chr1: 234961714-234962041; chr10: 32703471-32704423; chr13: 31100912-31101535; chr2: 216808192-216808391; chr12: 18476876-18477436; chr2: 120818881-120819190; chr19: 38673641-38674608; chr17: 36605585-36606403; chr7: 65736314-65736453; chr13: 51058670-51059041; chr11: 113766137-113766643; chr12: 26265265-26266147; chr5: 109673723-109674226; chr8: 10618285-10618795; chr19: 53244844-53245458; chr11: 105386196-105387277; chr21: 16248092-16248889; chr18: 55795530-55795975; chr3: 64598707-64599348; chr1: 196659363-196660153; chr4: 165952537-165954234; chr12: 124773668-124774705; chr6: 41666010-41666469; chr6: 159237124-159238595; chr9: 108544124-108545341; chr6: 13014688-13016135; chr16: 11443167-11443469; and chr9: 101265123-101265817.

A6.4. The method of embodiment A6, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; and chr1: 209819233-209819714.

A6.5. The method of embodiment A6.5, wherein the one or more loci are chosen from TABLE 4 having a median t-statistic between −18.0 and −9.0.

A6.6. The method of embodiment A6, wherein the one or more loci are chosen from TABLE 4 having a median t-statistic between −18.0 and −10.0.

A6.7. The method of any one of embodiments A1 to A6 and A6.5 to A6.6, wherein the one or more loci are chosen from loci in chromosome 21, 18 or 13.

A6.8. The method of any one of embodiments A5 to A6.7, wherein the one or more loci relatively less methylated in fetal nucleic acid than in maternal nucleic acid comprise a CpG density of about 800 CpG methylation sites per 50,000 base pairs, or less.

A6.9. The method of embodiment A6.8, wherein the CpG density is about 600 CpG methylation sites per 50,000 base pairs, or less.

A6.10. The method of embodiment A6.9, wherein the CpG density is about 400 CpG methylation sites per 50,000 base pairs, or less.

A6.11. The method of embodiment A6.9, wherein the CpG density is about 200 CpG methylation sites per 50,000 base pairs, or less.

A6.12. The method of any one of embodiments A5 to A6.11, wherein the one or more loci relatively less methylated in fetal nucleic acid than in maternal nucleic acid comprise a CpG density of about 16 CpG methylation sites per 1,000 base pairs, or less.

A6.13. The method of embodiment A6.12, wherein the CpG density is about 12 CpG methylation sites per 1,000 base pairs, or less.
A6.14. The method of embodiment A6.13, wherein the CpG density is about 8 CpG methylation sites per 1,000 base pairs, or less.
A6.15. The method of embodiment A6.14, wherein the CpG density is about 4 CpG methylation sites per 1,000 base pairs, or less.
A6.16. The method of any one of embodiments A5 to A6.15, wherein the one or more loci relatively less methylated in fetal nucleic acid than in maternal nucleic acid comprise a CpG density of about 0.016 CpG methylation sites per base pair, or less.
A6.17. The method of embodiment A6.16, wherein the CpG density is about 0.012 CpG methylation sites per base pair, or less.
A6.18. The method of embodiment A6.17, wherein the CpG density is about 0.008 CpG methylation sites per base pair, or less.
A6.19. The method of embodiment A6.18, wherein the CpG density is about 0.004 CpG methylation sites per base pair, or less.
A6.20. The method of any one of embodiments A5 to A6.19, wherein the one or more loci relatively less methylated in fetal nucleic acid contain at least 5 CpG methylation sites.
A6.21. The method of embodiment 6.20, wherein the one or more loci relatively less methylated in fetal nucleic acid contain at least 9 CpG methylation sites.
A6.22. The method of embodiment 6.22, wherein the one or more loci relatively less methylated in fetal nucleic acid contain at least 12 CpG methylation sites.
A6.23. The method of any one of embodiments A5 to A6.22, wherein the one or more loci relatively less methylated in fetal nucleic acid are about 5,000 base pairs or less.
A6.24. The method of embodiment A6.23, wherein the one or more loci relatively less methylated in fetal nucleic acid are about 2,000 base pairs or less.
A6.25. The method of embodiment A6.24, wherein the one or more loci relatively less methylated in fetal nucleic acid are about 1,000 base pairs or less.
A6.26. The method of embodiment A6.25, wherein the one or more loci relatively less methylated in fetal nucleic acid are about 750 base pairs or less.
A6.27. The method of embodiment A6.26, wherein the one or more loci relatively less methylated in fetal nucleic acid are about 500 base pairs or less.
A6.28. The method of embodiment A6.27, wherein the one or more loci relatively less methylated in fetal nucleic acid are about 250 base pairs or less.
A6.29. The method of any one of embodiments A5 to A6.28, wherein the one or more loci relatively less methylated in fetal nucleic acid comprise 0.1 genes per 1000 base pair, or less.
A6.30. The method of any one of embodiments A5 to A6.28, wherein the one or more loci relatively less methylated in fetal nucleic acid comprise 0.08 genes per 1000 base pair, or less.
A6.31. The method of any one of embodiments A5 to A6.28, wherein the one or more loci relatively less methylated in fetal nucleic acid comprise 0.06 genes per 1000 base pair, or less.
A6.32. The method of any one of embodiments A5 to A6.28, wherein the one or more loci relatively less methylated in fetal nucleic acid comprise 0.04 genes per 1000 base pair, or less.
A6.33. The method of any one of embodiments A5 to A6.28, wherein the one or more loci relatively less methylated in fetal nucleic acid comprise 0.02 genes per 1000 base pair, or less.
A6.34. The method of any one of embodiments A5 to A6.33, wherein each of the one or more loci relatively less methylated in fetal nucleic acid comprise at least 1 restriction endonuclease recognition sites per 1000 bp, wherein each of the at least one restriction endonuclease recognition sites can be specifically digested by at least one of the one or more methylation sensitive cleavage agents when the restriction endonuclease recognition site is non-methylated.
A6.35. The method of any one of embodiments A5 to A6.33, wherein each of the one or more loci relatively less methylated in fetal nucleic acid comprise at least 10 restriction endonuclease recognition sites per 1000 bp, wherein each of the at least one restriction endonuclease recognition site can be specifically digested by at least one of the one or more methylation sensitive cleavage agents when the restriction endonuclease recognition site is non-methylated.
A6.36. The method of any one of embodiments A5 to A6.33, wherein each of the one or more loci relatively less methylated in fetal nucleic acid comprise at least 20 restriction endonuclease recognition sites per 1000 bp, wherein each of the at least one restriction endonuclease recognition site can be specifically digested by at least one of the one or more methylation sensitive cleavage agents when the restriction endonuclease recognition site is non-methylated.
A6.37. The method of any one of embodiments A5 to A6.33, wherein each of the one or more loci relatively less methylated in fetal nucleic acid comprise at least 30 restriction endonuclease recognition sites per 1000 bp, wherein each of the at least one restriction endonuclease recognition site can be specifically digested by at least one of the one or more methylation sensitive cleavage agents when the restriction endonuclease recognition site is non-methylated.
A7. The method of embodiment A6.8, wherein the one or more loci are chosen from chromosome 13 in TABLE 4.
A7.1. The method of embodiment A6.8, wherein the one or more loci are chosen from chromosome 18 in TABLE 4.
A7.2. The method of embodiment A6.8, wherein the one or more loci are chosen from chromosome 21 in TABLE 4.
A7.3. The method of any one of embodiments A5 to A7.2, wherein the one or more loci one or more loci that are 60% or less methylated in fetal nucleic acid and 61% or greater methylated in maternal nucleic acid.
A7.4. The method of embodiment A7.3, wherein the loci are 70% or more methylated in the maternal nucleic acid.
A7.5. The method of embodiment A7.4, wherein the loci are 75% or more methylated in the maternal nucleic acid.
A7.6. The method of embodiment A7.5, wherein the loci are 80% or more methylated in the maternal nucleic acid.
A7.7. The method of any one of embodiments A5 to A7.6, wherein the one or more loci relatively less methylated in fetal nucleic acid than in maternal nucleic acid are 40% or less methylated in the fetal nucleic acid.
A7.8. The method of embodiment A7.7, wherein the loci are 30% or less methylated in the fetal nucleic acid.
A7.9. The method of embodiment A7.8, wherein the loci are 20% or less methylated in the fetal nucleic acid.
A7.10. The method of embodiment A7.9, wherein the loci are 10% or less methylated in the fetal nucleic acid.
A7.11. The method of any one of embodiments A5 to A7.10, wherein a difference in methylation status between fetal nucleic acid and maternal nucleic acid for the one or more loci relatively less methylated in fetal nucleic acid than in maternal nucleic acid is 5% or more.

A7.12. The method of embodiment A7.11, wherein a difference in methylation status is 10% or more.
A7.13. The method of embodiment A7.12, wherein a difference in methylation status is 20% or more.
A7.14. The method of embodiment A7.13, wherein a difference in methylation status is 40% or more.
A8. The method of any one of embodiments A2 to A7.10, wherein the enriching comprises selectively separating the digested nucleic acid fragments from non-digested nucleic acid.
A9. The method of embodiment A8, wherein the digested nucleic acid fragments are selectively separated according to molecular weight.
A9.1. The method of embodiment A8, wherein the digested nucleic acid fragments are selectively separated according to size.
A10. The method of any one of embodiments A8 to A9.1, wherein the digested nucleic acid fragments are selectively separated by a process comprising polyethylene glycol mediated precipitation.
A11. The method of any one of embodiments A8 to A9.1, wherein the digested nucleic acid fragments are selectively separated by a process comprising size exclusion chromatography.
A12. The method of embodiment A8, wherein the digested nucleic acid fragments are selectively separated by a process comprising contacting the fragments with a methyl-specific binding agent.
A12.1. The method of embodiment A12, wherein the contacting the fragments with the methyl-specific binding agent provides bound nucleic acid fragments and unbound nucleic acid fragments.
A12.2. The method of embodiment A12.1, wherein the bound nucleic acid fragments are selectively separated from the unbound nucleic acid fragments.
A12.3. The method of embodiments A12.1, comprising exposing the bound nucleic acid fragments, or a portion thereof, to conditions that dissociate the bound nucleic acids from the methyl-specific binding agent thereby providing one or more elution products.
A13. The method of any one of embodiments A12 to A12.3, wherein the methyl-specific binding agent comprises an antibody or a portion thereof
A14. The method of embodiment A13, wherein the antibody specifically binds an unmethylated portion of one or more nucleic acid fragments in the sample.
A15. The method of embodiment A13, wherein the antibody specifically binds a methylated portion of one or more nucleic acid fragments in the sample.
A16. The method of any one of embodiments A12 to A12.2, wherein the methyl-specific binding agent comprises a methyl-CpG binding domain protein or a portion thereof.
A17. The method of embodiment A16, wherein the methyl-CpG binding domain protein is chosen from MeCP2, MBD1, MBD2, MBD3 and MBD4.
A18. The method of any one of embodiments A1 to A17, wherein the one or more methylation sensitive cleavage agents comprise one or more restriction endonucleases.
A19. The method of embodiment A18, wherein the one or more restriction endonucleases are selected from a Type I, Type II, Type III, Type IV or Type V restriction endonuclease.
A20. The method of embodiment A18 or A19, wherein the one or more restriction endonucleases recognize or bind to a recognition sequence comprising 6 base pairs or less.
A21. The method of embodiment A18 or A19, wherein the one or more restriction endonucleases recognize or bind to a recognition sequence comprising 4 base pairs or less.
A22. The method of any one of embodiments A18 to A21, wherein the one or more restriction endonucleases produce overhangs.
A23. The method of any one of embodiments A22, wherein each of the digested nucleic acid fragments comprises one or more unpaired nucleotides at the 5' or 3' end of the fragment.
A24. The method of any one of embodiments A18 to A21, wherein the one or more restriction endonucleases produce blunt ends.
A25 The method of any one of embodiments A18 to A23, wherein one or more of the restriction endonucleases are selected from HHAI, HinP11 and HPAII.
A26 The method of any one of embodiments A18 to A25, wherein the average, mean, median or nominal length of the digested nucleic acid fragments is about 40 bases to about 100 bases.
A27. The method of any one of embodiments A2 to A26, wherein the enriching in (b) comprises amplifying the digested nucleic acid fragments relative to the non-digested nucleic acid.
A28. The method of any one of embodiments A1 to A27, wherein the digested nucleic acid fragments are amplified by a process comprising ligating one or more adaptors to one or both ends of each of the digested nucleic acid fragments.
A29. The method of embodiment A28, wherein the ligating comprises a blunt end ligation.
A30. The method of embodiment A28 or A29, comprising ligating the one or more adaptors to one or more unpaired nucleotides at the 5' or 3' end of the digested nucleic acid fragments.
A31. The method of any one of embodiments A28 to A30, wherein the one or more adaptors comprise one or more capture agents.
A32. The method of embodiment A31, wherein the one or more capture agents are selected from an antibody, an antigen and a member of a binding pair.
A33. The method of embodiment A31 or A32, wherein the one or more capture agents comprise biotin.
A34. The method of any one of embodiments A27 to A33, wherein the digested nucleic acid fragments are amplified by a process comprising a bridge amplification.
A35. The method of any one of embodiments A1 to A34, wherein the nucleic acid from the pregnant female comprises cell-free circulating nucleic acid.
A36. The method of embodiment A35, wherein the nucleic acid is from blood serum, blood plasma or urine.
A37. The method of any one of embodiments A1, A2 and A4 to A36, wherein the analyzing comprises determining an amount of fetal nucleic acid in the nucleic acid sample.
A38. The method of embodiment A37, wherein determining the amount of fetal nucleic acid comprises determining a ratio of fetal nucleic acid to a total amount of nucleic acid in the sample.
A39. The method of embodiment A38, wherein the ratio is a percent representation.
A40. The method of any one of embodiments A1, A2 and A4 to A39, wherein the analyzing comprises determining the presence of absence of a fetal aneuploidy.
A41. The method of embodiment A40, wherein the fetal aneuploidy is a trisomy.
A42. The method of embodiment A41, wherein the trisomy is a trisomy of chromosome 13, 18 or 21.

A43. The method of any one of embodiments A1, A2 and A4 to A42, wherein the analyzing comprises non-targeted sequencing of the digested nucleic acid fragments or modified variant thereof.

A44. The method of any one of embodiments A1, A2 and A4 to A42, wherein the analyzing comprises targeted sequencing of the digested nucleic acid fragments or a modified variant thereof.

A45. The method of any one of embodiments A1 to A44, which comprises contacting the digested nucleic acid fragments with an agent that modifies a methylated nucleotide to another moiety.

A46. The method of any one of embodiments A40 to A45, wherein determining the presence or absence of a fetal aneuploidy comprises obtaining counts of sequence reads mapped to portions of a reference genome, which sequence reads are normalized and which sequence reads are from the enriched hypomethylated nucleic acid or the enriched hypermethylated nucleic acid.

A47. The method of embodiment A46, wherein determining the presence or absence of a fetal aneuploidy comprises comparing the normalized counts of sequence reads for a target chromosome to the normalized counts of sequence reads for the reference chromosome, whereby a statistically significant difference between the counts for the target chromosome and the counts for the reference chromosome determines the presence of a fetal aneuploidy.

A48. The method of embodiment A47, wherein counts of sequence reads of about 3 to about 15 loci on the target chromosome and the reference chromosome is determined.

A49. The method of embodiment A47, wherein counts of sequence reads of about 16 or more loci on the target chromosome and the reference chromosome is determined.

A50. The method of any one of embodiments A37 to A49, wherein determining the amount of fetal nucleic acid comprises use of a mass spectrometry method.

A51. The method of any one of embodiments A37 to A49, wherein determining the amount of fetal nucleic acid comprises use of a sequencing method.

B1. A method for analyzing nucleic acid in a sample, comprising:
(a) enriching for hypomethylated nucleic acid present in a nucleic acid sample from a pregnant female, which nucleic acid comprises fetal nucleic acid and maternal nucleic acid, thereby generating enriched hypomethylated nucleic acid; and
(b) analyzing the enriched hypomethylated nucleic acid, which analyzing comprises determining the presence, absence or amount of a polynucleotide in one or more loci chosen from loci of Table 4.

B2. The method of embodiment B1, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; chr1: 209819233-209819714; chr15: 99270658-99271954; chr9: 110581951-110582676; chr11: 76039765-76040736; chr21: 37607430-37607980; chr2: 100226464-100227140; chr21: 40278885-40279778; chr20: 40125800-40126325; chr14: 96964341-96965236; chr1: 94566367-94567508; chr6: 32120324-32121235; chr6: 2158961-2159107; chr2: 85833089-85833413; chr4: 147936346-147936831; chr2: 33107594-33108530; chr22: 43407118-43407581; chr21: 39492468-39494149; chr9: 124359818-124360534; chr6: 164167085-164167560; chr4: 4674762-4675733; chr1: 23890894-23891476; chr15: 57844015-57844457; chr16: 68766035-68766853; chr1: 234961714-234962041; chr10: 32703471-32704423; chr13: 31100912-31101535; chr2: 216808192-216808391; chr12: 18476876-18477436; chr12: 120818881-120819190; chr19: 38673641-38674608; chr17: 36605585-36606403; chr7: 65736314-65736453; chr13: 51058670-51059041; chr11: 113766137-113766643; chr12: 26265265-26266147; chr5: 109673723-109674226; chr8: 10618285-10618795; chr19: 53244844-53245458; chr11: 105386196-105387277; chr21: 16248092-16248889; chr18: 55795530-55795975; chr3: 64598707-64599348; chr1: 196659363-196660153; chr4: 165952537-165954234; chr12: 124773668-124774705; chr6: 41666010-41666469; chr6: 159237124-159238595; chr9: 108544124-108545341; chr6: 13014688-13016135; chr16: 11443167-11443469; and chr9: 101265123-101265817.

B3. The method of embodiment B1, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; and chr1: 209819233-209819714.

B4. The method of embodiment B1, wherein the one or more loci are chosen from TABLE 4 having a median t-statistic between −18.0 and −7.0.
B5. The method of embodiment B1, wherein the one or more loci are chosen from TABLE 4 having a median t-statistic between −18.0 and −9.0.
B6. The method of embodiment B1, wherein the one or more loci are chosen from TABLE 4 having a median t-statistic between −18.0 and −10.0.
B6.1. The method of any one of embodiments B4 to B6, wherein the median t-statistic is determined by a t-test.
B7. The method of any one of embodiments B1 to B6.1, wherein the one or more loci are chosen from loci in chromosome 21, 18 or 13.
B8. The method of embodiment B7, wherein the one or more loci are chosen from chromosome 13 in TABLE 4.
B9. The method of embodiment B7, wherein the one or more loci are chosen from chromosome 18 in TABLE 4.
B10. The method of embodiment B7, wherein the one or more loci are chosen from chromosome 21 in TABLE 4.
B11. The method of any one of embodiments B1 to B10.2, wherein the one or more loci are relatively less methylated in fetal nucleic acid than in maternal nucleic acid.
B11.1. The method of any one of embodiments B11, wherein the one or more loci relatively less methylated in fetal nucleic acid than in maternal nucleic acid comprise a CpG density of about 800 CpG methylation sites per 50,000 base pairs, or less.
B11.2. The method of embodiment B11.1, wherein the CpG density is about 600 CpG methylation sites per 50,000 base pairs, or less.
B11.3. The method of embodiment B11.2, wherein the CpG density is about 400 CpG methylation sites per 50,000 base pairs, or less.
B11.4. The method of embodiment B11.3, wherein the CpG density is about 200 CpG methylation sites per 50,000 base pairs, or less.
B11.5. The method of any one of embodiments B11 to B11.4, wherein the one or more loci relatively less methylated in fetal nucleic acid than in maternal nucleic acid comprise a CpG density of about 16 CpG methylation sites per 1,000 base pairs, or less.
B11.6. The method of embodiment B11.5, wherein the CpG density is about 12 CpG methylation sites per 1,000 base pairs, or less.
B11.7. The method of embodiment B11.6, wherein the CpG density is about 8 CpG methylation sites per 1,000 base pairs, or less.
B11.8. The method of embodiment B11.7, wherein the CpG density is about 4 CpG methylation sites per 1,000 base pairs, or less.
B11.9. The method of any one of embodiments B11 to B11.8, wherein the one or more loci relatively less methylated in fetal nucleic acid than in maternal nucleic acid comprise a CpG density of about 0.016 CpG methylation sites per base pair, or less.
B11.10. The method of embodiment B11.9, wherein the CpG density is about 0.012 CpG methylation sites per base pair, or less.
B11.11. The method of embodiment B11.10, wherein the CpG density is about 0.008 CpG methylation sites per base pair, or less.
B11.12. The method of embodiment B11.11, wherein the CpG density is about 0.004 CpG methylation sites per base pair, or less.
B11.13. The method of any one of embodiments B11 to B11.12, wherein the one or more loci relatively less methylated in fetal nucleic acid contain at least 5 CpG methylation sites.
B11.14. The method of embodiment B11.13, wherein the one or more loci relatively less methylated in fetal nucleic acid contain at least 9 CpG methylation sites.
B11.15. The method of embodiment B11.14, wherein the one or more loci relatively less methylated in fetal nucleic acid contain at least 12 CpG methylation sites.
B11.16. The method of any one of embodiments B11 to B11.15, wherein the one or more loci relatively less methylated in fetal nucleic acid are about 5,000 base pairs or less.
B11.17. The method of embodiment B11.16, wherein the one or more loci relatively less methylated in fetal nucleic acid are about 2,000 base pairs or less.
B11.18. The method of embodiment B11.17, wherein the one or more loci relatively less methylated in fetal nucleic acid are about 1,000 base pairs or less.
B11.19. The method of embodiment B11.18, wherein the one or more loci relatively less methylated in fetal nucleic acid are about 750 base pairs or less.
B11.20. The method of embodiment B11.19, wherein the one or more loci relatively less methylated in fetal nucleic acid are about 500 base pairs or less.
B11.21. The method of embodiment B11.20, wherein the one or more loci relatively less methylated in fetal nucleic acid are about 250 base pairs or less.
B11.22. The method of any one of embodiments B11 to B11.21, wherein the one or more loci relatively less methylated in fetal nucleic acid comprise 0.1 genes per 1000 base pair, or less.
B11.23. The method of embodiment B11.22, wherein the one or more loci relatively less methylated in fetal nucleic acid comprise 0.08 genes per 1000 base pair, or less.
B11.24. The method of embodiment B11.23, wherein the one or more loci relatively less methylated in fetal nucleic acid comprise 0.06 genes per 1000 base pair, or less.
B11.25. The method of embodiment B11.24, wherein the one or more loci relatively less methylated in fetal nucleic acid comprise 0.04 genes per 1000 base pair, or less.
B11.26. The method of embodiment B11.25, wherein the one or more loci relatively less methylated in fetal nucleic acid comprise 0.02 genes per 1000 base pair, or less.
B11.27. The method of any one of embodiments B11 to B11.26, wherein each of the one or more loci relatively less methylated in fetal nucleic acid comprise at least 1 restriction endonuclease recognition sites per 1000 bp, wherein each of the at least one restriction endonuclease recognition sites can be specifically digested by at least one of the one or more methylation sensitive cleavage agents when the restriction endonuclease recognition site is non-methylated.
B11.28. The method of embodiment B11.27, wherein each of the one or more loci relatively less methylated in fetal nucleic acid comprise at least 10 restriction endonuclease recognition sites per 1000 bp.
B11.29. The method of embodiment B11.28, wherein each of the one or more loci relatively less methylated in fetal nucleic acid comprise at least 20 restriction endonuclease recognition sites per 1000 bp.
B11.30. The method of embodiment B11.29, wherein each of the one or more loci relatively less methylated in fetal nucleic acid comprise at least 30 restriction endonuclease recognition sites per 1000 bp.
B12. The method of any one of embodiments B1 to B11.30, wherein the analyzing comprises determining the presence or absence of one or more polynucleotides in the one or more loci relatively less methylated in fetal nucleic acid than in maternal nucleic acid.

B13. The method of any one of embodiments B1 to B12, wherein the analyzing comprises determining the amount of one or more polynucleotides in the one or more loci relatively less methylated in fetal nucleic acid than in maternal nucleic acid.

B14. The method of any one of embodiments B11 to B13, wherein a difference in methylation status between fetal nucleic acid and maternal nucleic acid for the one or more loci relatively less methylated in fetal nucleic acid than in maternal nucleic acid is 5% or more.

B14.1. The method of embodiment B14, wherein a difference in methylation status is 10% or more.

B14.2. The method of embodiment B14.1, wherein a difference in methylation status is 20% or more.

B14.3. The method of embodiment B14.2, wherein a difference in methylation status is 40% or more.

B14.4. The method of any one of embodiments B14 to B14.3, wherein the difference in methylation status between fetal nucleic acid and maternal nucleic acid is determined by a statistical method chosen from a t-test, Z-test, Chi-square, Wilcox, ANOVA, MANOVA, MANCOVA and logistic regression.

B14.5. The method of embodiment B14.4, wherein the difference in methylation status between fetal nucleic acid and maternal nucleic acid is determined by a t-test.

B14.6. The method of embodiment B14.5, wherein the difference in methylation status between fetal nucleic acid and maternal nucleic acid for the one or more loci relatively less methylated in fetal nucleic acid than in maternal nucleic acid comprise a median t-statistic between −18.0 and −7.0 or comprise a statistical difference comparable to a t-statistic between −18.0 and −7.0.

B15. The method of any one of embodiments B1 to B14.6, wherein the nucleic acid enriched for hypomethylated nucleic acid comprise one or more polynucleotides in one or more loci that are 60% or less methylated in fetal nucleic acid than in maternal nucleic acid.

B16. The method of any one of embodiments B11 to B15, wherein the one or more loci relatively less methylated in fetal nucleic acid than in maternal nucleic acid are 60% or more methylated in the maternal nucleic acid.

B16.1. The method of embodiment B16, wherein the loci are 70% or more methylated in maternal nucleic acid.

B16.2. The method of embodiment B16.1, wherein the loci are 75% or more methylated in maternal nucleic acid.

B16.3. The method of embodiment B16.2, wherein the loci are 80% or more methylated in maternal nucleic acid.

B16.4. The method of any one of embodiments B11 to B16.3, wherein the one or more loci relatively less methylated in fetal nucleic acid than in maternal nucleic acid are 40% or less methylated in fetal nucleic acid.

B16.5. The method of embodiment B16.4, wherein the loci are 30% or less methylated in fetal nucleic acid.

B16.6. The method of embodiment B16.5, wherein the loci are 20% or less methylated in fetal nucleic acid.

B16.7. The method of embodiment B16.6, wherein the loci are 10% or less methylated in fetal nucleic acid.

B17. A method for analyzing nucleic acid in a sample, comprising:
(a) enriching for hypomethylated nucleic acid present in a nucleic acid sample from a pregnant female, which nucleic acid comprises fetal nucleic acid and maternal nucleic acid; thereby generating enriched hypomethylated nucleic acid; and (b) analyzing the enriched hypomethylated nucleic acid, which analyzing comprises non-targeted analysis of substantially all of the hypomethylated nucleic acid.

B18. The method of any one of embodiments B1 to B17, wherein the enriching comprises exposing the nucleic acid sample to conditions that selectively separate the hypomethylated nucleic acid from methylated nucleic acid.

B19. The method of embodiment B18, wherein the enriching comprises contacting the nucleic acid in the nucleic acid sample with a binding agent that specifically associates with methylated nucleic acid, thereby generating separated and enriched hypomethylated nucleic acid.

B19.1. The method of embodiment B19, wherein the contacting the fragments with the binding agent provides bound nucleic acid fragments and unbound nucleic acid fragments.

B19.2. The method of embodiment B19.1, wherein the bound nucleic acid fragments are selectively separated from the unbound nucleic acid fragments.

B19.3. The method of embodiments B19.1, comprising exposing the bound nucleic acid fragments, or a portion thereof, to conditions that dissociate the bound nucleic acids from the binding agent thereby providing one or more elution products.

B20. The method of any one of embodiments B19 to B19.3, comprising amplifying the separated and enriched hypomethylated nucleic acid.

B21. The method of embodiment B20, wherein the amplification comprises ligating one or more adaptors to the enriched hypomethylated nucleic acid.

B22. The method of embodiment B20 or B21, wherein the amplifying comprises a targeted amplification.

B23. The method of embodiment B21 or B22, wherein the one or more adaptors comprise a capture agent.

B24. The method of any one of embodiments B20 to B23, wherein the enriched nucleic acid is amplified by a process comprising a bridge amplification.

B25. The method of any one of embodiments B18 to B24, wherein the conditions that separate hypomethylated nucleic acid from methylated nucleic acid comprise binding substantially all of the nucleic acid in the nucleic acid sample and selectively eluting the hypomethylated nucleic acid.

B26. The method of any one of embodiments B19.1 to B24, wherein the conditions that separate hypomethylated nucleic acid from methylated nucleic acid comprise binding substantially all of the methylated nucleic acid in the nucleic acid sample, wherein the unbound nucleic acid fragments comprises enriched hypomethylated nucleic acid.

B27. The method of any one of embodiments B19 to B26, wherein the binding agent, or a portion thereof, comprises a methyl-specific binding agent.

B28. The method of embodiment B27, wherein the methyl-specific binding agent comprises an antibody or a portion thereof.

B29. The method of embodiment B28, wherein the antibody, or portion thereof, specifically binds an unmethylated portion of one or more nucleic acid in the sample.

B30. The method of embodiment B28, wherein the antibody, or portion thereof, specifically binds a methylated portion of one or more nucleic acids in the sample.

B31. The method of embodiment B27, wherein the methyl-specific binding agent comprises a methyl-CpG binding domain protein or a portion thereof.

B32. The method of embodiments B27 or B31, wherein the methyl-CpG binding domain protein is chosen from MeCP2, MBD1, MBD2, MBD3 and MBD4.

B33. The method of any one of embodiments B1 to B32, wherein the enriching comprises digesting the nucleic acid sample with one or more methylation sensitive cleavage agents that specifically digest the nucleic acids at a recognition site comprising a methylation site.

B34. The method of B32 or B33, wherein the digesting produces digested nucleic acid fragment and non-digested nucleic acid fragments.

B35. The method of embodiment B34, wherein the enriching comprises selectively separating the digested nucleic acid fragments from non-digested nucleic acid.

B36. The method of any one of embodiments B33 to B35, wherein the one or more methylation sensitive cleavage agents comprise one or more restriction endonucleases.

B36.1. The method of embodiment B36, wherein the one or more restriction endonucleases digest the nucleic acids at an unmethylated methylation site.

B36.2. The method of embodiment B36, wherein the one or more restriction endonucleases digest the nucleic acids at a methylated methylation site.

B37. The method of any one of embodiments B36 to B36.2, wherein the one or more restriction endonucleases are selected from a Type I, Type II, Type III, Type IV or Type V restriction endonuclease.

B38. The method of any one of embodiments B36 to B37, wherein the one or more restriction endonucleases recognize or bind to a recognition sequence comprising 6 base pairs or less.

B39. The method of any one of embodiments B36 to B38, wherein the one or more restriction endonucleases recognize or bind to a recognition sequence comprising 4 base pairs or less.

B40. The method of any one of embodiments B36 to B39, wherein the one or more restriction endonucleases produce overhangs.

B41. The method of embodiment B40, wherein each of the digested nucleic acid fragments comprises one or more unpaired nucleotides at the 5' or 3' end of the fragment.

B42. The method of any one of embodiments B36 to B41, wherein one or more of the restriction endonucleases are selected from HHAI, HinP1I and HPAII.

B43. The method of any one of embodiments B36 to B39, wherein the one or more restriction endonucleases produce blunt ends.

B44. The method of any one of embodiments B36 to B43, wherein the average, mean, median or nominal length of the digested nucleic acid fragments is about 40 bases to about 100 bases.

B45. The method of any one of embodiments B34 to B44, wherein the enriching comprises amplifying the digested nucleic acid fragments relative to the non-digested nucleic acid.

B46. The method of embodiment B45, wherein the digested nucleic acid fragments are amplified by a process comprising ligating one or more adaptors to one or both ends of each of the digested nucleic acid fragments.

B47. The method of embodiment B46, wherein the ligating comprises a blunt end ligation.

B48. The method of embodiment B46 or B47, comprising ligating the one or more adaptors to one or more unpaired nucleotides at the 5' or 3' end of the digested nucleic acid fragments.

B49. The method of any one of embodiments B46 to B48, wherein the one or more adaptors comprise one or more capture agents.

B50. The method of embodiment B49, wherein the one or more capture agents are selected from an antibody, an antigen and a member of a binding pair.

B51. The method of embodiment B49 or B50, wherein the one or more capture agents comprise biotin.

B52. The method of any one of embodiments B45 to B51, wherein the digested nucleic acid fragments are amplified by a process comprising a bridge amplification.

B53. The method of any one of embodiments B1 to B52, wherein the nucleic acid from the pregnant female comprises cell-free circulating nucleic acid.

B54. The method of embodiment B53, wherein the nucleic acid is from blood serum, blood plasma or urine.

B55. The method of any one of embodiments B1 to B54, wherein the analyzing comprises determining an amount of fetal nucleic acid in the nucleic acid sample.

B56. The method of embodiment B55, wherein determining the amount of fetal nucleic acid comprises determining a ratio of fetal nucleic acid to a total amount of nucleic acid in the sample.

B57. The method of embodiment B56, wherein the ratio is a percent representation.

B58. The method of any one of embodiments B1 to B57, wherein the analyzing comprises determining the presence of absence of a fetal aneuploidy.

B59. The method of embodiment B58, wherein the fetal aneuploidy is a trisomy.

B60. The method of embodiment B59, wherein the trisomy is a trisomy of chromosome 13, 18 or 21.

B61. The method of any one of embodiments B1 to B60, wherein the analyzing comprises a target-based approach.

B62. The method of any one of embodiments B1 to B60, wherein the analyzing comprises a non-target-based approach.

B63. The method of any one of embodiments B1 to B62, wherein the analyzing comprises sequencing the enriched hypomethylated nucleic acid, or a portion thereof or sequencing the enriched hypermethylated nucleic acid, or a portion thereof.

B64. The method of embodiment B63, where the sequencing comprises non-targeted sequencing.

B65. The method of embodiment B63, where the sequencing comprises targeted sequencing.

B66. The method of any one of embodiments B1 to B65, which comprises contacting the enriched hypomethylated nucleic acid or the enriched hypermethylated nucleic acid with an agent that modifies a methylated nucleotide to another moiety.

B67. The method of any one of embodiments B58 to B66, wherein determining the presence or absence of a fetal aneuploidy comprises obtaining counts of sequence reads mapped to portions of a reference genome, which sequence reads are normalized and which sequence reads are from the enriched hypomethylated nucleic acid or the enriched hypermethylated nucleic acid.

B68. The method of embodiment B67, wherein determining the presence or absence of a fetal aneuploidy comprises comparing the normalized counts of sequence reads for a target chromosome to the normalized counts of sequence reads for the reference chromosome, whereby a statistically significant difference between the counts for the target chromosome and the counts for the reference chromosome determines the presence of a fetal aneuploidy.

B69. The method of embodiment B68, wherein counts of sequence reads of about 3 to about 15 loci on the target chromosome and the reference chromosome is determined.

B70. The method of embodiment B68, wherein counts of sequence reads of about 16 or more loci on the target chromosome and the reference chromosome is determined.

B71. The method of any one of embodiments B55 to B70, wherein determining the amount of fetal nucleic acid comprises use of a mass spectrometry method.

B72. The method of any one of embodiments B55 to B70, wherein determining the amount of fetal nucleic acid comprises use of a sequencing method.

B73. The method of embodiment B72, wherein the sequencing method comprises sequencing by synthesis.

B74. The method of any one of embodiments B1 to B73, wherein the analyzing comprises mass spectrometry.

B75. The method of embodiment B74, wherein the mass spectrometry analysis comprises a targeted-mass spectrometry.

C1. A method for enriching for a minority nucleic acid species in a sample, comprising:
(a) digesting nucleic acid in a nucleic acid sample from a pregnant female, which nucleic acid comprises a minority nucleic acid species and a majority nucleic acid species, with one or more methylation sensitive cleavage agents that specifically digest the nucleic acid at non-methylated recognition sites, thereby generating digested nucleic acid fragments; and
(b) analyzing the digested nucleic acid fragments.

C2. The method of embodiment C1, which comprises prior to (b) enriching the digested nucleic acid fragments relative to non-digested nucleic acid, thereby generating nucleic acid enriched for the minority nucleic acid species.

C3. A method for enriching for a minority nucleic acid species in a sample, comprising:
(a) digesting nucleic acid in a nucleic acid sample from a pregnant female, which nucleic acid comprises a minority nucleic acid species and a majority nucleic acid species, with one or more methylation sensitive cleavage agents that specifically digest the nucleic acid at non-methylated recognition sites, thereby generating digested nucleic acid fragments; and
(b) enriching the digested nucleic acid fragments relative to non-digested nucleic acid, thereby generating nucleic acid enriched for the minority nucleic acid species.

C4. The method of embodiment C3, comprising (c) analyzing the enriched minority nucleic acid species.

C4.1. The method of embodiment C1, C2 or C4, wherein the analyzing comprises a target-based analysis.

C4.2. The method of embodiment C1, C2 or C4, wherein the analyzing comprises a non-target-based analysis.

C4.3. The method of any one of embodiments C1, C2 and C4 to C4.2, wherein the analysis comprises sequencing.

C4.4. The method of embodiment C4.3, wherein the sequencing comprises sequencing a portion of the enriched minority nucleic acid species.

C4.5. The method of embodiment C4.4, comprising sequencing a portion of the enriched minority nucleic acid species that is hypomethylated.

C4.6. The method of embodiment C4.4, comprising sequencing a portion of the enriched minority nucleic acid species that is hypermethylated.

C4.7. The method of embodiment C4.3, comprising sequencing substantially all of the enriched minority nucleic acid species.

C4.8. The method of embodiment C4.3, wherein the sequencing method comprises sequencing by synthesis.

C4.9. The method of any one of embodiments C1, C2 and C4 to C4.2, wherein the analyzing comprises mass spectrometry.

C4.10. The method of embodiment C4.9, wherein the mass spectrometry analysis comprises a targeted-mass spectrometry.

C5. The method of any one of embodiments C1, C2 and C4 to C4.10, wherein the analyzing comprises determining the presence or absence of one or more polynucleotides in one or more loci relatively less methylated in the minority nucleic acid species than in the majority nucleic acid species.

C5.1. The method of any one of embodiments C1, C2 and C4 to C5, wherein the analyzing comprises determining the amount of one or more polynucleotides in one or more loci relatively less methylated in the minority nucleic acid species than in the majority nucleic acid species.

C5.2. The method of any one of embodiments C1, C2 and C4 to C5, wherein a difference in methylation status between the minority nucleic acid species and the majority nucleic acid species for the one or more loci relatively less methylated in the minority nucleic acid species than in the majority nucleic acid species is 5% or more.

C5.2.1. The method of embodiment C5.2, wherein the difference in methylation status between the minority nucleic acid species and the majority nucleic acid species for the one or more loci relatively less methylated in the minority nucleic acid species than in the majority nucleic acid species is determined by a statistical method chosen from a t-test, Z-test, Chi-square, Wilcox, ANOVA, MANOVA, MANCOVA and logistic regression.

C5.2.2. The method of embodiment C5.2.1, wherein the difference in methylation status between the minority nucleic acid species and the majority nucleic acid species is determined by a t-test.

C5.2.3. The method of embodiment C5.2.2, wherein the difference in methylation status between the minority nucleic acid species and the majority nucleic acid species for the one or more loci relatively less methylated in the minority nucleic acid species than in the majority nucleic acid species comprise a median t-statistic between −18.0 and −7.0 or comprise a statistical difference comparable to a t-statistic between −18.0 and −7.0.

C5.3. The method of any one of embodiments C2 to C5.2.3, wherein the nucleic acid enriched for the minority nucleic acid species comprise one or more polynucleotides in one or more loci that are 60% or less methylated in the minority nucleic acid species and about 61% or greater methylated in the majority nucleic acid species.

C6. The method of embodiment C5, wherein the one or more loci are chosen from loci in Table 2AB, Table 2CB, Table 3 and Table 4.

C6.1. The method of embodiment C6, wherein the one or more loci are chosen from loci having genomic coordinates from human reference genome hg18, NCBI Build 36.1 of: chr13: 19290394-19290768, chr13: 19887090-19887336; chr13: 20193675-20193897; chr13: 109232856-109235065; chr13: 109716455-109716604; chr13: 112724910-112725742; chr13: 112799123-112799379; chr18: 6919797-6919981; chr18: 13377536-13377654; chr18: 41671477-41673011; chr18: 58203013-58203282; chr18: 70133945-70134397; chr18: 71128742-71128974; chr18: 72664454-72664736; chr18: 74170347-74170489; chr18: 75596358-75596579; chr18: 75760343-75760820; chr21: 33327593-33328334; chr21: 35180938-35185436; chr21: 44529935-44530388; chr21: 45061293-45061853; chr21: 45202815-45202972; chr21: 45671984-45672098; chr21: 45754383-45754487; chr3: 9963364-9964023; chr5: 138757911-138758724; chr6: 35561812-35562252; chr12: 1642456-1642708; chr12: 56406249-56407788; and chr12: 56416146-56418794.

C6.2. The method of embodiment C6, wherein the one or more loci are chosen from loci having genomic coordinates from human reference genome hg18, NCBI Build 36.1 of: chr21: 9906600-9906800; chr21: 9907000-9907400; chr21: 9917800-9918450; chr21: 10010000-10015000; chr21: 13974500-13976000; chr21: 13989500-13992000; chr21: 13998500-14000100; chr21: 14017000-14018500; chr21: 14056400-14058100; chr21: 14070250-14070550; chr21: 14119800-14120400; chr21: 14304800-14306100; chr21: 16881500-16883000; chr21: 17905300-17905500; chr21: 23574000-23574600; chr21: 24366920-24367060; chr21: 25656000-25656900; chr21: 26830750-26830950; chr21: 26938800-26939200; chr21: 30176500-30176750; chr21: 31955000-31955300; chr21: 33272200-33273300; chr21: 33328000-33328500; chr21: 35185000-35186000; chr21: 36589000-36590500; chr21: 42399200-42399900; chr21: 42528400-42528600; chr21: 42598300-42599600; chr21: 42910000-42911000; chr21: 42945500-42946000; chr21: 42961400-42962700; chr21: 42978200-42979800; chr21: 43130800-43131500; chr21: 43446600-43447600; chr21: 43463000-43466100; chr21: 43545000-43546000; chr21: 43606000-43606500; chr21: 43902500-43903800; chr21: 44446500-44447500; chr21: 44614500-44615000; chr21: 44750400-44751000; chr21: 45145500-45146100; chr21: 45501000-45503000; chr21: 45571500-45573700; chr21: 45609000-45610600; chr21: 45670000-45677000; chr21: 45700500-45702000; chr21: 45753000-45755000; chr21: 45885000-45887000; chr21: 46111000-46114000; chr21: 46142000-46144500; chr21: 46227000-46233000; chr21: 46245000-46252000; chr21: 46280500-46283000; chr21: 46343500-46344200; chr21: 46368000-46378000; chr21: 46426700-46427500; and chr21: 46546914-46547404.

C6.3. The method of embodiment C6, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; chr1: 209819233-209819714; chr15: 99270658-99271954; chr9: 110581951-110582676; chr11: 76039765-76040736; chr21: 37607430-37607980; chr2: 100226464-100227140; chr21: 40278885-40279778; chr20: 40125800-40126325; chr14: 96964341-96965236; chr1: 94566367-94567508; chr6: 32120324-32121235; chr6: 2158961-2159107; chr2: 85833089-85833413; chr4: 147936346-147936831; chr2: 33107594-33108530; chr22: 43407118-43407581; chr21: 39492468-39494149; chr9: 124359818-124360534; chr6: 164167085-164167560; chr4: 4674762-4675733; chr1: 23890894-23891476; chr15: 57844015-57844457; chr16: 68766035-68766853; chr1: 234961714-234962041; chr10: 32703471-32704423; chr13: 31100912-31101535; chr2: 216808192-216808391; chr12: 18476876-18477436; chr12: 120818881-120819190; chr19: 38673641-38674608; chr17: 36605585-36606403; chr7: 65736314-65736453; chr13: 51058670-51059041; chr11: 113766137-113766643; chr12: 26265265-26266147; chr5: 109673723-109674226; chr8: 10618285-10618795; chr19: 53244844-53245458; chr11: 105386196-105387277; chr21: 16248092-16248889; chr18: 55795530-55795975; chr3: 64598707-64599348; chr1: 196659363-196660153; chr4: 165952537-165954234; chr12: 124773668-124774705; chr6: 41666010-41666469; chr6: 159237124-159238595; chr9: 108544124-108545341; chr6: 13014688-13016135; chr16: 11443167-11443469; and chr9: 101265123-101265817.

C6.4. The method of embodiment C6, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; and chr1: 209819233-209819714.

C6.5. The method of embodiment C6, wherein the one or more loci are chosen from TABLE 4 having a median t-statistic between −18.0 and −7.0.

C6.6. The method of embodiment C6, wherein the one or more loci are chosen from TABLE 4 having a median t-statistic between −18.0 and −9.0.

C6.7. The method of embodiment C6, wherein the one or more loci are chosen from TABLE 4 having a median t-statistic between −18.0 and −10.0.

C6.7.1. The method of any one of embodiments C6.5 to C6.7, wherein the median t-statistic is determined by a t-test.

C6.8. The method of any one of embodiments C1 to A6 and C6.5 to A6.7.1, wherein the one or more loci are chosen from loci in chromosome 21, 18 or 13.

C6.9. The method of any one of embodiments C5 to C6.8, wherein the one or more loci relatively less methylated in the minority nucleic acid species than in the majority nucleic acid comprise a CpG density of about 800 CpG methylation sites per 50,000 base pairs, or less.

C6.10. The method of embodiment C6.9, wherein the CpG density is about 600 CpG methylation sites per 50,000 base pairs, or less.

C6.11. The method of embodiment C6.10, wherein the CpG density is about 400 CpG methylation sites per 50,000 base pairs, or less.
C6.12. The method of embodiment C6.11, wherein the CpG density is about 200 CpG methylation sites per 50,000 base pairs, or less.
C6.13. The method of any one of embodiments C5 to C6.12, wherein the one or more loci relatively less methylated in the minority nucleic acid species than in the majority nucleic acid comprise a CpG density of about 16 CpG methylation sites per 1,000 base pairs, or less.
C6.14. The method of embodiment C6.13, wherein the CpG density is about 12 CpG methylation sites per 1,000 base pairs, or less.
C6.15. The method of embodiment C6.14, wherein the CpG density is about 8 CpG methylation sites per 1,000 base pairs, or less.
C6.16. The method of embodiment C6.15, wherein the CpG density is about 4 CpG methylation sites per 1,000 base pairs, or less.
C6.17. The method of any one of embodiments C5 to C6.16, wherein the one or more loci relatively less methylated in the minority nucleic acid species than in the majority nucleic acid comprise a CpG density of about 0.016 CpG methylation sites per base pair, or less.
C6.18. The method of embodiment C6.17, wherein the CpG density is about 0.012 CpG methylation sites per base pair, or less.
C6.19. The method of embodiment C6.18, wherein the CpG density is about 0.008 CpG methylation sites per base pair, or less.
C6.20. The method of embodiment C6.19, wherein the CpG density is about 0.004 CpG methylation sites per base pair, or less.
C6.21. The method of any one of embodiments C5 to C6.20, wherein the one or more loci relatively less methylated in the minority nucleic acid species contain at least 5 CpG methylation sites.
C6.22. The method of embodiment C6.21, wherein the one or more loci relatively less methylated in the minority nucleic acid species contain at least 9 CpG methylation sites.
C6.23. The method of embodiment 6.22, wherein the one or more loci relatively less methylated in the minority nucleic acid species contain at least 12 CpG methylation sites.
C6.24. The method of any one of embodiments C5 to C6.23, wherein the one or more loci relatively less methylated in the minority nucleic acid species are about 5,000 base pairs or less.
C6.25. The method of embodiment C6.24, wherein the one or more loci relatively less methylated in the minority nucleic acid species are about 2,000 base pairs or less.
C6.26. The method of embodiment C6.25, wherein the one or more loci relatively less methylated in the minority nucleic acid species are about 1,000 base pairs or less.
C6.27. The method of embodiment C6.26, wherein the one or more loci relatively less methylated in the minority nucleic acid species are about 750 base pairs or less.
C6.28. The method of embodiment C6.27, wherein the one or more loci relatively less methylated in the minority nucleic acid species are about 500 base pairs or less.
C6.29. The method of embodiment C6.28, wherein the one or more loci relatively less methylated in the minority nucleic acid species are about 250 base pairs or less.
C6.30. The method of any one of embodiments C5 to C6.29, wherein the one or more loci relatively less methylated in the minority nucleic acid species comprise 0.1 genes per 1000 base pair, or less.
C6.31. The method of embodiment C6.30, wherein the one or more loci relatively less methylated in the minority nucleic acid species comprise 0.08 genes per 1000 base pair, or less.
C6.32. The method of embodiment C6.31, wherein the one or more loci relatively less methylated in the minority nucleic acid species comprise 0.06 genes per 1000 base pair, or less.
C6.33. The method of embodiment C6.32, wherein the one or more loci relatively less methylated in the minority nucleic acid species comprise 0.04 genes per 1000 base pair, or less.
C6.34. The method of embodiment C6.33, wherein the one or more loci relatively less methylated in the minority nucleic acid species comprise 0.02 genes per 1000 base pair, or less.
C6.35. The method of any one of embodiments C5 to C6.34, wherein each of the one or more loci relatively less methylated in the minority nucleic acid species comprise at least 1 restriction endonuclease recognition sites per 1000 bp, wherein each of the at least one restriction endonuclease recognition sites can be specifically digested by at least one of the one or more methylation sensitive cleavage agents when the restriction endonuclease recognition site is non-methylated.
C6.36. The method of embodiment C6.35, wherein each of the one or more loci relatively less methylated in the minority nucleic acid species comprise at least 10 restriction endonuclease recognition sites per 1000 bp.
C6.37. The method of embodiment C6.36, wherein each of the one or more loci relatively less methylated in the minority nucleic acid species comprise at least 20 restriction endonuclease recognition sites per 1000 bp.
C6.38. The method of embodiment C6.37, wherein each of the one or more loci relatively less methylated in the minority nucleic acid species comprise at least 30 restriction endonuclease recognition sites per 1000 bp.
C7. The method of embodiment C6.8, wherein the one or more loci are chosen from chromosome 13 in TABLE 4.
C7.1. The method of embodiment C6.8, wherein the one or more loci are chosen from chromosome 18 in TABLE 4.
C7.2. The method of embodiment C6.8, wherein the one or more loci are chosen from chromosome 21 in TABLE 4.
C7.3. The method of any one of embodiments C5 to C7.2, wherein the one or more loci relatively less methylated in the minority nucleic acid species than in the majority nucleic acid species are 60% or more methylated in the majority nucleic acid species.
C7.4. The method of embodiment C7.3, wherein the loci are 70% or more methylated in the majority nucleic acid species.
C7.5. The method of embodiment C7.4, wherein the loci are 75% or more methylated in the majority nucleic acid species.
C7.6. The method of embodiment C7.5, wherein the loci are 80% or more methylated in the majority nucleic acid species.
C7.7. The method of any one of embodiments C5 to C7.6, wherein the one or more loci relatively less methylated in the minority nucleic acid species than in the majority nucleic acid species are 40% or less methylated in the minority nucleic acid species.
C7.8. The method of embodiment C7.7, wherein the loci are 30% or less methylated in the minority nucleic acid species.
C7.9. The method of embodiment C7.8, wherein the loci are 20% or less methylated in the minority nucleic acid species.

C7.10. The method of embodiment C7.9, wherein the loci are 10% or less methylated in the minority nucleic acid species.

C7.11. The method of any one of embodiments C5 to C7.10, wherein a difference in methylation status between the minority nucleic acid species and the majority nucleic acid species for the one or more loci relatively less methylated in the minority nucleic acid species than in the majority nucleic acid species is 5% or more.

C7.12. The method of embodiment C7.11, wherein a difference in methylation status is 10% or more.

C7.13. The method of embodiment C7.12, wherein a difference in methylation status is 20% or more.

C7.14. The method of embodiment C7.13, wherein a difference in methylation status is 40% or more.

C8. The method of any one of embodiments C2 to C7.14, wherein the enriching comprises selectively separating the digested nucleic acid fragments from non-digested nucleic acid.

C9. The method of embodiment C8, wherein the digested nucleic acid fragments are selectively separated according to molecular weight.

C9.1. The method of embodiment C8, wherein the digested nucleic acid fragments are selectively separated according to size.

C10. The method of any one of embodiments C8 to C9.1, wherein the digested nucleic acid fragments are selectively separated by a process comprising polyethylene glycol mediated precipitation.

C11. The method of any one of embodiments C8 to C9.1, wherein the digested nucleic acid fragments are selectively separated by a process comprising size exclusion chromatography.

C12. The method of embodiment C8, wherein the digested nucleic acid fragments are selectively separated by a process comprising contacting the fragments with a methyl-specific binding agent.

C12.1. The method of embodiment C12, wherein the contacting the fragments with the methyl-specific binding agent provides bound nucleic acid fragments and unbound nucleic acid fragments.

C12.2. The method of embodiment C12.1, wherein the bound nucleic acid fragments are selectively separated from the unbound nucleic acid fragments.

C12.3. The method of embodiments C12.1, comprising exposing the bound nucleic acid fragments, or a portion thereof, to conditions that dissociate the bound nucleic acids from the methyl-specific binding agent thereby providing one or more elution products.

C13. The method of any one of embodiments C12 to C12.3, wherein the methyl-specific binding agent comprises an antibody or a portion thereof C14. The method of embodiment C13, wherein the antibody specifically binds an unmethylated portion of one or more nucleic acid fragments in the sample.

C15. The method of embodiment C13, wherein the antibody specifically binds a methylated portion of one or more nucleic acid fragments in the sample.

C16. The method of any one of embodiments C12 to C12.2, wherein the methyl-specific binding agent comprises a methyl-CpG binding domain protein or a portion thereof.

C17. The method of embodiment C16, wherein the methyl-CpG binding domain protein is chosen from MeCP2, MBD1, MBD2, MBD3 and MBD4.

C18. The method of any one of embodiments C1 to C17, wherein the one or more methylation sensitive cleavage agents comprise one or more restriction endonucleases.

C19. The method of embodiment C18, wherein the one or more restriction endonucleases are selected from a Type I, Type II, Type III, Type IV or Type V restriction endonuclease.

C20. The method of embodiment C18 or C19, wherein the one or more restriction endonucleases recognize or bind to a recognition sequence comprising 6 base pairs or less.

C21. The method of embodiment C18 or C19, wherein the one or more restriction endonucleases recognize or bind to a recognition sequence comprising 4 base pairs or less.

C22. The method of any one of embodiments C18 to C21, wherein the one or more restriction endonucleases produce overhangs.

C23. The method of any one of embodiments C18 to C22, wherein each of the digested nucleic acid fragments comprises one or more unpaired nucleotides at the 5' or 3' end of the fragment.

C24. The method of any one of embodiments C18 to C21, wherein the one or more restriction endonucleases produce blunt ends.

C25. The method of any one of embodiments C18 to C23, wherein one or more of the restriction endonucleases are selected from HHAI, HinP1I and HPAII.

C26. The method of any one of embodiments C18 to C25, wherein the average, mean, median or nominal length of the digested nucleic acid fragments is about 40 bases to about 100 bases.

C27. The method of any one of embodiments C2 to C26, wherein the enriching in (b) comprises amplifying the digested nucleic acid fragments relative to the non-digested nucleic acid.

C28. The method of any one of embodiments C1 to C27, wherein the digested nucleic acid fragments are amplified by a process comprising ligating one or more adaptors to one or both ends of each of the digested nucleic acid fragments.

C29. The method of embodiment C28, wherein the ligating comprises a blunt end ligation.

C30. The method of embodiment C28 or C29, comprising ligating the one or more adaptors to one or more unpaired nucleotides at the 5' or 3' end of the digested nucleic acid fragments.

C31. The method of any one of embodiments C28 to C30, wherein the one or more adaptors comprise one or more capture agents.

C32. The method of embodiment C31, wherein the one or more capture agents are selected from an antibody, an antigen and a member of a binding pair.

C33. The method of embodiment C31 or C32, wherein the one or more capture agents comprise biotin.

C34. The method of any one of embodiments C27 to C33, wherein the digested nucleic acid fragments are amplified by a process comprising a bridge amplification.

C35. The method of any one of embodiments C1 to C34, wherein the nucleic acid from the pregnant female comprises cell-free circulating nucleic acid.

C36. The method of embodiment C35, wherein the nucleic acid is from blood serum, blood plasma or urine.

C37. The method of any one of embodiments C1, C2 and C4 to C36, wherein the analyzing comprises determining an amount of the minority nucleic acid species in the nucleic acid sample.

C38. The method of embodiment C37, wherein determining the amount of the minority nucleic acid species comprises determining a ratio of the minority nucleic acid species to a total amount of nucleic acid in the sample.

C39. The method of embodiment C38, wherein the ratio is a percent representation.

C40. The method of any one of embodiments C1, C2 and C4 to C39, wherein the analyzing comprises determining the presence of absence of a fetal aneuploidy.

C41. The method of embodiment C40, wherein the fetal aneuploidy is a trisomy.

C42. The method of embodiment C41, wherein the trisomy is a trisomy of chromosome 13, 18 or 21.

C43. The method of any one of embodiments C1, C2 and C4 to C42, wherein the analyzing comprises non-targeted sequencing of the digested nucleic acid fragments or modified variant thereof.

C44. The method of any one of embodiments C1, C2 and C4 to C42, wherein the analyzing comprises targeted sequencing of the digested nucleic acid fragments or a modified variant thereof.

C45. The method of any one of embodiments C1 to C44, which comprises contacting the digested nucleic acid fragments with an agent that modifies a methylated nucleotide to another moiety.

C46. The method of any one of embodiments C40 to C45, wherein determining the presence or absence of a fetal aneuploidy comprises obtaining counts of sequence reads mapped to portions of a reference genome, which sequence reads are normalized and which sequence reads are from the enriched hypomethylated nucleic acid or the enriched hypermethylated nucleic acid.

C47. The method of embodiment C46, wherein determining the presence or absence of a fetal aneuploidy comprises comparing the normalized counts of sequence reads for a target chromosome to the normalized counts of sequence reads for the reference chromosome, whereby a statistically significant difference between the counts for the target chromosome and the counts for the reference chromosome determines the presence of a fetal aneuploidy.

C48. The method of embodiment C47, wherein counts of sequence reads of about 3 to about 15 loci on the target chromosome and the reference chromosome is determined.

C49. The method of embodiment C47, wherein counts of sequence reads of about 16 or more loci on the target chromosome and the reference chromosome is determined.

C50. The method of any one of embodiments C37 to C49, wherein determining the amount of the minority nucleic acid species comprises use of a mass spectrometry method.

C51. The method of any one of embodiments C37 to C49, wherein determining the amount of the minority nucleic acid species comprises use of a sequencing method.

D1. A method for analyzing nucleic acid in a sample, comprising:
(a) enriching for hypomethylated nucleic acid present in a nucleic acid sample from a pregnant female, which nucleic acid comprises a minority nucleic acid species and a majority nucleic acid species, thereby generating enriched hypomethylated nucleic acid; and
(b) analyzing the enriched hypomethylated nucleic acid, which analyzing comprises determining the presence, absence or amount of a polynucleotide in one or more loci chosen from loci of Table 4.

D2. The method of embodiment D1, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1: 110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; chr1: 209819233-209819714; chr15: 99270658-99271954; chr9: 110581951-110582676; chr11: 76039765-76040736; chr21: 37607430-37607980; chr2: 100226464-100227140; chr21: 40278885-40279778; chr20: 40125800-40126325; chr14: 96964341-96965236; chr1: 94566367-94567508; chr6: 32120324-32121235; chr6: 2158961-2159107; chr2: 85833089-85833413; chr4: 147936346-147936831; chr2: 33107594-33108530; chr22: 43407118-43407581; chr21: 39492468-39494149; chr9: 124359818-124360534; chr6: 164167085-164167560; chr4: 4674762-4675733; chr1: 23890894-23891476; chr15: 57844015-57844457; chr16: 68766035-68766853; chr1: 234961714-234962041; chr10: 32703471-32704423; chr13: 31100912-31101535; chr2: 216808192-216808391; chr12: 18476876-18477436; chr12: 120818881-120819190; chr19: 38673641-38674608; chr17: 36605585-36606403; chr7: 65736314-65736453; chr13: 51058670-51059041; chr11: 113766137-113766643; chr12: 26265265-26266147; chr5: 109673723-109674226; chr8: 10618285-10618795; chr19: 53244844-53245458; chr11: 105386196-105387277; chr21: 16248092-16248889; chr18: 55795530-55795975; chr3: 64598707-64599348; chr1: 196659363-196660153; chr4: 165952537-165954234; chr12: 124773668-124774705; chr6: 41666010-41666469; chr6: 159237124-159238595; chr9: 108544124-108545341; chr6: 13014688-13016135; chr16: 11443167-11443469; and chr9: 101265123-101265817.

D3. The method of embodiment D1, wherein the one or more loci are chosen from loci having genomic coordinates from human reference genome hg19 of: chr17: 8512152-8512589; chr12: 13267398-13267724; chr3: 161138353-161138975; chr3: 151869156-151870687; chr9: 131317330-131317804; chr6: 18022909-18023559; chr4: 106476287-106477106; chr3: 134045674-134046244; chr6: 35115863-35116124; chr1: 143963833-143964046; chr12: 77024511-77024859; chr18: 46293373-46293973; chr8: 90912968-90913639; chr9: 127573329-127573696; chr3: 6108611-6109391; chr22: 33017833-33018590; chr3: 150064304-150065444; chr15: 32856228-32856444; chr14: 99941483-99941851; chr11: 117043564-117043818; chr12: 105837821-105838093; chr6: 44145412-44146058; chr20: 56555622-56556195; chr15: 67470797-67471606; chr4: 172550817-172551369; chr3: 72077846-72078294; chr10: 70478675-70479033; chr10: 27600544-27601168; chr7: 30971230-30971923; chr2: 27220151-27220511; chr1: 198668454-198668878; chr11: 10372877-10373954; chr8: 42912750-42913015; chr4: 74511731-74512313; chr12: 11760705-11760985; chr15: 67054128-67054469; chr3: 126292144-126292819; chr3: 132325316-132325885; chr12: 104999139-104999560; chr7: 680256-681378; chr1:

110419703-110420528; chr1: 144994257-144995559; chr3: 105678334-105678651; chr17: 54776398-54777625; chr7: 33761864-33762747; chr17: 840170-840475; chr12: 64215983-64216721; chr9: 16867882-16868157; chr12: 47358208-47358689; and chr1: 209819233-209819714.

D4. The method of embodiment D1, wherein the one or more loci are chosen from Table 4 having a median t-statistic between −18.0 and −7.0.

D5. The method of embodiment D1, wherein the one or more loci are chosen from Table 4 having a median t-statistic between −18.0 and −9.0.

D6. The method of embodiment D1, wherein the one or more loci are chosen from Table 4 having a median t-statistic between −18.0 and −10.0.

D6.1. The method of any one of embodiments D4 to D6, wherein the median t-statistic is determined by a t-test.

D7. The method of any one of embodiments D1 to D6.1, wherein the one or more loci are chosen from loci in chromosome 21, 18 or 13.

D8. The method of embodiment D7, wherein the one or more loci are chosen from chromosome 13 in Table 4.

D9. The method of embodiment D7, wherein the one or more loci are chosen from chromosome 18 in Table 4.

D10. The method of embodiment D7, wherein the one or more loci are chosen from chromosome 21 in Table 4.

D11. The method of any one of embodiments D1 to D10, wherein the one or more loci are relatively less methylated in the minority nucleic acid species than in the majority nucleic acid species.

D11.1. The method of embodiments D11, wherein the one or more loci relatively less methylated in the minority nucleic acid species than in the majority nucleic acid species comprise a CpG density of about 800 CpG methylation sites per 50,000 base pairs, or less.

D11.2. The method of embodiment D11.1, wherein the CpG density is about 600 CpG methylation sites per 50,000 base pairs, or less.

D11.3. The method of embodiment D11.2, wherein the CpG density is about 400 CpG methylation sites per 50,000 base pairs, or less.

D11.4. The method of embodiment D11.3, wherein the CpG density is about 200 CpG methylation sites per 50,000 base pairs, or less.

D11.5. The method of any one of embodiments D11 to D11.4, wherein the one or more loci relatively less methylated in the minority nucleic acid species than in the majority nucleic acid species comprise a CpG density of about 16 CpG methylation sites per 1,000 base pairs, or less.

D11.6. The method of embodiment D11.5, wherein the CpG density is about 12 CpG methylation sites per 1,000 base pairs, or less.

D11.7. The method of embodiment D11.6, wherein the CpG density is about 8 CpG methylation sites per 1,000 base pairs, or less.

D11.8. The method of embodiment D11.7, wherein the CpG density is about 4 CpG methylation sites per 1,000 base pairs, or less.

D11.9. The method of any one of embodiments D11 to D11.8, wherein the one or more loci relatively less methylated in the minority nucleic acid species than in the majority nucleic acid species comprise a CpG density of about 0.016 CpG methylation sites per base pair, or less.

D11.10. The method of embodiment D11.9, wherein the CpG density is about 0.012 CpG methylation sites per base pair, or less.

D11.11. The method of embodiment D11.10, wherein the CpG density is about 0.008 CpG methylation sites per base pair, or less.

D11.12. The method of embodiment D11.11, wherein the CpG density is about 0.004 CpG methylation sites per base pair, or less.

D11.13. The method of any one of embodiments D11 to D11.12, wherein the one or more loci relatively less methylated in the minority nucleic acid species contain at least 5 CpG methylation sites.

D11.14. The method of embodiment 11.13, wherein the one or more loci relatively less methylated in the minority nucleic acid species contain at least 9 CpG methylation sites.

D11.15. The method of embodiment 11.14, wherein the one or more loci relatively less methylated in the minority nucleic acid species contain at least 12 CpG methylation sites.

D11.16. The method of any one of embodiments D11 to D11.15, wherein the one or more loci relatively less methylated in the minority nucleic acid species are about 5,000 base pairs or less.

D11.17. The method of embodiment D11.16, wherein the one or more loci relatively less methylated in the minority nucleic acid species are about 2,000 base pairs or less.

D11.18. The method of embodiment D11.17, wherein the one or more loci relatively less methylated in the minority nucleic acid species are about 1,000 base pairs or less.

D11.19. The method of embodiment D11.18, wherein the one or more loci relatively less methylated in the minority nucleic acid species are about 750 base pairs or less.

D11.20. The method of embodiment D11.19, wherein the one or more loci relatively less methylated in the minority nucleic acid species are about 500 base pairs or less.

D11.21. The method of embodiment D11.20, wherein the one or more loci relatively less methylated in the minority nucleic acid species are about 250 base pairs or less.

D11.22. The method of any one of embodiments D11 to D11.21, wherein the one or more loci relatively less methylated in the minority nucleic acid species comprise 0.1 genes per 1000 base pair, or less.

D11.23. The method of embodiment D11.22, wherein the one or more loci relatively less methylated in the minority nucleic acid species comprise 0.08 genes per 1000 base pair, or less.

D11.24. The method of embodiment D11.23, wherein the one or more loci relatively less methylated in the minority nucleic acid species comprise 0.06 genes per 1000 base pair, or less.

D11.25. The method of embodiment D11.24, wherein the one or more loci relatively less methylated in the minority nucleic acid species comprise 0.04 genes per 1000 base pair, or less.

D11.26. The method of embodiment D11.25, wherein the one or more loci relatively less methylated in the minority nucleic acid species comprise 0.02 genes per 1000 base pair, or less.

D11.27. The method of any one of embodiments D11 to D11.26, wherein each of the one or more loci relatively less methylated in the minority nucleic acid species comprise at least 1 restriction endonuclease recognition sites per 1000 bp, wherein each of the at least one restriction endonuclease recognition sites can be specifically digested by at least one of the one or more methylation sensitive cleavage agents when the restriction endonuclease recognition site is non-methylated.

D11.28. The method of embodiment D11.27, wherein each of the one or more loci relatively less methylated in the minority nucleic acid species comprise at least 10 restriction endonuclease recognition sites per 1000 bp.

D11.29. The method of embodiment D11.28, wherein each of the one or more loci relatively less methylated in the minority nucleic acid species comprise at least 20 restriction endonuclease recognition sites per 1000 bp.

D11.30. The method of embodiment D11.29, wherein each of the one or more loci relatively less methylated in the minority nucleic acid species comprise at least 30 restriction endonuclease recognition sites per 1000 bp.

D12. The method of any one of embodiments D11 to D11.30, wherein the analyzing comprises determining the presence or absence of one or more polynucleotides in the one or more loci relatively less methylated in the minority nucleic acid species than in the majority nucleic acid species.

D13. The method of any one of embodiments D11 to D11.30, wherein the analyzing comprises determining the amount of one or more polynucleotides in the one or more loci relatively less methylated in the minority nucleic acid species than in the majority nucleic acid species.

D14. The method of any one of embodiments D11 to D13, wherein the difference in methylation status between the minority nucleic acid species and the majority nucleic acid species for the one or more loci relatively less methylated in the minority nucleic acid species than in the majority nucleic acid species is 5% or more.

D14.1. The method of embodiment D14, wherein a difference in methylation status is 10% or more.

D14.2. The method of embodiment D14.1, wherein a difference in methylation status is 20% or more.

D14.3. The method of embodiment D14.2, wherein a difference in methylation status is 40% or more.

D14.4. The method of embodiment D14.3, wherein the difference in methylation status between the minority nucleic acid species and the majority nucleic acid species for the one or more loci relatively less methylated in the minority nucleic acid species than in the majority nucleic acid species is determined by a statistical method chosen from a t-test, Z-test, Chi-square, Wilcox, ANOVA, MANOVA, MANCOVA and logistic regression.

D14.5. The method of embodiment D14.4, wherein the difference in methylation status between the minority nucleic acid species and the majority nucleic acid species is determined by a t-test.

D14.6. The method of embodiment D14.5, wherein the difference in methylation status between the minority nucleic acid species and the majority nucleic acid species for the one or more loci relatively less methylated in the minority nucleic acid species than in the majority nucleic acid species comprises a median t-statistic between −18.0 and −7.0 or comprise a statistical difference comparable to a t-statistic between −18.0 and −7.0.

D15. The method of any one of embodiments D1 to D14.6, wherein the nucleic acid enriched for hypomethylated nucleic acid comprise one or more polynucleotides in one or more loci that are 60% or less methylated in the minority nucleic acid species than in the majority nucleic acid species.

D15.1. The method of any one of embodiments D11 to D15, wherein the one or more loci relatively less methylated in the minority nucleic acid species than in the majority nucleic acid species are 60% or more methylated in the majority nucleic acid species.

D15.2. The method of embodiment D15.1, wherein the loci are 70% or more methylated in the majority nucleic acid species.

D15.3. The method of embodiment D15.2, wherein the loci are 75% or more methylated in the majority nucleic acid species.

D15.4. The method of embodiment D15.3, wherein the loci are 80% or more methylated in the majority nucleic acid species.

D16. The method of any one of embodiments D11 to D15.4, wherein the one or more loci relatively less methylated in the minority nucleic acid species than in the majority nucleic acid species are 40% or less methylated in the minority nucleic acid species.

D16.1. The method of embodiment D16, wherein the loci are 30% or less methylated in the minority nucleic acid species.

D16.2. The method of embodiment D16.1, wherein the loci are 20% or less methylated in the minority nucleic acid species.

D16.3. The method of embodiment D16.2, wherein the loci are 10% or less methylated in the minority nucleic acid species.

D17. A method for analyzing nucleic acid in a sample, comprising:

(a) enriching for hypomethylated nucleic acid present in a nucleic acid sample from a pregnant female, which nucleic acid comprises a minority nucleic acid species and a majority nucleic acid species, thereby generating enriched hypomethylated nucleic acid; and (b) analyzing the enriched hypomethylated nucleic acid, which analyzing comprises non-targeted analysis of substantially all of the hypomethylated nucleic acid.

D18. The method of any one of embodiments D1 to D17, wherein the enriching comprises exposing the nucleic acid sample to conditions that selectively separate the hypomethylated nucleic acid from methylated nucleic acid.

D19. The method of embodiment D18, wherein the enriching comprises contacting the nucleic acid in the nucleic acid sample with a binding agent that specifically associates with methylated nucleic acid, thereby generating separated and enriched hypomethylated nucleic acid.

D19.1. The method of embodiment D19, wherein the contacting the fragments with the binding agent provides bound nucleic acid fragments and unbound nucleic acid fragments.

D19.2. The method of embodiment D19.1, wherein the bound nucleic acid fragments are selectively separated from the unbound nucleic acid fragments.

D19.3. The method of embodiments D19.1, comprising exposing the bound nucleic acid fragments, or a portion thereof, to conditions that dissociate the bound nucleic acids from the binding agent thereby providing one or more elution products.

D20. The method of any one of embodiments D19 to D19.3, comprising amplifying the separated and enriched hypomethylated nucleic acid.

D21. The method of embodiment D20, wherein the amplification comprises ligating one or more adaptors to the enriched hypomethylated nucleic acid.

D22. The method of embodiment D20 or D21, wherein the amplifying comprises a targeted amplification.

D23. The method of embodiment D21 or D22, wherein the one or more adaptors comprise a capture agent.

D24. The method of any one of embodiments D20 to D23, wherein the enriched nucleic acid is amplified by a process comprising a bridge amplification.

D25. The method of any one of embodiments D18 to D24, wherein the conditions that separate hypomethylated nucleic acid from methylated nucleic acid comprise binding substantially all of the nucleic acid in the nucleic acid sample and selectively eluting the hypomethylated nucleic acid.

D26. The method of any one of embodiments D19.1 to D24, wherein the conditions that separate hypomethylated nucleic acid from methylated nucleic acid comprise binding substantially all of the methylated nucleic acid in the nucleic acid sample, wherein the unbound nucleic acid fragments comprises enriched hypomethylated nucleic acid.

D27. The method of any one of embodiments D19 to D26, wherein the binding agent, or a portion thereof, comprises a methyl-specific binding agent.

D28. The method of embodiment D27, wherein the methyl-specific binding agent comprises an antibody or a portion thereof.

D29. The method of embodiment D28, wherein the antibody, or portion thereof, specifically binds an unmethylated portion of one or more nucleic acid in the sample.

D30. The method of embodiment D28, wherein the antibody, or portion thereof, specifically binds a methylated portion of one or more nucleic acids in the sample.

D31. The method of embodiment D27, wherein the methyl-specific binding agent comprises a methyl-CpG binding domain protein or a portion thereof.

D32. The method of embodiments D27 or D31, wherein the methyl-CpG binding domain protein is chosen from MeCP2, MBD1, MBD2, MBD3 and MBD4.

D33. The method of any one of embodiments D1 to D32, wherein the enriching comprises digesting the nucleic acid sample with one or more methylation sensitive cleavage agents that specifically digest the nucleic acids at a recognition site comprising a methylation site.

D34. The method of D32 or D33, wherein the digesting produces digested nucleic acid fragment and non-digested nucleic acid fragments.

D35. The method of embodiment D34, wherein the enriching comprises selectively separating the digested nucleic acid fragments from non-digested nucleic acid.

D36. The method of any one of embodiments D33 to D35, wherein the one or more methylation sensitive cleavage agents comprise one or more restriction endonucleases.

D36.1. The method of embodiment D36, wherein the one or more restriction endonucleases digest the nucleic acids at an unmethylated methylation site.

D36.2. The method of embodiment D36, wherein the one or more restriction endonucleases digest the nucleic acids at a methylated methylation site.

D37. The method of any one of embodiments D36 to D36.2, wherein the one or more restriction endonucleases are selected from a Type I, Type II, Type III, Type IV or Type V restriction endonuclease.

D38. The method of any one of embodiments D36 to D37, wherein the one or more restriction endonucleases recognize or bind to a recognition sequence comprising 6 base pairs or less.

D39. The method of any one of embodiments D36 to D38, wherein the one or more restriction endonucleases recognize or bind to a recognition sequence comprising 4 base pairs or less.

D40. The method of any one of embodiments D36 to D39, wherein the one or more restriction endonucleases produce overhangs.

D41. The method of embodiment D40, wherein each of the digested nucleic acid fragments comprises one or more unpaired nucleotides at the 5' or 3' end of the fragment.

D42. The method of any one of embodiments D36 to D41, wherein one or more of the restriction endonucleases are selected from HHAI, HinP1I and HPAII.

D43. The method of any one of embodiments D36 to D39, wherein the one or more restriction endonucleases produce blunt ends.

D44. The method of any one of embodiments D36 to D43, wherein the average, mean, median or nominal length of the digested nucleic acid fragments is about 40 bases to about 100 bases.

D45. The method of any one of embodiments D34 to D44, wherein the enriching comprises amplifying the digested nucleic acid fragments relative to the non-digested nucleic acid.

D46. The method of embodiment D45, wherein the digested nucleic acid fragments are amplified by a process comprising ligating one or more adaptors to one or both ends of each of the digested nucleic acid fragments.

D47. The method of embodiment D46, wherein the ligating comprises a blunt end ligation.

D48. The method of embodiment D46 or D47, comprising ligating the one or more adaptors to one or more unpaired nucleotides at the 5' or 3' end of the digested nucleic acid fragments.

D49. The method of any one of embodiments D46 to D48, wherein the one or more adaptors comprise one or more capture agents.

D50. The method of embodiment D49, wherein the one or more capture agents are selected from an antibody, an antigen and a member of a binding pair.

D51. The method of embodiment D49 or D50, wherein the one or more capture agents comprise biotin.

D52. The method of any one of embodiments D45 to D51, wherein the digested nucleic acid fragments are amplified by a process comprising a bridge amplification.

D53. The method of any one of embodiments D1 to D52, wherein the nucleic acid from the pregnant female comprises cell-free circulating nucleic acid.

D54. The method of embodiment D53, wherein the nucleic acid is from blood serum, blood plasma or urine.

D55. The method of any one of embodiments D1 to D54, wherein the analyzing comprises determining an amount of feta nucleic acid in the nucleic acid sample.

D56. The method of embodiment D55, wherein determining the amount of feta nucleic acid comprises determining a ratio of feta nucleic acid to a total amount of nucleic acid in the sample.

D57. The method of embodiment D56, wherein the ratio is a percent representation.

D58. The method of any one of embodiments D1 to D57, wherein the analyzing comprises determining the presence of absence of a fetal aneuploidy.

D59. The method of embodiment D58, wherein the fetal aneuploidy is a trisomy.

D60. The method of embodiment D59, wherein the trisomy is a trisomy of chromosome 13, 18 or 21.

D61. The method of any one of embodiments D1 to D60, wherein the analyzing comprises a target-based approach.

D62. The method of any one of embodiments D1 to D60, wherein the analyzing comprises a non-target-based approach.

D63. The method of any one of embodiments D1 to D62, wherein the analyzing comprises sequencing the enriched hypomethylated nucleic acid, or a portion thereof or sequencing the enriched hypermethylated nucleic acid, or a portion thereof.

D64. The method of embodiment D63, where the sequencing comprises non-targeted sequencing.

D65. The method of embodiment D63, where the sequencing comprises targeted sequencing.

D66. The method of any one of embodiments D1 to D65, which comprises contacting the enriched hypomethylated nucleic acid or the enriched hypermethylated nucleic acid with an agent that modifies a methylated nucleotide to another moiety.

D67. The method of any one of embodiments D58 to D66, wherein determining the presence or absence of a fetal aneuploidy comprises obtaining counts of sequence reads mapped to portions of a reference genome, which sequence reads are normalized and which sequence reads are from the enriched hypomethylated nucleic acid or the enriched hypermethylated nucleic acid.

D68. The method of embodiment D67, wherein determining the presence or absence of a fetal aneuploidy comprises comparing the normalized counts of sequence reads for a target chromosome to the normalized counts of sequence reads for the reference chromosome, whereby a statistically significant difference between the counts for the target chromosome and the counts for the reference chromosome determines the presence of a fetal aneuploidy.

D69. The method of embodiment D68, wherein counts of sequence reads of about 3 to about 15 loci on the target chromosome and the reference chromosome is determined.

D70. The method of embodiment D68, wherein counts of sequence reads of about 16 or more loci on the target chromosome and the reference chromosome is determined.

D71. The method of any one of embodiments D55 to D70, wherein determining the amount of feta nucleic acid comprises use of a mass spectrometry method.

D72. The method of any one of embodiments D55 to D70, wherein determining the amount of feta nucleic acid comprises use of a sequencing method.

D73. The method of embodiment D72, wherein the sequencing method comprises sequencing by synthesis.

D74. The method of any one of embodiments D1 to D73, wherein the analyzing comprises mass spectrometry.

D75. The method of embodiment D74, wherein the mass spectrometry analysis comprises a targeted-mass spectrometry.

E1. A method for preparing a collection of amplification primers, comprising:
(a) selecting one or more genomic loci, wherein each locus comprises three or more features selected from:
  (i) a locus length of about 5000 contiguous base pairs, or less,
  (ii) a CpG density of 16 CpG methylation sites per 1000 base pairs, or less,
  (iii) a gene density of 0.1 genes per 1000 base pair, or less,
  (iv) at least 5 CpG methylation sites,
  (v) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases,
  (vi) at least 1 restriction endonuclease recognition site per 1000 base pairs, wherein the at least one restriction endonuclease recognition site can be specifically digested by a methylation sensitive cleavage agent,
  (vii) a locus comprising a methylation status of 40% or less in fetal nucleic acid,
  (viii) a locus comprising a methylation status of 60% or more in maternal nucleic acid, and
  (ix) a locus comprising a difference in methylation status of 5% or more between fetal nucleic acid and maternal nucleic acid; and
(b) preparing a plurality of oligonucleotide primer pairs, wherein each primer of each primer pair hybridizes to a portion of a strand of the locus selected in (a) for which the primer pair is specific, whereby a collection of amplification primers is prepared.

E1.1. The method of embodiment E1, wherein each of the primers of each of the primer pairs is specific for a target polynucleotide located in one or more of the loci selected in (a).

E1.2. The method of embodiment E1.1, wherein each of the primer pairs in configured for amplifying the target polynucleotide located in one or more of the loci selected in (a) for which the primer pair is specific.

E1.3. The method of embodiment E1.1 or E1.2, wherein each of the primers of the primer pair can hybridize to a portion of the target polynucleotide for which the primer is specific.

E1.4. The method of any one of embodiments E1.1 to E1.3, wherein each of the loci selected in
(a) comprise one or more target polynucleotides.

E1.5. The method of any one of embodiments E1.1 to E1.4, wherein each of the one or more target nucleic polynucleotides comprises at least one of the restriction endonuclease recognition sites in (a)(vi), wherein each of the primer pairs flank at least one of the restriction endonuclease recognition sites in (a)(vi).

E2. The method of any one of embodiments E1.4 or E1.5, wherein each locus comprises at least two target polynucleotides.

E3. The method of any one of embodiments E1 to E2, wherein the feature of (a)(i) is 2000 contiguous nucleotides, or less.

E4. The method of embodiment E3, wherein the feature of (a)(i) is 1000 contiguous nucleotides, or less.

E4.1. The method of embodiment E3, wherein the feature of (a)(i) is 750 contiguous nucleotides, or less.

E4.2. The method of embodiment E3, wherein the feature of (a)(i) is 500 contiguous nucleotides, or less.

E4.3. The method of embodiment E3, wherein the feature of (a)(i) is 250 contiguous nucleotides, or less.

E5. The method of any one of embodiments E1 to E4.3, wherein the CpG density of (a)(ii) is 12 CpG methylation sites per 1000 base pairs, or less.

E6. The method of embodiment E5, wherein the CpG density of (a)(ii) is 8 CpG methylation sites per 1000 base pairs, or less.

E7. The method of embodiment E6, wherein the CpG density of (a)(ii) is 4 CpG methylation sites per 1000 base pairs, or less.

E8. The method of any one of embodiments E1 to E7, wherein the CpG density of (a)(ii) is about 0.016 CpG methylation sites per base pair, or less.

E9. The method of embodiment E8, wherein the CpG density of (a)(ii) is about 0.012 CpG methylation sites per base pair, or less.

E10. The method of embodiment E9, wherein the CpG density of (a)(ii) is about 0.008 CpG methylation sites per base pair, or less.

E11. The method of embodiment E10, wherein the CpG density of (a)(ii) is about 0.004 CpG methylation sites per base pair, or less.

E12. The method of any one of embodiments E1 to E11, wherein the at least 5 CpG methylation sites of (a)(iv) are at least 9 CpG methylation sites.

E13. The method of embodiment E12, wherein the at least 5 CpG methylation sites of (a)(iv) are at least 12 CpG methylation sites.
E14. The method of any one of embodiments E1 to E13, wherein the gene density of (a)(iii) is 0.08 genes per 1000 base pair, or less.
E15. The method of embodiment E14, wherein the gene density of (a)(iii) is 0.06 genes per 1000 base pair, or less.
E16. The method of embodiment E15, wherein the gene density of (a)(iii) is 0.04 genes per 1000 base pair, or less.
E17. The method of embodiment E16, wherein the gene density of (a)(iii) is 0.02 genes per 1000 base pair, or less.
E18. The method of any one of embodiments E1 to E17, wherein the average, mean, median or absolute distance between each restriction endonuclease recognition site of (v) about 40 to about 100 base pairs.
E19. The method of any one of embodiments E1 to E18, the feature of (a)(vi) is at least 10 restriction endonuclease recognition site per 1000 base pairs
E20. The method of embodiment E19, wherein the feature of (a)(vi) is at least 20 restriction endonuclease recognition sites per 1000 bp.
E21. The method of embodiment E20, wherein the feature of (a)(vi) is at least 30 restriction endonuclease recognition sites per 1000 bp.
E21.1. The method of any one of embodiments E1 to E21, wherein genomic loci having features (vii), (viii) and (ix) are selected in (a).
E21.2. The method of any one of embodiments E1 to E21, wherein genomic loci having features (ii), (iv) and (ix) are selected in (a).
E21.3. The method of any one of embodiments E1 to E21, wherein genomic loci having features (ii), (vii) and (ix) are selected in (a).
E21.4. The method of any one of embodiments E1 to E21, wherein genomic loci having features (iii), (iv) and (ix) are selected in (a).
E21.5. The method of any one of embodiments E21.1 to E21.4, wherein genomic loci having feature (i) is selected in (a).
E21.6. The method of any one of embodiments E21.1 to E21.5, wherein genomic loci having feature (v) is selected in (a).
E21.7. The method of any one of embodiments E21.1 to E21.6, wherein genomic loci having feature (vi) is selected in (a).
E22. The method of any one of embodiments E1 to E21.7, wherein at least one of the oligonucleotide primers of each of the primer pairs comprises a non-native element.
E23. The method of any one of embodiments E1 to E21, wherein each of the oligonucleotide primers comprises a non-native element.
E24. The method of embodiment E22 or E23, wherein the non-native element comprises a heterologous nucleotide sequence.
E25. The method of embodiment E22 or E23, wherein the non-native element comprises an identifier.
E26. The method of embodiment E25, wherein the identifier comprises a label
E27. The method of any one of embodiments E22 to E26, wherein the non-native element comprises a binding agent.
E28. The method of embodiment E27, wherein the binding agent comprises a member of a binding pair.
E29. The method of any one of embodiments E22 to E28, wherein the non-native element comprises a non-native nucleotide.
E30. The method of embodiment E29, wherein the non-native nucleotide comprises a chemical modification.
E31. The method of any one of embodiments E1 to E30, wherein both of the oligonucleotide primers of each of the primer pairs comprises a hybridization sequence that is complimentary to a portion of the locus that the primer pair is configured to amplify.
E32. The method of embodiment E31, wherein the locus, which the primer pair is configured to amplify, is longer than the combined length of the hybridization sequences of the target specific primer pair.
E33. The method of embodiment E31 or E32, wherein each of the oligonucleotide primers of each of the primer pairs comprises a sequence tag.
E34. The method of embodiment E31 or E32, wherein each of the oligonucleotide primers of each of the primer pairs comprises an different hybridization sequence.
E35. The method of any one of embodiments E1 to E34, wherein each of the target polynucleotides comprises a length of about 500 nucleotides to about 30 nucleotides. (nucleosomes are 146 or 166)
E36. The method of embodiment E35, wherein each of the target polynucleotides comprise a length of about 1000 nucleotides to about 40 nucleotides.
E37. The method of embodiment E36, wherein the target polynucleotide is about 180 nucleotides to about 40 nucleotides.
E38. The method of any one of embodiments E1 to E37, wherein the target polynucleotide is single stranded.
E39. The method of any one of embodiments E1 to E37, wherein the target polynucleotide is double stranded.
E40. The method of any one of embodiments E1 to E37, wherein the target polynucleotide is circulating cell free DNA.
E41. The method of embodiment E40, wherein the circulating cell free DNA comprises a length of 360 nucleotides to about 40 nucleotides.
E41.1. The method of any one of embodiments E1 to E41, comprising contacting target polynucleotides with the collection of amplification primers under amplification conditions, thereby generating amplicons.
E42. The method of any one of embodiments E1 to E41, comprising:
 (a) digesting the target polynucleotides of a first sample and a second sample with the one or more methylation sensitive restriction endonucleases that specifically digest the target polynucleotides at the at least one restriction endonuclease recognition site when the at least one restriction endonuclease site is unmethylated, wherein each of the samples comprise one or more of the selected loci;
 (b) contacting each sample with the collection of oligonucleotide primers under amplification conditions, thereby providing target specific amplicons of undigested target polynucleotides; and
 (c) analyzing the target specific amplicons from each sample, wherein a differentially methylated locus is identified according to the analyzing.
E43. The method of embodiment E42, wherein the analyzing comprises determining an amount of the target specific amplicons from each sample.
E44. The method of embodiment E43, wherein the amount of target specific amplicons of the first sample is significantly different from the amount of target specific amplicons of the second sample.

E45. The method of any one of embodiments E42 to E44, wherein the first sample and the second sample are from different sources.

E46. The method of any one of embodiments E42 to E45, wherein the first sample and/or the second sample comprise circulating cell free nucleic acid.

E47. The method of any one of embodiments E42 to E46, wherein the analyzing comprises determining a methylation status of the one or more selected loci in the first sample.

E48. The method of any one of embodiment E42 to E47, wherein the analyzing comprises determining a methylation status of the one or more selected loci in the second sample.

E49. The method of any one of embodiments E42 to E48, wherein the first sample comprises a minority nucleic acid species.

E50. The method of any one of embodiments E42 to E49, wherein the second sample comprises a majority nucleic acid species.

E51. The method of any one of embodiments E42 to E50, wherein the first sample comprises fetal nucleic acid.

E52. The method of any one of embodiments E42 to E51, wherein the first sample comprises enriched fetal nucleic acid.

E53. The method of any one of embodiments E42 to E52, wherein the second sample comprises maternal nucleic acid.

E54. The method of any one of embodiments E50 to E53, wherein the analyzing comprises identifying one or more of the selected loci 60% or more methylated in the majority nucleic acid species relative to the minority nucleic acid species.

E55. The method of embodiment E54, wherein the analyzing comprises identifying one or more of the selected loci 70% or more methylated in the majority nucleic acid species relative to the minority nucleic acid species.

E56. The method of embodiment E55, wherein the analyzing comprises identifying one or more of the selected loci 75% or more methylated in the majority nucleic acid species relative to the minority nucleic acid species.

E57. The method of embodiment E56, wherein the analyzing comprises identifying one or more of the selected loci 80% or more methylated in the majority nucleic acid species relative to the minority nucleic acid species.

E58. The method of any one of embodiments E50 to E57, wherein the analyzing comprises identifying one or more of the selected loci 40% or less methylated in the minority nucleic acid species relative to the majority nucleic acid species.

E59. The method of embodiment E58, wherein the analyzing comprises identifying one or more of the selected loci 30% or less methylated in the minority nucleic acid species relative to the majority nucleic acid species.

E60. The method of embodiment E59, wherein the analyzing comprises identifying one or more of the selected loci 20% or less methylated in the minority nucleic acid species relative to the majority nucleic acid species.

E61. The method of embodiment E60, wherein the analyzing comprises identifying one or more of the selected loci 10% or less methylated in the minority nucleic acid species relative to the majority nucleic acid species.

E62. The method of any one of embodiments E50 to E61, wherein the analyzing comprises identifying one or more of the selected loci, wherein a difference in methylation status between the minority nucleic acid species and the majority nucleic acid species for the one or more selected loci is 5% or more.

E63. The method of embodiment E62, wherein the difference in methylation status is 10% or more.

E64. The method of embodiment E63, wherein the difference in methylation status is 20% or more.

E65. The method of embodiment E64, wherein the difference in methylation status is 40% or more.

E66. The method of any one of embodiments E42 to E65, wherein the methylation status of the one or more selected loci in the first sample is 15% or less methylated and the methylation status of the one or more loci in the second sample is 60% or greater.

E67. The method of any one of embodiments E42 to E66, wherein the one or more methylation sensitive restriction endonuclease comprises two or more methylation sensitive restriction endonucleases.

E68. The method of any one of embodiments E42 to E67, wherein the one or more methylation sensitive restriction endonuclease does not digest nucleic acid when the at least one restriction endonuclease recognition site is methylated.

E69. The method of any one of embodiments E42 to E68, wherein the differentially methylated locus identified in E42(d) is hypomethylated in the first sample.

E70. The method of any one of embodiments E42 to E69, wherein the differentially methylated locus identified in E42(d) is hypermethylated in the second sample.

E71. The collection of oligonucleotide primer pairs of any one of embodiments E42 to E70, wherein the analyzing comprises analyzing target polynucleotides that a cleaved by the one or more methylation sensitive restriction endonucleases.

E72. The collection of oligonucleotide primer pairs of any one of embodiments E42 to E70, wherein the analyzing comprises analyzing target polynucleotides that a not cleaved by the one or more methylation sensitive restriction endonucleases.

F1. A collection of oligonucleotide primer pairs for identifying the presence or absence of a hypomethylated locus prepared by a process comprising:
(a) selecting one or more genomic loci wherein each locus comprises three or more features selected from;
(i) 5000 contiguous base pairs, or less,
(ii) a CpG density of 16 CpG methylation sites per 1000 base pairs, or less,
(iii) a gene density of 0.1 genes per 1000 base pair, or less,
(iv) at least 5 CpG methylation sites,
(v) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases,
(vi) at least 1 restriction endonuclease recognition site per 1000 base pairs, wherein the at least one restriction endonuclease recognition sites can be specifically digested by a methylation sensitive cleavage agent,
(vii) a locus comprising a methylation status of 40% or less in fetal nucleic acid,
(viii) a locus comprising a methylation status of 60% or more in maternal nucleic acid, and
(ix) a locus comprising a difference in methylation status of 5% or more between fetal nucleic acid and maternal nucleic acid; and
(b) preparing a plurality of oligonucleotide primer pairs, wherein each primer of each primer pair hybridizes to a portion of a strand of the locus selected in (a) for which the primer pair is specific, whereby a collection of amplification primers is prepared.

F1.1. The collection of oligonucleotide primer pairs of embodiment F1, wherein each of the primers of each of the primer pairs is specific for a target polynucleotide located in one or more of the loci selected in (a).

F1.2. The collection of oligonucleotide primer pairs of embodiment F1.1, wherein each of the primer pairs in configured for amplifying the target polynucleotide located in one or more of the loci selected in (a) for which the primer pair is specific.

F1.3. The collection of oligonucleotide primer pairs of embodiment F1.1 or F1.2, wherein each of the primers of the primer pair can hybridize to a portion of the target polynucleotide for which the primer is specific.

F1.4. The collection of oligonucleotide primer pairs of any one of embodiments F1.1 to F1.3, wherein each of the loci selected in (a) comprise one or more target polynucleotides.

F1.5. The collection of oligonucleotide primer pairs of any one of embodiments F1.1 to F1.4, wherein each of the one or more target nucleic polynucleotides comprises at least one of the restriction endonuclease recognition sites in (a)(vi), wherein each of the primer pairs flank at least one of the restriction endonuclease recognition sites in (a)(vi).

F2. The collection of oligonucleotide primer pairs of any one of embodiments F1.4 or F1.5, wherein each locus comprises at least two target polynucleotides.

F3. The collection of oligonucleotide primer pairs of any one of embodiments F1 to F2, wherein the feature of (a)(i) is 2000 contiguous nucleotides, or less.

F4. The collection of oligonucleotide primer pairs of embodiment F3, wherein the feature of (a)(i) is 1000 contiguous nucleotides, or less.

F4.1. The collection of oligonucleotide primer pairs of embodiment F3, wherein the feature of (a)(i) is 750 contiguous nucleotides, or less.

F4.2. The collection of oligonucleotide primer pairs of embodiment F3, wherein the feature of (a)(i) is 500 contiguous nucleotides, or less.

F4.3. The collection of oligonucleotide primer pairs of embodiment F3, wherein the feature of (a)(i) is 250 contiguous nucleotides, or less.

F5. The collection of oligonucleotide primer pairs of any one of embodiments F1 to F4.3, wherein the CpG density of (a)(ii) is 12 CpG methylation sites per 1000 base pairs, or less.

F6. The collection of oligonucleotide primer pairs of embodiment F5, wherein the CpG density of (a)(ii) is 8 CpG methylation sites per 1000 base pairs, or less.

F7. The collection of oligonucleotide primer pairs of embodiment F6, wherein the CpG density of (a)(ii) is 4 CpG methylation sites per 1000 base pairs, or less.

F8. The collection of oligonucleotide primer pairs of any one of embodiments F1 to F7, wherein the CpG density of (a)(ii) is about 0.016 CpG methylation sites per base pair, or less.

F9. The collection of oligonucleotide primer pairs of embodiment F8, wherein the CpG density of (a)(ii) is about 0.012 CpG methylation sites per base pair, or less.

F10. The collection of oligonucleotide primer pairs of embodiment F9, wherein the CpG density of (a)(ii) is about 0.008 CpG methylation sites per base pair, or less.

F11. The collection of oligonucleotide primer pairs of embodiment F10, wherein the CpG density of (a)(ii) is about 0.004 CpG methylation sites per base pair, or less.

F12. The collection of oligonucleotide primer pairs of any one of embodiments F1 to F11, wherein the at least 5 CpG methylation sites of (a)(iv) are at least 9 CpG methylation sites.

F13. The collection of oligonucleotide primer pairs of embodiment F12, wherein the at least 5 CpG methylation sites of (a)(iv) are at least 12 CpG methylation sites.

F14. The collection of oligonucleotide primer pairs of any one of embodiments F1 to F13, wherein the gene density of (a)(iii) is 0.08 genes per 1000 base pair, or less.

F15. The collection of oligonucleotide primer pairs of embodiment F14, wherein the gene density of (a)(iii) is 0.06 genes per 1000 base pair, or less.

F16. The collection of oligonucleotide primer pairs of embodiment F15, wherein the gene density of (a)(iii) is 0.04 genes per 1000 base pair, or less.

F17. The collection of oligonucleotide primer pairs of embodiment F16, wherein the gene density of (a)(iii) is 0.02 genes per 1000 base pair, or less.

F18. The collection of oligonucleotide primer pairs of any one of embodiments F1 to F17, wherein the average, mean, median or absolute distance between each restriction endonuclease recognition site of (v) about 40 to about 100 base pairs.

F19. The collection of oligonucleotide primer pairs of any one of embodiments F1 to F18, the feature of (a)(vi) is at least 10 restriction endonuclease recognition site per 1000 base pairs F20. The collection of oligonucleotide primer pairs of embodiment F19, wherein the feature of (a)(vi) is at least 20 restriction endonuclease recognition sites per 1000 bp.

F21. The collection of oligonucleotide primer pairs of embodiment F20, wherein the feature of (a)(vi) is at least 30 restriction endonuclease recognition sites per 1000 bp.

F21.1. The collection of oligonucleotide primer pairs of any one of embodiments F1 to F21, wherein genomic loci having features (vii), (viii) and (ix) are selected in (a).

F21.2. The collection of oligonucleotide primer pairs of any one of embodiments F1 to F21.1, wherein genomic loci having features (ii), (iv) and (ix) are selected in (a).

F21.3. The collection of oligonucleotide primer pairs of any one of embodiments F1 to F21, wherein genomic loci having features (ii), (vii) and (ix) are selected in (a).

F21.4. The collection of oligonucleotide primer pairs of any one of embodiments F1 to F21, wherein genomic loci having features (iii), (iv) and (ix) are selected in (a).

F21.5. The collection of oligonucleotide primer pairs of any one of embodiments F21.1 to F21.4, wherein genomic loci having feature (i) is selected in (a).

F21.6. The collection of oligonucleotide primer pairs of any one of embodiments F21.1 to F21.5, wherein genomic loci having feature (v) is selected in (a).

F21.7. The collection of oligonucleotide primer pairs of any one of embodiments F21.1 to F21.6, wherein genomic loci having feature (vi) is selected in (a).

F22. The collection of oligonucleotide primer pairs of any one of embodiments F1 to F21.7, wherein at least one of the oligonucleotide primers of each of the primer pairs comprises a non-native element.

F23. The collection of oligonucleotide primer pairs of any one of embodiments F1 to F21, wherein each of the oligonucleotide primers comprises a non-native element.

F24. The collection of oligonucleotide primer pairs of embodiment F22 or F23, wherein the non-native element comprises a heterologous nucleotide sequence.

F25. The collection of oligonucleotide primer pairs of embodiment F22 or F23, wherein the non-native element comprises an identifier.

F26. The collection of oligonucleotide primer pairs of embodiment F25, wherein the identifier comprises a label F27. The collection of oligonucleotide primer pairs of any one of embodiments F22 to F26, wherein the non-native element comprises a binding agent.

F28. The collection of oligonucleotide primer pairs of embodiment F27, wherein the binding agent comprises a member of a binding pair.

F29. The collection of oligonucleotide primer pairs of any one of embodiments F22 to F28, wherein the non-native element comprises a non-native nucleotide.

F30. The collection of oligonucleotide primer pairs of embodiment F29, wherein the non-native nucleotide comprises a chemical modification.

F31. The collection of oligonucleotide primer pairs of any one of embodiments F1 to F30, wherein both of the oligonucleotide primers of each of the primer pairs comprises a hybridization sequence that is complimentary to a portion of the target sequence which the primer pair is configured to amplify.

F32. The collection of oligonucleotide primer pairs of embodiment F31, wherein the target sequence, which the primer pair is configured to amplify, is longer than the combined length of the hybridization sequences of the target specific primer pair.

F33. The collection of oligonucleotide primer pairs of embodiment F31 or F32, wherein each of the oligonucleotide primers of each of the primer pairs comprises aa sequence tag.

F34. The collection of oligonucleotide primer pairs of embodiment F31 or F32, wherein each of the oligonucleotide primers of each of the primer pairs comprises an different hybridization sequence.

F35. The collection of oligonucleotide primer pairs of any one of embodiments F1 to F34, wherein the target polynucleotide comprises a length of about 500 nucleotides to about 30 nucleotides. (nucleosomes are 146 or 166)

F36. The collection of oligonucleotide primer pairs of embodiment F35, wherein the target polynucleotide comprises a length of about 360 nucleotides to about 40 nucleotides.

F37. The collection of oligonucleotide primer pairs of embodiment F36, wherein the target polynucleotide comprises a length of about 180 nucleotides to about 40 nucleotides.

F38. The collection of oligonucleotide primer pairs of any one of embodiments F1 to F37, wherein the target polynucleotide is single stranded.

F39. The collection of oligonucleotide primer pairs of any one of embodiments F1 to F37, wherein the target polynucleotide is double stranded.

F40. The collection of oligonucleotide primer pairs of any one of embodiments F1 to F37, wherein the target polynucleotide is circulating cell free DNA.

F41. The collection of oligonucleotide primer pairs of F40, wherein the circulating cell free DNA comprises a length of 360 nucleotides to about 40 nucleotides.

F41.1. The collection of oligonucleotide primer pairs of any one of embodiments F1 to F41, comprising contacting target polynucleotides with the collection of amplification primers under amplification conditions, thereby generating amplicons.

F42. The collection of oligonucleotide primer pairs of any one of embodiments F1 to F41.1, wherein the process comprises:
(a) digesting the target polynucleotide of a first sample and a second sample with the one or more methylation sensitive restriction endonucleases that specifically digest the target polynucleotide at the at least one restriction endonuclease recognition site when the at least one restriction endonuclease site is unmethylated, wherein each of the samples comprise one or more of the selected loci;
(b) contacting each sample with the collection of oligonucleotide primers under amplification conditions, thereby providing target specific amplicons of undigested target polynucleotides; and
(c) analyzing the target specific amplicons from each sample, wherein a differentially methylated locus is identified according to the analyzing.

F43. The collection of oligonucleotide primer pairs of embodiment F42, wherein the analyzing comprises determining an amount of the target specific amplicons from each sample.

F44. The collection of oligonucleotide primer pairs of embodiment F43, wherein the amount of target specific amplicons of the first sample is significantly different from the amount of target specific amplicons of the second sample.

F45. The collection of oligonucleotide primer pairs of any one of embodiments F42 to F44, wherein the first sample and the second sample are from different sources.

F46. The collection of oligonucleotide primer pairs of any one of embodiments F42 to F45, wherein the first sample and/or the second sample comprise circulating cell free nucleic acid.

F47. The collection of oligonucleotide primer pairs of any one of embodiments F42 to F46, wherein the analyzing comprises determining a methylation status of the one or more selected loci in the first sample.

F48. The collection of oligonucleotide primer pairs of any one of embodiment F42 to F47, wherein the analyzing comprises determining a methylation status of the one or more selected loci in the second sample.

F49. The collection of oligonucleotide primer pairs of any one of embodiments F42 to F48, wherein the first sample comprises a minority nucleic acid species.

F50. The collection of oligonucleotide primer pairs of any one of embodiments F42 to F49, wherein the second sample comprises a majority nucleic acid species.

F51. The collection of oligonucleotide primer pairs of any one of embodiments F42 to F50, wherein the first sample comprises fetal nucleic acid.

F52. The collection of oligonucleotide primer pairs of any one of embodiments F42 to F51, wherein the first sample comprises enriched fetal nucleic acid.

F53. The collection of oligonucleotide primer pairs of any one of embodiments F42 to F52, wherein the second sample comprises maternal nucleic acid.

F54. The collection of oligonucleotide primer pairs of any one of embodiments F50 to F53, wherein the analyzing comprises identifying one or more of the selected loci 60% or more methylated in the majority nucleic acid species relative to the minority nucleic acid species.

F55. The collection of oligonucleotide primer pairs of embodiment F54, wherein the analyzing comprises identifying one or more of the selected loci 70% or more methylated in the majority nucleic acid species relative to the minority nucleic acid species.

F56. The collection of oligonucleotide primer pairs of embodiment F55, wherein the analyzing comprises identifying one or more of the selected loci 75% or more methylated in the majority nucleic acid species relative to the minority nucleic acid species.

F57. The collection of oligonucleotide primer pairs of embodiment F56, wherein the analyzing comprises identifying one or more of the selected loci 80% or more methylated in the majority nucleic acid species relative to the minority nucleic acid species.

F58. The collection of oligonucleotide primer pairs of any one of embodiments F50 to F57, wherein the analyzing comprises identifying one or more of the selected loci 40% or less methylated in the minority nucleic acid species relative to the majority nucleic acid species.

F59. The collection of oligonucleotide primer pairs of embodiment F58, wherein the analyzing comprises identifying one or more of the selected loci 30% or less methylated in the minority nucleic acid species relative to the majority nucleic acid species.

F60. The collection of oligonucleotide primer pairs of embodiment F59, wherein the analyzing comprises identifying one or more of the selected loci 20% or less methylated in the minority nucleic acid species relative to the majority nucleic acid species.

F61. The collection of oligonucleotide primer pairs of embodiment F60, wherein the analyzing comprises identifying one or more of the selected loci 10% or less methylated in the minority nucleic acid species relative to the majority nucleic acid species.

F62. The collection of oligonucleotide primer pairs of any one of embodiments F50 to F61, wherein the analyzing comprises identifying one or more of the selected loci, wherein a difference in methylation status between the minority nucleic acid species and the majority nucleic acid species for the one or more selected loci is 5% or more.

F63. The collection of oligonucleotide primer pairs of embodiment F62, wherein the difference in methylation status is 10% or more.

F64. The collection of oligonucleotide primer pairs of embodiment F63, wherein the difference in methylation status is 20% or more.

F65. The collection of oligonucleotide primer pairs of embodiment F64, wherein the difference in methylation status is 40% or more.

F66. The collection of oligonucleotide primer pairs of any one of embodiments F42 to F65, wherein the methylation status of the one or more selected loci in the first sample is 15% or less methylated and the methylation status of the one or more loci in the second sample is 60% or greater.

F67. The collection of oligonucleotide primer pairs of any one of embodiments F42 to F66, wherein the one or more methylation sensitive restriction endonuclease comprises two or more methylation sensitive restriction endonucleases.

F68. The collection of oligonucleotide primer pairs of any one of embodiments F42 to F67, wherein the one or more methylation sensitive restriction endonuclease does not digest nucleic acid when the at least one restriction endonuclease recognition site is methylated.

F69. The collection of oligonucleotide primer pairs of any one of embodiments F42 to F68, wherein the differentially methylated locus identified in F42(d) is hypomethylated in the first sample.

F70. The collection of oligonucleotide primer pairs of any one of embodiments F42 to F69, wherein the differentially methylated locus identified in F42(d) is hypermethylated in the second sample.

F71. The collection of oligonucleotide primer pairs of any one of embodiments F42 to F70, wherein the analyzing comprises analyzing target polynucleotides that a cleaved by the one or more methylation sensitive restriction endonucleases.

F72. The collection of oligonucleotide primer pairs of any one of embodiments F42 to F70, wherein the analyzing comprises analyzing target polynucleotides that a not cleaved by the one or more methylation sensitive restriction endonucleases.

G1. A collection of amplification primer pairs for identifying the presence or absence of a hypermethylated locus prepared by a process comprising:
  (a) selecting one or more genomic loci wherein each locus comprises three or more features selected from:
    (i) a locus length of about 5000 contiguous base pairs, or less,
    (ii) at least 5 CpG methylation sites,
    (iii) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases,
    (iv) at least 1 restriction endonuclease recognition site per 1000 base pairs, wherein the at least one restriction endonuclease recognition sites can be specifically digested by a methylation sensitive restriction endonuclease,
    (v) a locus comprising a methylation status of 60% or more in a minority nucleic acid species,
    (vi) a locus comprising a methylation status of 40% or less in a majority nucleic acid species, and
    (vii) a locus comprising a difference in methylation status of 5% or more between a minority nucleic acid species and a majority nucleic acid species; and
  (b) preparing a plurality of oligonucleotide primer pairs, wherein each primer of each primer pair hybridizes to a portion of a strand of the locus selected in (a) for which the primer pair is specific, whereby a collection of amplification primers is prepared.

G1.1. The collection of amplification primer pairs of embodiment G1, wherein each of the primers of each of the primer pairs is specific for a target polynucleotide located in one or more of the loci selected in (a).

G1.2. The collection of amplification primer pairs of embodiment G1.1, wherein each of the primer pairs in configured for amplifying the target polynucleotide located in one or more of the loci selected in (a) for which the primer pair is specific.

G1.3. The collection of amplification primer pairs of embodiment G1.1 or G1.2, wherein each of the primers of the primer pair can hybridize to a portion of the target polynucleotide for which the primer is specific.

G1.4. The collection of amplification primer pairs of any one of embodiments G1.1 to G1.3, wherein each of the loci selected in (a) comprise one or more target polynucleotides.

G2. The collection of amplification primer pairs of any one of embodiments G1.1 to G1.4, wherein each of the one or more target nucleic polynucleotides comprises at least one of the restriction endonuclease recognition sites in (a)(iv), wherein each of the primer pairs flank at least one of the restriction endonuclease recognition sites in (a)(iv).

G3. The collection of amplification primer pairs of any one of embodiments G1.4 or G2, wherein each locus comprises at least two target polynucleotides.

G4. The collection of amplification primer pairs of any one or embodiments G1 to G3, wherein the feature of (a)(i) is 2000 contiguous nucleotides, or less.

G5. The collection of amplification primer pairs of embodiment G4, wherein the feature of (a)(i) is 1000 contiguous nucleotides, or less.

G6. The collection of amplification primer pairs of embodiment G4, wherein the feature of (a)(i) is 750 contiguous nucleotides, or less.

G7. The collection of amplification primer pairs of embodiment G4, wherein the feature of (a)(i) is 500 contiguous nucleotides, or less.

G8. The collection of amplification primer pairs of embodiment G4, wherein the feature of (a)(i) is 250 contiguous nucleotides, or less.

G9. The collection of amplification primer pairs of any one of embodiments G1 to G8, wherein the at least 5 CpG methylation sites of (a)(ii) are at least 9 CpG methylation sites.

G10. The collection of amplification primer pairs of embodiment G9, wherein the at least 5 CpG methylation sites of (a)(ii) are at least 12 CpG methylation sites.

G11. The collection of amplification primer pairs of any one of embodiments G1 to G10, wherein the average, mean, median or absolute distance between each restriction endonuclease recognition site of (iii) is about 40 to about 100 base pairs.

G12. The collection of amplification primer pairs of any one of embodiments G1 to G11, wherein the feature of (a)(iv) is at least 10 restriction endonuclease recognition site per 1000 base pairs G13. The collection of amplification primer pairs of embodiment G12, wherein the feature of (a)(iv) is at least 20 restriction endonuclease recognition sites per 1000 bp.

G14. The collection of amplification primer pairs of embodiment G12, wherein the feature of (a)(iv) is at least 30 restriction endonuclease recognition sites per 1000 bp.

G14.1. The collection of amplification primer pairs of any one of embodiments G1 to G14, wherein genomic loci having features (ii), (iii) and (iv) are selected in (a).

G14.2. The collection of amplification primer pairs of any one of embodiments G1 to G14, wherein genomic loci having features (ii), (iii) and (vii) are selected in (a).

G14.3. The collection of amplification primer pairs of any one of embodiments G1 to G14, wherein genomic loci having features (ii), (iv) and (vii) are selected in (a).

G14.4. The collection of amplification primer pairs of any one of embodiments G1 to G14, wherein genomic loci having features (iii), (iv) and (vii) are selected in (a).

G14.5. The collection of amplification primer pairs of any one of embodiments G14.1 to G14.4, wherein genomic loci having feature (i) is selected in (a).

G14.6. The collection of amplification primer pairs of any one of embodiments G14.1 to G14.5, wherein genomic loci having feature (v) is selected in (a).

G14.7. The collection of amplification primer pairs of any one of embodiments G14.1 to G14.6, wherein genomic loci having feature (vi) is selected in (a).

G15. The collection of amplification primer pairs of any one of embodiments G1 to G14, wherein at least one of the amplification primers of each of the primer pairs comprises a non-native element.

G16. The collection of amplification primer pairs of any one of embodiments G1 to G15, wherein each of the amplification primers comprises a non-native element.

G17. The collection of amplification primer pairs of embodiment G15 or G16, wherein the non-native element comprises a heterologous nucleotide sequence.

G18. The collection of amplification primer pairs of embodiment G15 or G16, wherein the non-native element comprises an identifier.

G19. The collection of amplification primer pairs of embodiment G18, wherein the identifier comprises a label G20. The collection of amplification primer pairs of any one of embodiments G16 to G19, wherein the non-native element comprises a binding agent.

G21. The collection of amplification primer pairs of embodiment G20, wherein the binding agent comprises a member of a binding pair.

G22. The collection of amplification primer pairs of any one of embodiments G15 to G21, wherein the non-native element comprises a non-native nucleotide.

G23. The collection of amplification primer pairs of embodiment G22, wherein the non-native nucleotide comprises a chemical modification.

G24. The collection of amplification primer pairs of any one of embodiments G1 to G23, wherein both of the amplification primers of each of the primer pairs comprises a hybridization sequence that is complimentary to a portion of the target sequence which the primer pair is configured to amplify.

G25. The collection of amplification primer pairs of embodiment G24, wherein the target sequence, which the primer pair is configured to amplify, is longer than the combined length of the hybridization sequences of the target specific primer pair.

G26. The collection of amplification primer pairs of embodiment G24 or G25, wherein each of the amplification primers of each of the primer pairs comprises a sequence tag.

G27. The collection of amplification primer pairs of embodiment G24 or G25, wherein each of the amplification primers of each of the primer pairs comprises a different hybridization sequence.

G28. The collection of amplification primer pairs of any one of embodiments G1 to G27, wherein the target polynucleotide comprises a length of about 500 nucleotides to about 30 nucleotides.

G29. The collection of amplification primer pairs of embodiment G28, wherein the target polynucleotide comprises a length of about 360 nucleotides to about 40 nucleotides.

G30. The collection of amplification primer pairs of embodiment G28, wherein the target polynucleotide comprises a length of about 180 nucleotides to about 40 nucleotides.

G31. The collection of amplification primer pairs of any one of embodiments G1 to G30, wherein the target polynucleotide is single stranded.

G32. The collection of amplification primer pairs of any one of embodiments G1 to G31, wherein the target polynucleotide is double stranded.

G33. The collection of amplification primer pairs of any one of embodiments G1 to G32, wherein the target polynucleotide is a circulating cell free nucleic acid.

G34. The collection of amplification primer pairs of G33, wherein the circulating cell free nucleic acid comprises a length of about 500 nucleotides to about 30 nucleotides.

G35. The collection of amplification primer pairs of any one of embodiments G1 to G34, wherein the minority nucleic acid species and the majority nucleic acid species comprise one or more target polynucleotides.

G36. The collection of amplification primer pairs of any one of embodiments G1 to G35, wherein the process comprises:

(a) digesting the target polynucleotides of a first sample and a second sample with the one or more methylation sensitive restriction endonucleases that specifically digest the target polynucleotides at the at least one restriction endonuclease recognition site when the at least one restriction endonuclease recognition site is unmethylated, wherein each of the samples comprise one or more of the selected loci;

(b) contacting each of the samples with the collection of amplification primers under amplification conditions, thereby providing target specific amplicons of undigested target polynucleotides; and (c) analyzing the target specific amplicons from each sample, wherein one or more differentially methylated loci are identified according to the analyzing.

G37. The collection of amplification primer pairs of embodiment G36, wherein the analyzing comprises determining an amount of the target specific amplicons from each sample.

G38. The collection of amplification primer pairs of embodiment G37, wherein the amount of target specific amplicons of the first sample is significantly different from the amount of target specific amplicons of the second sample.

G39. The collection of amplification primer pairs of any one of embodiments G37 to G38, wherein the first sample and the second sample are from different sources.

G40. The collection of amplification primer pairs of any one of embodiments G36 to G39, wherein the first sample and/or the second sample comprise circulating cell free nucleic acid.

G41. The collection of amplification primer pairs of any one of embodiments G36 to G40, wherein the analyzing comprises determining a methylation status of the one or more selected loci in the first sample.

G42. The collection of amplification primer pairs of any one of embodiment G36 to G41, wherein the analyzing comprises determining a methylation status of the one or more selected loci in the second sample.

G43. The collection of amplification primer pairs of any one of embodiments G36 to G42, wherein the first sample comprises the minority nucleic acid species.

G44. The collection of amplification primer pairs of any one of embodiments G36 to G43, wherein the second sample comprises the majority nucleic acid species.

G45. The collection of amplification primer pairs of any one of embodiments G36 to G44, wherein the second sample does not include the minority nucleic acid species.

G46. The collection of amplification primer pairs of any one of embodiments G36 to G45, wherein the minority nucleic acid species is partially or entirely removed from the second sample.

G47. The collection of amplification primer pairs of any one of embodiments G1 to G46, wherein the minority nucleic acid species is fetal nucleic acid.

G48. The collection of amplification primer pairs of any one of embodiments G36 to G47, wherein the first sample is enriched for the minority nucleic acid species.

G49. The collection of amplification primer pairs of any one of embodiments G1 to G48, wherein the majority nucleic acid species is maternal nucleic acid.

G50. The collection of amplification primer pairs of any one of embodiments G1 to G49, wherein the feature of (a)(vi) is 65% or more in the minority species.

G51. The collection of amplification primer pairs of any one of embodiments G1 to G50, wherein the feature of (a)(vi) is 70% or more in the minority species.

G52. The collection of amplification primer pairs of any one of embodiments G1 to G51, wherein the feature of (a)(vi) is 75% or more in the minority species.

G53. The collection of amplification primer pairs of any one of embodiments G1 to G52, wherein the feature of (a)(vi) is 80% or more in the minority species.

G54. The collection of amplification primer pairs of any one of embodiments G1 to G53, wherein the feature of (a)(vii) is 40% or less in the majority nucleic acid species.

G55. The collection of amplification primer pairs of any one of embodiments G1 to G54, wherein the feature of (a)(vii) is 30% or less in the majority nucleic acid species.

G56. The collection of amplification primer pairs of any one of embodiments G1 to G55, wherein the feature of (a)(vii) is 20% or less in the majority nucleic acid species.

G57. The collection of amplification primer pairs of any one of embodiments G1 to G56, wherein the feature of (a)(vii) is 10% or less in the majority nucleic acid species.

G58. The collection of amplification primer pairs of any one of embodiments G1 to G57, wherein the feature of (a)(viii) is a difference in methylation status of 7.5% or more.

G59. The collection of amplification primer pairs of any one of embodiments G1 to G58, wherein the feature of (a)(viii) is a difference in methylation status of 10% or more.

G60. The collection of amplification primer pairs of any one of embodiments G1 to G59, wherein the feature of (a)(viii) is a difference in methylation status of 20% or more.

G61. The collection of amplification primer pairs of any one of embodiments G1 to G60, wherein the feature of (a)(viii) is a difference in methylation status of 40% or more.

G62. The collection of amplification primer pairs of any one of embodiments G36 to G61, wherein the methylation status of the one or more selected loci in the first sample is 60% or more and the methylation status of the one or more loci in the second sample is 40% or less.

G63. The collection of amplification primer pairs of any one of embodiments G36 to G62, wherein the one or more methylation sensitive restriction endonuclease comprises two or more methylation sensitive restriction endonucleases.

G64. The collection of amplification primer pairs of any one of embodiments G36 to G63, wherein the one or more methylation sensitive restriction endonucleases do not digest nucleic acid when the at least one restriction endonuclease recognition site is methylated.

G65. The collection of amplification primer pairs of any one of embodiments G36 to G64, wherein the differentially methylated locus identified in G36(c) is hypermethylated in the first sample.

G66. The collection of amplification primer pairs of any one of embodiments G36 to G65, wherein the differentially methylated locus identified in G36(c) is hypomethylated in the second sample.

G67. The collection of amplification primer pairs of any one of embodiments G36 to G66, wherein the analyzing comprises analyzing target polynucleotides that a not cleaved by the one or more methylation sensitive restriction endonucleases.

H1. A method of amplifying one or more target polynucleotides in a hypermethylated locus comprising: contacting a sample with one or more of the primer pairs of embodiments G1 to G67 under amplification conditions, thereby generating target specific amplicons.

H2. The method of embodiment H1, wherein the sample comprises circulating cell free nucleic acid obtained from a human subject.

H3. The method of embodiment H2, wherein the circulating cell free nucleic acid of the sample comprises one or more of the target polynucleotides.

H3.1. The method of any one of embodiments H1 to H3, wherein each of the primer pairs is configured for amplifying the target polynucleotide for which the primer pair is specific, wherein each of the primers of the primer pair hybridize to a portion of the target polynucleotide for which the primer pair is specific.

H3.2. The method of any one of embodiments H1 to H3, wherein each of the target polynucleotides comprise at least one of the restriction endonuclease restriction recognition sites in (a)(iv), wherein each of the primer pairs flank at least one of the restriction endonuclease sites in (a)(iv).

H4. The method of any one of embodiments H3 to H3.2, wherein the human subject is a pregnant female subject.

H5. The method of any one of embodiments H1 to H4, comprising, prior to contacting with the primer pairs, digesting sample nucleic acid with a methylation sensitive restriction endonuclease that specifically digests the target polynucleotide at the at least one restriction endonuclease recognition site when the at least one restriction endonuclease site is unmethylated.

H6. The method of embodiment H5, wherein the amplification conditions comprise amplifying target polynucleotides that were not cleaved by the one or more methylation sensitive restriction endonucleases.

H7. The method of any one of embodiments H1 to H6, wherein the amplification conditions comprise a known amount of one or more competitor nucleic acids.

H7.1. The method of embodiment H5 or H6, wherein the amplification conditions comprise amplifying the competitor nucleic acids, thereby providing competitor specific amplicons.

H8. The method of embodiment H7 or H7.1, wherein each of the one or more competitor nucleic acids comprise a nucleic acid sequence that is substantially identical to a target polynucleotide.

H9. The method of embodiment H8, wherein each of the one or more competitor nucleic acids comprises a feature that distinguishes the competitor nucleic acid from the target polynucleotide to which it is substantially identical to.

H10. The method of any one of embodiments H7 to H9, wherein each of which primer pairs is configured to specifically amplify one of the target polynucleotides and its competitor nucleic acid.

H11. The method of embodiment H10, comprising analyzing the target specific amplicons and the competitor specific amplicons.

H12. The method of embodiment H11, wherein the analyzing comprises determining the presence or absence of a genetic variation.

H13. The method of embodiment H12, wherein the genetic variation is a chromosome aneuploidy.

H14. The method of embodiment H13, wherein the chromosome aneuploidy is chosen from an aneuploidy of chromosome 13, 18 and 21.

H15. The method of embodiment H11, wherein the analyzing comprises determining the presence or absence of a cancer.

H16. The method of any one of embodiments of H11 to H15, wherein the analyzing comprises determining a ratio of target specific amplicons to competitor specific amplicons for each of the target polynucleotides in the sample.

H17. The method of any one of embodiments H11 to H16, wherein the analyzing comprises determining an amount of fetal nucleic acid in the sample.

H18. The method of embodiment H17, wherein the analyzing comprises normalizing each of which ratios to the amount of fetal nucleic acid in the sample.

H19. The method of any one of embodiments H16 to H18, wherein the amplification conditions comprise a portion of the fetal nucleic acid from the sample and each of which ratios is normalized according to the portion of fetal nucleic acid.

H20. The method of any one of embodiments H11 to H19, wherein the analysis comprises matrix assisted laser desorption ionization (MALDI) mass spectrometry.

H21. The method of any one of embodiments H11 to H20, wherein the analysis comprises sequencing the target specific amplicons.

H22. The method of any one of embodiments H11 to H21, wherein the analysis comprises sequencing the competitor polynucleotide specific amplicons.

H23. The method of any one of embodiments H11 to H22, wherein the amount of one or more target polynucleotides in the sample is determined according to the analysis.

H24. The method of any one of embodiments H11 to H23, wherein the analysis comprises comparing the ratios from two or more samples.

H25. The method of embodiment H24, wherein the two or more samples comprise one or more control samples.

H26. The method of embodiment H25, wherein the ratios from one or more of the samples are normalized to the one or more control samples.

H27. The method of any one of embodiments H1 to H26, wherein the methylation sensitive restriction endonuclease is selected from AatII, AccII, ACiI, AcII, AfeI, AgeI, AgeI-HF, Aor13HI, Aor51HI, AscI, AseI, BceAI, BmgBI, BsaAI, BsaHI, BsiEI, BspDI, BsrFI, BspT104I, BssHII, BstBI, BstUI, Cfr10I, ClaI, CpoI, EagI, Eco52I, FauI, FseI, FspI, DpnI, DpnII, HaeII, HaeIII, HapII, HfaI, HgaI, HhaI, HinP1I, HPAII, Hpy99I, HpyCH4IV, KasI, MaeII, McrBC, MluI, MspI, NaeI, NgoMIV, NotI, NotI-HF, NruI, NsbI, NtBsmAI, NtCviPII, PaeR7I, PluTI, PmlI, PmaCI, Psp1406I, PvuI, RsrII, SacII, SalI, SalI-HF, ScrFI, SfoI, SfrAI, SmaI, SnaBI, TspMI, ZraI and isoschizomers thereof.

H27.1. The method of any one of embodiments H1 to H27, wherein the methylation sensitive restriction endonuclease is selected from HpaII, HinP1I, HhaI, MaeII, BstUI and AciI.

H27.2. The method of any one of embodiments H1 to H27.1, wherein the methylation sensitive restriction endonuclease is selected from HHAI, HinP1I and HPAII.

H28. The method of any one of embodiments H1 to H27, wherein each locus comprises at least two target polynucleotides.

H29. The method of any one of embodiments H1 to H27, wherein the feature of (a)(i) is 2000 contiguous nucleotides, or less.

H30. The method of embodiment H29, wherein the feature of (a)(i) is 1000 contiguous nucleotides, or less.

H31. The method of embodiment H30, wherein the feature of (a)(i) is 750 contiguous nucleotides, or less.

H32. The method of embodiment H31, wherein the feature of (a)(i) is 500 contiguous nucleotides, or less.

H33. The method of embodiment H30, wherein the feature of (a)(i) is 250 contiguous nucleotides, or less.

H34. The method of any one of embodiments H1 to H33, wherein the at least 5 CpG methylation sites of (a)(ii) are at least 9 CpG methylation sites.

H35. The method of any one of embodiments H1 to H34, wherein the at least 5 CpG methylation sites of (a)(ii) are at least 12 CpG methylation sites.

H36. The method of any one of embodiments H1 to H35, wherein the average, mean, median or absolute distance between each restriction endonuclease recognition site of (iii) is about 40 to about 100 base pairs.
H37. The method of any one of embodiments H1 to H36, wherein the feature of (a)(iv) is at least 10 restriction endonuclease recognition site per 1000 base pairs
H38. The method of any one of embodiments H1 to H37, wherein the feature of (a)(iv) is at least 20 restriction endonuclease recognition sites per 1000 bp.
H39. The method of any one of embodiments H1 to H38, wherein the feature of (a)(iv) is at least 30 restriction endonuclease recognition sites per 1000 bp.
H40. The method of any one of embodiments H1 to H39, wherein the target polynucleotide comprises a length of about 500 nucleotides to about 30 nucleotides.
H41. The method of any one of embodiments H1 to H40, wherein the target polynucleotide comprises a length of about 360 nucleotides to about 40 nucleotides.
H42. The method of any one of embodiments H1 to H41, wherein the target polynucleotide comprises a length of about 180 nucleotides to about 40 nucleotides.
H43. The method of any one of embodiments H1 to H42, wherein the target polynucleotide is single stranded.
H44. The method of any one of embodiments H1 to H42, wherein the target polynucleotide is double stranded.
H45. The method of any one of embodiments H1 to H44, wherein the target polynucleotide is a circulating cell free nucleic acid.
H46. The method of any one of embodiments H1 to H45, wherein the circulating cell free nucleic acid comprises a length of about 500 nucleotides to about 30 nucleotides.
H47. The method of any one of embodiments H1 to H46, wherein the feature of (a)(v) is 65% or more in the minority species.
H48. The method of any one of embodiments H1 to H47, wherein the feature of (a)(v) is 70% or more in the minority species.
H49. The method of any one of embodiments H1 to H48, wherein the feature of (a)(v) is 75% or more in the minority species.
H50. The method of any one of embodiments H1 to H49, wherein the feature of (a)(v) is 80% or more in the minority species.
H51. The method of any one of embodiments H1 to H50, wherein the feature of (a)(vi) is 35% or less in the majority nucleic acid species.
H52. The method of any one of embodiments H1 to H51, wherein the feature of (a)(vi) is 30% or less in the majority nucleic acid species.
H53. The method of any one of embodiments H1 to H52, wherein the feature of (a)(vi) is 20% or less in the majority nucleic acid species.
H54. The method of any one of embodiments H1 to H53, wherein the feature of (a)(vi) is 10% or less in the majority nucleic acid species.
H55. The method of any one of embodiments H1 to H54, wherein the feature of (a)(vii) is a difference in methylation status of 7.5% or more.
H56. The method of any one of embodiments H1 to H55, wherein the feature of (a)(vii) is a difference in methylation status of 10% or more.
H57. The method of any one of embodiments H1 to H56, wherein the feature of (a)(vii) is a difference in methylation status of 20% or more.
H58. The method of any one of embodiments H1 to H57, wherein the feature of (a)(vii) is a difference in methylation status of 40% or more.
H59. The method of any one of embodiments H5 to H58, wherein the target polynucleotides of the sample are digested, prior to (b), with two or more methylation sensitive restriction endonucleases, wherein each of the two or more methylation sensitive restriction endonucleases recognize a different restriction endonuclease recognition sequence.
H60. The method of any one of embodiments H1 to H59, wherein the minority nucleic acid species is fetal nucleic acid.
H61. The method of any one of embodiments H1 to H60, wherein the majority nucleic acid species is maternal nucleic acid.
I1. A method for preparing a collection of amplification primers, comprising:
 (a) selecting one or more genomic loci wherein each locus comprises three or more features selected from:
  (i) a locus length of about 5000 contiguous base pairs, or less,
  (ii) at least 5 CpG methylation sites,
  (iii) a plurality of restriction endonuclease recognition sites wherein the average, mean, median or absolute distance between each restriction endonuclease recognition site on the locus is about 20 to about 125 base pairs, and each of the restriction endonuclease recognition sites is recognized by one or more methylation sensitive restriction endonucleases,
  (iv) at least 1 restriction endonuclease recognition site per 1000 base pairs, wherein the at least one restriction endonuclease recognition site can be specifically digested by a methylation sensitive restriction endonuclease,
  (v) a locus comprising a methylation status of 60% or more in fetal nucleic acid,
  (vi) a locus comprising a methylation status of 40% or less in maternal nucleic acid, and
  (vii) a locus comprising a difference in methylation status of 5% or more between fetal nucleic acid and maternal nucleic acid; and
 (b) preparing a plurality of oligonucleotide primer pairs, wherein each primer of each primer pair hybridizes to a portion of a strand of the locus selected in (a) for which the primer pair is specific, whereby a collection of amplification primers is prepared.
I1.1. The method of embodiment I1, wherein each of the primers of each of the primer pairs is specific for a target polynucleotide located in one or more of the loci selected in (a).
I1.2. The method of embodiment I1.1, wherein each of the primer pairs in configured for amplifying the target polynucleotide located in one or more of the loci selected in (a) for which the primer pair is specific.
I1.3. The method of embodiment I1.1 or I1.2, wherein each of the primers of the primer pair can hybridize to a portion of the target polynucleotide for which the primer is specific.
I1.4. The method of any one of embodiments I1.1 to I1.3, wherein each of the loci selected in (a) comprise one or more target polynucleotides.
I2. The method of any one of embodiments I1.1 to I1.4, wherein each of the one or more target nucleic polynucleotides comprises at least one of the restriction endonuclease recognition sites in (a)(iv), wherein each of the primer pairs flank at least one of the restriction endonuclease recognition sites in (a)(iv).

I3. The method of any one of embodiments I1.4 or I2, wherein each locus comprises at least two target polynucleotides.

I4. The method of any one or embodiments I1 to I3, wherein the feature of (a)(i) is 2000 contiguous nucleotides, or less.

I5. The method of embodiment I4, wherein the feature of (a)(i) is 1000 contiguous nucleotides, or less.

I6. The method of embodiment I4, wherein the feature of (a)(i) is 750 contiguous nucleotides, or less.

I7. The method of embodiment I4, wherein the feature of (a)(i) is 500 contiguous nucleotides, or less.

I8. The method of embodiment I4, wherein the feature of (a)(i) is 250 contiguous nucleotides, or less.

I9. The method of any one of embodiments I1 to I8, wherein the at least 5 CpG methylation sites of (a)(ii) are at least 9 CpG methylation sites.

I10. The method of embodiment I9, wherein the at least 5 CpG methylation sites of (a)(ii) are at least 12 CpG methylation sites.

I11. The method of any one of embodiments I1 to I10, wherein the average, mean, median or absolute distance between each restriction endonuclease recognition site of (iii) is about 40 to about 100 base pairs.

I12. The method of any one of embodiments I1 to I11, wherein the feature of (a)(iv) is at least 10 restriction endonuclease recognition sites per 1000 base pairs I13. The method of embodiment I12, wherein the feature of (a)(iv) is at least 20 restriction endonuclease recognition sites per 1000 bp.

I14. The method of embodiment I12, wherein the feature of (a)(iv) is at least 30 restriction endonuclease recognition sites per 1000 bp.

I14.1. The method of any one of embodiments I1 to I14, wherein genomic loci having features (ii), (iii) and (iv) are selected in (a).

I14.2. The method of any one of embodiments I1 to I14, wherein genomic loci having features (ii), (iii) and (vii) are selected in (a).

I14.3. The method of any one of embodiments I1 to I14, wherein genomic loci having features (ii), (iv) and (vii) are selected in (a).

I14.4. The method of any one of embodiments I1 to I14, wherein genomic loci having features (iii), (iv) and (vii) are selected in (a).

I14.5. The method of any one of embodiments I14.1 to I14.4, wherein genomic loci having feature (i) is selected in (a).

I14.6. The method of any one of embodiments I14.1 to I14.5, wherein genomic loci having feature (v) is selected in (a).

I14.7. The method of any one of embodiments I14.1 to I14.6, wherein genomic loci having feature (vi) is selected in (a).

I15. The method of any one of embodiments I1 to I14.7, wherein at least one of the amplification primers of each of the primer pairs comprises a non-native element.

I16. The method of any one of embodiments I1 to I15, wherein each of the amplification primers comprises a non-native element.

I17. The method of embodiment I15 or I16, wherein the non-native element comprises a heterologous nucleotide sequence.

I18. The method of embodiment I15 or I16, wherein the non-native element comprises an identifier.

I19. The method of embodiment I18, wherein the identifier comprises a label

I20. The method of any one of embodiments I16 to I19, wherein the non-native element comprises a binding agent.

I21. The method of embodiment I20, wherein the binding agent comprises a member of a binding pair.

I22. The method of any one of embodiments I15 to I21, wherein the non-native element comprises a non-native nucleotide.

I23. The method of embodiment I22, wherein the non-native nucleotide comprises a chemical modification.

I24. The method of any one of embodiments I1 to I23, wherein both of the amplification primers of each of the primer pairs comprises a hybridization sequence that is complimentary to a portion of the target sequence which the primer pair is configured to amplify.

I25. The method of embodiment I24, wherein the target sequence, which the primer pair is configured to amplify, is longer than the combined length of the hybridization sequences of the target specific primer pair.

I26. The method of embodiment I24 or I25, wherein each of the amplification primers of each of the primer pairs comprises a sequence tag.

I27. The method of embodiment I24 or I25, wherein each of the amplification primers of each of the primer pairs comprises a different hybridization sequence.

I28. The method of any one of embodiments I1 to I27, wherein the target polynucleotide comprises a length of about 500 nucleotides to about 30 nucleotides.

I29. The method of embodiment I28, wherein the target polynucleotide comprises a length of about 360 nucleotides to about 40 nucleotides.

I30. The method of embodiment I28, wherein the target polynucleotide comprises a length of about 180 nucleotides to about 40 nucleotides.

I31. The method of any one of embodiments I1 to I30, wherein the target polynucleotide is single stranded.

I32. The method of any one of embodiments I1 to I31, wherein the target polynucleotide is double stranded.

I33. The method of any one of embodiments I1 to I32, wherein the target polynucleotide is a circulating cell free nucleic acid.

I34. The method of I33, wherein the circulating cell free nucleic acid comprises a length of about 500 nucleotides to about 30 nucleotides.

I35. The method of any one of embodiments I1 to I34, wherein the minority nucleic acid species and the majority nucleic acid species comprise one or more target polynucleotides.

I35.1. The method of any one of embodiments I1 to I35, comprising contacting target polynucleotides with the collection of amplification primers under amplification conditions, thereby generating amplicons.

I36. The method of any one of embodiments I1 to I35.1, wherein the process comprises:
 (a) digesting the target polynucleotides of a first sample and a second sample with the one or more methylation sensitive restriction endonucleases that specifically digest the target polynucleotides at the at least one restriction endonuclease recognition site when the at least one restriction endonuclease recognition site is unmethylated, wherein each of the samples comprise one or more of the selected loci;
 (b) contacting each of the samples with the collection of amplification primers under amplification conditions, thereby providing target specific amplicons of undigested target polynucleotides; and
 (c) analyzing the target specific amplicons from each sample, wherein one or more differentially methylated loci are identified according to the analyzing.

I37. The method of embodiment I36, wherein the analyzing comprises determining an amount of the target specific amplicons from each sample.

I38. The method of embodiment I37, wherein the amount of target specific amplicons of the first sample is significantly different from the amount of target specific amplicons of the second sample.

I39. The method of any one of embodiments I37 to I38, wherein the first sample and the second sample are from different sources.

I40. The method of any one of embodiments I36 to I39, wherein the first sample and/or the second sample comprise circulating cell free nucleic acid.

I41. The method of any one of embodiments I36 to I40, wherein the analyzing comprises determining a methylation status of the one or more selected loci in the first sample.

I42. The method of any one of embodiment I36 to I41, wherein the analyzing comprises determining a methylation status of the one or more selected loci in the second sample.

I43. The method of any one of embodiments I36 to I42, wherein the first sample comprises the minority nucleic acid species.

I44. The method of any one of embodiments I36 to I43, wherein the second sample comprises the majority nucleic acid species.

I45. The method of any one of embodiments I36 to I44, wherein the second sample does not include the minority nucleic acid species.

I46. The method of any one of embodiments I36 to I45, wherein the minority nucleic acid species is partially or entirely removed from the second sample.

I47. The method of any one of embodiments I1 to I46, wherein the minority nucleic acid species is fetal nucleic acid.

I48. The method of any one of embodiments I36 to I47, wherein the first sample is enriched for the minority nucleic acid species.

I49. The method of any one of embodiments I1 to I48, wherein the majority nucleic acid species is maternal nucleic acid.

I50. The method of any one of embodiments I1 to I49, wherein the feature of (a)(vi) is 65% or more in the minority species.

I51. The method of any one of embodiments I1 to I50, wherein the feature of (a)(vi) is 70% or more in the minority species.

I52. The method of any one of embodiments I1 to I51, wherein the feature of (a)(vi) is 75% or more in the minority species.

I53. The method of any one of embodiments I1 to I52, wherein the feature of (a)(vi) is 80% or more in the minority species.

I54. The method of any one of embodiments I1 to I53, wherein the feature of (a)(vii) is 40% or less in the majority nucleic acid species.

I55. The method of any one of embodiments I1 to I54, wherein the feature of (a)(vii) is 30% or less in the majority nucleic acid species.

I56. The method of any one of embodiments I1 to I55, wherein the feature of (a)(vii) is 20% or less in the majority nucleic acid species.

I57. The method of any one of embodiments I1 to I56, wherein the feature of (a)(vii) is 10% or less in the majority nucleic acid species.

I58. The method of any one of embodiments I1 to I57, wherein the feature of (a)(viii) is a difference in methylation status of 7.5% or more.

I59. The method of any one of embodiments I1 to I58, wherein the feature of (a)(viii) is a difference in methylation status of 10% or more.

I60. The method of any one of embodiments I1 to I59, wherein the feature of (a)(viii) is a difference in methylation status of 20% or more.

I61. The method of any one of embodiments I1 to I60, wherein the feature of (a)(viii) is a difference in methylation status of 40% or more.

I62. The method of any one of embodiments I36 to I61, wherein the methylation status of the one or more selected loci in the first sample is 60% or more and the methylation status of the one or more loci in the second sample is 40% or less.

I63. The method of any one of embodiments I36 to I62, wherein the one or more methylation sensitive restriction endonucleases comprises two or more methylation sensitive restriction endonucleases.

I64. The method of any one of embodiments I36 to I63, wherein the one or more methylation sensitive restriction endonucleases do not digest nucleic acid when the at least one restriction endonuclease recognition site is methylated.

I65. The method of any one of embodiments I36 to I64, wherein the differentially methylated locus identified in I36(c) is hypermethylated in the first sample.

I66. The method of any one of embodiments I36 to I65, wherein the differentially methylated locus identified in I36(c) is hypomethylated in the second sample.

I67. The method of any one of embodiments I36 to I66, wherein the analyzing comprises analyzing target polynucleotides that are not cleaved by the one or more methylation sensitive restriction endonucleases.

TABLE 4

| Name | chr | start.pos | end.pos | median.tstat | num.cg | dmr.size |
|---|---|---|---|---|---|---|
| chr18_group026471 | chr18 | 46293373 | 46293973 | −16.9049 | 11 | 600 |
| chr21_group016566 | chr21 | 37607430 | 37607980 | −14.7907 | 9 | 550 |
| chr21_group018120 | chr21 | 40278885 | 40279778 | −14.7688 | 17 | 893 |
| chr21_group017525 | chr21 | 39492468 | 39494149 | −14.6283 | 42 | 1681 |
| chr13_group007242 | chr13 | 31100912 | 31101535 | −14.4812 | 17 | 623 |
| chr13_group018451 | chr13 | 51058670 | 51059041 | −14.4169 | 11 | 371 |
| chr21_group001690 | chr21 | 16248092 | 16248889 | −14.356 | 10 | 797 |
| chr18_group032258 | chr18 | 55795530 | 55795975 | −14.3543 | 9 | 445 |
| chr18_group005133 | chr18 | 10015219 | 10015998 | −14.0399 | 14 | 779 |
| chr18_group003796 | chr18 | 6929395 | 6930301 | −13.9235 | 34 | 906 |
| chr13_group058098 | chr13 | 1.11E+08 | 1.11E+08 | −13.5537 | 13 | 629 |
| chr18_group007329 | chr18 | 12730627 | 12731352 | −13.3425 | 22 | 725 |
| chr13_group021607 | chr13 | 57309494 | 57310128 | −13.3373 | 45 | 634 |
| chr13_group015272 | chr13 | 44626994 | 44628089 | −13.2862 | 18 | 1095 |
| chr13_group033223 | chr13 | 74794868 | 74795434 | −13.2319 | 21 | 566 |
| chr13_group006986 | chr13 | 30716719 | 30717655 | −13.1679 | 16 | 936 |

TABLE 4-continued

| Name | chr | start.pos | end.pos | median.tstat | num.cg | dmr.size |
|---|---|---|---|---|---|---|
| chr18__group009952 | chr18 | 20861481 | 20862471 | −13.1052 | 15 | 990 |
| chr13__group028529 | chr13 | 67768565 | 67769663 | −13.0609 | 25 | 1098 |
| chr21__group020707 | chr21 | 44224007 | 44224641 | −13.0236 | 12 | 634 |
| chr18__group027248 | chr18 | 48479243 | 48479837 | −12.9968 | 15 | 594 |
| chr18__group007476 | chr18 | 13165140 | 13166009 | −12.9397 | 24 | 869 |
| chr18__group012863 | chr18 | 25501864 | 25502512 | −12.8931 | 17 | 648 |
| chr13__group018472 | chr13 | 51103345 | 51104019 | −12.7903 | 12 | 674 |
| chr18__group044012 | chr18 | 72120483 | 72121032 | −12.7655 | 9 | 549 |
| chr18__group010402 | chr18 | 21561904 | 21563080 | −12.7457 | 16 | 1176 |
| chr13__group048991 | chr13 | 97637074 | 97637420 | −12.7035 | 12 | 346 |
| chr13__group005784 | chr13 | 29267938 | 29268338 | −12.6922 | 11 | 400 |
| chr13__group015332 | chr13 | 44786994 | 44787866 | −12.6809 | 9 | 872 |
| chr18__group018226 | chr18 | 34341274 | 34341773 | −12.6607 | 12 | 499 |
| chr21__group016480 | chr21 | 37402631 | 37403430 | −12.6429 | 13 | 799 |
| chr13__group029661 | chr13 | 69282527 | 69282971 | −12.5703 | 16 | 444 |
| chr13__group000629 | chr13 | 20451092 | 20451346 | −12.5243 | 18 | 254 |
| chr18__group023898 | chr18 | 42369133 | 42369884 | −12.5166 | 9 | 751 |
| chr18__group013875 | chr18 | 27058350 | 27058737 | −12.5157 | 25 | 387 |
| chr18__group006811 | chr18 | 11954410 | 11954802 | −12.4776 | 11 | 392 |
| chr18__group048470 | chr18 | 77693845 | 77695057 | −12.4703 | 16 | 1212 |
| chr18__group011804 | chr18 | 23407402 | 23408355 | −12.4504 | 15 | 953 |
| chr13__group050053 | chr13 | 99629352 | 99630505 | −12.368 | 18 | 1153 |
| chr13__group027591 | chr13 | 66559650 | 66560121 | −12.3624 | 11 | 471 |
| chr18__group012477 | chr18 | 24681277 | 24681560 | −12.1634 | 21 | 283 |
| chr18__group004618 | chr18 | 8685433 | 8686027 | −12.1533 | 11 | 594 |
| chr13__group041742 | chr13 | 87724610 | 87724935 | −12.0468 | 15 | 325 |
| chr13__group034306 | chr13 | 76273626 | 76274359 | −12.0449 | 11 | 733 |
| chr18__group029460 | chr18 | 51780586 | 51781707 | −11.947 | 15 | 1121 |
| chr21__group013506 | chr21 | 32969790 | 32970668 | −11.8622 | 22 | 878 |
| chr18__group009092 | chr18 | 19578272 | 19578799 | −11.8223 | 10 | 527 |
| chr18__group020671 | chr18 | 37504354 | 37505067 | −11.7929 | 27 | 713 |
| chr21__group020749 | chr21 | 44354088 | 44354771 | −11.7439 | 14 | 683 |
| chr13__group058232 | chr13 | 1.11E+08 | 1.11E+08 | −11.7365 | 12 | 266 |
| chr18__group021434 | chr18 | 38414514 | 38414774 | −11.7187 | 20 | 260 |
| chr18__group003854 | chr18 | 7158213 | 7158746 | −11.6762 | 12 | 533 |
| chr18__group010417 | chr18 | 21574212 | 21574792 | −11.5749 | 9 | 580 |
| chr13__group005598 | chr13 | 28698313 | 28699972 | −11.5709 | 55 | 1659 |
| chr13__group008848 | chr13 | 33403456 | 33404484 | −11.5396 | 13 | 1028 |
| chr18__group011930 | chr18 | 23781839 | 23782625 | −11.5035 | 17 | 786 |
| chr18__group001254 | chr18 | 3383219 | 3384353 | −11.5029 | 13 | 1134 |
| chr18__group026380 | chr18 | 46106736 | 46107453 | −11.4851 | 15 | 717 |
| chr13__group007429 | chr13 | 31366525 | 31367224 | −11.4812 | 15 | 699 |
| chr13__group055249 | chr13 | 1.07E+08 | 1.07E+08 | −11.4584 | 19 | 1161 |
| chr21__group013308 | chr21 | 32533210 | 32534126 | −11.4174 | 12 | 916 |
| chr18__group026566 | chr18 | 46489198 | 46489544 | −11.4117 | 10 | 346 |
| chr13__group022725 | chr13 | 58892436 | 58893336 | −11.3873 | 43 | 900 |
| chr13__group018362 | chr13 | 50908835 | 50909516 | −11.374 | 10 | 681 |
| chr13__group018280 | chr13 | 50759974 | 50760445 | −11.3679 | 28 | 471 |
| chr13__group023719 | chr13 | 60348376 | 60349193 | −11.2981 | 9 | 817 |
| chr13__group058567 | chr13 | 1.12E+08 | 1.12E+08 | −11.2957 | 17 | 981 |
| chr18__group014812 | chr18 | 28736700 | 28737682 | −11.2814 | 14 | 982 |
| chr18__group023870 | chr18 | 42276886 | 42277743 | −11.2393 | 10 | 857 |
| chr21__group020760 | chr21 | 44375297 | 44378110 | −11.2289 | 60 | 2813 |
| chr13__group013720 | chr13 | 41880223 | 41880778 | −11.1942 | 26 | 555 |
| chr18__group032656 | chr18 | 56456697 | 56457533 | −11.1926 | 14 | 836 |
| chr13__group034311 | chr13 | 76278769 | 76279385 | −11.1411 | 14 | 616 |
| chr21__group022744 | chr21 | 47468995 | 47470354 | −11.1342 | 29 | 1359 |
| chr21__group001757 | chr21 | 16580282 | 16580737 | −11.1324 | 14 | 455 |
| chr18__group005784 | chr18 | 10877619 | 10878377 | −11.0946 | 10 | 758 |
| chr13__group001376 | chr13 | 21926814 | 21927416 | −11.0909 | 11 | 602 |
| chr18__group000673 | chr18 | 1508897 | 1509216 | −11.0852 | 19 | 319 |
| chr13__group005021 | chr13 | 27957203 | 27958101 | −11.0774 | 18 | 898 |
| chr13__group008846 | chr13 | 33397997 | 33399054 | −11.0767 | 25 | 1057 |
| chr13__group019220 | chr13 | 52304127 | 52304727 | −11.0699 | 12 | 600 |
| chr18__group000568 | chr18 | 1406184 | 1407313 | −11.0346 | 44 | 1129 |
| chr18__group035537 | chr18 | 60905299 | 60905799 | −11.0089 | 12 | 500 |
| chr13__group018382 | chr13 | 50960770 | 50961124 | −11.007 | 10 | 354 |
| chr13__group003365 | chr13 | 25576343 | 25576804 | −11.0063 | 14 | 461 |
| chr18__group014785 | chr18 | 28613852 | 28614367 | −10.9802 | 23 | 515 |
| chr18__group005826 | chr18 | 10925452 | 10926684 | −10.9304 | 24 | 1232 |
| chr21__group020743 | chr21 | 44344531 | 44346583 | −10.93 | 59 | 2052 |
| chr18__group029859 | chr18 | 52635637 | 52636083 | −10.9189 | 11 | 446 |
| chr13__group015339 | chr13 | 44803459 | 44805711 | −10.8903 | 27 | 2252 |
| chr18__group000675 | chr18 | 1521568 | 1522349 | −10.8837 | 29 | 781 |
| chr13__group001236 | chr13 | 21749154 | 21749709 | −10.8642 | 34 | 555 |
| chr18__group013327 | chr18 | 26202137 | 26202705 | −10.8597 | 20 | 568 |
| chr21__group020032 | chr21 | 43171531 | 43172291 | −10.8457 | 20 | 760 |
| chr13__group014614 | chr13 | 43727693 | 43728741 | −10.8318 | 17 | 1048 |

TABLE 4-continued

| Name | chr | start.pos | end.pos | median.tstat | num.cg | dmr.size |
|---|---|---|---|---|---|---|
| chr13__group051184 | chr13 | 1.02E+08 | 1.02E+08 | −10.8312 | 22 | 301 |
| chr13__group035442 | chr13 | 78264557 | 78265072 | −10.8281 | 16 | 515 |
| chr21__group022183 | chr21 | 46850316 | 46851109 | −10.8105 | 23 | 793 |
| chr18__group000141 | chr18 | 371380 | 372207 | −10.7998 | 15 | 827 |
| chr18__group011942 | chr18 | 23807464 | 23808015 | −10.7956 | 20 | 551 |
| chr18__group001058 | chr18 | 2826620 | 2826938 | −10.7686 | 10 | 318 |
| chr18__group011237 | chr18 | 22656883 | 22657649 | −10.7459 | 13 | 766 |
| chr13__group053108 | chr13 | 1.04E+08 | 1.04E+08 | −10.7256 | 14 | 1151 |
| chr13__group001186 | chr13 | 21633464 | 21634359 | −10.7252 | 48 | 895 |
| chr21__group017681 | chr21 | 39731774 | 39733054 | −10.7057 | 11 | 1280 |
| chr13__group052468 | chr13 | 1.04E+08 | 1.04E+08 | −10.7028 | 12 | 991 |
| chr18__group000937 | chr18 | 2350847 | 2352093 | −10.702 | 29 | 1246 |
| chr18__group009474 | chr18 | 20036295 | 20036913 | −10.6996 | 14 | 618 |
| chr18__group035839 | chr18 | 61459045 | 61459767 | −10.6813 | 9 | 722 |
| chr13__group001080 | chr13 | 21252719 | 21253590 | −10.6786 | 14 | 871 |
| chr13__group054370 | chr13 | 1.06E+08 | 1.06E+08 | −10.646 | 10 | 682 |
| chr13__group055061 | chr13 | 1.07E+08 | 1.07E+08 | −10.6196 | 10 | 747 |
| chr21__group022114 | chr21 | 46777401 | 46777935 | −10.6196 | 25 | 534 |
| chr13__group043314 | chr13 | 89814855 | 89815673 | −10.6063 | 29 | 818 |
| chr13__group005730 | chr13 | 29129047 | 29129645 | −10.6013 | 12 | 598 |
| chr13__group015498 | chr13 | 45288386 | 45289249 | −10.5937 | 13 | 863 |
| chr13__group005692 | chr13 | 29051191 | 29051934 | −10.5812 | 14 | 743 |
| chr13__group050041 | chr13 | 99607654 | 99607814 | −10.5752 | 9 | 160 |
| chr18__group002740 | chr18 | 5410292 | 5410903 | −10.5614 | 9 | 611 |
| chr21__group020938 | chr21 | 44738781 | 44739795 | −10.5547 | 31 | 1014 |
| chr13__group054932 | chr13 | 1.07E+08 | 1.07E+08 | −10.5524 | 11 | 423 |
| chr21__group020955 | chr21 | 44752685 | 44754007 | −10.5505 | 31 | 1322 |
| chr18__group011640 | chr18 | 23097371 | 23098346 | −10.5497 | 12 | 975 |
| chr21__group010087 | chr21 | 27105562 | 27105734 | −10.5354 | 12 | 172 |
| chr18__group024383 | chr18 | 43097228 | 43097658 | −10.5166 | 11 | 430 |
| chr21__group014832 | chr21 | 35343544 | 35344171 | −10.5143 | 10 | 627 |
| chr18__group032667 | chr18 | 56483544 | 56484298 | −10.5098 | 29 | 754 |
| chr18__group007102 | chr18 | 12375499 | 12376286 | −10.4811 | 38 | 787 |
| chr21__group022052 | chr21 | 46682431 | 46682724 | −10.4769 | 9 | 293 |
| chr13__group017504 | chr13 | 48803858 | 48804411 | −10.4667 | 28 | 553 |
| chr21__group003082 | chr21 | 18728605 | 18729375 | −10.459 | 9 | 770 |
| chr13__group007493 | chr13 | 31430274 | 31431084 | −10.4293 | 9 | 810 |
| chr18__group035253 | chr18 | 60152941 | 60153270 | −10.4113 | 9 | 329 |
| chr13__group010751 | chr13 | 36788420 | 36789081 | −10.4028 | 36 | 661 |
| chr21__group020594 | chr21 | 44088881 | 44089479 | −10.397 | 17 | 598 |
| chr18__group005184 | chr18 | 10121856 | 10123068 | −10.3816 | 16 | 1212 |
| chr21__group015514 | chr21 | 36444991 | 36445543 | −10.3779 | 12 | 552 |
| chr13__group032630 | chr13 | 73860964 | 73861648 | −10.3647 | 10 | 684 |
| chr18__group001056 | chr18 | 2824960 | 2825882 | −10.3605 | 10 | 922 |
| chr21__group013362 | chr21 | 32723893 | 32724426 | −10.3426 | 9 | 533 |
| chr13__group016530 | chr13 | 47259035 | 47259654 | −10.3425 | 9 | 619 |
| chr13__group001283 | chr13 | 21808562 | 21809375 | −10.339 | 15 | 813 |
| chr21__group020291 | chr21 | 43676864 | 43677913 | −10.3383 | 21 | 1049 |
| chr13__group035110 | chr13 | 77458389 | 77458677 | −10.3275 | 11 | 288 |
| chr13__group015773 | chr13 | 45935600 | 45936019 | −10.3217 | 14 | 419 |
| chr13__group009158 | chr13 | 34208563 | 34208967 | −10.3168 | 9 | 404 |
| chr13__group055417 | chr13 | 1.08E+08 | 1.08E+08 | −10.2985 | 12 | 942 |
| chr13__group032539 | chr13 | 73635949 | 73636845 | −10.2761 | 11 | 896 |
| chr21__group020250 | chr21 | 43621575 | 43622219 | −10.2749 | 10 | 644 |
| chr21__group020127 | chr21 | 43460070 | 43460693 | −10.2675 | 15 | 623 |
| chr18__group000159 | chr18 | 449378 | 449797 | −10.2488 | 9 | 419 |
| chr18__group046745 | chr18 | 75551578 | 75552347 | −10.2475 | 9 | 769 |
| chr21__group015351 | chr21 | 36186618 | 36187267 | −10.247 | 13 | 649 |
| chr21__group015366 | chr21 | 36218936 | 36219309 | −10.2179 | 9 | 373 |
| chr13__group030914 | chr13 | 71588839 | 71589440 | −10.2151 | 12 | 601 |
| chr13__group058414 | chr13 | 1.12E+08 | 1.12E+08 | −10.2091 | 20 | 785 |
| chr13__group048134 | chr13 | 96392324 | 96393071 | −10.2021 | 25 | 747 |
| chr18__group013827 | chr18 | 26941361 | 26942489 | −10.1988 | 24 | 1128 |
| chr18__group001577 | chr18 | 3895108 | 3895854 | −10.1844 | 10 | 746 |
| chr13__group054916 | chr13 | 1.07E+08 | 1.07E+08 | −10.181 | 10 | 496 |
| chr21__group015353 | chr21 | 36190815 | 36191383 | −10.1599 | 12 | 568 |
| chr13__group003072 | chr13 | 24972946 | 24973610 | −10.1332 | 10 | 664 |
| chr21__group008687 | chr21 | 25532310 | 25533273 | −10.1259 | 12 | 963 |
| chr21__group021349 | chr21 | 45622219 | 45623300 | −10.1212 | 38 | 1081 |
| chr21__group011313 | chr21 | 29774445 | 29774845 | −10.112 | 23 | 400 |
| chr18__group032271 | chr18 | 55820879 | 55821179 | −10.1028 | 14 | 300 |
| chr21__group014816 | chr21 | 35303201 | 35304000 | −10.1017 | 34 | 799 |
| chr13__group059739 | chr13 | 1.13E+08 | 1.13E+08 | −10.0973 | 19 | 683 |
| chr13__group049750 | chr13 | 98919130 | 98920014 | −10.0958 | 18 | 884 |
| chr13__group001410 | chr13 | 22049016 | 22049287 | −10.0815 | 16 | 271 |
| chr18__group025521 | chr18 | 44601666 | 44602373 | −10.0764 | 13 | 707 |
| chr18__group032314 | chr18 | 55890984 | 55891490 | −10.0603 | 12 | 506 |
| chr13__group008998 | chr13 | 33728013 | 33728743 | −10.0579 | 11 | 730 |

TABLE 4-continued

| Name | chr | start.pos | end.pos | median.tstat | num.cg | dmr.size |
|---|---|---|---|---|---|---|
| chr21_group002419 | chr21 | 17935773 | 17936701 | −10.0451 | 18 | 928 |
| chr18_group046498 | chr18 | 75333425 | 75333854 | −10.0273 | 9 | 429 |
| chr13_group013764 | chr13 | 41995627 | 41996427 | −10.0232 | 15 | 800 |
| chr18_group041336 | chr18 | 68879856 | 68880633 | −10.0214 | 26 | 777 |
| chr18_group010870 | chr18 | 22251422 | 22252205 | −10.0125 | 9 | 783 |
| chr13_group059713 | chr13 | 1.13E+08 | 1.13E+08 | −10.0078 | 18 | 1048 |
| chr13_group008433 | chr13 | 32366585 | 32367276 | −10.0029 | 9 | 691 |
| chr13_group002412 | chr13 | 24043965 | 24044800 | −9.97771 | 16 | 835 |
| chr18_group048130 | chr18 | 77218126 | 77219495 | −9.97552 | 24 | 1369 |
| chr18_group030112 | chr18 | 52896008 | 52896224 | −9.95656 | 9 | 216 |
| chr21_group020768 | chr21 | 44388961 | 44390071 | −9.94057 | 15 | 1110 |
| chr18_group001155 | chr18 | 3118315 | 3119876 | −9.93163 | 15 | 1561 |
| chr21_group013608 | chr21 | 33171187 | 33171884 | −9.92344 | 12 | 697 |
| chr18_group009230 | chr18 | 19773525 | 19774091 | −9.91508 | 9 | 566 |
| chr21_group016594 | chr21 | 37681484 | 37681983 | −9.91004 | 22 | 499 |
| chr18_group043374 | chr18 | 71382419 | 71383037 | −9.9079 | 25 | 618 |
| chr18_group010054 | chr18 | 21211717 | 21212317 | −9.90534 | 10 | 600 |
| chr18_group020728 | chr18 | 37576753 | 37577413 | −9.89717 | 18 | 660 |
| chr13_group047570 | chr13 | 95467808 | 95468302 | −9.88968 | 19 | 494 |
| chr21_group014698 | chr21 | 34913489 | 34913641 | −9.88488 | 11 | 152 |
| chr21_group013639 | chr21 | 33227435 | 33228236 | −9.87963 | 9 | 801 |
| chr21_group022244 | chr21 | 46953901 | 46954278 | −9.87581 | 10 | 377 |
| chr13_group055396 | chr13 | 1.08E+08 | 1.08E+08 | −9.87575 | 16 | 1175 |
| chr13_group031363 | chr13 | 72051413 | 72052176 | −9.87032 | 11 | 763 |
| chr18_group007966 | chr18 | 13672958 | 13673998 | −9.86876 | 16 | 1040 |
| chr18_group040559 | chr18 | 67917252 | 67918467 | −9.85761 | 58 | 1215 |
| chr21_group017239 | chr21 | 39123584 | 39124433 | −9.85733 | 10 | 849 |
| chr18_group007063 | chr18 | 12264320 | 12264847 | −9.85543 | 23 | 527 |
| chr13_group035472 | chr13 | 78334657 | 78335658 | −9.85421 | 14 | 1001 |
| chr13_group059930 | chr13 | 1.14E+08 | 1.14E+08 | −9.84779 | 14 | 718 |
| chr13_group018144 | chr13 | 50374420 | 50375895 | −9.83765 | 20 | 1475 |
| chr13_group050023 | chr13 | 99548517 | 99549003 | −9.82977 | 9 | 486 |
| chr21_group020957 | chr21 | 44760695 | 44761480 | −9.82466 | 20 | 785 |
| chr13_group059671 | chr13 | 1.13E+08 | 1.13E+08 | −9.82017 | 10 | 318 |
| chr21_group018584 | chr21 | 41135433 | 41136215 | −9.81809 | 16 | 782 |
| chr21_group011677 | chr21 | 30457668 | 30458697 | −9.81185 | 13 | 1029 |
| chr13_group003376 | chr13 | 25588059 | 25588271 | −9.81032 | 11 | 212 |
| chr21_group020921 | chr21 | 44720747 | 44721418 | −9.80232 | 34 | 671 |
| chr13_group015404 | chr13 | 44977316 | 44978535 | −9.79638 | 25 | 1219 |
| chr18_group044472 | chr18 | 72976548 | 72977465 | −9.79434 | 9 | 917 |
| chr21_group018802 | chr21 | 41446056 | 41447102 | −9.77216 | 13 | 1046 |
| chr18_group043016 | chr18 | 70931181 | 70932070 | −9.76413 | 27 | 889 |
| chr18_group007912 | chr18 | 13606450 | 13607178 | −9.76217 | 11 | 728 |
| chr13_group007214 | chr13 | 31060338 | 31061122 | −9.75174 | 12 | 784 |
| chr18_group003865 | chr18 | 7173172 | 7173875 | −9.7498 | 22 | 703 |
| chr18_group010861 | chr18 | 22242369 | 22243526 | −9.74895 | 17 | 1157 |
| chr21_group017086 | chr21 | 38905563 | 38906275 | −9.74304 | 14 | 712 |
| chr18_group033255 | chr18 | 57514191 | 57515766 | −9.74236 | 14 | 1575 |
| chr18_group007294 | chr18 | 12640584 | 12641032 | −9.73868 | 9 | 448 |
| chr13_group015438 | chr13 | 45164058 | 45164816 | −9.73398 | 24 | 758 |
| chr18_group001245 | chr18 | 3359922 | 3360705 | −9.73395 | 20 | 783 |
| chr18_group023454 | chr18 | 41674767 | 41675427 | −9.73051 | 13 | 660 |
| chr18_group018372 | chr18 | 34642457 | 34642713 | −9.72191 | 11 | 256 |
| chr13_group004043 | chr13 | 26648845 | 26649035 | −9.7206 | 9 | 190 |
| chr13_group015451 | chr13 | 45191788 | 45192153 | −9.72008 | 9 | 365 |
| chr21_group020677 | chr21 | 44188252 | 44188886 | −9.71866 | 14 | 634 |
| chr21_group022746 | chr21 | 47474136 | 47474724 | −9.67003 | 9 | 588 |
| chr18_group015061 | chr18 | 29369327 | 29369858 | −9.66953 | 13 | 531 |
| chr18_group000215 | chr18 | 580125 | 580773 | −9.66819 | 43 | 648 |
| chr18_group026564 | chr18 | 46481134 | 46482577 | −9.66431 | 15 | 1443 |
| chr13_group009189 | chr13 | 34273934 | 34274477 | −9.66092 | 20 | 543 |
| chr18_group001271 | chr18 | 3452757 | 3453671 | −9.66056 | 24 | 914 |
| chr21_group014111 | chr21 | 33952243 | 33952776 | −9.65333 | 15 | 533 |
| chr21_group014635 | chr21 | 34728137 | 34728781 | −9.65065 | 12 | 644 |
| chr18_group012535 | chr18 | 24813196 | 24813345 | −9.63853 | 11 | 149 |
| chr21_group013388 | chr21 | 32796748 | 32797704 | −9.63533 | 9 | 956 |
| chr18_group010579 | chr18 | 21748440 | 21749304 | −9.62286 | 16 | 864 |
| chr13_group058138 | chr13 | 1.11E+08 | 1.11E+08 | −9.61589 | 32 | 1313 |
| chr18_group000130 | chr18 | 332543 | 333816 | −9.61376 | 23 | 1273 |
| chr13_group049008 | chr13 | 97670716 | 97671507 | −9.59749 | 10 | 791 |
| chr13_group018011 | chr13 | 49888180 | 49888624 | −9.59547 | 10 | 444 |
| chr21_group021215 | chr21 | 45279770 | 45280988 | −9.59209 | 23 | 1218 |
| chr21_group020060 | chr21 | 43269197 | 43269655 | −9.58398 | 12 | 458 |
| chr13_group007031 | chr13 | 30768945 | 30769315 | −9.58101 | 9 | 370 |
| chr13_group013721 | chr13 | 41884516 | 41884793 | −9.57669 | 12 | 277 |
| chr18_group003611 | chr18 | 6437781 | 6438416 | −9.57467 | 12 | 635 |
| chr21_group016536 | chr21 | 37527834 | 37528038 | −9.57002 | 9 | 204 |
| chr18_group032658 | chr18 | 56460879 | 56461310 | −9.5624 | 10 | 431 |

TABLE 4-continued

| Name | chr | start.pos | end.pos | median.tstat | num.cg | dmr.size |
|---|---|---|---|---|---|---|
| chr13__group016713 | chr13 | 47547468 | 47548756 | −9.56169 | 10 | 1288 |
| chr13__group014559 | chr13 | 43596219 | 43597457 | −9.56104 | 25 | 1238 |
| chr13__group018736 | chr13 | 51444439 | 51444797 | −9.55258 | 11 | 358 |
| chr18__group026706 | chr18 | 47025441 | 47026405 | −9.54771 | 15 | 964 |
| chr21__group005494 | chr21 | 21761062 | 21761792 | −9.54492 | 9 | 730 |
| chr21__group017004 | chr21 | 38569235 | 38569603 | −9.54065 | 9 | 368 |
| chr18__group023650 | chr18 | 41900873 | 41901287 | −9.53872 | 14 | 414 |
| chr18__group031277 | chr18 | 54244289 | 54244427 | −9.53707 | 11 | 138 |
| chr21__group022871 | chr21 | 47808017 | 47808378 | −9.53519 | 10 | 361 |
| chr18__group030357 | chr18 | 53170126 | 53171368 | −9.53518 | 9 | 1242 |
| chr18__group008948 | chr18 | 19179095 | 19179333 | −9.53274 | 9 | 238 |
| chr13__group054548 | chr13 | 1.06E+08 | 1.06E+08 | −9.5327 | 30 | 1095 |
| chr13__group001004 | chr13 | 20982072 | 20982685 | −9.53269 | 9 | 613 |
| chr13__group036576 | chr13 | 79883757 | 79884346 | −9.53215 | 12 | 589 |
| chr18__group003383 | chr18 | 6218233 | 6220246 | −9.53174 | 26 | 2013 |
| chr18__group007341 | chr18 | 12767077 | 12767273 | −9.52238 | 11 | 196 |
| chr13__group013596 | chr13 | 41496212 | 41496402 | −9.51912 | 10 | 190 |
| chr18__group008895 | chr18 | 18895686 | 18896241 | −9.50939 | 12 | 555 |
| chr13__group004973 | chr13 | 27903019 | 27904320 | −9.507 | 15 | 1301 |
| chr13__group049127 | chr13 | 97980285 | 97980869 | −9.49723 | 11 | 584 |
| chr21__group019770 | chr21 | 42589507 | 42590379 | −9.49358 | 15 | 872 |
| chr18__group045835 | chr18 | 74532349 | 74532959 | −9.48738 | 21 | 610 |
| chr21__group013360 | chr21 | 32719573 | 32720138 | −9.48097 | 17 | 565 |
| chr18__group030830 | chr18 | 53807036 | 53807781 | −9.47871 | 12 | 745 |
| chr21__group018067 | chr21 | 40128349 | 40128702 | −9.47846 | 18 | 353 |
| chr18__group033126 | chr18 | 57273036 | 57274250 | −9.47682 | 19 | 1214 |
| chr21__group018144 | chr21 | 40337124 | 40338425 | −9.47383 | 27 | 1301 |
| chr13__group015532 | chr13 | 45392487 | 45392699 | −9.47348 | 9 | 212 |
| chr13__group054188 | chr13 | 1.06E+08 | 1.06E+08 | −9.47017 | 11 | 814 |
| chr18__group006934 | chr18 | 12129474 | 12129974 | −9.46716 | 9 | 500 |
| chr18__group005055 | chr18 | 9835076 | 9836234 | −9.46461 | 20 | 1158 |
| chr18__group008530 | chr18 | 14798092 | 14798756 | −9.46336 | 11 | 664 |
| chr21__group022197 | chr21 | 46868542 | 46869575 | −9.46075 | 32 | 1033 |
| chr13__group032770 | chr13 | 74269126 | 74270530 | −9.44715 | 27 | 1404 |
| chr18__group004460 | chr18 | 8480680 | 8480966 | −9.4447 | 9 | 286 |
| chr21__group012507 | chr21 | 31612876 | 31613867 | −9.43948 | 13 | 991 |
| chr18__group005143 | chr18 | 10035101 | 10035631 | −9.43527 | 13 | 530 |
| chr13__group001107 | chr13 | 21290855 | 21291572 | −9.43093 | 23 | 717 |
| chr13__group058623 | chr13 | 1.12E+08 | 1.12E+08 | −9.4305 | 15 | 1068 |
| chr13__group032740 | chr13 | 56675570 | 56676201 | −9.43011 | 12 | 631 |
| chr18__group022059 | chr18 | 39211724 | 39212419 | −9.42912 | 29 | 695 |
| chr13__group004843 | chr13 | 27609752 | 27611471 | −9.42093 | 26 | 1719 |
| chr21__group020307 | chr21 | 43695642 | 43696757 | −9.41563 | 16 | 1115 |
| chr13__group016375 | chr13 | 46960145 | 46960472 | −9.41364 | 9 | 327 |
| chr21__group018569 | chr21 | 41109342 | 41111108 | −9.40767 | 22 | 1766 |
| chr18__group006053 | chr18 | 11145029 | 11147295 | −9.40567 | 30 | 2266 |
| chr18__group006795 | chr18 | 11920944 | 11921748 | −9.40474 | 18 | 804 |
| chr18__group005486 | chr18 | 10577970 | 10578656 | −9.39576 | 17 | 686 |
| chr21__group020751 | chr21 | 44356786 | 44357567 | −9.39573 | 12 | 781 |
| chr13__group059929 | chr13 | 1.14E+08 | 1.14E+08 | −9.39027 | 48 | 1021 |
| chr13__group007311 | chr13 | 31248832 | 31249554 | −9.38876 | 24 | 722 |
| chr13__group054209 | chr13 | 1.06E+08 | 1.06E+08 | −9.38866 | 11 | 1672 |
| chr13__group019283 | chr13 | 52494954 | 52495665 | −9.38485 | 10 | 711 |
| chr13__group008481 | chr13 | 32411359 | 32412463 | −9.38343 | 9 | 1104 |
| chr21__group017814 | chr21 | 39881854 | 39882725 | −9.38303 | 10 | 871 |
| chr18__group029449 | chr18 | 51752218 | 51753061 | −9.38029 | 31 | 843 |
| chr18__group000355 | chr18 | 878678 | 879684 | −9.37775 | 9 | 1006 |
| chr18__group007577 | chr18 | 13267266 | 13268604 | −9.37061 | 12 | 1338 |
| chr18__group003128 | chr18 | 5983065 | 5983693 | −9.36986 | 11 | 628 |
| chr21__group021385 | chr21 | 45681577 | 45681946 | −9.36569 | 15 | 369 |
| chr13__group049635 | chr13 | 98720836 | 98721414 | −9.36238 | 11 | 578 |
| chr21__group020972 | chr21 | 44780824 | 44781744 | −9.3593 | 31 | 920 |
| chr13__group001160 | chr13 | 21527020 | 21528093 | −9.35352 | 33 | 1073 |
| chr13__group001003 | chr13 | 20979990 | 20980206 | −9.35098 | 10 | 216 |
| chr18__group027191 | chr18 | 48301590 | 48302995 | −9.33864 | 37 | 1405 |
| chr13__group057364 | chr13 | 1.1E+08 | 1.1E+08 | −9.33026 | 9 | 502 |
| chr18__group006806 | chr18 | 11941924 | 11942352 | −9.32466 | 13 | 428 |
| chr18__group004661 | chr18 | 8800064 | 8800688 | −9.29632 | 11 | 624 |
| chr13__group016207 | chr13 | 46622342 | 46623241 | −9.29598 | 30 | 899 |
| chr21__group015122 | chr21 | 35908768 | 35909374 | −9.29175 | 9 | 606 |
| chr18__group021859 | chr18 | 38973438 | 38973721 | −9.2901 | 15 | 283 |
| chr13__group028564 | chr13 | 67799625 | 67800487 | −9.28649 | 15 | 862 |
| chr13__group005082 | chr13 | 28055198 | 28056420 | −9.28228 | 19 | 1222 |
| chr13__group050044 | chr13 | 99613134 | 99614179 | −9.27554 | 13 | 1045 |
| chr21__group017534 | chr21 | 39543266 | 39544487 | −9.27514 | 16 | 1221 |
| chr21__group021309 | chr21 | 45568236 | 45568788 | −9.27481 | 12 | 552 |
| chr18__group011722 | chr18 | 23241950 | 23242444 | −9.2748 | 11 | 494 |
| chr18__group045523 | chr18 | 74182105 | 74182845 | −9.27141 | 11 | 740 |

TABLE 4-continued

| Name | chr | start.pos | end.pos | median.tstat | num.cg | dmr.size |
|---|---|---|---|---|---|---|
| chr13__group059796 | chr13 | 1.14E+08 | 1.14E+08 | −9.26286 | 15 | 362 |
| chr21__group020835 | chr21 | 44550292 | 44551650 | −9.25488 | 16 | 1358 |
| chr18__group005117 | chr18 | 9994168 | 9994894 | −9.24492 | 11 | 726 |
| chr18__group043904 | chr18 | 71955844 | 71956352 | −9.24366 | 11 | 508 |
| chr18__group026267 | chr18 | 45862090 | 45863008 | −9.24299 | 12 | 918 |
| chr13__group003833 | chr13 | 26233232 | 26233902 | −9.23631 | 13 | 670 |
| chr13__group018087 | chr13 | 50173398 | 50174259 | −9.23453 | 18 | 861 |
| chr13__group014855 | chr13 | 44017640 | 44018241 | −9.23272 | 10 | 601 |
| chr13__group015508 | chr13 | 45319257 | 45319768 | −9.22953 | 9 | 511 |
| chr13__group003303 | chr13 | 25444030 | 25445127 | −9.22713 | 19 | 1097 |
| chr13__group003979 | chr13 | 26552443 | 26553072 | −9.22471 | 26 | 629 |
| chr18__group007910 | chr18 | 13603400 | 13604577 | −9.21949 | 17 | 1177 |
| chr18__group033853 | chr18 | 58209734 | 58210581 | −9.21811 | 9 | 847 |
| chr13__group016156 | chr13 | 46481878 | 46482416 | −9.21244 | 11 | 538 |
| chr18__group004791 | chr18 | 9064049 | 9064635 | −9.19919 | 10 | 586 |
| chr13__group050055 | chr13 | 99640685 | 99641358 | −9.19134 | 10 | 673 |
| chr13__group042731 | chr13 | 88876540 | 88877355 | −9.1896 | 37 | 815 |
| chr21__group010215 | chr21 | 27496662 | 27498497 | −9.18324 | 17 | 1835 |
| chr13__group015530 | chr13 | 45390044 | 45390330 | −9.17598 | 10 | 286 |
| chr18__group001123 | chr18 | 3038245 | 3038717 | −9.1748 | 24 | 472 |
| chr21__group014271 | chr21 | 34238235 | 34238796 | −9.16132 | 9 | 561 |
| chr13__group017949 | chr13 | 49792267 | 49793722 | −9.15677 | 49 | 1455 |
| chr13__group010104 | chr13 | 36025157 | 36025538 | −9.1503 | 16 | 381 |
| chr13__group015503 | chr13 | 45306224 | 45307108 | −9.14988 | 15 | 884 |
| chr18__group045433 | chr18 | 74092615 | 74093296 | −9.14759 | 23 | 681 |
| chr13__group018951 | chr13 | 51779826 | 51780609 | −9.14574 | 11 | 783 |
| chr21__group022137 | chr21 | 46806218 | 46806861 | −9.14564 | 17 | 643 |
| chr13__group060158 | chr13 | 1.14E+08 | 1.14E+08 | −9.13328 | 33 | 1306 |
| chr13__group018775 | chr13 | 51556190 | 51556905 | −9.13229 | 31 | 715 |
| chr13__group003186 | chr13 | 25201116 | 25201948 | −9.12907 | 21 | 832 |
| chr13__group034271 | chr13 | 76119193 | 76119948 | −9.12072 | 16 | 755 |
| chr21__group020999 | chr21 | 44820721 | 44821497 | −9.11717 | 20 | 776 |
| chr18__group001113 | chr18 | 3013769 | 3014439 | −9.11702 | 24 | 670 |
| chr21__group021746 | chr21 | 46193223 | 46193841 | −9.11547 | 17 | 618 |
| chr21__group020138 | chr21 | 43477079 | 43477764 | −9.11522 | 16 | 685 |
| chr13__group017378 | chr13 | 48437465 | 48438228 | −9.11236 | 20 | 763 |
| chr13__group025091 | chr13 | 62800651 | 62800881 | −9.1122 | 14 | 230 |
| chr21__group017989 | chr21 | 40047317 | 40047730 | −9.11218 | 14 | 413 |
| chr18__group009062 | chr18 | 19524608 | 19526096 | −9.1091 | 10 | 1488 |
| chr21__group020511 | chr21 | 43977015 | 43977804 | −9.10496 | 19 | 789 |
| chr18__group026546 | chr18 | 46442083 | 46443069 | −9.10112 | 13 | 986 |
| chr18__group032529 | chr18 | 56223305 | 56224594 | −9.10036 | 17 | 1289 |
| chr21__group018447 | chr21 | 40950994 | 40952220 | −9.09973 | 23 | 1226 |
| chr21__group022034 | chr21 | 46654091 | 46654678 | −9.09168 | 24 | 587 |
| chr18__group024933 | chr18 | 43978625 | 43979458 | −9.08893 | 15 | 833 |
| chr13__group043460 | chr13 | 90014905 | 90016195 | −9.08732 | 59 | 1290 |
| chr21__group014531 | chr21 | 34508204 | 34508911 | −9.08544 | 22 | 707 |
| chr21__group020008 | chr21 | 43109222 | 43109723 | −9.08422 | 10 | 501 |
| chr13__group045518 | chr13 | 92596388 | 92596645 | −9.08311 | 13 | 257 |
| chr18__group025779 | chr18 | 44954371 | 44955126 | −9.08159 | 10 | 755 |
| chr18__group000755 | chr18 | 1793062 | 1793432 | −9.07389 | 12 | 370 |
| chr18__group044050 | chr18 | 72193247 | 72193987 | −9.07126 | 11 | 740 |
| chr18__group009736 | chr18 | 20349488 | 20349966 | −9.07014 | 13 | 478 |
| chr18__group015073 | chr18 | 29390294 | 29391570 | −9.06867 | 16 | 1276 |
| chr21__group014289 | chr21 | 34258543 | 34259269 | −9.06609 | 14 | 726 |
| chr13__group019309 | chr13 | 52580050 | 52580541 | −9.06542 | 13 | 491 |
| chr21__group020748 | chr21 | 44351648 | 44353737 | −9.06429 | 37 | 2089 |
| chr13__group004501 | chr13 | 27252910 | 27253233 | −9.05795 | 15 | 323 |
| chr21__group010191 | chr21 | 27436937 | 27437476 | −9.05691 | 10 | 539 |
| chr18__group008012 | chr18 | 13790853 | 13791688 | −9.05607 | 12 | 835 |
| chr13__group059932 | chr13 | 1.14E+08 | 1.14E+08 | −9.05511 | 12 | 238 |
| chr18__group026588 | chr18 | 46543564 | 46544211 | −9.05059 | 13 | 647 |
| chr21__group015507 | chr21 | 36437304 | 36437738 | −9.05005 | 9 | 434 |
| chr18__group035335 | chr18 | 60331105 | 60331804 | −9.04373 | 11 | 699 |
| chr13__group057903 | chr13 | 1.11E+08 | 1.11E+08 | −9.03598 | 9 | 254 |
| chr18__group007124 | chr18 | 12402768 | 12404212 | −9.03446 | 17 | 1444 |
| chr21__group018160 | chr21 | 40393180 | 40393501 | −9.02285 | 11 | 321 |
| chr21__group014937 | chr21 | 35593762 | 35594627 | −9.02029 | 10 | 865 |
| chr18__group007690 | chr18 | 13369905 | 13370898 | −9.01685 | 9 | 993 |
| chr13__group060194 | chr13 | 1.14E+08 | 1.14E+08 | −9.01526 | 15 | 268 |
| chr13__group023758 | chr13 | 60678951 | 60679143 | −9.0152 | 12 | 192 |
| chr13__group015325 | chr13 | 44765643 | 44766220 | −9.01359 | 12 | 577 |
| chr13__group036022 | chr13 | 79264431 | 79265674 | −9.01023 | 17 | 1243 |
| chr18__group026776 | chr18 | 47255388 | 47257647 | −9.00927 | 22 | 2259 |
| chr13__group044899 | chr13 | 91869158 | 91870226 | −9.00807 | 16 | 1068 |
| chr13__group059680 | chr13 | 1.13E+08 | 1.13E+08 | −9.00482 | 9 | 605 |
| chr13__group003646 | chr13 | 25997197 | 25998260 | −9.00445 | 10 | 1063 |
| chr13__group015747 | chr13 | 45875156 | 45875756 | −8.99904 | 16 | 600 |

TABLE 4-continued

| Name | chr | start.pos | end.pos | median.tstat | num.cg | dmr.size |
|---|---|---|---|---|---|---|
| chr21__group020180 | chr21 | 43530145 | 43530944 | −8.99494 | 13 | 799 |
| chr18__group003410 | chr18 | 6242031 | 6242882 | −8.9893 | 16 | 851 |
| chr21__group022583 | chr21 | 47307529 | 47308022 | −8.98887 | 11 | 493 |
| chr13__group012073 | chr13 | 38984399 | 38984768 | −8.97996 | 13 | 369 |
| chr21__group022239 | chr21 | 46935507 | 46935981 | −8.97341 | 22 | 474 |
| chr13__group043709 | chr13 | 90353054 | 90353646 | −8.97259 | 16 | 592 |
| chr18__group003132 | chr18 | 5986236 | 5987650 | −8.97175 | 13 | 1414 |
| chr13__group058114 | chr13 | 1.11E+08 | 1.11E+08 | −8.96904 | 13 | 522 |
| chr21__group014838 | chr21 | 35356454 | 35356874 | −8.96667 | 14 | 420 |
| chr13__group036575 | chr13 | 79881364 | 79882418 | −8.96382 | 11 | 1054 |
| chr13__group006500 | chr13 | 30071388 | 30071845 | −8.96098 | 16 | 457 |
| chr21__group007005 | chr21 | 23581980 | 23582871 | −8.95062 | 32 | 891 |
| chr21__group014316 | chr21 | 34281114 | 34281962 | −8.94693 | 9 | 848 |
| chr18__group009969 | chr18 | 20920655 | 20921014 | −8.94421 | 9 | 359 |
| chr13__group006487 | chr13 | 30054247 | 30054521 | −8.94159 | 11 | 274 |
| chr13__group015387 | chr13 | 44925234 | 44925805 | −8.93024 | 9 | 571 |
| chr13__group008486 | chr13 | 32417154 | 32417780 | −8.92926 | 10 | 626 |
| chr13__group050078 | chr13 | 99724850 | 99725720 | −8.9273 | 11 | 870 |
| chr18__group009657 | chr18 | 20263075 | 20263918 | −8.92016 | 11 | 843 |
| chr21__group020050 | chr21 | 43206482 | 43207358 | −8.91638 | 20 | 876 |
| chr18__group003537 | chr18 | 6362876 | 6363921 | −8.91566 | 15 | 1045 |
| chr18__group008440 | chr18 | 14431923 | 14432715 | −8.91366 | 23 | 792 |
| chr13__group032429 | chr13 | 73222567 | 73223595 | −8.91134 | 11 | 1028 |
| chr18__group032031 | chr18 | 55439152 | 55440929 | −8.90891 | 19 | 1777 |
| chr21__group014972 | chr21 | 35708606 | 35709751 | −8.90082 | 18 | 1145 |
| chr18__group026519 | chr18 | 46387738 | 46388482 | −8.89985 | 13 | 744 |
| chr18__group006120 | chr18 | 11214176 | 11214893 | −8.89818 | 10 | 717 |
| chr18__group031549 | chr18 | 54743323 | 54744424 | −8.89682 | 11 | 1101 |
| chr13__group050630 | chr13 | 1.01E+08 | 1.01E+08 | −8.88781 | 14 | 319 |
| chr13__group009387 | chr13 | 34799235 | 34799605 | −8.88542 | 10 | 370 |
| chr18__group005698 | chr18 | 10793049 | 10794079 | −8.88365 | 17 | 1030 |
| chr13__group007434 | chr13 | 31370806 | 31371618 | −8.8808 | 17 | 812 |
| chr18__group017748 | chr18 | 33710816 | 33711541 | −8.88063 | 22 | 725 |
| chr21__group014009 | chr21 | 33847214 | 33848083 | −8.8776 | 9 | 869 |
| chr18__group039582 | chr18 | 66457551 | 66458055 | −8.87482 | 20 | 504 |
| chr13__group001995 | chr13 | 23367741 | 23368492 | −8.87427 | 14 | 751 |
| chr13__group052530 | chr13 | 1.04E+08 | 1.04E+08 | −8.86436 | 9 | 241 |
| chr21__group014899 | chr21 | 35446809 | 35447498 | −8.86251 | 24 | 689 |
| chr18__group026570 | chr18 | 46500340 | 46501353 | −8.85637 | 15 | 1013 |
| chr18__group005647 | chr18 | 10744964 | 10746565 | −8.85427 | 18 | 1601 |
| chr18__group000078 | chr18 | 146503 | 147773 | −8.85406 | 41 | 1270 |
| chr18__group039699 | chr18 | 66609251 | 66610179 | −8.8429 | 13 | 928 |
| chr21__group003224 | chr21 | 18879876 | 18880426 | −8.83734 | 10 | 550 |
| chr18__group007968 | chr18 | 13675301 | 13676210 | −8.83558 | 10 | 909 |
| chr18__group007494 | chr18 | 13181812 | 13182069 | −8.83503 | 13 | 257 |
| chr18__group013003 | chr18 | 25712832 | 25713374 | −8.83459 | 10 | 542 |
| chr13__group057700 | chr13 | 1.1E+08 | 1.1E+08 | −8.83214 | 12 | 556 |
| chr18__group003255 | chr18 | 6097860 | 6099196 | −8.82974 | 16 | 1336 |
| chr18__group024956 | chr18 | 44004238 | 44005178 | −8.8293 | 12 | 940 |
| chr21__group021834 | chr21 | 46426590 | 46428131 | −8.82649 | 22 | 1541 |
| chr18__group006487 | chr18 | 11554166 | 11555259 | −8.8236 | 9 | 1093 |
| chr18__group007331 | chr18 | 12741226 | 12742094 | −8.81771 | 17 | 868 |
| chr18__group006305 | chr18 | 11386772 | 11387767 | −8.81394 | 12 | 995 |
| chr21__group021327 | chr21 | 45597530 | 45598071 | −8.81121 | 9 | 541 |
| chr13__group050176 | chr13 | 1E+08 | 1E+08 | −8.81001 | 16 | 1011 |
| chr18__group009760 | chr18 | 20377622 | 20378954 | −8.80928 | 32 | 1332 |
| chr21__group015381 | chr21 | 36242719 | 36243755 | −8.80778 | 14 | 1036 |
| chr18__group004459 | chr18 | 8479988 | 8480202 | −8.80116 | 9 | 214 |
| chr21__group021015 | chr21 | 44860765 | 44861471 | −8.80054 | 17 | 706 |
| chr13__group052312 | chr13 | 1.04E+08 | 1.04E+08 | −8.79896 | 12 | 1088 |
| chr21__group019698 | chr21 | 42495066 | 42496104 | −8.79612 | 11 | 1038 |
| chr13__group054931 | chr13 | 1.07E+08 | 1.07E+08 | −8.79382 | 21 | 1069 |
| chr13__group006968 | chr13 | 30692604 | 30693548 | −8.79307 | 11 | 944 |
| chr13__group029755 | chr13 | 69558905 | 69559465 | −8.79083 | 32 | 560 |
| chr13__group032569 | chr13 | 73696171 | 73697090 | −8.79056 | 25 | 919 |
| chr18__group001352 | chr18 | 3649987 | 3651088 | −8.79055 | 12 | 1101 |
| chr13__group008961 | chr13 | 33640396 | 33641184 | −8.78689 | 28 | 788 |
| chr18__group030536 | chr18 | 53388313 | 53388739 | −8.78498 | 27 | 426 |
| chr13__group008484 | chr13 | 32415003 | 32415457 | −8.77992 | 12 | 454 |
| chr13__group016079 | chr13 | 46417301 | 46417967 | −8.7774 | 9 | 666 |
| chr18__group003552 | chr18 | 6382148 | 6383248 | −8.76339 | 12 | 1100 |
| chr21__group021181 | chr21 | 45229946 | 45230447 | −8.76167 | 10 | 501 |
| chr18__group005371 | chr18 | 10402888 | 10404469 | −8.75722 | 23 | 1581 |
| chr18__group013045 | chr18 | 25768465 | 25768836 | −8.75591 | 9 | 371 |
| chr13__group004346 | chr13 | 27105000 | 27106025 | −8.75161 | 10 | 1025 |
| chr18__group008903 | chr18 | 18949093 | 18949864 | −8.75155 | 11 | 771 |
| chr21__group022780 | chr21 | 47519136 | 47521078 | −8.75017 | 27 | 1942 |
| chr13__group019205 | chr13 | 52211690 | 52212971 | −8.74789 | 11 | 1281 |

TABLE 4-continued

| Name | chr | start.pos | end.pos | median.tstat | num.cg | dmr.size |
|---|---|---|---|---|---|---|
| chr13_group041366 | chr13 | 87193979 | 87194874 | −8.74747 | 21 | 895 |
| chr21_group022028 | chr21 | 46644747 | 46646416 | −8.74624 | 30 | 1669 |
| chr21_group008989 | chr21 | 25837339 | 25837669 | −8.74006 | 9 | 330 |
| chr21_group011712 | chr21 | 30527726 | 30528291 | −8.72647 | 20 | 565 |
| chr13_group014560 | chr13 | 43598310 | 43598775 | −8.72645 | 20 | 465 |
| chr18_group026544 | chr18 | 46437432 | 46437792 | −8.72449 | 9 | 360 |
| chr13_group055152 | chr13 | 1.07E+08 | 1.07E+08 | −8.72153 | 13 | 1126 |
| chr18_group032016 | chr18 | 55365701 | 55366706 | −8.71927 | 14 | 1005 |
| chr13_group015434 | chr13 | 45153410 | 45154524 | −8.71733 | 19 | 1114 |
| chr18_group009966 | chr18 | 20910567 | 20911711 | −8.71691 | 34 | 1144 |
| chr18_group000433 | chr18 | 976170 | 977008 | −8.71101 | 29 | 838 |
| chr13_group060333 | chr13 | 1.15E+08 | 1.15E+08 | −8.71072 | 29 | 1500 |
| chr13_group006994 | chr13 | 30727949 | 30729157 | −8.70368 | 29 | 1208 |
| chr21_group021549 | chr21 | 45925869 | 45926352 | −8.70276 | 11 | 483 |
| chr21_group019769 | chr21 | 42588368 | 42589201 | −8.69239 | 21 | 833 |
| chr13_group019304 | chr13 | 52572769 | 52573915 | −8.69046 | 15 | 1146 |
| chr18_group005024 | chr18 | 9709608 | 9710214 | −8.68951 | 10 | 606 |
| chr13_group057940 | chr13 | 1.11E+08 | 1.11E+08 | −8.68874 | 24 | 1092 |
| chr18_group014846 | chr18 | 28841076 | 28842288 | −8.68576 | 9 | 1212 |
| chr18_group048134 | chr18 | 77225407 | 77225973 | −8.68462 | 10 | 566 |
| chr21_group016588 | chr21 | 37667639 | 37668417 | −8.68455 | 51 | 778 |
| chr13_group049999 | chr13 | 99428450 | 99428752 | −8.68197 | 9 | 302 |
| chr13_group052389 | chr13 | 1.04E+08 | 1.04E+08 | −8.67748 | 11 | 208 |
| chr18_group007339 | chr18 | 12762121 | 12762665 | −8.67483 | 9 | 544 |
| chr18_group038841 | chr18 | 65085724 | 65085994 | −8.67363 | 22 | 270 |
| chr13_group058206 | chr13 | 1.11E+08 | 1.11E+08 | −8.66978 | 11 | 877 |
| chr18_group005344 | chr18 | 10374116 | 10375130 | −8.66763 | 12 | 1014 |
| chr21_group021387 | chr21 | 45683146 | 45684467 | −8.66419 | 29 | 1321 |
| chr13_group018020 | chr13 | 49922204 | 49922580 | −8.65678 | 15 | 376 |
| chr18_group000233 | chr18 | 604828 | 605378 | −8.65665 | 11 | 550 |
| chr18_group004488 | chr18 | 8500642 | 8501714 | −8.65546 | 17 | 1072 |
| chr13_group049609 | chr13 | 98685656 | 98686103 | −8.65515 | 9 | 447 |
| chr18_group040590 | chr18 | 68048256 | 68048751 | −8.65339 | 10 | 495 |
| chr21_group020754 | chr21 | 44361322 | 44362227 | −8.65141 | 18 | 905 |
| chr18_group006060 | chr18 | 11158195 | 11158746 | −8.64921 | 10 | 551 |
| chr13_group010991 | chr13 | 37150770 | 37151471 | −8.64723 | 10 | 701 |
| chr21_group004458 | chr21 | 20586362 | 20586978 | −8.64597 | 12 | 616 |
| chr18_group048252 | chr18 | 77370095 | 77371619 | −8.64583 | 20 | 1524 |
| chr18_group024420 | chr18 | 43133557 | 43134678 | −8.64432 | 10 | 1121 |
| chr21_group020441 | chr21 | 43846332 | 43848032 | −8.64376 | 16 | 1700 |
| chr13_group050741 | chr13 | 1.01E+08 | 1.01E+08 | −8.64358 | 9 | 306 |
| chr18_group006054 | chr18 | 11150212 | 11151502 | −8.64242 | 16 | 1290 |
| chr13_group058202 | chr13 | 1.11E+08 | 1.11E+08 | −8.63915 | 19 | 1365 |
| chr21_group020606 | chr21 | 44105149 | 44106617 | −8.63871 | 74 | 1468 |
| chr13_group004848 | chr13 | 27629400 | 27630736 | −8.63462 | 16 | 1336 |
| chr21_group014930 | chr21 | 35576609 | 35577583 | −8.63007 | 12 | 974 |
| chr18_group038954 | chr18 | 65295456 | 65296239 | −8.62375 | 28 | 783 |
| chr13_group005456 | chr13 | 28562373 | 28562902 | −8.62267 | 12 | 529 |
| chr13_group005679 | chr13 | 29025514 | 29026380 | −8.62183 | 23 | 866 |
| chr21_group014628 | chr21 | 34690433 | 34690874 | −8.62026 | 13 | 441 |
| chr13_group059951 | chr13 | 1.14E+08 | 1.14E+08 | −8.6174 | 19 | 1063 |
| chr21_group012761 | chr21 | 31902836 | 31903430 | −8.6132 | 16 | 594 |
| chr21_group003332 | chr21 | 19039306 | 19040209 | −8.60891 | 10 | 903 |
| chr18_group044182 | chr18 | 72546653 | 72547280 | −8.60753 | 10 | 627 |
| chr13_group058566 | chr13 | 1.12E+08 | 1.12E+08 | −8.60557 | 16 | 1213 |
| chr13_group025170 | chr13 | 62904024 | 62904349 | −8.60445 | 17 | 325 |
| chr21_group021018 | chr21 | 44871728 | 44872298 | −8.60275 | 22 | 570 |
| chr13_group008397 | chr13 | 32333985 | 32334519 | −8.60211 | 10 | 534 |
| chr13_group060525 | chr13 | 1.15E+08 | 1.15E+08 | −8.59823 | 21 | 1278 |
| chr21_group018266 | chr21 | 40708426 | 40709462 | −8.59163 | 25 | 1036 |
| chr13_group005399 | chr13 | 28471596 | 28472648 | −8.5906 | 10 | 1052 |
| chr21_group016433 | chr21 | 37356937 | 37357543 | −8.58989 | 9 | 606 |
| chr13_group060171 | chr13 | 1.14E+08 | 1.14E+08 | −8.58985 | 10 | 597 |
| chr13_group060415 | chr13 | 1.15E+08 | 1.15E+08 | −8.58939 | 19 | 883 |
| chr21_group000429 | chr21 | 10596510 | 10602783 | −8.5853 | 265 | 6273 |
| chr18_group045706 | chr18 | 74390764 | 74391692 | −8.58477 | 12 | 928 |
| chr21_group013647 | chr21 | 33259895 | 33260296 | −8.58298 | 16 | 401 |
| chr18_group043802 | chr18 | 71811566 | 71813197 | −8.58106 | 18 | 1631 |
| chr18_group046743 | chr18 | 75548990 | 75550159 | −8.58002 | 17 | 1169 |
| chr21_group020881 | chr21 | 44616671 | 44617184 | −8.58002 | 9 | 513 |
| chr13_group023762 | chr13 | 60711982 | 60712449 | −8.57947 | 9 | 467 |
| chr18_group026584 | chr18 | 46539449 | 46540148 | −8.57924 | 11 | 699 |
| chr13_group014594 | chr13 | 43702694 | 43703647 | −8.57748 | 30 | 953 |
| chr13_group060037 | chr13 | 1.14E+08 | 1.14E+08 | −8.57469 | 11 | 409 |
| chr13_group027555 | chr13 | 66499795 | 66500911 | −8.57288 | 9 | 1116 |
| chr21_group020639 | chr21 | 44140800 | 44141520 | −8.57037 | 10 | 720 |
| chr13_group048036 | chr13 | 96082576 | 96083341 | −8.57025 | 15 | 765 |
| chr18_group035653 | chr18 | 61157317 | 61157839 | −8.56905 | 21 | 522 |

TABLE 4-continued

| Name | chr | start.pos | end.pos | median.tstat | num.cg | dmr.size |
|---|---|---|---|---|---|---|
| chr13_group004527 | chr13 | 27278166 | 27278562 | −8.56875 | 13 | 396 |
| chr13_group031022 | chr13 | 71713833 | 71714827 | −8.56859 | 9 | 994 |
| chr13_group011331 | chr13 | 37729629 | 37730100 | −8.5678 | 22 | 471 |
| chr21_group002430 | chr21 | 17960429 | 17961147 | −8.56671 | 24 | 718 |
| chr21_group014185 | chr21 | 34156216 | 34157147 | −8.55999 | 9 | 931 |
| chr13_group007689 | chr13 | 31625783 | 31626898 | −8.55856 | 17 | 1115 |
| chr13_group015407 | chr13 | 44991514 | 44992282 | −8.55424 | 12 | 768 |
| chr18_group026458 | chr18 | 46262249 | 46262564 | −8.55269 | 10 | 315 |
| chr13_group016167 | chr13 | 46493562 | 46494579 | −8.55143 | 10 | 1017 |
| chr18_group011133 | chr18 | 22538851 | 22539371 | −8.54596 | 10 | 520 |
| chr13_group001085 | chr13 | 21258852 | 21259464 | −8.54442 | 20 | 612 |
| chr13_group013795 | chr13 | 42027974 | 42029163 | −8.54402 | 26 | 1189 |
| chr21_group021367 | chr21 | 45656545 | 45657642 | −8.5409 | 26 | 1097 |
| chr18_group011555 | chr18 | 22999923 | 23001209 | −8.54021 | 16 | 1286 |
| chr18_group001263 | chr18 | 3412513 | 3412872 | −8.53911 | 9 | 359 |
| chr21_group005740 | chr21 | 22074075 | 22074901 | −8.53882 | 17 | 826 |
| chr21_group020073 | chr21 | 43350577 | 43351809 | −8.53788 | 22 | 1232 |
| chr13_group014095 | chr13 | 42907649 | 42908489 | −8.53476 | 14 | 840 |
| chr18_group038127 | chr18 | 64171702 | 64172506 | −8.5306 | 11 | 804 |
| chr18_group017290 | chr18 | 32893221 | 32893615 | −8.53058 | 9 | 394 |
| chr18_group003299 | chr18 | 6145177 | 6147010 | −8.53058 | 33 | 1833 |
| chr13_group058171 | chr13 | 1.11E+08 | 1.11E+08 | −8.52931 | 9 | 339 |
| chr21_group000690 | chr21 | 11143251 | 11146515 | −8.52574 | 56 | 3264 |
| chr18_group043429 | chr18 | 71442099 | 71442414 | −8.52527 | 12 | 315 |
| chr18_group047163 | chr18 | 76000176 | 76000723 | −8.52452 | 11 | 547 |
| chr18_group003720 | chr18 | 6576010 | 6576313 | −8.52357 | 11 | 303 |
| chr21_group015267 | chr21 | 36076719 | 36077666 | −8.52298 | 14 | 947 |
| chr18_group046616 | chr18 | 75430012 | 75430692 | −8.52198 | 9 | 680 |
| chr13_group004614 | chr13 | 27365950 | 27367029 | −8.51919 | 9 | 1079 |
| chr18_group003433 | chr18 | 6264494 | 6264962 | −8.50597 | 9 | 468 |
| chr18_group016437 | chr18 | 31911079 | 31911739 | −8.50486 | 25 | 660 |
| chr13_group047482 | chr13 | 95399693 | 95400527 | −8.50424 | 9 | 834 |
| chr18_group027143 | chr18 | 48089509 | 48090229 | −8.50361 | 9 | 720 |
| chr13_group049112 | chr13 | 97908729 | 97910258 | −8.49866 | 15 | 1529 |
| chr18_group032678 | chr18 | 56513577 | 56514106 | −8.49819 | 15 | 529 |
| chr21_group011723 | chr21 | 30565706 | 30567318 | −8.49602 | 22 | 1612 |
| chr18_group035539 | chr18 | 60907986 | 60909247 | −8.49211 | 13 | 1261 |
| chr21_group020856 | chr21 | 44582345 | 44582917 | −8.49036 | 16 | 572 |
| chr18_group029456 | chr18 | 51773187 | 51774405 | −8.48751 | 16 | 1218 |
| chr18_group044058 | chr18 | 72209035 | 72209745 | −8.48467 | 11 | 710 |
| chr21_group021765 | chr21 | 46289886 | 46290397 | −8.48237 | 15 | 511 |
| chr21_group017970 | chr21 | 40029239 | 40030403 | −8.48211 | 12 | 1164 |
| chr18_group043493 | chr18 | 71518595 | 71519222 | −8.48035 | 10 | 627 |
| chr13_group013370 | chr13 | 41062764 | 41063484 | −8.47666 | 10 | 720 |
| chr13_group019588 | chr13 | 53353218 | 53353929 | −8.47358 | 12 | 711 |
| chr21_group022433 | chr21 | 47160765 | 47162336 | −8.47324 | 20 | 1571 |
| chr18_group007685 | chr18 | 13364998 | 13365556 | −8.47292 | 9 | 558 |
| chr18_group006342 | chr18 | 11417533 | 11418859 | −8.4683 | 9 | 1326 |
| chr13_group048170 | chr13 | 96706526 | 96707130 | −8.46636 | 12 | 604 |
| chr21_group016870 | chr21 | 38113857 | 38114360 | −8.4659 | 15 | 503 |
| chr18_group032266 | chr18 | 55810450 | 55811072 | −8.46528 | 16 | 622 |
| chr13_group000616 | chr13 | 20392406 | 20392757 | −8.46344 | 21 | 351 |
| chr18_group045867 | chr18 | 74695632 | 74696262 | −8.45988 | 12 | 630 |
| chr21_group022456 | chr21 | 47185748 | 47186534 | −8.45672 | 10 | 786 |
| chr18_group007147 | chr18 | 12441076 | 12442311 | −8.45614 | 18 | 1235 |
| chr13_group015952 | chr13 | 46242894 | 46244335 | −8.45211 | 34 | 1441 |
| chr13_group058047 | chr13 | 1.11E+08 | 1.11E+08 | −8.45007 | 24 | 608 |
| chr18_group022330 | chr18 | 39494889 | 39495482 | −8.44961 | 17 | 593 |
| chr18_group013535 | chr18 | 26541680 | 26543057 | −8.44513 | 15 | 1377 |
| chr18_group035348 | chr18 | 60377107 | 60377636 | −8.44256 | 13 | 529 |
| chr18_group000053 | chr18 | 109284 | 110173 | −8.44073 | 9 | 889 |
| chr21_group018256 | chr21 | 40693096 | 40693812 | −8.43729 | 9 | 716 |
| chr21_group011791 | chr21 | 30805689 | 30806775 | −8.43643 | 11 | 1086 |
| chr21_group021895 | chr21 | 46490004 | 46490382 | −8.43503 | 10 | 378 |
| chr21_group038141 | chr21 | 64188962 | 64189431 | −8.43477 | 9 | 469 |
| chr18_group001344 | chr18 | 3623354 | 3624317 | −8.43406 | 34 | 963 |
| chr21_group019775 | chr21 | 42608312 | 42609201 | −8.43404 | 19 | 889 |
| chr21_group000154 | chr21 | 9695395 | 9697376 | −8.43284 | 34 | 1981 |
| chr13_group060002 | chr13 | 1.14E+08 | 1.14E+08 | −8.42577 | 19 | 604 |
| chr21_group019822 | chr21 | 42692328 | 42693777 | −8.42575 | 22 | 1449 |
| chr13_group060024 | chr13 | 1.14E+08 | 1.14E+08 | −8.42499 | 12 | 542 |
| chr21_group020005 | chr21 | 43104542 | 43105422 | −8.42411 | 19 | 880 |
| chr21_group000340 | chr21 | 10138905 | 10140493 | −8.42336 | 19 | 1588 |
| chr18_group026578 | chr18 | 46516926 | 46518489 | −8.42164 | 23 | 1563 |
| chr13_group041754 | chr13 | 87738908 | 87739495 | −8.42105 | 19 | 587 |
| chr13_group058103 | chr13 | 1.11E+08 | 1.11E+08 | −8.41946 | 36 | 1689 |
| chr18_group006587 | chr18 | 11653665 | 11655212 | −8.41818 | 18 | 1547 |
| chr18_group005630 | chr18 | 10730747 | 10731013 | −8.41654 | 16 | 266 |

TABLE 4-continued

| Name | chr | start.pos | end.pos | median.tstat | num.cg | dmr.size |
|---|---|---|---|---|---|---|
| chr21__group012262 | chr21 | 31318992 | 31319937 | −8.41547 | 12 | 945 |
| chr13__group000945 | chr13 | 20910101 | 20910456 | −8.41494 | 10 | 355 |
| chr13__group008421 | chr13 | 32354834 | 32356349 | −8.41398 | 15 | 1515 |
| chr21__group013288 | chr21 | 32471237 | 32472468 | −8.41283 | 19 | 1231 |
| chr18__group018527 | chr18 | 34852765 | 34853181 | −8.41245 | 12 | 416 |
| chr13__group033237 | chr13 | 74815615 | 74816115 | −8.40996 | 23 | 500 |
| chr18__group007078 | chr18 | 12282624 | 12283427 | −8.40589 | 14 | 803 |
| chr21__group000489 | chr21 | 10792851 | 10793531 | −8.40426 | 9 | 680 |
| chr18__group024447 | chr18 | 43167042 | 43168708 | −8.3978 | 14 | 1666 |
| chr21__group021151 | chr21 | 45140257 | 45141396 | −8.39541 | 11 | 1139 |
| chr21__group022774 | chr21 | 47511657 | 47512862 | −8.39188 | 15 | 1205 |
| chr18__group003252 | chr18 | 6095385 | 6096088 | −8.39145 | 9 | 703 |
| chr13__group004764 | chr13 | 27501265 | 27502414 | −8.39102 | 9 | 1149 |
| chr18__group001073 | chr18 | 2854570 | 2856526 | −8.3897 | 28 | 1956 |
| chr21__group016649 | chr21 | 37852334 | 37852979 | −8.38735 | 12 | 645 |
| chr18__group003573 | chr18 | 6400553 | 6401964 | −8.38241 | 21 | 1411 |
| chr18__group040557 | chr18 | 67910311 | 67910902 | −8.3769 | 13 | 591 |
| chr18__group018591 | chr18 | 34909834 | 34911433 | −8.37617 | 19 | 1599 |
| chr18__group001099 | chr18 | 2913120 | 2913592 | −8.37428 | 15 | 472 |
| chr21__group020659 | chr21 | 44168969 | 44169815 | −8.37254 | 9 | 846 |
| chr13__group057472 | chr13 | 1.1E+08 | 1.1E+08 | −8.37103 | 15 | 749 |
| chr21__group009273 | chr21 | 26140679 | 26141857 | −8.36751 | 11 | 1178 |
| chr21__group022228 | chr21 | 46911913 | 46912440 | −8.36178 | 13 | 527 |
| chr18__group047209 | chr18 | 76050375 | 76051638 | −8.35878 | 10 | 1263 |
| chr18__group013018 | chr18 | 25733520 | 25734536 | −8.35792 | 9 | 1016 |
| chr21__group015009 | chr21 | 35791536 | 35791800 | −8.35518 | 10 | 264 |
| chr13__group001735 | chr13 | 22614660 | 22615553 | −8.35471 | 26 | 893 |
| chr21__group018117 | chr21 | 40275709 | 40276288 | −8.35395 | 13 | 579 |
| chr21__group021967 | chr21 | 46580772 | 46581687 | −8.35291 | 10 | 915 |
| chr18__group033193 | chr18 | 57446602 | 57446927 | −8.35104 | 15 | 325 |
| chr13__group059977 | chr13 | 1.14E+08 | 1.14E+08 | −8.35104 | 42 | 1380 |
| chr13__group004845 | chr13 | 27614097 | 27614857 | −8.35038 | 23 | 760 |
| chr21__group019969 | chr21 | 43033146 | 43033716 | −8.34962 | 11 | 570 |
| chr18__group026165 | chr18 | 45494349 | 45494960 | −8.34922 | 9 | 611 |
| chr13__group057950 | chr13 | 1.11E+08 | 1.11E+08 | −8.34898 | 17 | 1591 |
| chr21__group020988 | chr21 | 44798421 | 44799050 | −8.3435 | 13 | 629 |
| chr18__group007384 | chr18 | 12894116 | 12894348 | −8.34171 | 10 | 232 |
| chr21__group004910 | chr21 | 21101215 | 21101923 | −8.34164 | 12 | 708 |
| chr18__group037227 | chr18 | 63068442 | 63069694 | −8.34056 | 9 | 1252 |
| chr18__group003882 | chr18 | 7201662 | 7202582 | −8.34044 | 11 | 920 |
| chr21__group019687 | chr21 | 42482129 | 42483110 | −8.33869 | 14 | 981 |
| chr18__group040348 | chr18 | 67462377 | 67463454 | −8.33748 | 13 | 1077 |
| chr21__group014960 | chr21 | 35678053 | 35678800 | −8.3326 | 10 | 747 |
| chr18__group040704 | chr18 | 68180930 | 68181978 | −8.33209 | 12 | 1048 |
| chr13__group019245 | chr13 | 52390814 | 52392038 | −8.33055 | 20 | 1224 |
| chr18__group023879 | chr18 | 42312152 | 42312887 | −8.33002 | 15 | 735 |
| chr18__group045888 | chr18 | 74712772 | 74713622 | −8.32648 | 10 | 850 |
| chr18__group000283 | chr18 | 712896 | 713587 | −8.32415 | 32 | 691 |
| chr21__group014770 | chr21 | 35220794 | 35221266 | −8.32236 | 12 | 472 |
| chr13__group013852 | chr13 | 42114320 | 42114758 | −8.32153 | 13 | 438 |
| chr13__group019294 | chr13 | 52549276 | 52550069 | −8.32069 | 13 | 793 |
| chr13__group018563 | chr13 | 51218906 | 51219610 | −8.31734 | 9 | 704 |
| chr18__group001167 | chr18 | 3148327 | 3148822 | −8.3159 | 25 | 495 |
| chr18__group043827 | chr18 | 71843368 | 71844921 | −8.31564 | 28 | 1553 |
| chr18__group048512 | chr18 | 77771637 | 77772401 | −8.31351 | 11 | 764 |
| chr13__group058452 | chr13 | 1.12E+08 | 1.12E+08 | −8.3101 | 11 | 397 |
| chr13__group019654 | chr13 | 53416552 | 53416868 | −8.30933 | 9 | 316 |
| chr13__group016492 | chr13 | 47120390 | 47121102 | −8.30516 | 12 | 712 |
| chr21__group022659 | chr21 | 47374226 | 47374659 | −8.30489 | 13 | 433 |
| chr21__group016805 | chr21 | 38032999 | 38033311 | −8.30475 | 9 | 312 |
| chr18__group018243 | chr18 | 34365950 | 34366900 | −8.30403 | 12 | 950 |
| chr18__group022362 | chr18 | 39527614 | 39528347 | −8.30339 | 9 | 733 |
| chr13__group007781 | chr13 | 31707097 | 31707827 | −8.29869 | 10 | 730 |
| chr13__group055843 | chr13 | 1.08E+08 | 1.08E+08 | −8.29823 | 14 | 660 |
| chr13__group009236 | chr13 | 34393113 | 34393618 | −8.29802 | 14 | 505 |
| chr13__group019181 | chr13 | 52130726 | 52131236 | −8.29541 | 11 | 510 |
| chr21__group021717 | chr21 | 46151014 | 46151699 | −8.29523 | 11 | 685 |
| chr13__group050120 | chr13 | 99814931 | 99815423 | −8.29426 | 10 | 492 |
| chr18__group017059 | chr18 | 32584438 | 32585131 | −8.29312 | 15 | 693 |
| chr13__group013644 | chr13 | 41705559 | 41706314 | −8.28791 | 16 | 755 |
| chr18__group003444 | chr18 | 6274715 | 6276296 | −8.28787 | 14 | 1581 |
| chr21__group014104 | chr21 | 33944979 | 33945780 | −8.28181 | 22 | 801 |
| chr13__group007085 | chr13 | 30833431 | 30834544 | −8.28032 | 15 | 1113 |
| chr13__group059575 | chr13 | 1.13E+08 | 1.13E+08 | −8.27666 | 18 | 854 |
| chr13__group018363 | chr13 | 50914779 | 50915260 | −8.2722 | 13 | 481 |
| chr13__group036021 | chr13 | 79263264 | 79263938 | −8.27084 | 13 | 674 |
| chr13__group017753 | chr13 | 49323737 | 49324400 | −8.26656 | 12 | 663 |
| chr18__group024770 | chr18 | 43747479 | 43747746 | −8.2656 | 12 | 267 |

TABLE 4-continued

| Name | chr | start.pos | end.pos | median.tstat | num.cg | dmr.size |
|---|---|---|---|---|---|---|
| chr18__group003332 | chr18 | 6171372 | 6172270 | −8.26396 | 10 | 898 |
| chr18__group005973 | chr18 | 11073411 | 11074231 | −8.2619 | 9 | 820 |
| chr21__group001047 | chr21 | 15383439 | 15383722 | −8.26044 | 13 | 283 |
| chr18__group004414 | chr18 | 8433898 | 8435204 | −8.25832 | 13 | 1306 |
| chr13__group053849 | chr13 | 1.05E+08 | 1.05E+08 | −8.25666 | 14 | 1200 |
| chr21__group021139 | chr21 | 45078064 | 45079168 | −8.25602 | 58 | 1104 |
| chr13__group018175 | chr13 | 50432017 | 50432459 | −8.25583 | 16 | 442 |
| chr18__group017855 | chr18 | 33886605 | 33887273 | −8.25408 | 9 | 668 |
| chr18__group044661 | chr18 | 73153137 | 73153586 | −8.25173 | 9 | 449 |
| chr18__group025487 | chr18 | 44571821 | 44573023 | −8.2489 | 11 | 1202 |
| chr18__group025465 | chr18 | 44549071 | 44550233 | −8.2449 | 27 | 1162 |
| chr13__group059879 | chr13 | 1.14E+08 | 1.14E+08 | −8.24336 | 18 | 582 |
| chr13__group010335 | chr13 | 36302207 | 36302867 | −8.24181 | 10 | 660 |
| chr13__group050502 | chr13 | 1.01E+08 | 1.01E+08 | −8.24087 | 9 | 630 |
| chr13__group050135 | chr13 | 99850661 | 99851928 | −8.239 | 18 | 1267 |
| chr18__group004511 | chr18 | 8522573 | 8523840 | −8.2381 | 12 | 1267 |
| chr13__group036097 | chr13 | 79338868 | 79339655 | −8.23599 | 10 | 787 |
| chr13__group015577 | chr13 | 45467979 | 45468845 | −8.23582 | 17 | 866 |
| chr18__group005686 | chr18 | 10779246 | 10780445 | −8.23534 | 13 | 1199 |
| chr21__group020742 | chr21 | 44342578 | 44343924 | −8.23485 | 32 | 1346 |
| chr13__group008564 | chr13 | 32519953 | 32520514 | −8.23137 | 11 | 561 |
| chr13__group031055 | chr13 | 71746178 | 71747044 | −8.22985 | 10 | 866 |
| chr21__group012120 | chr21 | 31171042 | 31172007 | −8.22469 | 10 | 965 |
| chr13__group007121 | chr13 | 30896450 | 30897046 | −8.22464 | 9 | 596 |
| chr13__group001061 | chr13 | 21127605 | 21128375 | −8.22335 | 10 | 770 |
| chr13__group018141 | chr13 | 50367862 | 50368390 | −8.22305 | 14 | 528 |
| chr21__group022566 | chr21 | 47284838 | 47285376 | −8.22244 | 10 | 538 |
| chr18__group040796 | chr18 | 68275448 | 68276968 | −8.21905 | 12 | 1520 |
| chr18__group003910 | chr18 | 7231198 | 7231781 | −8.21299 | 23 | 583 |
| chr18__group047542 | chr18 | 76359373 | 76360500 | −8.21003 | 9 | 1127 |
| chr13__group058002 | chr13 | 1.11E+08 | 1.11E+08 | −8.20898 | 10 | 241 |
| chr13__group060143 | chr13 | 1.14E+08 | 1.14E+08 | −8.20185 | 12 | 984 |
| chr13__group060102 | chr13 | 1.14E+08 | 1.14E+08 | −8.2018 | 16 | 883 |
| chr18__group035414 | chr18 | 60660703 | 60661218 | −8.20175 | 10 | 515 |
| chr13__group001168 | chr13 | 21548925 | 21550259 | −8.20048 | 27 | 1334 |
| chr21__group020900 | chr21 | 44693746 | 44694064 | −8.19975 | 9 | 318 |
| chr13__group012327 | chr13 | 39580522 | 39581136 | −8.19964 | 23 | 614 |
| chr13__group001163 | chr13 | 21535637 | 21536111 | −8.19645 | 10 | 474 |
| chr13__group028346 | chr13 | 67585979 | 67586999 | −8.19057 | 12 | 1020 |
| chr13__group060556 | chr13 | 1.15E+08 | 1.15E+08 | −8.19041 | 11 | 555 |
| chr21__group022107 | chr21 | 46769734 | 46770402 | −8.18949 | 16 | 668 |
| chr18__group011790 | chr18 | 23380990 | 23381440 | −8.1891 | 9 | 450 |
| chr21__group020149 | chr21 | 43496543 | 43497045 | −8.18844 | 10 | 502 |
| chr13__group016504 | chr13 | 47159450 | 47159735 | −8.18831 | 9 | 285 |
| chr13__group049007 | chr13 | 97668684 | 97669123 | −8.18533 | 13 | 439 |
| chr18__group037050 | chr18 | 62873442 | 62874391 | −8.18492 | 20 | 949 |
| chr18__group026402 | chr18 | 46142495 | 46143285 | −8.18322 | 20 | 790 |
| chr13__group034462 | chr13 | 76593592 | 76594119 | −8.18319 | 15 | 527 |
| chr18__group009034 | chr18 | 19487561 | 19487927 | −8.18179 | 9 | 366 |
| chr13__group050740 | chr13 | 1.01E+08 | 1.01E+08 | −8.18033 | 15 | 653 |
| chr13__group031120 | chr13 | 71812167 | 71812489 | −8.17739 | 19 | 322 |
| chr13__group003184 | chr13 | 25189061 | 25189944 | −8.17425 | 12 | 883 |
| chr18__group008046 | chr18 | 13824887 | 13825595 | −8.16969 | 9 | 708 |
| chr21__group021035 | chr21 | 44921845 | 44922847 | −8.16785 | 16 | 1002 |
| chr13__group005337 | chr13 | 28410178 | 28410714 | −8.16566 | 11 | 536 |
| chr21__group000156 | chr21 | 9698170 | 9702329 | −8.16118 | 85 | 4159 |
| chr21__group015104 | chr21 | 35879115 | 35880143 | −8.15977 | 9 | 1028 |
| chr18__group005581 | chr18 | 10681882 | 10682619 | −8.15749 | 17 | 737 |
| chr13__group059957 | chr13 | 1.14E+08 | 1.14E+08 | −8.15574 | 31 | 1224 |
| chr21__group014565 | chr21 | 34549211 | 34549477 | −8.154 | 16 | 266 |
| chr13__group035127 | chr13 | 77491801 | 77492363 | −8.15091 | 11 | 562 |
| chr21__group013987 | chr21 | 33828718 | 33829959 | −8.1502 | 16 | 1241 |
| chr18__group012028 | chr18 | 24125973 | 24126889 | −8.14809 | 10 | 916 |
| chr18__group046453 | chr18 | 75290204 | 75291427 | −8.14433 | 10 | 1223 |
| chr21__group020493 | chr21 | 43913066 | 43914099 | −8.14408 | 10 | 1033 |
| chr13__group005133 | chr13 | 28098638 | 28099454 | −8.14228 | 11 | 816 |
| chr13__group054979 | chr13 | 1.07E+08 | 1.07E+08 | −8.14085 | 18 | 607 |
| chr13__group019092 | chr13 | 51913189 | 51913898 | −8.14035 | 10 | 709 |
| chr13__group059908 | chr13 | 1.14E+08 | 1.14E+08 | −8.13953 | 17 | 1203 |
| chr18__group033420 | chr18 | 57754001 | 57754895 | −8.13824 | 9 | 894 |
| chr18__group007507 | chr18 | 13191170 | 13192230 | −8.13573 | 15 | 1060 |
| chr21__group022500 | chr21 | 47223715 | 47224390 | −8.13553 | 10 | 675 |
| chr13__group008490 | chr13 | 32419638 | 32419947 | −8.12809 | 9 | 309 |
| chr18__group045961 | chr18 | 74800918 | 74801691 | −8.12678 | 14 | 773 |
| chr18__group045616 | chr18 | 74304348 | 74305742 | −8.1265 | 19 | 1394 |
| chr18__group006464 | chr18 | 11529198 | 11530088 | −8.12649 | 9 | 890 |
| chr13__group059914 | chr13 | 1.14E+08 | 1.14E+08 | −8.12625 | 12 | 461 |
| chr18__group003234 | chr18 | 6078539 | 6079405 | −8.12571 | 11 | 866 |

TABLE 4-continued

| Name | chr | start.pos | end.pos | median.tstat | num.cg | dmr.size |
|---|---|---|---|---|---|---|
| chr18__group005703 | chr18 | 10797758 | 10799148 | −8.12384 | 9 | 1390 |
| chr18__group017390 | chr18 | 33078163 | 33078719 | −8.12288 | 16 | 556 |
| chr18__group007118 | chr18 | 12396073 | 12397193 | −8.1214 | 31 | 1120 |
| chr18__group044544 | chr18 | 73050382 | 73050782 | −8.12051 | 9 | 400 |
| chr18__group045620 | chr18 | 74308426 | 74308548 | −8.11992 | 10 | 122 |
| chr13__group005734 | chr13 | 29138219 | 29138787 | −8.11752 | 11 | 568 |
| chr13__group013127 | chr13 | 40786650 | 40787608 | −8.11663 | 10 | 958 |
| chr13__group056731 | chr13 | 1.09E+08 | 1.09E+08 | −8.10795 | 9 | 565 |
| chr13__group028481 | chr13 | 67730044 | 67731131 | −8.10713 | 16 | 1087 |
| chr21__group001947 | chr21 | 17276551 | 17277760 | −8.10372 | 12 | 1209 |
| chr18__group032574 | chr18 | 56278935 | 56279391 | −8.10294 | 11 | 456 |
| chr18__group026367 | chr18 | 46073910 | 46074798 | −8.10172 | 10 | 888 |
| chr21__group006942 | chr21 | 23421842 | 23422734 | −8.10141 | 9 | 892 |
| chr18__group007686 | chr18 | 13366014 | 13366373 | −8.09957 | 9 | 359 |
| chr18__group035463 | chr18 | 60755591 | 60756602 | −8.0968 | 15 | 1011 |
| chr21__group016858 | chr21 | 38102333 | 38103616 | −8.09591 | 22 | 1283 |
| chr21__group008991 | chr21 | 25839322 | 25840093 | −8.09145 | 14 | 771 |
| chr18__group010913 | chr18 | 22307046 | 22307968 | −8.09143 | 17 | 922 |
| chr18__group034991 | chr18 | 59619656 | 59620122 | −8.09064 | 12 | 466 |
| chr18__group043141 | chr18 | 71094083 | 71094443 | −8.08986 | 13 | 360 |
| chr21__group022089 | chr21 | 46751423 | 46751728 | −8.08569 | 9 | 305 |
| chr21__group013965 | chr21 | 33805733 | 33805967 | −8.0827 | 9 | 234 |
| chr13__group001021 | chr13 | 21014566 | 21015373 | −8.0816 | 10 | 807 |
| chr21__group022479 | chr21 | 47208032 | 47208445 | −8.07928 | 10 | 413 |
| chr18__group022336 | chr18 | 39500899 | 39502460 | −8.07902 | 12 | 1561 |
| chr21__group022600 | chr21 | 47322827 | 47323507 | −8.0771 | 9 | 680 |
| chr18__group045018 | chr18 | 73586488 | 73586914 | −8.0746 | 11 | 426 |
| chr13__group013794 | chr13 | 42025339 | 42027592 | −8.07415 | 37 | 2253 |
| chr18__group047567 | chr18 | 76386814 | 76387902 | −8.07101 | 12 | 1088 |
| chr21__group013319 | chr21 | 32591370 | 32592158 | −8.0705 | 12 | 788 |
| chr13__group058072 | chr13 | 1.11E+08 | 1.11E+08 | −8.07034 | 15 | 629 |
| chr13__group011963 | chr13 | 38760426 | 38760801 | −8.06882 | 12 | 375 |
| chr13__group032533 | chr13 | 73627834 | 73628082 | −8.06695 | 10 | 248 |
| chr13__group026117 | chr13 | 64603380 | 64604193 | −8.06482 | 16 | 813 |
| chr21__group011663 | chr21 | 30392071 | 30392492 | −8.06255 | 12 | 421 |
| chr18__group040958 | chr18 | 68445999 | 68446931 | −8.06229 | 14 | 932 |
| chr13__group059723 | chr13 | 1.13E+08 | 1.13E+08 | −8.06087 | 15 | 1042 |
| chr18__group009883 | chr18 | 20681752 | 20683070 | −8.05775 | 26 | 1318 |
| chr18__group040565 | chr18 | 67943843 | 67944590 | −8.05739 | 9 | 747 |
| chr18__group045800 | chr18 | 74488023 | 74488448 | −8.05436 | 10 | 425 |
| chr13__group001308 | chr13 | 21833512 | 21834319 | −8.05406 | 13 | 807 |
| chr13__group021919 | chr13 | 57708255 | 57708486 | −8.05397 | 10 | 231 |
| chr13__group007168 | chr13 | 30963039 | 30964139 | −8.05377 | 13 | 1100 |
| chr18__group005941 | chr18 | 11041362 | 11042692 | −8.05253 | 11 | 1330 |
| chr18__group045645 | chr18 | 74334287 | 74335834 | −8.05093 | 16 | 1547 |
| chr18__group004300 | chr18 | 8062990 | 8063452 | −8.04349 | 30 | 462 |
| chr18__group026750 | chr18 | 47182074 | 47182808 | −8.04266 | 10 | 734 |
| chr21__group021219 | chr21 | 45286742 | 45287562 | −8.03607 | 17 | 820 |
| chr21__group008224 | chr21 | 25063813 | 25064358 | −8.03362 | 15 | 545 |
| chr21__group010225 | chr21 | 27539816 | 27540728 | −8.03338 | 10 | 912 |
| chr18__group004705 | chr18 | 8912113 | 8912918 | −8.03126 | 11 | 805 |
| chr13__group018960 | chr13 | 51787045 | 51788049 | −8.02981 | 9 | 1004 |
| chr18__group032408 | chr18 | 56069141 | 56069997 | −8.02786 | 12 | 856 |
| chr13__group059634 | chr13 | 1.13E+08 | 1.13E+08 | −8.0263 | 21 | 1173 |
| chr13__group056676 | chr13 | 1.09E+08 | 1.09E+08 | −8.02562 | 9 | 911 |
| chr13__group053080 | chr13 | 1.04E+08 | 1.04E+08 | −8.02513 | 9 | 1012 |
| chr18__group006589 | chr18 | 11657111 | 11658177 | −8.02488 | 15 | 1066 |
| chr13__group017849 | chr13 | 49449235 | 49450194 | −8.02488 | 9 | 959 |
| chr18__group011915 | chr18 | 23734467 | 23734949 | −8.02445 | 12 | 482 |
| chr18__group035706 | chr18 | 61264039 | 61264671 | −8.01884 | 12 | 632 |
| chr18__group044239 | chr18 | 72717791 | 72718126 | −8.01846 | 9 | 335 |
| chr18__group045311 | chr18 | 73966451 | 73967600 | −8.01753 | 33 | 1149 |
| chr13__group030651 | chr13 | 71302350 | 71303097 | −8.01672 | 20 | 747 |
| chr18__group048440 | chr18 | 77633878 | 77634136 | −8.01626 | 11 | 258 |
| chr21__group020335 | chr21 | 43725280 | 43726561 | −8.01471 | 29 | 1281 |
| chr13__group003008 | chr13 | 24901187 | 24901452 | −8.00725 | 9 | 265 |
| chr13__group056398 | chr13 | 1.09E+08 | 1.09E+08 | −8.00704 | 9 | 383 |
| chr18__group018610 | chr18 | 34929646 | 34930697 | −8.00618 | 15 | 1051 |
| chr13__group035529 | chr13 | 78549419 | 78550053 | −8.00527 | 13 | 634 |
| chr18__group031618 | chr18 | 54814515 | 54814590 | −8.00376 | 10 | 75 |
| chr13__group018813 | chr13 | 51614662 | 51615199 | −8.00161 | 9 | 537 |
| chr18__group047943 | chr18 | 76751451 | 76755402 | −8.00161 | 147 | 3951 |
| chr18__group031941 | chr18 | 55169238 | 55170849 | −8.00144 | 13 | 1611 |
| chr21__group014769 | chr21 | 35216473 | 35218075 | −8.00105 | 23 | 1602 |
| chr21__group010617 | chr21 | 28146254 | 28146505 | −8.00067 | 9 | 251 |
| chr13__group019559 | chr13 | 53325606 | 53325862 | −8.00056 | 12 | 256 |
| chr18__group015048 | chr18 | 29340762 | 29340929 | −7.99883 | 17 | 167 |
| chr13__group059873 | chr13 | 1.14E+08 | 1.14E+08 | −7.99741 | 15 | 1588 |

TABLE 4-continued

| Name | chr | start.pos | end.pos | median.tstat | num.cg | dmr.size |
|---|---|---|---|---|---|---|
| chr18__group033820 | chr18 | 58175270 | 58176839 | −7.99543 | 13 | 1569 |
| chr18__group024460 | chr18 | 43178154 | 43179314 | −7.99222 | 11 | 1160 |
| chr21__group000479 | chr21 | 10779090 | 10780085 | −7.99174 | 19 | 995 |
| chr21__group013668 | chr21 | 33317159 | 33318182 | −7.98948 | 13 | 1023 |
| chr21__group018149 | chr21 | 40353992 | 40354700 | −7.98856 | 16 | 708 |
| chr13__group020744 | chr13 | 55082953 | 55083091 | −7.98782 | 9 | 138 |
| chr18__group048149 | chr18 | 77244298 | 77246369 | −7.98733 | 51 | 2071 |
| chr18__group035126 | chr18 | 60021619 | 60022257 | −7.98382 | 9 | 638 |
| chr13__group059884 | chr13 | 1.14E+08 | 1.14E+08 | −7.98224 | 25 | 1430 |
| chr21__group014146 | chr21 | 34032871 | 34033860 | −7.97959 | 15 | 989 |
| chr21__group000207 | chr21 | 9852819 | 9853695 | −7.97811 | 9 | 876 |
| chr13__group042405 | chr13 | 88506787 | 88507297 | −7.97627 | 11 | 510 |
| chr13__group047500 | chr13 | 95411394 | 95411717 | −7.97517 | 16 | 323 |
| chr18__group044000 | chr18 | 72103378 | 72104099 | −7.97502 | 10 | 721 |
| chr21__group012195 | chr21 | 31242997 | 31244143 | −7.97469 | 9 | 1146 |
| chr18__group030083 | chr18 | 52866582 | 52867539 | −7.97154 | 11 | 957 |
| chr21__group003346 | chr21 | 19066480 | 19067040 | −7.97037 | 15 | 560 |
| chr13__group056561 | chr13 | 1.09E+08 | 1.09E+08 | −7.97034 | 17 | 520 |
| chr13__group059651 | chr13 | 1.13E+08 | 1.13E+08 | −7.96976 | 82 | 3572 |
| chr18__group024961 | chr18 | 44010630 | 44011762 | −7.96775 | 9 | 1132 |
| chr13__group013796 | chr13 | 42029466 | 42030223 | −7.96555 | 22 | 757 |
| chr18__group015307 | chr18 | 29938622 | 29938934 | −7.96362 | 9 | 312 |
| chr13__group059852 | chr13 | 1.14E+08 | 1.14E+08 | −7.96067 | 21 | 914 |
| chr13__group000574 | chr13 | 20213363 | 20213929 | −7.95939 | 10 | 566 |
| chr21__group017833 | chr21 | 39903268 | 39904221 | −7.95891 | 10 | 953 |
| chr18__group006031 | chr18 | 11125279 | 11126522 | −7.95364 | 13 | 1243 |
| chr18__group020265 | chr18 | 36638399 | 36639230 | −7.95312 | 10 | 831 |
| chr13__group007135 | chr13 | 30909117 | 30909625 | −7.95218 | 11 | 508 |
| chr13__group003522 | chr13 | 25797792 | 25798599 | −7.94848 | 13 | 807 |
| chr13__group052495 | chr13 | 1.04E+08 | 1.04E+08 | −7.9458 | 9 | 1003 |
| chr21__group001158 | chr21 | 15630345 | 15631358 | −7.94419 | 9 | 1013 |
| chr18__group012086 | chr18 | 24218499 | 24219334 | −7.94417 | 9 | 835 |
| chr13__group030838 | chr13 | 71495912 | 71497583 | −7.94401 | 13 | 1671 |
| chr18__group017101 | chr18 | 32639375 | 32640848 | −7.94386 | 13 | 1473 |
| chr21__group013466 | chr21 | 32925261 | 32926647 | −7.93904 | 15 | 1386 |
| chr21__group018190 | chr21 | 40454463 | 40455605 | −7.93875 | 31 | 1142 |
| chr13__group025071 | chr13 | 62767662 | 62767938 | −7.93805 | 14 | 276 |
| chr21__group004770 | chr21 | 20933587 | 20934048 | −7.93721 | 12 | 461 |
| chr13__group000635 | chr13 | 20461971 | 20462487 | −7.93322 | 12 | 516 |
| chr13__group028748 | chr13 | 68008835 | 68009112 | −7.93098 | 13 | 277 |
| chr18__group007127 | chr18 | 12406552 | 12407429 | −7.9306 | 15 | 877 |
| chr13__group053175 | chr13 | 1.05E+08 | 1.05E+08 | −7.93046 | 14 | 535 |
| chr21__group014448 | chr21 | 34420248 | 34421081 | −7.9291 | 9 | 833 |
| chr13__group044778 | chr13 | 91670196 | 91670536 | −7.92875 | 9 | 340 |
| chr13__group060457 | chr13 | 1.15E+08 | 1.15E+08 | −7.9282 | 13 | 596 |
| chr13__group058179 | chr13 | 1.11E+08 | 1.11E+08 | −7.92674 | 16 | 452 |
| chr13__group003137 | chr13 | 25119615 | 25120195 | −7.92628 | 10 | 580 |
| chr13__group031100 | chr13 | 71790921 | 71792011 | −7.92558 | 9 | 1090 |
| chr13__group059931 | chr13 | 1.14E+08 | 1.14E+08 | −7.92518 | 21 | 994 |
| chr21__group022511 | chr21 | 47232061 | 47232515 | −7.92481 | 9 | 454 |
| chr18__group001373 | chr18 | 3687969 | 3688206 | −7.92477 | 9 | 237 |
| chr18__group011220 | chr18 | 22635950 | 22636476 | −7.92284 | 9 | 526 |
| chr13__group010961 | chr13 | 37122259 | 37123190 | −7.92142 | 9 | 931 |
| chr21__group013356 | chr21 | 32709709 | 32711080 | −7.91932 | 31 | 1371 |
| chr18__group040913 | chr18 | 68399359 | 68400159 | −7.91915 | 10 | 800 |
| chr21__group000659 | chr21 | 11109021 | 11109622 | −7.91843 | 10 | 601 |
| chr13__group015195 | chr13 | 44403358 | 44404869 | −7.91701 | 23 | 1511 |
| chr18__group043000 | chr18 | 70804444 | 70804916 | −7.91474 | 9 | 472 |
| chr18__group046177 | chr18 | 75034639 | 75035377 | −7.91425 | 10 | 738 |
| chr13__group032589 | chr13 | 73743021 | 73743561 | −7.91017 | 11 | 540 |
| chr13__group060149 | chr13 | 1.14E+08 | 1.14E+08 | −7.90841 | 32 | 1224 |
| chr13__group015244 | chr13 | 44533986 | 44534473 | −7.90654 | 16 | 487 |
| chr13__group023993 | chr13 | 61166478 | 61167230 | −7.90464 | 12 | 752 |
| chr18__group038766 | chr18 | 64981701 | 64982392 | −7.90391 | 9 | 691 |
| chr13__group058097 | chr13 | 1.11E+08 | 1.11E+08 | −7.90258 | 28 | 1658 |
| chr18__group025205 | chr18 | 44236557 | 44237093 | −7.90176 | 19 | 536 |
| chr13__group017852 | chr13 | 49454048 | 49454899 | −7.90052 | 10 | 851 |
| chr13__group001384 | chr13 | 21935206 | 21935898 | −7.89867 | 11 | 692 |
| chr21__group022251 | chr21 | 46972703 | 46973546 | −7.89858 | 21 | 843 |
| chr13__group012933 | chr13 | 40588412 | 40589474 | −7.89808 | 20 | 1062 |
| chr18__group000040 | chr18 | 90242 | 91000 | −7.89746 | 14 | 758 |
| chr21__group021878 | chr21 | 46473475 | 46474229 | −7.89286 | 9 | 754 |
| chr13__group059973 | chr13 | 1.14E+08 | 1.14E+08 | −7.89262 | 20 | 890 |
| chr18__group017271 | chr18 | 32813072 | 32813371 | −7.89154 | 16 | 299 |
| chr21__group022010 | chr21 | 46626633 | 46627608 | −7.88605 | 14 | 975 |
| chr18__group003710 | chr18 | 6557084 | 6557972 | −7.88165 | 17 | 888 |
| chr18__group045996 | chr18 | 74863479 | 74864385 | −7.88154 | 18 | 906 |
| chr13__group013912 | chr13 | 42533430 | 42534587 | −7.8808 | 30 | 1157 |

TABLE 4-continued

| Name | chr | start.pos | end.pos | median.tstat | num.cg | dmr.size |
|---|---|---|---|---|---|---|
| chr18_group038142 | chr18 | 64190452 | 64191138 | −7.88015 | 11 | 686 |
| chr18_group026513 | chr18 | 46375096 | 46375671 | −7.87703 | 14 | 575 |
| chr13_group060144 | chr13 | 1.14E+08 | 1.14E+08 | −7.8765 | 13 | 706 |
| chr21_group015068 | chr21 | 35848284 | 35849741 | −7.87591 | 11 | 1457 |
| chr21_group022214 | chr21 | 46891378 | 46892009 | −7.87591 | 14 | 631 |
| chr21_group020685 | chr21 | 44197424 | 44198286 | −7.87556 | 13 | 862 |
| chr13_group058139 | chr13 | 1.11E+08 | 1.11E+08 | −7.87376 | 9 | 346 |
| chr18_group006190 | chr18 | 11278551 | 11279352 | −7.87299 | 15 | 801 |
| chr18_group032934 | chr18 | 56907727 | 56908513 | −7.87161 | 9 | 786 |
| chr13_group030885 | chr13 | 71544223 | 71544999 | −7.87087 | 9 | 776 |
| chr18_group048285 | chr18 | 77398595 | 77399965 | −7.8705 | 16 | 1370 |
| chr13_group057728 | chr13 | 1.1E+08 | 1.1E+08 | −7.87022 | 13 | 1021 |
| chr13_group059935 | chr13 | 1.14E+08 | 1.14E+08 | −7.87019 | 11 | 564 |
| chr13_group052164 | chr13 | 1.03E+08 | 1.03E+08 | −7.86795 | 25 | 1896 |
| chr21_group020004 | chr21 | 43100636 | 43101730 | −7.86773 | 15 | 1094 |
| chr13_group047581 | chr13 | 95481317 | 95481913 | −7.86511 | 10 | 596 |
| chr13_group049895 | chr13 | 99302249 | 99302997 | −7.86457 | 11 | 748 |
| chr18_group007590 | chr18 | 13279805 | 13281394 | −7.86376 | 18 | 1589 |
| chr13_group034148 | chr13 | 75813589 | 75814730 | −7.86327 | 25 | 1141 |
| chr13_group001353 | chr13 | 21904455 | 21905607 | −7.86285 | 11 | 1152 |
| chr21_group021852 | chr21 | 46449540 | 46450841 | −7.86282 | 21 | 1301 |
| chr21_group021107 | chr21 | 45032086 | 45032676 | −7.86259 | 15 | 590 |
| chr13_group005510 | chr13 | 28615805 | 28616087 | −7.86115 | 9 | 282 |
| chr18_group037848 | chr18 | 63822816 | 63823615 | −7.8601 | 17 | 799 |
| chr18_group015207 | chr18 | 29762291 | 29762814 | −7.85919 | 16 | 523 |
| chr21_group014029 | chr21 | 33871610 | 33872657 | −7.85909 | 15 | 1047 |
| chr18_group007015 | chr18 | 12220064 | 12220691 | −7.85867 | 17 | 627 |
| chr18_group006233 | chr18 | 11322935 | 11324196 | −7.8577 | 19 | 1261 |
| chr18_group004087 | chr18 | 7460427 | 7461100 | −7.8568 | 14 | 673 |
| chr18_group020248 | chr18 | 36622590 | 36623130 | −7.85647 | 10 | 540 |
| chr13_group055661 | chr13 | 1.08E+08 | 1.08E+08 | −7.85626 | 9 | 282 |
| chr13_group002522 | chr13 | 24151756 | 24152512 | −7.85237 | 10 | 756 |
| chr13_group053105 | chr13 | 1.04E+08 | 1.04E+08 | −7.84777 | 18 | 1492 |
| chr21_group018592 | chr21 | 41160059 | 41160764 | −7.84429 | 12 | 705 |
| chr18_group007911 | chr18 | 13604884 | 13606113 | −7.8431 | 17 | 1229 |
| chr18_group046524 | chr18 | 75359584 | 75360151 | −7.84265 | 9 | 567 |
| chr21_group016292 | chr21 | 37226347 | 37227518 | −7.83926 | 12 | 1171 |
| chr13_group049898 | chr13 | 99309251 | 99310668 | −7.83925 | 20 | 1417 |
| chr18_group003750 | chr18 | 6682623 | 6684133 | −7.83778 | 24 | 1510 |
| chr21_group012036 | chr21 | 31096872 | 31098196 | −7.83769 | 9 | 1324 |
| chr21_group015376 | chr21 | 36236154 | 36237377 | −7.83762 | 17 | 1223 |
| chr21_group001773 | chr21 | 16662991 | 16663363 | −7.83537 | 9 | 372 |
| chr18_group005777 | chr18 | 10870424 | 10871666 | −7.83446 | 12 | 1242 |
| chr13_group052280 | chr13 | 1.04E+08 | 1.04E+08 | −7.83425 | 17 | 610 |
| chr18_group033033 | chr18 | 57061177 | 57061745 | −7.83168 | 16 | 568 |
| chr18_group048428 | chr18 | 77622401 | 77623409 | −7.83106 | 25 | 1008 |
| chr18_group008044 | chr18 | 13821062 | 13822117 | −7.82943 | 10 | 1055 |
| chr21_group006131 | chr21 | 22519021 | 22519552 | −7.82899 | 14 | 531 |
| chr21_group020421 | chr21 | 43827853 | 43828835 | −7.82869 | 10 | 982 |
| chr13_group002024 | chr13 | 23488633 | 23489303 | −7.82731 | 11 | 670 |
| chr13_group018995 | chr13 | 51818806 | 51819764 | −7.82528 | 11 | 958 |
| chr13_group005201 | chr13 | 28273310 | 28273505 | −7.82426 | 12 | 195 |
| chr13_group058857 | chr13 | 1.12E+08 | 1.12E+08 | −7.82322 | 18 | 1091 |
| chr18_group032729 | chr18 | 56652212 | 56652902 | −7.8218 | 11 | 690 |
| chr18_group001236 | chr18 | 3329130 | 3329868 | −7.82116 | 9 | 738 |
| chr21_group006859 | chr21 | 23327851 | 23328406 | −7.82028 | 12 | 555 |
| chr13_group053178 | chr13 | 1.05E+08 | 1.05E+08 | −7.81809 | 11 | 1086 |
| chr18_group006494 | chr18 | 11559683 | 11560244 | −7.81587 | 17 | 561 |
| chr21_group021804 | chr21 | 46378515 | 46379089 | −7.81553 | 16 | 574 |
| chr13_group027046 | chr13 | 65904539 | 65905048 | −7.81237 | 23 | 509 |
| chr21_group016944 | chr21 | 38366592 | 38367455 | −7.81024 | 22 | 863 |
| chr18_group044210 | chr18 | 72640676 | 72641315 | −7.80722 | 15 | 639 |
| chr18_group002531 | chr18 | 5154663 | 5155674 | −7.80695 | 24 | 1011 |
| chr18_group035947 | chr18 | 61616678 | 61617179 | −7.79791 | 13 | 501 |
| chr18_group009371 | chr18 | 19931508 | 19932132 | −7.79785 | 14 | 624 |
| chr18_group039835 | chr18 | 66825955 | 66826645 | −7.79695 | 11 | 690 |
| chr18_group044501 | chr18 | 73007859 | 73009089 | −7.79643 | 12 | 1230 |
| chr13_group053077 | chr13 | 1.04E+08 | 1.04E+08 | −7.79562 | 14 | 942 |
| chr13_group010705 | chr13 | 36699825 | 36700231 | −7.79408 | 16 | 406 |
| chr18_group007555 | chr18 | 13241542 | 13242446 | −7.79289 | 9 | 904 |
| chr13_group056701 | chr13 | 1.09E+08 | 1.09E+08 | −7.79209 | 11 | 882 |
| chr21_group019694 | chr21 | 42489717 | 42490888 | −7.79177 | 15 | 1171 |
| chr13_group050472 | chr13 | 1E+08 | 1.01E+08 | −7.79168 | 13 | 1304 |
| chr18_group031263 | chr18 | 54230479 | 54231110 | −7.79056 | 9 | 631 |
| chr18_group045592 | chr18 | 74271232 | 74271600 | −7.78953 | 13 | 368 |
| chr18_group035091 | chr18 | 59987970 | 59988212 | −7.787 | 10 | 242 |
| chr13_group036154 | chr13 | 79396452 | 79397032 | −7.78681 | 9 | 580 |
| chr13_group005777 | chr13 | 29258382 | 29258994 | −7.78673 | 11 | 612 |

TABLE 4-continued

| Name | chr | start.pos | end.pos | median.tstat | num.cg | dmr.size |
|---|---|---|---|---|---|---|
| chr18__group003142 | chr18 | 5995700 | 5996625 | −7.78594 | 11 | 925 |
| chr18__group046533 | chr18 | 75369523 | 75370370 | −7.78444 | 19 | 847 |
| chr13__group060306 | chr13 | 1.15E+08 | 1.15E+08 | −7.78306 | 20 | 983 |
| chr21__group011665 | chr21 | 30396024 | 30396483 | −7.77982 | 14 | 459 |
| chr18__group009222 | chr18 | 19764495 | 19765447 | −7.77906 | 14 | 952 |
| chr13__group048819 | chr13 | 97433534 | 97434881 | −7.77835 | 11 | 1347 |
| chr13__group060324 | chr13 | 1.15E+08 | 1.15E+08 | −7.77795 | 28 | 956 |
| chr21__group022118 | chr21 | 46785381 | 46787522 | −7.77794 | 46 | 2141 |
| chr18__group039588 | chr18 | 66467396 | 66467935 | −7.77708 | 9 | 539 |
| chr18__group035426 | chr18 | 60689496 | 60690143 | −7.77454 | 17 | 647 |
| chr13__group052218 | chr13 | 1.03E+08 | 1.03E+08 | −7.77293 | 25 | 840 |
| chr21__group014504 | chr21 | 34483099 | 34483794 | −7.76866 | 10 | 695 |
| chr13__group007211 | chr13 | 31055369 | 31056218 | −7.76863 | 10 | 849 |
| chr21__group020596 | chr21 | 44092977 | 44093503 | −7.76618 | 13 | 526 |
| chr13__group060583 | chr13 | 1.15E+08 | 1.15E+08 | −7.76495 | 10 | 568 |
| chr13__group016445 | chr13 | 47040427 | 47041385 | −7.76444 | 9 | 958 |
| chr21__group022961 | chr21 | 48118017 | 48119683 | −7.7641 | 146 | 1666 |
| chr18__group044717 | chr18 | 73215476 | 73216759 | −7.76393 | 10 | 1283 |
| chr18__group025018 | chr18 | 44067025 | 44067774 | −7.76222 | 10 | 749 |
| chr13__group059817 | chr13 | 1.14E+08 | 1.14E+08 | −7.75992 | 22 | 655 |
| chr18__group010288 | chr18 | 21452266 | 21453542 | −7.75794 | 25 | 1276 |
| chr13__group056685 | chr13 | 1.09E+08 | 1.09E+08 | −7.75769 | 13 | 788 |
| chr13__group036336 | chr13 | 79575491 | 79576456 | −7.75284 | 9 | 965 |
| chr18__group025490 | chr18 | 44575160 | 44575485 | −7.74961 | 15 | 325 |
| chr21__group016572 | chr21 | 37618163 | 37618984 | −7.74915 | 24 | 821 |
| chr13__group006498 | chr13 | 30067223 | 30068317 | −7.74619 | 12 | 1094 |
| chr21__group008654 | chr21 | 25497853 | 25499124 | −7.74481 | 27 | 1271 |
| chr21__group006240 | chr21 | 22640297 | 22641175 | −7.74391 | 11 | 878 |
| chr18__group005612 | chr18 | 10711713 | 10713087 | −7.74337 | 11 | 1374 |
| chr18__group048242 | chr18 | 77359169 | 77360020 | −7.74278 | 19 | 851 |
| chr21__group005033 | chr21 | 21225859 | 21226895 | −7.74229 | 22 | 1036 |
| chr18__group011505 | chr18 | 22951621 | 22952510 | −7.74125 | 12 | 889 |
| chr18__group037594 | chr18 | 63552183 | 63552897 | −7.74043 | 25 | 714 |
| chr18__group008459 | chr18 | 14458944 | 14460664 | −7.73941 | 49 | 1720 |
| chr13__group060295 | chr13 | 1.14E+08 | 1.14E+08 | −7.73862 | 12 | 1090 |
| chr21__group008176 | chr21 | 25008513 | 25008807 | −7.73823 | 11 | 294 |
| chr18__group035107 | chr18 | 60003676 | 60004296 | −7.73661 | 10 | 620 |
| chr18__group018156 | chr18 | 34272808 | 34273753 | −7.7355 | 10 | 945 |
| chr18__group002723 | chr18 | 5373965 | 5375149 | −7.73495 | 10 | 1184 |
| chr18__group032539 | chr18 | 56237072 | 56237522 | −7.73349 | 15 | 450 |
| chr18__group030663 | chr18 | 53560227 | 53560633 | −7.72967 | 19 | 406 |
| chr13__group058109 | chr13 | 1.11E+08 | 1.11E+08 | −7.72952 | 10 | 612 |
| chr18__group003258 | chr18 | 6101161 | 6102032 | −7.72896 | 9 | 871 |
| chr13__group038667 | chr13 | 83439951 | 83440286 | −7.72583 | 9 | 335 |
| chr21__group018155 | chr21 | 40367143 | 40367877 | −7.72538 | 10 | 734 |
| chr18__group026478 | chr18 | 46303260 | 46303930 | −7.72378 | 9 | 670 |
| chr13__group001756 | chr13 | 22686121 | 22686438 | −7.72105 | 11 | 317 |
| chr13__group001961 | chr13 | 23298886 | 23300556 | −7.71961 | 30 | 1670 |
| chr18__group010568 | chr18 | 21719568 | 21720211 | −7.71849 | 24 | 643 |
| chr18__group025294 | chr18 | 44317432 | 44318645 | −7.71824 | 10 | 1213 |
| chr13__group045581 | chr13 | 92659929 | 92660929 | −7.71799 | 30 | 1000 |
| chr18__group039887 | chr18 | 66897457 | 66898152 | −7.71541 | 10 | 695 |
| chr13__group012266 | chr13 | 39489934 | 39490159 | −7.71391 | 15 | 225 |
| chr21__group020980 | chr21 | 44789093 | 44790417 | −7.71298 | 29 | 1324 |
| chr18__group006180 | chr18 | 11268656 | 11269497 | −7.71266 | 14 | 841 |
| chr18__group040955 | chr18 | 68442732 | 68443386 | −7.71155 | 10 | 654 |
| chr13__group013279 | chr13 | 40951148 | 40952144 | −7.70958 | 9 | 996 |
| chr18__group048529 | chr18 | 77828533 | 77829207 | −7.70943 | 12 | 674 |
| chr18__group003262 | chr18 | 6107377 | 6108352 | −7.70893 | 13 | 975 |
| chr21__group016514 | chr21 | 37485649 | 37486150 | −7.70819 | 13 | 501 |
| chr18__group044098 | chr18 | 72253122 | 72254224 | −7.70779 | 10 | 1102 |
| chr21__group021427 | chr21 | 45761754 | 45762371 | −7.70707 | 10 | 617 |
| chr13__group037429 | chr13 | 81553538 | 81554185 | −7.70706 | 10 | 647 |
| chr13__group015755 | chr13 | 45884246 | 45884397 | −7.70555 | 10 | 151 |
| chr13__group018970 | chr13 | 51797292 | 51799040 | −7.70545 | 19 | 1748 |
| chr13__group006367 | chr13 | 29933450 | 29933814 | −7.70529 | 11 | 364 |
| chr18__group005493 | chr18 | 10589022 | 10589334 | −7.70428 | 19 | 312 |
| chr13__group006587 | chr13 | 30155331 | 30156159 | −7.70362 | 10 | 828 |
| chr13__group060083 | chr13 | 1.14E+08 | 1.14E+08 | −7.70263 | 9 | 399 |
| chr18__group028295 | chr18 | 50097997 | 50098764 | −7.70224 | 9 | 767 |
| chr18__group005756 | chr18 | 10848658 | 10850460 | −7.69989 | 21 | 1802 |
| chr18__group035640 | chr18 | 61143902 | 61144807 | −7.6984 | 22 | 905 |
| chr18__group018574 | chr18 | 34893234 | 34894286 | −7.69677 | 11 | 1052 |
| chr18__group044586 | chr18 | 73090389 | 73091288 | −7.69625 | 13 | 899 |
| chr21__group022090 | chr21 | 46752808 | 46754233 | −7.69606 | 22 | 1425 |
| chr18__group017075 | chr18 | 32600221 | 32601601 | −7.69528 | 11 | 1380 |
| chr13__group035925 | chr13 | 79084301 | 79084733 | −7.69523 | 10 | 432 |
| chr18__group038442 | chr18 | 64533807 | 64534114 | −7.69386 | 10 | 307 |

TABLE 4-continued

| Name | chr | start.pos | end.pos | median.tstat | num.cg | dmr.size |
|---|---|---|---|---|---|---|
| chr13__group018234 | chr13 | 50657440 | 50657706 | −7.69143 | 16 | 266 |
| chr21__group001891 | chr21 | 17045851 | 17046329 | −7.6901 | 18 | 478 |
| chr13__group011606 | chr13 | 38211022 | 38212024 | −7.68996 | 17 | 1002 |
| chr18__group005726 | chr18 | 10817565 | 10819537 | −7.68883 | 15 | 1972 |
| chr13__group050033 | chr13 | 99578093 | 99579166 | −7.68869 | 9 | 1073 |
| chr13__group001679 | chr13 | 22475912 | 22476634 | −7.68859 | 13 | 722 |
| chr13__group001082 | chr13 | 21254650 | 21255639 | −7.6872 | 17 | 989 |
| chr21__group000356 | chr21 | 10163405 | 10163898 | −7.68457 | 12 | 493 |
| chr21__group016134 | chr21 | 37080793 | 37081285 | −7.68454 | 9 | 492 |
| chr21__group020762 | chr21 | 44378750 | 44379440 | −7.68256 | 10 | 690 |
| chr18__group025176 | chr18 | 44210849 | 44212103 | −7.68241 | 13 | 1254 |
| chr21__group019699 | chr21 | 42496523 | 42497695 | −7.68197 | 12 | 1172 |
| chr13__group060031 | chr13 | 1.14E+08 | 1.14E+08 | −7.6766 | 15 | 1138 |
| chr21__group013884 | chr21 | 33625140 | 33625934 | −7.67636 | 9 | 794 |
| chr13__group007418 | chr13 | 31353342 | 31354387 | −7.67571 | 11 | 1045 |
| chr13__group059376 | chr13 | 1.13E+08 | 1.13E+08 | −7.67462 | 32 | 1747 |
| chr13__group058084 | chr13 | 1.11E+08 | 1.11E+08 | −7.67088 | 9 | 679 |
| chr13__group015976 | chr13 | 46306509 | 46307189 | −7.67071 | 10 | 680 |
| chr13__group001350 | chr13 | 21900725 | 21901162 | −7.66985 | 15 | 437 |
| chr21__group019823 | chr21 | 42694171 | 42695002 | −7.66906 | 14 | 831 |
| chr18__group009275 | chr18 | 19830193 | 19830827 | −7.66883 | 12 | 634 |
| chr18__group009944 | chr18 | 20837209 | 20837990 | −7.66649 | 14 | 781 |
| chr13__group056743 | chr13 | 1.09E+08 | 1.09E+08 | −7.66467 | 12 | 1389 |
| chr13__group014098 | chr13 | 42910451 | 42911712 | −7.66451 | 10 | 1261 |
| chr13__group033552 | chr13 | 75145952 | 75147123 | −7.66422 | 12 | 1171 |
| chr13__group060183 | chr13 | 1.14E+08 | 1.14E+08 | −7.66331 | 9 | 564 |
| chr21__group020460 | chr21 | 43867424 | 43868357 | −7.66167 | 15 | 933 |
| chr18__group005263 | chr18 | 10262777 | 10263309 | −7.66088 | 9 | 532 |
| chr18__group036224 | chr18 | 61907722 | 61908549 | −7.66055 | 9 | 827 |
| chr18__group000600 | chr18 | 1436276 | 1437151 | −7.66031 | 13 | 875 |
| chr21__group022103 | chr21 | 46764904 | 46766116 | −7.65919 | 46 | 1212 |
| chr18__group003564 | chr18 | 6393241 | 6394634 | −7.65672 | 11 | 1393 |
| chr18__group040677 | chr18 | 68160442 | 68161121 | −7.65652 | 11 | 679 |
| chr13__group047456 | chr13 | 95374557 | 95375926 | −7.65588 | 14 | 1369 |
| chr18__group009931 | chr18 | 20800482 | 20801259 | −7.65552 | 11 | 777 |
| chr18__group025485 | chr18 | 44569313 | 44570022 | −7.65184 | 20 | 709 |
| chr18__group001394 | chr18 | 3714141 | 3714951 | −7.65171 | 10 | 810 |
| chr18__group035417 | chr18 | 60675433 | 60675809 | −7.65098 | 14 | 376 |
| chr13__group049626 | chr13 | 98709498 | 98710032 | −7.64981 | 9 | 534 |
| chr21__group017082 | chr21 | 38891636 | 38892205 | −7.64878 | 23 | 569 |
| chr13__group034288 | chr13 | 76208488 | 76209729 | −7.64786 | 39 | 1241 |
| chr18__group026407 | chr18 | 46149349 | 46149792 | −7.64784 | 10 | 443 |
| chr13__group007508 | chr13 | 31443290 | 31444425 | −7.64697 | 15 | 1135 |
| chr21__group018565 | chr21 | 41099363 | 41099866 | −7.64587 | 13 | 503 |
| chr13__group006984 | chr13 | 30711939 | 30712394 | −7.64575 | 10 | 455 |
| chr21__group021185 | chr21 | 45234107 | 45234562 | −7.6445 | 10 | 455 |
| chr13__group057845 | chr13 | 1.11E+08 | 1.11E+08 | −7.64395 | 10 | 588 |
| chr13__group054070 | chr13 | 1.06E+08 | 1.06E+08 | −7.64366 | 9 | 865 |
| chr18__group007027 | chr18 | 12231798 | 12232791 | −7.64179 | 11 | 993 |
| chr13__group045520 | chr13 | 92597667 | 92599020 | −7.64095 | 12 | 1353 |
| chr13__group057833 | chr13 | 1.11E+08 | 1.11E+08 | −7.64057 | 42 | 2497 |
| chr13__group005604 | chr13 | 28705770 | 28706126 | −7.64029 | 10 | 356 |
| chr18__group032033 | chr18 | 55451140 | 55451982 | −7.63993 | 9 | 842 |
| chr18__group009667 | chr18 | 20274997 | 20276312 | −7.63932 | 16 | 1315 |
| chr21__group021875 | chr21 | 46470887 | 46471782 | −7.63609 | 9 | 895 |
| chr21__group018226 | chr21 | 40510538 | 40511153 | −7.6334 | 20 | 615 |
| chr18__group046950 | chr18 | 75805981 | 75806580 | −7.6334 | 10 | 599 |
| chr18__group009918 | chr18 | 20775996 | 20776599 | −7.63162 | 12 | 603 |
| chr18__group037060 | chr18 | 62882968 | 62883677 | −7.63111 | 12 | 709 |
| chr18__group037027 | chr18 | 62852497 | 62853575 | −7.6291 | 9 | 1078 |
| chr18__group047905 | chr18 | 76705398 | 76705948 | −7.62867 | 13 | 550 |
| chr21__group018164 | chr21 | 40402177 | 40402853 | −7.62673 | 12 | 676 |
| chr13__group058133 | chr13 | 1.11E+08 | 1.11E+08 | −7.62513 | 17 | 853 |
| chr13__group051067 | chr13 | 1.02E+08 | 1.02E+08 | −7.62427 | 12 | 1168 |
| chr18__group044621 | chr18 | 73119135 | 73120406 | −7.6235 | 17 | 1271 |
| chr13__group001154 | chr13 | 21513572 | 21514858 | −7.62292 | 15 | 1286 |
| chr21__group020111 | chr21 | 43442035 | 43442699 | −7.62229 | 9 | 664 |
| chr18__group025206 | chr18 | 44237589 | 44238190 | −7.62142 | 11 | 601 |
| chr13__group010323 | chr13 | 36288332 | 36289327 | −7.62041 | 16 | 995 |
| chr13__group060546 | chr13 | 1.15E+08 | 1.15E+08 | −7.62008 | 9 | 471 |
| chr21__group020727 | chr21 | 44297876 | 44298399 | −7.61926 | 9 | 523 |
| chr18__group005602 | chr18 | 10703652 | 10704442 | −7.61853 | 9 | 790 |
| chr21__group020851 | chr21 | 44573379 | 44574461 | −7.61829 | 41 | 1082 |
| chr18__group001119 | chr18 | 3026889 | 3027689 | −7.61721 | 11 | 800 |
| chr13__group048493 | chr13 | 97075448 | 97076907 | −7.61667 | 12 | 1459 |
| chr21__group003163 | chr21 | 18808854 | 18809894 | −7.61666 | 12 | 1040 |
| chr21__group014527 | chr21 | 34502482 | 34504396 | −7.61654 | 23 | 1914 |
| chr18__group006995 | chr18 | 12193404 | 12193998 | −7.61373 | 10 | 594 |

TABLE 4-continued

| Name | chr | start.pos | end.pos | median.tstat | num.cg | dmr.size |
|---|---|---|---|---|---|---|
| chr21__group022590 | chr21 | 47313337 | 47315414 | −7.61194 | 21 | 2077 |
| chr13__group005704 | chr13 | 29072880 | 29073304 | −7.61119 | 12 | 424 |
| chr18__group044964 | chr18 | 73514526 | 73515441 | −7.60983 | 11 | 915 |
| chr21__group015234 | chr21 | 36040729 | 36041306 | −7.6085 | 11 | 577 |
| chr18__group044547 | chr18 | 73053237 | 73054170 | −7.60817 | 12 | 933 |
| chr13__group030567 | chr13 | 71212469 | 71213840 | −7.60787 | 9 | 1371 |
| chr18__group007379 | chr18 | 12889960 | 12890418 | −7.60714 | 10 | 458 |
| chr21__group015740 | chr21 | 36695916 | 36696511 | −7.60667 | 9 | 595 |
| chr13__group024896 | chr13 | 62509456 | 62509759 | −7.60589 | 9 | 303 |
| chr18__group045396 | chr18 | 74062562 | 74063301 | −7.60561 | 11 | 739 |
| chr13__group039201 | chr13 | 84026395 | 84026981 | −7.60504 | 11 | 586 |
| chr18__group048586 | chr18 | 77955384 | 77956183 | −7.60234 | 11 | 799 |
| chr13__group025189 | chr13 | 62926804 | 62927455 | −7.6021 | 15 | 651 |
| chr13__group007158 | chr13 | 30941760 | 30942160 | −7.59966 | 10 | 400 |
| chr21__group015689 | chr21 | 36637955 | 36638721 | −7.59801 | 9 | 766 |
| chr13__group052425 | chr13 | 1.04E+08 | 1.04E+08 | −7.59762 | 12 | 870 |
| chr18__group000234 | chr18 | 610324 | 611007 | −7.59734 | 12 | 683 |
| chr18__group048633 | chr18 | 78008647 | 78010352 | −7.59595 | 13 | 1705 |
| chr21__group018278 | chr21 | 40730779 | 40731718 | −7.59553 | 12 | 939 |
| chr18__group024854 | chr18 | 43905993 | 43907124 | −7.59457 | 16 | 1131 |
| chr18__group007729 | chr18 | 13409979 | 13410255 | −7.59412 | 10 | 276 |
| chr21__group022430 | chr21 | 47154230 | 47157953 | −7.59268 | 37 | 3723 |
| chr13__group003455 | chr13 | 25670483 | 25671849 | −7.5879 | 29 | 1366 |
| chr13__group026891 | chr13 | 65723811 | 65724644 | −7.58693 | 30 | 833 |
| chr18__group047548 | chr18 | 76367101 | 76368411 | −7.58638 | 26 | 1310 |
| chr21__group020225 | chr21 | 43577253 | 43577952 | −7.58386 | 10 | 699 |
| chr18__group043879 | chr18 | 71909711 | 71911064 | −7.58294 | 16 | 1353 |
| chr21__group011985 | chr21 | 31049805 | 31051024 | −7.58125 | 9 | 1219 |
| chr13__group055356 | chr13 | 1.07E+08 | 1.07E+08 | −7.58092 | 19 | 837 |
| chr18__group025554 | chr18 | 44700807 | 44701715 | −7.5798 | 17 | 908 |
| chr21__group021168 | chr21 | 45201067 | 45201695 | −7.57658 | 9 | 628 |
| chr18__group003839 | chr18 | 7119427 | 7119723 | −7.57571 | 15 | 296 |
| chr13__group059946 | chr13 | 1.14E+08 | 1.14E+08 | −7.57504 | 44 | 2052 |
| chr21__group015717 | chr21 | 36671422 | 36672595 | −7.57472 | 9 | 1173 |
| chr18__group006061 | chr18 | 11159340 | 11160036 | −7.57405 | 10 | 696 |
| chr18__group018687 | chr18 | 35001130 | 35002809 | −7.574 | 18 | 1679 |
| chr13__group001825 | chr13 | 23002043 | 23002885 | −7.57221 | 14 | 842 |
| chr13__group005491 | chr13 | 28597098 | 28598099 | −7.57217 | 13 | 1001 |
| chr13__group007857 | chr13 | 31809113 | 31810202 | −7.57188 | 11 | 1089 |
| chr21__group001245 | chr21 | 15723621 | 15724922 | −7.57044 | 13 | 1301 |
| chr18__group010079 | chr18 | 21237048 | 21238799 | −7.57038 | 13 | 1751 |
| chr13__group000434 | chr13 | 19938846 | 19939767 | −7.56689 | 27 | 921 |
| chr18__group011240 | chr18 | 22659977 | 22660637 | −7.56634 | 11 | 660 |
| chr21__group021148 | chr21 | 45131548 | 45132684 | −7.5663 | 21 | 1136 |
| chr13__group058649 | chr13 | 1.12E+08 | 1.12E+08 | −7.5662 | 9 | 989 |
| chr21__group014238 | chr21 | 34207255 | 34207867 | −7.56479 | 9 | 612 |
| chr18__group009456 | chr18 | 20012467 | 20013364 | −7.5642 | 20 | 897 |
| chr18__group043780 | chr18 | 71792233 | 71792881 | −7.56318 | 9 | 648 |
| chr21__group013345 | chr21 | 32682924 | 32683403 | −7.5625 | 10 | 479 |
| chr13__group015160 | chr13 | 44359042 | 44359470 | −7.56225 | 10 | 428 |
| chr21__group000929 | chr21 | 15095548 | 15096626 | −7.56206 | 60 | 1078 |
| chr18__group006193 | chr18 | 11281005 | 11282750 | −7.5619 | 14 | 1745 |
| chr21__group022199 | chr21 | 46873839 | 46875258 | −7.56095 | 32 | 1419 |
| chr13__group041749 | chr13 | 87730786 | 87732551 | −7.55988 | 24 | 1765 |
| chr21__group017660 | chr21 | 39706604 | 39707253 | −7.55852 | 11 | 649 |
| chr18__group035545 | chr18 | 60926355 | 60927535 | −7.55837 | 11 | 1180 |
| chr13__group008383 | chr13 | 32318714 | 32320794 | −7.55693 | 14 | 2080 |
| chr18__group039515 | chr18 | 66324393 | 66325149 | −7.55676 | 12 | 756 |
| chr21__group022275 | chr21 | 47001739 | 47002214 | −7.55627 | 9 | 475 |
| chr13__group060139 | chr13 | 1.14E+08 | 1.14E+08 | −7.55241 | 43 | 1994 |
| chr13__group049851 | chr13 | 99230291 | 99231217 | −7.55206 | 9 | 926 |
| chr18__group045456 | chr18 | 74113497 | 74113658 | −7.55047 | 9 | 161 |
| chr21__group022255 | chr21 | 46982673 | 46983485 | −7.54969 | 12 | 812 |
| chr18__group035939 | chr18 | 61607388 | 61608360 | −7.54614 | 14 | 972 |
| chr18__group036894 | chr18 | 62703841 | 62704489 | −7.54489 | 16 | 648 |
| chr18__group018503 | chr18 | 34826868 | 34827206 | −7.54428 | 11 | 338 |
| chr21__group005026 | chr21 | 21218865 | 21219216 | −7.54337 | 11 | 351 |
| chr21__group016289 | chr21 | 37222761 | 37224008 | −7.54233 | 11 | 1247 |
| chr18__group003141 | chr18 | 5995095 | 5995331 | −7.54209 | 9 | 236 |
| chr13__group030534 | chr13 | 71184526 | 71185479 | −7.54149 | 12 | 953 |
| chr13__group058624 | chr13 | 1.12E+08 | 1.12E+08 | −7.54077 | 19 | 1727 |
| chr21__group014283 | chr21 | 34253740 | 34254806 | −7.53865 | 11 | 1066 |
| chr18__group007719 | chr18 | 13399227 | 13400571 | −7.53642 | 13 | 1344 |
| chr18__group044463 | chr18 | 72969314 | 72970002 | −7.53621 | 9 | 688 |
| chr18__group018805 | chr18 | 35099344 | 35100105 | −7.53606 | 9 | 761 |
| chr18__group043700 | chr18 | 71719705 | 71720602 | −7.53534 | 9 | 897 |
| chr21__group007541 | chr21 | 24276680 | 24277633 | −7.53472 | 11 | 953 |
| chr18__group034990 | chr18 | 59616921 | 59617799 | −7.53455 | 17 | 878 |

TABLE 4-continued

| Name | chr | start.pos | end.pos | median.tstat | num.cg | dmr.size |
|---|---|---|---|---|---|---|
| chr21__group009178 | chr21 | 26035698 | 26036166 | −7.53356 | 11 | 468 |
| chr13__group035771 | chr13 | 78898548 | 78899576 | −7.53305 | 10 | 1028 |
| chr18__group047427 | chr18 | 76251487 | 76252403 | −7.53271 | 17 | 916 |
| chr13__group060297 | chr13 | 1.14E+08 | 1.14E+08 | −7.53229 | 15 | 1163 |
| chr13__group003121 | chr13 | 25102272 | 25103344 | −7.53156 | 10 | 1072 |
| chr13__group047243 | chr13 | 95067141 | 95067996 | −7.53018 | 10 | 855 |
| chr13__group039720 | chr13 | 84673731 | 84675016 | −7.52992 | 13 | 1285 |
| chr21__group021227 | chr21 | 45323291 | 45323936 | −7.52837 | 25 | 645 |
| chr13__group000996 | chr13 | 20965653 | 20966323 | −7.52758 | 42 | 670 |
| chr18__group044817 | chr18 | 73323590 | 73324198 | −7.5273 | 9 | 608 |
| chr21__group017875 | chr21 | 39939073 | 39939941 | −7.52637 | 20 | 868 |
| chr21__group006037 | chr21 | 22396990 | 22397681 | −7.52565 | 10 | 691 |
| chr21__group020854 | chr21 | 44578783 | 44579364 | −7.52463 | 12 | 581 |
| chr21__group019918 | chr21 | 42869637 | 42870081 | −7.52336 | 9 | 444 |
| chr13__group059948 | chr13 | 1.14E+08 | 1.14E+08 | −7.52124 | 59 | 2537 |
| chr18__group011822 | chr18 | 23442929 | 23443491 | −7.52099 | 9 | 562 |
| chr18__group044048 | chr18 | 72189716 | 72190213 | −7.52093 | 11 | 497 |
| chr18__group003354 | chr18 | 6192130 | 6193653 | −7.52029 | 14 | 1523 |
| chr18__group033101 | chr18 | 57214551 | 57215397 | −7.51989 | 9 | 846 |
| chr13__group024977 | chr13 | 62617000 | 62617600 | −7.51909 | 10 | 600 |
| chr18__group046788 | chr18 | 75591983 | 75593160 | −7.51868 | 12 | 1177 |
| chr18__group010659 | chr18 | 21978299 | 21978647 | −7.51846 | 14 | 348 |
| chr18__group040634 | chr18 | 68118341 | 68120664 | −7.51711 | 29 | 2323 |
| chr18__group033111 | chr18 | 57246832 | 57247789 | −7.51583 | 9 | 957 |
| chr21__group013468 | chr21 | 32927594 | 32928726 | −7.51389 | 11 | 1132 |
| chr18__group018823 | chr18 | 35116487 | 35117328 | −7.51186 | 11 | 841 |
| chr13__group059617 | chr13 | 1.13E+08 | 1.13E+08 | −7.51058 | 13 | 355 |
| chr18__group003294 | chr18 | 6139476 | 6140608 | −7.50953 | 10 | 1132 |
| chr13__group003540 | chr13 | 25862211 | 25862815 | −7.50621 | 11 | 604 |
| chr18__group003247 | chr18 | 6091214 | 6092495 | −7.50372 | 10 | 1281 |
| chr13__group009163 | chr13 | 34216316 | 34217700 | −7.50355 | 14 | 1384 |
| chr18__group046657 | chr18 | 75468106 | 75469006 | −7.50043 | 11 | 900 |
| chr13__group013729 | chr13 | 41955871 | 41956881 | −7.49993 | 9 | 1010 |
| chr13__group007473 | chr13 | 31407688 | 31410129 | −7.49829 | 30 | 2441 |
| chr18__group032578 | chr18 | 56286067 | 56286637 | −7.49733 | 10 | 570 |
| chr13__group028484 | chr13 | 67733248 | 67734164 | −7.49655 | 9 | 916 |
| chr21__group010839 | chr21 | 28933548 | 28933775 | −7.49441 | 9 | 227 |
| chr13__group003526 | chr13 | 25803389 | 25804599 | −7.49435 | 12 | 1210 |
| chr18__group025270 | chr18 | 44297230 | 44298152 | −7.49387 | 9 | 922 |
| chr21__group008387 | chr21 | 25229224 | 25229787 | −7.49357 | 9 | 563 |
| chr21__group008346 | chr21 | 25186128 | 25186378 | −7.49161 | 9 | 250 |
| chr13__group060329 | chr13 | 1.15E+08 | 1.15E+08 | −7.48794 | 31 | 1266 |
| chr13__group055279 | chr13 | 1.07E+08 | 1.07E+08 | −7.48583 | 13 | 774 |
| chr13__group059601 | chr13 | 1.13E+08 | 1.13E+08 | −7.48562 | 14 | 311 |
| chr18__group006804 | chr18 | 11934121 | 11934416 | −7.48503 | 10 | 295 |
| chr21__group006673 | chr21 | 23120671 | 23121072 | −7.4847 | 11 | 401 |
| chr18__group004655 | chr18 | 8785920 | 8786280 | −7.48452 | 18 | 360 |
| chr13__group013941 | chr13 | 42585373 | 42586468 | −7.4837 | 14 | 1095 |
| chr13__group014463 | chr13 | 43439012 | 43439730 | −7.48341 | 9 | 718 |
| chr13__group006800 | chr13 | 30435856 | 30436529 | −7.48275 | 9 | 673 |
| chr13__group002151 | chr13 | 23721304 | 23722106 | −7.48259 | 14 | 802 |
| chr18__group047463 | chr18 | 76286305 | 76289648 | −7.48247 | 35 | 3343 |
| chr18__group002072 | chr18 | 4527649 | 4528211 | −7.48199 | 12 | 562 |
| chr18__group048395 | chr18 | 77586418 | 77587350 | −7.48146 | 44 | 932 |
| chr13__group060470 | chr13 | 1.15E+08 | 1.15E+08 | −7.4801 | 13 | 611 |
| chr18__group003263 | chr18 | 6109278 | 6110888 | −7.47548 | 16 | 1610 |
| chr18__group048411 | chr18 | 77606823 | 77607409 | −7.47351 | 12 | 586 |
| chr13__group060451 | chr13 | 1.15E+08 | 1.15E+08 | −7.4734 | 22 | 700 |
| chr13__group019446 | chr13 | 53019556 | 53020464 | −7.4722 | 31 | 908 |
| chr18__group045533 | chr18 | 74199616 | 74200235 | −7.47031 | 9 | 619 |
| chr21__group000503 | chr21 | 10805701 | 10806441 | −7.46981 | 9 | 740 |
| chr21__group007645 | chr21 | 24387695 | 24388122 | −7.46955 | 9 | 427 |
| chr18__group035452 | chr18 | 60729987 | 60731183 | −7.46943 | 15 | 1196 |
| chr13__group006903 | chr13 | 30594145 | 30594444 | −7.46877 | 9 | 299 |
| chr13__group000534 | chr13 | 20139539 | 20139729 | −7.46868 | 10 | 190 |
| chr18__group035413 | chr18 | 60658906 | 60660365 | −7.46629 | 25 | 1459 |
| chr13__group059986 | chr13 | 1.14E+08 | 1.14E+08 | −7.46419 | 9 | 815 |
| chr18__group048414 | chr18 | 77608773 | 77609106 | −7.46196 | 17 | 333 |
| chr21__group020338 | chr21 | 43729118 | 43729642 | −7.45742 | 10 | 524 |
| chr13__group036110 | chr13 | 79351577 | 79352526 | −7.45717 | 9 | 949 |
| chr13__group031775 | chr13 | 72511948 | 72512562 | −7.45677 | 9 | 614 |
| chr13__group051943 | chr13 | 1.03E+08 | 1.03E+08 | −7.45662 | 10 | 1086 |
| chr13__group005010 | chr13 | 27944655 | 27946204 | −7.45616 | 14 | 1549 |
| chr18__group008561 | chr18 | 14927888 | 14929132 | −7.45437 | 13 | 1244 |
| chr18__group005030 | chr18 | 9742012 | 9742512 | −7.45415 | 11 | 500 |
| chr13__group058340 | chr13 | 1.12E+08 | 1.12E+08 | −7.45407 | 13 | 471 |
| chr13__group023061 | chr13 | 59355418 | 59355974 | −7.4539 | 9 | 556 |
| chr13__group043073 | chr13 | 89369957 | 89370509 | −7.45345 | 12 | 552 |

TABLE 4-continued

| Name | chr | start.pos | end.pos | median.tstat | num.cg | dmr.size |
|---|---|---|---|---|---|---|
| chr13__group047253 | chr13 | 95085945 | 95086233 | −7.45302 | 12 | 288 |
| chr21__group020605 | chr21 | 44102757 | 44103900 | −7.45283 | 22 | 1143 |
| chr18__group004458 | chr18 | 8478706 | 8479563 | −7.45175 | 14 | 857 |
| chr18__group006096 | chr18 | 11192943 | 11193521 | −7.45165 | 11 | 578 |
| chr18__group006062 | chr18 | 11160443 | 11161435 | −7.45148 | 9 | 992 |
| chr13__group003360 | chr13 | 25570030 | 25570477 | −7.44763 | 15 | 447 |
| chr21__group022409 | chr21 | 47132938 | 47134303 | −7.44746 | 10 | 1365 |
| chr13__group059922 | chr13 | 1.14E+08 | 1.14E+08 | −7.4473 | 18 | 337 |
| chr21__group021818 | chr21 | 46409969 | 46410275 | −7.44644 | 14 | 306 |
| chr18__group007108 | chr18 | 12387389 | 12388048 | −7.44468 | 9 | 659 |
| chr18__group003426 | chr18 | 6257748 | 6259115 | −7.44305 | 10 | 1367 |
| chr21__group000481 | chr21 | 10781419 | 10784823 | −7.44071 | 41 | 3404 |
| chr13__group012981 | chr13 | 40633079 | 40634897 | −7.43991 | 12 | 1818 |
| chr21__group005051 | chr21 | 21243725 | 21244357 | −7.4398 | 10 | 632 |
| chr21__group019717 | chr21 | 42518878 | 42519321 | −7.43961 | 10 | 443 |
| chr13__group003730 | chr13 | 26068105 | 26069273 | −7.43773 | 10 | 1168 |
| chr13__group029155 | chr13 | 68488704 | 68489823 | −7.43625 | 31 | 1119 |
| chr13__group003468 | chr13 | 25689986 | 25692093 | −7.43572 | 36 | 2107 |
| chr21__group014147 | chr21 | 34034362 | 34034773 | −7.4348 | 9 | 411 |
| chr13__group000054 | chr13 | 19202441 | 19203495 | −7.43468 | 29 | 1054 |
| chr18__group024827 | chr18 | 43881214 | 43882407 | −7.43422 | 15 | 1193 |
| chr18__group021095 | chr18 | 38006240 | 38006591 | −7.43189 | 15 | 351 |
| chr21__group021020 | chr21 | 44878465 | 44879188 | −7.43167 | 17 | 723 |
| chr21__group019966 | chr21 | 43025521 | 43026166 | −7.43119 | 19 | 645 |
| chr18__group027323 | chr18 | 48663917 | 48664547 | −7.43109 | 9 | 630 |
| chr13__group005020 | chr13 | 27955975 | 27956627 | −7.43014 | 11 | 652 |
| chr13__group024401 | chr13 | 61791727 | 61792644 | −7.42923 | 9 | 917 |
| chr13__group053007 | chr13 | 1.04E+08 | 1.04E+08 | −7.42872 | 13 | 567 |
| chr18__group005559 | chr18 | 10662929 | 10663708 | −7.42716 | 9 | 779 |
| chr18__group005413 | chr18 | 10453698 | 10454155 | −7.42556 | 18 | 457 |
| chr18__group030638 | chr18 | 53524848 | 53526628 | −7.42496 | 26 | 1780 |
| chr18__group003441 | chr18 | 6271427 | 6273603 | −7.424 | 44 | 2176 |
| chr18__group045983 | chr18 | 74849702 | 74850936 | −7.42256 | 18 | 1234 |
| chr18__group010722 | chr18 | 22098099 | 22099211 | −7.4219 | 18 | 1112 |
| chr21__group007714 | chr21 | 24473579 | 24473948 | −7.41979 | 9 | 369 |
| chr18__group015525 | chr18 | 30274829 | 30276562 | −7.41779 | 16 | 1733 |
| chr13__group007766 | chr13 | 31693834 | 31694581 | −7.41743 | 12 | 747 |
| chr21__group022163 | chr21 | 46830470 | 46830974 | −7.41726 | 9 | 504 |
| chr18__group019070 | chr18 | 35358855 | 35359574 | −7.41494 | 9 | 719 |
| chr13__group003032 | chr13 | 5903455 | 5904429 | −7.4137 | 11 | 974 |
| chr13__group060549 | chr13 | 1.15E+08 | 1.15E+08 | −7.41366 | 12 | 360 |
| chr18__group032991 | chr18 | 56976524 | 56976947 | −7.41342 | 10 | 423 |
| chr18__group036702 | chr18 | 62476970 | 62478335 | −7.41331 | 11 | 1365 |
| chr21__group020977 | chr21 | 44787305 | 44787625 | −7.41271 | 11 | 320 |
| chr13__group038859 | chr13 | 83676273 | 83676706 | −7.41185 | 16 | 433 |
| chr21__group008905 | chr21 | 25751091 | 25751561 | −7.41151 | 10 | 470 |
| chr18__group035309 | chr18 | 60278040 | 60278633 | −7.41 | 9 | 593 |
| chr18__group033269 | chr18 | 57542813 | 57543336 | −7.40997 | 11 | 523 |
| chr21__group014050 | chr21 | 33893674 | 33894237 | −7.40794 | 9 | 563 |
| chr13__group059678 | chr13 | 1.13E+08 | 1.13E+08 | −7.4078 | 12 | 1065 |
| chr18__group008877 | chr18 | 18810239 | 18811085 | −7.40769 | 17 | 846 |
| chr13__group055012 | chr13 | 1.07E+08 | 1.07E+08 | −7.40632 | 26 | 1488 |
| chr18__group047953 | chr18 | 76763765 | 76764459 | −7.40584 | 13 | 694 |
| chr18__group012073 | chr18 | 24200469 | 24201409 | −7.40482 | 19 | 940 |
| chr18__group043824 | chr18 | 71840120 | 71841002 | −7.4037 | 27 | 882 |
| chr13__group014942 | chr13 | 44115569 | 44116771 | −7.40142 | 13 | 1202 |
| chr21__group006433 | chr21 | 22858152 | 22858581 | −7.40025 | 10 | 429 |
| chr13__group060442 | chr13 | 1.15E+08 | 1.15E+08 | −7.40008 | 12 | 1501 |
| chr21__group020684 | chr21 | 44195120 | 44197005 | −7.39906 | 27 | 1885 |
| chr18__group004392 | chr18 | 8366627 | 8366986 | −7.39905 | 9 | 359 |
| chr18__group025301 | chr18 | 44322868 | 44324154 | −7.39785 | 12 | 1286 |
| chr18__group018761 | chr18 | 35069065 | 35069385 | −7.39778 | 9 | 320 |
| chr13__group049732 | chr13 | 98866275 | 98866598 | −7.39762 | 10 | 323 |
| chr18__group043726 | chr18 | 71740800 | 71741995 | −7.39672 | 14 | 1195 |
| chr18__group008119 | chr18 | 13889915 | 13890984 | −7.39297 | 13 | 1069 |
| chr13__group059836 | chr13 | 1.14E+08 | 1.14E+08 | −7.3929 | 26 | 1905 |
| chr13__group010177 | chr13 | 36113909 | 36114510 | −7.39201 | 10 | 601 |
| chr18__group006873 | chr18 | 12068224 | 12069077 | −7.3914 | 36 | 853 |
| chr13__group059976 | chr13 | 1.14E+08 | 1.14E+08 | −7.39124 | 27 | 795 |
| chr18__group015645 | chr18 | 30411042 | 30412095 | −7.38992 | 10 | 1053 |
| chr21__group010610 | chr21 | 28137734 | 28138578 | −7.38943 | 11 | 844 |
| chr21__group003301 | chr21 | 18957695 | 18958125 | −7.38894 | 11 | 430 |
| chr13__group058090 | chr13 | 1.11E+08 | 1.11E+08 | −7.38853 | 19 | 283 |
| chr13__group004712 | chr13 | 27456206 | 27457242 | −7.38783 | 10 | 1036 |
| chr13__group007708 | chr13 | 31640894 | 31641914 | −7.387 | 14 | 1020 |
| chr13__group016307 | chr13 | 46855266 | 46855773 | −7.38682 | 11 | 507 |
| chr13__group014558 | chr13 | 43595485 | 43595893 | −7.38652 | 9 | 408 |
| chr21__group014447 | chr21 | 34419007 | 34419831 | −7.38562 | 13 | 824 |

TABLE 4-continued

| Name | chr | start.pos | end.pos | median.tstat | num.cg | dmr.size |
|---|---|---|---|---|---|---|
| chr13_group047182 | chr13 | 94994576 | 94995812 | −7.38527 | 22 | 1236 |
| chr18_group000184 | chr18 | 535721 | 536063 | −7.38452 | 12 | 342 |
| chr18_group025462 | chr18 | 44545468 | 44546081 | −7.38417 | 14 | 613 |
| chr18_group006383 | chr18 | 11456870 | 11458521 | −7.38308 | 14 | 1651 |
| chr21_group009357 | chr21 | 26218240 | 26219064 | −7.38262 | 9 | 824 |
| chr21_group016488 | chr21 | 37435846 | 37437721 | −7.38162 | 22 | 1875 |
| chr18_group037457 | chr18 | 63391878 | 63392102 | −7.38131 | 9 | 224 |
| chr21_group020580 | chr21 | 44069182 | 44071900 | −7.38071 | 36 | 2718 |
| chr21_group000573 | chr21 | 10989922 | 10991859 | −7.37932 | 128 | 1937 |
| chr13_group053101 | chr13 | 1.04E+08 | 1.04E+08 | −7.37817 | 9 | 1333 |
| chr21_group022146 | chr21 | 46811810 | 46812381 | −7.37784 | 9 | 571 |
| chr21_group022179 | chr21 | 46847480 | 46847961 | −7.37476 | 14 | 481 |
| chr18_group005791 | chr18 | 10884628 | 10885628 | −7.37451 | 10 | 1000 |
| chr18_group042997 | chr18 | 70801786 | 70802542 | −7.37409 | 21 | 756 |
| chr13_group055490 | chr13 | 1.08E+08 | 1.08E+08 | −7.37377 | 9 | 225 |
| chr21_group009820 | chr21 | 26736952 | 26737517 | −7.37208 | 14 | 565 |
| chr18_group031544 | chr18 | 54737814 | 54739387 | −7.37051 | 24 | 1573 |
| chr21_group018573 | chr21 | 41114339 | 41115050 | −7.37012 | 9 | 711 |
| chr18_group038677 | chr18 | 64868021 | 64868870 | −7.36947 | 10 | 849 |
| chr18_group014693 | chr18 | 28466401 | 28466979 | −7.36937 | 17 | 578 |
| chr13_group059982 | chr13 | 1.14E+08 | 1.14E+08 | −7.36907 | 106 | 3789 |
| chr18_group007521 | chr18 | 13203016 | 13203619 | −7.36851 | 9 | 603 |
| chr18_group001649 | chr18 | 3960356 | 3961575 | −7.36821 | 9 | 1219 |
| chr18_group025463 | chr18 | 44546998 | 44547517 | −7.3668 | 18 | 519 |
| chr21_group006453 | chr21 | 22879842 | 22880323 | −7.36651 | 12 | 481 |
| chr18_group048167 | chr18 | 77272065 | 77272351 | −7.36149 | 12 | 286 |
| chr13_group052017 | chr13 | 1.03E+08 | 1.03E+08 | −7.35923 | 9 | 723 |
| chr13_group020678 | chr13 | 54841056 | 54841598 | −7.35804 | 14 | 542 |
| chr21_group020406 | chr21 | 43810346 | 43811737 | −7.35756 | 11 | 1391 |
| chr21_group020003 | chr21 | 43098901 | 43099665 | −7.3565 | 12 | 764 |
| chr18_group048239 | chr18 | 77355958 | 77356723 | −7.35629 | 18 | 765 |
| chr18_group047327 | chr18 | 76154558 | 76155688 | −7.35579 | 10 | 1130 |
| chr13_group020775 | chr13 | 55146115 | 55147089 | −7.35558 | 30 | 974 |
| chr21_group022682 | chr21 | 47398616 | 47399439 | −7.35454 | 21 | 823 |
| chr18_group048007 | chr18 | 76819234 | 76819849 | −7.35232 | 17 | 615 |
| chr21_group021518 | chr21 | 45877469 | 45878266 | −7.35175 | 10 | 797 |
| chr13_group000533 | chr13 | 20138783 | 20139009 | −7.35098 | 11 | 226 |
| chr21_group020430 | chr21 | 43836256 | 43837389 | −7.34823 | 25 | 1133 |
| chr13_group007735 | chr13 | 31668699 | 31670059 | −7.34815 | 9 | 1360 |
| chr13_group052651 | chr13 | 1.04E+08 | 1.04E+08 | −7.34762 | 10 | 929 |
| chr21_group017324 | chr21 | 39214548 | 39215390 | −7.34701 | 10 | 842 |
| chr18_group044980 | chr18 | 73539430 | 73540074 | −7.34582 | 12 | 644 |
| chr13_group053297 | chr13 | 1.05E+08 | 1.05E+08 | −7.34529 | 10 | 706 |
| chr13_group053368 | chr13 | 1.05E+08 | 1.05E+08 | −7.34505 | 19 | 792 |
| chr13_group058191 | chr13 | 1.11E+08 | 1.11E+08 | −7.34397 | 9 | 446 |
| chr18_group024700 | chr18 | 43545875 | 43546311 | −7.34296 | 23 | 436 |
| chr13_group004518 | chr13 | 27270236 | 27270684 | −7.34239 | 10 | 448 |
| chr21_group000508 | chr21 | 10810789 | 10811303 | −7.34217 | 11 | 514 |
| chr21_group019498 | chr21 | 42212363 | 42213258 | −7.34162 | 10 | 895 |
| chr21_group021266 | chr21 | 45412570 | 45413070 | −7.34122 | 20 | 500 |
| chr13_group000532 | chr13 | 20135457 | 20136179 | −7.34003 | 27 | 722 |
| chr18_group005683 | chr18 | 10776169 | 10777563 | −7.33956 | 10 | 1394 |
| chr13_group058563 | chr13 | 1.12E+08 | 1.12E+08 | −7.33838 | 10 | 599 |
| chr21_group013691 | chr21 | 33406121 | 33406793 | −7.3381 | 11 | 672 |
| chr13_group003134 | chr13 | 25114669 | 25115385 | −7.33502 | 17 | 716 |
| chr21_group000482 | chr21 | 10785153 | 10787763 | −7.33485 | 32 | 2610 |
| chr21_group016631 | chr21 | 37834317 | 37835056 | −7.33478 | 14 | 739 |
| chr13_group055236 | chr13 | 1.07E+08 | 1.07E+08 | −7.33471 | 9 | 727 |
| chr13_group039985 | chr13 | 84954799 | 84955591 | −7.33375 | 9 | 792 |
| chr18_group046786 | chr18 | 75588767 | 75589507 | −7.33361 | 9 | 740 |
| chr18_group034656 | chr18 | 59160472 | 59161223 | −7.33305 | 9 | 751 |
| chr18_group010344 | chr18 | 21506743 | 21507352 | −7.33089 | 9 | 609 |
| chr13_group003195 | chr13 | 25225343 | 25226324 | −7.3307 | 11 | 981 |
| chr13_group007388 | chr13 | 31329844 | 31330481 | −7.32935 | 16 | 637 |
| chr18_group000343 | chr18 | 866230 | 867512 | −7.32907 | 10 | 1282 |
| chr18_group044684 | chr18 | 73178985 | 73180072 | −7.32761 | 13 | 1087 |
| chr18_group020281 | chr18 | 36653770 | 36654018 | −7.32733 | 11 | 248 |
| chr13_group033176 | chr13 | 74742201 | 74743090 | −7.32517 | 9 | 889 |
| chr18_group038149 | chr18 | 64198195 | 64198769 | −7.3249 | 9 | 574 |
| chr13_group055700 | chr13 | 1.08E+08 | 1.08E+08 | −7.32047 | 9 | 773 |
| chr21_group022248 | chr21 | 46964022 | 46964512 | −7.32027 | 12 | 490 |
| chr13_group027872 | chr13 | 67043720 | 67044302 | −7.3202 | 10 | 582 |
| chr18_group032680 | chr18 | 56515318 | 56516638 | −7.3194 | 21 | 1320 |
| chr21_group001703 | chr21 | 16290292 | 16291355 | −7.31789 | 13 | 1063 |
| chr18_group047675 | chr18 | 76485529 | 76488900 | −7.31771 | 67 | 3371 |
| chr13_group004862 | chr13 | 27710225 | 27710549 | −7.31675 | 10 | 324 |
| chr18_group009375 | chr18 | 19934989 | 19936171 | −7.31662 | 10 | 1182 |
| chr18_group007878 | chr18 | 13565625 | 13566187 | −7.31547 | 13 | 562 |

TABLE 4-continued

| Name | chr | start.pos | end.pos | median.tstat | num.cg | dmr.size |
|---|---|---|---|---|---|---|
| chr13__group000940 | chr13 | 20906036 | 20906772 | −7.31407 | 11 | 736 |
| chr13__group037653 | chr13 | 81864995 | 81865363 | −7.3099 | 10 | 368 |
| chr18__group011095 | chr18 | 22499238 | 22500058 | −7.30844 | 9 | 820 |
| chr13__group014191 | chr13 | 42999076 | 42999689 | −7.30785 | 16 | 613 |
| chr21__group015927 | chr21 | 36885189 | 36885542 | −7.30776 | 14 | 353 |
| chr18__group010084 | chr18 | 21244015 | 21245047 | −7.30649 | 12 | 1032 |
| chr18__group028187 | chr18 | 49972332 | 49972580 | −7.30522 | 9 | 248 |
| chr13__group059670 | chr13 | 1.13E+08 | 1.13E+08 | −7.30369 | 10 | 940 |
| chr18__group046172 | chr18 | 75028775 | 75029751 | −7.30316 | 12 | 976 |
| chr13__group041512 | chr13 | 87444222 | 87444887 | −7.30253 | 36 | 665 |
| chr18__group001554 | chr18 | 3870561 | 3871904 | −7.30251 | 10 | 1343 |
| chr13__group016434 | chr13 | 47029531 | 47030243 | −7.30076 | 23 | 712 |
| chr18__group006637 | chr18 | 11701925 | 11703689 | −7.29942 | 17 | 1764 |
| chr18__group045638 | chr18 | 74327252 | 74327949 | −7.29815 | 15 | 697 |
| chr18__group009885 | chr18 | 20684774 | 20686189 | −7.29792 | 29 | 1415 |
| chr18__group015708 | chr18 | 30507842 | 30508230 | −7.2963 | 17 | 388 |
| chr18__group008587 | chr18 | 15000158 | 15000744 | −7.29554 | 11 | 586 |
| chr21__group001518 | chr21 | 16029708 | 16030524 | −7.2943 | 9 | 816 |
| chr18__group045963 | chr18 | 74804428 | 74805769 | −7.2926 | 24 | 1341 |
| chr18__group044065 | chr18 | 72220831 | 72221770 | −7.29128 | 9 | 939 |
| chr18__group014247 | chr18 | 27755019 | 27755993 | −7.29076 | 67 | 974 |
| chr13__group017483 | chr13 | 48747200 | 48747641 | −7.29031 | 15 | 441 |
| chr18__group026583 | chr18 | 46532775 | 46534300 | −7.29029 | 25 | 1525 |
| chr21__group010972 | chr21 | 29186181 | 29186579 | −7.28863 | 10 | 398 |
| chr18__group048131 | chr18 | 77221549 | 77221694 | −7.2881 | 9 | 145 |
| chr18__group047029 | chr18 | 75871395 | 75872342 | −7.28803 | 12 | 947 |
| chr21__group020024 | chr21 | 43147288 | 43147931 | −7.28802 | 17 | 643 |
| chr13__group060178 | chr13 | 1.14E+08 | 1.14E+08 | −7.28718 | 59 | 2866 |
| chr18__group007708 | chr18 | 13388219 | 13389319 | −7.28675 | 10 | 1100 |
| chr18__group044107 | chr18 | 72263552 | 72263936 | −7.28656 | 12 | 384 |
| chr21__group021013 | chr21 | 44855790 | 44856481 | −7.28619 | 12 | 691 |
| chr13__group059883 | chr13 | 1.14E+08 | 1.14E+08 | −7.28568 | 19 | 821 |
| chr13__group059820 | chr13 | 1.14E+08 | 1.14E+08 | −7.28489 | 21 | 1486 |
| chr18__group036002 | chr18 | 61681735 | 61683198 | −7.28389 | 12 | 1463 |
| chr21__group020457 | chr21 | 43863044 | 43865090 | −7.28303 | 26 | 2046 |
| chr13__group025405 | chr13 | 63242342 | 63242894 | −7.28245 | 14 | 552 |
| chr21__group014540 | chr21 | 34526000 | 34526650 | −7.28076 | 9 | 650 |
| chr18__group045315 | chr18 | 73970340 | 73971515 | −7.27641 | 13 | 1175 |
| chr13__group004016 | chr13 | 26617530 | 26617837 | −7.27568 | 13 | 307 |
| chr21__group011878 | chr21 | 30957356 | 30958327 | −7.27541 | 9 | 971 |
| chr21__group020588 | chr21 | 44081629 | 44082394 | −7.2734 | 16 | 765 |
| chr18__group007823 | chr18 | 13502512 | 13503362 | −7.27228 | 10 | 850 |
| chr18__group025243 | chr18 | 44271680 | 44273957 | −7.27205 | 21 | 2277 |
| chr18__group018232 | chr18 | 34348731 | 34349900 | −7.27137 | 13 | 1169 |
| chr18__group043718 | chr18 | 71733195 | 71734491 | −7.26741 | 14 | 1296 |
| chr13__group058044 | chr13 | 1.11E+08 | 1.11E+08 | −7.26719 | 16 | 983 |
| chr13__group003700 | chr13 | 26040732 | 26042021 | −7.2655 | 21 | 1289 |
| chr13__group042587 | chr13 | 88721332 | 88722049 | −7.2651 | 12 | 717 |
| chr13__group019010 | chr13 | 51832988 | 51834117 | −7.265 | 12 | 1129 |
| chr21__group022232 | chr21 | 46916158 | 46916640 | −7.26469 | 12 | 482 |
| chr21__group014286 | chr21 | 34256420 | 34257189 | −7.26451 | 13 | 769 |
| chr13__group059975 | chr13 | 1.14E+08 | 1.14E+08 | −7.26341 | 56 | 2439 |
| chr21__group015263 | chr21 | 36072334 | 36073036 | −7.26311 | 12 | 702 |
| chr21__group000257 | chr21 | 9907290 | 9908296 | −7.26277 | 18 | 1006 |
| chr18__group018828 | chr18 | 35120303 | 35120645 | −7.26198 | 10 | 342 |
| chr21__group021244 | chr21 | 45374965 | 45375552 | −7.26097 | 18 | 587 |
| chr21__group020115 | chr21 | 43445383 | 43446686 | −7.26006 | 12 | 1303 |
| chr13__group052268 | chr13 | 1.04E+08 | 1.04E+08 | −7.25965 | 29 | 2463 |
| chr18__group029969 | chr18 | 52745623 | 52747755 | −7.2593 | 19 | 2132 |
| chr13__group060184 | chr13 | 1.14E+08 | 1.14E+08 | −7.2587 | 16 | 988 |
| chr18__group048424 | chr18 | 77617278 | 77618460 | −7.25777 | 15 | 1182 |
| chr13__group029838 | chr13 | 69700428 | 69701529 | −7.25714 | 16 | 1101 |
| chr18__group012315 | chr18 | 24468520 | 24469748 | −7.25518 | 20 | 1228 |
| chr21__group013280 | chr21 | 32460594 | 32461158 | −7.25488 | 23 | 564 |
| chr21__group014978 | chr21 | 35728529 | 35729390 | −7.25469 | 9 | 861 |
| chr18__group048186 | chr18 | 77293800 | 77294558 | −7.25323 | 12 | 758 |
| chr13__group019281 | chr13 | 52491703 | 52492307 | −7.25249 | 10 | 604 |
| chr18__group048419 | chr18 | 77611853 | 77613625 | −7.25218 | 37 | 1772 |
| chr13__group005752 | chr13 | 29192884 | 29193090 | −7.25213 | 12 | 206 |
| chr13__group001940 | chr13 | 23270411 | 23270911 | −7.25113 | 33 | 500 |
| chr18__group039010 | chr18 | 65455818 | 65457614 | −7.25097 | 15 | 1796 |
| chr21__group021005 | chr21 | 44828984 | 44829564 | −7.24994 | 14 | 580 |
| chr18__group035634 | chr18 | 61137587 | 61138362 | −7.24672 | 12 | 775 |
| chr18__group045365 | chr18 | 74033743 | 74035488 | −7.24448 | 18 | 1745 |
| chr18__group048116 | chr18 | 77202668 | 77203731 | −7.24415 | 25 | 1063 |
| chr18__group048198 | chr18 | 77305153 | 77305540 | −7.24406 | 12 | 387 |
| chr21__group001016 | chr21 | 15353372 | 15354299 | −7.24355 | 29 | 927 |
| chr13__group032424 | chr13 | 73216493 | 73217129 | −7.24269 | 22 | 636 |

TABLE 4-continued

| Name | chr | start.pos | end.pos | median.tstat | num.cg | dmr.size |
|---|---|---|---|---|---|---|
| chr21__group013341 | chr21 | 32668073 | 32668393 | −7.24136 | 9 | 320 |
| chr13__group057360 | chr13 | 1.1E+08 | 1.1E+08 | −7.24105 | 10 | 420 |
| chr13__group016236 | chr13 | 46661098 | 46661446 | −7.24098 | 11 | 348 |
| chr18__group000029 | chr18 | 75535 | 76169 | −7.24084 | 34 | 634 |
| chr18__group033529 | chr18 | 57863382 | 57864450 | −7.24047 | 11 | 1068 |
| chr21__group020254 | chr21 | 43629126 | 43630546 | −7.24013 | 14 | 1420 |
| chr13__group060662 | chr13 | 1.15E+08 | 1.15E+08 | −7.23976 | 16 | 1244 |
| chr18__group004588 | chr18 | 8612052 | 8612731 | −7.23806 | 9 | 679 |
| chr13__group060424 | chr13 | 1.15E+08 | 1.15E+08 | −7.23746 | 20 | 1307 |
| chr13__group015495 | chr13 | 45281229 | 45281516 | −7.23605 | 11 | 287 |
| chr18__group007637 | chr18 | 13326008 | 13327401 | −7.23523 | 11 | 1393 |
| chr18__group044454 | chr18 | 72956539 | 72957161 | −7.235 | 10 | 622 |
| chr13__group060348 | chr13 | 1.15E+08 | 1.15E+08 | −7.23492 | 14 | 412 |
| chr21__group022233 | chr21 | 46917126 | 46919942 | −7.23438 | 33 | 2816 |
| chr18__group027270 | chr18 | 48533012 | 48533972 | −7.23368 | 14 | 960 |
| chr18__group004998 | chr18 | 9645022 | 9645573 | −7.23357 | 11 | 551 |
| chr21__group021505 | chr21 | 45860813 | 45861433 | −7.23306 | 10 | 620 |
| chr18__group018522 | chr18 | 34847054 | 34847931 | −7.23256 | 9 | 877 |
| chr21__group014498 | chr21 | 34477099 | 34478023 | −7.23128 | 11 | 924 |
| chr18__group008957 | chr18 | 19193385 | 19194090 | −7.23089 | 13 | 705 |
| chr18__group000138 | chr18 | 366596 | 367880 | −7.22985 | 20 | 1284 |
| chr13__group002996 | chr13 | 24888361 | 24888810 | −7.22865 | 9 | 449 |
| chr18__group025907 | chr18 | 45080438 | 45081357 | −7.22839 | 9 | 919 |
| chr13__group028800 | chr13 | 68071720 | 68072144 | −7.22827 | 22 | 424 |
| chr21__group002480 | chr21 | 18040157 | 18040879 | −7.22812 | 19 | 722 |
| chr13__group054953 | chr13 | 1.07E+08 | 1.07E+08 | −7.22666 | 9 | 537 |
| chr21__group022769 | chr21 | 47502778 | 47504454 | −7.22586 | 33 | 1676 |
| chr13__group042650 | chr13 | 88788343 | 88789495 | −7.22505 | 9 | 1152 |
| chr18__group035158 | chr18 | 60051757 | 60052464 | −7.22355 | 30 | 707 |
| chr21__group018161 | chr21 | 40394853 | 40395469 | −7.22184 | 10 | 616 |
| chr21__group014024 | chr21 | 33867046 | 33868050 | −7.22017 | 10 | 1004 |
| chr18__group003545 | chr18 | 6374224 | 6376629 | −7.22007 | 26 | 2405 |
| chr21__group022337 | chr21 | 47060626 | 47062008 | −7.21962 | 36 | 1382 |
| chr21__group020583 | chr21 | 44075903 | 44076501 | −7.21804 | 13 | 598 |
| chr13__group058915 | chr13 | 1.12E+08 | 1.12E+08 | −7.21747 | 13 | 1650 |
| chr18__group040684 | chr18 | 68166394 | 68167016 | −7.21722 | 21 | 622 |
| chr13__group048799 | chr13 | 97417365 | 97417621 | −7.21546 | 10 | 256 |
| chr13__group050778 | chr13 | 1.01E+08 | 1.01E+08 | −7.2154 | 12 | 806 |
| chr18__group046475 | chr18 | 75309804 | 75310219 | −7.21315 | 10 | 415 |
| chr18__group018660 | chr18 | 34975023 | 34976046 | −7.21303 | 11 | 1023 |
| chr13__group013850 | chr13 | 42107431 | 42108704 | −7.21185 | 13 | 1273 |
| chr21__group021760 | chr21 | 46264058 | 46265348 | −7.21144 | 39 | 1290 |
| chr13__group059356 | chr13 | 1.13E+08 | 1.13E+08 | −7.21107 | 21 | 732 |
| chr13__group013137 | chr13 | 40800063 | 40801057 | −7.21088 | 9 | 994 |
| chr21__group019715 | chr21 | 42513868 | 42514503 | −7.20964 | 9 | 635 |
| chr13__group032526 | chr13 | 73609600 | 73610790 | −7.20917 | 11 | 1190 |
| chr13__group029109 | chr13 | 68432007 | 68432342 | −7.20852 | 9 | 335 |
| chr18__group005098 | chr18 | 9962039 | 9962735 | −7.2076 | 13 | 696 |
| chr18__group048356 | chr18 | 77535490 | 77536489 | −7.20688 | 15 | 999 |
| chr21__group006014 | chr21 | 22366629 | 22367583 | −7.20646 | 9 | 954 |
| chr21__group000016 | chr21 | 9437054 | 9439684 | −7.20546 | 113 | 2630 |
| chr13__group004747 | chr13 | 27484720 | 27485828 | −7.20537 | 13 | 1108 |
| chr18__group037440 | chr18 | 63376158 | 63376636 | −7.20525 | 11 | 478 |
| chr18__group027479 | chr18 | 48925918 | 48926491 | −7.20524 | 10 | 573 |
| chr18__group007770 | chr18 | 13446128 | 13448859 | −7.20507 | 40 | 2731 |
| chr21__group021026 | chr21 | 44886586 | 44887065 | −7.20414 | 19 | 479 |
| chr13__group045605 | chr13 | 92687311 | 92687686 | −7.20389 | 10 | 375 |
| chr13__group047711 | chr13 | 95602538 | 95604042 | −7.20333 | 20 | 1504 |
| chr18__group048386 | chr18 | 77576638 | 77577484 | −7.2029 | 13 | 846 |
| chr18__group003001 | chr18 | 5868698 | 5869362 | −7.20278 | 9 | 664 |
| chr13__group041618 | chr13 | 87602587 | 87603187 | −7.20079 | 17 | 600 |
| chr18__group010033 | chr18 | 21184005 | 21184782 | −7.20018 | 11 | 777 |
| chr21__group021831 | chr21 | 46424476 | 46424939 | −7.19989 | 22 | 463 |
| chr13__group059925 | chr13 | 1.14E+08 | 1.14E+08 | −7.19895 | 61 | 3174 |
| chr18__group032017 | chr18 | 55373196 | 55374365 | −7.19831 | 17 | 1169 |
| chr18__group007491 | chr18 | 13179563 | 13180566 | −7.198 | 10 | 1003 |
| chr13__group005274 | chr13 | 28339249 | 28339990 | −7.19687 | 15 | 741 |
| chr21__group020822 | chr21 | 44537386 | 44537623 | −7.19471 | 10 | 237 |
| chr21__group015048 | chr21 | 35827824 | 35828686 | −7.19288 | 12 | 862 |
| chr18__group002665 | chr18 | 5319140 | 5319915 | −7.19104 | 9 | 775 |
| chr13__group005046 | chr13 | 27985397 | 27986581 | −7.19056 | 13 | 1184 |
| chr18__group007319 | chr18 | 12701385 | 12701904 | −7.19026 | 13 | 519 |
| chr18__group007504 | chr18 | 13187625 | 13188809 | −7.189 | 10 | 1184 |
| chr18__group007604 | chr18 | 13292900 | 13293287 | −7.1884 | 10 | 387 |
| chr13__group002950 | chr13 | 24801658 | 24802488 | −7.18809 | 14 | 830 |
| chr13__group047617 | chr13 | 95514390 | 95515038 | −7.18709 | 9 | 648 |
| chr13__group030552 | chr13 | 71200243 | 71201419 | −7.18683 | 13 | 1176 |
| chr21__group014106 | chr21 | 33946789 | 33948002 | −7.18566 | 20 | 1213 |

TABLE 4-continued

| Name | chr | start.pos | end.pos | median.tstat | num.cg | dmr.size |
|---|---|---|---|---|---|---|
| chr13__group004985 | chr13 | 27914553 | 27915323 | −7.18416 | 17 | 770 |
| chr13__group058504 | chr13 | 1.12E+08 | 1.12E+08 | −7.18197 | 11 | 871 |
| chr21__group021408 | chr21 | 45712949 | 45713759 | −7.18154 | 12 | 810 |
| chr18__group042171 | chr18 | 69876206 | 69876867 | −7.18132 | 16 | 661 |
| chr21__group021741 | chr21 | 46181083 | 46181809 | −7.17882 | 9 | 726 |
| chr13__group056732 | chr13 | 1.09E+08 | 1.09E+08 | −7.17846 | 13 | 1957 |
| chr13__group029787 | chr13 | 69619016 | 69619578 | −7.17645 | 11 | 562 |
| chr21__group022176 | chr21 | 46844455 | 46845193 | −7.17638 | 11 | 738 |
| chr21__group000228 | chr21 | 9876255 | 9880228 | −7.17533 | 110 | 3973 |
| chr13__group040283 | chr13 | 85276248 | 85276586 | −7.17454 | 9 | 338 |
| chr13__group032393 | chr13 | 73184421 | 73184884 | −7.17415 | 23 | 463 |
| chr18__group012314 | chr18 | 24463968 | 24468180 | −7.17399 | 52 | 4212 |
| chr21__group000682 | chr21 | 11130080 | 11131615 | −7.17265 | 14 | 1535 |
| chr18__group003453 | chr18 | 6286108 | 6287580 | −7.17212 | 10 | 1472 |
| chr13__group025920 | chr13 | 64349228 | 64349649 | −7.17168 | 13 | 421 |
| chr21__group022460 | chr21 | 47189223 | 47190058 | −7.16811 | 11 | 835 |
| chr18__group000313 | chr18 | 831452 | 832693 | −7.1679 | 21 | 1241 |
| chr13__group053789 | chr13 | 1.05E+08 | 1.05E+08 | −7.16784 | 12 | 1447 |
| chr13__group003004 | chr13 | 24896584 | 24898107 | −7.16707 | 14 | 1523 |
| chr13__group029767 | chr13 | 69585852 | 69586452 | −7.16672 | 9 | 600 |
| chr21__group016845 | chr21 | 38091212 | 38091734 | −7.16456 | 12 | 522 |
| chr18__group017719 | chr18 | 33663136 | 33663362 | −7.16433 | 12 | 226 |
| chr18__group031907 | chr18 | 55137366 | 55138522 | −7.16366 | 9 | 1156 |
| chr13__group048001 | chr13 | 96022771 | 96023427 | −7.16307 | 9 | 656 |
| chr18__group000212 | chr18 | 575543 | 576247 | −7.16167 | 15 | 704 |
| chr21__group003188 | chr21 | 18839169 | 18840938 | −7.16134 | 18 | 1769 |
| chr13__group050823 | chr13 | 1.01E+08 | 1.01E+08 | −7.16015 | 23 | 1371 |
| chr13__group055387 | chr13 | 1.07E+08 | 1.07E+08 | −7.15853 | 9 | 628 |
| chr18__group007049 | chr18 | 12248920 | 12249776 | −7.15838 | 10 | 856 |
| chr13__group028677 | chr13 | 67931385 | 67932148 | −7.15822 | 18 | 763 |
| chr21__group000524 | chr21 | 10846738 | 10849738 | −7.15796 | 32 | 3000 |
| chr21__group020973 | chr21 | 44783677 | 44784605 | −7.15795 | 10 | 928 |
| chr13__group032560 | chr13 | 73677678 | 73678339 | −7.15767 | 11 | 661 |
| chr18__group007300 | chr18 | 12645811 | 12646506 | −7.15689 | 12 | 695 |
| chr13__group017804 | chr13 | 49383876 | 49385120 | −7.15585 | 12 | 1244 |
| chr13__group001723 | chr13 | 22588119 | 22588960 | −7.15552 | 9 | 841 |
| chr13__group055437 | chr13 | 1.08E+08 | 1.08E+08 | −7.15451 | 13 | 1132 |
| chr13__group013148 | chr13 | 40810176 | 40811182 | −7.15426 | 13 | 1006 |
| chr21__group020453 | chr21 | 43857602 | 43860060 | −7.15371 | 34 | 2458 |
| chr18__group046727 | chr18 | 75533278 | 75534339 | −7.15269 | 11 | 1061 |
| chr18__group044019 | chr18 | 72130044 | 72131125 | −7.15218 | 14 | 1081 |
| chr21__group016710 | chr21 | 37938801 | 37939735 | −7.15182 | 9 | 934 |
| chr21__group016549 | chr21 | 37561803 | 37562444 | −7.15181 | 12 | 641 |
| chr18__group044349 | chr18 | 72845010 | 72846183 | −7.15151 | 15 | 1173 |
| chr21__group016730 | chr21 | 37961020 | 37961601 | −7.15051 | 11 | 581 |
| chr18__group012287 | chr18 | 24434257 | 24435450 | −7.14991 | 14 | 1193 |
| chr18__group005936 | chr18 | 11033645 | 11034668 | −7.14926 | 9 | 1023 |
| chr13__group054211 | chr13 | 1.06E+08 | 1.06E+08 | −7.14826 | 17 | 607 |
| chr21__group021820 | chr21 | 46411464 | 46412295 | −7.14704 | 26 | 831 |
| chr13__group005011 | chr13 | 27946805 | 27947702 | −7.14434 | 12 | 897 |
| chr21__group015201 | chr21 | 36008288 | 36009461 | −7.14409 | 13 | 1173 |
| chr21__group021513 | chr21 | 45869346 | 45869761 | −7.14374 | 9 | 415 |
| chr18__group008458 | chr18 | 14457799 | 14458169 | −7.14197 | 17 | 370 |
| chr18__group024221 | chr18 | 42900792 | 42902001 | −7.14085 | 12 | 1209 |
| chr21__group022757 | chr21 | 47486306 | 47488401 | −7.14064 | 35 | 2095 |
| chr21__group019799 | chr21 | 42661254 | 42661854 | −7.13914 | 16 | 600 |
| chr18__group047173 | chr18 | 76009792 | 76010960 | −7.13902 | 11 | 1168 |
| chr13__group026707 | chr13 | 65499232 | 65500199 | −7.13743 | 20 | 967 |
| chr13__group030758 | chr13 | 71414299 | 71415563 | −7.13622 | 11 | 1264 |
| chr13__group051821 | chr13 | 1.03E+08 | 1.03E+08 | −7.13605 | 9 | 760 |
| chr18__group007888 | chr18 | 24690061 | 24690688 | −7.1359 | 11 | 627 |
| chr21__group018852 | chr21 | 41514913 | 41515674 | −7.13574 | 15 | 761 |
| chr13__group030856 | chr13 | 71511873 | 71512541 | −7.13391 | 10 | 668 |
| chr18__group010295 | chr18 | 21459163 | 21459770 | −7.13207 | 15 | 607 |
| chr18__group033170 | chr18 | 57375660 | 57376586 | −7.13187 | 13 | 926 |
| chr13__group058161 | chr13 | 1.11E+08 | 1.11E+08 | −7.13137 | 12 | 827 |
| chr13__group004360 | chr13 | 27118499 | 27119215 | −7.13089 | 11 | 716 |
| chr13__group007549 | chr13 | 31490989 | 31491826 | −7.13088 | 9 | 837 |
| chr21__group000517 | chr21 | 10822699 | 10826716 | −7.13037 | 56 | 4017 |
| chr13__group044508 | chr13 | 91401051 | 91401372 | −7.13022 | 20 | 321 |
| chr18__group047335 | chr18 | 76162051 | 76164075 | −7.1298 | 25 | 2024 |
| chr18__group007082 | chr18 | 12293853 | 12294717 | −7.1296 | 11 | 864 |
| chr18__group004841 | chr18 | 9285020 | 9285201 | −7.12899 | 9 | 181 |
| chr13__group052277 | chr13 | 1.04E+08 | 1.04E+08 | −7.12757 | 10 | 541 |
| chr18__group007751 | chr18 | 13431928 | 13432233 | −7.12723 | 11 | 305 |
| chr13__group015791 | chr13 | 45964973 | 45965679 | −7.12628 | 32 | 706 |
| chr18__group044328 | chr18 | 72825232 | 72825850 | −7.12604 | 11 | 618 |
| chr18__group047754 | chr18 | 76558125 | 76560115 | −7.12476 | 26 | 1990 |

TABLE 4-continued

| Name | chr | start.pos | end.pos | median.tstat | num.cg | dmr.size |
|---|---|---|---|---|---|---|
| chr18__group024724 | chr18 | 43627298 | 43627612 | −7.12386 | 11 | 314 |
| chr13__group060496 | chr13 | 1.15E+08 | 1.15E+08 | −7.12301 | 10 | 363 |
| chr21__group022007 | chr21 | 46622032 | 46623408 | −7.12065 | 11 | 1376 |
| chr13__group000160 | chr13 | 19495090 | 19495845 | −7.12017 | 9 | 755 |
| chr13__group053189 | chr13 | 1.05E+08 | 1.05E+08 | −7.12006 | 16 | 663 |
| chr13__group004516 | chr13 | 27268021 | 27269261 | −7.11958 | 13 | 1240 |
| chr13__group005728 | chr13 | 29127020 | 29127988 | −7.11952 | 14 | 968 |
| chr21__group016715 | chr21 | 37943802 | 37944511 | −7.11717 | 10 | 709 |
| chr18__group001348 | chr18 | 3639839 | 3640032 | −7.11622 | 9 | 193 |
| chr18__group002778 | chr18 | 5540569 | 5541008 | −7.11515 | 12 | 439 |
| chr13__group006492 | chr13 | 30058603 | 30059262 | −7.11509 | 10 | 659 |
| chr18__group007550 | chr18 | 13236170 | 13237164 | −7.11506 | 14 | 994 |
| chr18__group000176 | chr18 | 515252 | 515641 | −7.11441 | 20 | 389 |
| chr13__group053670 | chr13 | 1.05E+08 | 1.05E+08 | −7.11255 | 9 | 570 |
| chr18__group046759 | chr18 | 75565043 | 75566648 | −7.11253 | 18 | 1605 |
| chr18__group046687 | chr18 | 75496776 | 75497488 | −7.11235 | 9 | 712 |
| chr21__group022238 | chr21 | 46933460 | 46933855 | −7.11222 | 9 | 395 |
| chr21__group021406 | chr21 | 45708718 | 45709906 | −7.11195 | 18 | 1188 |
| chr13__group058152 | chr13 | 1.11E+08 | 1.11E+08 | −7.11029 | 15 | 813 |
| chr18__group003635 | chr18 | 6466025 | 6466622 | −7.10934 | 11 | 597 |
| chr18__group012364 | chr18 | 24513949 | 24514775 | −7.10857 | 29 | 826 |
| chr21__group011857 | chr21 | 30936490 | 30937030 | −7.10821 | 9 | 540 |
| chr13__group036438 | chr13 | 79712732 | 79713526 | −7.10772 | 9 | 794 |
| chr13__group006858 | chr13 | 30522258 | 30523565 | −7.1074 | 16 | 1307 |
| chr18__group009437 | chr18 | 19996968 | 19998211 | −7.1053 | 28 | 1243 |
| chr21__group020232 | chr21 | 43591250 | 43591737 | −7.10476 | 10 | 487 |
| chr18__group012297 | chr18 | 24445134 | 24445788 | −7.10402 | 9 | 654 |
| chr18__group048225 | chr18 | 77343005 | 77343742 | −7.10394 | 9 | 737 |
| chr13__group030027 | chr13 | 70189062 | 70189783 | −7.10285 | 14 | 721 |
| chr13__group016566 | chr13 | 47383545 | 47384081 | −7.10217 | 21 | 536 |
| chr13__group013768 | chr13 | 41999234 | 42000400 | −7.10133 | 12 | 1166 |
| chr18__group006675 | chr18 | 11738667 | 11740284 | −7.10127 | 17 | 1617 |
| chr18__group007545 | chr18 | 13232054 | 13233432 | −7.1009 | 24 | 1378 |
| chr13__group060544 | chr13 | 1.15E+08 | 1.15E+08 | −7.09973 | 15 | 260 |
| chr18__group047039 | chr18 | 75883139 | 75884181 | −7.0972 | 13 | 1042 |
| chr13__group013772 | chr13 | 42004057 | 42005490 | −7.09548 | 15 | 1433 |
| chr13__group035260 | chr13 | 78024850 | 78025042 | −7.09385 | 14 | 192 |
| chr21__group008676 | chr21 | 25518984 | 25520077 | −7.09323 | 13 | 1093 |
| chr18__group040388 | chr18 | 67512491 | 67513569 | −7.09311 | 11 | 1078 |
| chr13__group007513 | chr13 | 31448277 | 31449136 | −7.09206 | 9 | 859 |
| chr21__group016672 | chr21 | 37881979 | 37883143 | −7.09171 | 17 | 1164 |
| chr21__group022093 | chr21 | 46756924 | 46757980 | −7.09158 | 10 | 1056 |
| chr18__group047351 | chr18 | 76179443 | 76181058 | −7.09082 | 16 | 1615 |
| chr13__group024400 | chr13 | 61790027 | 61791273 | −7.09007 | 11 | 1246 |
| chr13__group057358 | chr13 | 1.1E+08 | 1.1E+08 | −7.08999 | 10 | 578 |
| chr21__group012895 | chr21 | 32055964 | 32057094 | −7.08916 | 13 | 1130 |
| chr21__group018257 | chr21 | 40694115 | 40694861 | −7.08748 | 14 | 746 |
| chr13__group000854 | chr13 | 20822180 | 20823195 | −7.08623 | 11 | 1015 |
| chr21__group021296 | chr21 | 45527867 | 45528368 | −7.08556 | 12 | 501 |
| chr18__group035703 | chr18 | 61255456 | 61256811 | −7.08523 | 18 | 1355 |
| chr21__group009309 | chr21 | 26170406 | 26170568 | −7.08512 | 10 | 162 |
| chr18__group042355 | chr18 | 70068084 | 70069722 | −7.08407 | 12 | 1638 |
| chr21__group014434 | chr21 | 34402565 | 34403591 | −7.08378 | 9 | 1026 |
| chr21__group022207 | chr21 | 46883167 | 46883798 | −7.08348 | 9 | 631 |
| chr18__group010503 | chr18 | 21655917 | 21657119 | −7.08326 | 17 | 1202 |
| chr21__group019644 | chr21 | 42439219 | 42440018 | −7.08322 | 9 | 799 |
| chr13__group060630 | chr13 | 1.15E+08 | 1.15E+08 | −7.08289 | 12 | 754 |
| chr21__group022243 | chr21 | 46947026 | 46949298 | −7.08115 | 34 | 2272 |
| chr21__group000518 | chr21 | 10827121 | 10829037 | −7.08064 | 34 | 1916 |
| chr18__group018537 | chr18 | 34865760 | 34867459 | −7.08061 | 23 | 1699 |
| chr13__group055635 | chr13 | 1.08E+08 | 1.08E+08 | −7.08043 | 9 | 1009 |
| chr21__group020410 | chr21 | 43815584 | 43816769 | −7.07935 | 15 | 1185 |
| chr18__group047193 | chr18 | 76029512 | 76030675 | −7.07855 | 17 | 1163 |
| chr21__group022063 | chr21 | 46719488 | 46721450 | −7.07798 | 54 | 1962 |
| chr13__group006766 | chr13 | 11858745 | 11860026 | −7.07728 | 15 | 1281 |
| chr13__group008747 | chr13 | 32888625 | 32888963 | −7.07682 | 11 | 338 |
| chr21__group017351 | chr21 | 39240955 | 39241898 | −7.0757 | 9 | 943 |
| chr18__group006021 | chr18 | 11116362 | 11116978 | −7.0757 | 13 | 616 |
| chr13__group031056 | chr13 | 71748179 | 71748669 | −7.07356 | 15 | 490 |
| chr18__group047037 | chr18 | 75880154 | 75881177 | −7.07332 | 9 | 1023 |
| chr18__group037658 | chr18 | 63620318 | 63621780 | −7.07274 | 12 | 1462 |
| chr21__group003180 | chr21 | 18827529 | 18828747 | −7.07263 | 13 | 1218 |
| chr13__group001009 | chr13 | 20988525 | 20990333 | −7.07247 | 88 | 1808 |
| chr21__group014245 | chr21 | 34212130 | 34213056 | −7.07126 | 9 | 926 |
| chr13__group059945 | chr13 | 1.14E+08 | 1.14E+08 | −7.07102 | 81 | 5274 |
| chr13__group004581 | chr13 | 27332818 | 27333617 | −7.07065 | 17 | 799 |
| chr13__group053844 | chr13 | 1.05E+08 | 1.05E+08 | −7.06904 | 9 | 367 |
| chr13__group002592 | chr13 | 24232959 | 24233414 | −7.06772 | 10 | 455 |

TABLE 4-continued

| Name | chr | start.pos | end.pos | median.tstat | num.cg | dmr.size |
|---|---|---|---|---|---|---|
| chr21__group022321 | chr21 | 47044246 | 47045063 | −7.06465 | 15 | 817 |
| chr13__group050198 | chr13 | 1E+08 | 1E+08 | −7.06429 | 23 | 1331 |
| chr21__group014512 | chr21 | 34489623 | 34490594 | −7.06397 | 9 | 971 |
| chr18__group048370 | chr18 | 77556647 | 77557213 | −7.06312 | 9 | 566 |
| chr18__group007576 | chr18 | 13265264 | 13266933 | −7.06151 | 22 | 1669 |
| chr18__group022303 | chr18 | 39465916 | 39466646 | −7.06102 | 15 | 730 |
| chr18__group018719 | chr18 | 35030054 | 35030762 | −7.0606 | 15 | 708 |
| chr21__group019961 | chr21 | 43013326 | 43013735 | −7.06044 | 9 | 409 |
| chr18__group026219 | chr18 | 45670076 | 45670542 | −7.05954 | 9 | 466 |
| chr18__group047332 | chr18 | 76159668 | 76160440 | −7.05942 | 18 | 772 |
| chr13__group050187 | chr13 | 1E+08 | 1E+08 | −7.05878 | 9 | 719 |
| chr18__group048233 | chr18 | 77349141 | 77349775 | −7.05694 | 12 | 634 |
| chr18__group007820 | chr18 | 13499831 | 13500669 | −7.0561 | 13 | 838 |
| chr21__group003429 | chr21 | 19274065 | 19275096 | −7.0542 | 24 | 1031 |
| chr13__group013262 | chr13 | 40930427 | 40931141 | −7.05266 | 15 | 714 |
| chr21__group016560 | chr21 | 37582110 | 37583834 | −7.05265 | 23 | 1724 |
| chr13__group060480 | chr13 | 1.15E+08 | 1.15E+08 | −7.05188 | 17 | 842 |
| chr18__group004094 | chr18 | 7467726 | 7468435 | −7.05171 | 10 | 709 |
| chr21__group022528 | chr21 | 47251876 | 47252635 | −7.05116 | 11 | 759 |
| chr18__group024336 | chr18 | 43041916 | 43042962 | −7.05029 | 9 | 1046 |
| chr13__group032315 | chr13 | 73104679 | 73105319 | −7.05001 | 10 | 640 |
| chr13__group052545 | chr13 | 1.04E+08 | 1.04E+08 | −7.04948 | 15 | 720 |
| chr18__group045559 | chr18 | 74233885 | 74234466 | −7.04788 | 12 | 581 |
| chr21__group018125 | chr21 | 40285176 | 40285618 | −7.04627 | 12 | 442 |
| chr18__group048345 | chr18 | 77525759 | 77526699 | −7.04548 | 9 | 940 |
| chr18__group000001 | chr18 | 10731 | 13867 | −7.04538 | 60 | 3136 |
| chr18__group045567 | chr18 | 74241498 | 74241978 | −7.04529 | 14 | 480 |
| chr21__group015835 | chr21 | 36786588 | 36789682 | −7.04491 | 24 | 3094 |
| chr21__group016551 | chr21 | 37565048 | 37566048 | −7.0436 | 12 | 1000 |
| chr13__group052367 | chr13 | 1.04E+08 | 1.04E+08 | −7.04264 | 10 | 1001 |
| chr13__group059924 | chr13 | 1.14E+08 | 1.14E+08 | −7.04213 | 41 | 1993 |
| chr18__group035340 | chr18 | 60351703 | 60352376 | −7.04183 | 19 | 673 |
| chr18__group048113 | chr18 | 77198287 | 77199244 | −7.04059 | 20 | 957 |
| chr13__group048868 | chr13 | 97484469 | 97485419 | −7.04005 | 10 | 950 |
| chr13__group059330 | chr13 | 1.13E+08 | 1.13E+08 | −7.0395 | 11 | 660 |
| chr13__group060265 | chr13 | 1.14E+08 | 1.14E+08 | −7.03926 | 9 | 1388 |
| chr18__group031742 | chr18 | 54960162 | 54960608 | −7.03917 | 9 | 446 |
| chr21__group003229 | chr21 | 18883746 | 18884067 | −7.03767 | 11 | 321 |
| chr18__group013081 | chr18 | 25820386 | 25820896 | −7.03707 | 13 | 510 |
| chr13__group004529 | chr13 | 27280465 | 27281269 | −7.0365 | 12 | 804 |
| chr21__group014863 | chr21 | 35401695 | 35402713 | −7.03605 | 10 | 1018 |
| chr21__group020035 | chr21 | 43174498 | 43175429 | −7.03602 | 20 | 931 |
| chr13__group031063 | chr13 | 71758206 | 71759183 | −7.03531 | 10 | 977 |
| chr18__group048371 | chr18 | 77560089 | 77560618 | −7.03522 | 11 | 529 |
| chr21__group019326 | chr21 | 42010213 | 42010698 | −7.03414 | 10 | 485 |
| chr13__group028360 | chr13 | 67607742 | 67608591 | −7.03394 | 9 | 849 |
| chr13__group032910 | chr13 | 74445312 | 74446167 | −7.03203 | 12 | 855 |
| chr21__group020572 | chr21 | 44061230 | 44062689 | −7.03168 | 25 | 1459 |
| chr18__group004165 | chr18 | 7574755 | 7575284 | −7.03092 | 22 | 529 |
| chr21__group010066 | chr21 | 27054210 | 27055217 | −7.02996 | 12 | 1007 |
| chr21__group006005 | chr21 | 22358330 | 22358815 | −7.02982 | 13 | 485 |
| chr18__group048342 | chr18 | 77522335 | 77523288 | −7.02937 | 12 | 953 |
| chr13__group000810 | chr13 | 20780336 | 20781440 | −7.02857 | 22 | 1104 |
| chr18__group009212 | chr18 | 19753418 | 19754144 | −7.02829 | 17 | 726 |
| chr13__group025815 | chr13 | 63952796 | 63953462 | −7.02761 | 20 | 666 |
| chr21__group021617 | chr21 | 46017899 | 46018452 | −7.02496 | 11 | 553 |
| chr21__group015208 | chr21 | 36016239 | 36016905 | −7.02421 | 9 | 666 |
| chr21__group015198 | chr21 | 36003727 | 36006181 | −7.0237 | 26 | 2454 |
| chr13__group060282 | chr13 | 1.14E+08 | 1.14E+08 | −7.02344 | 15 | 1456 |
| chr13__group057669 | chr13 | 1.1E+08 | 1.1E+08 | −7.02179 | 10 | 1092 |
| chr13__group001763 | chr13 | 22709340 | 22710008 | −7.02117 | 11 | 668 |
| chr13__group034141 | chr13 | 75807809 | 75808597 | −7.02067 | 9 | 788 |
| chr13__group002058 | chr13 | 23595573 | 23595786 | −7.0201 | 9 | 213 |
| chr21__group022440 | chr21 | 47169116 | 47170388 | −7.02001 | 15 | 1272 |
| chr18__group017185 | chr18 | 48138213 | 48138797 | −7.01989 | 10 | 584 |
| chr18__group006140 | chr18 | 11232201 | 11233208 | −7.01961 | 12 | 1007 |
| chr18__group000197 | chr18 | 559758 | 560243 | −7.01957 | 11 | 485 |
| chr13__group060423 | chr13 | 1.15E+08 | 1.15E+08 | −7.01946 | 13 | 926 |
| chr13__group059960 | chr13 | 1.14E+08 | 1.14E+08 | −7.01863 | 17 | 466 |
| chr18__group031143 | chr18 | 54114365 | 54115417 | −7.01848 | 10 | 1052 |
| chr13__group030738 | chr13 | 71391133 | 71392338 | −7.01785 | 13 | 1205 |
| chr13__group007535 | chr13 | 31476377 | 31477635 | −7.017 | 9 | 1258 |
| chr18__group006809 | chr18 | 11951388 | 11951754 | −7.01692 | 9 | 366 |
| chr21__group022767 | chr21 | 47497306 | 47498806 | −7.01671 | 20 | 1500 |
| chr21__group019213 | chr21 | 41877668 | 41878526 | −7.01639 | 10 | 858 |
| chr13__group034351 | chr13 | 76444823 | 76445372 | −7.01437 | 14 | 549 |
| chr13__group003593 | chr13 | 25939928 | 25940726 | −7.01321 | 25 | 798 |
| chr13__group001531 | chr13 | 22297777 | 22298579 | −7.01265 | 13 | 802 |

TABLE 4-continued

| Name | chr | start.pos | end.pos | median.tstat | num.cg | dmr.size |
|---|---|---|---|---|---|---|
| chr13__group060474 | chr13 | 1.15E+08 | 1.15E+08 | −7.01111 | 15 | 917 |
| chr21__group018154 | chr21 | 40365760 | 40366343 | −7.01052 | 11 | 583 |
| chr13__group056606 | chr13 | 1.09E+08 | 1.09E+08 | −7.00892 | 15 | 296 |
| chr18__group038576 | chr18 | 64744060 | 64744590 | −7.00855 | 11 | 530 |
| chr13__group049086 | chr13 | 97839883 | 97840086 | −7.00772 | 9 | 203 |
| chr18__group047213 | chr18 | 76054258 | 76054995 | −7.00763 | 11 | 737 |
| chr21__group022803 | chr21 | 47547796 | 47550311 | −7.00727 | 41 | 2515 |
| chr21__group016486 | chr21 | 37431584 | 37431942 | −7.00665 | 9 | 358 |
| chr13__group059877 | chr13 | 1.14E+08 | 1.14E+08 | −7.00568 | 18 | 1056 |
| chr13__group007685 | chr13 | 31620860 | 31621433 | −7.0056 | 13 | 573 |
| chr13__group050086 | chr13 | 99737295 | 99737906 | −7.00548 | 17 | 611 |
| chr21__group013599 | chr21 | 33159865 | 33160711 | −7.00348 | 11 | 846 |
| chr21__group022087 | chr21 | 46745875 | 46750482 | −7.00333 | 81 | 4607 |
| chr18__group039534 | chr18 | 66400866 | 66401812 | −7.00316 | 11 | 946 |
| chr13__group006936 | chr13 | 30646463 | 30647022 | −7.00287 | 9 | 559 |
| chr18__group007815 | chr18 | 13494922 | 13496009 | −7.00278 | 15 | 1087 |
| chr13__group009456 | chr13 | 34921809 | 34922776 | −7.00233 | 12 | 967 |
| chr18__group014738 | chr18 | 28511760 | 28512636 | −7.00207 | 9 | 876 |
| chr18__group047843 | chr18 | 76653647 | 76654261 | −6.99889 | 9 | 614 |
| chr18__group032275 | chr18 | 55827962 | 55828609 | −6.99844 | 11 | 647 |
| chr21__group005268 | chr21 | 21496086 | 21496405 | −6.99787 | 9 | 319 |
| chr18__group025148 | chr18 | 44184731 | 44185689 | −6.99603 | 9 | 958 |
| chr13__group005128 | chr13 | 28093687 | 28095147 | −6.99507 | 16 | 1460 |
| chr13__group028693 | chr13 | 67945426 | 67945713 | −6.99382 | 10 | 287 |
| chr18__group048249 | chr18 | 77367192 | 77367904 | −6.99352 | 11 | 712 |
| chr18__group012506 | chr18 | 24743252 | 24743606 | −6.99129 | 9 | 354 |
| chr18__group009601 | chr18 | 20192921 | 20193862 | −6.99046 | 12 | 941 |
| chr13__group002234 | chr13 | 23822566 | 23823054 | −6.99028 | 19 | 488 |
| chr13__group044895 | chr13 | 91860260 | 91860980 | −6.99008 | 14 | 720 |
| chr21__group013427 | chr21 | 32881906 | 32882615 | −6.98998 | 10 | 709 |
| chr18__group003109 | chr18 | 5967297 | 5967961 | −6.98844 | 9 | 664 |
| chr18__group045186 | chr18 | 73811306 | 73812626 | −6.98816 | 15 | 1320 |
| chr13__group000446 | chr13 | 19956689 | 19957630 | −6.98793 | 17 | 941 |
| chr21__group008888 | chr21 | 25728149 | 25729862 | −6.98504 | 11 | 1713 |
| chr13__group057357 | chr13 | 1.1E+08 | 1.1E+08 | −6.98184 | 11 | 539 |
| chr13__group006997 | chr13 | 30731170 | 30732090 | −6.9817 | 12 | 920 |
| chr18__group010273 | chr18 | 21437988 | 21439289 | −6.98125 | 11 | 1301 |
| chr21__group004115 | chr21 | 20164142 | 20164287 | −6.98068 | 10 | 145 |
| chr13__group004995 | chr13 | 27927151 | 27927729 | −6.97914 | 11 | 578 |
| chr13__group057388 | chr13 | 1.1E+08 | 1.1E+08 | −6.97854 | 12 | 702 |
| chr18__group010313 | chr18 | 21479295 | 21480277 | −6.97788 | 10 | 982 |
| chr18__group035986 | chr18 | 61666128 | 61667539 | −6.97782 | 10 | 1411 |
| chr13__group008558 | chr13 | 32502384 | 32502725 | −6.97661 | 14 | 341 |
| chr18__group017438 | chr18 | 33162840 | 33163645 | −6.97598 | 11 | 805 |
| chr13__group047170 | chr13 | 94984207 | 94985254 | −6.97533 | 10 | 1047 |
| chr18__group007596 | chr18 | 13285556 | 13286318 | −6.97482 | 9 | 762 |
| chr21__group020699 | chr21 | 44211765 | 44212460 | −6.97434 | 9 | 695 |
| chr18__group001393 | chr18 | 3712621 | 3713813 | −6.97366 | 11 | 1192 |
| chr18__group001242 | chr18 | 3349484 | 3350996 | −6.973 | 37 | 1512 |
| chr13__group059997 | chr13 | 1.14E+08 | 1.14E+08 | −6.97278 | 15 | 1118 |
| chr18__group021513 | chr18 | 38519500 | 38520153 | −6.97239 | 13 | 653 |
| chr18__group008341 | chr18 | 14177128 | 14178574 | −6.97231 | 62 | 1446 |
| chr13__group009006 | chr13 | 33764826 | 33765665 | −6.97144 | 13 | 839 |
| chr18__group048117 | chr18 | 77205372 | 77206657 | −6.97056 | 29 | 1285 |
| chr18__group047583 | chr18 | 76400412 | 76401674 | −6.97055 | 12 | 1262 |
| chr18__group024820 | chr18 | 43872470 | 43873185 | −6.97026 | 10 | 715 |
| chr18__group018867 | chr18 | 35154061 | 35154654 | −6.96995 | 10 | 593 |
| chr21__group022802 | chr21 | 47545624 | 47547362 | −6.96819 | 29 | 1738 |
| chr18__group048446 | chr18 | 77642308 | 77644992 | −6.9681 | 44 | 2684 |
| chr18__group024916 | chr18 | 43961035 | 43962259 | −6.96767 | 12 | 1224 |
| chr13__group059959 | chr13 | 1.14E+08 | 1.14E+08 | −6.96699 | 46 | 3193 |
| chr21__group022810 | chr21 | 47556674 | 47558051 | −6.96692 | 15 | 1377 |
| chr13__group020551 | chr13 | 54494325 | 54495953 | −6.96661 | 14 | 1628 |
| chr13__group013421 | chr13 | 41120026 | 41120678 | −6.96612 | 12 | 652 |
| chr13__group024900 | chr13 | 62515343 | 62518524 | −6.96582 | 45 | 3181 |
| chr21__group010197 | chr21 | 27451898 | 27452911 | −6.96362 | 12 | 1013 |
| chr13__group019210 | chr13 | 52248304 | 52249519 | −6.96352 | 10 | 1215 |
| chr13__group059889 | chr13 | 1.14E+08 | 1.14E+08 | −6.96277 | 26 | 1480 |
| chr18__group003012 | chr18 | 5878372 | 5878902 | −6.96148 | 10 | 530 |
| chr13__group017514 | chr13 | 48849357 | 48850328 | −6.9602 | 11 | 971 |
| chr13__group058041 | chr13 | 1.11E+08 | 1.11E+08 | −6.95938 | 15 | 902 |
| chr18__group018517 | chr18 | 34841401 | 34842180 | −6.95758 | 15 | 779 |
| chr18__group009021 | chr18 | 19461719 | 19462575 | −6.9571 | 9 | 856 |
| chr13__group044589 | chr13 | 91492166 | 91493487 | −6.95637 | 10 | 1321 |
| chr13__group016870 | chr13 | 47742592 | 47743087 | −6.95599 | 10 | 495 |
| chr13__group029390 | chr13 | 68744996 | 68745468 | −6.95493 | 10 | 472 |
| chr13__group004020 | chr13 | 26620445 | 26621169 | −6.9542 | 9 | 724 |
| chr13__group055273 | chr13 | 1.07E+08 | 1.07E+08 | −6.95407 | 9 | 182 |

TABLE 4-continued

| Name | chr | start.pos | end.pos | median.tstat | num.cg | dmr.size |
|---|---|---|---|---|---|---|
| chr18__group046813 | chr18 | 75621882 | 75624694 | −6.954 | 30 | 2812 |
| chr21__group022560 | chr21 | 47277928 | 47279003 | −6.95336 | 12 | 1075 |
| chr21__group014391 | chr21 | 34353308 | 34354241 | −6.95189 | 10 | 933 |
| chr13__group004061 | chr13 | 26669972 | 26671121 | −6.95046 | 10 | 1149 |
| chr21__group013976 | chr21 | 33817507 | 33818443 | −6.94879 | 11 | 936 |
| chr13__group004826 | chr13 | 27572487 | 27573167 | −6.9484 | 10 | 680 |
| chr13__group028185 | chr13 | 67419022 | 67419674 | −6.94787 | 10 | 652 |
| chr18__group006879 | chr18 | 12075717 | 12076817 | −6.94747 | 18 | 1100 |
| chr21__group013888 | chr21 | 33629242 | 33630662 | −6.9473 | 11 | 1420 |
| chr21__group022721 | chr21 | 47442943 | 47443828 | −6.94513 | 18 | 885 |
| chr13__group059900 | chr13 | 1.14E+08 | 1.14E+08 | −6.9451 | 29 | 1712 |
| chr18__group018839 | chr18 | 35128325 | 35128851 | −6.9448 | 9 | 526 |
| chr18__group011215 | chr18 | 22627550 | 22628257 | −6.94466 | 12 | 707 |
| chr21__group019935 | chr21 | 42908286 | 42908863 | −6.94329 | 14 | 577 |
| chr21__group022768 | chr21 | 47499168 | 47502312 | −6.9432 | 47 | 3144 |
| chr18__group030643 | chr18 | 53529965 | 53531414 | −6.94303 | 21 | 1449 |
| chr13__group058148 | chr13 | 1.11E+08 | 1.11E+08 | −6.94136 | 19 | 1048 |
| chr13__group060280 | chr13 | 1.14E+08 | 1.14E+08 | −6.9394 | 10 | 162 |
| chr21__group020896 | chr21 | 44689668 | 44690232 | −6.93853 | 10 | 564 |
| chr18__group044545 | chr18 | 73051156 | 73052385 | −6.93779 | 12 | 1229 |
| chr13__group058622 | chr13 | 1.12E+08 | 1.12E+08 | −6.93708 | 28 | 2055 |
| chr21__group021404 | chr21 | 45707278 | 45707911 | −6.93646 | 11 | 633 |
| chr18__group048074 | chr18 | 77147440 | 77147846 | −6.93618 | 9 | 406 |
| chr18__group005695 | chr18 | 10790685 | 10791070 | −6.9326 | 17 | 385 |
| chr18__group047662 | chr18 | 76473986 | 76474862 | −6.9315 | 10 | 876 |
| chr21__group017928 | chr21 | 39983265 | 39983997 | −6.92907 | 9 | 732 |
| chr13__group059445 | chr13 | 1.13E+08 | 1.13E+08 | −6.92738 | 12 | 558 |
| chr18__group025619 | chr18 | 44767251 | 44768314 | −6.92737 | 9 | 1063 |
| chr21__group014255 | chr21 | 34220331 | 34221266 | −6.92732 | 9 | 935 |
| chr18__group003633 | chr18 | 6462176 | 6462961 | −6.92714 | 12 | 785 |
| chr13__group025331 | chr13 | 63108667 | 63109120 | −6.92521 | 11 | 453 |
| chr21__group015229 | chr21 | 36036177 | 36037626 | −6.92432 | 17 | 1449 |
| chr13__group060075 | chr13 | 1.14E+08 | 1.14E+08 | −6.92318 | 11 | 784 |
| chr18__group007848 | chr18 | 13528350 | 13529764 | −6.92092 | 12 | 1414 |
| chr13__group002552 | chr13 | 24189662 | 24190051 | −6.92085 | 9 | 389 |
| chr13__group006508 | chr13 | 30079062 | 30080472 | −6.92075 | 17 | 1410 |
| chr13__group058463 | chr13 | 1.12E+08 | 1.12E+08 | −6.92061 | 9 | 692 |
| chr13__group059611 | chr13 | 1.13E+08 | 1.13E+08 | −6.92045 | 10 | 633 |
| chr18__group044689 | chr18 | 73183883 | 73185144 | −6.9199 | 22 | 1261 |
| chr18__group007531 | chr18 | 13212305 | 13213602 | −6.91985 | 18 | 1297 |
| chr21__group013644 | chr21 | 33247239 | 33248605 | −6.91954 | 26 | 1366 |
| chr18__group045692 | chr18 | 74379337 | 74379813 | −6.91816 | 10 | 476 |
| chr13__group060268 | chr13 | 1.14E+08 | 1.14E+08 | −6.917 | 45 | 854 |
| chr18__group003431 | chr18 | 6262064 | 6263304 | −6.91633 | 10 | 1240 |
| chr18__group047362 | chr18 | 76191680 | 76192819 | −6.91595 | 18 | 1139 |
| chr18__group006798 | chr18 | 11925638 | 11926507 | −6.91583 | 13 | 869 |
| chr18__group021800 | chr18 | 38870342 | 38870630 | −6.91468 | 10 | 288 |
| chr13__group060588 | chr13 | 1.15E+08 | 1.15E+08 | −6.91456 | 14 | 1295 |
| chr21__group000521 | chr21 | 10836111 | 10841560 | −6.91453 | 69 | 5449 |
| chr18__group048254 | chr18 | 77372704 | 77373353 | −6.91443 | 12 | 649 |
| chr21__group021890 | chr21 | 46484335 | 46485000 | −6.91382 | 9 | 665 |
| chr13__group000739 | chr13 | 20705306 | 20706649 | −6.91288 | 10 | 1343 |
| chr18__group047653 | chr18 | 76464630 | 76465208 | −6.9123 | 10 | 578 |
| chr18__group048484 | chr18 | 77721618 | 77722073 | −6.9122 | 10 | 455 |
| chr18__group039167 | chr18 | 65684511 | 65685058 | −6.9117 | 9 | 547 |
| chr13__group044603 | chr13 | 91505690 | 91506481 | −6.91109 | 9 | 791 |
| chr18__group047631 | chr18 | 76444685 | 76446485 | −6.91095 | 25 | 1800 |
| chr18__group003543 | chr18 | 6370469 | 6371210 | −6.90963 | 9 | 741 |
| chr21__group020936 | chr21 | 44737662 | 44737981 | −6.90784 | 9 | 319 |
| chr18__group026213 | chr18 | 45655349 | 45656272 | −6.90677 | 12 | 923 |
| chr18__group025275 | chr18 | 44301007 | 44302136 | −6.90655 | 13 | 1129 |
| chr13__group052808 | chr13 | 1.04E+08 | 1.04E+08 | −6.90531 | 9 | 751 |
| chr18__group047880 | chr18 | 76684095 | 76686824 | −6.90494 | 53 | 2729 |
| chr13__group001609 | chr13 | 22388114 | 22389451 | −6.90476 | 15 | 1337 |
| chr21__group016742 | chr21 | 37973127 | 37974658 | −6.90436 | 14 | 1531 |
| chr21__group022060 | chr21 | 46714985 | 46716324 | −6.90389 | 21 | 1339 |
| chr18__group005811 | chr18 | 10901987 | 10903294 | −6.90321 | 10 | 1307 |
| chr18__group047594 | chr18 | 76412136 | 76412824 | −6.90303 | 12 | 688 |
| chr18__group017236 | chr18 | 32775753 | 32776359 | −6.90135 | 9 | 606 |
| chr21__group022685 | chr21 | 47403979 | 47404543 | −6.89869 | 33 | 564 |
| chr21__group019833 | chr21 | 42731981 | 42733433 | −6.89851 | 25 | 1452 |
| chr13__group016034 | chr13 | 46370257 | 46371598 | −6.89678 | 9 | 1341 |
| chr13__group055706 | chr13 | 1.08E+08 | 1.08E+08 | −6.89667 | 9 | 516 |
| chr18__group038161 | chr18 | 64212016 | 64212555 | −6.89615 | 11 | 539 |
| chr13__group023821 | chr13 | 60802874 | 60803702 | −6.89418 | 10 | 828 |
| chr18__group047497 | chr18 | 76324564 | 76325422 | −6.89323 | 9 | 858 |
| chr18__group031970 | chr18 | 55200447 | 55201384 | −6.89203 | 10 | 937 |
| chr13__group019313 | chr13 | 52583804 | 52584915 | −6.89012 | 13 | 1111 |

TABLE 4-continued

| Name | chr | start.pos | end.pos | median.tstat | num.cg | dmr.size |
|---|---|---|---|---|---|---|
| chr13__group008032 | chr13 | 31985306 | 31985793 | −6.88917 | 9 | 487 |
| chr18__group011216 | chr18 | 22629784 | 22630788 | −6.88859 | 13 | 1004 |
| chr13__group040285 | chr13 | 85279446 | 85280045 | −6.88815 | 10 | 599 |
| chr18__group047363 | chr18 | 76193209 | 76193967 | −6.88785 | 10 | 758 |
| chr13__group026412 | chr13 | 64982056 | 64982702 | −6.88667 | 9 | 646 |
| chr18__group045760 | chr18 | 74447256 | 74449059 | −6.88573 | 30 | 1803 |
| chr13__group059834 | chr13 | 1.14E+08 | 1.14E+08 | −6.8852 | 18 | 850 |
| chr13__group011053 | chr13 | 37222116 | 37222683 | −6.88508 | 9 | 567 |
| chr13__group060235 | chr13 | 1.14E+08 | 1.14E+08 | −6.88155 | 17 | 1343 |
| chr13__group049073 | chr13 | 97793655 | 97794950 | −6.8813 | 14 | 1295 |
| chr18__group047621 | chr18 | 76436068 | 76437151 | −6.88068 | 17 | 1083 |
| chr18__group008196 | chr18 | 13971828 | 13972450 | −6.8806 | 9 | 622 |
| chr18__group047240 | chr18 | 76078091 | 76080294 | −6.88047 | 34 | 2203 |
| chr13__group000268 | chr13 | 19683418 | 19683844 | −6.8799 | 9 | 426 |
| chr18__group025276 | chr18 | 44302760 | 44303803 | −6.87948 | 10 | 1043 |
| chr13__group019301 | chr13 | 52565041 | 52565313 | −6.87901 | 10 | 272 |
| chr21__group005078 | chr21 | 21272029 | 21273369 | −6.87853 | 22 | 1340 |
| chr18__group005015 | chr18 | 9688137 | 9688742 | −6.87845 | 11 | 605 |
| chr13__group035155 | chr13 | 77553657 | 77554042 | −6.87716 | 12 | 385 |
| chr13__group020514 | chr13 | 54447769 | 54448041 | −6.87704 | 11 | 272 |
| chr18__group004815 | chr18 | 9100957 | 9101489 | −6.87608 | 20 | 532 |
| chr21__group021770 | chr21 | 46308559 | 46309494 | −6.87601 | 24 | 935 |
| chr13__group045559 | chr13 | 92635324 | 92636821 | −6.87593 | 19 | 1497 |
| chr21__group014917 | chr21 | 35530564 | 35531943 | −6.87483 | 17 | 1379 |
| chr13__group042455 | chr13 | 88564811 | 88565532 | −6.87424 | 9 | 721 |
| chr18__group046394 | chr18 | 75237698 | 75238324 | −6.87389 | 14 | 626 |
| chr13__group002509 | chr13 | 24141367 | 24142526 | −6.87353 | 9 | 1159 |
| chr21__group020331 | chr21 | 43720795 | 43721790 | −6.87337 | 9 | 995 |
| chr18__group037660 | chr18 | 63625083 | 63626002 | −6.87335 | 9 | 919 |
| chr13__group060147 | chr13 | 1.14E+08 | 1.14E+08 | −6.87318 | 14 | 832 |
| chr13__group059878 | chr13 | 1.14E+08 | 1.14E+08 | −6.87147 | 19 | 1240 |
| chr21__group016682 | chr21 | 37906261 | 37907121 | −6.87142 | 11 | 860 |
| chr21__group022148 | chr21 | 46813755 | 46815037 | −6.8706 | 10 | 1282 |
| chr21__group000522 | chr21 | 10841870 | 10845343 | −6.86874 | 43 | 3473 |
| chr18__group044355 | chr18 | 72850584 | 72851853 | −6.86782 | 12 | 1269 |
| chr21__group022110 | chr21 | 46772617 | 46773296 | −6.86753 | 10 | 679 |
| chr21__group022185 | chr21 | 46852245 | 46853878 | −6.86478 | 20 | 1633 |
| chr13__group007325 | chr13 | 31263879 | 31264773 | −6.86389 | 14 | 894 |
| chr18__group017260 | chr18 | 32800795 | 32801698 | −6.86288 | 11 | 903 |
| chr21__group000270 | chr21 | 9967771 | 9968828 | −6.8627 | 36 | 1057 |
| chr13__group005008 | chr13 | 27941378 | 27942906 | −6.8621 | 13 | 1528 |
| chr18__group007688 | chr18 | 13367397 | 13368209 | −6.86192 | 11 | 812 |
| chr18__group040194 | chr18 | 67285285 | 67286662 | −6.86163 | 14 | 1377 |
| chr13__group023668 | chr13 | 60207389 | 60207878 | −6.86058 | 10 | 489 |
| chr13__group016239 | chr13 | 46664614 | 46665406 | −6.85981 | 13 | 792 |
| chr18__group038090 | chr18 | 64135052 | 64135560 | −6.85927 | 14 | 508 |
| chr13__group047620 | chr13 | 95517304 | 95518835 | −6.85921 | 12 | 1531 |
| chr18__group025141 | chr18 | 44173444 | 44174485 | −6.85917 | 11 | 1041 |
| chr13__group006716 | chr13 | 30283588 | 30284439 | −6.85786 | 15 | 851 |
| chr18__group032912 | chr18 | 56880745 | 56882016 | −6.85782 | 10 | 1271 |
| chr18__group044056 | chr18 | 72201985 | 72202600 | −6.85558 | 10 | 615 |
| chr21__group019607 | chr21 | 42396250 | 42397029 | −6.8549 | 12 | 779 |
| chr13__group013097 | chr13 | 40747010 | 40747904 | −6.8548 | 10 | 894 |
| chr18__group004678 | chr18 | 8844645 | 8844978 | −6.85304 | 11 | 333 |
| chr13__group057822 | chr13 | 1.11E+08 | 1.11E+08 | −6.85204 | 9 | 192 |
| chr21__group007651 | chr21 | 24393418 | 24394269 | −6.85094 | 23 | 851 |
| chr21__group004780 | chr21 | 20946301 | 20946963 | −6.84919 | 12 | 662 |
| chr18__group020854 | chr18 | 37719454 | 37720032 | −6.8482 | 11 | 578 |
| chr18__group007091 | chr18 | 12309306 | 12309781 | −6.84812 | 10 | 475 |
| chr13__group016334 | chr13 | 46903408 | 46905190 | −6.84653 | 13 | 1782 |
| chr13__group034346 | chr13 | 76440513 | 76440833 | −6.84486 | 13 | 320 |
| chr18__group046898 | chr18 | 75705047 | 75706273 | −6.84266 | 16 | 1226 |
| chr13__group031099 | chr13 | 71789076 | 71789680 | −6.84232 | 15 | 604 |
| chr18__group010376 | chr18 | 21536034 | 21537060 | −6.84183 | 9 | 1026 |
| chr21__group020607 | chr21 | 44107343 | 44108498 | −6.84165 | 12 | 1155 |
| chr18__group048159 | chr18 | 77256526 | 77258094 | −6.84122 | 24 | 1568 |
| chr21__group006429 | chr21 | 22852409 | 22853797 | −6.841 | 15 | 1388 |
| chr13__group059306 | chr13 | 1.13E+08 | 1.13E+08 | −6.84078 | 25 | 890 |
| chr18__group008468 | chr18 | 14479225 | 14479340 | −6.84047 | 13 | 115 |
| chr13__group003742 | chr13 | 26076917 | 26077879 | −6.84022 | 10 | 962 |
| chr18__group010345 | chr18 | 21507765 | 21508226 | −6.83922 | 11 | 461 |
| chr18__group003111 | chr18 | 5969017 | 5970141 | −6.83883 | 15 | 1124 |
| chr18__group003817 | chr18 | 7038101 | 7038943 | −6.83694 | 11 | 842 |
| chr18__group045636 | chr18 | 74325424 | 74326176 | −6.83604 | 19 | 752 |
| chr13__group057904 | chr13 | 1.11E+08 | 1.11E+08 | −6.83588 | 12 | 567 |
| chr18__group048437 | chr18 | 77630820 | 77631379 | −6.83546 | 13 | 559 |
| chr13__group005720 | chr13 | 29112201 | 29112995 | −6.83474 | 10 | 794 |
| chr13__group059267 | chr13 | 1.13E+08 | 1.13E+08 | −6.83461 | 34 | 2136 |

TABLE 4-continued

| Name | chr | start.pos | end.pos | median.tstat | num.cg | dmr.size |
|---|---|---|---|---|---|---|
| chr18__group043795 | chr18 | 71805120 | 71806329 | −6.83453 | 10 | 1209 |
| chr13__group006682 | chr13 | 30251156 | 30252217 | −6.8344 | 9 | 1061 |
| chr13__group014062 | chr13 | 42818641 | 42818996 | −6.8333 | 12 | 355 |
| chr13__group007424 | chr13 | 31361406 | 31362640 | −6.8327 | 9 | 1234 |
| chr18__group007514 | chr18 | 13195575 | 13196279 | −6.83253 | 16 | 704 |
| chr13__group005581 | chr13 | 28677282 | 28678271 | −6.83224 | 11 | 989 |
| chr18__group048182 | chr18 | 77289992 | 77290366 | −6.8322 | 9 | 374 |
| chr21__group012030 | chr21 | 31092370 | 31093351 | −6.83215 | 9 | 981 |
| chr13__group017950 | chr13 | 49795810 | 49796520 | −6.83186 | 11 | 710 |
| chr18__group023009 | chr18 | 41061677 | 41062779 | −6.83143 | 15 | 1102 |
| chr13__group022014 | chr13 | 57847969 | 57848609 | −6.83022 | 10 | 640 |
| chr21__group019685 | chr21 | 42478953 | 42480216 | −6.82997 | 13 | 1263 |
| chr18__group046482 | chr18 | 75317736 | 75319759 | −6.82929 | 18 | 2023 |
| chr13__group021962 | chr13 | 57790804 | 57791369 | −6.82923 | 9 | 565 |
| chr18__group002830 | chr18 | 5684687 | 5685044 | −6.82867 | 11 | 357 |
| chr13__group059631 | chr13 | 1.13E+08 | 1.13E+08 | −6.82852 | 9 | 622 |
| chr13__group004036 | chr13 | 26639323 | 26639681 | −6.82811 | 12 | 358 |
| chr18__group048422 | chr18 | 77615453 | 77615968 | −6.82787 | 10 | 515 |
| chr21__group003223 | chr21 | 18878640 | 18879546 | −6.82638 | 31 | 906 |
| chr18__group005742 | chr18 | 10832514 | 10833816 | −6.82634 | 17 | 1302 |
| chr13__group019704 | chr13 | 53478770 | 53479477 | −6.82586 | 9 | 707 |
| chr13__group025845 | chr13 | 64119335 | 64120336 | −6.82571 | 10 | 1001 |
| chr18__group033357 | chr18 | 57684243 | 57684904 | −6.82562 | 18 | 661 |
| chr21__group000714 | chr21 | 11168504 | 11170843 | −6.82533 | 56 | 2339 |
| chr13__group050581 | chr13 | 1.01E+08 | 1.01E+08 | −6.82405 | 13 | 1302 |
| chr13__group058313 | chr13 | 1.11E+08 | 1.11E+08 | −6.82364 | 12 | 393 |
| chr13__group058121 | chr13 | 1.11E+08 | 1.11E+08 | −6.82253 | 11 | 311 |
| chr13__group002824 | chr13 | 24610380 | 24611202 | −6.81936 | 9 | 822 |
| chr21__group022346 | chr21 | 47072447 | 47072950 | −6.81923 | 9 | 503 |
| chr18__group011861 | chr18 | 23530072 | 23530311 | −6.81906 | 10 | 239 |
| chr13__group056690 | chr13 | 1.09E+08 | 1.09E+08 | −6.81855 | 16 | 1495 |
| chr18__group014946 | chr18 | 29130710 | 29131084 | −6.81807 | 9 | 374 |
| chr18__group040718 | chr18 | 68193976 | 68194776 | −6.81713 | 9 | 800 |
| chr18__group042422 | chr18 | 70169281 | 70169677 | −6.81707 | 9 | 396 |
| chr18__group046673 | chr18 | 75484612 | 75485470 | −6.81592 | 13 | 858 |
| chr13__group048987 | chr13 | 97619581 | 97620075 | −6.81492 | 9 | 494 |
| chr13__group016421 | chr13 | 47011962 | 47012604 | −6.81367 | 26 | 642 |
| chr13__group047736 | chr13 | 95626382 | 95627724 | −6.81347 | 9 | 1342 |
| chr21__group021374 | chr21 | 45668937 | 45670040 | −6.813 | 22 | 1103 |
| chr21__group000514 | chr21 | 10817187 | 10818681 | −6.81088 | 19 | 1494 |
| chr13__group039554 | chr13 | 84446420 | 84447287 | −6.80973 | 10 | 867 |
| chr21__group018558 | chr21 | 41082851 | 41083939 | −6.80939 | 13 | 1088 |
| chr18__group006486 | chr18 | 11551689 | 11552899 | −6.80895 | 12 | 1210 |
| chr21__group008126 | chr21 | 24947311 | 24947902 | −6.80808 | 11 | 591 |
| chr18__group003541 | chr18 | 6366863 | 6368778 | −6.8076 | 12 | 1915 |
| chr13__group059832 | chr13 | 1.14E+08 | 1.14E+08 | −6.80754 | 14 | 552 |
| chr21__group022303 | chr21 | 47026649 | 47029066 | −6.80732 | 42 | 2417 |
| chr18__group047889 | chr18 | 76693010 | 76694499 | −6.80723 | 16 | 1489 |
| chr21__group003770 | chr21 | 19671678 | 19672879 | −6.80643 | 10 | 1201 |
| chr18__group005136 | chr18 | 10018580 | 10019055 | −6.80634 | 14 | 475 |
| chr13__group030823 | chr13 | 71483094 | 71483755 | −6.80585 | 9 | 661 |
| chr13__group000598 | chr13 | 20354976 | 20355488 | −6.80546 | 21 | 512 |
| chr18__group008956 | chr18 | 19191424 | 19191775 | −6.8009 | 11 | 351 |
| chr21__group000520 | chr21 | 10830188 | 10835746 | −6.79781 | 75 | 5558 |
| chr13__group060132 | chr13 | 1.14E+08 | 1.14E+08 | −6.79773 | 9 | 299 |
| chr13__group032893 | chr13 | 74419573 | 74420587 | −6.79682 | 12 | 1014 |
| chr13__group060592 | chr13 | 1.15E+08 | 1.15E+08 | −6.79654 | 12 | 439 |
| chr21__group000516 | chr21 | 10819850 | 10822349 | −6.79596 | 35 | 2499 |
| chr13__group059534 | chr13 | 1.13E+08 | 1.13E+08 | −6.79515 | 9 | 706 |
| chr21__group007985 | chr21 | 24795308 | 24796218 | −6.79432 | 10 | 910 |
| chr21__group022115 | chr21 | 46778775 | 46783358 | −6.79292 | 64 | 4583 |
| chr13__group052006 | chr13 | 1.03E+08 | 1.03E+08 | −6.79281 | 9 | 642 |
| chr18__group001471 | chr18 | 3792908 | 3794079 | −6.78926 | 14 | 1171 |
| chr13__group055219 | chr13 | 1.07E+08 | 1.07E+08 | −6.78919 | 21 | 1478 |
| chr21__group022556 | chr21 | 47273730 | 47275433 | −6.78914 | 16 | 1703 |
| chr13__group043304 | chr13 | 89740160 | 89740512 | −6.78893 | 17 | 352 |
| chr18__group043033 | chr18 | 70960379 | 70960655 | −6.7877 | 12 | 276 |
| chr13__group040295 | chr13 | 85294271 | 85295064 | −6.78693 | 10 | 793 |
| chr21__group000527 | chr21 | 10853003 | 10858794 | −6.78605 | 82 | 5791 |
| chr18__group045711 | chr18 | 74395786 | 74396553 | −6.78602 | 13 | 767 |
| chr13__group060367 | chr13 | 1.15E+08 | 1.15E+08 | −6.78573 | 33 | 830 |
| chr13__group059081 | chr13 | 1.13E+08 | 1.13E+08 | −6.78564 | 28 | 2959 |
| chr18__group044672 | chr18 | 73166271 | 73167173 | −6.78523 | 12 | 902 |
| chr13__group026549 | chr13 | 65216478 | 65217507 | −6.78269 | 9 | 1029 |
| chr18__group042504 | chr18 | 70242060 | 70242943 | −6.78103 | 15 | 883 |
| chr21__group011136 | chr21 | 29483594 | 29484657 | −6.78069 | 15 | 1063 |
| chr13__group060458 | chr13 | 1.15E+08 | 1.15E+08 | −6.78027 | 9 | 825 |
| chr13__group035168 | chr13 | 77599583 | 77599779 | −6.77878 | 10 | 196 |

TABLE 4-continued

| Name | chr | start.pos | end.pos | median.tstat | num.cg | dmr.size |
|---|---|---|---|---|---|---|
| chr18__group033769 | chr18 | 58124245 | 58125275 | −6.77744 | 9 | 1030 |
| chr13__group013985 | chr13 | 42657399 | 42658150 | −6.77715 | 18 | 751 |
| chr18__group018611 | chr18 | 34931059 | 34931378 | −6.77658 | 9 | 319 |
| chr18__group005045 | chr18 | 9808390 | 9809168 | −6.77627 | 16 | 778 |
| chr13__group056686 | chr13 | 1.09E+08 | 1.09E+08 | −6.77573 | 9 | 501 |
| chr21__group021356 | chr21 | 45635148 | 45635971 | −6.77374 | 19 | 823 |
| chr13__group007674 | chr13 | 31609208 | 31609975 | −6.77231 | 10 | 767 |
| chr13__group053977 | chr13 | 1.05E+08 | 1.05E+08 | −6.77114 | 9 | 1278 |
| chr13__group006753 | chr13 | 30320755 | 30321485 | −6.77084 | 9 | 730 |
| chr21__group006810 | chr21 | 23275552 | 23276046 | −6.77054 | 13 | 494 |
| chr13__group008382 | chr13 | 32317166 | 32318249 | −6.77018 | 10 | 1083 |
| chr18__group004497 | chr18 | 8508388 | 8509671 | −6.76957 | 13 | 1283 |
| chr18__group018514 | chr18 | 34838466 | 34839943 | −6.7692 | 13 | 1477 |
| chr18__group007544 | chr18 | 13229764 | 13231713 | −6.7679 | 16 | 1949 |
| chr21__group003418 | chr21 | 19256540 | 19256881 | −6.76735 | 10 | 341 |
| chr18__group048385 | chr18 | 77575590 | 77576278 | −6.76723 | 11 | 688 |
| chr21__group000686 | chr21 | 11135088 | 11136511 | −6.76587 | 13 | 1423 |
| chr13__group027245 | chr13 | 66146818 | 66147426 | −6.76445 | 12 | 608 |
| chr21__group012438 | chr21 | 31518834 | 31519781 | −6.76411 | 17 | 947 |
| chr18__group007846 | chr18 | 13524694 | 13526294 | −6.76293 | 19 | 1600 |
| chr18__group043488 | chr18 | 71510677 | 71511839 | −6.76182 | 15 | 1162 |
| chr18__group048199 | chr18 | 77306389 | 77307689 | −6.76017 | 14 | 1300 |
| chr21__group019930 | chr21 | 42898535 | 42898872 | −6.75909 | 9 | 337 |
| chr13__group050248 | chr13 | 1E+08 | 1E+08 | −6.75897 | 18 | 812 |
| chr21__group000528 | chr21 | 10859153 | 10860812 | −6.75859 | 32 | 1659 |
| chr13__group001270 | chr13 | 21790505 | 21791009 | −6.7571 | 14 | 504 |
| chr13__group058186 | chr13 | 1.11E+08 | 1.11E+08 | −6.75668 | 10 | 331 |
| chr13__group059865 | chr13 | 1.14E+08 | 1.14E+08 | −6.75655 | 13 | 693 |
| chr21__group014435 | chr21 | 34404197 | 34405153 | −6.75497 | 11 | 956 |
| chr21__group020391 | chr21 | 43796715 | 43797045 | −6.75429 | 9 | 330 |
| chr21__group022687 | chr21 | 47406185 | 47407232 | −6.75421 | 18 | 1047 |
| chr13__group024681 | chr13 | 62132120 | 62132873 | −6.75332 | 9 | 753 |
| chr21__group013423 | chr21 | 32874615 | 32875044 | −6.75246 | 11 | 429 |
| chr21__group017380 | chr21 | 39268479 | 39269541 | −6.75221 | 10 | 1062 |
| chr18__group001238 | chr18 | 3330631 | 3331010 | −6.75195 | 9 | 379 |
| chr13__group058875 | chr13 | 1.12E+08 | 1.12E+08 | −6.75191 | 9 | 481 |
| chr18__group030753 | chr18 | 53731685 | 53732492 | −6.75175 | 10 | 807 |
| chr18__group002930 | chr18 | 5796031 | 5796272 | −6.74708 | 9 | 241 |
| chr13__group000421 | chr13 | 19920066 | 19921076 | −6.7461 | 12 | 1010 |
| chr13__group050379 | chr13 | 1E+08 | 1E+08 | −6.74597 | 10 | 959 |
| chr18__group013046 | chr18 | 25769188 | 25769537 | −6.74512 | 10 | 349 |
| chr21__group000689 | chr21 | 11140216 | 11141188 | −6.74451 | 17 | 972 |
| chr18__group007952 | chr18 | 13648403 | 13649733 | −6.74392 | 16 | 1330 |
| chr13__group050069 | chr13 | 99666103 | 99666761 | −6.74388 | 9 | 658 |
| chr18__group044318 | chr18 | 72816204 | 72817638 | −6.74377 | 37 | 1434 |
| chr18__group007851 | chr18 | 13532625 | 13533127 | −6.74248 | 9 | 502 |
| chr13__group018172 | chr13 | 50420507 | 50421106 | −6.74231 | 11 | 599 |
| chr18__group044327 | chr18 | 72824306 | 72824889 | −6.74188 | 10 | 583 |
| chr21__group000157 | chr21 | 9702915 | 9704816 | −6.74168 | 48 | 1901 |
| chr18__group007922 | chr18 | 13622622 | 13623526 | −6.73907 | 13 | 904 |
| chr18__group024914 | chr18 | 43958215 | 43959932 | −6.73728 | 15 | 1717 |
| chr13__group006568 | chr13 | 30135836 | 30136681 | −6.73505 | 13 | 845 |
| chr18__group044046 | chr18 | 72177927 | 72178298 | −6.73439 | 9 | 371 |
| chr18__group048214 | chr18 | 77327403 | 77329049 | −6.734 | 24 | 1646 |
| chr13__group049840 | chr13 | 99215812 | 99216108 | −6.73386 | 9 | 296 |
| chr13__group059875 | chr13 | 1.14E+08 | 1.14E+08 | −6.73317 | 22 | 1707 |
| chr18__group033370 | chr18 | 57702447 | 57702919 | −6.73297 | 12 | 472 |
| chr18__group002910 | chr18 | 5772224 | 5773305 | −6.732 | 14 | 1081 |
| chr13__group013809 | chr13 | 42053633 | 42054999 | −6.73091 | 12 | 1366 |
| chr13__group028201 | chr13 | 67437242 | 67438110 | −6.73078 | 13 | 868 |
| chr13__group032320 | chr13 | 73110402 | 73111715 | −6.73055 | 14 | 1313 |
| chr13__group054539 | chr13 | 1.06E+08 | 1.06E+08 | −6.7293 | 9 | 425 |
| chr21__group014125 | chr21 | 33965259 | 33965875 | −6.72919 | 10 | 616 |
| chr13__group042234 | chr13 | 88328670 | 88329437 | −6.72909 | 11 | 767 |
| chr18__group032925 | chr18 | 56896736 | 56898521 | −6.72907 | 13 | 1785 |
| chr13__group033524 | chr13 | 75119688 | 75119826 | −6.72863 | 13 | 138 |
| chr13__group000774 | chr13 | 20747482 | 20748025 | −6.72803 | 10 | 543 |
| chr13__group058826 | chr13 | 1.12E+08 | 1.12E+08 | −6.72724 | 14 | 1058 |
| chr18__group035988 | chr18 | 61668859 | 61669768 | −6.7266 | 23 | 909 |
| chr13__group052104 | chr13 | 1.03E+08 | 1.03E+08 | −6.72651 | 10 | 1070 |
| chr21__group022707 | chr21 | 47425219 | 47426301 | −6.72599 | 28 | 1082 |
| chr13__group002916 | chr13 | 24731498 | 24731781 | −6.72596 | 19 | 283 |
| chr18__group005913 | chr18 | 11013871 | 11014587 | −6.72546 | 10 | 716 |
| chr18__group032554 | chr18 | 56257092 | 56257747 | −6.72507 | 9 | 655 |
| chr13__group014639 | chr13 | 43767988 | 43768539 | −6.72424 | 10 | 551 |
| chr18__group043356 | chr18 | 71355221 | 71356150 | −6.72407 | 9 | 929 |
| chr21__group020967 | chr21 | 44775347 | 44776177 | −6.7237 | 9 | 830 |
| chr18__group026831 | chr18 | 47418520 | 47418838 | −6.72182 | 11 | 318 |

TABLE 4-continued

| Name | chr | start.pos | end.pos | median.tstat | num.cg | dmr.size |
|---|---|---|---|---|---|---|
| chr13__group007395 | chr13 | 31335163 | 31335828 | −6.72159 | 9 | 665 |
| chr13__group058167 | chr13 | 1.11E+08 | 1.11E+08 | −6.71972 | 15 | 638 |
| chr13__group060116 | chr13 | 1.14E+08 | 1.14E+08 | −6.719 | 19 | 955 |
| chr13__group039973 | chr13 | 84943693 | 84943896 | −6.71888 | 11 | 203 |
| chr21__group021323 | chr21 | 45589951 | 45591430 | −6.71553 | 26 | 1479 |
| chr21__group014275 | chr21 | 34241128 | 34241577 | −6.7139 | 9 | 449 |
| chr18__group045573 | chr18 | 74247878 | 74248739 | −6.71126 | 14 | 861 |
| chr21__group020304 | chr21 | 43693037 | 43693712 | −6.71112 | 14 | 675 |
| chr18__group032101 | chr18 | 55580679 | 55581181 | −6.70937 | 16 | 502 |
| chr13__group005414 | chr13 | 28482435 | 28483033 | −6.70898 | 11 | 598 |
| chr13__group056776 | chr13 | 1.09E+08 | 1.09E+08 | −6.70889 | 17 | 782 |
| chr13__group038517 | chr13 | 83275402 | 83276017 | −6.70865 | 9 | 615 |
| chr18__group044044 | chr18 | 72168202 | 72168772 | −6.70815 | 11 | 570 |
| chr18__group005116 | chr18 | 9992136 | 9993414 | −6.70402 | 10 | 1278 |
| chr13__group031550 | chr13 | 72249104 | 72249598 | −6.70385 | 17 | 494 |
| chr13__group038186 | chr13 | 82831648 | 82832397 | −6.70274 | 13 | 749 |
| chr18__group007767 | chr18 | 13442507 | 13444458 | −6.70161 | 19 | 1951 |
| chr13__group019701 | chr13 | 53475643 | 53476058 | −6.70036 | 9 | 415 |
| chr18__group046502 | chr18 | 75339057 | 75339765 | −6.70028 | 12 | 708 |
| chr18__group010819 | chr18 | 22189025 | 22189762 | −6.69896 | 9 | 737 |
| chr13__group058108 | chr13 | 1.11E+08 | 1.11E+08 | −6.69789 | 9 | 354 |
| chr13__group048405 | chr13 | 96984015 | 96984441 | −6.69754 | 15 | 426 |
| chr21__group000762 | chr21 | 14424159 | 14425086 | −6.69671 | 12 | 927 |
| chr18__group048146 | chr18 | 77240504 | 77241684 | −6.69615 | 23 | 1180 |
| chr13__group048092 | chr13 | 96222029 | 96222877 | −6.69588 | 12 | 848 |
| chr18__group045764 | chr18 | 74454128 | 74454862 | −6.69545 | 13 | 734 |
| chr21__group005950 | chr21 | 22299868 | 22300856 | −6.69517 | 15 | 988 |
| chr18__group008514 | chr18 | 14658090 | 14658684 | −6.69458 | 14 | 594 |
| chr13__group059892 | chr13 | 1.14E+08 | 1.14E+08 | −6.69458 | 21 | 1376 |
| chr18__group035089 | chr18 | 59986621 | 59987165 | −6.69455 | 13 | 544 |
| chr18__group044004 | chr18 | 72109624 | 72110270 | −6.69416 | 15 | 646 |
| chr21__group000513 | chr21 | 10816216 | 10816875 | −6.69415 | 10 | 659 |
| chr13__group005800 | chr13 | 29290233 | 29290761 | −6.69372 | 10 | 528 |
| chr13__group003978 | chr13 | 26547383 | 26547892 | −6.69345 | 11 | 509 |
| chr13__group010293 | chr13 | 36244581 | 36245544 | −6.69344 | 9 | 963 |
| chr21__group000913 | chr21 | 15068826 | 15070117 | −6.6934 | 36 | 1291 |
| chr18__group045643 | chr18 | 74331705 | 74331886 | −6.69312 | 9 | 181 |
| chr18__group007718 | chr18 | 13397726 | 13398905 | −6.69302 | 12 | 1179 |
| chr13__group008390 | chr13 | 32326498 | 32327648 | −6.69259 | 12 | 1150 |
| chr21__group000483 | chr21 | 10788127 | 10788927 | −6.69245 | 14 | 800 |
| chr18__group024710 | chr18 | 43559833 | 43560824 | −6.69201 | 9 | 991 |
| chr18__group003527 | chr18 | 6350961 | 6351796 | −6.69184 | 13 | 835 |
| chr21__group022733 | chr21 | 47454881 | 47458847 | −6.6909 | 51 | 3966 |
| chr18__group026701 | chr18 | 47016894 | 47017934 | −6.69033 | 13 | 1040 |
| chr13__group057952 | chr13 | 1.11E+08 | 1.11E+08 | −6.68899 | 11 | 908 |
| chr18__group048321 | chr18 | 77440896 | 77441278 | −6.6881 | 9 | 382 |
| chr21__group021000 | chr21 | 44823788 | 44824567 | −6.68753 | 11 | 779 |
| chr13__group058445 | chr13 | 1.12E+08 | 1.12E+08 | −6.68751 | 17 | 1013 |
| chr21__group020142 | chr21 | 43487866 | 43488231 | −6.68616 | 9 | 365 |
| chr18__group028931 | chr18 | 51037870 | 51038525 | −6.6841 | 22 | 655 |
| chr21__group021407 | chr21 | 45710225 | 45712548 | −6.68396 | 41 | 2323 |
| chr13__group060587 | chr13 | 1.15E+08 | 1.15E+08 | −6.6828 | 11 | 681 |
| chr13__group040052 | chr13 | 85037615 | 85038081 | −6.6819 | 9 | 466 |
| chr13__group035970 | chr13 | 79139066 | 79142020 | −6.68162 | 28 | 2954 |
| chr13__group032612 | chr13 | 73789808 | 73790900 | −6.68056 | 13 | 1092 |
| chr21__group022204 | chr21 | 46879633 | 46880462 | −6.67997 | 14 | 829 |
| chr21__group021757 | chr21 | 46256649 | 46257080 | −6.67964 | 9 | 431 |
| chr21__group022704 | chr21 | 47420847 | 47421584 | −6.67868 | 14 | 737 |
| chr13__group028883 | chr13 | 68170099 | 68170716 | −6.67829 | 9 | 617 |
| chr18__group025255 | chr18 | 44284175 | 44285774 | −6.67744 | 10 | 1599 |
| chr13__group060247 | chr13 | 1.14E+08 | 1.14E+08 | −6.67354 | 10 | 251 |
| chr21__group000511 | chr21 | 10814190 | 10815395 | −6.67315 | 13 | 1205 |
| chr21__group004747 | chr21 | 20905491 | 20906039 | −6.67129 | 13 | 548 |
| chr18__group025201 | chr18 | 44232845 | 44233367 | −6.67127 | 9 | 522 |
| chr21__group022720 | chr21 | 47442017 | 47442635 | −6.6704 | 13 | 618 |
| chr18__group007859 | chr18 | 13543845 | 13544861 | −6.67033 | 16 | 1016 |
| chr21__group020388 | chr21 | 43791196 | 43792331 | −6.66997 | 17 | 1135 |
| chr18__group005622 | chr18 | 10724210 | 10725155 | −6.66795 | 11 | 945 |
| chr13__group030766 | chr13 | 71428014 | 71428579 | −6.66776 | 9 | 565 |
| chr21__group000499 | chr21 | 10802442 | 10803288 | −6.66741 | 15 | 846 |
| chr13__group048196 | chr13 | 96736637 | 96737162 | −6.66723 | 9 | 525 |
| chr13__group039710 | chr13 | 84660445 | 84661038 | −6.66703 | 34 | 593 |
| chr18__group048088 | chr18 | 77167696 | 77168548 | −6.66676 | 12 | 852 |
| chr18__group008831 | chr18 | 18700364 | 18700749 | −6.66648 | 11 | 385 |
| chr13__group006717 | chr13 | 30284925 | 30286304 | −6.66641 | 16 | 1379 |
| chr18__group035143 | chr18 | 60036445 | 60037659 | −6.66465 | 13 | 1214 |
| chr21__group020926 | chr21 | 44726925 | 44727387 | −6.6639 | 10 | 462 |
| chr18__group033896 | chr18 | 58259642 | 58261091 | −6.66176 | 11 | 1449 |

TABLE 4-continued

| Name | chr | start.pos | end.pos | median.tstat | num.cg | dmr.size |
|---|---|---|---|---|---|---|
| chr18_group003093 | chr18 | 5952607 | 5953822 | −6.6611 | 10 | 1215 |
| chr13_group059822 | chr13 | 1.14E+08 | 1.14E+08 | −6.66084 | 14 | 776 |
| chr13_group019875 | chr13 | 53648298 | 53648969 | −6.66019 | 9 | 671 |
| chr13_group000172 | chr13 | 19517034 | 19518877 | −6.65987 | 39 | 1843 |
| chr13_group007731 | chr13 | 31662897 | 31663632 | −6.65974 | 9 | 735 |
| chr13_group053843 | chr13 | 1.05E+08 | 1.05E+08 | −6.65926 | 10 | 526 |
| chr13_group056585 | chr13 | 1.09E+08 | 1.09E+08 | −6.65869 | 20 | 447 |
| chr18_group006599 | chr18 | 11666362 | 11667371 | −6.65837 | 11 | 1009 |
| chr21_group020910 | chr21 | 44707850 | 44708576 | −6.65833 | 10 | 726 |
| chr18_group007033 | chr18 | 12235782 | 12237171 | −6.65809 | 12 | 1389 |
| chr21_group002045 | chr21 | 17422574 | 17423222 | −6.6567 | 17 | 648 |
| chr18_group005594 | chr18 | 10695908 | 10697032 | −6.65655 | 16 | 1124 |
| chr21_group014309 | chr21 | 34274903 | 34275490 | −6.65621 | 9 | 587 |
| chr21_group004974 | chr21 | 21167170 | 21168034 | −6.6549 | 14 | 864 |
| chr13_group022344 | chr13 | 58361564 | 58362010 | −6.65355 | 11 | 446 |
| chr13_group060244 | chr13 | 1.14E+08 | 1.14E+08 | −6.65343 | 21 | 1595 |
| chr18_group048358 | chr18 | 77538098 | 77539980 | −6.65305 | 18 | 1882 |
| chr13_group007363 | chr13 | 31306000 | 31306653 | −6.65291 | 14 | 653 |
| chr18_group046809 | chr18 | 75616581 | 75618950 | −6.65204 | 44 | 2369 |
| chr18_group048462 | chr18 | 77664477 | 77664874 | −6.65201 | 12 | 397 |
| chr18_group039491 | chr18 | 66290995 | 66292045 | −6.65192 | 20 | 1050 |
| chr18_group000056 | chr18 | 112257 | 112390 | −6.6518 | 10 | 133 |
| chr21_group021855 | chr21 | 46452653 | 46454200 | −6.65095 | 16 | 1547 |
| chr21_group012429 | chr21 | 31501659 | 31502357 | −6.65072 | 16 | 698 |
| chr13_group002364 | chr13 | 23985256 | 23986806 | −6.65029 | 15 | 1550 |
| chr18_group044894 | chr18 | 73418740 | 73419203 | −6.65016 | 13 | 463 |
| chr13_group056790 | chr13 | 1.09E+08 | 1.09E+08 | −6.64964 | 10 | 800 |
| chr13_group034250 | chr13 | 76072546 | 76073165 | −6.64912 | 9 | 619 |
| chr21_group020327 | chr21 | 43715156 | 43716647 | −6.64848 | 14 | 1491 |
| chr21_group020076 | chr21 | 43376017 | 43377038 | −6.64726 | 23 | 1021 |
| chr18_group041078 | chr18 | 68566185 | 68566794 | −6.64669 | 9 | 609 |
| chr18_group006850 | chr18 | 12043780 | 12044466 | −6.64628 | 9 | 686 |
| chr18_group026528 | chr18 | 46404644 | 46406154 | −6.64616 | 25 | 1510 |
| chr21_group022641 | chr21 | 47357035 | 47358245 | −6.64597 | 10 | 1210 |
| chr18_group047380 | chr18 | 76211307 | 76211930 | −6.64581 | 9 | 623 |
| chr13_group001432 | chr13 | 22176170 | 22176609 | −6.64563 | 17 | 439 |
| chr18_group009485 | chr18 | 20050171 | 20051106 | −6.64456 | 10 | 935 |
| chr13_group060371 | chr13 | 1.15E+08 | 1.15E+08 | −6.64339 | 11 | 539 |
| chr18_group006224 | chr18 | 11313590 | 11314388 | −6.64318 | 12 | 798 |
| chr18_group003502 | chr18 | 6329215 | 6329698 | −6.64278 | 9 | 483 |
| chr13_group022956 | chr13 | 59219506 | 59220227 | −6.64247 | 9 | 721 |
| chr13_group004708 | chr13 | 27452251 | 27453331 | −6.64236 | 9 | 1080 |
| chr21_group022612 | chr21 | 47332476 | 47333473 | −6.64104 | 10 | 997 |
| chr21_group022680 | chr21 | 47391547 | 47392189 | −6.64072 | 12 | 642 |
| chr13_group026370 | chr13 | 64928658 | 64929126 | −6.63999 | 11 | 468 |
| chr21_group020942 | chr21 | 44742938 | 44743398 | −6.63876 | 11 | 460 |
| chr13_group056774 | chr13 | 1.09E+08 | 1.09E+08 | −6.6385 | 10 | 1503 |
| chr13_group001592 | chr13 | 22366188 | 22367270 | −6.63807 | 16 | 1082 |
| chr18_group006598 | chr18 | 11664921 | 11665850 | −6.63744 | 10 | 929 |
| chr21_group021265 | chr21 | 45411331 | 45411974 | −6.63572 | 24 | 643 |
| chr21_group022188 | chr21 | 46855411 | 46856520 | −6.63542 | 9 | 1109 |
| chr18_group048204 | chr18 | 77312845 | 77316023 | −6.63299 | 57 | 3178 |
| chr13_group055250 | chr13 | 1.07E+08 | 1.07E+08 | −6.6328 | 14 | 354 |
| chr18_group003452 | chr18 | 6284258 | 6285423 | −6.63273 | 23 | 1165 |
| chr13_group059329 | chr13 | 1.13E+08 | 1.13E+08 | −6.63221 | 11 | 723 |
| chr13_group060578 | chr13 | 1.15E+08 | 1.15E+08 | −6.63217 | 19 | 1828 |
| chr18_group011024 | chr18 | 22421394 | 22422258 | −6.63167 | 9 | 864 |
| chr13_group005106 | chr13 | 28073878 | 28075172 | −6.63115 | 17 | 1294 |
| chr13_group031411 | chr13 | 72098816 | 72099565 | −6.63001 | 16 | 749 |
| chr13_group060281 | chr13 | 1.14E+08 | 1.14E+08 | −6.6295 | 12 | 623 |
| chr21_group022636 | chr21 | 47353672 | 47354242 | −6.62933 | 10 | 570 |
| chr21_group021477 | chr21 | 45818186 | 45819444 | −6.62821 | 17 | 1258 |
| chr13_group041646 | chr13 | 87629152 | 87629854 | −6.6281 | 11 | 702 |
| chr21_group020654 | chr21 | 44162810 | 44163743 | −6.62766 | 17 | 933 |
| chr18_group048363 | chr18 | 77544781 | 77545539 | −6.62684 | 16 | 758 |
| chr13_group059823 | chr13 | 1.14E+08 | 1.14E+08 | −6.62638 | 10 | 882 |
| chr13_group016447 | chr13 | 47043816 | 47044532 | −6.6262 | 10 | 716 |
| chr18_group018593 | chr18 | 34912698 | 34913265 | −6.62561 | 10 | 567 |
| chr18_group047049 | chr18 | 75894449 | 75895177 | −6.62561 | 9 | 728 |
| chr18_group026526 | chr18 | 46402464 | 46402829 | −6.62416 | 10 | 365 |
| chr13_group015646 | chr13 | 45641369 | 45642357 | −6.62079 | 11 | 988 |
| chr13_group054206 | chr13 | 1.06E+08 | 1.06E+08 | −6.62047 | 9 | 840 |
| chr21_group007169 | chr21 | 23889805 | 23890763 | −6.6204 | 9 | 958 |
| chr18_group014368 | chr18 | 27914637 | 27915030 | −6.61944 | 9 | 393 |
| chr21_group022247 | chr21 | 46960520 | 46961501 | −6.61806 | 15 | 981 |
| chr18_group024962 | chr18 | 44012702 | 44013990 | −6.61737 | 11 | 1288 |
| chr18_group011862 | chr18 | 23532795 | 23533780 | −6.61714 | 13 | 985 |
| chr13_group058803 | chr13 | 1.12E+08 | 1.12E+08 | −6.61702 | 26 | 1926 |

TABLE 4-continued

| Name | chr | start.pos | end.pos | median.tstat | num.cg | dmr.size |
|---|---|---|---|---|---|---|
| chr13_group029729 | chr13 | 69518126 | 69518634 | −6.61701 | 11 | 508 |
| chr13_group059366 | chr13 | 1.13E+08 | 1.13E+08 | −6.61695 | 19 | 1837 |
| chr18_group005789 | chr18 | 10881709 | 10882497 | −6.61568 | 9 | 788 |
| chr18_group048063 | chr18 | 77115886 | 77116711 | −6.61532 | 10 | 825 |
| chr13_group019244 | chr13 | 52389893 | 52390268 | −6.61502 | 9 | 375 |
| chr13_group018986 | chr13 | 51808907 | 51809545 | −6.61424 | 9 | 638 |
| chr13_group013791 | chr13 | 42022511 | 42023611 | −6.61371 | 12 | 1100 |
| chr18_group007707 | chr18 | 13386588 | 13387783 | −6.61296 | 26 | 1195 |
| chr13_group007176 | chr13 | 30977431 | 30978382 | −6.61284 | 12 | 951 |
| chr21_group004485 | chr21 | 20616807 | 20618682 | −6.61273 | 32 | 1875 |
| chr18_group044348 | chr18 | 72843476 | 72844690 | −6.61092 | 21 | 1214 |
| chr21_group013457 | chr21 | 32916866 | 32917320 | −6.61073 | 9 | 454 |
| chr18_group047995 | chr18 | 76807308 | 76807922 | −6.61016 | 11 | 614 |
| chr18_group047678 | chr18 | 76491070 | 76491674 | −6.61014 | 13 | 604 |
| chr21_group021326 | chr21 | 45595962 | 45596396 | −6.60946 | 9 | 434 |
| chr18_group025476 | chr18 | 44558856 | 44560637 | −6.60906 | 33 | 1781 |
| chr13_group000604 | chr13 | 20368826 | 20370251 | −6.6087 | 19 | 1425 |
| chr21_group000912 | chr21 | 15067127 | 15068430 | −6.60845 | 19 | 1303 |
| chr13_group000720 | chr13 | 20679609 | 20680334 | −6.60806 | 9 | 725 |
| chr13_group003799 | chr13 | 26144436 | 26145112 | −6.60774 | 12 | 676 |
| chr21_group019771 | chr21 | 42591751 | 42592070 | −6.6077 | 10 | 319 |
| chr13_group006905 | chr13 | 30596525 | 30598019 | −6.60705 | 14 | 1494 |
| chr13_group001699 | chr13 | 22538774 | 22539558 | −6.60561 | 11 | 784 |
| chr18_group047902 | chr18 | 76703457 | 76704009 | −6.60491 | 10 | 552 |
| chr18_group048173 | chr18 | 77275966 | 77276534 | −6.60419 | 16 | 568 |
| chr13_group001417 | chr13 | 22058060 | 22058180 | −6.60336 | 9 | 120 |
| chr13_group060078 | chr13 | 1.14E+08 | 1.14E+08 | −6.60192 | 9 | 378 |
| chr21_group004939 | chr21 | 21132013 | 21132542 | −6.60129 | 13 | 529 |
| chr21_group002061 | chr21 | 17442622 | 17443678 | −6.60063 | 11 | 1056 |
| chr18_group018711 | chr18 | 35022553 | 35023152 | −6.60043 | 10 | 599 |
| chr13_group004912 | chr13 | 27846185 | 27846693 | −6.59841 | 9 | 508 |
| chr13_group049303 | chr13 | 98273869 | 98274837 | −6.59691 | 10 | 968 |
| chr21_group000657 | chr21 | 11106389 | 11107549 | −6.59605 | 36 | 1160 |
| chr13_group016326 | chr13 | 46896192 | 46896784 | −6.59603 | 10 | 592 |
| chr13_group060448 | chr13 | 1.15E+08 | 1.15E+08 | −6.5948 | 30 | 1554 |
| chr18_group003791 | chr18 | 6920592 | 6920858 | −6.59476 | 12 | 266 |
| chr21_group009158 | chr21 | 26018297 | 26019071 | −6.5945 | 10 | 774 |
| chr18_group046882 | chr18 | 75688991 | 75691504 | −6.59427 | 37 | 2513 |
| chr13_group002069 | chr13 | 23629338 | 23630085 | −6.59424 | 18 | 747 |
| chr18_group032959 | chr18 | 56949719 | 56950296 | −6.59327 | 11 | 577 |
| chr13_group014462 | chr13 | 43438324 | 43438536 | −6.59029 | 9 | 212 |
| chr18_group045320 | chr18 | 73975331 | 73975863 | −6.58983 | 9 | 532 |
| chr13_group050548 | chr13 | 1.01E+08 | 1.01E+08 | −6.58972 | 10 | 1103 |
| chr18_group048305 | chr18 | 77418183 | 77419978 | −6.58969 | 21 | 1795 |
| chr18_group047108 | chr18 | 75952699 | 75954611 | −6.58928 | 22 | 1912 |
| chr13_group004348 | chr13 | 27108006 | 27109076 | −6.58899 | 9 | 1070 |
| chr13_group059647 | chr13 | 1.13E+08 | 1.13E+08 | −6.58872 | 9 | 621 |
| chr21_group020725 | chr21 | 44257758 | 44258579 | −6.58739 | 20 | 821 |
| chr18_group024673 | chr18 | 43416882 | 43417526 | −6.58736 | 14 | 644 |
| chr21_group022312 | chr21 | 47035702 | 47036670 | −6.58705 | 11 | 968 |
| chr13_group016088 | chr13 | 46424214 | 46424563 | −6.58483 | 10 | 349 |
| chr18_group048100 | chr18 | 77181395 | 77182099 | −6.58474 | 15 | 704 |
| chr18_group015299 | chr18 | 29917276 | 29918200 | −6.58402 | 9 | 924 |
| chr21_group017094 | chr21 | 38925312 | 38926014 | −6.5834 | 14 | 702 |
| chr18_group046529 | chr18 | 75365474 | 75366537 | −6.58222 | 11 | 1063 |
| chr21_group022485 | chr21 | 47211299 | 47212267 | −6.58188 | 9 | 968 |
| chr13_group056736 | chr13 | 1.09E+08 | 1.09E+08 | −6.5817 | 10 | 577 |
| chr13_group000037 | chr13 | 19172028 | 19175135 | −6.58158 | 52 | 3107 |
| chr21_group009351 | chr21 | 26212395 | 26212911 | −6.58141 | 18 | 516 |
| chr18_group047961 | chr18 | 76770797 | 76771470 | −6.58036 | 13 | 673 |
| chr21_group021196 | chr21 | 45249684 | 45250492 | −6.57932 | 27 | 808 |
| chr21_group020328 | chr21 | 43717135 | 43718145 | −6.57914 | 12 | 1010 |
| chr13_group001539 | chr13 | 22310863 | 22311474 | −6.57878 | 10 | 611 |
| chr13_group049624 | chr13 | 98706509 | 98707392 | −6.57861 | 14 | 883 |
| chr21_group021458 | chr21 | 45797380 | 45798737 | −6.57825 | 29 | 1357 |
| chr21_group016323 | chr21 | 37250197 | 37251811 | −6.57698 | 15 | 1614 |
| chr13_group060612 | chr13 | 1.15E+08 | 1.15E+08 | −6.57671 | 9 | 314 |
| chr21_group020959 | chr21 | 44762691 | 44763571 | −6.57623 | 18 | 880 |
| chr18_group043831 | chr18 | 71848640 | 71850264 | −6.57588 | 19 | 1624 |
| chr21_group022732 | chr21 | 47452972 | 47454433 | −6.57547 | 45 | 1461 |
| chr13_group057746 | chr13 | 1.1E+08 | 1.1E+08 | −6.57532 | 11 | 320 |
| chr18_group042850 | chr18 | 70639139 | 70639619 | −6.57487 | 12 | 480 |
| chr18_group040926 | chr18 | 68409913 | 68411014 | −6.57434 | 9 | 1101 |
| chr18_group026385 | chr18 | 46119019 | 46119295 | −6.57356 | 9 | 276 |
| chr18_group018808 | chr18 | 35101610 | 35102190 | −6.5725 | 12 | 580 |
| chr13_group000065 | chr13 | 19239271 | 19239568 | −6.57165 | 10 | 297 |
| chr21_group007234 | chr21 | 23950561 | 23951769 | −6.57073 | 23 | 1208 |
| chr18_group025470 | chr18 | 44554604 | 44555557 | −6.57033 | 19 | 953 |

TABLE 4-continued

| Name | chr | start.pos | end.pos | median.tstat | num.cg | dmr.size |
|---|---|---|---|---|---|---|
| chr18__group009240 | chr18 | 19784858 | 19785859 | −6.5698 | 10 | 1001 |
| chr21__group017603 | chr21 | 39657663 | 39658702 | −6.56942 | 9 | 1039 |
| chr18__group024061 | chr18 | 42643572 | 42644225 | −6.56812 | 21 | 653 |
| chr13__group028188 | chr13 | 67422786 | 67423190 | −6.56731 | 16 | 404 |
| chr18__group041839 | chr18 | 69501139 | 69501369 | −6.56693 | 10 | 230 |
| chr21__group005532 | chr21 | 21797278 | 21798381 | −6.56589 | 16 | 1103 |
| chr13__group058596 | chr13 | 1.12E+08 | 1.12E+08 | −6.56586 | 10 | 1089 |
| chr21__group021823 | chr21 | 46415268 | 46415842 | −6.56513 | 9 | 574 |
| chr13__group016554 | chr13 | 47340774 | 47341919 | −6.5642 | 9 | 1145 |
| chr21__group022575 | chr21 | 47297522 | 47299427 | −6.56333 | 15 | 1905 |
| chr18__group031967 | chr18 | 55196383 | 55197345 | −6.56252 | 9 | 962 |
| chr18__group006109 | chr18 | 11204614 | 11205047 | −6.56236 | 10 | 433 |
| chr21__group016604 | chr21 | 37711141 | 37711578 | −6.56206 | 11 | 437 |
| chr21__group020660 | chr21 | 44170946 | 44171620 | −6.56177 | 12 | 674 |
| chr21__group013453 | chr21 | 32912514 | 32913662 | −6.56173 | 13 | 1148 |
| chr13__group004533 | chr13 | 27284051 | 27284910 | −6.56098 | 15 | 859 |
| chr18__group032094 | chr18 | 55573216 | 55574168 | −6.55887 | 10 | 952 |
| chr18__group035366 | chr18 | 60430337 | 60431077 | −6.55869 | 9 | 740 |
| chr13__group055272 | chr13 | 1.07E+08 | 1.07E+08 | −6.55837 | 12 | 771 |
| chr18__group014718 | chr18 | 28489734 | 28491557 | −6.55689 | 19 | 1823 |
| chr21__group014436 | chr21 | 34405918 | 34407523 | −6.55663 | 26 | 1605 |
| chr21__group013612 | chr21 | 33175197 | 33175555 | −6.55649 | 9 | 358 |
| chr18__group045726 | chr18 | 74411821 | 74412455 | −6.55455 | 10 | 634 |
| chr21__group022573 | chr21 | 47294577 | 47296686 | −6.55444 | 23 | 2109 |
| chr18__group003100 | chr18 | 5960511 | 5961298 | −6.55422 | 9 | 787 |
| chr18__group015722 | chr18 | 30526804 | 30526995 | −6.55373 | 15 | 191 |
| chr13__group050117 | chr13 | 99810923 | 99811524 | −6.55075 | 10 | 601 |
| chr18__group047743 | chr18 | 76549810 | 76550113 | −6.55031 | 10 | 303 |
| chr18__group018594 | chr18 | 34913919 | 34916122 | −6.5492 | 21 | 2203 |
| chr13__group006700 | chr13 | 30266757 | 30268603 | −6.54896 | 22 | 1846 |
| chr18__group034063 | chr18 | 58461712 | 58462904 | −6.54845 | 11 | 1192 |
| chr13__group002163 | chr13 | 23736025 | 23736759 | −6.54787 | 15 | 734 |
| chr13__group023015 | chr13 | 59301176 | 59301898 | −6.54763 | 10 | 722 |
| chr13__group002446 | chr13 | 24079390 | 24079711 | −6.54651 | 9 | 321 |
| chr13__group058604 | chr13 | 1.12E+08 | 1.12E+08 | −6.5451 | 16 | 756 |
| chr18__group006822 | chr18 | 11971986 | 11972742 | −6.54446 | 20 | 756 |
| chr18__group008463 | chr18 | 14473671 | 14474143 | −6.54386 | 21 | 472 |
| chr21__group006342 | chr21 | 22761573 | 22762494 | −6.54321 | 9 | 921 |
| chr13__group059673 | chr13 | 1.13E+08 | 1.13E+08 | −6.54293 | 15 | 868 |
| chr13__group027955 | chr13 | 67156807 | 67157702 | −6.54207 | 10 | 895 |
| chr21__group021488 | chr21 | 45834291 | 45835497 | −6.54156 | 17 | 1206 |
| chr18__group048359 | chr18 | 77540888 | 77542497 | −6.53989 | 20 | 1609 |
| chr21__group020680 | chr21 | 44190680 | 44191657 | −6.53948 | 18 | 977 |
| chr13__group058252 | chr13 | 1.11E+08 | 1.11E+08 | −6.53819 | 9 | 677 |
| chr21__group020294 | chr21 | 43681034 | 43682136 | −6.53813 | 20 | 1102 |
| chr18__group016099 | chr18 | 31324044 | 31324765 | −6.53749 | 12 | 721 |
| chr18__group018868 | chr18 | 35155295 | 35155990 | −6.53723 | 11 | 695 |
| chr21__group016774 | chr21 | 38000391 | 38002140 | −6.53707 | 23 | 1749 |
| chr18__group003288 | chr18 | 6132863 | 6134336 | −6.53684 | 15 | 1473 |
| chr13__group004818 | chr13 | 27553890 | 27554565 | −6.5368 | 13 | 675 |
| chr13__group004557 | chr13 | 27309770 | 27310743 | −6.53567 | 9 | 973 |
| chr13__group056310 | chr13 | 1.09E+08 | 1.09E+08 | −6.53547 | 26 | 543 |
| chr13__group003630 | chr13 | 25978765 | 25979655 | −6.53468 | 11 | 890 |
| chr21__group022863 | chr21 | 47737794 | 47738466 | −6.53312 | 11 | 672 |
| chr13__group004807 | chr13 | 27541230 | 27542491 | −6.53235 | 16 | 1261 |
| chr21__group020381 | chr21 | 43782466 | 43782820 | −6.53186 | 12 | 354 |
| chr18__group048151 | chr18 | 77247458 | 77248745 | −6.53099 | 15 | 1287 |
| chr21__group012512 | chr21 | 31621038 | 31621689 | −6.52983 | 11 | 651 |
| chr13__group060289 | chr13 | 1.14E+08 | 1.14E+08 | −6.52979 | 17 | 911 |
| chr13__group040545 | chr13 | 85573751 | 85574296 | −6.52861 | 13 | 545 |
| chr13__group050567 | chr13 | 1.01E+08 | 1.01E+08 | −6.5284 | 11 | 648 |
| chr18__group043906 | chr18 | 71957896 | 71958313 | −6.52779 | 14 | 417 |
| chr18__group032936 | chr18 | 56910927 | 56912207 | −6.52604 | 16 | 1280 |
| chr13__group010261 | chr13 | 36211285 | 36212607 | −6.52572 | 9 | 1322 |
| chr21__group021410 | chr21 | 45714897 | 45715456 | −6.52565 | 13 | 559 |
| chr13__group041258 | chr13 | 87011181 | 87011666 | −6.52528 | 9 | 485 |
| chr13__group016133 | chr13 | 46461242 | 46462579 | −6.52511 | 10 | 1337 |
| chr13__group058684 | chr13 | 1.12E+08 | 1.12E+08 | −6.5238 | 9 | 692 |
| chr18__group047491 | chr18 | 76318373 | 76319721 | −6.52362 | 16 | 1348 |
| chr18__group025467 | chr18 | 44551395 | 44552270 | −6.52321 | 18 | 875 |
| chr18__group025460 | chr18 | 44541841 | 44544322 | −6.5224 | 33 | 2481 |
| chr13__group007362 | chr13 | 31304791 | 31305666 | −6.52074 | 15 | 875 |
| chr18__group047436 | chr18 | 76259288 | 76260375 | −6.51998 | 14 | 1087 |
| chr21__group022759 | chr21 | 47490293 | 47491279 | −6.51979 | 11 | 986 |
| chr13__group024901 | chr13 | 62519048 | 62520203 | −6.51977 | 13 | 1155 |
| chr21__group010663 | chr21 | 28318361 | 28318749 | −6.51512 | 9 | 388 |
| chr21__group007627 | chr21 | 24365938 | 24366849 | −6.51505 | 11 | 911 |
| chr18__group044061 | chr18 | 72212335 | 72212993 | −6.51445 | 18 | 658 |

TABLE 4-continued

| Name | chr | start.pos | end.pos | median.tstat | num.cg | dmr.size |
|---|---|---|---|---|---|---|
| chr13__group058051 | chr13 | 1.11E+08 | 1.11E+08 | −6.51295 | 12 | 793 |
| chr21__group022237 | chr21 | 46928486 | 46930146 | −6.51287 | 40 | 1660 |
| chr18__group026244 | chr18 | 45764518 | 45765676 | −6.50978 | 9 | 1158 |
| chr21__group022684 | chr21 | 47402652 | 47403616 | −6.50917 | 14 | 964 |
| chr13__group059938 | chr13 | 1.14E+08 | 1.14E+08 | −6.50836 | 24 | 685 |
| chr18__group046512 | chr18 | 75347399 | 75348251 | −6.50802 | 9 | 852 |
| chr13__group024544 | chr13 | 61986223 | 61986946 | −6.50779 | 9 | 723 |
| chr21__group022642 | chr21 | 47358847 | 47360519 | −6.50741 | 19 | 1672 |
| chr21__group007538 | chr21 | 24273517 | 24274176 | −6.5071 | 14 | 659 |
| chr13__group059860 | chr13 | 1.14E+08 | 1.14E+08 | −6.50601 | 9 | 528 |
| chr13__group056584 | chr13 | 1.09E+08 | 1.09E+08 | −6.5059 | 10 | 429 |
| chr21__group000208 | chr21 | 9854176 | 9854682 | −6.50301 | 9 | 506 |
| chr18__group025231 | chr18 | 44259280 | 44260447 | −6.50212 | 25 | 1167 |
| chr13__group013124 | chr13 | 40782344 | 40783402 | −6.502 | 10 | 1058 |
| chr13__group005502 | chr13 | 28608746 | 28610140 | −6.50121 | 12 | 1394 |
| chr13__group040887 | chr13 | 86225191 | 86226618 | −6.50118 | 9 | 1427 |
| chr21__group002273 | chr21 | 17681625 | 17682230 | −6.49825 | 9 | 605 |
| chr18__group047212 | chr18 | 76053477 | 76053908 | −6.49819 | 10 | 431 |
| chr13__group039251 | chr13 | 84076190 | 84076581 | −6.498 | 9 | 391 |
| chr18__group043029 | chr18 | 70950787 | 70951503 | −6.49775 | 9 | 716 |
| chr21__group000492 | chr21 | 10795486 | 10796962 | −6.49743 | 19 | 1476 |
| chr21__group021837 | chr21 | 46431972 | 46432394 | −6.49738 | 9 | 422 |
| chr18__group021501 | chr18 | 38506474 | 38507094 | −6.4973 | 9 | 620 |
| chr21__group018524 | chr21 | 41046609 | 41047567 | −6.49707 | 12 | 958 |
| chr13__group048035 | chr13 | 96078806 | 96079467 | −6.497 | 12 | 661 |
| chr13__group015175 | chr13 | 44379792 | 44380648 | −6.49649 | 10 | 856 |
| chr18__group018532 | chr18 | 34858127 | 34859594 | −6.49618 | 11 | 1467 |
| chr13__group025963 | chr13 | 64414859 | 64416317 | −6.49569 | 12 | 1458 |
| chr18__group005620 | chr18 | 10721262 | 10722035 | −6.494 | 10 | 773 |
| chr13__group008092 | chr13 | 32035485 | 32035718 | −6.49372 | 11 | 233 |
| chr21__group022121 | chr21 | 46790652 | 46791286 | −6.49365 | 13 | 634 |
| chr21__group010223 | chr21 | 27530921 | 27531558 | −6.49307 | 9 | 637 |
| chr18__group048387 | chr18 | 77577889 | 77579197 | −6.49174 | 13 | 1308 |
| chr18__group013747 | chr18 | 26826448 | 26826948 | −6.49015 | 12 | 500 |
| chr21__group000043 | chr21 | 9483205 | 9484633 | −6.48945 | 43 | 1428 |
| chr18__group042719 | chr18 | 70489318 | 70489792 | −6.48926 | 9 | 474 |
| chr21__group012578 | chr21 | 31691743 | 31692604 | −6.48802 | 9 | 861 |
| chr13__group025901 | chr13 | 64314691 | 64314994 | −6.48796 | 10 | 303 |
| chr18__group047688 | chr18 | 76501003 | 76501773 | −6.48785 | 9 | 770 |
| chr13__group007457 | chr13 | 31391499 | 31393465 | −6.4878 | 18 | 1966 |
| chr18__group046483 | chr18 | 75320229 | 75321470 | −6.4872 | 12 | 1241 |
| chr18__group018606 | chr18 | 34925998 | 34927186 | −6.48674 | 11 | 1188 |
| chr18__group008047 | chr18 | 13825986 | 13827120 | −6.486 | 27 | 1134 |
| chr18__group045634 | chr18 | 74322485 | 74323167 | −6.48563 | 16 | 682 |
| chr18__group011246 | chr18 | 22676640 | 22677470 | −6.48505 | 10 | 830 |
| chr18__group008467 | chr18 | 14478225 | 14478588 | −6.48473 | 9 | 363 |
| chr21__group000915 | chr21 | 15077072 | 15078221 | −6.48312 | 43 | 1149 |
| chr18__group007857 | chr18 | 13542218 | 13542662 | −6.4807 | 11 | 444 |
| chr21__group000550 | chr21 | 10884748 | 10885120 | −6.48025 | 16 | 372 |
| chr21__group014551 | chr21 | 34537011 | 34537743 | −6.47955 | 10 | 732 |
| chr13__group029153 | chr13 | 68483587 | 68484479 | −6.47865 | 15 | 892 |
| chr18__group044359 | chr18 | 72853860 | 72855141 | −6.47786 | 13 | 1281 |
| chr18__group048081 | chr18 | 77157593 | 77158850 | −6.47778 | 21 | 1257 |
| chr21__group000648 | chr21 | 11094617 | 11095036 | −6.47711 | 9 | 419 |
| chr18__group018161 | chr18 | 34277227 | 34279292 | −6.4767 | 13 | 2065 |
| chr13__group004564 | chr13 | 27318923 | 27319772 | −6.47558 | 14 | 849 |
| chr21__group003179 | chr21 | 18826050 | 18826694 | −6.47535 | 11 | 644 |
| chr21__group013454 | chr21 | 32914207 | 32914688 | −6.47363 | 10 | 481 |
| chr18__group021260 | chr18 | 38192929 | 38193205 | −6.47356 | 14 | 276 |
| chr13__group038489 | chr13 | 83241372 | 83241959 | −6.47291 | 20 | 587 |
| chr18__group035353 | chr18 | 60387436 | 60388444 | −6.47156 | 12 | 1008 |
| chr13__group050784 | chr13 | 1.01E+08 | 1.01E+08 | −6.47144 | 9 | 216 |
| chr13__group058210 | chr13 | 1.11E+08 | 1.11E+08 | −6.47133 | 11 | 379 |
| chr18__group008843 | chr18 | 18724911 | 18725119 | −6.46971 | 11 | 208 |
| chr21__group014256 | chr21 | 34221632 | 34223099 | −6.46842 | 10 | 1467 |
| chr21__group022117 | chr21 | 46784420 | 46784893 | −6.46777 | 10 | 473 |
| chr21__group020846 | chr21 | 44566772 | 44567009 | −6.46748 | 9 | 237 |
| chr18__group007732 | chr18 | 13412790 | 13414304 | −6.46739 | 13 | 1514 |
| chr13__group000039 | chr13 | 19183152 | 19183958 | −6.46585 | 19 | 806 |
| chr18__group047321 | chr18 | 76149141 | 76150063 | −6.46428 | 11 | 922 |
| chr18__group046761 | chr18 | 75568665 | 75569828 | −6.46362 | 11 | 1163 |
| chr18__group044875 | chr18 | 73392636 | 73393895 | −6.46194 | 12 | 1259 |
| chr18__group007921 | chr18 | 13620807 | 13622101 | −6.46168 | 13 | 1294 |
| chr18__group038160 | chr18 | 64210363 | 64211034 | −6.46032 | 10 | 671 |
| chr13__group059088 | chr13 | 1.13E+08 | 1.13E+08 | −6.45998 | 21 | 1479 |
| chr18__group048372 | chr18 | 77560939 | 77561362 | −6.45857 | 11 | 423 |
| chr21__group022653 | chr21 | 47368951 | 47370362 | −6.45766 | 20 | 1411 |
| chr13__group000829 | chr13 | 20796939 | 20797842 | −6.45712 | 12 | 903 |

TABLE 4-continued

| Name | chr | start.pos | end.pos | median.tstat | num.cg | dmr.size |
|---|---|---|---|---|---|---|
| chr13__group028124 | chr13 | 67347089 | 67348070 | −6.45573 | 12 | 981 |
| chr13__group060564 | chr13 | 1.15E+08 | 1.15E+08 | −6.4556 | 15 | 684 |
| chr21__group000653 | chr21 | 11099601 | 11100900 | −6.45548 | 19 | 1299 |
| chr18__group010026 | chr18 | 21169435 | 21170432 | −6.45369 | 10 | 997 |
| chr13__group045429 | chr13 | 92494682 | 92495389 | −6.45361 | 13 | 707 |
| chr13__group024483 | chr13 | 61912886 | 61913697 | −6.45317 | 23 | 811 |
| chr21__group022029 | chr21 | 46647118 | 46648439 | −6.45303 | 15 | 1321 |
| chr13__group059574 | chr13 | 1.13E+08 | 1.13E+08 | −6.45141 | 42 | 2370 |
| chr21__group020262 | chr21 | 43644152 | 43645604 | −6.44876 | 12 | 1452 |
| chr18__group000101 | chr18 | 269121 | 269576 | −6.44843 | 9 | 455 |
| chr13__group012336 | chr13 | 39614078 | 39614547 | −6.44841 | 12 | 469 |
| chr21__group014708 | chr21 | 35009173 | 35009825 | −6.44781 | 18 | 652 |
| chr18__group040832 | chr18 | 68315005 | 68316385 | −6.44476 | 12 | 1380 |
| chr18__group025039 | chr18 | 44087186 | 44088411 | −6.44435 | 15 | 1225 |
| chr18__group007864 | chr18 | 13550441 | 13551637 | −6.4436 | 20 | 1196 |
| chr13__group006709 | chr13 | 30276749 | 30278190 | −6.4436 | 15 | 1441 |
| chr18__group048366 | chr18 | 77548964 | 77550416 | −6.44201 | 40 | 1452 |
| chr21__group020870 | chr21 | 44598440 | 44599471 | −6.44184 | 13 | 1031 |
| chr18__group043902 | chr18 | 71951022 | 71951898 | −6.44134 | 13 | 876 |
| chr13__group001191 | chr13 | 21644560 | 21645272 | −6.44085 | 11 | 712 |
| chr18__group039837 | chr18 | 66828477 | 66829166 | −6.44078 | 9 | 689 |
| chr21__group022234 | chr21 | 46921546 | 46922878 | −6.44019 | 22 | 1332 |
| chr21__group020458 | chr21 | 43865472 | 43866469 | −6.44017 | 12 | 997 |
| chr13__group009648 | chr13 | 35281410 | 35281713 | −6.43955 | 10 | 303 |
| chr21__group022031 | chr21 | 46650936 | 46651748 | −6.43761 | 13 | 812 |
| chr13__group059632 | chr13 | 1.13E+08 | 1.13E+08 | −6.43746 | 9 | 1176 |
| chr18__group044351 | chr18 | 72847072 | 72847709 | −6.43694 | 12 | 637 |
| chr18__group025555 | chr18 | 44703009 | 44703453 | −6.43418 | 11 | 444 |
| chr13__group034348 | chr13 | 76442867 | 76443082 | −6.43381 | 9 | 215 |
| chr18__group030265 | chr18 | 53068555 | 53069573 | −6.43318 | 14 | 1018 |
| chr18__group017627 | chr18 | 33484608 | 33485785 | −6.43314 | 28 | 1177 |
| chr18__group040700 | chr18 | 68176507 | 68177873 | −6.43254 | 9 | 1366 |
| chr13__group018054 | chr13 | 50019750 | 50020103 | −6.43198 | 11 | 353 |
| chr13__group059998 | chr13 | 1.14E+08 | 1.14E+08 | −6.43136 | 14 | 1069 |
| chr21__group008041 | chr21 | 24862318 | 24863234 | −6.43078 | 11 | 916 |
| chr21__group014505 | chr21 | 34484291 | 34485799 | −6.42993 | 21 | 1508 |
| chr21__group022795 | chr21 | 47535862 | 47536360 | −6.42982 | 9 | 498 |
| chr18__group005508 | chr18 | 10615068 | 10615453 | −6.42909 | 11 | 385 |
| chr21__group022851 | chr21 | 47633614 | 47633910 | −6.42788 | 11 | 296 |
| chr21__group021879 | chr21 | 46474573 | 46475042 | −6.42732 | 10 | 469 |
| chr21__group000668 | chr21 | 11116706 | 11116879 | −6.4271 | 10 | 173 |
| chr21__group003308 | chr21 | 18983044 | 18983498 | −6.42682 | 9 | 454 |
| chr18__group009225 | chr18 | 19768305 | 19769154 | −6.42583 | 10 | 849 |
| chr13__group039280 | chr13 | 84106871 | 84107678 | −6.42552 | 13 | 807 |
| chr18__group033360 | chr18 | 57687227 | 57687774 | −6.42493 | 12 | 547 |
| chr13__group031701 | chr13 | 72420030 | 72420669 | −6.42405 | 9 | 639 |
| chr18__group007005 | chr18 | 12207904 | 12208599 | −6.42379 | 16 | 695 |
| chr13__group000656 | chr13 | 20496256 | 20496811 | −6.42374 | 10 | 555 |
| chr13__group015402 | chr13 | 44970311 | 44971639 | −6.42291 | 16 | 1328 |
| chr18__group047006 | chr18 | 75850469 | 75850983 | −6.42082 | 9 | 514 |
| chr21__group014140 | chr21 | 33991904 | 33992721 | −6.42024 | 11 | 817 |
| chr13__group058631 | chr13 | 1.12E+08 | 1.12E+08 | −6.41993 | 12 | 923 |
| chr18__group045884 | chr18 | 74709320 | 74709794 | −6.41854 | 13 | 474 |
| chr18__group045708 | chr18 | 74393082 | 74394280 | −6.41806 | 13 | 1198 |
| chr18__group047230 | chr18 | 76068633 | 76069540 | −6.418 | 11 | 907 |
| chr21__group000120 | chr21 | 9663703 | 9665222 | −6.41777 | 14 | 1519 |
| chr18__group024828 | chr18 | 43882800 | 43883361 | −6.41766 | 9 | 561 |
| chr13__group007482 | chr13 | 31421132 | 31421642 | −6.41714 | 9 | 510 |
| chr18__group044620 | chr18 | 73118128 | 73118741 | −6.41688 | 9 | 613 |
| chr18__group003654 | chr18 | 6483426 | 6484474 | −6.41603 | 13 | 1048 |
| chr18__group025443 | chr18 | 44527853 | 44528686 | −6.41597 | 13 | 833 |
| chr21__group010205 | chr21 | 27471619 | 27472191 | −6.4146 | 9 | 572 |
| chr13__group060000 | chr13 | 1.14E+08 | 1.14E+08 | −6.41377 | 25 | 2257 |
| chr13__group057876 | chr13 | 1.11E+08 | 1.11E+08 | −6.41326 | 10 | 231 |
| chr18__group013341 | chr18 | 26218634 | 26218882 | −6.41301 | 12 | 248 |
| chr13__group005063 | chr13 | 28034188 | 28034320 | −6.41282 | 10 | 132 |
| chr21__group019912 | chr21 | 42859971 | 42860513 | −6.41039 | 13 | 542 |
| chr13__group016179 | chr13 | 46507473 | 46508550 | −6.4094 | 16 | 1077 |
| chr21__group022799 | chr21 | 47541394 | 47542327 | −6.40915 | 12 | 933 |
| chr18__group042988 | chr18 | 70790516 | 70791885 | −6.409 | 10 | 1369 |
| chr21__group004022 | chr21 | 19958723 | 19959534 | −6.40848 | 9 | 811 |
| chr21__group020444 | chr21 | 43849763 | 43851592 | −6.40759 | 22 | 1829 |
| chr13__group003213 | chr13 | 25262016 | 25262493 | −6.40642 | 10 | 477 |
| chr13__group001620 | chr13 | 22399010 | 22399854 | −6.4064 | 12 | 844 |
| chr13__group023087 | chr13 | 59391593 | 59391831 | −6.40633 | 9 | 238 |
| chr13__group015939 | chr13 | 46204996 | 46205439 | −6.40611 | 9 | 443 |
| chr13__group037428 | chr13 | 81552863 | 81553062 | −6.40496 | 10 | 199 |
| chr13__group004116 | chr13 | 26725436 | 26726842 | −6.40451 | 19 | 1406 |

TABLE 4-continued

| Name | chr | start.pos | end.pos | median.tstat | num.cg | dmr.size |
|---|---|---|---|---|---|---|
| chr13_group018838 | chr13 | 51653718 | 51654963 | −6.4042 | 23 | 1245 |
| chr18_group018715 | chr18 | 35025201 | 35025901 | −6.40382 | 11 | 700 |
| chr21_group020352 | chr21 | 43743733 | 43744183 | −6.40351 | 9 | 450 |
| chr18_group005381 | chr18 | 10414411 | 10414754 | −6.4026 | 11 | 343 |
| chr21_group022811 | chr21 | 47559059 | 47560829 | −6.4025 | 21 | 1770 |
| chr18_group044373 | chr18 | 72872057 | 72872661 | −6.40135 | 10 | 604 |
| chr21_group020426 | chr21 | 43831819 | 43833653 | −6.40096 | 27 | 1834 |
| chr21_group020021 | chr21 | 43134250 | 43135973 | −6.40088 | 27 | 1723 |
| chr18_group041084 | chr18 | 68572599 | 68573636 | −6.40058 | 9 | 1037 |
| chr18_group046500 | chr18 | 75335545 | 75336722 | −6.40038 | 13 | 1177 |
| chr18_group025228 | chr18 | 44255822 | 44257042 | −6.39903 | 18 | 1220 |
| chr18_group015607 | chr18 | 30374338 | 30375250 | −6.39869 | 25 | 912 |
| chr21_group019947 | chr21 | 42939706 | 42940801 | −6.39861 | 12 | 1095 |
| chr13_group019335 | chr13 | 52688904 | 52689506 | −6.39604 | 15 | 602 |
| chr21_group000233 | chr21 | 9885709 | 9886767 | −6.39353 | 9 | 1058 |
| chr21_group021304 | chr21 | 45552556 | 45552829 | −6.39262 | 11 | 273 |
| chr18_group032524 | chr18 | 56212657 | 56213652 | −6.39248 | 10 | 995 |
| chr13_group006575 | chr13 | 30141811 | 30142777 | −6.39172 | 9 | 966 |
| chr18_group024342 | chr18 | 43051286 | 43052667 | −6.39124 | 11 | 1381 |
| chr21_group008341 | chr21 | 25179165 | 25179811 | −6.3876 | 10 | 646 |
| chr21_group017991 | chr21 | 40049495 | 40050406 | −6.3871 | 14 | 911 |
| chr13_group060251 | chr13 | 1.14E+08 | 1.14E+08 | −6.38683 | 14 | 1124 |
| chr21_group022075 | chr21 | 46732919 | 46734542 | −6.38545 | 21 | 1623 |
| chr13_group015250 | chr13 | 44549355 | 44550330 | −6.38491 | 14 | 975 |
| chr21_group019793 | chr21 | 42652035 | 42653014 | −6.3846 | 13 | 979 |
| chr18_group012084 | chr18 | 24215402 | 24217071 | −6.3843 | 16 | 1669 |
| chr13_group059821 | chr13 | 1.14E+08 | 1.14E+08 | −6.38288 | 51 | 2863 |
| chr13_group050783 | chr13 | 1.01E+08 | 1.01E+08 | −6.3826 | 10 | 645 |
| chr18_group047225 | chr18 | 76064304 | 76065273 | −6.38205 | 9 | 969 |
| chr21_group001498 | chr21 | 16008476 | 16009081 | −6.38124 | 10 | 605 |
| chr18_group008760 | chr18 | 15315677 | 15316105 | −6.3792 | 9 | 428 |
| chr18_group005313 | chr18 | 10336747 | 10337392 | −6.37856 | 14 | 645 |
| chr18_group047648 | chr18 | 76459087 | 76460688 | −6.37842 | 15 | 1601 |
| chr18_group045397 | chr18 | 74063688 | 74064307 | −6.37815 | 14 | 619 |
| chr18_group018691 | chr18 | 35006560 | 35007126 | −6.37793 | 13 | 566 |
| chr13_group056621 | chr13 | 1.09E+08 | 1.09E+08 | −6.37788 | 12 | 512 |
| chr21_group016609 | chr21 | 37758307 | 37758658 | −6.37721 | 13 | 351 |
| chr18_group047072 | chr18 | 75920423 | 75921164 | −6.37716 | 12 | 741 |
| chr13_group059911 | chr13 | 1.14E+08 | 1.14E+08 | −6.37701 | 10 | 453 |
| chr18_group007692 | chr18 | 13372563 | 13373239 | −6.3768 | 9 | 676 |
| chr13_group058987 | chr13 | 1.13E+08 | 1.13E+08 | −6.37604 | 9 | 910 |
| chr18_group045960 | chr18 | 74799103 | 74800379 | −6.37601 | 38 | 1276 |
| chr13_group024403 | chr13 | 61793445 | 61794408 | −6.3751 | 12 | 963 |
| chr18_group025614 | chr18 | 44761146 | 44761944 | −6.37297 | 9 | 798 |
| chr13_group038626 | chr13 | 83397106 | 83397626 | −6.37288 | 11 | 520 |
| chr21_group020996 | chr21 | 44814741 | 44815316 | −6.37277 | 10 | 575 |
| chr21_group014110 | chr21 | 33950033 | 33951913 | −6.37241 | 21 | 1880 |
| chr18_group007537 | chr18 | 13223601 | 13224721 | −6.37225 | 12 | 1120 |
| chr18_group007800 | chr18 | 13477754 | 13478763 | −6.37136 | 11 | 1009 |
| chr13_group007647 | chr13 | 31581476 | 31583103 | −6.36879 | 14 | 1627 |
| chr18_group032052 | chr18 | 55504781 | 55505185 | −6.36671 | 9 | 404 |
| chr13_group010850 | chr13 | 37007717 | 37008246 | −6.36663 | 9 | 529 |
| chr21_group015038 | chr21 | 35817496 | 35819903 | −6.36644 | 30 | 2407 |
| chr21_group013831 | chr21 | 33579160 | 33579898 | −6.36589 | 13 | 738 |
| chr13_group060301 | chr13 | 1.14E+08 | 1.14E+08 | −6.36577 | 12 | 1279 |
| chr18_group001481 | chr18 | 3804475 | 3805445 | −6.36554 | 9 | 970 |
| chr13_group059961 | chr13 | 1.14E+08 | 1.14E+08 | −6.36371 | 76 | 5037 |
| chr18_group008420 | chr18 | 14393603 | 14394072 | −6.35731 | 17 | 469 |
| chr18_group032300 | chr18 | 55868881 | 55869842 | −6.35568 | 9 | 961 |
| chr18_group030498 | chr18 | 53331313 | 53333089 | −6.35398 | 16 | 1776 |
| chr18_group047414 | chr18 | 76238955 | 76239709 | −6.35379 | 14 | 754 |
| chr13_group059367 | chr13 | 1.13E+08 | 1.13E+08 | −6.35365 | 17 | 1610 |
| chr13_group010847 | chr13 | 37002659 | 37003182 | −6.35348 | 9 | 523 |
| chr18_group000172 | chr18 | 503387 | 503733 | −6.35338 | 11 | 346 |
| chr21_group012099 | chr21 | 31149681 | 31150366 | −6.35322 | 11 | 685 |
| chr21_group003300 | chr21 | 18956586 | 18957017 | −6.35318 | 10 | 431 |
| chr13_group005457 | chr13 | 28563204 | 28563787 | −6.35247 | 9 | 583 |
| chr13_group029261 | chr13 | 68598337 | 68598933 | −6.35169 | 10 | 596 |
| chr21_group020608 | chr21 | 44109019 | 44109343 | −6.3516 | 11 | 324 |
| chr13_group060580 | chr13 | 1.15E+08 | 1.15E+08 | −6.34918 | 9 | 551 |
| chr18_group025310 | chr18 | 44331885 | 44332747 | −6.34865 | 9 | 862 |
| chr13_group017911 | chr13 | 49593229 | 49593600 | −6.34847 | 10 | 371 |
| chr18_group036621 | chr18 | 62388241 | 62388525 | −6.34839 | 9 | 284 |
| chr18_group005946 | chr18 | 11046554 | 11048348 | −6.34565 | 19 | 1794 |
| chr18_group046661 | chr18 | 75471840 | 75473126 | −6.34519 | 11 | 1286 |
| chr18_group036014 | chr18 | 61692424 | 61693934 | −6.34416 | 19 | 1510 |
| chr18_group003346 | chr18 | 6184459 | 6185296 | −6.34293 | 9 | 837 |
| chr13_group050509 | chr13 | 1.01E+08 | 1.01E+08 | −6.34152 | 10 | 552 |

TABLE 4-continued

| Name | chr | start.pos | end.pos | median.tstat | num.cg | dmr.size |
|---|---|---|---|---|---|---|
| chr21__group015027 | chr21 | 35807062 | 35807948 | −6.34138 | 10 | 886 |
| chr13__group059639 | chr13 | 1.13E+08 | 1.13E+08 | −6.34124 | 15 | 660 |
| chr18__group039839 | chr18 | 66830343 | 66830632 | −6.34053 | 12 | 289 |
| chr21__group012741 | chr21 | 31875435 | 31875749 | −6.34025 | 10 | 314 |
| chr13__group055174 | chr13 | 1.07E+08 | 1.07E+08 | −6.33895 | 16 | 418 |
| chr21__group020581 | chr21 | 44072539 | 44073085 | −6.33799 | 12 | 546 |
| chr13__group059080 | chr13 | 1.13E+08 | 1.13E+08 | −6.33789 | 19 | 1791 |
| chr21__group017945 | chr21 | 40003105 | 40003881 | −6.33763 | 9 | 776 |
| chr13__group058738 | chr13 | 1.12E+08 | 1.12E+08 | −6.33758 | 12 | 1193 |
| chr13__group022929 | chr13 | 59187466 | 59187992 | −6.33755 | 9 | 526 |
| chr18__group006495 | chr18 | 11560717 | 11561662 | −6.33657 | 9 | 945 |
| chr13__group060560 | chr13 | 1.15E+08 | 1.15E+08 | −6.33393 | 27 | 1521 |
| chr21__group020602 | chr21 | 44099352 | 44100670 | −6.33344 | 10 | 1318 |
| chr13__group030722 | chr13 | 71370763 | 71371507 | −6.33136 | 9 | 744 |
| chr13__group007571 | chr13 | 13256545 | 13257536 | −6.33121 | 10 | 991 |
| chr18__group047162 | chr18 | 75998824 | 75999727 | −6.33006 | 22 | 903 |
| chr13__group060302 | chr13 | 1.14E+08 | 1.14E+08 | −6.32929 | 17 | 1116 |
| chr21__group018056 | chr21 | 40115628 | 40116320 | −6.32806 | 16 | 692 |
| chr13__group038882 | chr13 | 83710933 | 83711159 | −6.32798 | 9 | 226 |
| chr13__group035111 | chr13 | 77461370 | 77462300 | −6.32698 | 15 | 930 |
| chr21__group003050 | chr21 | 18699822 | 18700253 | −6.32681 | 11 | 431 |
| chr18__group010335 | chr18 | 21499606 | 21501003 | −6.32584 | 11 | 1397 |
| chr18__group030879 | chr18 | 53856326 | 53857232 | −6.32544 | 18 | 906 |
| chr13__group027482 | chr13 | 66417098 | 66419090 | −6.32465 | 26 | 1992 |
| chr18__group002755 | chr18 | 5488944 | 5489177 | −6.3236 | 12 | 233 |
| chr21__group021016 | chr21 | 44866312 | 44866729 | −6.32231 | 10 | 417 |
| chr18__group016939 | chr18 | 32463806 | 32465486 | −6.32187 | 14 | 1680 |
| chr18__group040662 | chr18 | 68146589 | 68147499 | −6.32171 | 9 | 910 |
| chr18__group048114 | chr18 | 77199581 | 77200006 | −6.32098 | 13 | 425 |
| chr18__group020771 | chr18 | 37628891 | 37629524 | −6.3207 | 9 | 633 |
| chr18__group032270 | chr18 | 55819257 | 55820329 | −6.31991 | 10 | 1072 |
| chr18__group046885 | chr18 | 75694677 | 75695986 | −6.31869 | 12 | 1309 |
| chr18__group007774 | chr18 | 13452470 | 13454126 | −6.3181 | 27 | 1656 |
| chr21__group017671 | chr21 | 39723128 | 39723501 | −6.31547 | 9 | 373 |
| chr18__group003844 | chr18 | 7136434 | 7136975 | −6.31235 | 16 | 541 |
| chr21__group021011 | chr21 | 44849347 | 44850471 | −6.31224 | 19 | 1124 |
| chr21__group010299 | chr21 | 27637720 | 27637954 | −6.30913 | 10 | 234 |
| chr18__group046303 | chr18 | 75154123 | 75155369 | −6.30785 | 11 | 1246 |
| chr13__group025945 | chr13 | 64385735 | 64386054 | −6.30592 | 21 | 319 |
| chr13__group002021 | chr13 | 23457867 | 23458364 | −6.30546 | 13 | 497 |
| chr13__group000896 | chr13 | 20869871 | 20870721 | −6.3045 | 12 | 850 |
| chr13__group053932 | chr13 | 1.05E+08 | 1.05E+08 | −6.30285 | 9 | 495 |
| chr21__group020998 | chr21 | 44816066 | 44817110 | −6.30222 | 20 | 1044 |
| chr13__group026730 | chr13 | 65532229 | 65533643 | −6.3022 | 22 | 1414 |
| chr18__group044688 | chr18 | 73182685 | 73183540 | −6.30204 | 9 | 855 |
| chr13__group042307 | chr13 | 88409557 | 88409825 | −6.30004 | 9 | 268 |
| chr18__group046289 | chr18 | 75133513 | 75133921 | −6.29859 | 17 | 408 |
| chr13__group000730 | chr13 | 20694759 | 20695143 | −6.29804 | 12 | 384 |
| chr13__group001471 | chr13 | 22224108 | 22224439 | −6.29779 | 9 | 331 |
| chr13__group050224 | chr13 | 1E+08 | 1E+08 | −6.29731 | 10 | 993 |
| chr13__group050166 | chr13 | 1E+08 | 1E+08 | −6.29677 | 10 | 377 |
| chr21__group007609 | chr21 | 24343400 | 24344184 | −6.2967 | 9 | 784 |
| chr18__group017220 | chr18 | 32762014 | 32763012 | −6.29636 | 10 | 998 |
| chr18__group046632 | chr18 | 75445182 | 75446012 | −6.29538 | 13 | 830 |
| chr21__group000497 | chr21 | 10800006 | 10800869 | −6.29287 | 12 | 863 |
| chr18__group040384 | chr18 | 67506862 | 67507926 | −6.29247 | 17 | 1064 |
| chr18__group017256 | chr18 | 32796039 | 32797399 | −6.29191 | 15 | 1360 |
| chr13__group059744 | chr13 | 1.13E+08 | 1.13E+08 | −6.29111 | 9 | 201 |
| chr13__group058916 | chr13 | 1.12E+08 | 1.12E+08 | −6.28941 | 9 | 1069 |
| chr18__group025477 | chr18 | 44561136 | 44562525 | −6.28921 | 30 | 1389 |
| chr18__group009527 | chr18 | 20109636 | 20110019 | −6.2882 | 11 | 383 |
| chr13__group057743 | chr13 | 1.1E+08 | 1.1E+08 | −6.28737 | 10 | 711 |
| chr21__group022745 | chr21 | 47470758 | 47473493 | −6.28533 | 33 | 2735 |
| chr21__group007193 | chr21 | 23912571 | 23913896 | −6.28405 | 9 | 1325 |
| chr13__group006286 | chr13 | 29843750 | 29844942 | −6.28358 | 11 | 1192 |
| chr18__group010828 | chr18 | 22204366 | 22205063 | −6.28335 | 17 | 697 |
| chr21__group013984 | chr21 | 33824026 | 33825194 | −6.28201 | 9 | 1168 |
| chr13__group049502 | chr13 | 98527422 | 98527743 | −6.28063 | 9 | 321 |
| chr18__group017498 | chr18 | 33340545 | 33341098 | −6.28036 | 12 | 553 |
| chr21__group022119 | chr21 | 46788076 | 46789299 | −6.27986 | 25 | 1223 |
| chr13__group058898 | chr13 | 1.12E+08 | 1.12E+08 | −6.27887 | 12 | 770 |
| chr13__group013110 | chr13 | 40761826 | 40762645 | −6.27826 | 12 | 819 |
| chr13__group000611 | chr13 | 20384169 | 20384981 | −6.27811 | 14 | 812 |
| chr18__group022326 | chr18 | 39488758 | 39489577 | −6.2764 | 9 | 819 |
| chr21__group016859 | chr21 | 38103965 | 38104795 | −6.27576 | 12 | 830 |
| chr13__group060336 | chr13 | 1.15E+08 | 1.15E+08 | −6.27538 | 9 | 509 |
| chr21__group003264 | chr21 | 18918814 | 18919466 | −6.27484 | 9 | 652 |
| chr18__group008800 | chr18 | 18511330 | 18512337 | −6.27321 | 10 | 1007 |

TABLE 4-continued

| Name | chr | start.pos | end.pos | median.tstat | num.cg | dmr.size |
|---|---|---|---|---|---|---|
| chr18__group006896 | chr18 | 12092582 | 12093098 | −6.2725 | 12 | 516 |
| chr21__group013937 | chr21 | 33772802 | 33774288 | −6.27169 | 13 | 1486 |
| chr18__group018510 | chr18 | 34834679 | 34835397 | −6.27146 | 10 | 718 |
| chr18__group045811 | chr18 | 74496758 | 74498178 | −6.27124 | 13 | 1420 |
| chr13__group018891 | chr13 | 51721572 | 51722565 | −6.27077 | 12 | 993 |
| chr21__group014114 | chr21 | 33953937 | 33954571 | −6.26913 | 13 | 634 |
| chr21__group022170 | chr21 | 46837744 | 46838495 | −6.2685 | 15 | 751 |
| chr21__group007560 | chr21 | 24300610 | 24301379 | −6.26768 | 9 | 769 |
| chr21__group019624 | chr21 | 42418848 | 42419797 | −6.2662 | 11 | 949 |
| chr21__group021780 | chr21 | 46321345 | 46321622 | −6.26563 | 15 | 277 |
| chr18__group006728 | chr18 | 11803700 | 11804880 | −6.26511 | 17 | 1180 |
| chr21__group012375 | chr21 | 31443711 | 31444651 | −6.26399 | 17 | 940 |
| chr18__group008019 | chr18 | 13796609 | 13796931 | −6.25796 | 9 | 322 |
| chr21__group020864 | chr21 | 44590257 | 44591966 | −6.25762 | 25 | 1709 |
| chr18__group033283 | chr18 | 57575526 | 57576125 | −6.25694 | 14 | 599 |
| chr18__group005986 | chr18 | 11086183 | 11086504 | −6.25683 | 10 | 321 |
| chr13__group040628 | chr13 | 85778903 | 85779400 | −6.25651 | 13 | 497 |
| chr21__group022839 | chr21 | 47602084 | 47602950 | −6.2556 | 24 | 866 |
| chr18__group048246 | chr18 | 77363231 | 77364659 | −6.25427 | 18 | 1428 |
| chr18__group047550 | chr18 | 76370069 | 76370734 | −6.25409 | 9 | 665 |
| chr18__group027303 | chr18 | 48636030 | 48636698 | −6.25351 | 16 | 668 |
| chr13__group049590 | chr13 | 98616762 | 98617238 | −6.2534 | 10 | 476 |
| chr18__group043061 | chr18 | 70992590 | 70993846 | −6.25296 | 17 | 1256 |
| chr21__group022692 | chr21 | 47410862 | 47411552 | −6.25232 | 14 | 690 |
| chr13__group001206 | chr13 | 21678091 | 21678860 | −6.25168 | 15 | 769 |
| chr21__group014728 | chr21 | 35050778 | 35051595 | −6.25159 | 9 | 817 |
| chr21__group020923 | chr21 | 44724225 | 44724689 | −6.25144 | 10 | 464 |
| chr13__group059950 | chr13 | 1.14E+08 | 1.14E+08 | −6.251 | 22 | 1415 |
| chr18__group015407 | chr18 | 30135898 | 30136349 | −6.25063 | 9 | 451 |
| chr18__group037452 | chr18 | 63386642 | 63387101 | −6.25002 | 10 | 459 |
| chr13__group025389 | chr13 | 63201488 | 63201842 | −6.24677 | 9 | 354 |
| chr18__group018842 | chr18 | 35130491 | 35131327 | −6.24656 | 12 | 836 |
| chr21__group006607 | chr21 | 23047817 | 23049042 | −6.24633 | 9 | 1225 |
| chr18__group045482 | chr18 | 74137640 | 74138134 | −6.24498 | 10 | 494 |
| chr18__group027702 | chr18 | 49267103 | 49267672 | −6.23955 | 13 | 569 |
| chr18__group024851 | chr18 | 43902107 | 43903056 | −6.23857 | 10 | 949 |
| chr21__group021738 | chr21 | 46178655 | 46179384 | −6.23656 | 10 | 729 |
| chr13__group060279 | chr13 | 1.14E+08 | 1.14E+08 | −6.23598 | 25 | 2157 |
| chr13__group056679 | chr13 | 1.09E+08 | 1.09E+08 | −6.23511 | 9 | 1110 |
| chr18__group047819 | chr18 | 76626122 | 76627305 | −6.23507 | 16 | 1183 |
| chr13__group055472 | chr13 | 1.08E+08 | 1.08E+08 | −6.23169 | 11 | 1145 |
| chr21__group014651 | chr21 | 34749930 | 34751086 | −6.23123 | 9 | 1156 |
| chr18__group006801 | chr18 | 11929280 | 11929698 | −6.22928 | 10 | 418 |
| chr21__group000953 | chr21 | 15148408 | 15148717 | −6.22865 | 12 | 309 |
| chr18__group010725 | chr18 | 22102362 | 22102792 | −6.22808 | 9 | 430 |
| chr18__group047472 | chr18 | 76300751 | 76301636 | −6.22772 | 10 | 885 |
| chr18__group006295 | chr18 | 11377830 | 11379511 | −6.22746 | 15 | 1681 |
| chr18__group007742 | chr18 | 13423720 | 13425136 | −6.22728 | 11 | 1416 |
| chr18__group021608 | chr18 | 38638185 | 38638859 | −6.22725 | 9 | 674 |
| chr13__group059885 | chr13 | 1.14E+08 | 1.14E+08 | −6.22594 | 10 | 754 |
| chr18__group047086 | chr18 | 75931164 | 75932132 | −6.2258 | 11 | 968 |
| chr18__group046194 | chr18 | 75052378 | 75053837 | −6.22547 | 16 | 1459 |
| chr21__group022250 | chr21 | 46966739 | 46968314 | −6.22529 | 16 | 1575 |
| chr13__group057908 | chr13 | 1.11E+08 | 1.11E+08 | −6.2248 | 10 | 1059 |
| chr21__group020310 | chr21 | 43699548 | 43700580 | −6.22297 | 12 | 1032 |
| chr13__group019005 | chr13 | 51825530 | 51826472 | −6.2229 | 22 | 942 |
| chr13__group026804 | chr13 | 65635062 | 65635622 | −6.22272 | 11 | 560 |
| chr13__group008763 | chr13 | 32984157 | 32984635 | −6.22185 | 10 | 478 |
| chr18__group002248 | chr18 | 4769287 | 4770692 | −6.22129 | 11 | 1405 |
| chr18__group010180 | chr18 | 21336815 | 21337631 | −6.22085 | 21 | 816 |
| chr13__group003350 | chr13 | 25559198 | 25559870 | −6.22084 | 9 | 672 |
| chr21__group022049 | chr21 | 46677404 | 46679684 | −6.22041 | 31 | 2280 |
| chr21__group006652 | chr21 | 23101535 | 23102422 | −6.22 | 9 | 887 |
| chr18__group018520 | chr18 | 34844358 | 34845611 | −6.21833 | 15 | 1253 |
| chr18__group043991 | chr18 | 72096098 | 72097200 | −6.21828 | 12 | 1102 |
| chr21__group022695 | chr21 | 47414379 | 47415418 | −6.21814 | 12 | 1039 |
| chr18__group018190 | chr18 | 34304238 | 34304840 | −6.21725 | 9 | 602 |
| chr13__group024506 | chr13 | 61938065 | 61939370 | −6.21656 | 13 | 1305 |
| chr13__group045625 | chr13 | 92705267 | 92706157 | −6.21633 | 11 | 890 |
| chr18__group048105 | chr18 | 77186015 | 77187219 | −6.21583 | 13 | 1204 |
| chr21__group008342 | chr21 | 25180335 | 25181431 | −6.21508 | 12 | 1096 |
| chr21__group022918 | chr21 | 48033200 | 48034510 | −6.21485 | 13 | 1310 |
| chr13__group053756 | chr13 | 1.05E+08 | 1.05E+08 | −6.21453 | 12 | 1493 |
| chr13__group060440 | chr13 | 1.15E+08 | 1.15E+08 | −6.21435 | 12 | 705 |
| chr13__group008385 | chr13 | 32322259 | 32323553 | −6.21377 | 11 | 1294 |
| chr13__group007672 | chr13 | 31606162 | 31607245 | −6.21341 | 11 | 1083 |
| chr18__group000753 | chr18 | 1790788 | 1791081 | −6.21013 | 9 | 293 |
| chr13__group039238 | chr13 | 84060793 | 84061548 | −6.20986 | 10 | 755 |

TABLE 4-continued

| Name | chr | start.pos | end.pos | median.tstat | num.cg | dmr.size |
|---|---|---|---|---|---|---|
| chr21__group020384 | chr21 | 43784828 | 43785283 | −6.20836 | 12 | 455 |
| chr18__group006897 | chr18 | 12093532 | 12094033 | −6.20835 | 23 | 501 |
| chr21__group022177 | chr21 | 46845555 | 46846642 | −6.20828 | 13 | 1087 |
| chr21__group022694 | chr21 | 47412862 | 47414015 | −6.20785 | 17 | 1153 |
| chr21__group008193 | chr21 | 25028224 | 25028703 | −6.2072 | 10 | 479 |
| chr13__group039282 | chr13 | 84109245 | 84110570 | −6.20487 | 12 | 1325 |
| chr21__group003187 | chr21 | 18836767 | 18837821 | −6.20329 | 13 | 1054 |
| chr13__group004759 | chr13 | 27494330 | 27495597 | −6.20216 | 10 | 1267 |
| chr18__group017561 | chr18 | 33397701 | 33398505 | −6.19934 | 9 | 804 |
| chr18__group008484 | chr18 | 14543331 | 14543661 | −6.19885 | 21 | 330 |
| chr13__group060317 | chr13 | 1.15E+08 | 1.15E+08 | −6.19841 | 13 | 901 |
| chr18__group046499 | chr18 | 75334284 | 75335149 | −6.19752 | 11 | 865 |
| chr21__group014464 | chr21 | 34436252 | 34436741 | −6.19617 | 9 | 489 |
| chr21__group022135 | chr21 | 46803461 | 46805420 | −6.19359 | 28 | 1959 |
| chr21__group017704 | chr21 | 39754503 | 39755732 | −6.19298 | 10 | 1229 |
| chr13__group005716 | chr13 | 29100661 | 29101401 | −6.19261 | 11 | 740 |
| chr21__group021450 | chr21 | 45788566 | 45788853 | −6.19204 | 9 | 287 |
| chr13__group060402 | chr13 | 1.15E+08 | 1.15E+08 | −6.19143 | 11 | 955 |
| chr18__group045574 | chr18 | 74249061 | 74250574 | −6.18858 | 9 | 1513 |
| chr18__group042441 | chr18 | 70187007 | 70188569 | −6.18856 | 18 | 1562 |
| chr13__group004645 | chr13 | 27394501 | 27395909 | −6.18823 | 12 | 1408 |
| chr18__group002496 | chr18 | 5123105 | 5123745 | −6.18795 | 9 | 640 |
| chr18__group007886 | chr18 | 13576144 | 13576866 | −6.1873 | 11 | 722 |
| chr18__group042780 | chr18 | 70555713 | 70557524 | −6.18671 | 15 | 1811 |
| chr13__group011362 | chr13 | 37789892 | 37790580 | −6.18619 | 10 | 688 |
| chr13__group025962 | chr13 | 64411884 | 64414552 | −6.18444 | 28 | 2668 |
| chr13__group050963 | chr13 | 1.02E+08 | 1.02E+08 | −6.18147 | 14 | 693 |
| chr13__group015427 | chr13 | 45129420 | 45129720 | −6.17969 | 11 | 300 |
| chr13__group042577 | chr13 | 88710546 | 88710991 | −6.17927 | 9 | 445 |
| chr13__group004954 | chr13 | 27886752 | 27887765 | −6.17832 | 11 | 1013 |
| chr18__group014056 | chr18 | 27453222 | 27454228 | −6.17782 | 10 | 1006 |
| chr13__group032519 | chr13 | 73560700 | 73561470 | −6.17771 | 15 | 770 |
| chr21__group022069 | chr21 | 46726821 | 46728144 | −6.1776 | 20 | 1323 |
| chr18__group013531 | chr18 | 26536059 | 26536586 | −6.17746 | 9 | 527 |
| chr18__group048072 | chr18 | 77141642 | 77144871 | −6.17634 | 37 | 3229 |
| chr18__group046011 | chr18 | 74877639 | 74879786 | −6.17624 | 24 | 2147 |
| chr21__group013920 | chr21 | 33723358 | 33724698 | −6.17563 | 15 | 1340 |
| chr18__group016912 | chr18 | 32441220 | 32441874 | −6.17544 | 12 | 654 |
| chr18__group018536 | chr18 | 34864405 | 34865363 | −6.17519 | 10 | 958 |
| chr13__group046267 | chr13 | 93683324 | 93683848 | −6.17499 | 13 | 524 |
| chr13__group027103 | chr13 | 65986573 | 65987538 | −6.17157 | 9 | 965 |
| chr13__group003683 | chr13 | 26028282 | 26029692 | −6.17085 | 10 | 1410 |
| chr18__group045541 | chr18 | 74212470 | 74212937 | −6.17078 | 9 | 467 |
| chr21__group000181 | chr21 | 9828976 | 9830820 | −6.16745 | 20 | 1844 |
| chr18__group007605 | chr18 | 13293722 | 13294389 | −6.1673 | 10 | 667 |
| chr21__group016850 | chr21 | 38095495 | 38096193 | −6.16658 | 9 | 698 |
| chr13__group012548 | chr13 | 39939402 | 39940005 | −6.1664 | 9 | 603 |
| chr13__group024405 | chr13 | 61795444 | 61796779 | −6.16515 | 18 | 1335 |
| chr18__group023117 | chr18 | 41178406 | 41178768 | −6.16512 | 10 | 362 |
| chr18__group006690 | chr18 | 11757326 | 11757879 | −6.16453 | 9 | 553 |
| chr18__group006114 | chr18 | 11208415 | 11208814 | −6.1645 | 9 | 399 |
| chr18__group045156 | chr18 | 73767307 | 73769087 | −6.16394 | 22 | 1780 |
| chr13__group039480 | chr13 | 84346966 | 84347517 | −6.16357 | 9 | 551 |
| chr13__group030516 | chr13 | 71163445 | 71165039 | −6.16127 | 13 | 1594 |
| chr13__group060230 | chr13 | 1.14E+08 | 1.14E+08 | −6.16116 | 14 | 1075 |
| chr18__group018889 | chr18 | 35178891 | 35179661 | −6.15989 | 9 | 770 |
| chr21__group006997 | chr21 | 23562894 | 23563106 | −6.15932 | 10 | 212 |
| chr21__group017960 | chr21 | 40019832 | 40021360 | −6.15597 | 15 | 1528 |
| chr18__group048223 | chr18 | 77338679 | 77341124 | −6.15464 | 32 | 2445 |
| chr21__group001068 | chr21 | 15450682 | 15451372 | −6.15111 | 12 | 690 |
| chr21__group021771 | chr21 | 46310285 | 46310548 | −6.15099 | 10 | 263 |
| chr18__group007569 | chr18 | 13254489 | 13255348 | −6.14823 | 9 | 859 |
| chr21__group022801 | chr21 | 47544212 | 47545320 | −6.14792 | 16 | 1108 |
| chr13__group055042 | chr13 | 1.07E+08 | 1.07E+08 | −6.14626 | 10 | 650 |
| chr13__group000253 | chr13 | 19663554 | 19664404 | −6.14552 | 11 | 850 |
| chr13__group005095 | chr13 | 28065374 | 28065787 | −6.14412 | 11 | 413 |
| chr18__group047046 | chr18 | 75890993 | 75892123 | −6.1439 | 11 | 1130 |
| chr13__group050572 | chr13 | 1.01E+08 | 1.01E+08 | −6.14193 | 10 | 989 |
| chr13__group060226 | chr13 | 1.14E+08 | 1.14E+08 | −6.14045 | 21 | 1403 |
| chr18__group047192 | chr18 | 76027060 | 76028905 | −6.1399 | 27 | 1845 |
| chr13__group060462 | chr13 | 1.15E+08 | 1.15E+08 | −6.13886 | 27 | 1347 |
| chr21__group000526 | chr21 | 10850776 | 10852682 | −6.1377 | 28 | 1906 |
| chr18__group007954 | chr18 | 13651012 | 13652225 | −6.1376 | 9 | 1213 |
| chr13__group005047 | chr13 | 27987546 | 27988105 | −6.13708 | 11 | 559 |
| chr21__group022568 | chr21 | 47286343 | 47288685 | −6.13621 | 33 | 2342 |
| chr13__group060553 | chr13 | 1.15E+08 | 1.15E+08 | −6.13591 | 11 | 305 |
| chr21__group000681 | chr21 | 11128401 | 11129690 | −6.13542 | 14 | 1289 |
| chr21__group022081 | chr21 | 46739791 | 46740873 | −6.13494 | 11 | 1082 |

TABLE 4-continued

| Name | chr | start.pos | end.pos | median.tstat | num.cg | dmr.size |
|---|---|---|---|---|---|---|
| chr18_group003838 | chr18 | 7118373 | 7118702 | −6.13349 | 9 | 329 |
| chr13_group045699 | chr13 | 92811527 | 92812400 | −6.13342 | 10 | 873 |
| chr13_group019579 | chr13 | 53344321 | 53346765 | −6.13322 | 16 | 2444 |
| chr13_group057327 | chr13 | 1.1E+08 | 1.1E+08 | −6.13315 | 10 | 1005 |
| chr18_group046261 | chr18 | 75110384 | 75111219 | −6.13097 | 10 | 835 |
| chr13_group015761 | chr13 | 45896485 | 45897033 | −6.13064 | 13 | 548 |
| chr13_group004573 | chr13 | 27324901 | 27325813 | −6.13058 | 10 | 912 |
| chr21_group016664 | chr21 | 37872280 | 37872664 | −6.13057 | 11 | 384 |
| chr21_group022164 | chr21 | 46832084 | 46834741 | −6.13003 | 26 | 2657 |
| chr18_group016951 | chr18 | 32475108 | 32476064 | −6.12969 | 9 | 956 |
| chr18_group002042 | chr18 | 4477381 | 4477998 | −6.12933 | 22 | 617 |
| chr18_group010363 | chr18 | 21523203 | 21524065 | −6.12788 | 10 | 862 |
| chr21_group014328 | chr21 | 34292650 | 34293402 | −6.12712 | 9 | 752 |
| chr18_group043419 | chr18 | 71423367 | 71424280 | −6.1246 | 12 | 913 |
| chr18_group045896 | chr18 | 74721415 | 74721797 | −6.12428 | 13 | 382 |
| chr13_group058667 | chr13 | 1.12E+08 | 1.12E+08 | −6.12399 | 10 | 1380 |
| chr21_group021886 | chr21 | 46480059 | 46480976 | −6.12262 | 11 | 917 |
| chr18_group014159 | chr18 | 27593349 | 27594255 | −6.12209 | 9 | 906 |
| chr21_group000510 | chr21 | 10812986 | 10813880 | −6.12173 | 14 | 894 |
| chr18_group047602 | chr18 | 76420827 | 76421607 | −6.12019 | 12 | 780 |
| chr18_group009291 | chr18 | 19847457 | 19847994 | −6.12011 | 11 | 537 |
| chr18_group005465 | chr18 | 10516567 | 10517574 | −6.11997 | 10 | 1007 |
| chr13_group059981 | chr13 | 1.14E+08 | 1.14E+08 | −6.11972 | 12 | 679 |
| chr13_group015816 | chr13 | 46020310 | 46021551 | −6.11933 | 14 | 1241 |
| chr18_group006689 | chr18 | 11755163 | 11756012 | −6.11827 | 13 | 849 |
| chr18_group045874 | chr18 | 74701417 | 74702214 | −6.11771 | 15 | 797 |
| chr13_group006526 | chr13 | 30096072 | 30096511 | −6.11761 | 9 | 439 |
| chr21_group022307 | chr21 | 47031252 | 47032445 | −6.11649 | 12 | 1193 |
| chr18_group043694 | chr18 | 71713124 | 71713928 | −6.1163 | 10 | 804 |
| chr18_group002507 | chr18 | 5132686 | 5133223 | −6.11596 | 11 | 537 |
| chr18_group032492 | chr18 | 56158059 | 56158875 | −6.11463 | 9 | 816 |
| chr18_group048073 | chr18 | 77145768 | 77147071 | −6.11457 | 17 | 1303 |
| chr18_group006405 | chr18 | 11478823 | 11479889 | −6.11354 | 9 | 1066 |
| chr13_group059974 | chr13 | 1.14E+08 | 1.14E+08 | −6.11253 | 12 | 268 |
| chr18_group006078 | chr18 | 11174117 | 11174558 | −6.11155 | 9 | 441 |
| chr13_group024409 | chr13 | 61799995 | 61802263 | −6.11072 | 21 | 2268 |
| chr18_group048241 | chr18 | 77358157 | 77358765 | −6.10936 | 11 | 608 |
| chr18_group018612 | chr18 | 34931722 | 34932488 | −6.10801 | 10 | 766 |
| chr18_group010532 | chr18 | 21682422 | 21683537 | −6.10763 | 9 | 1115 |
| chr21_group022217 | chr21 | 46895911 | 46896291 | −6.10756 | 9 | 380 |
| chr13_group006272 | chr13 | 29829798 | 29830633 | −6.1075 | 9 | 835 |
| chr21_group021336 | chr21 | 45608350 | 45608690 | −6.10619 | 9 | 340 |
| chr13_group002098 | chr13 | 23673389 | 23673921 | −6.10577 | 9 | 532 |
| chr18_group034864 | chr18 | 59447913 | 59449097 | −6.10502 | 9 | 1184 |
| chr21_group014560 | chr21 | 34545387 | 34545997 | −6.10169 | 10 | 610 |
| chr18_group032768 | chr18 | 56736983 | 56737636 | −6.10068 | 10 | 653 |
| chr21_group022734 | chr21 | 47459470 | 47460298 | −6.09851 | 9 | 828 |
| chr13_group010362 | chr13 | 36339857 | 36340695 | −6.09741 | 13 | 838 |
| chr18_group048213 | chr18 | 77326021 | 77326796 | −6.09711 | 10 | 775 |
| chr13_group059563 | chr13 | 1.13E+08 | 1.13E+08 | −6.09671 | 16 | 1170 |
| chr21_group020177 | chr21 | 43525910 | 43527369 | −6.0961 | 10 | 1459 |
| chr13_group058168 | chr13 | 1.11E+08 | 1.11E+08 | −6.09553 | 12 | 909 |
| chr18_group047732 | chr18 | 76538831 | 76540055 | −6.09454 | 12 | 1224 |
| chr18_group003023 | chr18 | 5888948 | 5890098 | −6.09352 | 11 | 1150 |
| chr18_group006917 | chr18 | 12112774 | 12113619 | −6.09327 | 12 | 845 |
| chr21_group020407 | chr21 | 43812309 | 43813171 | −6.09235 | 10 | 862 |
| chr18_group009213 | chr18 | 19757292 | 19758656 | −6.09145 | 22 | 1364 |
| chr21_group022150 | chr21 | 46815796 | 46816708 | −6.09117 | 14 | 912 |
| chr18_group008316 | chr18 | 14149611 | 14151261 | −6.0909 | 19 | 1650 |
| chr18_group006238 | chr18 | 11328436 | 11328876 | −6.08871 | 9 | 440 |
| chr13_group049785 | chr13 | 98980799 | 98981490 | −6.08825 | 12 | 691 |
| chr21_group014556 | chr21 | 34541069 | 34542169 | −6.08811 | 10 | 1100 |
| chr13_group019288 | chr13 | 52506752 | 52507954 | −6.08751 | 10 | 1202 |
| chr13_group059685 | chr13 | 1.13E+08 | 1.13E+08 | −6.08705 | 10 | 530 |
| chr21_group016067 | chr21 | 37021222 | 37022159 | −6.08664 | 9 | 937 |
| chr13_group022019 | chr13 | 57860676 | 57861281 | −6.08468 | 30 | 605 |
| chr21_group021821 | chr21 | 46412614 | 46414124 | −6.08415 | 16 | 1510 |
| chr18_group001407 | chr18 | 3729126 | 3729883 | −6.0832 | 10 | 757 |
| chr13_group007398 | chr13 | 31337393 | 31338717 | −6.08294 | 10 | 1324 |
| chr13_group036425 | chr13 | 79692939 | 79693478 | −6.08286 | 14 | 539 |
| chr21_group007903 | chr21 | 24703119 | 24704303 | −6.08087 | 9 | 1184 |
| chr21_group022517 | chr21 | 47239513 | 47240325 | −6.07742 | 9 | 812 |
| chr18_group008022 | chr18 | 13798845 | 13799811 | −6.07695 | 9 | 966 |
| chr18_group045931 | chr18 | 74755822 | 74756547 | −6.07581 | 10 | 725 |
| chr18_group048287 | chr18 | 77400994 | 77401900 | −6.07032 | 9 | 906 |
| chr18_group024736 | chr18 | 43675999 | 43676905 | −6.07032 | 20 | 906 |
| chr13_group059322 | chr13 | 1.13E+08 | 1.13E+08 | −6.06917 | 12 | 605 |
| chr18_group045977 | chr18 | 74832279 | 74832770 | −6.06803 | 9 | 491 |

TABLE 4-continued

| Name | chr | start.pos | end.pos | median.tstat | num.cg | dmr.size |
|---|---|---|---|---|---|---|
| chr18__group045515 | chr18 | 74171760 | 74172440 | −6.06737 | 9 | 680 |
| chr21__group014724 | chr21 | 35043505 | 35043858 | −6.06345 | 11 | 353 |
| chr13__group053302 | chr13 | 1.05E+08 | 1.05E+08 | −6.06252 | 11 | 566 |
| chr18__group046941 | chr18 | 75795054 | 75796373 | −6.06136 | 11 | 1319 |
| chr18__group006807 | chr18 | 11945890 | 11946677 | −6.05913 | 9 | 787 |
| chr18__group007747 | chr18 | 13429126 | 13430041 | −6.059 | 13 | 915 |
| chr13__group003009 | chr13 | 24901917 | 24902088 | −6.05824 | 9 | 171 |
| chr18__group046008 | chr18 | 74875430 | 74876389 | −6.05795 | 12 | 959 |
| chr13__group003003 | chr13 | 24895356 | 24896163 | −6.05707 | 9 | 807 |
| chr13__group010928 | chr13 | 37089033 | 37089661 | −6.05705 | 9 | 628 |
| chr21__group000229 | chr21 | 9880576 | 9882201 | −6.05611 | 33 | 1625 |
| chr18__group005129 | chr18 | 10009790 | 10010855 | −6.05453 | 15 | 1065 |
| chr13__group020229 | chr13 | 54085294 | 54086226 | −6.05389 | 9 | 932 |
| chr13__group047371 | chr13 | 95248976 | 95249423 | −6.0533 | 9 | 447 |
| chr18__group009121 | chr18 | 19634662 | 19635555 | −6.05242 | 9 | 893 |
| chr18__group048436 | chr18 | 77629407 | 77630183 | −6.0522 | 11 | 776 |
| chr13__group058305 | chr13 | 1.11E+08 | 1.11E+08 | −6.05209 | 20 | 947 |
| chr18__group045962 | chr18 | 74802095 | 74802644 | −6.05204 | 9 | 549 |
| chr13__group060252 | chr13 | 1.14E+08 | 1.14E+08 | −6.04974 | 12 | 938 |
| chr13__group001512 | chr13 | 22280683 | 22281479 | −6.04957 | 10 | 796 |
| chr13__group005357 | chr13 | 28430454 | 28432765 | −6.04876 | 28 | 2311 |
| chr18__group044047 | chr18 | 72184339 | 72184922 | −6.0487 | 12 | 583 |
| chr21__group008739 | chr21 | 25580698 | 25581924 | −6.04262 | 34 | 1226 |
| chr18__group018822 | chr18 | 35115256 | 35115796 | −6.0413 | 9 | 540 |
| chr21__group020609 | chr21 | 44109740 | 44110663 | −6.03945 | 16 | 923 |
| chr21__group022796 | chr21 | 47536716 | 47539774 | −6.03862 | 43 | 3058 |
| chr21__group014693 | chr21 | 34868188 | 34868914 | −6.03849 | 10 | 726 |
| chr21__group022058 | chr21 | 46710899 | 46711935 | −6.0378 | 15 | 1036 |
| chr18__group018958 | chr18 | 35249674 | 35250821 | −6.03666 | 10 | 1147 |
| chr13__group029040 | chr13 | 68343593 | 68344132 | −6.03286 | 16 | 539 |
| chr18__group047024 | chr18 | 75866758 | 75867573 | −6.03191 | 9 | 815 |
| chr21__group022085 | chr21 | 46742978 | 46744028 | −6.03157 | 20 | 1050 |
| chr21__group020575 | chr21 | 44065477 | 44066335 | −6.03045 | 11 | 858 |
| chr18__group047547 | chr18 | 76364925 | 76365731 | −6.03036 | 10 | 806 |
| chr13__group059913 | chr13 | 1.14E+08 | 1.14E+08 | −6.02905 | 18 | 1173 |
| chr21__group020569 | chr21 | 44057291 | 44057854 | −6.02582 | 10 | 563 |
| chr21__group020753 | chr21 | 44359871 | 44360927 | −6.02547 | 11 | 1056 |
| chr13__group060487 | chr13 | 1.15E+08 | 1.15E+08 | −6.02469 | 25 | 1935 |
| chr21__group022755 | chr21 | 47483995 | 47484551 | −6.02457 | 10 | 556 |
| chr18__group045665 | chr18 | 74356095 | 74356803 | −6.02061 | 9 | 708 |
| chr13__group059553 | chr13 | 1.13E+08 | 1.13E+08 | −6.01946 | 11 | 906 |
| chr21__group020548 | chr21 | 44037392 | 44038590 | −6.0169 | 17 | 1198 |
| chr13__group042836 | chr13 | 89001754 | 89002103 | −6.01632 | 10 | 349 |
| chr18__group038331 | chr18 | 64403495 | 64404953 | −6.01572 | 16 | 1458 |
| chr21__group020319 | chr21 | 43707417 | 43708632 | −6.0134 | 19 | 1215 |
| chr13__group010569 | chr13 | 36550601 | 36551051 | −6.01319 | 9 | 450 |
| chr18__group001084 | chr18 | 2880101 | 2881156 | −6.01218 | 12 | 1055 |
| chr13__group059386 | chr13 | 1.13E+08 | 1.13E+08 | −6.01179 | 9 | 463 |
| chr18__group021709 | chr18 | 38764337 | 38764807 | −6.00993 | 9 | 470 |
| chr18__group005663 | chr18 | 10759375 | 10760447 | −6.00596 | 11 | 1072 |
| chr18__group034972 | chr18 | 59579532 | 59580296 | −6.0042 | 9 | 764 |
| chr13__group058255 | chr13 | 1.11E+08 | 1.11E+08 | −6.00266 | 9 | 852 |
| chr18__group019974 | chr18 | 36321411 | 36321701 | −6.00241 | 10 | 290 |
| chr13__group032751 | chr13 | 74235970 | 74236454 | −6.00167 | 11 | 484 |
| chr13__group055248 | chr13 | 1.07E+08 | 1.07E+08 | −6.00163 | 11 | 973 |
| chr18__group024708 | chr18 | 43554766 | 43555196 | −6.00107 | 10 | 430 |
| chr13__group050175 | chr13 | 1E+08 | 1E+08 | −5.99985 | 12 | 1300 |
| chr21__group022210 | chr21 | 46885536 | 46886901 | −5.99951 | 15 | 1365 |
| chr21__group021430 | chr21 | 45765158 | 45766243 | −5.99782 | 9 | 1085 |
| chr13__group059638 | chr13 | 1.13E+08 | 1.13E+08 | −5.99779 | 16 | 1377 |
| chr18__group044996 | chr18 | 73558804 | 73559248 | −5.99757 | 13 | 444 |
| chr18__group047031 | chr18 | 75873577 | 75874167 | −5.99746 | 9 | 590 |
| chr18__group048374 | chr18 | 77563552 | 77564518 | −5.99664 | 11 | 966 |
| chr21__group020584 | chr21 | 44076934 | 44078125 | −5.99572 | 11 | 1191 |
| chr18__group045507 | chr18 | 74158520 | 74159224 | −5.99292 | 9 | 704 |
| chr13__group002332 | chr13 | 23954423 | 23955490 | −5.99101 | 9 | 1067 |
| chr21__group000891 | chr21 | 14981578 | 14982696 | −5.98715 | 12 | 1118 |
| chr18__group008473 | chr18 | 14486866 | 14487750 | −5.98712 | 22 | 884 |
| chr21__group020611 | chr21 | 44112195 | 44113509 | −5.98631 | 23 | 1314 |
| chr21__group021555 | chr21 | 45934512 | 45935407 | −5.9859 | 9 | 895 |
| chr13__group023117 | chr13 | 59433026 | 59433849 | −5.98208 | 16 | 823 |
| chr21__group022235 | chr21 | 46925847 | 46926971 | −5.98081 | 13 | 1124 |
| chr13__group028544 | chr13 | 67780048 | 67780581 | −5.97848 | 9 | 533 |
| chr18__group001560 | chr18 | 3878874 | 3879882 | −5.97756 | 10 | 1008 |
| chr18__group007533 | chr18 | 13215118 | 13215833 | −5.97532 | 12 | 715 |
| chr18__group046647 | chr18 | 75458828 | 75460216 | −5.97416 | 11 | 1388 |
| chr21__group022272 | chr21 | 46996674 | 47000074 | −5.97412 | 52 | 3400 |
| chr18__group033965 | chr18 | 58331275 | 58332082 | −5.97408 | 9 | 807 |

TABLE 4-continued

| Name | chr | start.pos | end.pos | median.tstat | num.cg | dmr.size |
|---|---|---|---|---|---|---|
| chr13__group058600 | chr13 | 1.12E+08 | 1.12E+08 | −5.97141 | 18 | 1903 |
| chr18__group003913 | chr18 | 7233446 | 7234405 | −5.97055 | 10 | 959 |
| chr18__group008768 | chr18 | 15330243 | 15330851 | −5.96943 | 18 | 608 |
| chr13__group004806 | chr13 | 27540186 | 27540747 | −5.96886 | 10 | 561 |
| chr13__group049328 | chr13 | 98305546 | 98306300 | −5.96704 | 10 | 754 |
| chr13__group034657 | chr13 | 76869086 | 76869737 | −5.96584 | 10 | 651 |
| chr21__group022536 | chr21 | 47257206 | 47258180 | −5.96128 | 11 | 974 |
| chr13__group060631 | chr13 | 1.15E+08 | 1.15E+08 | −5.96101 | 9 | 764 |
| chr18__group035164 | chr18 | 60055913 | 60057124 | −5.95938 | 9 | 1211 |
| chr18__group045945 | chr18 | 74783768 | 74784511 | −5.95864 | 9 | 743 |
| chr18__group024763 | chr18 | 43737298 | 43738168 | −5.9575 | 9 | 870 |
| chr21__group001014 | chr21 | 15351723 | 15352130 | −5.95435 | 9 | 407 |
| chr18__group045112 | chr18 | 73706403 | 73707235 | −5.95391 | 12 | 832 |
| chr21__group000523 | chr21 | 10845644 | 10846233 | −5.95355 | 9 | 589 |
| chr18__group035561 | chr18 | 60964978 | 60965621 | −5.95334 | 11 | 643 |
| chr21__group022572 | chr21 | 47292241 | 47294031 | −5.95283 | 19 | 1790 |
| chr18__group048181 | chr18 | 77289068 | 77289328 | −5.95279 | 11 | 260 |
| chr21__group000063 | chr21 | 9540118 | 9540877 | −5.95112 | 25 | 759 |
| chr21__group021424 | chr21 | 45753273 | 45754037 | −5.94997 | 14 | 764 |
| chr21__group022486 | chr21 | 47212995 | 47213702 | −5.94954 | 15 | 707 |
| chr18__group042963 | chr18 | 70765880 | 70766857 | −5.94881 | 9 | 977 |
| chr18__group047324 | chr18 | 76152031 | 76153022 | −5.94695 | 12 | 991 |
| chr18__group025939 | chr18 | 45121106 | 45121568 | −5.94569 | 13 | 462 |
| chr13__group050188 | chr13 | 1E+08 | 1E+08 | −5.94373 | 15 | 1287 |
| chr18__group006666 | chr18 | 11730891 | 11731845 | −5.94255 | 10 | 954 |
| chr21__group021848 | chr21 | 46446799 | 46447570 | −5.94209 | 12 | 771 |
| chr18__group048142 | chr18 | 77236653 | 77237509 | −5.94184 | 13 | 856 |
| chr13__group013115 | chr13 | 40767066 | 40768106 | −5.94136 | 10 | 1040 |
| chr18__group007812 | chr18 | 13489441 | 13490711 | −5.93924 | 10 | 1270 |
| chr18__group030049 | chr18 | 52830597 | 52831362 | −5.93877 | 9 | 765 |
| chr18__group047357 | chr18 | 76186122 | 76187750 | −5.93828 | 10 | 1628 |
| chr18__group047752 | chr18 | 76556723 | 76557384 | −5.93818 | 19 | 661 |
| chr21__group022819 | chr21 | 47569290 | 47571044 | −5.9368 | 15 | 1754 |
| chr18__group006686 | chr18 | 11750037 | 11751177 | −5.93395 | 16 | 1140 |
| chr21__group014314 | chr21 | 34278076 | 34279565 | −5.93351 | 9 | 1489 |
| chr13__group059912 | chr13 | 1.14E+08 | 1.14E+08 | −5.93252 | 36 | 1518 |
| chr18__group043626 | chr18 | 71650404 | 71651015 | −5.9305 | 9 | 611 |
| chr21__group021330 | chr21 | 45602503 | 45603239 | −5.93018 | 13 | 736 |
| chr21__group012225 | chr21 | 31277966 | 31278421 | −5.93007 | 10 | 455 |
| chr18__group017327 | chr18 | 32940948 | 32941468 | −5.9267 | 9 | 520 |
| chr21__group020312 | chr21 | 43701551 | 43702059 | −5.92562 | 10 | 508 |
| chr13__group057744 | chr13 | 1.1E+08 | 1.1E+08 | −5.92538 | 13 | 1102 |
| chr18__group007917 | chr18 | 13616354 | 13617218 | −5.92181 | 12 | 864 |
| chr13__group028959 | chr13 | 68259998 | 68260501 | −5.91703 | 14 | 503 |
| chr18__group042668 | chr18 | 70444577 | 70445349 | −5.91417 | 10 | 772 |
| chr13__group010380 | chr13 | 36358623 | 36360568 | −5.91173 | 14 | 1945 |
| chr21__group021017 | chr21 | 44870068 | 44870457 | −5.90798 | 9 | 389 |
| chr13__group003018 | chr13 | 24911579 | 24913352 | −5.90745 | 21 | 1773 |
| chr13__group059971 | chr13 | 1.14E+08 | 1.14E+08 | −5.90683 | 29 | 2272 |
| chr21__group000258 | chr21 | 9908867 | 9910374 | −5.90648 | 17 | 1507 |
| chr13__group005033 | chr13 | 27968728 | 27969509 | −5.90602 | 9 | 781 |
| chr18__group000028 | chr18 | 72674 | 73921 | −5.90467 | 33 | 1247 |
| chr18__group025238 | chr18 | 44265282 | 44266708 | −5.90413 | 11 | 1426 |
| chr13__group060241 | chr13 | 1.14E+08 | 1.14E+08 | −5.90366 | 18 | 1124 |
| chr21__group009348 | chr21 | 26208063 | 26208771 | −5.90279 | 16 | 708 |
| chr18__group048205 | chr18 | 77317008 | 77318366 | −5.90049 | 13 | 1358 |
| chr18__group026973 | chr18 | 47742174 | 47742921 | −5.89925 | 9 | 747 |
| chr13__group007548 | chr13 | 31490294 | 31490687 | −5.89602 | 10 | 393 |
| chr13__group007644 | chr13 | 31579030 | 31579686 | −5.89584 | 15 | 656 |
| chr21__group002065 | chr21 | 17445561 | 17446064 | −5.89277 | 9 | 503 |
| chr18__group047064 | chr18 | 75911285 | 75912439 | −5.88992 | 9 | 1154 |
| chr13__group059326 | chr13 | 1.13E+08 | 1.13E+08 | −5.88825 | 24 | 2427 |
| chr13__group028436 | chr13 | 67687702 | 67687961 | −5.88667 | 9 | 259 |
| chr18__group024989 | chr18 | 44039887 | 44040956 | −5.88545 | 13 | 1069 |
| chr21__group019893 | chr21 | 42824143 | 42825001 | −5.88478 | 11 | 858 |
| chr18__group005502 | chr18 | 10607478 | 10608213 | −5.88458 | 22 | 735 |
| chr13__group049605 | chr13 | 98681884 | 98682550 | −5.88103 | 12 | 666 |
| chr21__group017665 | chr21 | 39715301 | 39715946 | −5.88002 | 9 | 645 |
| chr18__group047733 | chr18 | 76541006 | 76541725 | −5.87851 | 14 | 719 |
| chr13__group006560 | chr13 | 30127876 | 30128622 | −5.87562 | 12 | 746 |
| chr13__group013745 | chr13 | 41972173 | 41973251 | −5.87338 | 11 | 1078 |
| chr13__group007733 | chr13 | 31665865 | 31666631 | −5.87326 | 9 | 766 |
| chr13__group059320 | chr13 | 1.13E+08 | 1.13E+08 | −5.8725 | 10 | 770 |
| chr13__group013608 | chr13 | 41632906 | 41633175 | −5.8723 | 9 | 269 |
| chr13__group019027 | chr13 | 51854716 | 51855368 | −5.87105 | 10 | 652 |
| chr21__group003143 | chr21 | 18792889 | 18793317 | −5.87091 | 11 | 428 |
| chr18__group024988 | chr18 | 44036922 | 44038730 | −5.86731 | 15 | 1808 |
| chr18__group048183 | chr18 | 77290836 | 77291748 | −5.86562 | 19 | 912 |

TABLE 4-continued

| Name | chr | start.pos | end.pos | median.tstat | num.cg | dmr.size |
|---|---|---|---|---|---|---|
| chr13_group002989 | chr13 | 24882686 | 24883063 | −5.86414 | 14 | 377 |
| chr18_group000776 | chr18 | 1852015 | 1852283 | −5.86335 | 13 | 268 |
| chr21_group000666 | chr21 | 11114822 | 11115670 | −5.86175 | 11 | 848 |
| chr13_group059934 | chr13 | 1.14E+08 | 1.14E+08 | −5.85773 | 14 | 795 |
| chr18_group047065 | chr18 | 75912866 | 75913564 | −5.85719 | 11 | 698 |
| chr18_group009920 | chr18 | 20780515 | 20780977 | −5.85652 | 9 | 462 |
| chr18_group007847 | chr18 | 13526717 | 13527945 | −5.85612 | 13 | 1228 |
| chr18_group045511 | chr18 | 74167811 | 74168556 | −5.85568 | 11 | 745 |
| chr13_group059838 | chr13 | 1.14E+08 | 1.14E+08 | −5.85552 | 12 | 564 |
| chr18_group010544 | chr18 | 21692621 | 21694169 | −5.85421 | 18 | 1548 |
| chr18_group048139 | chr18 | 77231214 | 77232819 | −5.85402 | 11 | 1605 |
| chr18_group048248 | chr18 | 77365686 | 77366683 | −5.85317 | 9 | 997 |
| chr18_group037747 | chr18 | 63720658 | 63721803 | −5.85066 | 9 | 1145 |
| chr18_group048445 | chr18 | 77640715 | 77641869 | −5.84676 | 13 | 1154 |
| chr18_group045521 | chr18 | 74177098 | 74177787 | −5.84665 | 11 | 689 |
| chr21_group008174 | chr21 | 25005728 | 25007077 | −5.84508 | 10 | 1349 |
| chr18_group007957 | chr18 | 13653748 | 13654696 | −5.84492 | 11 | 948 |
| chr18_group043509 | chr18 | 71532218 | 71532932 | −5.84467 | 9 | 714 |
| chr21_group014250 | chr21 | 34216775 | 34217627 | −5.84366 | 10 | 852 |
| chr18_group045635 | chr18 | 74323499 | 74324688 | −5.84267 | 24 | 1189 |
| chr18_group045505 | chr18 | 74156128 | 74157127 | −5.84088 | 12 | 999 |
| chr18_group044383 | chr18 | 72881886 | 72882602 | −5.84021 | 12 | 716 |
| chr18_group045729 | chr18 | 74414891 | 74415672 | −5.83748 | 9 | 781 |
| chr18_group018717 | chr18 | 35026764 | 35027521 | −5.8354 | 9 | 757 |
| chr18_group021144 | chr18 | 38054371 | 38054909 | −5.83331 | 10 | 538 |
| chr13_group004702 | chr13 | 27446283 | 27446806 | −5.83212 | 10 | 523 |
| chr13_group051675 | chr13 | 1.03E+08 | 1.03E+08 | −5.83152 | 9 | 835 |
| chr21_group020941 | chr21 | 44741617 | 44742565 | −5.82976 | 9 | 948 |
| chr21_group022160 | chr21 | 46826475 | 46827325 | −5.82969 | 11 | 850 |
| chr21_group022524 | chr21 | 47247977 | 47249057 | −5.82869 | 12 | 1080 |
| chr21_group000603 | chr21 | 11046703 | 11048190 | −5.82612 | 13 | 1487 |
| chr13_group013128 | chr13 | 40790204 | 40791435 | −5.82584 | 15 | 1231 |
| chr18_group012762 | chr18 | 25323233 | 25323661 | −5.82394 | 9 | 428 |
| chr13_group060498 | chr13 | 1.15E+08 | 1.15E+08 | −5.82341 | 9 | 701 |
| chr13_group058662 | chr13 | 1.12E+08 | 1.12E+08 | −5.81824 | 12 | 1356 |
| chr21_group000133 | chr21 | 9676384 | 9677500 | −5.81524 | 11 | 1116 |
| chr13_group059904 | chr13 | 1.14E+08 | 1.14E+08 | −5.81433 | 9 | 718 |
| chr13_group001920 | chr13 | 23238227 | 23238841 | −5.81403 | 10 | 614 |
| chr18_group037476 | chr18 | 63413568 | 63414219 | −5.8131 | 9 | 651 |
| chr18_group044765 | chr18 | 73262578 | 73264682 | −5.81227 | 16 | 2104 |
| chr18_group032930 | chr18 | 56903942 | 56904918 | −5.81101 | 14 | 976 |
| chr13_group018782 | chr13 | 51574216 | 51575241 | −5.80821 | 9 | 1025 |
| chr13_group059562 | chr13 | 1.13E+08 | 1.13E+08 | −5.80416 | 11 | 546 |
| chr21_group008864 | chr21 | 25705240 | 25706037 | −5.80412 | 9 | 797 |
| chr13_group059882 | chr13 | 1.14E+08 | 1.14E+08 | −5.80323 | 21 | 1734 |
| chr18_group013015 | chr18 | 25730109 | 25730453 | −5.80319 | 9 | 344 |
| chr13_group059557 | chr13 | 1.13E+08 | 1.13E+08 | −5.80208 | 20 | 1951 |
| chr13_group059364 | chr13 | 1.13E+08 | 1.13E+08 | −5.80193 | 11 | 712 |
| chr13_group059279 | chr13 | 1.13E+08 | 1.13E+08 | −5.80022 | 9 | 347 |
| chr21_group020298 | chr21 | 43684698 | 43686180 | −5.79949 | 11 | 1482 |
| chr13_group002262 | chr13 | 23850760 | 23850940 | −5.79727 | 10 | 180 |
| chr18_group045569 | chr18 | 74244562 | 74245600 | −5.79635 | 13 | 1038 |
| chr13_group059325 | chr13 | 1.13E+08 | 1.13E+08 | −5.79454 | 13 | 1287 |
| chr18_group046996 | chr18 | 75842162 | 75843116 | −5.7922 | 9 | 954 |
| chr18_group006017 | chr18 | 11111192 | 11112391 | −5.79207 | 11 | 1199 |
| chr13_group057513 | chr13 | 1.1E+08 | 1.1E+08 | −5.78539 | 9 | 611 |
| chr21_group021403 | chr21 | 45705144 | 45706444 | −5.78195 | 24 | 1300 |
| chr13_group005235 | chr13 | 28301692 | 28302204 | −5.7818 | 9 | 512 |
| chr13_group058991 | chr13 | 1.13E+08 | 1.13E+08 | −5.78107 | 9 | 355 |
| chr18_group047323 | chr18 | 76150976 | 76151357 | −5.77785 | 9 | 381 |
| chr13_group055054 | chr13 | 1.07E+08 | 1.07E+08 | −5.77765 | 10 | 830 |
| chr13_group058892 | chr13 | 1.12E+08 | 1.12E+08 | −5.77648 | 10 | 966 |
| chr18_group005473 | chr18 | 10526912 | 10527424 | −5.77596 | 10 | 512 |
| chr18_group015255 | chr18 | 29804607 | 29805134 | −5.77443 | 9 | 527 |
| chr18_group011209 | chr18 | 22621154 | 22621669 | −5.77439 | 10 | 515 |
| chr18_group044343 | chr18 | 72836530 | 72837776 | −5.76873 | 16 | 1246 |
| chr13_group024061 | chr13 | 61229074 | 61229771 | −5.76839 | 9 | 697 |
| chr18_group048589 | chr18 | 77957628 | 77959648 | −5.76721 | 21 | 2020 |
| chr18_group048234 | chr18 | 77350208 | 77350977 | −5.76556 | 9 | 769 |
| chr18_group006783 | chr18 | 11880770 | 11881666 | −5.76484 | 9 | 896 |
| chr18_group047955 | chr18 | 76766191 | 76767231 | −5.76307 | 13 | 1040 |
| chr18_group008091 | chr18 | 13865682 | 13866118 | −5.76189 | 9 | 436 |
| chr21_group011167 | chr21 | 29533820 | 29535751 | −5.76145 | 17 | 1931 |
| chr18_group047748 | chr18 | 76553042 | 76554395 | −5.76107 | 12 | 1353 |
| chr21_group000286 | chr21 | 9988826 | 9989265 | −5.75661 | 9 | 439 |
| chr18_group008055 | chr18 | 13832084 | 13832849 | −5.75623 | 10 | 765 |
| chr21_group022097 | chr21 | 46760490 | 46761449 | −5.75224 | 10 | 959 |
| chr13_group019376 | chr13 | 52849377 | 52849774 | −5.75052 | 13 | 397 |

TABLE 4-continued

| Name | chr | start.pos | end.pos | median.tstat | num.cg | dmr.size |
|---|---|---|---|---|---|---|
| chr13__group044301 | chr13 | 91147982 | 91148515 | −5.74902 | 9 | 533 |
| chr18__group036202 | chr18 | 61887269 | 61888069 | −5.74536 | 10 | 800 |
| chr21__group022693 | chr21 | 47411896 | 47412449 | −5.74525 | 11 | 553 |
| chr21__group007128 | chr21 | 23844211 | 23844682 | −5.74475 | 9 | 471 |
| chr21__group020432 | chr21 | 43838332 | 43838745 | −5.7404 | 9 | 413 |
| chr13__group059615 | chr13 | 1.13E+08 | 1.13E+08 | −5.73091 | 9 | 651 |
| chr21__group019821 | chr21 | 42689391 | 42690386 | −5.72559 | 16 | 995 |
| chr13__group036149 | chr13 | 79390798 | 79391429 | −5.72529 | 9 | 631 |
| chr13__group035668 | chr13 | 78782891 | 78783400 | −5.72409 | 10 | 509 |
| chr18__group044918 | chr18 | 73456563 | 73456971 | −5.72367 | 10 | 408 |
| chr18__group024906 | chr18 | 43950584 | 43951351 | −5.71933 | 9 | 767 |
| chr21__group021828 | chr21 | 46420021 | 46420963 | −5.71872 | 17 | 942 |
| chr18__group006669 | chr18 | 11733915 | 11735210 | −5.71811 | 9 | 1295 |
| chr13__group004341 | chr13 | 27098314 | 27099497 | −5.71808 | 14 | 1183 |
| chr13__group060288 | chr13 | 1.14E+08 | 1.14E+08 | −5.71648 | 26 | 1792 |
| chr21__group020316 | chr21 | 43705052 | 43705896 | −5.71644 | 9 | 844 |
| chr18__group004872 | chr18 | 9333478 | 9333688 | −5.71592 | 9 | 210 |
| chr18__group048221 | chr18 | 77336082 | 77337860 | −5.71556 | 23 | 1778 |
| chr13__group013832 | chr13 | 42087636 | 42088124 | −5.71477 | 11 | 488 |
| chr18__group047155 | chr18 | 75992307 | 75993165 | −5.70952 | 11 | 858 |
| chr21__group022172 | chr21 | 46840213 | 46840992 | −5.70687 | 13 | 779 |
| chr13__group053554 | chr13 | 1.05E+08 | 1.05E+08 | −5.70675 | 14 | 756 |
| chr21__group021402 | chr21 | 45702857 | 45703698 | −5.70638 | 9 | 841 |
| chr18__group045717 | chr18 | 74402010 | 74402715 | −5.70349 | 10 | 705 |
| chr13__group006584 | chr13 | 30151724 | 30153083 | −5.70166 | 10 | 1359 |
| chr13__group047213 | chr13 | 95034465 | 95035506 | −5.69917 | 9 | 1041 |
| chr18__group023708 | chr18 | 42029597 | 42030713 | −5.69257 | 9 | 1116 |
| chr18__group018648 | chr18 | 34963177 | 34964437 | −5.68695 | 11 | 1260 |
| chr21__group000470 | chr21 | 10771836 | 10772750 | −5.68086 | 13 | 914 |
| chr18__group045583 | chr18 | 74259812 | 74260140 | −5.67763 | 9 | 328 |
| chr13__group019806 | chr13 | 53580664 | 53581223 | −5.6774 | 10 | 559 |
| chr18__group029001 | chr18 | 51152655 | 51152908 | −5.67205 | 9 | 253 |
| chr13__group052801 | chr13 | 1.04E+08 | 1.04E+08 | −5.67169 | 9 | 522 |
| chr13__group024808 | chr13 | 62359170 | 62359852 | −5.66887 | 10 | 682 |
| chr21__group000758 | chr21 | 14409143 | 14410566 | −5.66788 | 23 | 1423 |
| chr21__group000158 | chr21 | 9708554 | 9709366 | −5.66503 | 11 | 812 |
| chr18__group013041 | chr18 | 25764823 | 25765763 | −5.65829 | 13 | 940 |
| chr13__group049158 | chr13 | 98068953 | 98069474 | −5.65799 | 13 | 521 |
| chr13__group011693 | chr13 | 38324448 | 38325781 | −5.65083 | 10 | 1333 |
| chr13__group060303 | chr13 | 1.14E+08 | 1.14E+08 | −5.64889 | 14 | 855 |
| chr21__group021514 | chr21 | 45870478 | 45871888 | −5.64833 | 13 | 1410 |
| chr21__group022710 | chr21 | 47429654 | 47430680 | −5.6439 | 13 | 1026 |
| chr18__group047545 | chr18 | 76362113 | 76363395 | −5.63874 | 11 | 1282 |
| chr13__group047205 | chr13 | 95024474 | 95024946 | −5.63846 | 14 | 472 |
| chr18__group031940 | chr18 | 55167468 | 55168207 | −5.63807 | 9 | 739 |
| chr21__group000099 | chr21 | 9647787 | 9648550 | −5.63351 | 9 | 763 |
| chr13__group036001 | chr13 | 79238379 | 79238602 | −5.63326 | 9 | 223 |
| chr13__group019805 | chr13 | 53579710 | 53580278 | −5.63157 | 11 | 568 |
| chr18__group026590 | chr18 | 46547865 | 46548459 | −5.62851 | 12 | 594 |
| chr13__group042365 | chr13 | 88462822 | 88463523 | −5.62822 | 10 | 701 |
| chr18__group008472 | chr18 | 14485922 | 14486207 | −5.61644 | 9 | 285 |
| chr13__group006494 | chr13 | 30060989 | 30062126 | −5.61642 | 16 | 1137 |
| chr21__group004164 | chr21 | 20229764 | 20230205 | −5.61515 | 9 | 441 |
| chr13__group001858 | chr13 | 23111052 | 23111901 | −5.599 | 10 | 849 |
| chr13__group059999 | chr13 | 1.14E+08 | 1.14E+08 | −5.59417 | 13 | 463 |
| chr18__group046726 | chr18 | 75532114 | 75532939 | −5.59335 | 10 | 825 |
| chr18__group007588 | chr18 | 13277573 | 13278517 | −5.58478 | 10 | 944 |
| chr18__group019014 | chr18 | 35302408 | 35303495 | −5.58282 | 9 | 1087 |
| chr21__group022705 | chr21 | 47422449 | 47423244 | −5.57415 | 9 | 795 |
| chr13__group048037 | chr13 | 96085838 | 96086352 | −5.56895 | 10 | 514 |
| chr18__group023975 | chr18 | 42517139 | 42517803 | −5.56884 | 10 | 664 |
| chr13__group055376 | chr13 | 1.07E+08 | 1.07E+08 | −5.55193 | 10 | 422 |
| chr13__group002006 | chr13 | 23387495 | 23388182 | −5.53539 | 9 | 687 |
| chr18__group047370 | chr18 | 76198965 | 76200234 | −5.52968 | 12 | 1269 |
| chr13__group015222 | chr13 | 44476455 | 44476689 | −5.52545 | 13 | 234 |
| chr18__group007923 | chr18 | 13623832 | 13624484 | −5.51511 | 9 | 652 |
| chr18__group019065 | chr18 | 35355327 | 35356559 | −5.49092 | 9 | 1232 |
| chr13__group060320 | chr13 | 1.15E+08 | 1.15E+08 | −5.48233 | 14 | 817 |
| chr13__group057176 | chr13 | 1.1E+08 | 1.1E+08 | −5.47204 | 12 | 795 |
| chr18__group036624 | chr18 | 62392731 | 62393283 | −5.47186 | 13 | 552 |
| chr13__group022815 | chr13 | 59040763 | 59041615 | −5.46551 | 11 | 852 |
| chr21__group015114 | chr21 | 35897073 | 35897718 | −5.46358 | 11 | 645 |
| chr18__group018582 | chr18 | 34901554 | 34902029 | −5.45775 | 12 | 475 |
| chr13__group007643 | chr13 | 31576507 | 31578481 | −5.45428 | 19 | 1974 |
| chr21__group018151 | chr21 | 40361421 | 40361883 | −5.44577 | 10 | 462 |
| chr18__group034479 | chr18 | 58994197 | 58995474 | −5.43621 | 9 | 1277 |
| chr21__group021451 | chr21 | 45790238 | 45791046 | −5.43091 | 12 | 808 |
| chr13__group059564 | chr13 | 1.13E+08 | 1.13E+08 | −5.4194 | 11 | 907 |

TABLE 4-continued

| Name | chr | start.pos | end.pos | median.tstat | num.cg | dmr.size |
|---|---|---|---|---|---|---|
| chr13__group058867 | chr13 | 1.12E+08 | 1.12E+08 | −5.41237 | 9 | 718 |
| chr18__group029346 | chr18 | 51576392 | 51576847 | −5.39431 | 9 | 455 |
| chr21__group013002 | chr21 | 32157293 | 32157978 | −5.39084 | 10 | 685 |
| chr18__group046801 | chr18 | 75608124 | 75609001 | −5.37562 | 9 | 877 |
| chr21__group022649 | chr21 | 47365567 | 47366433 | −5.37341 | 13 | 866 |
| chr13__group060290 | chr13 | 1.14E+08 | 1.14E+08 | −5.36458 | 9 | 592 |

TABLE 5

| Name | DMR Start | DMR End_ | Size | mean.tstat | mean.diff | Chr |
|---|---|---|---|---|---|---|
| chr13__group001152 | 47242642 | 47243375 | 733 | −18.39194896 | −65.04772831 | chr13 |
| chr18__group002279 | 77128686 | 77129194 | 508 | −15.92751691 | −76.12359512 | chr18 |
| chr21__group000669 | 37802796 | 37802920 | 124 | −14.85848967 | −70.19048592 | chr21 |
| chr13__group001055 | 45961151 | 45961376 | 225 | −14.52536947 | −72.8660151 | chr13 |
| chr13__group000837 | 41556123 | 41556559 | 436 | −14.41181464 | −76.22794022 | chr13 |
| chr21__group001287 | 45507539 | 45507920 | 381 | −13.65151696 | −73.79595082 | chr21 |
| chr13__group000996 | 44980514 | 44981274 | 760 | −13.35405184 | −67.95304154 | chr13 |
| chr21__group000407 | 33346730 | 33347176 | 446 | −13.27481502 | −65.11458163 | chr21 |
| chr13__group002079 | 99714609 | 99715308 | 699 | −12.64399132 | −67.72369515 | chr13 |
| chr13__group002706 | 114015757 | 114016232 | 475 | −12.45799036 | −75.86615906 | chr13 |
| chr13__group002387 | 109792952 | 109793498 | 546 | −12.08695033 | −48.56177338 | chr13 |
| chr18__group000425 | 9735310 | 9735670 | 360 | −11.90890159 | −69.09064631 | chr18 |
| chr18__group001458 | 46579707 | 46580634 | 927 | −11.88258159 | −69.77613844 | chr18 |
| chr21__group000744 | 38737064 | 38737693 | 629 | −11.82876443 | −64.29898552 | chr21 |
| chr13__group002671 | 113652077 | 113652335 | 258 | −11.66741064 | −59.83995008 | chr13 |
| chr18__group002064 | 72191316 | 72191934 | 618 | −11.65088321 | −65.35422759 | chr18 |
| chr21__group000870 | 40356442 | 40358137 | 1695 | −11.60664769 | −63.58086422 | chr21 |
| chr18__group001384 | 45912085 | 45912442 | 357 | −11.36213307 | −68.16862277 | chr18 |
| chr13__group002326 | 107143426 | 107144053 | 627 | −11.34199552 | −64.74414067 | chr13 |
| chr13__group000220 | 25283521 | 25283889 | 368 | −11.33778351 | −62.36569075 | chr13 |
| chr18__group000468 | 10032629 | 10033220 | 591 | −11.26843364 | −65.05501365 | chr18 |
| chr21__group001047 | 43482158 | 43484549 | 2391 | −11.17459478 | −61.09681895 | chr21 |
| chr18__group001918 | 60903751 | 60904250 | 499 | −11.11767014 | −62.97175155 | chr18 |
| chr13__group001167 | 47325529 | 47326847 | 1318 | −11.09332481 | −56.90120868 | chr13 |
| chr13__group002694 | 113917444 | 113917909 | 465 | −11.08612587 | −56.524238 | chr13 |
| chr18__group000141 | 2972224 | 2972717 | 493 | −11.02284003 | −63.47862984 | chr18 |
| chr21__group001177 | 44818620 | 44820068 | 1448 | −11.01945247 | −66.72935383 | chr21 |
| chr13__group002145 | 100085097 | 100085374 | 277 | −10.99247843 | −38.43675878 | chr13 |
| chr13__group002022 | 99128593 | 99129024 | 431 | −10.98079521 | −62.76054996 | chr13 |
| chr21__group001384 | 46285309 | 46286064 | 755 | −10.94388726 | −65.6313201 | chr21 |
| chr13__group002729 | 114207429 | 114207770 | 341 | −10.93640318 | −58.72388163 | chr13 |
| chr21__group001283 | 45503812 | 45504128 | 316 | −10.87300518 | −61.54462763 | chr21 |
| chr13__group000317 | 27579604 | 27579946 | 342 | −10.8609601 | −67.7146906 | chr13 |
| chr13__group002755 | 114557557 | 114558163 | 606 | −10.85791406 | −65.63923565 | chr13 |
| chr13__group001393 | 52352179 | 52352817 | 638 | −10.83714493 | −57.87931836 | chr13 |
| chr18__group002129 | 74162566 | 74163659 | 1093 | −10.8195408 | −42.66574101 | chr18 |
| chr21__group001292 | 45540991 | 45541565 | 574 | −10.81816839 | −58.15595132 | chr21 |
| chr21__group001396 | 46331232 | 46331472 | 240 | −10.77984709 | −57.6696574 | chr21 |
| chr13__group002545 | 111845403 | 111846045 | 642 | −10.7705166 | −71.97711474 | chr13 |
| chr21__group001470 | 47312028 | 47312160 | 132 | −10.76828269 | −44.81041674 | chr21 |
| chr18__group001699 | 55498674 | 55499306 | 632 | −10.75927045 | −66.30696456 | chr18 |
| chr21__group001307 | 45592549 | 45593181 | 632 | −10.72677238 | −61.73195138 | chr21 |
| chr21__group001258 | 45336547 | 45337622 | 1075 | −10.70893808 | −63.58539905 | chr21 |
| chr21__group001499 | 47788663 | 47789945 | 1282 | −10.66597233 | −60.72910502 | chr21 |
| chr21__group001238 | 45254376 | 45255612 | 1236 | −10.54010834 | −63.35916067 | chr21 |
| chr21__group000463 | 34524008 | 34524881 | 873 | −10.52944668 | −66.57298921 | chr21 |
| chr13__group000354 | 28020829 | 28021618 | 789 | −10.45396274 | −68.74696978 | chr13 |
| chr18__group001477 | 47002515 | 47003346 | 831 | −10.43668822 | −65.57930483 | chr18 |
| chr18__group001910 | 60805252 | 60805835 | 583 | −10.3396226 | −64.14358935 | chr18 |
| chr13__group002020 | 99106773 | 99107296 | 523 | −10.28813726 | −55.24926251 | chr13 |
| chr18__group001902 | 60765364 | 60766636 | 1272 | −10.28476262 | −61.74559736 | chr18 |
| chr21__group000729 | 38597759 | 38598577 | 818 | −10.20691991 | −71.0653834 | chr21 |
| chr13__group002503 | 111228253 | 111228526 | 273 | −10.19993662 | −61.34012207 | chr13 |
| chr21__group001487 | 47673664 | 47674403 | 739 | −10.07270424 | −62.1765764 | chr21 |
| chr13__group000073 | 21567837 | 21568105 | 268 | −10.06560545 | −62.70226276 | chr13 |
| chr18__group001837 | 60118020 | 60118330 | 310 | −10.05666314 | −45.78237085 | chr18 |
| chr13__group001210 | 49079717 | 49080414 | 697 | −10.04995406 | −62.95900973 | chr13 |
| chr18__group002156 | 74634139 | 74634581 | 442 | −10.03245079 | −61.78970015 | chr18 |
| chr21__group000990 | 43145495 | 43146565 | 1070 | −9.955407708 | −66.38512218 | chr21 |
| chr13__group002650 | 113437992 | 113438446 | 454 | −9.877188826 | −58.14838467 | chr13 |
| chr13__group002454 | 110993243 | 110994351 | 1108 | −9.8764326 | −55.55290417 | chr13 |
| chr13__group002674 | 113664324 | 113664844 | 520 | −9.873186928 | −59.67724766 | chr13 |
| chr18__group000586 | 13136102 | 13136978 | 876 | −9.870565374 | −55.75839326 | chr18 |
| chr18__group002172 | 74767978 | 74768360 | 382 | −9.858932463 | −59.92145568 | chr18 |

TABLE 5-continued

| Name | DMR Start | DMR End | Size | mean.tstat | mean.diff | Chr |
|---|---|---|---|---|---|---|
| chr21__group001112 | 43954489 | 43955438 | 949 | −9.843310101 | −62.13721727 | chr21 |
| chr21__group001209 | 45077195 | 45077890 | 695 | −9.786478595 | −63.7188637 | chr21 |
| chr13__group001346 | 51578389 | 51578743 | 354 | −9.750684295 | −53.99917988 | chr13 |
| chr21__group000737 | 38629494 | 38630973 | 1479 | −9.695982997 | −59.28551446 | chr21 |
| chr18__group000598 | 13464868 | 13465835 | 967 | −9.630900641 | −58.85587975 | chr18 |
| chr18__group001434 | 46443970 | 46444249 | 279 | −9.613284198 | −58.34208949 | chr18 |
| chr18__group000315 | 7370705 | 7371487 | 782 | −9.552408256 | −49.71140664 | chr18 |
| chr13__group002734 | 114261800 | 114262177 | 377 | −9.552136767 | −66.8246575 | chr13 |
| chr13__group001320 | 51287828 | 51288553 | 725 | −9.549267971 | −55.02772399 | chr13 |
| chr13__group002158 | 100310241 | 100311033 | 792 | −9.541230599 | −45.71776059 | chr13 |
| chr13__group002133 | 100027442 | 100028142 | 700 | −9.506681845 | −60.3675195 | chr13 |
| chr21__group000360 | 32637575 | 32638443 | 868 | −9.477129658 | −58.33695274 | chr21 |
| chr13__group000407 | 28538881 | 28539268 | 387 | −9.471258558 | −52.88622512 | chr13 |
| chr18__group001451 | 46549726 | 46550108 | 382 | −9.465522562 | −54.8505642 | chr18 |
| chr18__group001654 | 54788900 | 54789176 | 276 | −9.463784817 | −36.0336351 | chr18 |
| chr21__group001221 | 45146825 | 45147292 | 467 | −9.45412142 | −62.72749199 | chr21 |
| chr21__group001459 | 46969944 | 46971551 | 1607 | −9.429922946 | −61.92783806 | chr21 |
| chr13__group002056 | 99545041 | 99545597 | 556 | −9.422007926 | −56.57705152 | chr13 |
| chr18__group000171 | 3177791 | 3178272 | 481 | −9.393705 | −58.71158806 | chr18 |
| chr18__group000732 | 20811381 | 20811849 | 468 | −9.390128708 | −46.24123787 | chr18 |
| chr21__group001020 | 43341081 | 43341829 | 748 | −9.363711759 | −66.40743115 | chr21 |
| chr21__group000711 | 38352550 | 38353375 | 825 | −9.356736152 | −55.5988808 | chr21 |
| chr13__group000603 | 33000796 | 33001355 | 559 | −9.349515489 | −43.47287432 | chr13 |
| chr21__group001016 | 43319300 | 43320207 | 907 | −9.319060926 | −56.46845033 | chr21 |
| chr21__group001081 | 43739547 | 43740084 | 537 | −9.310430086 | −44.31473312 | chr21 |
| chr13__group002344 | 107404832 | 107405784 | 952 | −9.306806621 | −59.26900623 | chr13 |
| chr21__group000742 | 38729857 | 38730861 | 1004 | −9.302054273 | −52.70258537 | chr21 |
| chr21__group000842 | 40123419 | 40124069 | 650 | −9.299800657 | −60.36021292 | chr21 |
| chr18__group002194 | 74839885 | 74840286 | 401 | −9.260709941 | −57.189939 | chr18 |
| chr18__group001288 | 43784948 | 43785507 | 559 | −9.255326772 | −58.14710727 | chr18 |
| chr18__group002088 | 72782968 | 72783511 | 543 | −9.244997831 | −55.31614938 | chr18 |
| chr18__group001011 | 31803129 | 31804139 | 1010 | −9.239512396 | −39.33343809 | chr18 |
| chr21__group000604 | 36417762 | 36418947 | 1185 | −9.226034669 | −60.19434304 | chr21 |
| chr21__group001398 | 46334045 | 46334575 | 530 | −9.184872967 | −55.63656857 | chr21 |
| chr18__group000848 | 23306498 | 23306769 | 271 | −9.172550049 | −58.08073401 | chr18 |
| chr13__group001577 | 70681595 | 70682349 | 754 | −9.172279091 | −41.36922459 | chr13 |
| chr18__group001443 | 46467107 | 46467595 | 488 | −9.143040577 | −48.58064259 | chr18 |
| chr21__group000725 | 38580421 | 38580649 | 228 | −9.13677136 | −59.03456726 | chr21 |
| chr21__group001295 | 45557711 | 45558670 | 959 | −9.109238083 | −47.82119077 | chr21 |
| chr18__group000936 | 29232383 | 29232797 | 414 | −9.063098538 | −58.41393518 | chr18 |
| chr18__group001941 | 61638900 | 61639535 | 635 | −9.058100004 | −61.3986068 | chr18 |
| chr18__group000032 | 518792 | 519699 | 907 | −8.985975594 | −52.64995804 | chr18 |
| chr13__group002034 | 99194933 | 99195669 | 736 | −8.981708737 | −55.40745505 | chr13 |
| chr21__group000199 | 26933982 | 26935234 | 1252 | −8.98084455 | −52.33810095 | chr21 |
| chr21__group000773 | 38918896 | 38919969 | 1073 | −8.965101846 | −54.64350843 | chr21 |
| chr13__group002748 | 114518518 | 114518841 | 323 | −8.948154528 | −44.98734749 | chr13 |
| chr21__group001409 | 46386632 | 46387009 | 377 | −8.944196335 | −55.51509133 | chr21 |
| chr18__group001241 | 43407677 | 43408455 | 778 | −8.92854939 | −50.04485828 | chr18 |
| chr13__group001065 | 45991122 | 45991445 | 323 | −8.915948449 | −53.38989609 | chr13 |
| chr13__group000390 | 28491265 | 28492638 | 1373 | −8.890516641 | −36.43523327 | chr13 |
| chr13__group002656 | 113527233 | 113528850 | 1617 | −8.883746931 | −55.59592014 | chr13 |
| chr13__group000635 | 33589621 | 33590002 | 381 | −8.829596188 | −45.40127717 | chr13 |
| chr18__group000140 | 2971014 | 2971515 | 501 | −8.822842181 | −52.85092816 | chr18 |
| chr21__group000806 | 39748213 | 39748878 | 665 | −8.783886568 | −52.7471035 | chr21 |
| chr21__group001135 | 44250990 | 44251388 | 398 | −8.779637199 | −53.05701038 | chr21 |
| chr21__group001201 | 44994599 | 44994936 | 337 | −8.767658097 | −61.72321133 | chr21 |
| chr13__group001391 | 52338951 | 52339297 | 346 | −8.766011857 | −54.46518805 | chr13 |
| chr13__group002644 | 113379709 | 113380562 | 853 | −8.75362873 | −53.48264092 | chr13 |
| chr21__group000452 | 34400145 | 34400987 | 842 | −8.74996012 | −34.80684009 | chr21 |
| chr13__group000040 | 21049971 | 21050518 | 547 | −8.666456394 | −58.32789435 | chr13 |
| chr13__group002750 | 114544309 | 114544556 | 247 | −8.648578186 | −62.15635845 | chr13 |
| chr21__group000988 | 43132389 | 43133155 | 766 | −8.617440804 | −55.84886339 | chr21 |
| chr21__group001187 | 44876290 | 44877156 | 866 | −8.613182289 | −63.82230415 | chr21 |
| chr13__group002539 | 111829383 | 111829767 | 384 | −8.610575243 | −60.12601333 | chr13 |
| chr21__group000940 | 42213548 | 42214461 | 601 | −8.606417329 | −36.42376223 | chr21 |
| chr21__group001158 | 44528684 | 44529639 | 955 | −8.543794599 | −47.38738569 | chr21 |
| chr21__group001477 | 47476997 | 47477654 | 657 | −8.532848673 | −46.98037339 | chr21 |
| chr13__group002634 | 113237697 | 113238411 | 714 | −8.486041114 | −63.1528534 | chr13 |
| chr13__group000084 | 21619829 | 21620580 | 751 | −8.482703655 | −57.03925273 | chr13 |
| chr13__group002172 | 100611663 | 100612546 | 883 | −8.461433431 | −32.39739364 | chr13 |
| chr21__group000830 | 39869603 | 39870768 | 1165 | −8.454831631 | −53.08980471 | chr21 |
| chr21__group001076 | 43689385 | 43689956 | 571 | −8.450716967 | −52.44050072 | chr21 |
| chr21__group000686 | 38066526 | 38067493 | 967 | −8.43289293 | −40.67552134 | chr21 |
| chr18__group002297 | 77283700 | 77284321 | 621 | −8.400824534 | −62.61321281 | chr18 |
| chr21__group001181 | 44834072 | 44835055 | 983 | −8.375423908 | −57.00162931 | chr21 |
| chr13__group000605 | 33002060 | 33003102 | 1042 | −8.345075377 | −40.72665221 | chr13 |
| chr13__group002165 | 100547192 | 100547859 | 667 | −8.336527938 | −48.22413571 | chr13 |
| chr13__group001472 | 53423763 | 53424344 | 581 | −8.332477304 | −38.22297695 | chr13 |

TABLE 5-continued

| Name | DMR Start | DMR End | Size | mean.tstat | mean.diff | Chr |
|---|---|---|---|---|---|---|
| chr18_group000463 | 9969190 | 9969757 | 567 | −8.292361223 | −62.91302734 | chr18 |
| chr21_group001362 | 46125842 | 46127678 | 1836 | −8.284079018 | −53.83072094 | chr21 |
| chr13_group002356 | 107571517 | 107572305 | 788 | −8.260743994 | −48.66622141 | chr13 |
| chr13_group002541 | 111836898 | 111837606 | 708 | −8.252240651 | −52.40225752 | chr13 |
| chr21_group001493 | 47717335 | 47717995 | 660 | −8.245339139 | −55.5372467 | chr21 |
| chr21_group001300 | 45573752 | 45574204 | 452 | −8.239429325 | −55.5508674 | chr21 |
| chr21_group001415 | 46451018 | 46451327 | 309 | −8.222686546 | −45.97032586 | chr21 |
| chr21_group001301 | 45576999 | 45578097 | 1098 | −8.204166678 | −61.86931142 | chr21 |
| chr18_group001809 | 59001400 | 59001977 | 577 | −8.187663397 | −32.24305168 | chr18 |
| chr13_group000394 | 28495600 | 28496569 | 969 | −8.180642844 | −36.74316983 | chr13 |
| chr21_group001015 | 43316011 | 43316607 | 596 | −8.174392103 | −57.49209554 | chr21 |
| chr13_group001266 | 50216962 | 50217550 | 588 | −8.169598401 | −53.51236395 | chr13 |
| chr13_group002583 | 112707657 | 112711587 | 3930 | −8.163330684 | −49.84995961 | chr13 |
| chr21_group000877 | 40376221 | 40377543 | 1322 | −8.132204098 | −54.86952268 | chr21 |
| chr21_group001335 | 45795088 | 45795408 | 320 | −8.125430669 | −58.34639577 | chr21 |
| chr13_group000090 | 21648765 | 21649379 | 614 | −8.119915946 | −54.916639 | chr13 |
| chr18_group001671 | 55103164 | 55104312 | 1148 | −8.113175501 | −42.10968749 | chr18 |
| chr18_group002344 | 77709704 | 77710610 | 906 | −8.109337771 | −57.25498272 | chr18 |
| chr21_group000562 | 36042331 | 36042565 | 234 | −8.094550453 | −24.21435877 | chr21 |
| chr13_group000462 | 29105140 | 29105830 | 690 | −8.083800067 | −38.10162833 | chr13 |
| chr13_group002584 | 112711972 | 112713457 | 1485 | −8.074042289 | −47.40036246 | chr13 |
| chr18_group001414 | 46307622 | 46308320 | 698 | −8.051503129 | −40.53953039 | chr18 |
| chr18_group001109 | 35146450 | 35147255 | 805 | −8.045886767 | −35.06961769 | chr18 |
| chr18_group000537 | 11987478 | 11987956 | 478 | −8.011263356 | −55.19983902 | chr18 |
| chr13_group002250 | 102568510 | 102568872 | 362 | −8.002856467 | −41.82024959 | chr13 |
| chr21_group001363 | 46128037 | 46129688 | 1651 | −8.002732923 | −43.33003689 | chr21 |
| chr13_group000023 | 20716207 | 20716728 | 521 | −7.998646792 | −46.99361982 | chr13 |
| chr21_group000818 | 39848132 | 39849414 | 1282 | −7.991244277 | −46.11095386 | chr21 |
| chr18_group001712 | 55862468 | 55863002 | 534 | −7.987817304 | −54.91394196 | chr18 |
| chr13_group001296 | 50701261 | 50701779 | 518 | −7.987127117 | −43.70423193 | chr13 |
| chr13_group000237 | 25505937 | 25506383 | 446 | −7.980970329 | −54.65305141 | chr13 |
| chr13_group000209 | 25085217 | 25086158 | 941 | −7.963068932 | −50.75890562 | chr13 |
| chr18_group001869 | 60489607 | 60489816 | 209 | −7.917527424 | −51.05165198 | chr18 |
| chr13_group002184 | 100640734 | 100642451 | 1717 | −7.910238263 | −40.37220292 | chr13 |
| chr18_group000725 | 20772097 | 20772711 | 614 | −7.899805331 | −51.98311617 | chr18 |
| chr13_group002166 | 100548217 | 100548553 | 336 | −7.877625439 | −49.86397914 | chr13 |
| chr18_group001665 | 55094804 | 55096737 | 1933 | −7.856000573 | −52.37240719 | chr18 |
| chr21_group000612 | 36576990 | 36577843 | 853 | −7.854106928 | −44.51982871 | chr21 |
| chr13_group002589 | 112717522 | 112718025 | 503 | −7.849567892 | −45.00076978 | chr13 |
| chr13_group002607 | 112761806 | 112762053 | 247 | −7.843104485 | −45.71044588 | chr13 |
| chr21_group001377 | 46269633 | 46269741 | 108 | −7.838404161 | −49.74759175 | chr21 |
| chr13_group002658 | 113547154 | 113547395 | 241 | −7.836178614 | −48.56718518 | chr13 |
| chr21_group001524 | 47971569 | 47972021 | 452 | −7.802944932 | −60.5452142 | chr21 |
| chr13_group002372 | 109148607 | 109149254 | 647 | −7.801788075 | −26.31153544 | chr13 |
| chr18_group002167 | 74716251 | 74717253 | 1002 | −7.781361742 | −57.08446083 | chr18 |
| chr21_group001157 | 44524329 | 44525096 | 767 | −7.7806853 | −62.74294271 | chr21 |
| chr13_group000457 | 29063895 | 29064821 | 926 | −7.760192773 | −45.08262521 | chr13 |
| chr13_group002606 | 112757945 | 112761434 | 3489 | −7.757878299 | −50.10676689 | chr13 |
| chr13_group000920 | 43148291 | 43149406 | 1115 | −7.754613127 | −37.59555158 | chr13 |
| chr18_group001554 | 48680123 | 48680632 | 509 | −7.742479548 | −52.04606056 | chr18 |
| chr18_group001454 | 46558035 | 46558432 | 397 | −7.728239128 | −55.83677577 | chr18 |
| chr18_group000490 | 10483146 | 10483580 | 434 | −7.726423092 | −53.94073586 | chr18 |
| chr21_group001343 | 45923813 | 45924286 | 473 | −7.715420245 | −56.418237 | chr21 |
| chr18_group002286 | 77165800 | 77166485 | 685 | −7.704384606 | −58.00791107 | chr18 |
| chr13_group000289 | 26586395 | 26586933 | 538 | −7.699885169 | −55.30715164 | chr13 |
| chr18_group001672 | 55104994 | 55106507 | 1513 | −7.672778137 | −41.54643946 | chr18 |
| chr21_group001328 | 45770125 | 45770867 | 742 | −7.672246373 | −40.4247514 | chr21 |
| chr21_group000695 | 38076763 | 38077971 | 1208 | −7.661119731 | −36.33245759 | chr21 |
| chr18_group002293 | 77266961 | 77267951 | 990 | −7.634700037 | −53.11920248 | chr18 |
| chr21_group001297 | 45563132 | 45563607 | 475 | −7.630774749 | −51.44913467 | chr21 |
| chr13_group002328 | 107145190 | 107146546 | 1356 | −7.614136558 | −54.83938849 | chr13 |
| chr21_group001380 | 46274100 | 46275015 | 915 | −7.610938411 | −51.44875941 | chr21 |
| chr18_group002334 | 77558154 | 77559328 | 1174 | −7.594449103 | −39.6735955 | chr18 |
| chr18_group000997 | 30350769 | 30351686 | 917 | −7.589417151 | −27.98979231 | chr18 |
| chr13_group002169 | 100608370 | 100609048 | 678 | −7.585617735 | −25.26896582 | chr13 |
| chr21_group001401 | 46346385 | 46346623 | 238 | −7.582653679 | −54.56890394 | chr21 |
| chr18_group000777 | 21199464 | 21199797 | 333 | −7.552550622 | −38.58286513 | chr18 |
| chr18_group001662 | 55020074 | 55020378 | 304 | −7.52236947 | −44.77514608 | chr18 |
| chr21_group001012 | 43305546 | 43306028 | 482 | −7.513932804 | −47.12216907 | chr21 |
| chr13_group001887 | 95655149 | 95655549 | 400 | −7.505720325 | −45.87949927 | chr13 |
| chr21_group000447 | 34394947 | 34396167 | 1220 | −7.490673461 | −35.47986338 | chr21 |
| chr13_group001045 | 45903663 | 45904254 | 591 | −7.490084979 | −48.47396401 | chr13 |
| chr13_group002594 | 112723177 | 112724441 | 1264 | −7.478161229 | −35.50870594 | chr13 |
| chr21_group001289 | 45522545 | 45522771 | 226 | −7.46831357 | −51.94523251 | chr21 |
| chr21_group001312 | 45626659 | 45627440 | 781 | −7.467580303 | −57.4023678 | chr21 |
| chr13_group000139 | 23535545 | 23535734 | 189 | −7.467204177 | −55.1352546 | chr13 |
| chr21_group001272 | 45433860 | 45434411 | 551 | −7.459807944 | −56.95683204 | chr21 |
| chr13_group002251 | 102569182 | 102569894 | 712 | −7.45187497 | −34.55623352 | chr13 |

TABLE 5-continued

| Name | DMR Start | DMR End_ | Size | mean.tstat | mean.diff | Chr |
|---|---|---|---|---|---|---|
| chr21__group001107 | 43944544 | 43945247 | 703 | −7.408060319 | −49.52563075 | chr21 |
| chr21__group001051 | 43537974 | 43538849 | 875 | −7.383613414 | −48.95640069 | chr21 |
| chr21__group001288 | 45509085 | 45509718 | 633 | −7.37657314 | −50.10457116 | chr21 |
| chr13__group002680 | 113816268 | 113817066 | 798 | −7.357155839 | −37.4336906 | chr13 |
| chr21__group000380 | 33027167 | 33027716 | 549 | −7.341068614 | −46.30265434 | chr21 |
| chr13__group001925 | 96206379 | 96206766 | 387 | −7.326027733 | −49.6760011 | chr13 |
| chr13__group000399 | 28501446 | 28502923 | 1477 | −7.316700643 | −38.44790605 | chr13 |
| chr18__group001328 | 44774444 | 44775576 | 1132 | −7.308752653 | −38.74103553 | chr18 |
| chr21__group000350 | 32546263 | 32546926 | 663 | −7.308727759 | −44.04199938 | chr21 |
| chr18__group001670 | 55101832 | 55102032 | 200 | −7.256974193 | −27.31976441 | chr18 |
| chr21__group000689 | 38070092 | 38070679 | 587 | −7.245508244 | −35.27535447 | chr21 |
| chr21__group000691 | 38072845 | 38073567 | 722 | −7.243380042 | −35.89192438 | chr21 |
| chr13__group000194 | 24845628 | 24846415 | 787 | −7.233393336 | −41.12797945 | chr13 |
| chr18__group002124 | 74101754 | 74102074 | 320 | −7.229406946 | −49.66217969 | chr18 |
| chr21__group001220 | 45145759 | 45146214 | 455 | −7.216653417 | −52.91917265 | chr21 |
| chr13__group002770 | 114831265 | 114831567 | 302 | −7.209461375 | −57.53024036 | chr13 |
| chr13__group001253 | 50125187 | 50125863 | 676 | −7.198431899 | −57.68042887 | chr13 |
| chr21__group001056 | 43575605 | 43575870 | 265 | −7.189850363 | −47.8837593 | chr21 |
| chr21__group001195 | 44914703 | 44915394 | 691 | −7.180506751 | −52.34807566 | chr21 |
| chr18__group001664 | 55021510 | 55021669 | 159 | −7.176378135 | −44.36163875 | chr18 |
| chr18__group001666 | 55097101 | 55098391 | 1290 | −7.170617096 | −44.73389603 | chr18 |
| chr18__group000714 | 20716700 | 20717693 | 993 | −7.146016584 | −37.53074357 | chr18 |
| chr13__group001499 | 58207706 | 58208915 | 1209 | −7.134787755 | −33.84596021 | chr13 |
| chr13__group002679 | 113807379 | 113807864 | 485 | −7.13245886 | −43.97158338 | chr13 |
| chr13__group002335 | 107186469 | 107186687 | 218 | −7.116623849 | −23.75464539 | chr13 |
| chr13__group002175 | 100621000 | 100621752 | 752 | −7.08565626 | −41.56510906 | chr13 |
| chr13__group002447 | 110950803 | 110951418 | 615 | −7.072874782 | −45.55712789 | chr13 |
| chr13__group001858 | 93879908 | 93880952 | 1044 | −7.059205313 | −30.15916476 | chr13 |
| chr13__group002574 | 112330611 | 112331007 | 396 | −7.051573147 | −43.00577031 | chr13 |
| chr13__group001100 | 46751498 | 46751812 | 314 | −7.049715251 | −58.30783768 | chr13 |
| chr21__group001128 | 44166891 | 44167283 | 392 | −7.046058888 | −43.37429142 | chr21 |
| chr21__group000420 | 33783760 | 33784889 | 1129 | −7.036579683 | −33.73634151 | chr21 |
| chr13__group000520 | 30945560 | 30946325 | 765 | −7.023949006 | −52.50912549 | chr13 |
| chr13__group002616 | 112985185 | 112985683 | 498 | −6.998497282 | −46.1533405 | chr13 |
| chr21__group000625 | 36900972 | 36901461 | 489 | −6.997438986 | −50.17593425 | chr21 |
| chr13__group002741 | 114301844 | 114302184 | 340 | −6.985616957 | −55.79348298 | chr13 |
| chr21__group000698 | 38080168 | 38081984 | 1816 | −6.974562459 | −35.27578779 | chr21 |
| chr13__group002721 | 114162726 | 114163098 | 372 | −6.972518741 | −48.87343429 | chr13 |
| chr21__group001111 | 43952782 | 43953266 | 484 | −6.947512747 | −51.08853379 | chr21 |
| chr13__group001734 | 79182090 | 79182725 | 635 | −6.931417531 | −33.32958417 | chr13 |
| chr13__group001882 | 95364233 | 95365328 | 1095 | −6.925270344 | −20.08606459 | chr13 |
| chr13__group000029 | 20875719 | 20876170 | 451 | −6.900016973 | −34.35762142 | chr13 |
| chr18__group000574 | 12911200 | 12912120 | 920 | −6.892928141 | −51.02929837 | chr18 |
| chr13__group002596 | 112726118 | 112726885 | 767 | −6.891544797 | −44.8373475 | chr13 |
| chr18__group001769 | 56939143 | 56940153 | 1010 | −6.888613817 | −35.5017386 | chr18 |
| chr18__group001808 | 59000646 | 59001049 | 403 | −6.885286215 | −33.4965757 | chr18 |
| chr21__group001453 | 46902588 | 46903711 | 1123 | −6.878355304 | −49.2557533 | chr21 |
| chr18__group002249 | 76733501 | 76734715 | 1214 | −6.874579391 | −30.94670393 | chr18 |
| chr13__group002185 | 100642999 | 100644801 | 1802 | −6.872779522 | −36.41162346 | chr13 |
| chr18__group001041 | 32956374 | 32957367 | 993 | −6.866298109 | −34.76041777 | chr18 |
| chr21__group000450 | 34398446 | 34399243 | 797 | −6.862686973 | −35.51953333 | chr21 |
| chr18__group002310 | 77397568 | 77397978 | 410 | −6.861904629 | −59.70231969 | chr18 |
| chr13__group000397 | 28498679 | 28499290 | 611 | −6.848875386 | −32.3738284 | chr13 |
| chr18__group001673 | 55107349 | 55108291 | 942 | −6.834584119 | −30.76088397 | chr18 |
| chr18__group002203 | 74962220 | 74963311 | 1091 | −6.831344856 | −30.71051823 | chr18 |
| chr13__group002355 | 107569644 | 107570136 | 492 | −6.791060316 | −52.23003552 | chr13 |
| chr18__group001573 | 49866573 | 49867697 | 1124 | −6.790894758 | −29.06204299 | chr18 |
| chr21__group001303 | 45579451 | 45580003 | 552 | −6.775753514 | −58.7422961 | chr21 |
| chr13__group002587 | 112715161 | 112716339 | 1178 | −6.772926587 | −45.80821993 | chr13 |
| chr21__group001217 | 45122629 | 45122970 | 341 | −6.737329391 | −47.56879318 | chr21 |
| chr13__group001876 | 95353962 | 95356005 | 2043 | −6.734806346 | −47.33755222 | chr13 |
| chr13__group000378 | 28367040 | 28368384 | 1344 | −6.708754199 | −31.71215305 | chr13 |
| chr13__group002212 | 101169937 | 101170300 | 363 | −6.672741328 | −47.3352739 | chr13 |
| chr21__group000699 | 38082354 | 38083353 | 999 | −6.659688576 | −35.58474443 | chr21 |
| chr21__group000942 | 42218345 | 42219021 | 676 | −6.609299201 | −41.18927259 | chr21 |
| chr18__group000816 | 22239955 | 22240667 | 712 | −6.575392479 | −42.5606315 | chr18 |
| chr13__group002188 | 100649131 | 100650238 | 1107 | −6.567868538 | −50.31034823 | chr13 |
| chr13__group002576 | 112547370 | 112548710 | 1340 | −6.567743245 | −43.49866554 | chr13 |
| chr18__group000057 | 905117 | 905876 | 759 | −6.484042303 | −40.65014919 | chr18 |
| chr13__group001733 | 79181165 | 79181588 | 423 | −6.484015868 | −44.80924788 | chr13 |
| chr21__group001383 | 46283780 | 46284468 | 688 | −6.425178251 | −32.08626906 | chr21 |
| chr21__group001243 | 45274637 | 45275319 | 682 | −6.421546914 | −48.83414174 | chr21 |
| chr21__group001174 | 44803308 | 44803697 | 389 | −6.415163712 | −49.17205094 | chr21 |
| chr13__group001932 | 96293996 | 96294460 | 464 | −6.40694812 | −42.3393559 | chr13 |
| chr18__group001767 | 56935173 | 56935836 | 663 | −6.394031339 | −31.21396585 | chr18 |
| chr21__group000445 | 34391928 | 34392544 | 616 | −6.360719895 | −36.05052741 | chr21 |
| chr21__group001471 | 47392740 | 47393477 | 737 | −6.322512735 | −27.80043103 | chr21 |
| chr21__group000696 | 38078318 | 38079295 | 977 | −6.290131968 | −30.96710244 | chr21 |

TABLE 5-continued

| Name | DMR Start | DMR End | Size | mean.tstat | mean.diff | Chr |
|---|---|---|---|---|---|---|
| chr18_group000377 | 9017330 | 9018102 | 772 | −6.278636256 | −45.75108205 | chr18 |
| chr18_group002328 | 77548049 | 77548854 | 805 | −6.269577119 | −26.67068957 | chr18 |
| chr21_group001367 | 46131932 | 46132925 | 993 | −6.179939458 | −34.57117312 | chr21 |
| chr21_group000655 | 37572196 | 37572667 | 471 | −6.12840127 | −37.38186941 | chr21 |
| chr18_group000058 | 906367 | 907244 | 877 | −6.126413388 | −26.69351508 | chr18 |
| chr13_group002513 | 111318089 | 111318913 | 824 | −6.073179093 | −39.75542158 | chr13 |
| chr13_group002593 | 112721363 | 112722077 | 714 | −5.907511589 | −42.66114358 | chr13 |
| chr13_group000636 | 33591173 | 33591597 | 424 | −5.677537951 | −43.6518728 | chr13 |
| chr18_group000555 | 12420729 | 12421378 | 649 | N/A | −56.00242497 | chr18 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology. —Certain embodiments of the technology are set forth in the claim(s) that follow(s).

What is claimed is:

1. A collection of amplification primer pairs for identifying the presence or absence of a hypermethylated locus or a hypomethylated locus prepared by a process comprising:
   (a) selecting one or more genomic loci wherein each locus comprises three or more features selected from:
      (i) a locus length of about 5000 contiguous base pairs, or less,
      (ii) at least 5 CpG methylation sites,
      (iii) a plurality of restriction endonuclease recognition sites wherein the mean, median or absolute distance between each restriction endonuclease recognition site on the locus is about 20 to about 125 base pairs, and each of the restriction endonuclease recognition sites is recognized by one or more methylation-sensitive restriction endonucleases,
      (iv) at least 1 restriction endonuclease recognition site per 1000 base pairs, wherein the at least one restriction endonuclease recognition site can be specifically digested by a methylation-sensitive restriction endonuclease,
      (v) a locus comprising a methylation status of 60% or more in a minority nucleic acid species,
      (vi) a locus comprising a methylation status of 40% or less in a majority nucleic acid species, and
      (vii) a locus comprising a difference in methylation status of 5% or more between a minority nucleic acid species and a majority nucleic acid species; and
   (b) preparing a plurality of oligonucleotide primer pairs, wherein each primer of each primer pair hybridizes to a portion of a strand of the locus selected in (a) for which the primer pair is specific, whereby a collection of amplification primers is prepared,
   wherein at least one of the amplification primers of each of the primer pairs comprises a non-native element, and
   wherein the one or more genomic loci are on chromosome 13, 18, or 21, and
   wherein the genomic loci comprise SEQ ID NO: 85.

2. The collection of amplification primer pairs of claim 1, wherein genomic loci having feature (iv) are selected in (a).

3. The collection of amplification primer pairs of claim 1, wherein the feature of (a)(i) is 500 contiguous nucleotides, or less.

4. The collection of amplification primer pairs of claim 1, wherein the at least 5 CpG methylation sites of (a)(ii) are at least 9 CpG methylation sites.

5. The collection of amplification primer pairs of claim 1, wherein the mean, median or absolute distance between each restriction endonuclease recognition site of (iii) is about 40 to about 100 base pairs.

6. The collection of amplification primer pairs of claim 1, wherein the feature of (a)(iv) is at least 10 restriction endonuclease recognition sites per 1000 base pairs.

7. The collection of amplification primer pairs of claim 1, wherein genomic loci having features (ii), (iii) and (iv) are selected in (a).

8. The collection of amplification primer pairs of claim 1, wherein genomic loci having features (ii), (iii) and (vii) are selected in (a).

9. The collection of amplification primer pairs of claim 1, wherein genomic loci having features (ii), (iv) and (vii) are selected in (a).

10. The collection of amplification primer pairs of claim 1, wherein genomic loci having features (iii), (iv) and (vii) are selected in (a).

11. The collection of amplification primer pairs of claim 1, wherein genomic loci having feature (i) are selected in (a).

12. The collection of amplification primer pairs of claim 1, wherein genomic loci having feature (v) are selected in (a).

13. The collection of amplification primer pairs of claim 1, wherein genomic loci having feature (vi) are selected in (a).

* * * * *

SEQUENCE LISTING

<160> NUMBER OF SEQ ID NOS: 85

<210> SEQ ID NO 1
<211> LENGTH: 374
<212> TYPE: DNA
<213> ORGANISM: Homo sapiens

<400> SEQUENCE: 1

```
tagtaaggca ccgaggggtg gctcctctcc ctgcagcggc tgtcgcttac catcctgtag      60
accgtgacct cctcacacag cgccaggacg aggatcgcgg tgagccagca ggtgactgcg     120
atcctggagc tggtcgcagc aggccatcct gcacgcggtg gaggcgcccc ctgcaggccg     180
cagcgcatcc ccagcttctg gacgcactgt gagcggttat gcagcagcac gctcatatga     240
gatgccccgc agggtgctat gcaggcccac gtccccacaa agcccatggc aggcgcccgg     300
gtgccggagc acgcacttgg ccccatggat ctctgtgccc agggctcagc caggcatctg     360
gccgctaaag gttt                                                       374
```

<210> SEQ ID NO 2
<211> LENGTH: 246
<212> TYPE: DNA
<213> ORGANISM: Homo sapiens

<400> SEQUENCE: 2

```
tctcatctga gcgctgtctt tcaccagagc tctgtaggac tgaggcagta gcgctggccc     60
gcctgcgaga gcccgaccgt ggacgatgcg tcgcgcccct tcccatcgcg cctgggcggg    120
cccgcctgcc ctcggctgag cccggttttcc ctaccccggg gcacctcccc tcgcccgcac   180
ccggccccag tccctcccag gcttgcgggt agagcctgtc tttgcccaga aggccgtctc    240
caagct                                                               246

<210> SEQ ID NO 3
<211> LENGTH: 222
<212> TYPE: DNA
<213> ORGANISM: Homo sapiens

<400> SEQUENCE: 3
cagtccccga ggccctcccc ggtgactcta accagggatt tcagcgcgcg gcgcggggct     60
gcccccaggc gtgacctcac ccgtgctctc tccctgcaga atctcctacg acccggcgag    120
gtaccccagg tacctgcctg aagcctactg cctgtgccgg ggctgcctga ccgggctgtt    180
cggcgaggag gacgtgcgct cccgcagcgc ccctgtctac at                       222

<210> SEQ ID NO 4
<211> LENGTH: 2209
<212> TYPE: DNA
<213> ORGANISM: Homo sapiens

<400> SEQUENCE: 4
agagagacat tttccacgga ggccgagttg tggcgcttgg ggttgtgggc gaaggacggg     60
gacacggggg tgaccgtcgt ggtggaggag aaggtctcgg aactgtgcg gcggcggccc    120 ccctgcgggt ctgcgcggat gaccttggcg ccgcggtggg ggtccggggg ctggctggcc   180
tgcaggaagg cctcgactcc cgacacctgc tccatgaggc tcagcctctt cacgcccgac   240
gtcgggctgg ccacgcgggc agcttctggc ttcggggggg ccgcgatagg ttgcggcggg   300
gtggcggcca caccaaaagc catctcggtg tagtcaccat tgtccccggt gtccgaggac   360
aacgatgagg cggcgcccgg gccctgggcg gtggcaacgg ccgaggcggg gggcaggcgg   420
tacagctccc ccggggccgg cggcggtggc ggcggctgca gagacgacga cggggacgcg   480
gacggacgcg ggggcaacgg cggatacggg gaggaggcct cggggacag gaggccgtcc    540 aaggagccca cggggtggcc gctcggggcg cccggcttag gagacttggg ggagctgaag    600
tcgaggttca tgtagtcgga gagcggagac cgctgccggc tgtcgctgct ggtgcccggg    660
gtgcctgagc ccagcgacga ggccgggctg ctggcggaca agagcgagga ggacgaggcc   720
gccgacgcca gcagggagg cgcgggcggc gacaggcggg cccggggctc gccaaagtcg    780
atgttgatgt actcgccggg gctcttgggc tccggtggca gtgggtactc gtgcatgctg    840
ggcaggctgg gcagcccctc cagggacagg cgcgtgggcc tcaccgcccg gccgcgctgg    900
cccaagaagc cctccgggcg gccgccgcta ggccgcacgg gcgaaggcac tacagggtga    960
gggggctgcg tggggccggc cccgaaggcg ctggccgcct ggctgggccc tggcgtggcc   1020
tgaggctcca gacgctcctc ctccaggatg cgcccacgg gggagctcat gagcacgtac    1080
tggtcgctgt cccgccaca ggtgtagggg gccttgtagg agcggggcaa ggagctgtag    1140
cagcagccgg gaacgcccct gagcggctcc ccgccggggt gcagggctgc ggagaagaag   1200
tcggggcggg tgccgtggt gaccgcgtcg ctggggaca cgttgaggta gtccccgttg    1260
ggcagcagct tgccatctgc atgctccatg gacagcttgg aaccgcacca catgcgcatg   1320
tacccactgt cctcggggga gctctcggcg ggcgagctgg ccttgtagcc gccccgctc    1380
```

```
gccgggaatg tcctgcccgc cgcagaggtg ggtgctggcc ccgcaggccc cgcagaaggc    1440
acggcggcgg cggcggcggc ggcggccctg ggctgcaaga tctgcttggg ggcggacacg    1500
ctggcggggc tcatgggcat gtagtcgtcg ctcctgcagc tgccgctccc actgcccgcg    1560
agggccgcgc cgggcgtcat gggcatgtag ccgtcgtctg cccccaggtt gctgctggag    1620
ctcctgtggg agccgatctc gatgtctccg tagtcctctg ggtaggggtg gtaggccacc    1680
ttgggagagg acgcggggca ggacgggcag aggcggcccg cgctgcccga gaaggtggcc    1740
cgcatcaggg tgtattcatc cagcgaggca gaggagggct ggggcaccgg ccgctgccgg    1800
gctggcgtgg tcagggagta ggtcctcttg cgcagccctc ggtccaggtc ctgggccgcg    1860
tcccccgaga cccggcggta ggagcggcca cagtggctca ggggcctgtc catggtcatg    1920
tacccgtaga actcaccgcc gccgccgccg tctcggccg ggggcgtctc cgcgatggac    1980
tcgggcgtgt tgcttcggtg gctgcagaag gcgcgcaggt cgcctgggct ggagccgtac    2040
tcgtccaggg acatgaagcc ggggtcgctg ggggagcccg aggcggaggc gctgccgctg    2100
gagggccgct ggccggggcc gtggtgcagc ggatgcggca gaggcgggtg cgggccgggc    2160
ggcggcgggt aggagcccga gccgtggccg ctgctggacg acagggagc                2209

<210> SEQ ID NO 5
<211> LENGTH: 149
<212> TYPE: DNA
<213> ORGANISM: Homo sapiens

<400> SEQUENCE: 5
taacctaaag aatgaagtca tgccccggcc tgcacccggg aaactgcaca cagcgaaaga      60
tcgccactga gataaagagc tgaaagctat tccccaattc agctgtttca gccgtgcggt     120
ctcacaatgg gctcacagac ggcagcatc                                       149

<210> SEQ ID NO 6
<211> LENGTH: 832
<212> TYPE: DNA
<213> ORGANISM: Homo sapiens

<400> SEQUENCE: 6
gtttccacaa tccacctcgt agctggggcg tgccgcttgc ctcggcttgt cccggcagaa      60
cactcttacc tttaatggcg actgaaaagt tgccacgagt tcctgatcat tgtggtaggt     120
gctgcgtgaa gctgagacgt gcgtgagcca catcccaggg ggctttgagc ccccaccgcg     180
gcggcggctg aggggaggct tgtcgtactc gcacaggagg acacagggct gcagtgttca     240
ctccagggcc tcttatcatt gggatctgag gaattttccg agaggaagtg cgaattaaca     300
atgatgaaag gtttgtgagt gagtgacagg cacgttctat tgagcactgc atggggcatt     360
atgtgccacc agagacgggg gcagaggtca agagccctcg agggctggga gagttcggag     420
gatagaagtc atcagagcac aatgaagcca gaccctgcag ccgccttccc cttcggggc     480 ttccttagaa tgcagcattg cggggactga gctgtcccag gtgaagggg gccgtcacgg     540 tgtgtggacg cccctcggct cagccctcta agagactcgg cagccaggat gggctcaagg     600
catgagccct caaaggaggt taggaaggag cgagggagaa aagatatgct tgtgtgacgt     660
cctggccgaa gtgagaacaa ttgtatcaga taatgagtca tgtcccattg aggggtgccg     720
acaaggactc gggaggaggc cacgagccc tgtactgagg agacgcccac agggagcctc     780
gggggcccag cgtcccggga tcactggatg gtaaagccgc cctgcctggc gt             832
```

<210> SEQ ID NO 7
<211> LENGTH: 256
<212> TYPE: DNA
<213> ORGANISM: Homo sapiens

<400> SEQUENCE: 7

| | | | | | |
|---|---|---|---|---|---|
| tccagctgca | gcgagggcgg | ccaggccccc | ttctccgacc | tgcagggta | gcgcggcctc | 60 |
| ggcgccggag | acccgcgcgc | tgtctggggc | tgcggtggcg | tggggagggc | gcggcccccg | 120 |
| gacgccccga | ggaaggggca | cctcaccgcc | cccacccaga | gcgcctggcc | gtgcgggctg | 180 |
| cagaggaccc | ctccggggca | gaggcaggtt | ccacggaaga | ccccggcccg | ctggggcttc | 240 |
| cccggagact | ccagag | | | | | 256 |

<210> SEQ ID NO 8
<211> LENGTH: 184
<212> TYPE: DNA
<213> ORGANISM: Homo sapiens

<400> SEQUENCE: 8

| | | | | | |
|---|---|---|---|---|---|
| acttactgct | tccaaaagcg | ctgggcacag | ccttatatga | ctgaccccgc | ccccgagtcc | 60 |
| caggccgccc | catgcaaccg | cccaaccgcc | caaccgccac | tccaaaggtc | accaaccact | 120 |
| gctccaggcc | acgggctgcc | tctccccacg | gctctagggc | ccttcccctc | caccgcaggc | 180 |
| tgac | | | | | | 184 |

<210> SEQ ID NO 9
<211> LENGTH: 118
<212> TYPE: DNA
<213> ORGANISM: Homo sapiens

<400> SEQUENCE: 9

| | | | | | |
|---|---|---|---|---|---|
| tgccacaccc | aggtaccgcc | cgcccgcgcg | agagccgggc | aggtgggccg | cggatgctcc | 60 |
| cagaggccgg | cccagcagag | cgatggactt | ggacaggcta | agatggaagt | gacctgag | 118 |

<210> SEQ ID NO 10
<211> LENGTH: 1534
<212> TYPE: DNA
<213> ORGANISM: Homo sapiens

<400> SEQUENCE: 10

| | | | | | |
|---|---|---|---|---|---|
| tcgccagcgc | agcgctggtc | catgcaggtg | ccacccgagg | tgagcgcgga | ggcaggcgac | 60 |
| gcggcagtgc | tgccctgcac | cttcacgcac | ccgcaccgcc | actacgacgg | gccgctgacg | 120 |
| gccatctggc | gcgcgggcga | gccctatgcg | ggcccgcagg | tgttccgctg | cgctgcggcg | 180 |
| cggggcagcg | agctctgcca | gacggcgctg | agcctgcacg | gccgcttccg | gctgctgggc | 240 |
| aacccgcgcc | gcaacgacct | ctcgctgcgc | gtcgagcgcc | tcgccctggc | tgacgaccgc | 300 |
| cgctacttct | gccgcgtcga | gttcgccggc | gacgtccatg | accgctacga | gagccgccac | 360 |
| ggcgtccggc | tgcacgtgac | aggcgaggcg | gcgtgggagc | gggtccccgg | cctcccttcc | 420 |
| cgccctcccg | cctgccccgc | cccaagggct | acgtgggtgc | caggcgctgt | gctgagccag | 480 |
| gaagggcaac | gagacccagc | cctctcctct | accccaggga | tctcacacct | gggggtagtt | 540 |
| taggaccacc | tgggagcttg | acacaaatgc | agaatccagg | tccaggaag | ggctgaggtg | 600 |
| ggcccgggaa | taggcattgc | cgtgactctc | gtagagtgac | tgtccccagt | ggctctcaga | 660 |
| cgaagaggcg | agaaagacaa | gtgaatggca | atcctaaata | tgccaagagg | tgcaatgtgg | 720 |
| tgtgtgctac | cagcccggaa | agacactcgc | agccctcta | cccaggggtg | cacagacagc | 780 |

```
ccaccaagta gtgcctagca ctttgccaga ccctgatata caaagatgcc tgaaccaggg      840
tcccgtccct agagcagtgg ctctccactc tagcccccac cctgctctgc gacaataatg      900
gccacttagc atttgctagg gagccgggac ctagtccaag cacccacaag catgaatttg      960
ccaaatcttt tcagcaacct cttaaggcaa ctgctatcat gatcctcact ttacacatgg     1020
agaagcagaa gcagagatga tagaatcttt cgcccaaggc cacatctgta ttgggacggg     1080
ggcagcctgg cacccaagtg cccattcctc ccttctgacc agcccccacc cctccggctc     1140
tggcgtccaa agggctaagg ggaggggtgc ccttgtgaca gtcacccgcc ttctcccctg     1200
cagccgcgcc gcggatcgtc aacatctcgg tgctgcccag tccggctcac gccttccgcg     1260
cgctctgcac tgccgaaggg gagccgccgc ccgccctcgc ctggtccggc ccggccctgg     1320
gcaacagctt ggcagccgtg cggagcccgc gtgagggtca cggccaccta gtgaccgccg     1380
aactgcccgc actgacccat gacggccgct acacgtgtac ggccgccaac agcctgggcc     1440
gctccgaggc cagcgtctac ctgttccgct ccatggcgc cagcggggcc tcgacggtcg      1500
ccctcctgct cggcgctctc ggcttcaagg cgct                                 1534

<210> SEQ ID NO 11
<211> LENGTH: 269
<212> TYPE: DNA
<213> ORGANISM: Homo sapiens

<400> SEQUENCE: 11
atgaacttca agggcgacat catcgtggtc tacgtcagcc agacctcgca ggagggcgcg       60
gcggcggctg cggagcccat gggccgcccg gtgcaggagg agaccctggc gcgccgagac      120
tccttcgcgg ggaacggccc cgcgcttccc gacccgtgcg gcggccccga ggggctgcgg      180
gagccggaga aggcctcgag gccggtgcag gagcaaggcg gggccaaggc ttgagcgccc      240
cccatggctg ggagcccgaa gctcggagc                                        269

<210> SEQ ID NO 12
<211> LENGTH: 282
<212> TYPE: DNA
<213> ORGANISM: Homo sapiens

<400> SEQUENCE: 12
tcagtgttat gtggggagcg ctagatcgtg cacacagtag gcgtcaggaa gtgttttccc       60
cagtaattta ttctccatgg tactttgcta aagtcatgaa ataactcaga ttttgttttc      120
caaggaagga gaaaggccca gaatttaaga gcaggcagac acacaaccgg gcaccccag       180 accctggccc ttccagcagt caggaattga cttgccttcc aaagcccag cccggagctt       240 gaggaacgga ctttcctgcg caggggatc ggggcgcact cg                          282

<210> SEQ ID NO 13
<211> LENGTH: 142
<212> TYPE: DNA
<213> ORGANISM: Homo sapiens

<400> SEQUENCE: 13
gtggaaacac aacctgcctt ccattgtctg cgcctccaaa acacaccccc cgcgcatccg       60
tgaagctgtg tgtttctgtg ttactacagg ggccggctgt ggaaatccca cgctccagac      120
cgcgtgccgg gcaggcccag cc                                               142

<210> SEQ ID NO 14
```

<211> LENGTH: 741
<212> TYPE: DNA
<213> ORGANISM: Homo sapiens

<400> SEQUENCE: 14

```
tccacacctc gggcagtcac taggaaaagg gtcgccaact gaaaggcctg caggaaccag    60
gatgatacct gcgtcagtcc cgcggctgct gcgagtgcgc gctctcctgc caggggggacc   120
tcagaccctc ctttacagca caccgagggc cctgcagaca cgcgagcggg ccttcagttt   180
gcaaaccctg aaagcgggcg cggtccacca ggacgatctg gcagggctct gggtgaggag   240
gccgcgtctt tatttggggt cctcgggcag ccacgttgca gctctggggg aagactgctt   300
aaggaacccg ctctgaactg cgcgctggtg tcctctccgg ccctcgcttc cccgaccccg   360
cacaggctaa cgggagacgc gcaggcccac cccaccggct ggagaccccg gcacggcccg   420
catccgccag gattgaagca gctggcttgg acgcgcgcag ttttcctttg gcgacattgc   480
agcgtcggtg cggccacaat ccgtccactg gttgtgggaa cggttggagg tcccccaaga   540
aggagacacg cagagctctc cagaaccgcc tacatgcgca tggggcccaa acagcctccc   600
aaggagcacc caggtccatg cacccgagcc caaaatcaca gacccgctac gggcttttgc   660
acatcagctc caaacacctg agtccacgtg cacaggctct cgcacagggg actcacgcac   720
ctgagttcgc gctcacagat c                                              741
```

<210> SEQ ID NO 15
<211> LENGTH: 4498
<212> TYPE: DNA
<213> ORGANISM: Homo sapiens

<400> SEQUENCE: 15

```
ctgccctcgc ggatctcccc cggcctcgcc ggcctccgcc tgtcctccca ccaccctctc    60
cgggccagta ccttgaaagc gatgggcagg gtcttgttgc agcgccagtg cgtaggcagc   120
acggagcaga ggaagttggg gctgtcggtg cgcaccagct cgcccgggtg gtcggccagc   180
acctccacca tgctgcggtc gccgctcctc agcttgccgg ccagggcagc gccggcgtcc   240
ggggcgccca gcggcaacgc ctcgctcatc ttgcctgggc tcagcgcggt ggaaggcggc   300
gtgaagcggc ggctcgtgct ggcatctacg gggatacgca tcacaacaag ccgattgagt   360
taggaccctg caaacagctc ctaccagacg gcgacagggg cgcggatctt cagcaagcag   420
ctcccgggag accaacatac acgttcaggg gcctttatta ctgcgggggg tggggggggg   480
cgggggtggt taggggagga gggagactaa gttactaaca gtccaggagg ggaaaacgtt   540
ctggttctgc ggatcggcct ctgacccagg atgggctcct agcaaccgat tgcttagtgc   600
attaaaaagt ggagactatc ttccacgaat cttgcttgca gaggttaagt tctgtctttg   660
gctgttagaa aagttcctga aggcaaaatt ctcatacact tcctaaaata tttatgcgaa   720
gagtaaaacg atcagcaaac acattatttg gaagttccag tagttaatgc ctgtcagttt   780
tttgcaggtg agttttgtct aaagtcccaa cagaacacaa ttatctcccg taacaaggcc   840
acttttatca tgcaaaactg gcttcagtcc cgaaaagcaa gagctgagac ttccaaaggt   900
agtgctacta atgtatgtgc acgtatatat aaatatatac atatgctcta cttcataaaa   960
tatttacaat acaatctgtg gagaatttaa acacaacaga aatccattaa tgtacgctgc  1020
agattttttt aagtagcctt gaaaatcagc ttcagtagtt ggagcagtgc tgagctagaa  1080
gtacttgtca tgttctctgt tctctcaatg aattctgtca aaacgctcag tgcagaaaat  1140
tcagcgtttc agagatcttc agctaatctt aaaacaacaa tcataagaag gcccagtcga  1200
```

-continued

```
tgacactcag ggttctacag ctctcccaca tctgtgaact cgggtttggg gatgttggtt    1260
aagtttgtgg ctggtcctct ggtttgttgg gagttgagca gccgcagagt cacacacatg    1320
caaacacgca ctcttcggaa ggcagccact gtctacatca gctgggtgac tcagccctga    1380
ctcgggcagc agcgagacga tactcctcca ccgtcgccca gcacccgccg gttagctgct    1440
ccgaggcacg aacacccacg agcgccgcgt aaccgcagca ggtggagcgg gccttgaggg    1500
agggctccgc ggcgcagatc gaaacagatc gggcggctcg ggttacacac gcacgcacat    1560
cctgccacgc acactgccac gcacacgcaa cttcacggct cgcctcggac cacagagcac    1620
tttctccccc tgttgtaaaa ggaaaacaat tggggaaaag ttcgcagcca ggaaagaagt    1680
tgaaaacatc cagccaagaa gccagttaat tcaaaaggaa gaagggggaa aaacaaaaaa    1740
aaacaacaaa aaaaggaagg tccaacgcag gccaaggaga agcagcagag gttgacttcc    1800
ttctggcgtc cctaggagcc ccggaaagaa gtgcctggcg gcgcagggcc gggcagcgtg    1860
gtgccctggc tgggtccggc gcgcggggcg ccgtcccgcc cgcgcccgct ggctctatga    1920
atgagagtgc ctggaaatga acgtgctttt actgtaagcc cggccggagg aattccattc    1980
cctcagctcg tttgcatagg ggcggccggc ggccaatcac aggcctttcc ggtatcagcc    2040
agggcgcggc tcgccgccgc cggctcctgg aattggcccg cgcgccccg ccgccgcgcc    2100 gcgcgctact gtacgcagcc cgggcgggga gtcggaggcc accccgcgc cccgcatcca    2160 agcctgcatg ctggcccggg gccccgcccg cgtgcggacc cctttccgca gccacacgca    2220
ggcttgtgcg gctccgcgag tggccacggt ccggagacct ggaaaaagaa agcaggcccc    2280
gccggcccga ggaggacccg gccggcgcgc cgcacccgga gaggcccggc cccgcgagcc    2340
gctgcaggca ggcgcagtgg ccgccacgag gctcccgaac cgggctgcag cccgcggacg    2400
gccccagatc ctgcgcggcc gcccagggcc aggcctccgc ttccagggcg ggggtgcgat    2460
ttggccgcgg ggcccggggg agccactccg cgctcctgca ccgtccggct ggcagctgcg    2520
gcgaagcggc gctgattcct tgcatgaggc cggacggcgt ccgcgcgtgc cgtttgctct    2580
cagcgtcttc ccttgggtcg gtttctgtaa tgggtgtttt ttaccgctgc gcccgggccg    2640
cggctcgatc cctccgcgcg tctcacttgc tgcgtgcgtc agcggccagc gaagagtttc    2700
ctagtcagga aagaccccaa gaacgcgcgg ctggaaggaa agttgaaagc agccacgcgg    2760
cttgctcccg ggccttgtag cgccggcacc cgcagcagcc ggacagcctg cccgggcccc    2820
gcgtctcccc tccggctccc cggaagcggc ccccgctcct ctccccgccc ccgtgcgctc    2880
gagcggcccc aggtgcggaa cccacccccgg cttcgcgtgc gggcggccgc ttccccctgc    2940
gccggtcccc gcggtgctgc gggcattttc gcggagctcg gagggccccg ccccggtcc    3000 ggcgtgcgct gccaactccg accccgcccg gcggggctcc ctcccagcgg aggctgctcc    3060
cgtcaccatg agtccctcca cgccctccct gccgggccct gcacctcccg ggcctctca    3120 tccaccccgg ggctgcaacc cagtccccgg atcccgccc cgttccaccg cgggctgctt    3180
tgtggtcccc gcggagcccc tcaattaagc tccccggcgc ggggtccct cgccgacctc    3240 acggggcccc tgacgcccgc tcctcccctcc cccagggcta gggtgctgtg gccgctgccg    3300
cgcagggact gtccccgggc gttgccgcgg gcccggacga aggaggggc cggggttgac    3360 tggcgtggag gccttttccg ggcgggcccg gactgcgcgg agctgtcggg acgcgccgcg    3420
ggctctggcg gacgccaggg ggcagcagcc gccctccctg gacgccgcgc gcagtccccg    3480
gagctcccgg aacgcccccg acggcgcggg gctgtgcggc ccgcctcgtg gccttcgggt    3540
```

| | |
|---|---|
| cgcccgggaa gaactagcgt tcgaggataa aagacaggaa gccgcccag agcccacttg | 3600 |
| agctggaacg gccaaggcgc gtttccgagg ttccaatata gagtcgcagc cggccaggtg | 3660 |
| gggactctcg gaccaggcct ccccgctgtg cggcccggtc ggggtctctt cccgaagccc | 3720 |
| ctgttcctgg ggcttgactc gggccgctct tggctatctg tgcttcagga gcccgggctt | 3780 |
| ccgggggggct aaggcgggcg gccgcggcc tcaaccctct ccgcctccgc tcccctggg | 3840 |
| cactgccagc acccgagttc agttttgttt taatggacct ggggtctcgg aaagaaaact | 3900 |
| tactacattt ttctttaaa atgatttttt taagcctaat tccagttgta aatccccccc | 3960 |
| tccccccgcc caaacgtcca ctttctaact ctgtccctga gaagagtgca tcgcgcgcgc | 4020 |
| ccgcccgccc gcaggggccg cagcgccttt gcctgcgggt tcggacgcgg cccgctctag | 4080 |
| aggcaagttc tgggcaaggg aaaccttttc gcctggtctc caatgcattt ccccgagatc | 4140 |
| ccacccaggg ctcctggggc cacccccacg tgcatccccc gaaccccg agatgcggga | 4200 |
| gggagcacga gggtgtggcg gctccaaaag taggcttttg actccagggg aaatagcaga | 4260 |
| ctcgggtgat ttgcccctcg gaaaggtcca gggaggctcc tctgggtctc gggccgcttg | 4320 |
| cctaaaaccc taaaccccgc gacggggggct gcgagtcgga ctcgggctgc ggtctcccag | 4380 |
| gagggagtca agttccttta tcgagtaagg aaagttggtc ccagccttgc atgcaccgag | 4440 |
| tttagccgtc agaggcagcg tcgtgggagc tgctcagcta ggagtttcaa ccgataaa | 4498 |

<210> SEQ ID NO 16
<211> LENGTH: 453
<212> TYPE: DNA
<213> ORGANISM: Homo sapiens

<400> SEQUENCE: 16

| | |
|---|---|
| ttcggaagtg agagttctct gagtcccgca cagagcgagt ctctgtcccc agccccaag | 60 |
| gcagctgccc tggtgggtga gtcaggccag gcccggagac ttcccgagag cgagggaggg | 120 |
| acagcagcgc ctccatcaca gggaagtgtc cctgcgggag gccctggccc tgattgggcg | 180 |
| ccggggcgga gcggcctttg ctctttgcgt ggtcgcgggg gtataacagc ggcgcgcgtg | 240 |
| gctcgcagac cggggagacg ggcggccgca cagccgcgc ggaggcccca cagccccgcc | 300 |
| gggacccgag gccaagcgag gggctgccag tgtcccggga cccaccgcgt ccgccccagc | 360 |
| cccgggtccc cgcgcccacc ccatggcgac ggacgcggcg ctacgccggc ttctgaggct | 420 |
| gcaccgcacg gagatcgcgg tggccgtgga cag | 453 |

<210> SEQ ID NO 17
<211> LENGTH: 560
<212> TYPE: DNA
<213> ORGANISM: Homo sapiens

<400> SEQUENCE: 17

| | |
|---|---|
| acgcacactg ggggtgtgat ggaaaggggg acgcgatgga taggggtggg cgcacactgg | 60 |
| gggacgcgac gggagggggt gagcacacac tgggggtgtg atggagaggg cgacgcaata | 120 |
| gggaggggtg ggcgcacacc agggacgcga tgatggggac gggtgggcgc acaccaggtg | 180 |
| gcatgatggg gaggagtggg tacacaccat ggggggcgtg atggggaggc gtgggcgtac | 240 |
| accggggggc gcgatgggga ggggtgggcg cacaccgggg gacgcgatgg aggcggtggg | 300 |
| tgcacacggg gcgcgatggg tgggagtagg tgcacactga gggcacgatt gggagacac | 360 |
| gaaggagagg ggtgggcgca cactggggga cgcgatggcc gggacacgat gcggagaagt | 420 |
| gggtgaatac cggggtcgcg atgggcgccc tggaaggacg gcagtgctgc tcacaggggc | 480 |

```
caggccctc agagcgcgcc ccttgggggt aaccccagac gcttgttccc gagccgactc        540
cgtgcactcg acacaggatc                                                  560

<210> SEQ ID NO 18
<211> LENGTH: 157
<212> TYPE: DNA
<213> ORGANISM: Homo sapiens

<400> SEQUENCE: 18
ccacagggtg gggtgcgccc acctgccctg tccatgtggc cttgggcctg cggggagag         60 ggaatcagga cccacagggc gagcccctc cgtagcccgc ggcaccgact ggatctcagt        120 gaacaccgt cagcccatcc agaggctaga aggggga                                 157

<210> SEQ ID NO 19
<211> LENGTH: 114
<212> TYPE: DNA
<213> ORGANISM: Homo sapiens

<400> SEQUENCE: 19
ttgaggtctc tgtgcatgct tgtgcgtacc ctggactttg ccgtgagggg tggccagtgc        60
tctgggtgcc tttgccagac aactggtctg ccgggccgag cattcatgct ggtc            114

<210> SEQ ID NO 20
<211> LENGTH: 104
<212> TYPE: DNA
<213> ORGANISM: Homo sapiens

<400> SEQUENCE: 20
tgacgcgccc ctctccccgc agctccacct ggttgcgctc aacagccccc tgtcaggcgg        60
catgcggggc atccgcgggg ccgacttcca gtgcttccag cagg                       104

<210> SEQ ID NO 21
<211> LENGTH: 659
<212> TYPE: DNA
<213> ORGANISM: Homo sapiens

<400> SEQUENCE: 21
aacacactgt ctcgcactag gtgctcgcgg aagagcgcgg cgtcgatgct gcggctcagg        60
ttgatgggcg atggcggccg cagatccagc tcgctcagcg atggcgccgg tcccacaccg       120
ttgcgggaca gtcccgggcc accctggggt ccgcgaccca acgacgcagc cgagccccag       180
gcgcctgaac tgggcgtggc cagctgccca ctctccgccg ggttgcggat gaggctcttg       240
ctgatgtcca agctgcctgc accaacgttg ctgggccctg catagcagtt attgggtcgc       300
tccggcacct cgctctttcc tgacggcgcc gggcacgcca gacgcatcag cttagccag        360 caagcgtgct ccgtgggcgg cctgggtctc gcggcagcca ccgcggccaa cgccagggcg       420
agcgcccatg tcagctccag gaggcgcagc cagaagtgga cacccacca ggcccacgag        480 aagcggccca cgcggcctgg gcccgggtac agccagagcg cagccgccag ctgcaagccg       540
ctagccagca gccccagcgc gcccgccaca gccaacagcc gagggccgg gctggcatcc       600 cagccccgtg ggccgtccag caggcggcga cggcacaggc agagcgtgcc cagagccac       659

<210> SEQ ID NO 22
<211> LENGTH: 813
<212> TYPE: DNA
<213> ORGANISM: Homo sapiens
```

<400> SEQUENCE: 22

| | | | | | |
|---|---|---|---|---|---|
| gtctgcacga | agcccgcggc | ggcctgcagg | gggcccagcg | actcgtccag | ggaaccggtg | 60
| cgcaggagca | gccgggggcg | cggcgcgccg | gccgcccttg | ggggactctg | gggccggggg | 120
| cgcagctcga | tctgacgctt | gggcactgtc | cggggcctgg | cgggcgcggc | gccctcctcc | 180
| agagccacct | ccacacactc | gaactgcgct | ggggcggcag | gacttggccc | acggggccgc | 240
| agctctaggt | aggtggccca | gcgggagcca | ccatcgggga | cctggactg  | gcgtgggacc | 300
| gcggcgggag | acgctggccc | cggcggcaag | gggctgatga | aggccggctc | cgtgaactgt | 360
| tgttgcgcct | cgcgatcgtc | tgcgccgag  | cagccgaaca | ggggtccgac | gccgaagatg | 420
| acttccatct | cccccgacgg | cagcgtgcgc | agctggggct | ggggtggccg | tgggccggaa | 480
| cctgggcctc | gcgggaaacc | cgagccggcc | ccgtgccgct | ggcggctatt | ctgggcgctg | 540
| acggacaggc | gaggctgcgc | gcccgccccc | cgcccaggag | ccacccaggg | ccaattcgct | 600
| gggcctttcg | cgtccggccc | aacgtccggg | ggctccggag | aacctggagc | cgtgtagtag | 660
| gagcctgacg | aaccggagga | gtcctggcgc | cgcgcggggg | ccgtgggcag | ctgcctcggg | 720
| atcccaggca | gggctggcgg | ggcgagcgcg | gtcagcatgg | tggggccgga | cgccgtgcac | 780
| tatctccctc | gcattcgcct | ccgctggtgg | cgc | | | 813

<210> SEQ ID NO 23
<211> LENGTH: 440
<212> TYPE: DNA
<213> ORGANISM: Homo sapiens

<400> SEQUENCE: 23

| | | | | | |
|---|---|---|---|---|---|
| ctggagagaa | ctatacgggc | tgtgggagtc | accgggcgac | tatcaccggg | cctccttttcc | 60
| acatcctcct | ccgggaaggg | acccgttcc  | gggcctcgac | cggcgcagac | tgggctgacc | 120
| cactttcttg | ggcccactga | gtcacctcga | aacctccagg | ccggtagcgg | ggaggagagg | 180
| aggagcaggc | gggggtgcca | aggtgtgggc | tgcgccctgg | ttaggggggcg | agcccggctt | 240
| gtttatgagg | aggagcgcgg | aggaggatcc | agacacacag | gcttgcgcgc | ccagactcgc | 300
| ccggccagcg | gctggcggcc | tccgacgtca | ccaaaaccggt | tgggtgagag | ggcagagagc | 360
| agggggaagg | gccgcagtcc | cgcccgcgcc | ccccggcacg | caccgtacat | cttgccctcg | 420
| tctgacagga | tgatcttccg | | | | | 440

<210> SEQ ID NO 24
<211> LENGTH: 252
<212> TYPE: DNA
<213> ORGANISM: Homo sapiens

<400> SEQUENCE: 24

| | | | | | |
|---|---|---|---|---|---|
| gagtgcggag | tgaaggggtg | cactgggcac | tcagcgcggc | ccttgggagg | cagggccgcc | 60
| ccagcctgcc | ctcctgtctg | ggaaggccgt | ccagaagcag | gagccccggg | gaaaacaact | 120
| ggctggacgg | ggcggccttc | agtgtctctc | ccagcctgag | agtcgcttcc | caccacctgg | 180
| gcacgaacct | gctctgcgat | ctccggcaag | ttcctgcgcc | tcctgtcggt | aaaatgcaga | 240
| tcgtggcgtc | tt | | | | | 252

<210> SEQ ID NO 25
<211> LENGTH: 1539
<212> TYPE: DNA
<213> ORGANISM: Homo sapiens

<400> SEQUENCE: 25

```
tcttctttcc gcccctaggg ggcacaagcg ggcatgtcca agcgcctagg agcccgtacc      60 gctgggacc  tcccctttccg cgaacccga  gcgggtagac ccagagcaat ccgagtgtgg    120
aaacaatgga gaggggcgt   gttgagctgg ggtctccatg cctcgttggg gagagggagg    180
tgagtttgtg tcttctggaa ggcgtggggg ctgtgccctc gtgggggtag gaagtgctcc     240
cgtggggcgg ggtgcggatc ggagaggtga gtgggtgcgt ctgtccagcg gtccgcccgg    300
tgtggtcgtg cccggcccgc gtggggatgg gggtgtctct cccgctgggc aactatacca    360
gcgcaaccgg ggcgtcggcg cggcccacgc tagcggcgct gctccggcgg cgggggctgg    420
gcgtggcggt gatgctgggc gtggtggccg cgctgggcgt ggtggccgcg ctgccgccct    480
cacccgggca gccgtgctgg agaaggatgt cggcgcacag ctggcttcca gcctggcggg    540
cgtagaacag cgccgtgcgg ccctgggcgt cacgggccgc cacgtccgcg ccgtactaga    600
gggcggaaac ggccgcgtga ccgcgcgtcc ccagggcgcc cacacccggc gccgcctccc    660
ccacatggcc aagcctactt ccggggtccc tctgggaatt tcgggctttc ccgcgccagg    720
cgttttccga gatgaagcct caaagacccc cttttcctccc cccagctcac gtacccacag    780
cagcagttgc gtgatgacga cgtgggcgag ctcggccgcc aggtggagtg gggagcgcag    840
ctgtgggtcc tctacgctgg tgtcgagcgg cccgtgtcgc gcatgggcca aaagcaggag    900
aacggtagcc acgtcctggg cctgcacggc ggcccacagc tggcggccca gcggctcctc    960
cgaggtgctc agcggcgcca ggaacagtag ctgctcgtac ttggcgcgaa tccacgactc   1020
gcgctcctcc ctgcaagacc agggatcaac ggaaaaggct ctaggacccc ccagccagga   1080
cttctgcccc tacccacggg accgtctcag gttcgcacac cctcagcaac cctcccccg    1140 ctctgttccc tcacgcttac cgcgaagagt cccgcgaggg cttggcacgg cctcgcgtgt   1200
cgctttccca cacgcggttg gccgtgtcgt tgccaatagc cgtcagcacc agggtcagct   1260
cccgtggcca gtcgtccaag tccagcgagc gaacgcggga caggtgtgtg cccaggttgc   1320
ggtggatgcc agaacactcg atgcagatga gggcgcccag gttcaagctg cccacgtgg   1380 ggtctgcgga aggagcgtag aggtcggctc ccagccgggc agcacaggca ccccggcatt   1440
cactacactc cctagccct ccgctgcctc ctggcactca ctgggggccc cgcagtccac   1500
gcagattgaa ttccccttgg cgttccggat cgcctggat                         1539

<210> SEQ ID NO 26
<211> LENGTH: 2648
<212> TYPE: DNA
<213> ORGANISM: Homo sapiens

<400> SEQUENCE: 26
agccaggtcc agccccgcg  cctgacaccg gccggacgtt cccggggcgc cgcagctgcg      60
gcgggaactc tgggatccgg agccatctgc tcccacccgc tccggagcca accccgggg    120 gccgcctccg ctcccggacc cgcctcctct cccgggagtg tgagccgaac caagagtctc    180
ctgcctatct cctccagtag gaaaatagta ataataatag acaccctgcc cccgtaaaaa    240
acactacctt ccccgtaccg cctcccaagt ctcccggggt acggattgcc tttgcagcag    300
ttccgcccca cctgactcac tccagggtca gccccgggtg ggtttcaatg cggctctggg    360
gagggggtgg gcagtggggg aagtgaggct tcctatccgc cccctctcac ttcacattta    420
aatattctgc acgttccagc cccgcgcgac tcgcgtaccg cccaatccgc cttcaccgca    480
cgaaaaacat cactagcctg ctctcagccc aggggacgac tagtccctgg cgagaagctg    540
```

-continued

| | |
|---|---|
| cctgcaaggt cactgtcatg ccacctgccc caagtgctca ggggaaactg aggcttcctc | 600 |
| atccccttca ccttcaacgt cgctctaaac acggcaaagc cccgtttcca tgctcccaga | 660 |
| gttcagctga ggctggaagt ggggtcctgg gcttctctgg gagcaatttt ctagtcactc | 720 |
| tgatcaagga cgttactttc ccagaaagct ctgaggctga gtccctctga aatcaagtcc | 780 |
| tttctcctgt cgcacaatgt agctactcgc cccgcttcag gactcctatt ctttgcccca | 840 |
| atccttgaca gaggggtgag cttggttcat ccgcccaccc cagagaaaag cttccctagt | 900 |
| ttcctggacc tcgctcctcc accccaagct gagcattcca ggtacccttc cctccctgtt | 960 |
| ctcaagccct gactcaactc actaggggaa gcgcggagct cggcgcccag cagctccctg | 1020 |
| gacccgctgc cagaagacag gctgggggt ccggaaggg gcccggagcc aggaggccct | 1080 |
| cctgtgctct tggtgaagat gccgctgata aacttgagca tcttgcggtc acgagtggat | 1140 |
| gctcggcccc cctcccggcc ccgtttcagc cccggagctg gaggctccag agtgattgga | 1200 |
| ggtgcaggcc cggggggctg cgcggaagca gcggtgacag cagtggctgg actcggagtt | 1260 |
| ggtgggaggg ttagcggagg aggagagccg gcaggcggtc ccggatgcaa gtcactgttg | 1320 |
| tccaaggtct tactcttgcc tttccgaggg gacaacttcc ctcgggctcc agccccagcc | 1380 |
| ccgaccccac cagaggtcga agctgtagag cccctcccc cggcggcggc ggcggtggcg | 1440 |
| gcggcagaga ccgaagctcc agtcccggcg ctgctctttg accccttgac cctgggcttg | 1500 |
| ccctcgcttt cgggccatga caggcggcta cccgcgccct tgcccccgcc ggctttggct | 1560 |
| ccactcgtgg tcacggtctt gcaaggcttg ggagccggcg gaggaggcgc caccttgagc | 1620 |
| ctccggctgc cggtgccagg gtgcggagag gatgagccag gatgccgcc gcccgcccgg | 1680 |
| ccttcgggct ccgggccgcc ccagctcggg ctgctgagca ggggggcgccg ggaggaggtg | 1740 |
| ggggcgcccc caggcttggg gtcggggctc agtcccccgg agagcggggg tcccggaggg | 1800 |
| acggcccaga gggagaggcg gcggccggga gcggggaga ctgggcgggc cggactggcc | 1860 |
| ggagccgggg acagggctgg gggctccgcg ccccccggtgc ccgcgctgct cgtgctgatc | 1920 |
| cacagcgcat cctgccggtg gaagagacgt tcgtgccgct tcttgcccgg ctcctccgcg | 1980 |
| cctcggggggc tgccaggatc cccagtctcg gagcctctgg caccggcggc gccggccgcg | 2040 |
| gccgcagacg gagaaggcgg cggcggaggc accgactcga gcttaaccag ggtcagcgag | 2100 |
| atgaggtagg tcgttgtccg gcgctgaagc gcgcccgcgc cccggctcat ggggcccgga | 2160 |
| gaccccgag ctggggaggg gaggggactc ccccggactg cctcagggg gcccggccat | 2220 |
| ggggccgccc tgctcgctgc ccccagcccc cggaccccgc tgagccccg gcccggctcc | 2280 |
| gctgtcgccg ccgcctccgc cgcctccgct tgcgcccccc tcccatcaca tggggcgccc | 2340 |
| cctccccatg ctccccgccc tgcgccccca ccctcttgga gccccgggac cttggtgctg | 2400 |
| ctccagggag gcgcgccgga ccgtccaccc cggcctgggt ggggggcgctg agatgggtgg | 2460 |
| gggagggcgg ggaggacagt agtgggggca aatgggggag agagaggaaa agggagcaga | 2520 |
| aaagggggacc ggaggctagg ggaaacgaac ctgtgcgggg gaggcagggg cggggaattg | 2580 |
| ggactcaagg gacagggggcc gcggatgcgg tcggaaagag ggtctagagg agggtgggaa | 2640 |
| gctagtgg | 2648 |

<210> SEQ ID NO 27
<211> LENGTH: 200
<212> TYPE: DNA
<213> ORGANISM: Homo sapiens

<400> SEQUENCE: 27

```
ggccgggcaa aaagccgccg caacaaaaag ctgcgctgac gggcggaaaa agccgcggcg    60
gcggagccaa aaagccgggg cggcaaaaag ccacggtggc gggcgcaaac agccgcaaaa   120
agccgcggtg gtgggggcaa aatcagtggg agcaggggca aaaaacaca aaaagccgcg   180 gcggcggggg caaaaagcca                                              200
```

<210> SEQ ID NO 28
<211> LENGTH: 400
<212> TYPE: DNA
<213> ORGANISM: Homo sapiens

<400> SEQUENCE: 28

```
tggctttgct ggagtgtgat gtgataggaa atgtgcagcc aaagacaaaa gaagatgtaa    60
gtaggcttga ctcattgcag ctaagaaccc agatgttacc ttgagggtat taactaataa   120
gcagtttaaa tcagaatggc acattctgat ttgttttttg tatgttcaca tttggcaggc   180
atagatactg tttgaaaaga gaaagtcag tacatagagg taacaagctt aaatatgtgc    240
caagtctaga aacaagagac taggggggata aggacctttc gaaattaaat gcaagatttg   300
aaaactgatt ggctggggga tgaggcaaag gcaggtctttt aaggtcaatc cctgttttgc   360
tttaagttgt tagcgggtgg ttttatcata tattgtagaa                         400
```

<210> SEQ ID NO 29
<211> LENGTH: 650
<212> TYPE: DNA
<213> ORGANISM: Homo sapiens

<400> SEQUENCE: 29

```
ttcctgggaa tgtcagctaa cctgagccta ggggcctgag cccaagggca gactgaggct    60
cccccagcac agggaggtgc tgcctgtgac aaggggtagt gctggcacag tgcaggctac   120
tccctagaaa gatcagcttg aatatgcagg aagagcagga ccctcgggct gaggcagagg   180
tggaatggga agtgcatggt ggtaatttag ttctccagag gccagaagta ggaggagcgg   240
ttggaatgct gatggcccaa agggaaaccc tggactaccc tggcctccca caggactctc   300
atagtaattg cggctccctg cagtggtgag gccagaagga gtgttgccca atgctgtcat   360
catccagtcc accccccacc caccatcaac agatgagtat ggtcatgagt gtggtcacct   420
catcagtcat ttgctcagtt gtgaaaaaga aattgttcag agaagagcaa agtgtttttc   480
catgagccaa aggtcagcca agttatgcta atgaggagga ctggagacag cgtgtcacag   540
acaccgagaa ggagcactgg gcaagggcac ttctcccagg gcagagccca caagaagcgt   600
cctggcacca gacactcagg gaactgaagg ctggcagggg cccgcccagt               650
```

<210> SEQ ID NO 30
<211> LENGTH: 5000
<212> TYPE: DNA
<213> ORGANISM: Homo sapiens

<400> SEQUENCE: 30

```
tccccccagc tgggtataag caaactttcc tgtctatggg ccgcagagac caccatctag    60
ttcccccgcc aaaactttac atgattttaa ttctcctgat gaagatgaga ggataacagc   120
caacagagag ggcagaggat gggatgggac tcccttgctc agagacctca cctctaggtc   180
tttacctcct attgagaaata agtcagttct gtagtaagaa ctctgtgtcc acggcaaccc   240
caaacagaat cctagcgctc ttgtgattct tgtagaatgg ggaatagaac gagcttggcc   300
```

```
caagactgca cagacttaaa aacatactat tctttgaaaa tggcaatcat taaaaagtca    360
ggaaacaaca ggtgctggag aggatgtgga gaaataggaa cacttttaca ctgttggtgg    420
gactgtaaac tagttcaacc atggtggaag tcagtgtggc gattcctcag ggatctagaa    480
ctagaaatac catttgaccc agccatccca ttactgggta tacccaaag ggactataaa    540 tcatgctgct atacagacac atgcacacgt atgtttactg cagcactatt cacaatagca    600
aagacttgga accaacccaa atgtccaaca atgatagact ggattaagaa aatgtggcac    660
atatacacca tggaatacta tgcagccata aaaaatgatg agttcatgtc ctttgtaggg    720
acatggatga aattggaaat cattctcagt aaactatcgc aagaacaaaa aaccaaacac    780
tgcatattct cactcatagg tgggaactga acaatgagaa cacgtggacc caggaagggg    840
aacatcacac tctggggact gttgtggggt gggggaggg gggagggata gcattgggag    900
atataccaaa tgctagatga ggagtttgtg ggtgcagcgc accagcatgt cacacgttta    960
catatgtaac taacctgcac attgtgcaca tgtaccctaa aacttaaagt ataataaaaa   1020
aaatactgtt ctgccataca tacagatact cattaaagat gagggagaag gcatggggt   1080 gggggagaat gtaccaaaac caaagaccac aggataataa cctcagagca gagactatct   1140
ctctagttat tttttctttt gtatgtaatg agaggattta ttatttactc tgatgaagaa   1200
gtttacatca agtgttcagc ttcctttgtg ggttacagag aataaccaga gggctcagtt   1260
atgctctctg aataactatg tttgcttagt gttttctaaa caatattaaa tttcactaaa   1320
atagacaagg ttgataggac ttgggggcat aactcattga ctcaagctat cattttatag   1380
gattgtgaga aaacaaatag atgaacattt aaaatacact catattctcg ctagaaaaga   1440
ggattttgaa tattcttaca tcaaagacat ggtaaatgtt taaggcaatg aatatgctaa   1500
ttaccatgat ttgatcatta tgcaatgtaa aatgtactga acatcacat tgtacctcat   1560 aaatatgtac aatttattat gtgcgaatta aaattttgag tataagaaaa aataaacttc   1620
aattgtaaga aaacaaccca acttttaaaa aacgggcaaa atacgtgaac agatacttca   1680
ctaatagaga tttgcaactg gcaaataagc aaatgaaaaa ctggtcatca tcactatcta   1740
ttagagaaat gcagattaaa actacaataa gaaacaatgc tgcccgtcca gacgcattgt   1800
tttgaccgtt tccaacttgt cccagccctt cccggggcat cgctgggggac cctacgccga   1860 cgtccccct ccgcccgcgc cccaagggcc gactgggcaa attgggagac ccgcccgcg    1920 gggcgaccca acttttcgga acagcacccc accgcccacc cccgcagacc cccggacccc   1980
cgctcccggc ggagactcag ggaacccgc accccaagcc cttctaaatc gtgcagcgtg    2040
agtgtgacgg ccaagagcgg atgcagcccg ggatcgcccg caccttcccg tgggcggaag   2100
cgcaggagcc agctggggag ggggcgcccct agaggagcgg ctagaaagca gacacgggga   2160
actcaggtca tcctgggggg ggacaagaca acgagagccg ggcgcctcgg gggcggcgcg   2220
ggagcctccg caggaccggg cgggcgcccc ggctggcgcg ggcggggggc gcgcccccctt   2280 tacctgcggc tccggctcct aggccatttc ctcacgcggc ggcggccggg actgagctaa   2340
caccactcag gccggccggg tttgaatgag gaggagcggg cgcggagagg aggggacggg   2400
gagggcggag ggagggaggg aggcgtcgcg gagttttttct cggccttttg tgcggacacc   2460
tcccggattc cgcgcccgca cccggccccc caaaagacac ggggagccgc gggcgagggg   2520
ttcagccatc cgccgaggcg cctagtgcct tcgcgcctcc aagaccccc cccaacaaaa    2580 aggagcgtcc cccacccta cccccgcccg gaggacttag ggcctgggct cacctcgggc   2640
gcggagctaa gtgtaggcgc cggggggtccc tagagccgcc ggggcgcagc gagtccggcg   2700
```

-continued

```
ctgggtaact gttgggtcag aaactgttca ggtagcagct gttgtgccct cccttggccc      2760
cgccgctcgg agacgcccg ccccctgcct tgaacggccg cccggccccg cccagcgcc        2820 cacgtgacta gcataggcgc gccccgttc cgcccgccgc cgcagactcc gcctccggga       2880
cgcgagcgag cggcgagcgc gcgcactacc agttcttgct cggcgactcc cgcgcacgcg      2940
cgcgccgtgc caccctcccc gcacccctcc tcccgccatc cggcttaacg tggcgggcgc      3000
gcgccgcggc agtagccgtg acaggtaccc ggcggggcgg gggggagg ggttggcccg        3060 cgagggtgtg cgcaggcaca gacccgggtc ctgtccccgc cgcccctcc tctgcaaggt       3120 gtgcctgggc gaggggaggg gcccgcgcc cgaaccctg ggtcacccc gaattacaaa         3180 caaaaacctt aacgccattg ctcgcgggtt agaaggcagc tgtgcgtgct caggaaaaga     3240
agccacgcac aagagaccgc acgcggcgtg gatacagtga cacgaaacac ccaaaatctc      3300 tttgaaagg gaaccaggc acagtggctc atgcctataa tcccagcact ttcggggcc         3360 aaggcgctca cctaaacccg agagttcaag accagcctgg gcaatacagc gaaaccctgt     3420
ctctacgaaa aatataaaaa ttagctgggc atagggctgg gcacggtggc tcacgcctgt     3480
aatcccagca tttggaggc cgaggcgggc ggatcacgag gtcaggagtt ccagaccatc      3540
ctggctaaca cagtgaaacc ttctctctac taaaaataca aaaaaatta gccgggcgtg      3600 gtggcaggtg cctgtagtcc tagcacttg ggaggttgag gcaggagaat ggcatgaatc      3660
agggagcgga ggctgcagtg agctgagatt gcgccactgc actccagcct gggggacaga    3720
gtgagactcc gtctcaaaaa aaaaaataat aattagctgg gcatggtggc tggcacacat    3780
ggtcccagct actcaggagg ctgaggtgga aggatctctt gatcccgggg aggtcaaggc     3840
tgcagtgagc caagatggca tcaccgcact ccagcctggg ccacagaccc tgtctcaaaa    3900
aaaaaagaga aagtggggaa gaaatgtaa tacaaattaa tataccaaca gcaattagtg     3960
agtacttttt ccatggagct gggagaggga ataaatgttt gtaaaattaa aatgttctac    4020
gctagaaatc aactttcctt ctatgctttc tttacttcac cccttatagc tacttagtaa    4080
atctcacaaa tcctatcctt ctgatctctc tgaaatgtat gtacccttc ccttctattc     4140 tcaccaccca tgtttctttg tttccttcta gcctgtgtaa taatctcata atcgcacctc    4200
ctgtacctgc cttctttcta gtccagaata cgttttccta aattccacca ataaccatcc    4260
tgctactgct ttgtgtgaaa ttctccaaaa aaaattttac ttttcaaaa taagtcaggc     4320 tccctctctt aggatacaaa accacaccat ggtcccagcc aatctttcag cctgattcac    4380
tcagtatata tttattgacc tctcctttct cccaagcact tggctagata ataattaaag    4440
agtgcggcac aaaacaaatt ggattcctcc cctcatggag cttgtatttt cacaggaagc    4500
acagacatta ataaattaa aacacaaaaa aatagacaag catataatta cagtatgtat     4560
cctagagaaa tatcactcat gcagaaagca tacacaagga tgcagcactg tttccaatag    4620
cgaaaagcta gaaacaacct acatgttcac caaaagaaaa tggccacata aactatacca    4680
tatccaaatt atccaaattt tagaatatag acaacaggtt gggcgcggtg gctcacacct    4740
gtaatcccag cactttggga agccgaggcg ggtggatcac aaggtcagga gttcaagacc    4800
agcctggcca acatggtgaa accccgtctc ctctaaaaaa acaaaaaaat cagctgggca    4860
ctgtggcagg agcctgtaat cccagctact gaggagactg aggcaggaga atcgcttgaa    4920
ccctggaggc agaggttgca gtgagccaag atcgcgccac tgcactctag cctgggtgac    4980
agagcaagac tccatctcag                                                5000
```

<210> SEQ ID NO 31
<211> LENGTH: 1500
<212> TYPE: DNA
<213> ORGANISM: Homo sapiens

<400> SEQUENCE: 31

| | | | | | |
|---|---|---|---|---|---|
| tgtaggagtc | ctccggtgct | ggagtccaga | gcacagtgag | gctgggtcct | cccgtgccat | 60 |
| agtgtagggc | atggcgggac | agggatcctg | ccctgcgata | gtccagtgct | tgagtccgca | 120 |
| gtaaggcaat | ggtcctccaa | tgctggagtt | cacggcgttg | tggggtcggg | gtcctttggt | 180 |
| gacttagtcc | agggcgtacc | agggcggggg | tccacagttg | ccatagtgag | gatcttggag | 240 |
| gaaggtggtt | cctgccttgc | tgtagtccgg | ggagcagggg | gcagggtcc | tctcttgtca | 300 |
| gagtctctgg | cgcggggtgg | gggtggaggt | gggggttttc | ctatgcgata | gcccacgggt | 360 |
| cggtgaagcc | gggtcctccc | gtgcctttgt | ccagggcgca | gggggggcgag | ggtcttcggt | 420 |
| ggtggagtcc | gcggagcggc | aggacggggg | tcctccagtg | ccatattcca | gggcgcggcg | 480 |
| gagtggggga | cctgtcctgc | agtggtccag | ggcatgtggg | agtggtggtc | ctgctgtgcc | 540 |
| tcagtccagt | gcgcggtggg | acggcggtcc | tgctgtgctg | tagtgcagga | cgcggtggcg | 600 |
| caggggtagt | ccagagagcg | ccgtggcagg | gggtcctcca | gtgctggaat | ccagtgcaag | 660 |
| gcgggtcagg | ggtcttaccg | tgccgaagtc | ggtggcaagg | gtcctcccgt | gccatagtct | 720 |
| agggggcgac | ggggcagggt | tctctagtgc | aggtgtccag | ggtgtggcag | ggcaggagtc | 780 |
| ctcttgtgca | ggagtccagg | acgtagccga | ggagtcctcc | aatgtcagag | tccagggctc | 840 |
| tgcggggccg | ggttcccca | tgccagagtg | tagggcgcgt | tcaggtgagg | gtcttggcgt | 900 |
| gcagtaatcc | agggtgcggt | ggggcagggg | tagtccagac | ctccatggcg | ggcgtccctc | 960 |
| tgtgcaggag | cccagtgcct | ggcggatcgg | gggtccttct | gtgctgtagt | ccagggcacc | 1020 |
| gcaaggtgtg | ggtcctctgg | tgccctagtc | caggggcgg | cgagtcagag | gttctcccgt | 1080 |
| gtctcagtct | agggcctggt | aggactgggg | tcctggagtc | cacgtggtag | cccaagttgc | 1140 |
| cgcaggacca | ggtactctgg | aaccacagtc | cagggcgctg | aggggcagga | gtagttcagg | 1200 |
| gcgagccggg | gcccaggtcc | tcgggagcca | gagtccaggg | tgtggagggg | tgggggttct | 1260 |
| gcagtggcac | agtccaggac | accgcgggc | gggacagggc | gggatcctc | ccgtgcctta | 1320 |
| gtccagggct | gagccgcggg | agaggtcctt | cagtagcaca | gtctagcgca | cggcgttgca | 1380 |
| ggtgtcctcc | agtgcctgag | gccacggcag | gtcgcgggtc | ccactgtgct | ctagttcagg | 1440 |
| gcggagtggg | tctgaggtct | tctcctgcct | cagtctaggg | cgctggagag | cggggatcct | 1500 |

<210> SEQ ID NO 32
<211> LENGTH: 2500
<212> TYPE: DNA
<213> ORGANISM: Homo sapiens

<400> SEQUENCE: 32

| | | | | | |
|---|---|---|---|---|---|
| gggttggtcc | tagaaagcgt | gaggatcgcc | gagtgcactg | ccctcccagc | ctagggtcca | 60 |
| ctcttccttg | gcccgagccc | agagctcggg | gtttcaggcg | ctgggccctg | tgcagctgcc | 120 |
| cagaataggc | tgagcggcag | gttcccgccc | tggcaaggga | tccagcagtg | gaatcctcac | 180 |
| tgctgttggc | tgcgggcaag | gtcagcgggg | tttccatcgc | tgctggtggg | agccacctgg | 240 |
| cggtggtagc | tgcaagtgag | cgcgtggcag | agactggcag | ggctggtccc | agacaccctg | 300 |
| agggtctctg | ggtgcatcgc | cctaccaccc | tagggtctgc | tcttccttag | cctgctccca | 360 |
| ggacgcggtg | tacgagggct | agactctgag | cagcctccag | gatgggctg | agcagcggat | 420 |

```
tcctgccctg ctgcagctac agtctgaatt aggcgccacc gcagtatctg gccctggggt    480
acgtgctact gggtggcatg gacagagatg ggggctgcca cagctgctat ggggctgagc    540
agccgattct cgccctgctg cagcgggcga ccgctgcaat ccccagcgct atgggaccga    600
ccacctgact tagatgcctt ggaggcatcc ggtcctgggg tcttgctgct ggtgtctgcg    660
ggcagggtca cggctgccac tactactgct gtgcgccatg ggcaggtgcc agctgcagct    720
gagtccgagg cagatgctgt cagggctggt ctgaggttgc ctaagggtgg ctgagtgcac    780
cacgcttcca ccccagggtc cgttattcct aggccggctc ccagattgca gggttgtggg    840
cgttggacac tgtgcagcca tgaggatctg gttgggtgca gattcccgcc ctcctgcagc    900
tgagaagcca atctcataac aggcgctgca gtgacctctg gctctgcggt ccgcgctgct    960
gctggagctg gcagagaaca gagctgccac cgctgctgct tccaggagtg tgcagctggc   1020
agctgcagct gagcccgtgg cggaggctgg aaggcttat tccagaagcc ttgagggtcc    1080
ccgaatgcac cgcccctcca ccctaaggtc cagtcttcct tgcccgcgcc cagagagttg   1140
gattgcaggc gctgagcaca gtgcaggtgc tgggatgggg ctaagctgaa agtttccgcc   1200
ctctggctgc tgcggggccg acagcctgag ttatgcgccg cggcggcttt tggtcatggg   1260
atccgcactg ccggtggctt gcacagggtc gggggctgcc acagctgcta tagttcaccg   1320
tgtgcacgtg gcagccgccc ctgagcccac cgctgaggct gcagggctgg tccggtccca   1380
gacggcctga gggccatttg cccgcgccca gatccgggtg gctgcgctgg gcactgtgca   1440
gcctcccgga atccgctgaa gggcacgttc ccgctctcct acagctgtgg gccgactgcc   1500
tgattttggc cactaggtgg agtctggctc tagggtttcg aggccgctgg tgttggtggg   1560
cggagtccgg gtttgccacc gctgcgctcc atgagcaggt agcagctgca gcggagcttt   1620
agaccgaggc tggcagggct ggccccagac ggcctgaggg tcaggagtg cagggtcctc    1680 ccaccctagg tccgctcttc ctttcccctt acccagagcg ggttgtgcgg gctctgggct   1740
ctgtgccggc gctgggctct gtgcagccgc cgagatgggg ctgagcagcg gatttcctcc   1800
ctgctgcagc tggaggacga ttacctgcac tagccgctga ggcggcatct ggccctgggt   1860
tactgcagct ggtgacgcgg gcagggtcag ggttggttgc aggtggcagc tgctgctaaa   1920
cccattgcga gcctcagggt caccaagttc accgtccttt catcatagta tctgatcttt   1980
ggcccgcgcc cagagtgcgg actggcctgc gctggggact gcatagcttc tggggccgg    2040 tcagcgccag tttcacgtcc tcctgcagct gcgtggccta aggtcttagg cgccgcggcg   2100
ctatctggcc ctgctgtcga cgctgctggt ggtggggaca gggtcaaggg ttgccactgc   2160
tgctcccgtg cgccatcggc aggtggcagt tgcagatgag cccacaattg aggctgttgg   2220
ggctgctccc aggttgttag agggtcgccg agttcaccga catgccaccc taggttacgc   2280
tcttggcccg cacccagagc gccgggttac gggtcctggg ccctgtgcag ccacggggat   2340
ggtgctgagt gcaggttccc gtcttcctga gatgcgggc gaccactgga attagcctct   2400
gtggtggtat ctgaccctag gtccgagct gctggtggcg tgggcggggt cgaagtcgcc    2460
tctgttgctg cggcgtgcca tttgcaccgt cctctggtac                         2500
```

<210> SEQ ID NO 33
<211> LENGTH: 1600
<212> TYPE: DNA
<213> ORGANISM: Homo sapiens

<400> SEQUENCE: 33

-continued

```
aaatactcta ctgaaaaaac agaaatagta aatgaataca gtaaagtttt agaatacaaa      60
atcagcatag aaaaatcagt cgcatttcta tacccaacag cataccatct gaaaaaggaa     120
tcaagaaacc aatcccattt aaaatagcta taaaaaaatg cctgggaata aactaagcca     180
aataaatatg tctaaaatga aaactataaa acattgataa aaatcaattg aaaaagatac     240
aaataaaggg aaagttatcc cattttatg aattagaagt attaatactg ttaaaatgac     300
catcatactc aaatcagtct ataggtccaa tacaatctct aacaaatttc caatgtaatt     360
cttcagagat gttaaaaaag gttttaaaaa tcgttctgcg gatgttaaaa ggattttttaa    420
aacgcttttt tcgttctgca ggcgaaggct gtggccgtgc tcccgccggc cagttcccag     480
cagcagcgca ttgcccctgc tccacgcctt cgctccaggc ccgcaggggc gcagccccgc     540
gggaatcagc actgagccgg tcccgccgcc gccccagtgt ccgggctgcg actgcgggga     600
gccgatcgcc cagcgattgg aggagggcga cgaggccttc cgccagagcg agtaccagaa     660
agcagccggg ctcttccgct ccacgctggc ccggctggcg cagcccgacc gcggtcagtg     720
cctgaggctg gggaacgcgc tggcccgcgc cgaccgcctc ccggtggccc tgggcgcgtt     780
ctgtgtcgcc ctgcggctcg aggcgctgcg gccggaggag ctgggagagc tggcagagct     840
ggcgggcggc ctggtgtgcc ccggcctgcg cgaacggcca ctgttcacgg ggaagccggg     900
cggcgagctt gaggcgccag gctagggagg gccggccctg gagcccggcg cgccccgcga     960
cctgctcggc tgcccgcggc tgctgcacaa gccggtgaca ctgccctgcg ggctcacggt    1020
ctgcaagcgc tgcgtggagc cggggccgag cggccacagg cgctgcgcgt gaacgtggtg    1080
ctgagccgca agctggagag gtgcttcccg gccaagtgcc cgctgctcag gctggagggt    1140
caggcgcgga gcctgcagcg ccagcagcag cccgaggccg cgctgctcag gtgcgaccag    1200
gccctgtagc tgtgacttgg ctgtggggct ggcccgcctc cctgacccct gtcaggcgga    1260
gcagctggag ctgacccacg ggcctgggct ttcgagcgct ttgtccaggc gctaatgatg    1320
ggaaggtgaa aggtggggt ggccacaccc tgcagtcagg gtggcaggtg tcagaggcca    1380
catgcaaccc actggttttg tcttttccag gatgctgata agtttcccgc ggccccccgga   1440
gcagctctgt aaggccctgt aattgccttt cgttcccttc tgctctattg aggagtggga    1500
agatgacaaa gtgttttgc tcaacccgaa ggaaaatgca catgggagga cacaccgggt    1560
tactatttga gtagcccaga caggagagca gcggtctgct                           1600
```

<210> SEQ ID NO 34
<211> LENGTH: 1500
<212> TYPE: DNA
<213> ORGANISM: Homo sapiens

<400> SEQUENCE: 34

```
tgggtggatt gcttgagccc aggagttcga gaccagcctg gacaaaatgg cagaaactcc      60
atgtctacaa aaaatacaaa aattagccgg gcatgatgtt ctgcgcctgt agtcccagct     120
actcaggagg ctgaggtggg aggatcgctt gagcccagga ggcggagttt gcagtgagct     180
gagatgtcac tgcattccag cctgggagac agagccagac tctgtctcaa agaaaaaaaa    240
gaaaaaaaaa aagaaaaga aaaacgaaa ttgtattctg aatacatctt ctaaaacact      300
acatttactt gcactatatt aaactggttt tatcctgacc acaattgcag gtgaaagata    360
ccactgttgt tctatttttc tggtaagtag agtgagccat gtcttcccca gggaagacg     420
cctcctaaaa atttgtagga ccacctttgg ttttcttcca gatatttttt ttgtcatcgc    480
ttttcctgcg cccaattccc atctgtctag ccctcgctgcc tccgctggtc tttttcgcga    540
```

```
gcctctcccc agccgcaggt attcgtctgg gctgcagccc ctcccatctc ctggggcgtg      600
accacctgtc caggccccgc ccccgtccaa cccgcggaga cccgccccct tccccggaca      660
ccgggttcag cgcccgagcg tgcgagcgcg tccccgctcg tcgcccggct cggcgtcggg      720
agcgcgctct gtgtggtcgc tgctgcagtg ttgttgtggc tgtgagaagg cggcggcggc      780
ggcggagcag cagccggacc agactcccta gtagctcagg cgctgccctg cgccggccct      840
ggcagggagc ctggtgagat ggtggaggag gaggctgtgc cgtggctggc cttgctgtgt      900
cctgctgcct ggttagaacc ccatccccgt ccccgtctc ctccgggggg tgaggaggag       960
ctggaagagg ggccggcctc tgtccggccc ggccaggcgg cagtcaccct ctgaggaggc     1020
agcgcccggg gagggcctc ccaggcggcc gccgccgcca gggggaggcg ctgggagtgg      1080
gagtgggagc gggacctcag ctgccaagct cggcccggac cctaggtgcg ggggaggcgg     1140
ggtcccgggc tcgggctgcc tgcccggacc tggcggggat gggcccgtgc ggctccgggt     1200
gtgggacgta ccctcagagc gcccgggggtt attcccactg actccaggga ggtgagtgtg    1260
cgcccttcgc tccctgccgt gtctgtgagg gtccatcgtt gccggagact ggaggtcggg     1320
ggccatggga gccccggggc gaacggtgcg gacatgggcc ttgtggaaag gaggagtgac     1380
cgcctgagcg tgcagcagga catcttcctg acctggtaat aattaggtga aaggatggt     1440 tgggggcggt cggcgtaact cagggaacac tggtcaggct gctccccaaa cgattacggt     1500
```

<210> SEQ ID NO 35
<211> LENGTH: 1700
<212> TYPE: DNA
<213> ORGANISM: Homo sapiens

<400> SEQUENCE: 35

```
gtctctagga caccctaaga tggcggcgag ggagacggtg aaggttggct cccgcctgtc       60
tgggctctga tcctctgtct cccccctccc ctgcggccgg ctcatggcct ggcggaggcc      120
cgaaccaaag acctccgcac cgccgtgtac aacgccgccc gtgacggcaa gggggcagct      180
gctccagaag ctgctcagca gccggagccg ggaggaactg gacgagctga ctggctaggt      240
ggccggcggg gggacgccgc tgctcatcgc cgccctgctac ggccacctgg acgtggtgga     300
gtacctggtg gacccgtgcg cgcgagcgt ggaggccggt ggctcggtgc acttcgatgg      360
cgagaccatg gagggtgcgc cgccgctgtg ggcgcggacc acctgacgt ggtgcggagc      420 ctgctgcgcc gcggggcctc ggtgaactgc accacgcgca ccaactccac gcccctccgc      480
gccgcctgct tcgagggcct cctggaggtg gtgcgctacc tggtcggcga gcaccaggcc      540
aacctggagg tggccaaccg gcacggccac atgtgcctca tgatctcgtg ctacaagggc      600
caccgtgaga tcgcccgcta cctgctggag cagggcgccc aggtgaactg cgcagcgcc     660 aagggcaaca cggccctgca caactgtgcc gagaccagca gcctggagat cctgcagctg      720
ctgctggggt gcaaggccag catgaacgt gatagctacg catgacccc gttgctcccg       780 gccagcgtga cgggccacac caacatcgtg gagtacctca tccaggagca gcccggccag      840
gagcagctca taggggtaga ggctcagctt aggctgcccc aagaaggctc ctccaccagc      900 cagggtgtg cgcagcctca gggggctccg tgctgcatct tctcccctga ggtactgaac      960
ggggaatctt accaaagctg ctgtcccacc agccgggaag ctgccatgga agccttggaa     1020
ttgctgggat ctacctatgt ggataagaaa cgagatctgc ttggggcccct taaacactgg     1080 aggcgggcca tggagctgcg tcaccagggg ggtgagtacc tgcccaaact ggagcccca     1140
```

```
cagctggtcc tggcctatga ctattccagg gaggtcaaca ccaccgagga gctggaggcg    1200
ctgatcaccg acgccgatga gatgcgtatg caggccttgt tgatccggga gcgcatcctc    1260
agtccctcgc accccgacac ttcctattgt atccgttaca ggggcgcagt gtacgccgac    1320
tcggggaata tcgagtgcta catccgcttg tggaagtacg ccctggacat gcaacagagc    1380
aacctggagc ctctgagccc catgagcgcc agcagcttcc tctccttcgc cgaactcttc    1440
tcctacgtgc tgcaggaccc ggctgccaaa gcagcctgg gcacccagat cggcttttgca    1500 gacctcatgg gggtcctcac caaaggggtc cgggaagtgg aatgggccct gcagctgctc    1560
agggagccta gagactcggc ccagttcaac aaggcgctgg ccatcatcct ccacctgctc    1620
tacctgctgg agaaagtgga gtgcaccccc agccaggagc acctgaagca ccagaccatc    1680
tatcgcctgc tcaagtgcgc                                                1700

<210> SEQ ID NO 36
<211> LENGTH: 300
<212> TYPE: DNA
<213> ORGANISM: Homo sapiens

<400> SEQUENCE: 36
taaaaataaa ttgtaataaa tatgccggcg gatggtagag atgccgaccc taccgaggag      60
cagatggcag aaacagagag aaacgacgag gagcagttcg aatgccagga acggctcaag     120
tgccaggtgc aggtgggggc ccccgaggag gaggaggagg acgcgggcct ggtggccaag     180
gccgaggccg tggctgcagg ctggatgctc gatttcctcc gcttctctct tgccgagct     240 ttccgcgacg gccgctcgga ggacttctgc aggatccgca acagggcaga ggctattatt     300

<210> SEQ ID NO 37
<211> LENGTH: 600
<212> TYPE: DNA
<213> ORGANISM: Homo sapiens

<400> SEQUENCE: 37
cgccaccacg tgcgggtagc gccgcatcgc cccagccgtg ttccttggtc tccgtctccg      60
ccgcgcccgc ctggtgaact ggagcacagg gaccatagtt ctggaaattt atccttttc     120 tctccatgga ttcagcagca gtgtctaaaa gaaaaaaatt catcaatcat ttatgtatat     180
tttaatataa aggtaaaaca ctgcgaacca gtggaaccgg atagaaagta attcagtttt     240
acagaacaca actgtttttc aggctctttt attaaatata aagagccat atatatttct     300 gtggaattcc cctttttactt aagaattcat tatcagcgaa ttagtttaag gaggctgttt     360
tgttagaggc tgtggttgca ttcaaaaatt ggaataggaa caatgacttg taaaaattca     420 acatttttatt ttatttttga gatgggtct cgctctgtcg cccaggctgt agtgcagtgg     480
cgcgatctcg gctcactgca acctcagcct cccgggttta aggaattctc tgcttcagcc     540
tcctgaatag ctgggattac aggcgcatgc caccaagccc agctaatttt ttttgtattt     600

<210> SEQ ID NO 38
<211> LENGTH: 1300
<212> TYPE: DNA
<213> ORGANISM: Homo sapiens

<400> SEQUENCE: 38
ccctgaacag tcagagttta ctgcccactt ttgctggagg agaagctcct gaacaactag      60
agagactgtg gttcccaaag agcagcctgt aggcctgagg actgctctat gaccggcgtc     120
agtccctgcc tccctccctc cgtccctcct tccctccttc cttcccaggc cttctctgac     180
```

```
taccagatcc agcagatgac ggccaacttt gtggatcagt ttggcttcaa tgatgaggag      240
tttgcagacc atgacaacaa catcaagtga gtccacttgg atgcccctg cacgaggcac       300 gactccccct cctcgctgct gaagtcccat ggggcagct cccttagtcc ttgccgggag       360
ataacaggtg tttccagttg catgagggtg ctgaggcccc cagtgagaac caggggagga     420
gcactgaggc ctcagatgag caccggggga ggagccctga ggcccagat gagcaccagg      480 ggaggagcac tgaggcccca gatgagcacc ggggaggag cgttgaagcc ccagatgagc      540
accagaggag gagagctgag gccccagatg agcccgggg gaggagctct gaggccccag      600
acgagcaccg ggggaggagc gccgaggccc cagatgagca ccgggggagg agcgccgagg     660
ccccagatga gcagtggggg aggagccccg aggcccccag atgagcagtg ggcggggcag     720
ggagcgccga ggccatcccc cttgctcttg cagcgcccca tttgacagga tcgcggagat     780
caacttcaac atcgacactg acgaggacag tgtgagcgag cggggctgtg cggggtcatg     840
caggcaccct gttcccaggc agctcaggcc gcgcccatgg ctcggtctgt ggtgggcctg     900
tgcggtgggg ctgggagagg cccctctgtg gagctaggaa cagtcgcttt tcttgaccct     960
ccccatcatg ccctccagcc catggcgccc acatcctgaa ctaagcccct ctgggagccc    1020
tgtggggaga gcgcctcctg tctcccccag accctctgga aactgacctt ggcgttttac    1080
tctgcagccc agcgcggctc tgaggcctgc tgcagcgacc gcatccagca ctttgatgag    1140
aacgaggaca tctcggagga cagcgacact tgctgtgctg cccaggtgaa ggccagagcc    1200
aggtgcgggg cctgcccatc cccccaaagc ctctgccgag gaggtgcagc ccccagaaca    1260
cccgtcagat gcccagacgc cctgctgttt gttatgccgg                          1300

<210> SEQ ID NO 39
<211> LENGTH: 1500
<212> TYPE: DNA
<213> ORGANISM: Homo sapiens

<400> SEQUENCE: 39
attgccgtac tttgcttccc tttgtatgta tttcttgtat gctgccgagt cactgatggc       60
tagctctgtc tggcaagtaa ttcaaaaatg ctgtttatgt agaaaggaaa ggtagggact      120
ttaccacact ctgtcattaa agggagcaat tgaagaacaa aggaactgag taaatacta     180 tatattgcct tttgtgttgc gaaacactgt agcacaaaca catttgtgtt cagccaaatg      240
ttttacttcc ttttgtaata acgcatatag taggttgtct ccacatatgt acaagaatcc      300
atattttatt taaacgtata tagtcaattg ttcatattta taggctgcaa acatttctca      360
atctcaaaga cttttacata tccactccca cacagctatt tgttattatt ttaaaagttc      420
ttaaattaaa aaaaaaaata aaatatacta atatctctgt tggttgattt tattaagcaa      480
cttaggattt caacacagtt taaatcatat tgatgactca gatcctggca ggtcttacaa      540
ttcctgtgaa atgagagcac agctaataaa aatattaagc aattacttt attaaaatca      600 tagggttttt ttcattatca catagaaatg attgatctat acagattggt ctcactcatg      660
tgtcttttgg gctgcttggg agcttcatgt agaagtggaa agtccccttt gctcttcctt      720
cgaccaaggt ggggaaaatg aaggcataga atacaatcta gggctattaa agaattgctg      780
gcattacttc tctctatcac gtgtgagcct ggctgcctgc ttcctgaggt agggatcca      840 ggatgagact gtgccggagc ctgttccac aactgcattt ggagatccgt cttattgatt      900
agcgggggaa aggggtgggg atcaggagtg tgaggtgagg ggaggaccaa ctgacgactg     960
```

```
gctcaatgaa gcacaagaca tttcttccg aaagatgtc aaacaactga gaaacagcca   1020
gagaggaagt agaaaggtgg aaaaatgagg agaccctgga agaaatgaag gcatttccta   1080
tgagacagcc ttggggcttt tttcttttct tcttttttt ttgcttccat catctgacct    1140
gcaaaggcta gagtgacagc gtcatgcaaa tgctgcagtc cagcaggtct gggagagggt   1200
ggatgctaga ctgtgagtta atgttaatga tgagcgcagt gaaaatacca gccgctgcca   1260 cccctgctc acagaagcgc tctgagtcag catcagatgc tttgcctcgc ctctcgctgt    1320
gtatctgtat gcctgtgtgc gcgcgcgtgc tcgctcgggc atccgtgtct agccgagggg   1380 aggggtggc gtgtgagtgc gtggagggta aaagccagtc agtcagtgag aagcaaaggt    1440
acgttggaga gcaactaaaa tctgactgat ttccatcttt ggagcatcag atgtattccc   1500
```

<210> SEQ ID NO 40
<211> LENGTH: 200
<212> TYPE: DNA
<213> ORGANISM: Homo sapiens

<400> SEQUENCE: 40

```
gcagcctcct cctgaaaaat gtaagccatt tccactttgt aaagctacgt ttatattcca      60
ccacgatacg atggaaaaga aacccaagg caatttaata tacgggttgg gaagaaagtt     120
ttgctgatgg aactacatta gcctccactc cagcaaagca acaaggaac cacactaaag     180 aaatgtactg aatcttttaa                                                200
```

<210> SEQ ID NO 41
<211> LENGTH: 600
<212> TYPE: DNA
<213> ORGANISM: Homo sapiens

<400> SEQUENCE: 41

```
tcattatccg attgattttc ctggtatcac atcacttaag tttaagtagc tcttatgtta      60
cttagtaatg actgcaaaac acgagttgtg atgcgggcaa tttggataca acaaaaagaa    120
gccattaagt ttgttcgtta gttaacaggt gaaagctctc aagttattaa ggataaaaat    180
gctagtatat atatatatgg tttggaacta tactgcggat tttggatcat atccgccatg    240
gataagggag gaatactata atcaggtttg ttttaaattc catgtctaat gacttcgtta    300
tctagatcac ctgtagagct gttttattg taggagtttt ccttggtttt aatcttttga     360 tttgttttc atgttaatac tgaaattttt aaaaattgca tattgtactt cctatatgaa    420
aattttacta tgtatttta tttttatttt cctttccctt taggaagaat tagttttgttc   480 cctgacagag ttagagtaag ggcaaattac ttgtctctat aaacaactca gatgtttga    540 gccggtgttg tagggttat cttttctgg ttttgcattt tattatagga catagtgctt     600
```

<210> SEQ ID NO 42
<211> LENGTH: 140
<212> TYPE: DNA
<213> ORGANISM: Homo sapiens

<400> SEQUENCE: 42

```
agaaagaaga aatccggtaa aaggatgtgt tattgagttt gcagttggtg tttgatcttg      60
cacagatttt ctcaggggcc ttaagaccgg tgccttggaa ctgccatctg gcatagaca     120 gaagggagca tttatacgcc                                                140
```

<210> SEQ ID NO 43
<211> LENGTH: 900

<212> TYPE: DNA
<213> ORGANISM: Homo sapiens

<400> SEQUENCE: 43

```
cgaagatggc ggaggtgcag gtcctggtgc tcgatggtcg aggccatctc ctggtccgcc      60
tggcggccat cgtggctaaa caggtactgc tgggccggaa agtggtggtc gtacgctgcg     120
aaggcatcaa catttctggc aatttctaca gaaacaagtt gaagtacctg gtttcctcc      180
gcaagcggat gaacacccac ctttcccgag gtccctacca cttccgggcc ccccagccgc     240
atcttctggc ggaccgtgcg aggtatgccg ccccacaaga ccaagcgagg ccaggcttct     300
ctggaccgcc tcaaggtgtt tgaccgcatc caccgccct acgacaagaa aaagcggatg     360
gtgttcctgc tccctcaagg ttgtgcgtct gaagcctaca gaaagtttg cctatctggg     420
gcgcctggct cacgaggttg gctggaagta ccaggcagtg acagccaccc tggaggagaa     480
gaggaaagag aaagccaaga tccactaccg gaagaagaaa cagctcatga ggctacggaa     540
acaggccgag aagaacatgg agaagaaaat tgacaaatac acagaggtcc tcaagaccca     600
cagactcctg gtctgagccc aataaagact gttaattcct catgcgtggc ctgcccttcc     660
tccatcgtcg ccctggaatg tacgggaccc aggggcagca gcagtccagg cgccacaggc     720
agcctcggac acaggaagct gggagcaagg aaagggtctt agtcactgcc tcccgaagtt     780
gcttgaaagc actcggagaa ctgtgcaggt gtcatttatc tatgaccaat aggaagagca     840
accagttact attagtgaaa gggagccaga agactgattg gagggcccta tcttgtgagc     900
```

<210> SEQ ID NO 44
<211> LENGTH: 200
<212> TYPE: DNA
<213> ORGANISM: Homo sapiens

<400> SEQUENCE: 44

```
cataacaaga gtcattctaa tgtgattata aaggacccga agctttgctt ttaaaattca      60
atacttaggt agaaagaaaa tgataacttt ttcccttga tttttattca ctatttttat     120
aacactagca gccctgagac accggattgg aaatatctat gcctcttgat gttacctggg     180
caccactgca tcacagtcct                                                  200
```

<210> SEQ ID NO 45
<211> LENGTH: 400
<212> TYPE: DNA
<213> ORGANISM: Homo sapiens

<400> SEQUENCE: 45

```
aatagtaatt gccaacagtc aagatatgta ctaccaccaa attccgtgtt atttgtgatc      60
aaaagatata cacagatact tgaaaactga tttctacgtt gcatatggga aaaatacctc     120
atttttctca gctgtccatt attttgaga tattatgtgc agtgatagta agaacaagca     180
gatttggaac acatcagcaa taattttttc aatcagagtc ctgccaaaat gaaagaattt     240
gacagtatcc ggcaccctgt actcatgctt ggcttctgta gaaactgtgg cttgcaaaag     300
ggcagctggg tactgtgttt tggtacctca ttctttaaac gtataatggg aatctggttg     360
gttcaggaaa acccttgcct acttattatt actctgtttt                           400
```

<210> SEQ ID NO 46
<211> LENGTH: 250
<212> TYPE: DNA
<213> ORGANISM: Homo sapiens

<400> SEQUENCE: 46

```
ggcccatact taatgtattt ttaaacgttt taacatttac taatatagaa ccttctattg    60
cctatttcct tctggtttat tcccttcct tctgtcattg aagaaatggt tctagtggta   120
gaaatactcc acgattgaga agaatgtggg aagaaaggag ggctggtggg taagaattgc   180
tcatgatgtc tccctctgaa ttctgtgctc tcacaatgac actccaatgt gtggtttgac   240
gcctggaaga                                                          250
```

<210> SEQ ID NO 47
<211> LENGTH: 300
<212> TYPE: DNA
<213> ORGANISM: Homo sapiens

<400> SEQUENCE: 47

```
aagacctgga gtttccatta caccgaattg gcacttaata actgttgtcg gagcatttct    60
taagccacat tttcgtaaag tggctttaaa attgctctgc cagtaggcag gttgctaaga   120
tggtcagaga caaacttctg aacgactctt gtaaatata cagaaatatt ttcagaactt    180
ttatcagtaa aattacaaaa cgtgttgcaa ggaaggtgct tgtgataaca ctgtccccag   240
aaccttagtg aagttaccaa ctggtggaaa attttctctt gcactcggct taaaaatcat   300
```

<210> SEQ ID NO 48
<211> LENGTH: 1100
<212> TYPE: DNA
<213> ORGANISM: Homo sapiens

<400> SEQUENCE: 48

```
aagtaacggg atcaaattaa ttattatttt ggtggccgcc tctcttctcc accccaagcc    60
aggcaagact caccctcggc cctgcccgcc ccagcatttc aaatggaata cctaggtggc   120
ccaggggac ccctgacccc tatatcctgt ttctttctgc ctgctttgct actttctcc    180
ttgataaaag gagagagtga gagataatta acaaaaaaca tggccccagg acaatgaaac   240
aactggcctt ggccggccag aaatgtatcc tggttttcta ggtgaacttt ctcccatcaa   300
tctttccttt aacctctctg ttagtggaag caataggaac accctcccc tcccctgagc    360
aaatgctttc ttttgactgg aaacaaaaca ggggctcggc gaaggctgag gtgaaatctg   420
ggtggcatgg gcgccgcaca atggggccgc tgttccccgg cccggggcttg tgttttacaa   480
caggggaggg gcgggcgtga atggtctgat gattggaaca atccccccga ttcaggccta   540
caaacgcatc ttctgttcca caccgagggg acagaaagga gaaagtgac aaagaacgcg   600
gggcggggg aattaaaaca aaatgcgctc gactaaaaaa tctctcatat cctgcatatt   660
ccagaaagcg gctctatgga gagccttc aggaggcctc agccatatct gaatggcttt    720
ctctggcctc tgatttattg atgaagctga agcgacttgc tggagaaagg cctggagcct    780
tctttgtctc cgagatgaag tacaataggc cacaggggcg agatctcttg tgatgctctc   840
gggtcctgcc tttctcttgc cctctcctcc ctgcaaatac cagcagcggt gacaaacgat   900
tggtggtgtg cctgggagag ccggtgacaa gactgggcca cttgaggtct ccttaagagg   960
gtattatggc cagggcgacg tttgtgctgt gaagatggca cactccattt tgtcaatggc  1020
tctcatcggc ccagataatc gccccctgcc tgcctgtcag gggcgcagcc ggccgattca  1080
tggcgccctc ggagaaagta                                              1100
```

<210> SEQ ID NO 49
<211> LENGTH: 500

<212> TYPE: DNA
<213> ORGANISM: Homo sapiens

<400> SEQUENCE: 49

```
ccggcacggc cgcatccgc caggattgaa gcagctggct tggacgcgcg cagttttcct      60
ttggcgacat tgcagcgtcg gtgcggccac aatccgtcca ctggttgtgg gaacggttgg    120
aggtccccca agaaggagac acgcagagct ctccagaacc gcctacatgc gcatggggcc    180
caaacagcct cccaaggagc acccaggtcc atgcacccga gcccaaaatc acagaccccg    240
tacgggcttt tgcacatcag ctccaaacac ctgagtccac gtgcacaggc tctcgcacag    300
gggactcacg cacctgagtt cgcgctcaca gatccacgca caccggtgct tgcacacgca    360
agggcctaga actgcaaagc agcggcctct ctggaccgcc tccctccggc cctcctgagc    420
cctactgagc cctgctgagt cctggaggcc ctgtgacccg gtgtccttgg accgcaagca    480
tcctggttta ccatccctac                                                 500
```

<210> SEQ ID NO 50
<211> LENGTH: 1000
<212> TYPE: DNA
<213> ORGANISM: Homo sapiens

<400> SEQUENCE: 50

```
ggacgcggcc cgctctagag gcaagttctg ggcaagggaa acctttttcgc ctggtctcca    60
atgcatttcc ccgagatccc acccagggct cctggggcca cccccacgtg catccccgg    120
aaccccgag atgcgggagg gagcacgagg gtgtggcggc tccaaaagta ggcttttgac    180
tccagggga atagcagact cgggtgattt gccccctcgga aaggtccagg gaggctcctc    240
tgggtctcgg gccgcttgcc taaaaccccta aaccccgcga cggggggctgc gagtcggact    300
cgggctgcgg tctcccagga gggagtcaag ttcctttatc gagtaaggaa agttggtccc    360
agccttgcat gcaccgagtt tagccgtcag aggcagcgtc gtgggagctg ctcagctagg    420
agtttcaacc gataaacccc gagtttgaag cccgacaaaa agctgatagc aatcacagct    480
tttgctcctt gactcgatgg gatcgcggga catttgggtt ccccggagc ggcgcaggct    540
gttaactgcg cagcgcggtg ccctcttgaa aagaagaaac agaccaacct ctgcccttcc    600
ttactgagga tctaaaatga atggaaagag gcaggggctc cggggaaagg gaacccctta    660
gtcggccggg catttacgg agcctgcact ttcaaggaca gccacagcgt gtacgaagtg    720
aggaattcct ttccaccaag agcgctcatt ttagcgacaa tacagaattc cccttccttt    780
gcctaaggga gaaggaaag gaaacattac caggttcatt cccagtgttt ccctggagta    840
atgctagaat ttacttttgt cataatgcaa aattaaaaaa aaaaaaaata caacgaagcg    900
atacgttggg cggatgctac gtgacagatt tttccaaatt ttgttgcggg gagagggagg    960
gaggagaatt gaaaacggct cacaacagga atgaaatgta                          1000
```

<210> SEQ ID NO 51
<211> LENGTH: 1500
<212> TYPE: DNA
<213> ORGANISM: Homo sapiens

<400> SEQUENCE: 51

```
aaacgtttaa aatatatttc taaacagaat gggccaattc agtcacagta actgttgatc      60
tccatagcag agcaacccac aaagacagaa ctgatttttt tcccataatc aggggtgaaa    120
aatatacaac ttgtttctga accaaaacca caatttctgc agtttaaaat gtttcactgc    180
```

| | |
|---|---|
| taatatggcc ctggtagaaa ttatgtagtt tcttttcttc tttaaaaaaa aaaaaaatta | 240 |
| aaaaaatttc ctaagacact aaatgctcca tctggaatgt agattctgat cacaaagcag | 300 |
| ctcagttaac ctaaaaaata aaaaattccc atcacctgtc tcagtagggc ctgagagtag | 360 |
| tgtggggaac cccagctttg gtatggagag tcatggcccc ttgaaccaga tagagacctt | 420 |
| gaatagccat agctggtgct tctctcagga taaactctga tgtaggaagt atcaccctca | 480 |
| tgagagtgga atttggtcat ccagttgacg cagggcatat tccatgtctt cttttctgag | 540 |
| acacccaacc atccccactc catccttctg cacatccgtg taacaggcat ccccagcttc | 600 |
| tcgcgtgtga tccttcaggt cctgccagct gcctgatgga agaagtccat ttcttccata | 660 |
| aatagcatcc tctgcatctc gagggtcctc gaagcgcacg gaggcgaagg gcacaaggcc | 720 |
| gtaccggctc ttgagctcga tctcgcggat gcggctgtac ttgtagaaca ggtcctgcgg | 780 |
| ctccttctcg cgcacgtggg tcggaaggtt tccccacgta gatgcacccg tcgccctccc | 840 |
| agccgcgctc gtgtccgccc agccggacaa ccgcaccgcc cgacgctgct ggccagccgc | 900 |
| agcccgcatc cgcccgtatc gccgccgctg ccgcctcagc acggctgccc ccgcagcgtc | 960 |
| tgttttgttt tattctaaca gggtctctct ctgtcgccca ggctggagtg cagtggcgtg | 1020 |
| atcttggctc cctgcaacct ctgcctcccg ggttcaagcg attcacctgc ctcagcctcc | 1080 |
| caagtagtgg gcattatagg tgccagctaa ccatggccgg ctaatttttt tttttttttt | 1140 |
| tttttttttt tgagacagag tcttgctctg tcacccaggc tggagtgcag tggcgcgatc | 1200 |
| tcggctccct gcaacctccg cctcctgggt tcaagcgatt ctcctgcctc agcctcctga | 1260 |
| gtagctggga ttacagctat gtacagcgat gtctgcaaag atagggattt aacagcactc | 1320 |
| atatcttcat gttcataaaa aagtcctaca cgcgtgatgt acgtctagat ctttccttt | 1380 |
| gtcacaggat atagcacggt agttacggat atagtctccg cagtgcctgg gtttgactca | 1440 |
| gcttccccac gtactgtcct gcgcatattt tgtgtctcag tttcctcatc tttaaggtag | 1500 |

<210> SEQ ID NO 52
<211> LENGTH: 700
<212> TYPE: DNA
<213> ORGANISM: Homo sapiens

<400> SEQUENCE: 52

| | |
|---|---|
| cacatttcag agctgaggtg ctggtgcggg caggtctcct gagctggggg gtcagctgtg | 60 |
| tggccagtga tggtgacgcc tcaggccgtg catggccggg gaggcggccc tgcctctgca | 120 |
| ctcttttgac tccatgacta ctggtgtctt cggacgccag agtcggggga gcaaccatgg | 180 |
| ggcaccgccc ctgcctgggg aggcagcacg aggcctgagc ccagcttaca gggggacatc | 240 |
| caccccccgct gagagcccca ccttcacggc gaggatctgt agaagaagac atttgatatt | 300 |
| actcggcaaa aaaacaaga aacgaaaaca caaaagagc tcctctgaag aagaaaaggt | 360 |
| atttgcgctg tggtccacct agaaataatg ttgttggcac aactagagca ttcctcagtc | 420 |
| attcaggagc actccctgcc ggtgcgtcca catgtcccaa ccccgataga tgaggcgctg | 480 |
| ttcgcccgtg gaggggtcag gttgtcgtga ccttatcttt acccttaggc cgtccatccc | 540 |
| ggggcctggg gttcctgcg ccagtcacgg tgggctgtgt aggtggccat gtgttcggtc | 600 |
| tttccccagg aggtacgtac catgtgctgg gaggcctgga ggctgagccg cccccgcgc | 660 |
| ctatgagttg caccctcaca gcggcggcca aacctcctgc | 700 |

<210> SEQ ID NO 53
<211> LENGTH: 200

<212> TYPE: DNA
<213> ORGANISM: Homo sapiens

<400> SEQUENCE: 53

```
caggcttgag cggtgactgg gagacccgg gaatggaaat ggcgctcaaa tgctggtgtg    60
gtgtccgcag gggaacggcc cgcgggtgtg tggagtctgc gccctgtgg cttcagctgc   120
gtcggggac tgcgggaatc ttccagactc cagtttaaat cagagaggtg tgtccacgaa   180
aagagtcaaa ctaaaacatt                                              200
```

<210> SEQ ID NO 54
<211> LENGTH: 1300
<212> TYPE: DNA
<213> ORGANISM: Homo sapiens

<400> SEQUENCE: 54

```
aacgagacag tgcaaaaagc cgctgcctgg tgacctggca tgcagactcg ccctcccac    60
ttgcacggtg atccactgaa gacaacagct gcctctgtac tcacgctccc ccacactccc   120
ctccttcctg ccctggtttc tccatcccta gatgccatcc catgcccaa accatccgcc   180
aagcacaata acctcgcccc cacccacccc atgaggtcac tcgagttgac aaccagataa   240
cagttttgt tttgttttgt tttgttttgt tttgtttgtt tttgagacgg gtctcgctc    300
tgttgcccag gctggagtgc aatgacgtta tctcggctca ccacaacctc cgcctccgg    360
gttcaagaga ttcttctgcc tcagctgcct gagtagctgg gactacaggc gcgtgccacc   420
attctcagct aacttttgta ttttttagtag agacagggtt tcattatatt ggccaggctg   480
gtctcgaact cctgacctct tgatccgccc acctcagcct ctcaaagtgc agggattaca   540
ggcgtgagcc accgcgccca atagcaattt gatgacccat ccctccact gctgggaaaa   600
ggctgggcac cgcccacact ccatgcagct ctctttccct ggctcggaat cgctgcaggc   660
gccacagacc agacgcgcac tgttccccac tcctgcttat cggccgcgcg gcatcccctt   720
gtcgcagcac tccagcatcc atgcagccgc gcggcacccc gtcttcggag cactccagaa   780
tccatgcaga gcgcagcacc ccacatccag agcgctccag aatccatgaa gcacgcggca   840
ccccctcgtc agagtgctcc agaatccatg aagtgcgcag caccccttaa tcggagcgct   900
ctagaacccg tgcagcgagc agcacccac cccggagcg ctccagaatc catgaagcca   960
gcagcacccc acacccggag tgctccagaa tccacgcagc acgtggcatc tcctcgtcat  1020
agcgttctag aatccatgca gcgagcagta ccccacaccg ggagcgctcc agaatccacg  1080
cagcgtctgg cacatctta tcagagcgct ccagagtcca tgcagccaca gtcctccaac  1140
ggaccctgag attgtttctg caaaaggcca tgccttcata aatctgaaaa tttggaaaac  1200
atccttctac ttatatcctt acaacccacc attcaagctg tagaagcctt tctggaaccc  1260
caagcagaag gatatccaaa atgtaaaaac ggtggggcct                        1300
```

<210> SEQ ID NO 55
<211> LENGTH: 1000
<212> TYPE: DNA
<213> ORGANISM: Homo sapiens

<400> SEQUENCE: 55

```
atagtgcgac tgttccgaag tctttatcac agttactggt gatgcttttt tccagatgtc    60
ctcgacgtgc acccatgaag ggctccacct gagagtgcca gggtcctccg tgggatgggg   120
ctggaggggg tgctcttgcc gtcctgggct cccaagcagc cataggaaca ataggtgat    180
```

```
gggtcccag agatagaggc cagtgacagc agcgctttga accccctcaca cgggcacggg      240 ccctctggca gggatgggcg tcccggtcac acggagatgg gggctgctgc tgcctgcagg      300
tagaggaagg gacgtgtttg gcagtcctgt gaccctgggg cacctcgcct ccccacggc      360 cggctctgct tgtaaacaga caagtgcaca agcgcagccc ggtgaaggca cagcggtccc      420
aggaggcatc tgggctgcac cccagcgagc cgcccataca cgtggagatg ccggccaagg      480
ccctgcagca cacggcagag gaaggcgcga tgggagccat gctgggcccg gaaggtgccg      540
ccgcccggag ctgtagccat cactccagct cttctttaa gtgttcccag aaattgtgac      600
ccaccaaaat ctgagagcac ccgacagtaa gccagaggac cttgatgtga gatcccagca      660
cggtgtgggg gcggactgtg gtgggtgctg tctcggcccc cacccttcc acaggtcggt      720 gtgcacatcc cacggcgcct gctaagctgc agtcttctcc aaaggggtca ctctccgtgg      780
gaagggagcc acccgccccc gggtgatgtc cccagtcagt gactgacgac agtccccagc      840
cgaggtgagg gaccagctcc tgcatccctc actccggggc ttgcctgtgg gccagggtgg      900
gggcgagcct cagcagagac cgcgtccccc ttgcctgtcc tgccctgcct cccctgcctc      960
ccccgcgcct ctgctgagca cgcccagagg gagctgcttg                           1000
```

<210> SEQ ID NO 56
<211> LENGTH: 500
<212> TYPE: DNA
<213> ORGANISM: Homo sapiens

<400> SEQUENCE: 56

```
cacttgaaaa gcacaactca tggtgccaaa gctctgacac ggactccact ggagctgtgg       60 gcaggggtg ccaaggtacc gagttccaag ccgttgttat ttgagagcgt gcccccccgcc      120 atgagagcag gtgggggggac ataaagtgac acaggatgga ctggccaaag gctgaggacg      180
atcacttacc tcacaggatg atgccacccc cacggacagg caaggagctc tcaccttccc      240
caggacccca gctgccacca gagctccaga tggccctggg ggtgtctgta aagcctgtga      300
ccgtccacca ggtggagacc aggctggcca ggggagggag aggaagtgac cactggccct      360
ggcactggct ggccggctcc agcaggcccg aaggggaggg aggagcctgg gtgcaccaga      420
ctctctcaat aagcagcacc cagacactta acagatggaa agcggtggct tggaactcac      480
ttccaacgaa acaatagcac                                                 500
```

<210> SEQ ID NO 57
<211> LENGTH: 1300
<212> TYPE: DNA
<213> ORGANISM: Homo sapiens

<400> SEQUENCE: 57

```
agcacctcct accccaccct ccccattcct gccatcccca gggtccaggg agcccagatt       60
ccagggaagg gttgcattag ctcccactcg gagtcctgat gcagcagaga cagacagagg      120
ccctgggaga agtgagcatg aattattaag acaagacaag ggtgaggccc cagagagggg      180
gtggcggaag ggtcatgttc atgcagcgag agttgcttcg agcttgaacc gcgtatccag      240
gagtcaagca gattgcaact ggcgagaggc cttcagaaat gccccgtgag agtcctgtgt      300
gcagagctcc atctcagcac acttcctgtt cttttggttc gtcgatttt gcattttcag      360 tccctgtga tccattattt ataacagtgg agattggcct cagacactag cagtgaggaa      420
aacaaaagcg aagctacgca gaaaaatgac aagagtgatg agcacagcag tcatgacaaa      480
tgagccctgt gcggaggccc gggatccgcg cagatgccgg cgcgggggaa atgggccctg      540
```

```
aaatcccacc gtcaggccag gcagctctga gcgtgacctg gagggctgtt cagacggtct    600
gggtagccgt gtcctgcgca tgaacatcct ccgtcgggga aggaattccc cacggattat    660
cagagctgct ccctccaccc cccgccacgt cccacgcggg ccacatcaac tccctctgca    720
gcctctggcc agcggctgag ccctccgtgt ctccctcgt taatgcctcc ttcaccatcc     780
cctcctgaag tttccccat tgcatacacg cgctgaggcc cacccggtat caaggactcc     840
cattgcttgc gaaaaagatt ccaccctct tagaacagag accagggccg ctgtagcaaa     900
tggccataaa tgccacagct taaaacaaca gaaacggatt atctcgcagc tctggaggat    960
ggagtccaaa atctgaatcg ctgggctgaa atccaggtgt gggcagggcc gcgctccctc   1020
tagaggctcc cccggagatt cccttccttg cctcttccag ctgctggtgg ctgccagcag   1080
tttgggaatt gcggccgcat cacaccacct ttctgtttgt tgttgacatc cccgcctccc   1140
ctgcctgcgg ggtcttagat gtctctctcc ttcccactga gtttcactcc acatttgaat   1200
tggattaact catgccatgt taggcaaacg tgcccctcaa atccttccac ttaacagaca   1260
tttattgaag gttcctgtgt gcggggccca agagaaggga                         1300
```

<210> SEQ ID NO 58
<211> LENGTH: 1600
<212> TYPE: DNA
<213> ORGANISM: Homo sapiens
<400> SEQUENCE: 58

```
ccatcttcct aggcctgcgt ttcccccaca ccggggactt gtgctggaaa gaaaagctgc     60
gttggcagcc aggagccggg gaaactgtcc agggaggcat cctctgcgat gaaggcgggg   120
cctcggcgtg gcccgttccg cgctctgtcc agccctggag aagccccacc ctcaccgagc   180
tcgaaatacc ccctccctga gagccgagac tcatggccgg gacccccttgg acagaagatg  240 cggatgctaa cccggcgctt ccaccacagc cccggcggca ctggggagcg agcgcggcca   300
tcccgcgcgt aggtggtgtt tctctgcagg cgccagtttc accgcgggcg cccaggatcc   360
tcaacggttc tgttgtgatg tgattcccct cttcgacttc gtcattcagc ctcagtccct   420
cagtccccaa ataccgaaag gcagtctttt tttttttttt ttgagacgga gtttcactct   480
tgttgcccag gctggagtgc aatggtgcga tctcggttca ctgcaacctc cgtctccctg   540
gctcaagcga ttctcccggc tcagcctccc gagtagctgg gattacaggc acctgccacc   600
acgcccggct aatttttgt attttagta gagacggggt ttcaccatgt tggccaggat    660
ggtctggaac tcctgatctc aggtgatcca cccgcctctg cctcccaaag tgctgggatt    720
acaggcgtga gccaccgcgc ccggcctttt tttcttttt cttttgaagt taatgaactt     780
gaattttatt ttatttacag aatagccccc atgagatact tgaagacccg gtgccaagcg    840
acagtgttga ccccaggtgg tcagtcctgc ctggccccctt ccgagggatg cgccttcacc   900
ataaccatgt cacggacagg cgtgtgggca agggggcatc gctgtatttt tcacaactct    960
ttccactgaa cacgacaatg acattttca ccacccgtat gcatcaacca aatgaaaaga   1020
tgagcctgtg acattcccgt gcgtagagtt acagcttttc ttttcaaaac gaaccttcag  1080
tttggagccg aagcggaagc acgtggcgtc tgacgtctcc agggagaccc gccgccctcg   1140
ctgccgcctc accgcgcttc tgttttgcag gtaatcttca gcaagtactg caactccagc   1200
gacatcatgg acctgttctg catcgccacc ggctgcctc ggtgagtgcg cgctgcgggc    1260 tctgccggt gacgccacgc ggcctcctcg ccttttcggg atggctggga ggggcgggaa    1320
```

| | |
|---|---:|
| gaggcgctga agggcccgag gcaccggcct tctacaaggg gctcttcgaa atcaatcaat | 1380 |
| gcgcagaatc ccgagggagg ctcagccgcc ctccgggcct ctctgcctcc acaggtgatg | 1440 |
| gctgtgtcca caaggaggaa accgtcgggc tgaattaaac agaaccgccc tcctaagagt | 1500 |
| gtgggttttt ctgccgggcg tggtgtctca cacctgtaat cccaacactt tgagaggccg | 1560 |
| aggtgggcag atcacctgag gtcaggagtt cgagaccagc | 1600 |

<210> SEQ ID NO 59
<211> LENGTH: 700
<212> TYPE: DNA
<213> ORGANISM: Homo sapiens

<400> SEQUENCE: 59

| | |
|---|---:|
| tgctgcaccc ccgctgccct ccctcccgct ggccggcagc accttctcca cccgggcccc | 60 |
| tctgctcaca gcgctccccg cccccgtctc cccgagggggc ggggagccag gacatggccc | 120 |
| tgaaagccta gccctggcct tgacctcccc agagcgccct ccccaccctc cgccctctgc | 180 |
| caaccctggc ccctgccctg gccccgtcct tgtcctctgc tgctgccctt ggggtcgcgc | 240 |
| cccgcagact gggctgtgcg tgggggtcct ggcggcctgt gccgtcccac gcctacgggg | 300 |
| atgggcgagg tccttcttgg ggcttctctt acccactctc cagtcacctg agggcgctgc | 360 |
| ttccctgcgg ccaccccagg tttctgtgca gccgaagcct ctgcctctgc ggccgggtga | 420 |
| tcccaagacc ccggggtcca gggaggcacg ggatctgctc ccccggtccc aaatgcaccg | 480 |
| gctgcgcctt aggagggacg gcctccaccc atggcgctgg cgcccagggg ccgctcctcg | 540 |
| gactacagca cttgctcgtc gccctgcgcc ctgtttagtt ctcatcacca gcagcctgga | 600 |
| ctagggcccct ggtccttctg gcctccttcc acagcccgct gcacatctca cccacttccc | 660 |
| cgaggtgctg tcattgttta gctgggcccc tcagcctccg | 700 |

<210> SEQ ID NO 60
<211> LENGTH: 1000
<212> TYPE: DNA
<213> ORGANISM: Homo sapiens

<400> SEQUENCE: 60

| | |
|---|---:|
| caggtgccgg ccaccacacc cggctaattt ttgtgttttt agtggagaca gggtttcgcc | 60 |
| atgttggccg ggctggtctc aaactcctga cctcatgtga tccacccgcc tcggccttcc | 120 |
| aaagtgctgg gattacaagt gtaagccact gcgcccggcc aagagtgaag ttctgatagc | 180 |
| tggggtaaga aaggccgtgg gaacagccgg tttcagacac gctgggtcta agacgctgcg | 240 |
| tctggcgctg ctcggcatcc aatgggagcc gtggagaagc caggcgagtg cgtagggcgg | 300 |
| agccagcgca caggaaatag gacgtgatga ggtcaaccgg ctggtccaag tgtgacggga | 360 |
| agtagaggat gcaagcaccg agccccgggg cccccagcat tggcggggag gagctcgcgg | 420 |
| tgcgggagaa gcaggggacc cgcgcatcctg gagaccaggt ggagccagtg cgcccggaag | 480 |
| gggcgtggcc cgctgacagc cgcccaggag gccggggggag gcctgagcc gagggccgcg | 540 |
| cgtggcaatg tggagagaca ttttggtgga gtcatggggc cacagcctga ttggtgagaa | 600 |
| caggaaggga aattgcagat gggcctggc ccctggctc ccgcatactc caggaccagg | 660 |
| gctgagtcat cgttcaccgt gtgtgaccag ggccccgtgt ggccggctgt cactcggtat | 720 |
| ccagttaccc tggcagacc actggcggca ccccccagcc agaggccgca gcaacacaca | 780 |
| cgcctgcagc gaccaggcc ggactgcatg ccccgtgggg gaactgaggg cgtttcagta | 840 |
| acagagtgtt aggggacacg ggttgggtgg cttggaaagg gcctaaggtg gggtttgttt | 900 |

| | |
|---|---:|
| tagattgggg tggtgagggc gcagggggccc ggtaggattc tctaacaggg cagcagccac | 960 |
| tcatttagca acaggagagg cgtccagcgt ttcgtgggct | 1000 |

<210> SEQ ID NO 61
<211> LENGTH: 3100
<212> TYPE: DNA
<213> ORGANISM: Homo sapiens

<400> SEQUENCE: 61

| | |
|---|---:|
| acccaaccac aggcctcctc tctgagccac gggtgagcgg tgcaggttct gctgttctgg | 60 |
| agggcctgag tcccacccag cacctcataa acagggtcct ccccagggct gctgcagtag | 120 |
| gcatcaacgc cagggtgcaa aatgcctcag ggagccaagg ctgagccagg ggagtgagaa | 180 |
| ggagcatgtg gaagtgcgtt ttggagaggc agctgcgcag gctgtcagca ggctccggcc | 240 |
| gcttctatag acagcatgac accaagggca gtgacctcat tccacaggct gagtccagcc | 300 |
| agccagccaa gcatcaccag ccagacgatt gaccctaacg gaccaaccaa cccgtaacga | 360 |
| cccctcctac cataaccagt agccagccag cccataacca gccaacttat ctataaccag | 420 |
| ccacctgacc atagccaaac aaccagccgg cccaccagta gcattcagcc cctcagctgg | 480 |
| ccctgagggt ttggagacag gtcgagggtc atgcctgtct gtccaggaga cagtcacagg | 540 |
| cccccgaaag ctctgcccca cttggtgtgt gggagaagag gccggcaggt gaccgaagca | 600 |
| tctctgttct gataaccggg acccgccctg tctctgccaa cccagcagg gacggcaccc | 660 |
| tctgggcagc tccacatggc acgtttggat ttcaggttcg atccgaccgg gacaagttcg | 720 |
| tcatcttcct cgatgtgaag cacttctccc cggaggacct caccgtgaag gtgcaggacg | 780 |
| actttgtgga gatccacgga aagcacaacg agcgccaggt gagcccaggc actgagaggt | 840 |
| gggagagggg ggcgagttgg gcgcgaggac aaggggggtca cggcgggcac gaccgggcct | 900 |
| gcacacctgc accatgcctt caaccctggg agagggacgc tctccagggg accccgaatc | 960 |
| aggcctggct tttccccaag ggagggggccg tgcccacctg agcacagcca gccctcccg | 1020 |
| gtgacagagg tcaccattcc cgagctaatg tggctcaggg atccaggtta gggtcccttc | 1080 |
| ccgggctgca cccagccgtc gccagctcca tccctgtcac ctggatgcca gggtggtctt | 1140 |
| agaaagaacc ccaggaagtg gggagtgcccc gggtggccgc ctcctagcca gtgtacatct | 1200 |
| tcacatgaac cctacctgag gaagccagtc cccgacggca tagctgcatc cgcttggaat | 1260 |
| gctttacagg cattgacacc ttcgcctcac agcagcactt tggaaccagt gtcctcatta | 1320 |
| ttccagggca cggctgggga acaagggggt cctcagcctg ctgggtccca cagctagtac | 1380 |
| cgggcaggtg gacgggagct tctccccaca gtcaccctga tgccccgctc ttgctcggct | 1440 |
| ggaggcctcg gatctccgtg tgttgaggg agccgggca ctggagcccct ggtgacctgc | 1500 |
| atctcctggc ggagccggga agagctcatg gactgtcaca gatggacagt gccccgcggg | 1560 |
| ggctggagag cagagtgggg ctggaaggtg gaactcttag ccaaagtctt ggtttctttt | 1620 |
| ggccagggtc ctctttcaat ggctggagaa ggtggtgctg gggggtgaac gctgacctcc | 1680 |
| tcatgtgctg cccctccctc gcctgggccc ggtaaagccc ccacgtagcc ccagccagcc | 1740 |
| tggaacatgc ttcctgagct cccagctctt ggtctttgca cccagtggag gaggaggtca | 1800 |
| gcccagggag ctgagtctgc ggtttagggc gtccagggga cgtggaagca tgtgggtcgt | 1860 |
| ctggccacat taggtagggc tgcagagacc tgggctagag cagtcctgcg gggtctggaa | 1920 |
| ggggaagact ggctgaggtg cggggcctgg tctggaatga tcctgcgatt ttggagtgaa | 1980 |

-continued

```
gccatggagc gggaagagac aaccccccgc ggggaatagc ccggcaagtg gccacgaggc    2040
caggctgagg tccagagaag caggggcatg aatccataaa tcccaggggg cctggccatg    2100
ggatgtgctg gctgcacccg gccccctgtga gagccccgc aggctggccc ccttctgcag    2160
tcagtggggc tggggcagct tctctggcat ggggcgaggc agccgcctgc acagtggccc    2220
ccctgactgt gcgccccac cctctccagg acgaccacgg ctacatttcc cgtgagttcc     2280
accgccgcta ccgcctgccg tccaacgtgg accagtcggc cctctcttgc tccctgtctg    2340
ccgatggcat gctgaccttc tgtggcccca agatccagac tggcctggat ccacccacg     2400 ccgagcgagc catccccgtg tcgcggggag agaagcccac ctcggctccc tcgtcctaag    2460
caggcattgc ctcggctggc tccctgcag ccctggccca tcatgggggg agcaccctga     2520
gggcggggtg tctgtcttcc tttgcttccc ttttttcctt tccaccttct cacatggaat    2580
gagggtttga gagagcagcc aggagagctt agggtctcag ggtgtcccag accccgacac    2640
cggccagtgg cggaagtgac cgcacctcac actcctttag atagcagcct ggctcccctg    2700
gggtgcaggc gcctcaactc tgctgagggt ccagaaggag ggggtgaccct ccggccaggt   2760 gcctcctgac acacctgcag cctccctccg cggcgggccc tgcccacacc tcctggggcg    2820
cgtgaggccc gtggggccgg gcttctgtg cacctgggct ctcgcggcct cttctctcag     2880
accgtcttcc tccaaccccct ctatgtagtg ccgctcttgg gacatgggt cgcccatgag    2940 agcgcagccc gcggcaatca ataaacagca ggtgatacaa gcaacccgcc gtctgctggt    3000
gctgtctcca tcaggggcgc gaggggcagg agggcggcgc cgggagggag gacagcgggg   3060
tctcctgctc gcgttggacc cggtggcctc ggaacgatgg                         3100
```

<210> SEQ ID NO 62
<211> LENGTH: 1000
<212> TYPE: DNA
<213> ORGANISM: Homo sapiens

<400> SEQUENCE: 62

```
ttttttgtgtt tttagtagag atgggatttc accatgttgg ccaggctggt ctcaaactcc    60
tggcctcatg caatcctcct gcctcagtag tagtagttgg gattacaggt gtgagctgcc    120
atgcccagct gcaggtgcgg aagctggggg cctcagagac tgtggactcc tggccggtga    180
ggagcggcat gggccgggag agctgactct tcagcgggac tgaggtggct ggagcgtgac    240 ccttttcctga gggcaaacag ggagggcctt ggagcccggc gctcaggaca ggcccctgct    300
ggcccggcag cctgagcttc cacactttc cagggcgtct cgagttcgcc cacagagctg     360
ttgtttcagg ataaaaaatg cccttgtatt ccacgttcca gttcagaggc ccgtctgttc    420
ccaagagcgg aggcgtcagc cgcatgagtc ccaccggaag ccgggttgcc gggtccccgt    480
ccctgccctg cagacgacgc attccggagc ccccttggga agctgcctgg ctctcccagg    540
cctggctgcc ttcgcacgag ggctccgagg catgctcatc ctacgtgact gcccgagtgt    600
gcacacgcct ggccgtgtgt gggcgtgtgc ctggggcccg agctcaggag caaggcctgc    660
gtggacctgt tgtctgaaac aagccagtag acagctgcgt caatgcaggc aagctgaaca    720
gggctgcttt ttcagcctga caaccccagg ggctgaacag gagctggggg aggagcaagg    780
ggccgttccc ctgccccaca gcacagcaca cgaccccgcc ttggaacctg ggcccgggg    840 tgaatcgagg gtcctggagc aagaggggct gctccacagg agagcctgtc ccgccacccc    900
tcagccacca gattcggggc tgctggactt gttctcaaac ctgcacagtg agtgacagct    960
gctgagacgg aggtctcagg cagtgcaggt gaatcagcat                         1000
```

<210> SEQ ID NO 63
<211> LENGTH: 500
<212> TYPE: DNA
<213> ORGANISM: Homo sapiens

<400> SEQUENCE: 63

```
tccttatttt ttagttctca agccctgtag ggtgttttcg gtcgcagttg tttgggctgt     60
ggtcctgacc ctcctgagtt ccagtggctc tgttcaggag agctgcctgg ggccgggact    120
tctgaaacac acactgagcc acaggccggc ccggcggctt gggttcaccg ccgcctcttt    180
gtgtgtgatg tcctgggata ggcccgtgca cgttcagatg acactgtaca tataaataac    240
ttgtagccga gaacaggatg gggcggggag gaggggaggg cagaacgtac cacagcagca    300
gaagtcactg tggatgcctt cgtaagttgc atggaaggtt tttaaaccta gccctgccga    360
gcagccctct cctggtccgg gagaacgatg gggagagagc tggcgttcag ctttcatcac    420
tggagccgtt ccttcttccg gccccccgag ggcctgtcca tgatcacact ttgtcttgtt    480
tcggggtgg ccctgtgac                                                  500
```

<210> SEQ ID NO 64
<211> LENGTH: 1300
<212> TYPE: DNA
<213> ORGANISM: Homo sapiens

<400> SEQUENCE: 64

```
ggaacggaga gccgccaggc ccaaacctcc cagaatttgc gcagtattct cggcctagag     60
agcgaggagt ggccttggcg aggtccctct ttggctcttc tggcttagcc ggggttttaa    120
acttgttatc tgcaaagcag aaggaaagtc agccctgat gtaagtgtca agtaaaataa    180
atcggatggg tccttcctg tttggcgagg aatgctacac taaggggac tgcgttcaaa     240
tgggcagtct ttgctggaaa cctcgcctcc gcgcgcttc cctcgctcgg attcaggcgc    300
ttttacgtta agggttgaat ttttgtgtca acaggcacct cgggaggtcg cctagacaac    360
tgagcggagc aactgagata accccgcta cgtgtggagt gacctagtcc attaacttgc     420
cccagcacgc ccgctgagtc cgcaaaatat aggatgcct cgggttttag atgaacccaa     480
agctaagatt tcttccctct ctggaattag caagcagccc gccctgccca actccctgg    540
aagcgcgcgt gctcgccagg cctcgggacg cctgcgcggg cgcccttgca ctggcaccag    600
ggctccgggg taggggcgca ccgatctgcc caagcctctg caggcactgg aggaaggcga    660
gccctccacc cgctcaacag gccccagtgc cggccttttcc ttccagtctc aactccaccc    720
ggggggccgg gggctccaca gttaaaaact ccacgccacg gagatcgcag gtaagctgct    780
ggctcaacga ggtgtgctaa atgggattaa agatcctgga ccgtggccag gcgcggcggc    840
tcaagcctgt aatcccagcg atcagggagg ccgccgcggg aggattgctt gagcccagga    900
gtttgagacc agcttgggca acatagcgag acaccgtctc tacaaaaaaa taacaaatag    960
tggggcgtga tggcgcgcgc ctgtagtctc agctacttgg gcggtcgaga tgggaggatc   1020
gatcgagtct gggaggtcga ggctgcagtg agccaggatc accgccaaga tcgcgccact   1080
gcattccagc ctgggcgaca gagggagacc ctgtctcaaa acaaacaaa aaatcctaga   1140
ccgtttacaa acagccttcc gtctcttcct ggtcaagtcc taaccctggc taacctcgcc   1200
gtctacagcc tgaattttgg caaccgaaag gcagcgccgg cgccacgtgc acacgggctg   1260
ggccgctccg ccagctgcca gggccactgc cgcgctcact                         1300
```

<210> SEQ ID NO 65
<211> LENGTH: 1000
<212> TYPE: DNA
<213> ORGANISM: Homo sapiens

<400> SEQUENCE: 65

```
cacagcccag cttcaagcct ggccgaccag gggtttggca tgaagacccc ggcagggctg      60
gggctgtgct ggaatccacc cggaagtttc ctgccccttg ggctgcccac caggtccct     120
ttctgctctg atcaagctgg acaaaacgtc gtggggccac agcacagggg gccaacgcaa     180
gctgggatcg tcagacgtta ggaaatccca aggaagaaga gaaaggggac acattcggga     240
gacgtcggca cacgctcgaa gcagcggaca ggcacctctc tgtggacaag gcagactggg     300
cggccgagat ccgcataga tgcctgcttc ctccacgacc tccacgtgtg gctggcccag     360
tccgggtccc cctcacctcc tctgtctgtc ttggtggcct cacgccgtgg gctgtgatgc     420
cggctacgct gcttgggtgg ccaagggtct gagctgcaag acgccagcc tgggtctctc      480
ccgagctctc ccacgtcctg tctgctcctc ctccgagctc ccggttgact ctcacgactg     540
caccagcctc tcccccagga aggcgtggaa acaacctcct ctcccaggc ccgctctgcc      600
tcctgcgttt caaggcaaat ccgttcctcc aggagatgat gcaaccacat cctgttggag     660
cccagagaag tgcggatgca gcccggggct ctttctttcc tagaaccctg cctgggagtg     720
gcttccctga actaaggaca gagactttgt cttcgttgcc tctcggcctg tgggcactga     780
gcatacagta ggtgctcagt aaatgcttgc aggccgatgc ccagagccat tagccctcat     840
catggtgagc tcggcagccg tgttggggc tgggctgggc ctaggtgtgc gtggggcgg       900
tgctggtctg ctttgctggg agccatggac accggaggaa cagggcccca tcagtgcggt     960
cagagtgcaa actcggagcg tccttctctg gaaaacgaat                          1000
```

<210> SEQ ID NO 66
<211> LENGTH: 500
<212> TYPE: DNA
<213> ORGANISM: Homo sapiens

<400> SEQUENCE: 66

```
gggaggggc gtggccagca ggcagctggg tggggctgag ccagggcgat ccgaccccga       60
accggagctt ttagcacttt gagtcccgtt actcagaggt ctcctgcagc cgggaatccc     120
actgtgctgt ggtccctggc agccagcacc caccccagc ttctccgtca aggttgagga      180
cggagcactc ctgcctctga ttaactggac gcaggagaag cagttgcttt aatccggagc     240
cttgagttgg gacagataat gagtcattca accagatttt ccaaggacac actaactttg     300
gtatgatgcg tgtgtgcccc tgaatccacg tggtcaggaa agcccaggga acactggcct     360
gtgactcact gagcaggttc ccttgttacc ccgaggggtg atttactcct ctgacagtga     420
cacggacact gtgcgtccat tccccgggcg ggcagaggac actccagat gcccacgagg       480
ggcccagcaa gcactggcca                                                 500
```

<210> SEQ ID NO 67
<211> LENGTH: 600
<212> TYPE: DNA
<213> ORGANISM: Homo sapiens

<400> SEQUENCE: 67

```
ctgcaggacc tgctcgttca cagatgttct cctagaagca gaagctgttt cttgttgcaa      60
acaaatttgc tgtgtcctgt cttaggagtc tcacctgaat ttaccaagga tgcatctgtg    120
```

```
cttggggatg gctcggtttg aggggtctga ggagcggctc ccctggatcc tttcctcccc    180
aggagcccac ctgccgagct gtcagcgtca gccccacatc tcaagatgag gaaatggagg    240
tcgaagccat gcacacgcag gcgtcctgct gacatgcagg ccaggcgggt gcctctgtat    300
tcagcagcct cagggctgtg gccagttcag gcagcagagg ggcctcatcc cggtgcttcc    360
ctgcaggcag ttgtggggcc ggcctgcagc aggggctcag acagggcctt gggagaggga    420
gggatcacag aggtgtccag tgacaggcag ggcgggcaga gcccatgggg ccttgggctc    480
ctcactcctt cggtcagtca gggtgacatc tggagccacc tccattaatg gtgggttatg    540
atttggttcc catgcagccc gtgccagctc gctgggagga ggacgaggac gcctgtgatc    600

<210> SEQ ID NO 68
<211> LENGTH: 600
<212> TYPE: DNA
<213> ORGANISM: Homo sapiens

<400> SEQUENCE: 68
caggaaccac gggacctgct gcctagcggc cctgttccac ccttggccgc tcgcaaaatg    60
tttaggcttc ataaggtttg cccagggtca caaatttaac tcacagcaaa caatgaaatc    120
agcgcatgat tttcgagccc tcgtggtcac cctcccttcc tcctgccctt tcctgcatgg    180
gcagcagcag ggtgaggagc tgctctcccc aggcccaggc tggagtccct cagacgacct    240
gccggccagg gtaccccct gccccacac agcgcctgac agagcccccc acactggggg    300
aacgtgggga cccaagcagg ggcagcggcc tcaccgggca ggcggcgacc tgcatcatgg    360
cgtccagccc accctcgggt gcatccaggt ttccggaaat cagctgcttc ccgacctcgg    420
tctgaaactg gttggagttg ttggtcagct tcagcacgtg cctgaaggca acgggggct    480 ggcactcttt ctccttgttg gggcatgggt ttcgcagctt atcagggtgc gtgttcacga    540
acggcagcac ggtcttgtcc acgaaggacc cgaagcctgc agggcacatg gaggggctgg    600

<210> SEQ ID NO 69
<211> LENGTH: 2000
<212> TYPE: DNA
<213> ORGANISM: Homo sapiens

<400> SEQUENCE: 69
gctggggaac tgaaggaagg gctgtggagc ctgaagcctg ggcctggcct gtgctgcggc    60
cgcaccgctg ggtgatgcag gagccactcc acctccctgg caccccagcc tcatccggca    120
acctgggagc gtgggcctcc tgcccctcca gggaggccct ggccgtgtcc tcatggggcc    180
cctccaggtc cttgtggctc caggtcggga cagtggctgt gagatctgac cctcccgttc    240
cccctccacc aagtaggaga aaccccggag catgagccct cgtccttcac cgtcccgggg    300 acaggggac ccccagatgc tgcacggctg acaggccaac gtggcagaag ctccagcttc    360
acaggaagcc agtgaccatg agagtctgta gctgtaacga agccacagag ctgtggcttt    420
cttccccctt cagctctagg aaaggttatc tgccctgcac agatctccgg aggcctggct    480
gggctctgag agcatcagac tgattatcgt aagaaaataa tctctgcaga cacattcctt    540
gctagaagca ggggacaaag cccagcttca agacaattc cacacacgcc ctccctgccc    600
tgcacagctg cctgccgggt gggagcagag cccttgcagc cgggctcagg ggcctgggca    660
gggacagcgt gtggcagggg cacagctgag acagagagcct caaagcgaca ccaacccgac    720
gtgaagctac agttgaggag acacagctgc cccattcccc gggcctcatc tccacagtga    780
```

```
gacgctggac tctctccctg acccaccgtc tcttagaacc tcccctccat ccggagcagt    840
tcggcagccc cagggcagcc aggggaaccc tgccgagtgc ctctgggccg ccacagaccg    900
cagagcccgc gggagccttg ctcacacagc ctcaggtcca ctgtggtctt ggggaaagc    960 cctgtcctgg gacaggggag ccgggggtcc tggccctgga ccaccatctg ggaccacgt   1020 tgtcacgcct gcaaagctcc ctgccccacc cccatgtgcc ggctggtgtt gacaccttg   1080 tagagtggga acctgcctcc gaccccagcc tgcagccaca gggcaggtta tagaccaggt   1140
gagagggcgc cgcgcccaga accaaggagc acaagtccgc agtgcccatg agatcctcat   1200
gctggccggc gcaggagcca tcctcggcct ctgcaggtcc tcgtgggaaa ccgcgggggc   1260
acgtggggcg gctgcagggt ccgcaaagcc ggctgtttgc gaagggcgca gctccacctg   1320
gaacagccga ggccgcccac gcgcttcccg cgggatcaga gcagcctcca cggctgttgt   1380
ctcaggcacc acgggatgcc tttcttcgtt tcaatagctg tgggaaagcc tcaatcggtc   1440
ctgaaagaac ccagatgtgc agcaatgaca aggccttctc tgagactcta gaaccttctg   1500
ccatctcaga caggagggag ccgtgaggca ggcgggagat ttgcagtcag caaaggacgg   1560
gcaggtgggg cagctgcaca cccagggccc tctccacggt cttcccgggc ccacccctcc   1620
cgcggtcctg ggtcatccac ctgctggcct cactctgccc acgcggccag gtcccaccgg   1680
cccctgagct caacagacca aagctggccc gaccccaccc ccaagaagaa tgaaacaatt   1740 ttttttttacc tcttgcagaa aagtaaaaga tcatttattc attctgtttc tagatagcaa   1800
aactaagtgt caaaagcacc ttctgcacac agtctgcaca cactggccgg tggtcctgtt   1860
cccgcaaggt tgagctgtgt tccagagaca tgggtcctcc gggtgatgag gagccgctgg   1920
agggccctga gctgcacgtg ctaatgatta acgcccgtc cgtgctggcc ggtttctcaa   1980
atgcctcctg acgattgcgc                                               2000

<210> SEQ ID NO 70
<211> LENGTH: 2200
<212> TYPE: DNA
<213> ORGANISM: Homo sapiens

<400> SEQUENCE: 70
ggcctgagga gtcaaacggt gcaaaccctg ccccactctg tttgggaagc acctgctgtg     60
tggcaggcgc tgcgcttggt gctggggata gaccatgggg aagaaacaca cagaacctgc    120
cctgctctca aggaacaggc cctggggggcg gccaggggca gagacccaag gcagacaccc    180
acacagtggc gtaatgacag tgcttatggt ggggacctgg ctgcacagca ggtcagcaag    240
gggatgttca ggtgacactg ggggcacgga gacccagggg agagtggatt gacagagggg    300
acgctgggca aatgtcccga ggctgaggtg gagttgcggg aaggaggagg ctgccgggca    360
gaggcgcaga gagctttgca ggtgttggca gagaccagca ggccctgcga ggcctggggt    420
gtgtcctcag ctgggagggc catagaagga tctgggcttg cagatgctgg tgcagactgg    480
aggcctgggg tgtgagagtc caggcggggc tcctgccaac acccagggga gtgggcctgg    540
gccaggtgga ccgggagctg gcacggtggt caggtgcttg gaggctgcgt ccacgctgg     600 ggacctggag gtgtgtgagg aggtgtctgt tgctcctggg gctgccgcct gcagggctgg    660
gtgtgcagca gtgcggggca atgaagtggg cgggttctgg gatggtggac gttcccttg    720 ttgggaacgt gttggtgcca agctgccatt tgagtttggc tctgaggggt ctgggcaggg    780
gacacacagg gaatcacaca ggatggagtg agttcccagg gacccagggt ggcttggcct    840
gagaacagct cccactccca gatgtgtggg aagccctcgg caccaagcct cagcctctcc    900
```

```
atctgtgaaa tggagacaac gtcactggac ttgcaggctg tccatgaggg tgatgcgatc    960
agaaagggtg gagttcctga acgccccggg gtcggggtct cacagcagga gcttagctgg   1020
tgtcggcatc tcctggaccc gtcctcagct ccgagcgccc agtcctgcca cctgtgtcca   1080
agtctgcact gtgcccacga ggccctcaag gccgcagaca gccccacact tctcggacgc   1140
cgccccagca cggtccttgt gtgaggtgga cactccttct ggacgccgcc ccagcacggt   1200
ccttgtgtga ggtggacact ccttctggac gccgcccag tacggtcctt gtgtgaggtg   1260
gacactcctt ctagggaagg agtagtaact cttgggtggt cgggtagttg ccatggaaag   1320
gggcagtaat gcccaggtat tgccgtggca accgtaaact gacatggcgc actggagggc   1380
gtgcctcatg gaaagctacc tgtgcccctg ccctgtgtta gctaggcctc aatgtggtcc   1440
agtatctgag caccgcctcc tgcctcagat gttcccgtct gtcacccat taccagggcg   1500
gcacttcggg tcctttccag ccatcattgt cctggcattg ccacagtgga cactgccaca   1560
caggcttgtg tgcttgcgcg tacccaggtc ctcacctctc tgggataaac caggcacgtg   1620
gcggccgccc cattttccac ccgccagcgg tggaggagtt gcccagcctt gcaggaaaac   1680
agctctcatg ccagcagcgg agcatcctat tcaagttttc tcaggctgc cagcacaaat    1740
gctgcatgcc gggcggcttc ctcagcagac cgttgtttct ctgcgtcctg gaggctggac   1800
gtcccaggtc ccgtgtggc aggcccggtt cctcccgcag cctctccttg gcttgtgggc    1860
ggcgtctcct ccctgggtcc tcgcagggcc acccctccgt gtgtctgtgt cctccctccc   1920
cttataagga ccccaggcag actggatcag ggcctgccct aaggactgaa ttttacctta   1980
atcacctctt taaaagctgt ctccaaatac agtcaccttc tggggtcctg gctgttaggg   2040
ctttgatgca tggatttggg ggacaccgct cagcccctaa cagccccat cctctgcctg    2100
cctttaccat ggggctgagc ccagccctgc aggagtcccc tggtttgatg tctgctgtgg   2160
ccacggcgac cctcaggctg ctccagccgc acttgtgctt                         2200

<210> SEQ ID NO 71
<211> LENGTH: 1600
<212> TYPE: DNA
<213> ORGANISM: Homo sapiens

<400> SEQUENCE: 71
ggggagtctc caggggctgg ggctggagcc gcatcagaga ggaaaggggt gtttgaaaaa     60
ggggcagggc ctgggaccca ggaaactgtt cttccagaga caccgtgaa gctgagcttt    120
gcctctcagg gaagctgtga ccccacgggt gctgcccaga gagatcgggc caggtggagc   180
caagatggac tggaattccc cgacggggac aaggggccgg acgaggctga cttgccctgt   240
ctgatgaatg gtcaggtttg ctttttctcc tgaaaacacg aggcagtgat cccggccagc   300
taattccagc agactggaga cgggatggtg gagaatgagg ctgtgggcgg aagagcaga    360
tgggactcgc cagcatcctc acggcagggc gcgctattg ccctccctcc cctcctactc    420
tctggggtcc caggagcccc agatacgcaa tgctgccagg cgatttctgg cgccccgcag   480
accccctgccc ctggagttgg gccaggtccc ggctggagca aagggggctc cttcaagccc   540
gctcctccct gtcaaacccg aggagcctga caggcgcagc gtcaccagcg tcaccgggcc   600
atagtgagcg gccaagccag cgtcaccggg ccatagtgag cggccaagcc agcgtcaccg   660
ggccatagtg agccgccaag ccagcgtcac cgggccatag tgagccgcca agccagtgtc   720
accgggccat agtgagcggc caagccttgg tctgccagag ccggccgcac cagaaggatt   780
```

| | |
|---|---|
| tctgggtccc cagtcctgga ggagcacacg gtttacacca ggccttggga ggggaagagg | 840 |
| caaggcgtgg gcccagccct cactccccag gagaaaccct gtttgagcgg cagaggagac | 900 |
| tggagagacc ccagggcggg gatccctgag aggagagaaa cccggaattc atccacggag | 960 |
| gcgttcaccc agaggagacc cggagcttct ccaggagagg ctggattgct ccaacagggg | 1020 |
| ccctgaggag ctgatggcaa gagcggaagg cagctctgac tcgtgcgtct gactccaggt | 1080 |
| gtggccgttg ggctacagt gggaccagcc tgttgtcact gaacccacaa agtgcctccg | 1140 |
| agcgcgggtg gagagagggg gacctcccac cgtctgctgg ccttgaatct tgaatctaat | 1200 |
| tcccgtctgt gctttgatgg gagaggcact gggagcgggc ggcttttttca gttccttttta | 1260 |
| tcttgaatgg cctttggggg attttcacag attctgagtt caaagcccag ggaggtgtgg | 1320 |
| gaacgtgaca ttcctcaccg cattcctcac cgcattcctc tgtaaaccag gcggtgttgg | 1380 |
| cacccatgag cctgtgtctt ctatgacatc aggagtttta tccctcacgt cagaaatcag | 1440 |
| ggttccaggc gccttggttt ttcttggcgc cagcggcttg gctatagaag aaaaactgaa | 1500 |
| ggggccaggt gcggtggctc acacctgtaa tcccagcact ttggaaggcc aaggcgggtg | 1560 |
| gatcacgagg tcaggggttc gagaccagcc aacatggcaa | 1600 |

<210> SEQ ID NO 72
<211> LENGTH: 7000
<212> TYPE: DNA
<213> ORGANISM: Homo sapiens

<400> SEQUENCE: 72

| | |
|---|---|
| gctcctcagg gggaggttcg gggcctttgg tctctggact tgggcagcag aaaggaaaca | 60 |
| tccctggggg cctgtggtga ccccatcct ccccagggtg gtctggcagg ggacactgtt | 120 |
| ttccaaagca aagccagagc gccaagggct ctcgggattc acgagatcca catttatccc | 180 |
| aagttagaac agcacatctg tgcgtgcaaa cttcattctg acttcggccg gctgtccttc | 240 |
| ttgcccaaag caccgtgagg cctcatccct gcatccctgt tgcttctttc atgtgggatg | 300 |
| agaacccagg aaggggctga gtgtgactcc tctggttttt agagagcact gcccccgccc | 360 |
| cgccccctcc tgcttcccca ccttttcaca gttgcctggc tggggcgtaa gtgaattgac | 420 |
| agcatttagt ttgagtgact ttcgagttac ttttttttctt tttttgagac agagtctcgc | 480 |
| tctgtcgccc agggtggact gcagtggtgt aatcttggct cactgcaacc tctacctccc | 540 |
| gggttcaagc gattctcaca tctcagcctc tggagtagct ggaattacag gcgcccgcca | 600 |
| ccacacctgg ctaatttttg tgtttttagt agagatgggg tttcaccatg ttggccaggc | 660 |
| tggtctcgaa ctcctgacct caggtgatcc gcctgccttg gcctcccaaa gtgctgggat | 720 |
| tacaggtgtg agccaccgag cctggcctgg agttattttg ggagagggca gcccctggtt | 780 |
| cagcgtggcg aggctgcgct tgctctcccg ggcgggcgtc cacaccctcc tcgccgagat | 840 |
| ggagaagccc aaaccctgc agcgctcccc catcacgtcc ggccctggaa gccccggaa | 900 |
| accctgccac gccctgagtg ggagagcgca ggtccctttc cggccctgga gcccccaga | 960 |
| aacccttggg tgccaggcct ggccgggaca gcagcgacac tgcatgctca gcccttgcgt | 1020 |
| gagaccacgg gagtgtccgc cctctgcacg tgctgctgat tgcccacttc gtccagcagg | 1080 |
| tttgggagct tgtggctgca tcctcctgca gacacttgcc cattctgggg cctcctctct | 1140 |
| gtcttttctc ctctgttgag gggtctggga ggaggcctt ggagggtacc catgctgctg | 1200 |
| ggactgatgc tccccgcggt ggaaggagct gcctcttgaa cagcaggggg ctgagcagag | 1260 |
| gggaggggat gcggggggtgc cgtgcacaca ggtgctctca ggacgcaggg gcttctcagc | 1320 |

```
cctgctgtcc cagggctgca ctccagcagg gcagactcct gaggtgcaga cacccccagct    1380 tcacgctcac acttctggaa ggcgatgtct gtgcgtttgc tttctgctgc agtttaaaaa    1440
gccgggctct ctccggagcg tgtgtagggc ctggtcactg gaatatctgg actcagtgtt    1500
aatggcagcc acgctggggg ctgggcccag ctttctgttc tccgtgtggg tgccatatcc    1560
acctccatcg cagcccttt  tctctcgacc ttttaaatca cagtgtcacc tcccccctgct   1620 gtcctgccag tggcccctgg aggcttctcc ccacccctt  cttctgggc  aattcttaag    1680 gctggcattg aatcaggagg ccagatgtgg ccctagtaa  ctcaccagca gtccctgagg    1740
cttctggctc ccctggccca ccagcctccc atgtctgcct caggcctctt gacccgcctg    1800
gcactgacca gactgtgtgc ccgggtgccg tgcccatggg ctccgcctcc cccaggcagg    1860 cccctcttg  ctccgcggcc acccctgctc ttgacctcac acctctgcgg tgtgtctgga    1920
cacaccagca ccacggcggg cggggagcgg aattctccag gtggggtggg caggccggcg    1980
ggtgttgagg tctctgtgca tgcttgtgcg taccctggac tttgccgtga ggggtggcca    2040
gtgctctggg tgcctttgcc agacaactgg tctgccgggc cgagcattca tgctggtcgc    2100
catcacgtga ctcccatgcg ccctggccct ggggttgggt ctgcaggact gagaaccagc    2160 ggaaggggg  cgaggcctcg ggaatgcgcc ggcaactggc gatgagctca ggcctgacta    2220
atgagcccag gtgactcata cacccggggc ctggatgagt ctgactgggt caggacttcc    2280
ctgcttgttc tgtcctggga gatgttgtcc ctggccctgc agagccggga ggacacgagg    2340
cctcctgggt cacagccaac gcagcctact cctgcccact gctcgcgccg gccaaggccc    2400
gtcggcacca cctcctccat gaagccttcc tgactgcccc catccctctg tgggcagctc    2460
gagtgtgcat cttgagtgct gtgcaggttg gggtccggcg ctcctgcagg caggcggcgt    2520
ctgggcctgg gggctctcag agtttgagga gcgtgtggtg agggtggcct cgggcctcaa    2580
agacgcagcg ctgtgggaac cgggagactg gctgagcccg ctctgaggaa ggtggggcca    2640
ggggcaccct cagctgaccc ggcgtgcagg ggtgaccagc caggcgtggc caaggatggg    2700
gtctctggga tcaggagact tcagtagcag ccaggaccga ggccaccagt ttccaccctg    2760
gcattttcca tcttttgaag gactggaaac gattggattc tttaactttt ttaagttgag    2820
gtgaaattca caacgcataa aattaaccat cttaaagcga acaattcggt gacatttagt    2880
acagccagaa ggctgtgcag ccatcaccac tgcccaactc tagaacattc acacgccgga    2940
gagagggagc cctgggccat cacgcagcca ccgcccggcc ccaagaacct gcgagtccac    3000
tttccacctc tggatcggcg gttctggacg ttcatgcagg tggttcccgc agtgcgaggc    3060
cttttgtttc gggctcctct cacaagcctc acgtttccag gtacgtcgtg gtgttgtgca    3120
gacccacaat tcatcccttt tcatgggtgt gtaatagtcc accatagatt ctctacgttt    3180
taaagcatgt tttatgtgcc tgaaatgtct ctgcactcga gactatagct tgctttcttt    3240
cttttctttt tttttttta atttgagacg gagtcttgct ctgttttcag gctgagtgc     3300 agtggtgcga tctcggctca ctataacctc tgcctccag  gttcaactga ttcttttgcc    3360
tcagcctccc gagtagctgg gactataggc gcgcaccccc acccggccaa ttttttgta     3420 tttttagtag agatggggtt tcatcatgtt ggccaggatg gtctcgatct tccgaccttg    3480
tgatctgccc gcctcggcct cccaaattgt tgggattaca ggcgtgagcc accgcgccca    3540
gccgagacta cagcttttctt taactgcatc cctggaggga tctgagagtc tctttccctg    3600
tctcctttcc tttggaaaac atttcagcca gggctcccca agatgaaagg ccagagtccc    3660
```

```
aggcatgggc gttgcaggtg cacagttgcc acggggagct gtgggtgatg gtcgctgtca    3720
gcgatggctg ctgcaggtcc ctgtgaggaa ggggcagtgc cacagcagga ggagagggag    3780
tcagcggacg ttgattggca gtgcccgccc attccatcat tcagtcaccc actgtgcacc    3840
cagcacccag gctcggctgc atagaacatg gcccaggaag gctccacttc ctgtctcctc    3900
ttctcccctc tccagtctca tgatggggct ggaggcatct tctagttttg agttctgagc    3960
taatgaacat gctcatgagc aggcggcagg atcccaggac ggtggagctg ggagcctgac    4020
tgcgggtgac ggacaggctc tggcagcccc tgtcagcatc ctctccaggg catgtgaaag    4080
ccagtgtgtc ctcagctgcc agtgcccct ccccacctcc tctgggccca tgtgcacggg     4140
acctgggctc ccccaaccaa gcctgcccgc cttggttcag cagaacggct cctgtctcta    4200
cagcggtgcc aggccaggag tgctgtgtct gtgaagcggg gtcatggttt tggggccctc    4260
atctccctcg cgccctctca ttggggaccc cccgtctccc tagcgccctc tcgtcctctc    4320
ctgcatgtgc tgtgtctgtg aagcggggtc atggttttgg ggcccccgt ctccctagcg     4380
ttctctcgcc ctctccagca tgtgaagtgg ggtcatggtt tggggcccc catctcccta     4440
gcgccctctc gttggggacc cccgtctccc tagcgccct ctcgccctcg cctgcatgtg     4500
ctgtgtccat gaagtggggt catggtttgg ggcccccta tctttctagc accctctcgc     4560
cctctcctgt atgtgaagtg gggtcatggt ttggggccg ccatctttct agcgccctct     4620
cgccttctcc tgagcgtgtg gaactctgtg gtggtcagag ctaaggttct gaataggtcg    4680
aagcacctcc ccggtgcctc tcaccctgaa tgctctggga ggacacagcc ttttcatagg    4740
ctacgactga catggcagga ggggcctgcc tgccacccgg gtcctctgct gcctgctgct    4800
tgctggggag ggggctcgag actgggatcc tgggcttctg ctccagctgt gcccaaggga    4860
gctgctgagg agggacccggg tggggcatcc actctgggca ggttcagggt cattcttggt   4920
gaccccgggt ccggttacaa aggctgatgg agcgcgtggg tggctgccta agtctctgga    4980
agcccaagaa tgtggagatg gcgcgtctcg gcccggggtc tcgtggctgg tctgggagaa    5040
cttgccttta tttctaggca ggaggctgca ctgcaaggga gcgtcagtgg cccggctggc    5100
tttccccggc cctcagcccg cactcgtcca ccaaagcaag ctcctttgtg gggctgccct    5160
gggaagccgg gatcacgagg ctctgccggc cgtggtcacc ccatgaggca gggtcagctc    5220
gggagcaagg cggatcagat ggaacagaac acgtagacca cctcgcccgc ccttagtcag    5280
ctgggccatt gaaaatcaag tccgtagaaa gacctagaaa taagtcccgg ggtgcccttg    5340
cctgttgacg ggcgggccga gcaggactgt tctcaggcag gcactggtct cttggcttcc    5400
aggtggtttg tttgctggtt tgaggctggg ggtgacgctc ctgtgcggga ggaggtcgca    5460
ttccattcat agcggcttat ctgggctgtc aggcaggcct ggagggagc ctgcctctgt     5520
gctctccaag ggtgggcgac ggacagacag ggtgtcccac cccttctggg ccaaggacag    5580
agggtcagtg tttgcagaga cctggggagg cccaggtgac ctccaccgag cacctgctgt    5640
gtgcagggcc agtgctggct gcagagacag cggagcgtgt gtggacccgg cggcccaggg    5700
gagggggca ggcaggaccc ggcggcccag gggaggggg caggcaggac ccggcggccc      5760
aggggaggtg ggcaggcagg acccggcggc caggggagg gggcaggca ggacccggcg      5820
gcccagggga ggggcaggc aggacccggc ggcccagggg agggggcag gcaggactcg      5880
gcggcccagg ggaggggggc aggcaggacc aggcggccct gggggtcagg ggtggaggcc    5940
aggcctagac ggcccacagg agggtggact cattctgacc gattcctgga agcccccgga    6000
aagtggtgat gttctggagg gcccagcaga ccccaaggcc cccaagacaa tcccagctgg    6060
```

```
ctctctgcgg ctctcggtgt ctgccatttg agacaatttg ggcacaggca gggcaggccg      6120
tcgcggacgg tctaagccgc gcgcattggt gggggcagca gagcccctgc tctcagctcc      6180
tcggggtaca gcgggggtac caggcgggtg agtgggtggg tggtcactgc tcctgccaag      6240
ggcagccctg gtttggtttg cacttgctgc cctggtgacg gctgctctca ttcctgcccc      6300
attgctaaca agggtgtcat aagctacttt cccggcccac atcctattaa gcccatggag      6360
accctcccac agctgagcct gctgtgggct gcaggccctg gcggtgccc acctcggtcc       6420 ccactggcct ccttccagca ctttagagca gacacaggtt ggagataagg aaagttccag      6480
agcacagact ggaacaagcc ccaggcctct ccctgcccca gcagggcctc cctggatttg      6540
ggggacaggt gccctcatgg ggggtcctga aggtcagagc tggggctggg gctgggctgg      6600
cggaggtggc cttggcggag ccacattcc agggtctcag tgagagtctg tggcaggcag       6660
ccttgcagat gccgctgagg accccccac ttcatgttgt gggtgatgtg gtccattgat       6720
tgcctccagg tttaaatcag gtggatattt acctagcggc ctcctctccc tctgcacagg     6780
gcctggagtg ggatggactg gggtgctcag ctggaggctc tgcagacaca gccccctggg     6840
ctatgcaggc cctgctggga gccacattgc cattttcat cacccacttt ttgggtgaga      6900
accccctcga gtcctaacat ctgccgcatc tcagagcctg tggctccagt cagagcatct     6960
ggaccatact gctggggtca gagcgcggca ggacaatggc                            7000

<210> SEQ ID NO 73
<211> LENGTH: 1500
<212> TYPE: DNA
<213> ORGANISM: Homo sapiens

<400> SEQUENCE: 73
tgccaccacc atcttcaggt agagcttctc tctcctcctt gctgggcggg gcccctccct        60
ggggaagcct gcaggaccca gacagccaag gactctcgcc cgccgcagcc gctcccagcc       120
agcagctcca acgccctgac gtccgcctgc gcacgccact tctgcacccc ctggtgatgg       180
gctccctggg caagcacgcg gcccctccg ccttctcctc tgggctcccg gcgcactgt        240 ctcaggtcgc agtcaccact ttaaccaggg acagcggtgc ttgggtctcc cacgtggcta      300
actctgtggg gccgggtctt gctaataact ctgccctgct cggggctgac cccgaggccc     360
ccgccggtcg ctgcctgccc ctgccaccct ccctgccagt ctgcgccac ctgggcatct       420 cacgcttctg gctgcccaac cacctccacc acgagagcgg cgagcaggtg cgggccgggg      480
cacgggcgtg gggggcctg ctgcagacgc actgccaccc cttcctcgcc tggttcttct       540
gcctgctgct ggtccccca tgcggcagcg tcccgccgcc cgcccgcca cctgctgcc         600 agttctgcga ggccctgcag gatgcgtgtt ggagccgcct gggcggggc cggctgcccg       660 tcgcctgtgc ctcgctcccg acccaggagg atgggtactg tgtgctcatt gggccggctg      720
caggtaactg gccggccccg atctccccac cctttccttt ttgccttgcc aggtaagtgt      780
gggcggggct gacgtgagcc tggtacaggt tccccccaca tcgaatctct acgttcaggg      840
gcccgtggcc ctcgggaggt gggagagctg ggagtgaggc ctcctgtgtg ggagggaggc     900
cggcgtctgg acaggaagag ggctggatga accgcagccc atgtgtccag gtgccacctg     960
ggcctggagc tccctgagca ttttagcgca tttagtcctc agcacggtcc cgagatacc     1020 tgccatgccc cgagtcacag aggggaaact gaggcgtggg gcagtggcgt gactcacccc   1080
agggagccga gattcccgct caggtgtggc tgcatcgacc ttgctccggt cactaagctg    1140
```

| | |
|---|---|
| cacggttcga tgcgcttcct gggagcccca gcgtgctcgg gccaagggtg ctgccgcgtg | 1200 |
| ggcagtgcag agaccctacc agcgtgggga ccagggaggt ctgcagggcc cgtcctgaga | 1260 |
| gggagccttt catgtccccc tccccatcct gaagcacaca gcctccctgc cacagtgggg | 1320 |
| gccgcttctg ggcccagggg acgttgcccc atcaccgtgt ggcctggcct tgttgctggc | 1380 |
| tggacagttg ggggcaggaa gaggagggaa aggggactc tttaacctcc tgggggcagg | 1440 |
| ggcagcccag aaaggacccc agcagatccc tcctctgtgt ccgggagtag acggggcccc | 1500 |

<210> SEQ ID NO 74
<211> LENGTH: 2000
<212> TYPE: DNA
<213> ORGANISM: Homo sapiens

<400> SEQUENCE: 74

| | |
|---|---|
| gggctccaca gcggcctgtc tcctcacagg gttcagccca gtctgctctc actcatttgc | 60 |
| tgattcattc tttcattcag ccagtcaata gtcatggccc ctcctgtgtg ccgggtggcc | 120 |
| atggatattg ccctgggtaa cacacagcct ggccctgtgg agcagacagt ggggacagcc | 180 |
| atgtggacag ggtgcaggtg gatggcaatg gcagctgggt caggaggggc tgagggccgt | 240 |
| ggggaaaggt gcagaatcaa tagggcatc cggactgggg tgcaggcctg ggggctggga | 300 |
| tttctagggt ggaggtcacc tctgagggag acagagcaag gccctgggag attagaaggt | 360 |
| cgaaggtcgc cgtgttgagg tcaggggccc tgaattggag ccgcggcaaa ggagagggca | 420 |
| ggtcagggca cgtggtgagt gattgctgcg gcttctgagc acggctgggt ctgtggggcc | 480 |
| tgagcagagg tgaccgcga tccggcgcca cggcaggcag gactcccac ccttgctgct | 540 |
| gcctacaccc ccagggcagc ccagagtcg ggggcgcagc tccctgcttg ccagttcaga | 600 |
| gcccagcccc tctcacccag cccagaggag gacacagatg gaggagggc acccggaggg | 660 |
| tccccccgcc gacaggcccc acgtctccca cctgcaggac aatgaagtgg ccgccttgca | 720 |
| gccccccgtg gtgcagctgc acgacagcaa ccccctaccg cggcgggagc accccaccc | 780 |
| caccgcgcgg ccctggcggg cagatgacat cctggccagc ccccctcgcc tgcccgagcc | 840 |
| ccagccctac cccggagccc cgcaccacag ctcctacgtg cacctgccgg cggcgcgacc | 900 |
| cacaagccca cccgcccaca gccaccgcga cttccagccg gtggtgagtg ccccccaaa | 960 |
| gtgggcttgg ctccatctag cccctcggct ctcggcagca gaagagggcc cagccctgc | 1020 |
| agagctgctg ggggtcccag gcttcggcca tgggtggggg tctggcggct cagggccact | 1080 |
| cagggcggct tggctggccc tgggacttgc cctctggtgg ccaagcagtg gtcatgaaag | 1140 |
| tccagccgct gtcacatcct tgaggaaccg gcgtacctcc gcctacagcg gcagctgggg | 1200 |
| gcacccacgt ggcccggggc tgctctgacc tggcagcgta tggggctgc tgcctgggcc | 1260 |
| cctcagtgtg tcacttgcgc gcctcccgct cagcgcccct cggccgtgcc tgtccacaca | 1320 |
| ggtgcggggc cggggtggtg cgccggggc ctgggtgcag ggggcagcgt gggacacagc | 1380 |
| ccgtgacgcg cccctctccc cgcagctcca cctggttgcg ctcaacagcc ccctgtcagg | 1440 |
| cggcatgcgg ggcatccgcg gggccgactt ccagtgcttc cagcaggcgc gggccgtggg | 1500 |
| gctggcgggc accttccgcg ccttcctgtc ctcgcgcctg caggacctgt acagcatcgt | 1560 |
| gcgccgtgcc gaccgcgcag ccgtgcccat cgtcaacctc aaggtgggtc agtccagtcc | 1620 |
| tgagggcgcg ggctcctcgg cccccacttg acctctgggg tgaactccca gcggggagct | 1680 |
| cccctctagg gcctctggag gccaccatgt tacagacact ggcgcctagg ctggcgactt | 1740 |
| cagggcaggc tccgggtggg tcacacccct ccaggctcag gccaggcctc tgcatccctg | 1800 |

```
ggcactgcca cgtcccccag ggcatcccat gaggccccc  cgtggccccc tgacccccg     1860 ctcccccggc agtgccctc  agagggtccc atgctgctgg accaagtgtc cacacaggtg    1920
atagggctca catacaagcc tggaatcagg aaccgtcctt tgggcctcta gtgccatgcg    1980
ggctggtggc ccctctgcca                                                2000

<210> SEQ ID NO 75
<211> LENGTH: 2000
<212> TYPE: DNA
<213> ORGANISM: Homo sapiens

<400> SEQUENCE: 75
gcctggagtg tagtcctgct gaaggccaga gaccacacac tccacccaga ctccggatct      60
ccctccccag caggggggatg gaggccctgc cgctgggagt gctggtgtta tgtggaaggg    120
ctgggcttct ccagggctcc tgggaggcct aaacatcttg caaggttttg acgttaatta    180
ctattatgat tgctttctgt gtgttactgt tttccccaca ctttagccag ctaatgtgga    240
gctacagaag gccctcgccc ctacccctcc agatgtccca gcccatgaca agcaggaagg    300
ccgggtgctg ggagacttcc tggggctgga tctgacatca ttccaagcag atgataacct    360
gccttcccga tttccaaacc cacagcaaga caccctggag ttatttataa atgcgagccc    420
ctgggtgcac ttctgacggg accagcaccc tgacggccat gagagggtgg agacagcgca    480
ccccgagctc agggaggcag gaaactctgg acctggaggc cgggcaccat gagggacacg    540
ctgcaggccc agctgctgcc gcctggggcg gggctgccct gcaggctccg ggaaaaccca    600
gaaccaggcc ggatcagcgt gtgtcaagag gcggggcgtg agagatgagc tgctttttt    660 cttcacaggg ttggcaggaa ctgcaaataa tagaaagtct ttagggtcta acacgctgcc    720
ctgaaaacac tatcattact ttcctaatga ctaactgtgt ctttcagccg gcggggcagg    780
cagctgaggc cgcaggctcc cgcagaggac cggggagggc tggcagcctg taatctgggg    840
gcgctgacag tgctctgccc agaccctcgc gccagctcca gctccagcac agcagccctg    900
ggtccctctg gcccctgcc  cgcagagtcc aggtgtggca gaggccgccc agtatccctt    960
ctcctcctcc ttttctaaaa acagagtctc acgatgtttc ccatgcgggt ctccaacgcc   1020
tgggctcaag cgatccttct gcctcggcct cccaaagcgt tgggattaag gggcgagcca   1080 ccgcgccccgg cccaccttcc cttctggttc atttccagta aggtcctgtc cacagcgtcc   1140
ttcccagcat tcccaccagg ctgcaggcct tggcctccct ccctccatt  ctcattctcc   1200 ccgaaaccgc caagcgcgtc caaagcacgg gttcgcaag  cgccccccc  gccccactcc   1260 acattccctt ccccgccgac tcagcctccg tagctcgcgg acggcccctc ctcacgccag   1320
cccaggcttt ttttttttt  ttttcttcta ttttaaggtt gtcttttaat gacacaagcg   1380
acatttggag acaaaaggac acatctcttc ctgacccacc tccaacccca gctgacggcc   1440
gccctgagcc tggcgtagac ggcccggaac gttccctgcg tgggttccgt ccatcccgaa   1500
cccctgtccc cgcgccggct ccgggggtgc tcgggggggcc gcgtggggtc tgtgacgtcg   1560
cctcgaggct gcatcccggt gacccggcag ccctggcgc  tcgcgggagg cgggcgggcg   1620
cggaccccag gctttagggc gcgattcctg cagctggctg ccggcccgag gttctggggt   1680
gtctgaggtc tcgggcgggg cgaggacgtt tctccggctc agccccccca cctcctgccc   1740
tgccgccccc cacacccagc tccccacgga cgcaagagg  cgcctcccac cccggcgagg   1800
acccgcgggg aaacgggggcc caggcgcggc gactgcggag gacgcgcctc ggccccagcg   1860
```

```
cctggtcct cggggcgtcc ggctgcccct tgcccgaggcc ggggcgggcg ctcagcgccg    1920
cggaagaaac gcccgggcgg ggacgcacag cgaggcgggc tccgcgggaa gtaccgggaa    1980
aacggcgcgg agcggaacag                                                2000
```

<210> SEQ ID NO 76
<211> LENGTH: 3000
<212> TYPE: DNA
<213> ORGANISM: Homo sapiens

<400> SEQUENCE: 76

```
tggagcaatc ccagagaggc tgaggtgttc aggctggccc cagatgcaca cgagcgtgaa      60
gcctgttcag aagccagctc ctcacaccct ctccctgcc agaggctcca gcacccctc      120 ccctctcctc tccctccct tccctgtggt cctcctgccc accccacccc cgtctgcatg      180
tgcaccgtca cggagatgcg tgtactaggg cggaggtcgg ggacagtcgt cagaaggaca     240
caggaaagaa gggaacagga atcccataac agaacattat ccggcaggag taattaacac     300
aggcaggact ggaggctttg ttttgttttg cttaaaaaac agtggtattt aaattaatgg     360
gcatgggaag actattcagt gaaagacatc ggtcattgag gtatctattc aaaaacacgg     420
tttagtactc tgccacacac cgaacgcaac gccacagcag ccatagaagc gtgtgtggct     480
gtttaacgtg gtcttttggg ggagggcatc ctaggcagag caggcgtgga agggaaggcg     540
gcggacggaa caaaacgcgg gcacgcaacg gctgctgcgc cggatctgag gcagggccag     600
cctgtgggag cagcaacatc gctcgcagga cagcgatgga gccccacga atccgcgtga     660 aagcagcaac cacctagaaa tgaacgtaca gctgcttaga aacagaatac ggatgacccg     720
aaagacttcc cgatggtagt caccagcata caggacctga cacgggcgtg cgggcagggt     780
gtgccgctac ggggtccctg gcgcacctgc taccccctgct acccgcattc accgcacgcg     840
gagggtgcgg gccgtgaagg ttatacatgc aaatatcctt ccaccagcca gttctccttc     900
caggaatctg ccacccgacc cttgtgttgt gcacagacat ggtccaggtg tttgcgacgt     960
gattgtttat cagagagaga gaagggaaat ctccaggctc gctgtagctg caggagctct    1020 ggggggctgcg cccatcgtgg agacggatag ctgtctctca tgaacacagg acagcaagtc    1080
cggctgcggc cacagaagac tcgccctcct ggacgcagcg tcttccttcc tcagccccac    1140
actggaggtg gccagtgcca tccacagcag aaggggccag ccgggaccag gctcacgccg    1200
tggaattctg ctctgtggta agaggaagag cgatagctgg aacccagcgc cgtcgcacac    1260
acagcgggga agagtctcag aaatgttact ttgagtcaaa aagctggaca aaaaaaggcg    1320
caagccagat ggtgctgaag aggccacagg aggctggcag ccaggggtc tggcacctca    1380 ctcggaggcg cagtgggccc gtccggaatt agtggccata cggcaagtgc cgagtggaca    1440
tcaaaccgtc acttcagact cctgcgcttc actgcctgtc ggttatgcct gggttttgaa    1500
atcaagtcac agaacacctg gaatgtggtg tttacgcaga acaaagcggg tgcctcggag    1560
gagagagcct agggacaggg gcacctcccg gtgtgggtgc ccagggttgc agggtggctt    1620
cctctgtctg cgcggttttc agagcccag ggtcctgcct gcccggctgc ctggaggcgg    1680
cccacatcct gctctgcgcc gccgaatctc agcctgaaca gcttcgctgg tgtttgtgtt    1740
gacttatttg ttcttttttt tttttttttt ttttaaataa aggattccga tgctgttaca    1800
gtcaataaaa gccacaggtc tgggtgacct acaaatgtgt gtgtctgact ttctgcagtt    1860
taaatcgcca ctgagcctta aggcgtctgg cccgcgcatt gaggaatcca cgtgggtctc    1920
ggggtcccca tgcctgccca gctccctgct tcagcctggg cgggtctggc gggcatttct    1980
```

```
gcgagcctgt ccctgggccc gcctcctggc cagacttcca gaaacattgt ccacatcccc   2040
gttgcacgtc cccccgtcac cggaaactgc agcccacagc actgggaaga acccgggagg   2100
caggcgttag gacggggtgg ccgagacagg gaagggagcc atggcggacg tcctcaccca   2160
agccagggct tcctgcccct gtggtactga caggagcccc gcaggacgtg gggttggctt   2220
tgggcagctc ggtggacact tctctttcag atcctgccac agcaaagctc acgagactca   2280
cttcttccca ttggaattca ctaagaacaa attcaacaat tcagacgccc agctggagg    2340 tttattttat ggattttacc tgtgcggtat ttagggttgt gtttatgaat aaaggtgtgc   2400
gttctggcaa gtagaaatac agagcttgtc tttcacccaa gtatctgtaa ctttctccaa   2460
tgcagacact aaaatgcaat aaaaacaaac caaacccatt aaacatgaat tagatgaggc   2520
aggctgatgg gaggttgtgg gattaacagg ccgtcagcgg attgaagctg cgcacatcgc   2580
tgggatgctg ctgcgggagg attcggtcta atccgggagc atctggctgg gcagtgggca   2640
gcgtctgcag tcgtggctgc ttgaaggtat gaaggttgtg gcctttgctt ccccccatca   2700
ggctgcccca ccctggaccc cacccagacc cctcgggcac cctgggtca tcttcagctc    2760 ccccttctct tccttccttc tcttccgcct gggcccctac tgtgacccga ggtcagcaga   2820
ggaccctggc aggtggctgc tccctgggac tcgactgtgc aggtgaggct tggggtgacc   2880
gctgctcctg ctcctgctcc tctcgccgtc cccaccctcc tccatcatgc tgtcaacatg   2940
catgtgggct gcagccctca gcctgcagga cgctgtcagt gcagctcctc agtggccagg   3000

<210> SEQ ID NO 77
<211> LENGTH: 2500
<212> TYPE: DNA
<213> ORGANISM: Homo sapiens

<400> SEQUENCE: 77
atcttgtctt ccttgtccca gtcctggaac cagccactgc cccagcagct cctgtgtgtg     60
gtggcatgtt ctggaagcca ggatgcatgg tgctcctggg ctgctgtggg tcctgggctg    120
ctgtgggtcc cgagctgctg tgggtcctgg gctgcacccc tgcagaacac ttccttccat    180
gttcagctcc ctatatggaa ccccagttcc agccccacag cacagggtcc cccagttctt    240
cctgcctcag gtgtgcacca cgaggaatcc aactgccagt atctgtgcgt ggcctcccgc    300
cgggaggagg ctgccggagg ctctgagctc tagccccaca gcactggcac atcctagatt    360
tccgggaaga cacggcctcc tccccagggg aaggtggtgg tgcccacacc cagagcattc    420
attcctgcag tggagacaga gggacctgcc tctccaactg tgggtgtcag gagccaaggc    480
gcatggtaaa tggggctctc tgtgaggcca ggtgcacggc cccatctcca gcagcagcgg    540
ccatgccacc cagctgcact ctgtggggga ggtgccatga ttgacggggg ccctcccctg    600
tgtccagtgt cctcctccct ccacgggccc ctctgcacac cgtcctcaca gtctccctct    660
gcacaccgtc ctcacagcct ccctctgcac accatcctca tggtctccct ctgcacaccg    720
tcctcacagc ctccctctgc acaccgtcct cacagcctcc ctctgcacac cgtcctcaca   780
gcctccctct gcacaccatc ctcatggtct ccctctcctt ccacagaccc ctctgctcgc    840
catcctgacg gcctccctct ccctccacgg acccctctac acactgtcct cccagcctcc    900
ctctacacgc catcctcaca gcctccctct ccctccacgg gccctctac acaccgtcct    960 cacgcctcc ctccctcc acgggcccct ctgcacaccg tcctcacagc ctccctctcc    1020
ctccacgggc ccctctgcac gccgtcctca cggcctccct ctgcctccac gggcccctct   1080
```

```
gcacgccgtc ctcacggcct ccctctgcct ccacgggccc ctctgcatgc cgtcctcacg      1140
gcctccctct ctctccacgg gcccctctgc acgccgtcct cacggcctcc ctctctctcc      1200
acgggcccct ctgcacgccg tcctcacagc cttcctcttt ttccacagac ccctctgcac      1260
gccgtcctca cggcctccct ctccctccac gggcccctct gcatgccgtc ctcacagcct      1320
caccgacgtc accattgctg gccccgcttc aggtgacagg ccacagtagc acctgtcagc      1380
tctgtcccgc tgctggacag ggagatactg ggccactcag cccagcgggg aacgtgtgtc      1440
ccgaaactgc cttgggctcg ccatcagaac tgtggcagca tcttccagcg ttccttttaa      1500
caggctgccg ttggaatagg agtcacggag caattgcagt gctaagtttt ctttaagtca      1560
cacaattgaa ggaggcttta ttttcacac atttcttcca gagtttcctg gtagcctgag       1620
tgcatgggtg atgcccctg agttatttat caggggcagc cagctgccct ccccgggc        1680
acttacagtc agcccatctc tgtcctggtc aggtgggcgc caaggaagac ccggctcagg      1740
gcctctgtat gggcagcctg gcttgtacac acacccctcc ccaccagcag attctgaatt      1800
ctcccttctt catgcacacc gggaaggtcc cttctgcact cataccggga aggtaggcag      1860
gtttcggtag tgtctgcctc cagtgttttc ctcctcctgc tctatgacat catctttctg      1920
tgatttttt tttcttgcag gaagttggaa gcatcatcgg gaaggtaatt attgattgaa       1980
tctctgcctc tcctggggtc tctgtaaggg gatggtgagg atggcagcct ccctgggtac      2040
taggtggcac ccagtaggtg cgcctttccc agttggtggg tggtctgtgt tccatgaaga      2100
caggacccca gaggtgtcgc ctttatgctg tatgacattg aagctggtcc ctggctctgc      2160
gtggcctgag gggaaggggt tcactccagc tggtcacctc gctgccccct gcccgtggcc      2220
ttggtggcca gtccttcttt cccggttgaa gaccccacga agaatgattt ctcacgcctt      2280
cttcagccgg ctgtgtagtc tgggtggtct ccaggagtgc cagtgaggc agcagccccc       2340
agacaattcc tttccaaatc agggctggcc cggggaagt aaggcccagt ttggaagcct       2400
gctgccccgg gaggccgagc agtgagggcc acctccctgt cttcatcaca ttttcaccgc      2460
ttccgggggt ccttcccctc agtcccacca tgggggcgcc                           2500
```

<210> SEQ ID NO 78
<211> LENGTH: 6000
<212> TYPE: DNA
<213> ORGANISM: Homo sapiens

<400> SEQUENCE: 78

```
gctggacacc tctgagagcg tggccctgag gctgaagccc tacggggccc tcgtggacaa        60
agtcaagtcc ttcaccaagc gcttcatcga caacctgagg gacaggtagg agggacgccc       120
cgtgaccttc ctcctgtgct ctgggcctc ttggagggag gggtggggc ccaggggaac        180
acgggtgcga cggcctcaac ctcctaaggt tgggcgagcg ttgccctgac cggggcccct       240
cccgcgccc tccagagtga ggccggggcc ctttccggcg ccctccagag tgagctggtc       300
tgagcctctc ccagcgcctt ccagagtgag ctggtttgag accctgctcg cggggtggc       360
acctgttcag cagggccgag gtgacagtga ggctgagatg tagggaagag aggctcccgc       420
aggctgaccg agagggctca gcgcactggc ccagacacgc agtcctgcct ggtgcgcggg      480
agcccctcac taaccacctg accctggtt tgttccgtgg gcagtgagag cctctacctg       540
ggtcctggat cccacgttct gaaggtcccc gactcgggag ccaggagggg tgtcgctctg      600
cagccccagg gccccaggc ttggttctgg gcttgggaca cggcaccctc tgctccacgt       660
tcctccatct gtgcgtgtgg ctgaggacag accggggga gagggagtc ggtcctgtgg        720
```

```
gtgcacaggg ccgctgaggg gggggcatgt agaacgggc tcccccactg agacgggtcc    780
tggcagtggg gacacagctt agccggcgta ggaaccccg tcctccttga ccctgctgac    840
tggccgctgg gccggagcct cccgccacca gaagggcac agtcagaggc tgccggtaac    900
agcagggtgg accttccagc ccacaccgtg cccagcagga gccattggta ccaggaaccc    960
tgagcttagt ggacatggcc aggcccgtgc ggcagtgttt gggggggggt ctggctgtgg   1020
atggcaccgg ggaggggcgg ccgcgtggcc cagcgtcccc cgagtcgccc ttgttgcctt   1080
tactcagtct ccccatgact cagtttccca cctgtgaaat ggggcggagt catccccatg   1140
tcgctgccac tggattcctg caggcgccgt ggtcactctg ctgaatggat gggagggtgg   1200
gtggggcaga ggtgggccca ccccaggctg gggcagagca gacccctgag agcctcaggc   1260
tcaggtgctc agagggcagc gagggggctg ctcagatccc cggggtgcct ccttcccca    1320
ctgtcatgct gccccactgc aggcccaagg accccacccc agcagggcca cacactcagg   1380
gctcctggtc tgagggcctg agggatcggg gcgcaggtcg cttgctggcc acacccgcct   1440
gcacagcctt ccaggagggc cggcctcagg ccacagggc aagtccagct gtgtgtcagc    1500
cacggccagg gtggggcagc ctgtccatct gggtgacgtc gcgccctggg acgggtagcg   1560
atggcgccag gggccgcccg cctcacgccc gccgtgcctg ttcctggcag gtactaccgc   1620
tgtgaccgaa acctggtgtg gaacgcaggc gcgctgcact acagtgacga ggtggagatc   1680
atccaaggcc tcacgcgcat gcctggcggc cgcgacgcac tcaaaagcag cgtggacgcg   1740
gtcaagtact ttgggaaggg cacctacacc gactgcgcta tcaagaaggg gctggagcag   1800
ctcctcgtgg ggtgagtggc ccccagcctc ctgcccacgc cagttctcac gcgtggtacc   1860
cagcctgggc tggggttggc ctgggtccc tgtgcggctt cagctgcagc ctccctgttc    1920
tcttggaggc tgcacggcct ccctgaccca ctttgtgggc aggaaagaga cggagacaga   1980
cagagacaga gagaaacaga aacagggaga aacagacaca gagagagaca gagacagaga   2040
gagatagaga cagagacaga gagagacaga gacaaagagt gacagaggga ccaagacagg   2100
cagacagaga caaacagaga cagagacaga gacacagaga gagacacaga gagacagaga   2160
cgggaacaga gacaggcaga cagagacaga gagagacaga gacagaaaca gagacagagg   2220
gacagagaca ggcagagaga gacagagaga cagagacaga gacagacaaa cagagacaga   2280
gagacagaaa cagggacaga gacagaaaga gagagagaca gagggaaaca gagagagaca   2340
gagacagata gaaaaagaca gaggcagaga gaagcagaga cagagaaaca aagacagtca   2400
gagacagaca gagacagaga cagaaacaga gacagagaga cagagacaga ggggcagaga   2460
caggcagaca gagagacaga gacagagaca gcgaaacaga gacagaaaca tacagagaca   2520
gagagacaga gagaagcaga gacagacaga ggcagagaga cagagagaag cagagacagg   2580
gacagagaca gagacagaaa tagagagata gagacagagg gacagagaca gagagataga   2640
gacagagagg gagacagaga gatagaagca gagagagaga gacaaagaca gaggcagaga   2700
gacagagaga gaagcacaga cagagacaga cagagagaca gggacagaca gagacagaga   2760
gaccggaaac agaggcagag agactgagag actgagagag acgggtggt tttcccaca    2820
gcatcaacac caagcagggc taggatcact gaaacagact catcagaccc gaagcatgcg   2880
ctttctcggg gttttctgg actgagggt tcctctcat cccagtgtcc agctgtgggg     2940
acgcagggge cgcaagcccc ggagtgtcca gagggaacg tggcctcccc acacccagcc   3000
cttcacgagg cctcaggatc ccagtggggg tacccgagge tgccctgtcc agccaggcgg   3060
```

```
tgcgggggt   ttggggagag   cctctccccg   aggtcggtct   cagagggcca   catggccggt    3120
gtgggccgga  cattcccttt   ccaatggttg   tgcccacttc   cctccagagt   tggtgccaag    3180
ctgggacctg  ggggacttgg   agtctcagga   agtcgtccgc   tgtctgcagg   gggtgcatgg    3240
gggatgtggc  cacacacgtc   agagtgcggc   cccctgtgga   agccacagac   agacacgact    3300
cccctaaatg  agctcgccct   tctggccgag   atgctcagcg   tccccagcag   gctgcccgac    3360
tgccctgcga  tactgccctc   cttcctgctg   ctcccacttt   cccttcgggg   gggttggatt    3420
tggggcattc  agggatcgcc   ctgttgtttg   ctcatcacac   ccatttcctg   caagagccac    3480
ggtgaccgag  cagccttgag   ttgaggcagc   ttgtgggtag   acgcggcggg   catctcggag    3540
gggcacgctc  cctgccaccc   tcagcctcca   ctcactggtc   aggggctttg   cgccccaggg    3600
caccccagga  accgagcctc   ctttggggtc   atgggtgcct   ctcctgggag   ggcgtggatt    3660
ttccaaagca  gtttagagaa   atgagaccca   caggcgttat   ttcccatggt   gaggttcttt    3720
tcagtaaccc  ccaccgtata   gccaggatca   gcaaagagag   gcggctcctc   ccggtgagac    3780
agggaccagc  acctcccgga   caggcttggg   tctccctcca   gttcccccac   ctagtctcga    3840
ggtctcacgc  tgccctctcc   tgtccagggg   ctcccacctg   aaggagaata   agtacctgat    3900
tgtggtgacc  gacgggcacc   ccctggaggg   ctacaaggaa   ccctgtgggg   ggctggagga    3960
tgctgtgaac  gaggccaagc   acctgggcgt   caaagtcttc   tcggtggcca   tcacacccga    4020
ccacctggta  ggcaccggcc   ccccccggca   gatgccccca   accacaggga   gtggcggctg    4080
caaggccccc  ggcagctggg   accgtctttt   ggtcctcggg   agggtgtggg   ttctccagcc    4140 ggccacccctt gccctgaga   ggccagcccc   tcctgctgag   gagcctggag   cgccccagcc    4200
cagcctcccc  tctggccctg   tgggaagcgg   ccccggccgt   caggggtccc   agccctgctc    4260 agcccacccct gaacactgcc   cccaggagcc   gcgtctgagc   atcatcgcca   cggaccacac    4320
gtaccggcgc  aacttcacgg   cggctgactg   gggccagagc   cgcgacgcag   aggaggccat    4380
cagccagacc  atcgacacca   tcgtggacat   gatcgtgagg   ccctgcccca   ggagacgggg    4440
aggcccgcgg  cggccgcagg   tggaaagtaa   ttctgcgttt   ccatttctct   ttccagaaaa    4500
ataacgtgga  gcaagtggta   agagccctcc   ccaccacccc   cagccgtgag   tctgcacacg    4560
tccacccaca  cgtccacctg   tgtgttcagg   acgcatgtcc   ctatgcatat   ccgcccatgt    4620
gcccgggaca  catgtcccct   gcgtgtctgc   ccgtgtgccc   gggatgtgtg   tccccctgcg    4680
tgtccacctg  tgtgtctgcc   catgtgcctg   ggacatgtgt   ccgcctgtgc   gtccatccgt    4740
gtgtccgtct  gccatgtgc    ctgggtcgca   tgtcaccctg   tgtcccagcc   gtatgtccgt    4800
ggctttccca  ctgactcgtc   tccatgcttt   cccccacag    tgctgctcct   tcgaatgcca    4860
ggtgagtgtg  ccccccgacc   cctgaccccg   cgccctgcac   cctgggaacc   tgagtctggg    4920
gtcctggctg  accgtcccct   ctgccttgca   gcctgcaaga   ggacctccgg   ggctccgggg    4980 cgacccccggc tttgaggtga   gtggtgactc   ctgctcctcc   catgtgttgt   ggggcctggg    5040
agtgggggtg  gcaggaccaa   agcctcctgg   gcacccaagt   ccaccatgag   gatccagagg    5100
ggacggcggg  ggtccagatg   gagggggacgg  cggggttcca   gatggagggg   acggcgggag    5160
tccagatgga  ggggatggcg   gggtccagat   ggaggggacg   gcggggtcca   gatggagggg    5220
acggcggggt  ccagatggag   gggatggcgg   ggtccagatg   gaggggacgg   cggggtccag    5280
atggagggga  cggcggggtc   cagatggagg   ggacgtcggg   gctccagatg   gaggggacgg    5340
cgggagtcca  gatggagggg   acggcggggt   ccagatggag   gggacggcgg   ggtccagatg    5400
gaggggacgg  cggggtccag   atggagggga   cgtcggggct   ccagatggag   gggacggcgg    5460
```

```
gagtccagat ggaggggacg gcgtggtcca gatggagggg acggcggggt ccagatggag    5520
gggacgtcgg ggctccagat ggaggggacg gcggggtcc agatggaggg gacggcgggg     5580
tccagatgga ggggacggcg gggtccagat ggaggggacg gcgggtcca gatggagggg     5640 acggcggggt ccagatggag gggacggcgg ggtccagatg gaggggacgg cgggagtcca    5700
gatggagggg acggcgtggt ccagatggag gggacggcgg ggtccagatg gaggggacgt    5760
cggggctcca gatggagggg acggcggggt ccagatggag gggatgtcgg ggtccagatg    5820
gaagggacgg cggggtccag caggcaggct ccggccgtgc agggtgtgga ctgtcccggg    5880
ggcgctgggg gcttctgagg gtgtctctgt ccgccctgcc ctcagccgca ctctgttcag    5940
aaggaccttt ctggaggtag gagggtgaga atgtgggtcc cctgcttctg tgtggctcac    6000

<210> SEQ ID NO 79
<211> LENGTH: 7000
<212> TYPE: DNA
<213> ORGANISM: Homo sapiens

<400> SEQUENCE: 79
ggccggggag gcggggaggc tgccccaaga gtaaaagcct ttctgacgtg cgcaggacgc      60
ggccctgact ggtctaactg actctttctc ttctcctcag cttgctgtgg tgagacccag     120
gctctagctc ctgagagaat ggatcccggg ggtcggggag cgaggcctgg gtcccacaca     180
tgtcacagga cagcacatgg cactctggtc cccgcccgca gctccctgca cctgcccgcc     240
ccctctgggg cctgctccaa gccagcaggg ttcccgggtg ttgggctggg ccccgcccctc    300 tttcacccat aactgaaata accaggagca ggcttggggg ggtccctgct ccatcattct     360
ggcccacagg ccccacccta gcctggctga gcaacgccag ccctgaccag ccgccggaca     420
gagcagcctt tacggggcca tgggaggggg tgggcttttc tggggctgag acgggggggac   480 cccaacgtgt caggtgagga tgtggcagcc aaggaggggc cagggcggtg gaggggaggg    540
gccagggcac tggaggggag gggcgtgctc tgctgacacc gccccgcct gcagaatgca     600 agtgcggccc catcgacctc ctgttcgtgc tggacagctc agagagcatt ggcctgcaga     660
acttcgagat tgccaaggac ttcgtcgtca aggtcatcga ccggctgagc cggacgagc     720 tggtcaaggt gaggcctcgc cccgcccggc tttctcaagc ccaggtgcac cccgaccctg     780
ccggccgccc ctgcccgcgc cagacctcag cctcccgagg ccaccgctgc atccctgtga    840
cttccctact catgacaagg atgccaggca cgcgccagcc cgtccaggcc tccagctcca    900
cctggcgagg ctggcccatt gtacacaggc gccccagatg agggagggtc tccccctctc    960
cttgaagggc ggtagtctgg ggtcctgagt gctgggtgtg ggcttgtccc tcgtggacag   1020
aacccaggag ggcttcatcc accaaggaag attgctttgc agggtaccca ggtcccgggg   1080
gctgtgccac cctctgggca cccggagcca atcgcagggt acccaggtcc cggggggctgt 1140 gccaccctct gtgcacccag agccaatcgc agggacccca ggtcctgagg tcctgggggc  1200
catgccaccc tctgggcacc cgcagccaat agagtcaccc ttgggaagct tatgcggacc   1260
tggggcagca ctcgcgtcct gaccccggtg ccggtccac agttcgagcc agggcagtcg   1320
tacgcgggtg tggtgcagta cagccacagc cagatgcagg agcacgtgag cctgcgcagc   1380
cccagcatcc ggaacgtgca ggagctcaag gagtgagtgc cccacgcggc caggaccctc   1440 ccaccccctcg ccccgaccgc tgttcccacg gcaggtcggc cctgaccct gatcccaggt   1500 gggctcggcc ccgcggcagg cctggcccca accggccctt cctgcccttt gctatgcaga   1560
```

| | |
|---|---|
| gccatcaaga gcctgcagtg gatggcgggc ggcaccttca cgggggaggc cctgcagtac | 1620 |
| acgcgggacc agctgctgcc gcccagcccg aacaaccgca tcgccctggt catcactgac | 1680 |
| gggcgctcag acactcagag ggacaccaca ccgctcaacg tgctctgcag ccccggcatc | 1740 |
| caggtggggt ggccaccccc aggctgcacc tgcccgcct agggcgcccc gccagccagg | 1800 |
| gtggccttgt ccccagaaag acgagggcag agcaggctgc gccacaccga tactgtctgt | 1860 |
| ccccacaggt ggtctccgtg gcatcaaag acgtgtttga cttcatccca ggctcagacc | 1920 |
| agctcaatgt catttcttgc caaggcctgg caccatccca gggccggccc ggcctctcgc | 1980 |
| tggtcaagga gaactatgca gagctgctgg aggatgcctt cctgaagaat gtcaccgccc | 2040 |
| agatctgcat aggtgcgcat ggggccaccc gggcagtccc agatctgcgt aggtgcgcgc | 2100 |
| ggggccgccc gggcagtccc agatctgcgt aggtgcacgc ggggccgccc gggcagtccc | 2160 |
| agatctgcgt aggtgcacgc ggggccgccc agggccgtcc cagatctgtg taggtgcgcg | 2220 |
| caggcgccca gggctgtccc agaggcctcc tcccagctca ctgttacctc caggggcacg | 2280 |
| gccaccctgt aggtgcgcac ggggccgcct ggggctgtcc cacaggcatc ctcctcccgg | 2340 |
| ctcgctgtga cttccggggg cacggccacc cctgtgctcg gccgggaggt cctgtgacat | 2400 |
| ctccttgcgg ggttataggt ggagcagtgg gctcacactg cacggctttt ctcttttaca | 2460 |
| gacaagaagt gtccagatta cacctgcccc agtgagtacc tcggcggccg ggacacgtgg | 2520 |
| ggaggagggc accgtggttg ggcgagggc tctgagagga cggggctctg gaggagggc | 2580 |
| ctggcggtca cgagagtagg tgcatggctc actccggtgg ctgagcacca ccgtgccgtg | 2640 |
| ccctctctgg ggagcttaga cgctctctgg ccggcccact gcggctgcat caccagggcc | 2700 |
| tcatgctaac ggctgcccac cccgccccgc agtcacgttc tcctccccgg ctgacatcac | 2760 |
| catcctgctg gacggctccg ccagcgtggg cagccacaac tttgacacca ccaagcgctt | 2820 |
| cgccaagcgc ctggccgagc gcttcctcac agcgggcagg acggacccg cccacgacgt | 2880 |
| gcgggtggcg gtggtgcagt acagcggcac gggccagcag cgcccagagc gggcgtcgct | 2940 |
| gcagttcctg cagaactaca cggccctggc cagtgccgtc gatgccatgg actttatcaa | 3000 |
| cgacgccacc gacgtcaacg atgccctggg ctatgtgacc cgcttctacc gcgaggcctc | 3060 |
| gtccggcgct gccaagaaga ggctgctgct cttctcagat ggcaactcgc agggcgccac | 3120 |
| gccctgcc atcgagaagg ccgtgcagga agcccagcgg gcaggcatcg agatcttcgt | 3180 |
| ggtggtcgtg ggccgccagg tgaatgagcc ccacatccgc gtcctggtca ccggcaagac | 3240 |
| ggccgagtac gacgtggcct acggcgagag ccacctgttc cgtgtcccca gctaccaggc | 3300 |
| cctgctccgc ggtgtcttcc accagacagt ctccaggaag gtggcgctgg gctagcccac | 3360 |
| cctgcacgcc ggcaccaaac cctgtcctcc caccctcc cactcatcac taaacagagt | 3420 |
| aaaatgtgat gcgaattttc ccgaccaacc tgattcgcta gatttttttt aaggaaaagc | 3480 |
| ttggaaagcc aggacacaac gctgctgcct gctttgtgca gggtcctccg gggctcagcc | 3540 |
| ctgagttggc atcacctgcg cagggccctc tggggctcag ccctgagcta gtgtcacctg | 3600 |
| cacagggccc tctgaggctc agccctgagc tggcgtcacc tgtgcagggc cctctggggc | 3660 |
| tcagccctga gctggcctca cctggggttcc ccacccggg ctcctctgcc ctgccctcct | 3720 |
| gcccgccctc cctcctgcct gcgcagctcc ttccctaggc acctctgtgc tgcatcccac | 3780 |
| cagcctgagc aagacgccct ctcggggcct gtgccgcact agcctccctc tcctctgtcc | 3840 |
| ccatagctgg ttttcccac caatcctcac ctaacagtta ctttacaatt aaactcaaag | 3900 |
| caagctcttc tcctcagctt ggggcagcca ttggcctctg tctcgttttg ggaaaccaag | 3960 |

```
gtcaggaggc cgttgcagac ataaatctcg gcgactcggc cccgtctcct gagggtcctg    4020
ctggtgaccg gcctggacct tggccctaca gccctggagg ccgctgctga ccagcactga    4080
ccccgacctc agagagtact cgcaggggcg ctggctgcac tcaagaccct cgagattaac    4140
ggtgctaacc ccgtctgctc ctccctcccg cagagactgg ggcctggact ggacatgaga    4200
gccccttggt gccacagagg gctgtgtctt actagaaaca acgcaaacct ctccttcctc    4260
agaatagtga tgtgttcgac gttttatcaa aggccccctt tctatgttca tgttagtttt    4320
gctccttctg tgttttttc tgaaccatat ccatgttgct gacttttcca aataaaggtt    4380
ttcactcctc tccctgtggt tatcttcccc acaaagtaaa atcctgccgt gtgcccaaa    4440 ggagcagtca caggaggttg gggggcgtgt gcgtgcgtgc tcactcccaa cccccatcac    4500
caccagtccc aggccagaac cagggctgcc cttggctaca gctgtccatc catgcccctt    4560
atctgcgtct cgtcggtga catggagacc atgctgcacc tgtggacaga gaggagctga    4620
gaaggcaaca ccctgggctt tggggtcggg agcagatcag gcctcagtgg gctggggccg    4680
gccacatcca ccgaggtcaa ccacagaggc cggccacagg ttctaggctt ggtactgaaa    4740 taccctggg agctcggaag gggagttgag atactgcagg gcccatagga agaagtcttg    4800
ggaggctcca ccttttgggc agaggaagaa gtcttgggag gctccacctt tggggcagag    4860
caagaagagg gcggagggca gaggcagcga gggctcatcc tcaaaagaaa gaagttagtg    4920
gcccctgaat cccagaatcc ggggtgcacg gctgttctgg gggccgctag gggactaaga    4980
ggatcggccg agggctgggc tggaggaggg cagcagggat gggcggcgag ggtgagggtg    5040
gggcttcctg aaggccttca cctgcgggga ccccggcgag ccccccaggt gccacaggca    5100
gggacacgcc tcgctcgatg cgtcacacca tgtggccacc agagctgcgg gaaaatgctg    5160
gggaccctgc atttccgttt caggtggcga acaagcgccc ctcacagaac tgcaggtaga    5220
gacgggcccg gggcagacgc agtgaggcgg tgggcggggc ccggggcaga tgcagtgagg    5280
cggtgggcgg ggcccggggc agaggcagcg agcggtgggc ggggcccggg gcagacgcag    5340
tgaggcggtg ggcggggccc ggggcagagg cagcgggtgg tggccgggc ccggggcaga    5400 cgcagtgagg cggtgggcgg ggcccgggt agtcgcagta ggtggtgggc ggggcccggg    5460
gcagacgcag tgaggtggtg ggcggggccc ggggcagacg cagtgaggcg gtgggagggg    5520 cccgggggcag acgcagtgag gcggtgggcg gggcccgggt cagaggcaac gggtggtggg    5580
cggggcccgg ggcagacgca gtgaggcggt gggcggggcc cggggcagat gcagtgaggc    5640
ggtgggcggg gcccggggca gatgcagtga ggcggtggga gggccccggg gcagacgcag    5700
tgaggcggtg gcggggccc ggggcagacg cagtgaggcg gtgggcgggg ccggggcag    5760 acgcagtgag gcagttgcca gcctctctca gctgcctcat gggattcgca ctgcagctgc    5820
ggccctggcg cgacaagggc tggacttggc cagcgggacg gtccctcacg gcgctgaggc    5880
ccacactctg cgtggagcct ccccgtgccc aggctaccct gcaaggtcct cggagaggct    5940
tcctccagcc ccagccccca cacagctccg gcccaggccc gctcttcccc atcccagttg    6000
ctttgcgctg tatacggcca ggtgaccccg agccggccct gagccctcgt cccggcttcc    6060
tcccctgtaa gctgggtgaa ggactccatg gcacccacct gagagggttg tggcgaggcc    6120
caggcccctc gtgccacac ggccggcggc ccatgcctgg caggggctgg gaggaggctg    6180
gggcgaccag aggggagcgg cctgtcctgg aggaggccca gggaccctgg tgagagggtc    6240
tctcccaagt gctctctatg ggaccccctt cctctgcgcc cgtccttcac ggacctctcc    6300
```

| | |
|---|---|
| gggtcacccc tgggctgcac actgggttca ggggggcctt gaggtggggc ccctgttccc | 6360 |
| aagtcccggc ggggtttctc ctgaacctca acccatcctc acctgcgggc attcccatcc | 6420 |
| cccaacgcct gggtcaccag gattccaggc aggaggggcg gtgggggtta ccaaggcccg | 6480 |
| ggttgccatg cagaaccccc agccaccacg cagacccca cggggcccag ggaagctcct | 6540 |
| ggtctcacac tgcacctcac acttcctgtg ggggcagact ccaaggtccc ggcctctcat | 6600 |
| cttgtagaaa ctgaggcaca ggagggacac acactcccac ggccggtcac cgtgccccc | 6660 |
| acacctccca ctggactgac acctggccag gctccggaca cccgtggcac agcctcagcc | 6720 |
| cctgcggccc ctgctccgtg gcccccaggc cccagctccc atgtgcacgt cctgcctcag | 6780 |
| gcctggaggc ccctcggccc caaataatca gacaattcaa cagcaaaact actttttca | 6840 |
| ggctggcagg actctgggca accccctgca acagccccct gccctatcac agccacctt | 6900 |
| gcctcccagg cacggagacc ccaccatcag gtcccagcct tggttcatcc ccaagcaccc | 6960 |
| tgtgtgttgg gatggcgatg ctggctgagc ccctgcatcc | 7000 |

```
<210> SEQ ID NO 80
<211> LENGTH: 2500
<212> TYPE: DNA
<213> ORGANISM: Homo sapiens

<400> SEQUENCE: 80
```

| | |
|---|---|
| agggcgtttg ggaacacccc tcccggaggg gtgaggcggc ccagcctgcg gctgccagag | 60 |
| gacacaggtt ctgctgcgga acctgcagac atggccataa caggccacag tgctcgggcc | 120 |
| cacacagcct ggacccacat ggccctgtgt cacctcctca ggggcaggct tcagggcctc | 180 |
| gaccctagag gctgcccctc ggttctgctc catggacggc gcaggcaggc ccaggcctgt | 240 |
| gacgagttca cggaagctcc aggatgaccc ccgctctgcg ccctcctcca gcattccaga | 300 |
| ccacaaacca ctctgggcta aaacgaggca tcgccagagc atcccacttc ctcggaaagc | 360 |
| tgcggtctgg ggacgcgtct tggccctgaa gaggctccag atggctccca tcaggcctct | 420 |
| ccgcctacgt gcggccgaca tggagtgaca gagcgtcggg gacacagaat tcagagctgg | 480 |
| gcctggggct gctttgagat actgatggct gccagggggc acagagaccc gtcctgcaga | 540 |
| cagggctgtg agggccacag ggggcctcgg ggagaggcag tgggagggag acagtgggg | 600 |
| gcctccagct gggtgagcag ctggagcgag ggggcccgg ggcttgtgat ggtgctgccg | 660 |
| acctagagg tgccggcccc acgatggaga gcacgtagtg ccccccggga gtcaggaggc | 720 |
| cgggcctgac ctcgggggct gcagccaggg gaggccggca ccagataa ccccaaaga | 780 |
| actgcaggcc ctgaggcgag gccagagtgg gggcggggc aggtcccagc cgaggaggtg | 840 |
| ctccgtgctg cctcagcaga acccatgatg ggctggccca aggctctgaa ggtgaaagg | 900 |
| cctcacacat tctgccccgg ctgacgcctt ccttgggcca gtgctcgggg gtgtgtaaca | 960 |
| aacgccaaga cgcattgtaa agaaggaagc ctgcgtttcc atcaccggct taatatcaaa | 1020 |
| caaaagtgca attttgaaaa tgtagtccaa ggttttctgt ggtgcggaaa tggccaggcc | 1080 |
| agacctccgt gggtggtcct tcgtgtccac gtcagcgccc tacatccaca ctgtgggcac | 1140 |
| catgacctca catgcggagc ggagcagggc cggcgcccgg agagccaggc tggtcacgaa | 1200 |
| cgaggcctag agggcgtcag gccccaaagc actcacaggc ttctcctctg tcctcgggc | 1260 |
| cttcagacac ctgcatgcgc cgattcagcc cccgcgcgc gccgattccc ctggccatgg | 1320 |
| ggtttccaaa gtgtgtgctc agaggacagt ttcctccagg atgacctgtc agtggctctc | 1380 |
| tgtgccgggg acgtcgcgtg ctgggtcccg gtctgaatgc ttcctaacga tttacccagt | 1440 |

```
tccttttctc cactcaggag gcgtttgctg agaggcacag gctgagcccc cgtgctgatg        1500
ccacgaccga gggaacgggt ctccctgtcg gcgtgaactg acccggccag gcgtccactg        1560
ccactcggac tgtctcccag gcacgtggcg cccacacggg cagaacacgc cctccacaca        1620
cgcggcttcg ggcagaacac gaggcgcccc ccacacacgc ggcttcgggg cttgtcatga        1680
aaaaagctga atgctggggg tgcagctttc accaacagaa tcccgtttgg aagggacgcg        1740
gtgagacatg atccacccta agttgtgatc ctgggtgagc cgccgtccac accctgctga        1800
gggtcccttc acccacttta ttctccagaa aaccctgccc atcagggctg agtcccacgc        1860
cttccctctc cgtccaggcc tggctttgac ctctggggtc gtgtggggca caggggacac        1920
cctatccagg cagaggccct acggctatct ggaggaagtg gtgggagctg gcttctgcc         1980 tggaggatgc acccgagggg gtcacagtcc acacagagac acgggtgc cttccagatg          2040 gctgagccag tccagcccag aagggcctgg gggttggggg ctgcacctgg cctgtcccca        2100
ccagcagggc tcagggcttc ccaaggtgtg tggggacgg ggcagcacct ctcaaccagg         2160
tcacctgaaa cccgaactga aaggcatcct aagttaagac attaactccc attgtcaagg       2220
tgccatcgtc aattctgtct ccaaatcctt ctttgttatt tcatgtattc acagagtgac        2280
gctccgtgtt tcgttcagcc tgcaggcctg cagaagctgc atctcgggat ggccaagagc        2340
ccggccaggc cccacggctg cacccaggac gggattcatg ccccatgcct ggcttctcac        2400
gaccacagag tgcctttccc gggactggat ggaggcagag tgagagaaga gcctggagca       2460
agtgttttgg accacagtga tcaaacacgg agcccgtggg                              2500
```

<210> SEQ ID NO 81
<211> LENGTH: 700
<212> TYPE: DNA
<213> ORGANISM: Homo sapiens

<400> SEQUENCE: 81

```
aagaaaggcc agaccgggca cggtggctca cgcctgtaat cccaacactt ggggaggccg         60
aggcgggcag atcacctgag gtcaggagtt cgagaccagc ctggccaaca gggtgaaacc        120
ccgtctctac taaaaataca aaaaaaatt agccgggcgt ggtggcaggc acctgtaatc        180
ccagctaatc gggaggctga ggcaggagaa aatcacttga acctgggagg cggaggctgc        240
agtgagctga gatcgcgcca ctgcactcca gcctgggtga gggagcgaga ctgtctcaaa        300
aaaaaaaaaa aaaaaaaaaa aaaggaaag aaaggcccgg tgagatgctt tctcttaaac         360
acggccctgc acgttgagtt gctgcctcct gtggcctatt tcacgtttat gcaaagtcgg        420
gcgcctgatg cggggctcac ccgccacaag caggggtcct ggtgctgctc atggaagggg        480
ccctacccag cccgcgggc actggctggg acggggctgc ccaggtccgc ccaggatcca         540
aacacccagc cccgcccagc ggcccttcct ggcctgcagt ggaggctgta atgggcaggg       600
gtggtgggaa tccagctca cagggcgcct gctcttagaa gggcggcatc tgggtccaga         660
ggtcagaaac gtcagatgcc catcccagaa gtggcgggga                              700
```

<210> SEQ ID NO 82
<211> LENGTH: 10000
<212> TYPE: DNA
<213> ORGANISM: Homo sapiens

<400> SEQUENCE: 82

```
gggtgaatga gtagatgtat gggtgagtag gtgggtaggt gggtagatgg atgggtgggt         60
```

-continued

```
gggcgagtgt gtggttagat gatggatggc tgaatggatg agtgggggga tggatgggtg      120
agtgggtgta tgtatggatg ggttagtggg tgggtggatg aatggatggg tgcataaagg      180
atggatggat gaatgagtta gtgggttggc agatggatgg atgggtgagt cagtggatag      240
atggatgggt gggtggatag aggatggatg gttgggtagg tgatggtggg atgagtggat      300
agatgggtat gtgagtgagt gggggatgg gtaggtgggt ggatggatgg ttaggtgaat        360
gagtggatgg acagacggac agtgggtgga tggatgagtg aacgatggaa ccgatggatg      420
aatgggtggg tgggtagagg atggacggac aggtgagtgg gtgggtggat ggatagatgg      480
gtaagtgagt ggatagatag atgggtgggt ggacagagga tgggtggatg aatggatggg      540
ttagtgggtg gctgggtgga tggatgatgg atgggtgact gggtggatgg atggatgggt      600
tagtgggtgg ctgggtggat agatggatgg gtgattgggc gaatgggcga atgggtggat      660
gggtgggcgt ggagttggtg ggtacatgat aatgggtgg aatacccatg gattggaatg       720
agctgttttg gctgctattt ctgggacacc cagctctgcc aggcccctac ccctctggtg      780
ggccaggctc tgacggtggc cactcatggc ctttctagct ctggtgccag catagggaag      840
gaggaggcac agccttgtct tactccttgc acctgttagc ccccccccc gccaagggag        900 gacccgtggt tggggacagc acaggggcc ctgctgtgtg cagggactgt ccctggggcc       960
actgaagccc acctgttctt gttccttctc aggcggatcc tggtcccct ggtgagccag      1020 gccctcgggg gccaagagga gtcccaggac ccgaggtagg ttggtggcca gtccccatgc    1080
cctcccccca acctgccagg ccaacacaca cccaagcctc gtggttctgc ccacggtgga    1140
cccacgtatc agtgggcagt ggcctgggag agactcagcc acccagcctt ggccccagag    1200
tctcagcctc atccttcctt ccccaggtg agcccggccc cctggagac ccggtctca       1260 cggtaggtgt cacatggggc agaaccagtg tccttctcct gccaaaacta gacaccaaga    1320
gcagcagggg tgggggaagg tcagctggca cggtcagaga gcaagatcag tggaggaggt    1380
cagagggcaa ggtcagagag caagcttggt tggggaaggt cacagggcaa ggttggtggg    1440
gggaggaggg tggcagcgag gttggtaggg acaggacccg ccagcctccc cgcatggctg    1500
cctccacacg tgggctggaa tgtcccggga ccccaggcc aggaccttgc tgtggaaact     1560 cttctgggc cccgggggga ctaccctgcc tgccgtgtgc attgcaggag tgtgacgtca      1620
tgacctacgt gagggagacc tgcggtgct gcggtgaggc actgcccacg gcagggtcgg    1680
ggcccatgca ccgggtggag ggcgggagtg cagcagggct gggtcatcgc tgggtcctgc    1740
atgtgcacgt gaccctaggg tctgaggtct ccccggtacc ccccgatgac cctgccaccc    1800
ccccagactg tgagaagcgc tgtggcgccc tggacgtggt cttcgtcatc gacagctccg    1860
agagcattgg gtacaccaac ttcacactgg agaagaactt cgtcatcaac gtggtcaaca    1920
ggctgggtgc catcgctaag gaccccaagt ccgagacagg tcagcggggc aggggcgggt    1980
gcagcattgc ggggggccgg gcggggcgtg ggaggcgatg agatgggaga agtccagacg    2040
cgtccctcca acgagggcct ctgcatggct gggatgccc agaccccga ggcctctggc      2100 aacgacctca cgcgtgcggc ttgcagggac gcgtgtgggc gtggtgcagt acagccacga    2160
gggcaccttt gaggccatcc agctggacga cgaacgtatc gactccctgt cgagcttcaa    2220
ggaggctgtc aagaacctcg agtggattgc gggcggcacc tggacaccct cagccctcaa    2280
gtttgcctac gaccgcctca tcaaggagag ccggcgccag aagacacgtg tgtttgcggt    2340
ggtcatcacg gacgggcgcc acgacccteg ggacgatgac ctcaacttgc gggcgctgtg    2400
cgaccgcgac gtcacagtga cggccatcgg catcggggac atgttccacg agaagcacga    2460
```

```
gagtgaaaac ctctactcca tcgcctgcga caagccacag caggtgcgca acatgacgct   2520
gttctccgac ctggtcgctg agaagttcat cgatgacatg gaggacgtcc tctgcccggg   2580
tgagcgtgtg ggcgcggggc agtcggccga ggagcagcag gccccagccg ctgtctagcg   2640
tgagccccag ggacacccct cacctgaggg atgaatgtgc agcccaggat cttgggctgt   2700
gggtgggaag gggtcgggcc ctctcggggc tgcagggcag aggccagctg caccctgagc   2760
ctgtctaggc agatcagtga acggccgctg agggttcgct agggactgac cctggcctgg   2820
cccggcctct ctcctctctt ccagaccctc agatcgtgtg cccagacctt ccctgccaaa   2880
caggtaatgc agggcaccct gagccaccac cccagactag caaagcagcc ctggtgtcct   2940
tcctcctcga gggccgggct gggggagggg ccgtgcaggg acccggggggg cggcggagcc   3000
actgcggagg ctgctcctta gggagatggc cccaggatgg cagcacaggg gaggaggggc   3060
ttggggaagg caggctccca ggaacgcagg aacagcatca cgaggccatg aggtgggtgc   3120
tgctagcctg gcgctgtgct cggcatgtgg ccactggtct tgaaggccca ccatgggcct   3180
tgcagtctcc ctcagctgcc gcccagctcc catgggctgg ccgtgcatgt gccactcgga   3240
ggaagccctg gattcagtga gtgaaaccat cccggggtgg aagcactgac accccccagc   3300
accagcaggt cttgctccaa ccctggcctg cctcggagct gcagctgcgg ctctcacatc   3360
tctgggagtg ggggagccca tgtcccggat gtggcccacg tgggtgtgaa gctggagctg   3420
ggggtgccgt ccaggctctg ctggacgtgg tgctgccccc atggtgcact gctgcaccgt   3480
acctgggccc acaggaggtc cccggggggcg ttaggagctg agtcccctc agtgagccgt   3540
cccctccagg agtgtgaggg tagggatgcc atggagacag ggtgggaggg tccgacctgg   3600
aggaccacag ggaggaaacc tcagggtctg cggtacgaag tcagcgcttc ctcagcacgc   3660
gggtcgcggt gtgcgttcgg gcgttccatg gggagctccc ggtgggtgag ctgggccact   3720
gagcacattc acaggccctg aggctgcccc aggggaggag ccgtggactc agagccgagg   3780
ttccccatac gtgctgcgac agagaaccta gggcttgcac ctgggtctgg ctgcccttca   3840
gcaggcgggc agcctctggc cccacaacag tgggctgtgc ttctgccgcc aaggtgcagg   3900
cgtcctcccc cagggtccac atcagcagca ggggcacctg accctgagg gcaggaacca   3960
gaccttggct cctccaccca ccccctcgtt cctgatgggg cagggaagtc tcgggacccc   4020
atgatgggcg acatggcgat ggtcactgtg ggtgctttgc tatcaggtgg ggggccttcc   4080
tctccactct gggtccagtg tgagtggccg ctatggcttc ccctccactc caggttctat   4140
cgtgagtggg tgggtgctgc gtctgtggat gtcacgtgac cttcctctt tagcctatca   4200
ttgtagttgg gagttagtta gcccgttgag cgtcattgaa tttccagtgt tgagccagcc   4260
ctgcgtgccc gggataaacc cacctggccg tggtgtgtgg ccctgtttat gcacgtgggc   4320
cctgattcgc tgatgcctgc ctgagggttt gcgcttatcg gcgacatcag cctgcacttt   4380
tcttttctcg tgatctctct ggttctggcc tcagggtgac gtgggcctcg tagggtcctg   4440
tggtggctcc tccccagacg gtgacatgga gtgagcccat tctccctcct gggagtgggt   4500
cactcaggcc accagagcac cacagggaaa gcagccaggg aggacacgga ggcccttgaa   4560
gctctggcct cttctgaggc ctccaggacc tgacagtgag tgggagcagc cctgcagaaa   4620
cccctcccct cctctcggcc gccctgacac ctcatccccg acactcagag ctcatcctcc   4680
ttcccagctg tttccaattt caaagtgaac tcgaccttgt ggctccagga gatgcagcag   4740
ggacagtgtt aaatcggctt tcaccagccc acacggccag gcatcctcct cggccctcct   4800
```

```
gggcactggg tggacaccac tgctgtggc ctggccctgg ccttctccag acagccctgt    4860 ccacccaaa gcccagccac cctgggcctg cagcaggcct gtggagttct cagttgcgtg    4920
gggaccagag ggtgctggag aaacaaacca gacgcagctg aaggcagtca gggcagggcg    4980
caatcagcga taagagctgc ataggggcca cagcgtaacc tgagctccag tcggtggaaa    5040
gaaaaggcag agacgttgca gaggccaggt ctgctcaggg aagacagtt ctgggtgtag     5100 aggactcaca tcccagagag gctgaggaag ggtttaccac cgcaagcttt ctcaggcggg    5160
ctcttgaggg gtggctgggg tcttcctggc gacgggcctg cggcactgga agccctactg    5220
gagtttggcc tgtctccggc acaggtttgg acggagctgt tttgtgctga aaggttttct    5280
cggggtccgt ggtgtccccc aaaggtgcca ccgtgcgggt ctcctagctc cctgccagct    5340
tcctgtccct gtgctcactg cccccacgcc tcctgccaag gccgagccac acacccgctc    5400
cacctgcatt tcctctaccg actcgccagc ccaaatgccg ctcttcactc tggcctcgct    5460
gagcggctgc ccgaggagga gctctaggcc gacgcccacc gcaggcctta cagtcttctc    5520
tggacgctcc cttgcagatg caccgtgcc tgcggcgag ccccggtca ccttcctccg       5580 cacggaagag gggccggacg ccaccttccc caggaccatt cccctgatcc aacagttgct    5640
aaacgccacg gagctcacgc aggacccggc cgcctactcc cagctggtgg ccgtgctggt    5700
ctacaccgcc gagcgggcca agttcgccac cggggtagag cggcaggact ggatggagct    5760
gttcattgac acctttaagc tggtgcacag ggacatcgtg ggggaccccg agaccgcgct    5820
ggccctctgc taaagcccgg gcacccgccc agccgggctg ggccctccct gccacactag    5880
cttcccaggg ctgcccccga caggctggct ctcagtggag gccagagatc tggaatcggg    5940
gtcagcgggg ctacagtcct tccaggggct ctggggcagc tcccagcctc ttcccatgct    6000 ggtgccacc gtgtcccttg ctgcggctgc atcttccagt ctctcctccg tcttcctgtg     6060
gccgctctct ttataagaac cctggtcatt gaatttaagg cccaccccaa gtccagaatg    6120
acctcgcaag accccttaact cactcccgtc tgcagagtcc ttctttgctg catcaggtca   6180
ccctcacagg ctccagggtt tgggtgtgga agtctttgga ggcccttact tagcggccca   6240
gctgggctgc cgtgcgtctg ggatggggct gagggagggt gctgcccagg tgctggagga   6300
tgttccagca ccaggttcca gcggagcctc ggaaacaggc cccagaggct ggtgagcctc    6360
gctgggtgtg ggcactaatc ccgtgcatgg tgactcgtgg gcgctcacgg cccacctggt    6420
ggcaggtgaa ggcttccggt tgggcagcag atagtcctgg gggaagctgg cagtcctggc    6480
accatgacgt atctgggctg gtgtcatgca cagtagggcg aatggccaca gctgcctgcc    6540
agcagccctg atcccggggt gtctgcaccc ttccagccca acctctgggt ctccaaaagc    6600
acagtcgggg gagcatccac caggcacaac ctctgcggtc ctcagaggac tgagcagaga    6660
atcccagggt ccacaatgtt ggggagcggc agggatcacc atccaaaggg agcggccccc    6720
acggcgagct gaccccgacg ttctgactgc aggagccctc atccaggctg gctcctgcc    6780 gggcacggct gtgaccattt ctcagggcca ggttctcgtc cccacaccca ctgcacaggg    6840
caggccaggc tggtcttccc actgtgggga tgaaggatcc tccacaggag gaggagagca   6900
gagtccacag acatcccaac agcctcagcc tccctgtgcc tggccggccc ccacagcttc    6960
cccgtctcct ccaggcccca cagacactga tgaatggaca gagacccca aaaccagctg     7020 cccttgcat gtctgtctcc atatgtttgg tgacagcagt gaaaatgtta ttagttttga    7080
gggggtttgg gaagcccagc ggtacctgag gagtttctgg acatttaagc cggttcctag    7140
gtgtggcctt aacagggagg ctgccccttcc tttcactgaa tgagctgcgt cactcataag   7200
```

```
ctcactgagg gaaccccatc tgccagctcg tgcgtgctca gacgcgtcc  atgtctcaag   7260
cgttctgtga aggctgcggt gcagcgtgag gtcaccctgc tgtgttcaga gctttgctca   7320
ctgcctgcgg ggctggaccg ttgcacctcc agggccccca gaaaccgagt tcgggtcag    7380
ggtcctctgt gtgcattcct gggggtccat gtaccagctg tgacgacgtc caggggttgg   7440
gctgagaagc agacaccctt ggggaaactg gctctgtccc tcccctcccc catcccagga   7500
gctgaggtct tggtgaggcc acagggccag gtccacgcaa ggactgtccg tgtcctgtcc   7560
tgtggtctct ggcccacgt  gacacccaca cgtgtggtag gcagcctggc ctgggttgtg   7620
gctatggcca ggcccccaag ctgtccccga tgcccagggc tggtgaccac ccaggcaggt   7680
gggggcccca cttggtaaca gagtcatagg gcagaaccca cctgggctgc cacagaaggt   7740
ctggctgccc ctgtgcccac tgctccccac catggccaat cagaagagtc aggggctcct   7800
ggtctttccg ggagggacgt ggcccagcca gctctaggtg ttctgagcag ctctgggacc   7860
cagcgattga ggggtcaggc tgggggtgtc agagccaggg tcctccttaa gtacctccca   7920
cactacacag acagtggccc ttttgtgggc agcaaattct tgagccatga aaggatgctt   7980
tgggccccttc cctcccagg  agggcagcct gtgcagggat ggtgctcagc aggtggacag   8040
ggcctggggc ctgtgtcagg gtctcaggcc tgggagcacc agcagaggag atggcggctc   8100
ccagcagtgc cgcctgaaag tgtcttgggc taaggaccca cacccagggc tgccctgcag   8160
aaacgccccc gcagagccca gtggtctgtg aggttgcagg cagggtgcga atggaagggc   8220
acaggtgcgg ggctggcacc tgcccggtcc tgcccacctc cctccgccc  agcccgcacc   8280
tgcgtctccc cacagagctg tccgtggcac agtgcacgca gcggcccgtg gacatcgtct   8340
tcctgctgga cggctccgag cggctgggtg agcagaactt ccacaaggcc cggcgcttcg   8400
tggagcaggt ggcgcggcgg ctgacgctgg cccggaggga cgacgaccct ctcaacgcac   8460
gcgtggcgct gctgcagttt ggtggcccccg cgagcagca ggtggccttc ccgctgagcc   8520
acaacctcac ggccatccac gaggcgctgg agaccacaca atacctgaac tccttctcgc   8580
acgtgggcgc aggcgtggtg cacgccatca atgccatcgt gcgcagcccg cgtggcgggg   8640
cccggaggca cgcagagctg tccttcgtgt tcctcacgga cggcgtcacg ggcaacgaca   8700
gtctgcacga gtcggcgcac tccatgcgca agcagaacgt ggtacccacc gtgctggcct   8760
tgggcagcga cgtggacatg gacgtgctca ccacgctcag cctgggtgac cgcgccgccg   8820
tgttccacga gaaggactat gacagcctgg cgcaacccgg cttcttcgac cgcttcatcc   8880
gctggatctg ctagcgccgc cgcccgggcc ccgcagtcga gggtcgtgag cccaccccgt   8940
ccatggtgct aagcgggccc gggtcccaca cggccagcac cgctgctcac tcggacgacg   9000
ccctgggcct gcacctctcc agctcctccc acggggtccc cgtagcccg  ccccccgccc   9060
agccccaggt ctccccaggc cctccgcagg ctgcccggcc tccctccccc tgcagccatc   9120
ccaaggctcc tgacctacct ggcccctgag ctctggagca agcccctgacc caataaaggc   9180
tttgaaccca ttgcgtgcct gcttgcgagc ttctgtgcgc aggagagacc tcaaaggtgt   9240
cttgtggcca ggagggaaac actgcagctg tcgctcgccc accagggtca atggctcccc   9300
cgggcccagc cctgacctcc taggacatca actgcaggtg ctggctgacc ccgcctgtgc   9360
agaccccaca gccttgatca gcaaactctc cctccagccc cagccaggcc caaagtgctc   9420
taagaagtgt caccatggct gagggtcttc tgtgggtgga cgcatgatta acactagacg   9480
gggagacagc aggtgctgag cctgttgtgt tctgtgtgga gatctcagtg agttttgct    9540
```

| | |
|---|---|
| gttcagaccc cagggtcctt caggctcagc tcaggagccc cacagtgaac cagaggctcc | 9600 |
| acaggcaggt gctgacctga caggagtggg cttggtggcc atcacagggc accacagaca | 9660 |
| cagcttgaac aactaccagt atcggccaca ggcctggagg catcagccgg ccatgcttc | 9720 |
| ctctggaggg ctagaggagg actagagaag ggcctgcccc ggcctctccc cagcatccca | 9780 |
| gggttcctga tctcctggat aaggatacaa gtcaccacac tggactgggg ctcagcctgc | 9840 |
| tctagaatac ctcacctaag tcacagtgga ccaggctcag cctgctctaa ggtgagctta | 9900 |
| cccgagacac tggaccagag atcagcctat cctgggataa gctcacccga gtcacactgg | 9960 |
| accagggctc agcctattcc gggatgagct cacccgagtc | 10000 |

<210> SEQ ID NO 83
<211> LENGTH: 800
<212> TYPE: DNA
<213> ORGANISM: Homo sapiens

<400> SEQUENCE: 83

| | |
|---|---|
| gacacttcca tgactgcagc tgaccagtcc acctgccagc ggttgaccac tcccacttcg | 60 |
| ccagcgaccg aaggggaggg gaggggcctc acctgagggc aacagcagaa cccaccacct | 120 |
| ggtcttgctt tactcagacc tgaggtgtg aaaggtgccc gtgacctccc gcatcaggga | 180 |
| gctggccgcc accctcgact cccggggagc aggcgtcccg cgaccccctc atctaccagg | 240 |
| ccatctgagc tgggcggcgc ctcacctccg ctcccggggg agccggcctc agggtaggca | 300 |
| tgcgccctgg gtgggagcag gtcgtggccg ccgccctcct ggcagctctg gctgagcagc | 360 |
| cgccgcagca tctgattctc cttcaggagg cgcacctgct tcttcaggtc cgcgttctcg | 420 |
| ctcaggagcc ggctcatcag ctcgccgcct tcagccatgg cgggtgcgtc cctccttgtc | 480 |
| cctcacggct cctgcagccc catggaggtg ggagcccaga gccgcaggc accacagaaa | 540 |
| cagcccaggc acggagttcc gtagccacca ccgccttcca cgccttgtga tgtcactgcc | 600 |
| ctagtgatga ggtgcccagc accctgcctg ccccgcgat ggctcatggc cccgttgagg | 660 |
| cagtgaagct ggaggcccgt ggcgtgcaca gcagccact cccacattat gaccagggcc | 720 |
| cgagaatgcc aaggacatta ggcagctacg ggatgtagcg actgtactcc aagaggggcg | 780 |
| tccaagccac tccccattga | 800 |

<210> SEQ ID NO 84
<211> LENGTH: 490
<212> TYPE: DNA
<213> ORGANISM: Homo sapiens

<400> SEQUENCE: 84

| | |
|---|---|
| atgtctgcag ggaagaagca gggggaccct gaataaagtt tccgtttttc ctatttgtta | 60 |
| aagtgataga gcattatagg accagagaac aggtgtgtct gtacactgtg caggtccccg | 120 |
| gggcaggctc tgagtccgtc tgcacacggt gcgggtcccc ggggcgcgcc ctgagcccgt | 180 |
| ctgcacacgg tgcgggtccc cggggcgcgc cctgagcccg tctgcacacg gtgcgggtcc | 240 |
| ccggggcgcg ccctgagccc gtctgcacac ggtgcgggtc ccggggcgc gccctgagcc | 300 |
| cgtctgcaca cggtgcgggt ccccggggcg cgccctgagc cgtctgcac acggtgcggg | 360 |
| tccccggggc gcgccctgag cccgtctgta cacggtgcgg tccccgggg cgcgccctga | 420 |
| gtctctacta aaaatacaaa aattagccag gcgtggtggt tcaagcctgt aatcccagct | 480 |
| ccttgggagg | 490 |

```
<210> SEQ ID NO 85
<211> LENGTH: 601
<212> TYPE: DNA
<213> ORGANISM: Homo sapiens

<400> SEQUENCE: 85
cggtgccagg ctgtaccaga ggctgggcca cacttcgcag ttcagcctgt ctccccatac      60
accttcccac caaggttccc aacttctctg gctttgcagg gtcctgactg cagactagac     120
tgactaacta gatgatgtgc attgattgtt tccgacttcc aggagaatgt ggggtgccca     180
gggtgcctgg gttagagaag gaaccaaaag tttccttgga tcctcatcag ggaattgtgg     240
tgtgatacag ggcggtgaag gggctccagt ttcacagaga agtgaagaac gagtgtgcct     300 cttttatgg gacctttgga atgacaggaa tggaagcctg agccctctcc acccagcact      360
gccctgtcac tgccccggga cgtccacgtg ggctctggga atgctccttt gctgagacag     420
gcttgggtag tacaagttca agccctcctc tgttgaaatg tgtgtgctct gtttagccaa     480
gaggtgtctg catccgagct atgcagagca aagtattatt agagccggca tcagtgtgtc     540
tgtaactgaa cccagctctc cctagcaacc gttgccaaca acacatctaa cagaaggatg     600
c                                                                     601
```